US011472769B2

(12) United States Patent
Ren et al.

(10) Patent No.: US 11,472,769 B2
(45) Date of Patent: Oct. 18, 2022

(54) SSAO INHIBITORS AND USE THEREOF

(71) Applicant: Eccogene (Shanghai) Co., Ltd., Shanghai (CN)

(72) Inventors: Zaifang Ren, Shanghai (CN); Xuefeng Sun, Shanghai (CN); Qing Xu, Shanghai (CN)

(73) Assignee: Eccogene (Shanghai) Co., Ltd., Shanghai (CN)

( * ) Notice: Subject to any disclaimer, the term of this patent is extended or adjusted under 35 U.S.C. 154(b) by 17 days.

(21) Appl. No.: 17/082,323

(22) Filed: Oct. 28, 2020

(65) Prior Publication Data

US 2021/0147360 A1 May 20, 2021

(30) Foreign Application Priority Data

Oct. 29, 2019 (WO) ................ PCT/CN2019/113957
Apr. 26, 2020 (WO) ................ PCT/CN2020/087022

(51) Int. Cl.

*C07D 211/46* (2006.01)
*C07D 309/06* (2006.01)
*C07D 211/32* (2006.01)
*C07C 317/32* (2006.01)
*C07D 307/14* (2006.01)
*C07D 319/12* (2006.01)

(52) U.S. Cl.

CPC .......... *C07D 211/46* (2013.01); *C07C 317/32* (2013.01); *C07D 211/32* (2013.01); *C07D 307/14* (2013.01); *C07D 309/06* (2013.01); *C07D 319/12* (2013.01)

(58) Field of Classification Search

CPC .................................................... C07D 211/46
See application file for complete search history.

(56) References Cited

U.S. PATENT DOCUMENTS

| | | | |
|---|---|---|---|
| 8,426,587 B2 | 4/2013 | McDonald et al. | |
| 9,302,986 B2 * | 4/2016 | Deodhar ............... | C07C 323/62 |
| 2013/0143860 A1 | 6/2013 | Yoshihara et al. | |
| 2015/0158813 A1 | 6/2015 | Deodhar et al. | |

FOREIGN PATENT DOCUMENTS

| | | |
|---|---|---|
| CN | 107935993 A | 4/2018 |
| CN | 108003166 A | 5/2018 |
| CN | 108047213 A | 5/2018 |
| CN | 109251166 A | 1/2019 |
| CN | 109810041 A | 5/2019 |
| WO | WO 2007/120528 A2 | 10/2007 |
| WO | WO 2009/066152 A2 | 5/2009 |
| WO | WO 2012/124696 A1 | 9/2012 |
| WO | WO 2013/163675 A1 | 11/2013 |
| WO | WO 2017/022861 A1 | 2/2017 |
| WO | WO 2017/148518 A1 | 9/2017 |
| WO | WO 2017/148519 A1 | 9/2017 |
| WO | WO 2017/194453 A1 | 11/2017 |
| WO | WO 2018/028517 A1 | 2/2018 |
| WO | WO 2018/073154 A1 | 4/2018 |
| WO | WO 2018/149226 A1 | 8/2018 |
| WO | WO 2018/196677 A1 | 11/2018 |
| WO | WO 2018/233633 A1 | 12/2018 |
| WO | WO 2019/024924 A1 | 2/2019 |
| WO | WO 2019/101086 A1 | 5/2019 |
| WO | WO 2019/241751 A1 | 12/2019 |
| WO | WO 2020/086747 A2 | 4/2020 |

OTHER PUBLICATIONS

Wolff, Manfred E. "Burger's Medicinal Chemistry, 5ed, Part I", John Wiley & Sons, 1995, pp. 975-977.*
Banker, G.S. etal, "Modern Pharmaceutics, 3ed.", Marcel Dekker, New York, 1996, pp. 451 and 596.*
Rautio et al. "Prodrugs: design and clinical Applications" Nature Reviews Drug Discovery 2008, 7, 255-270.*
Beaumont "Design of Ester Prodrugs to Enhance Oral Absorption of Poorly Permeable Compounds: Challenges to the Discovery Scientist" Current Drug Metabolism, 2003, 4, 461-485.*
Malmborg "Predicting human exposure of active drug after oral prodrug administration, using a joined in vitro/in silico-in vivo extrapolation and physiologically-based pharmacokinetic modeling approach" Journal of Pharmacological and Toxicological Methods 67 (2013) 203-213.*
Dunkel "Semicarbazide-sensitive amine oxidase/vascular adhesion protein-1: a patent survey" Expert Opin. Ther. Patents (2011) 21 (9) 1453-1471.*

(Continued)

*Primary Examiner* — David K O'Dell
(74) *Attorney, Agent, or Firm* — Cooley LLP; Chen Chen; Heng Zhang

(57) ABSTRACT

The application relates to a compound of Formula (I') or (I):

(I')

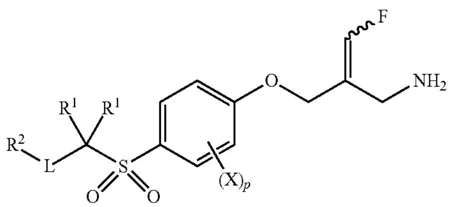

or (I)

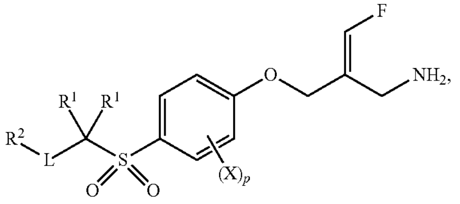

or a pharmaceutically acceptable salt, hydrate, solvate, prodrug, stereoisomer, or tautomer thereof, which modulates the activity of SSAO, a pharmaceutical composition comprising a compound of Formula (I') or (I), and a method of treating or preventing a disease in which SSAO plays a role.

22 Claims, No Drawings

(56) References Cited

OTHER PUBLICATIONS

Pannecoeck "Vascular adhesion protein-1: Role in human pathology and application as a biomarker" Critical Reviews in Clinical Laboratory Sciences (2015), 52(6), 284-300.*

Vakal "Human Copper-Containing Amine Oxidases in Drug Design and Development" Molecules (2020), 25(6), 1293.*

Bligt-Linden, et al. "Novel pyridazinone inhibitors for vascular adhesion protein-1 (VAP-1): old target-new inhibition mode." J Med Chem. Dec. 27, 2013;56(24):9837-48. doi: 10.1021/jm401372d.

Dunkel, et al. "Semicarbazide-sensitive amine oxidase/vascular adhesion protein-1: a patent survey." Expert Opin Ther Pat. Sep. 2011;21(9):1453-71. doi: 10.1517/13543776.2011.594040.

Inoue, et al. "Novel 1H-imidazol-2-amine derivatives as potent and orally active vascular adhesion protein-1 (VAP-1) inhibitors for diabetic macular edema treatment." Bioorg Med Chem. Jul. 1, 2013;21(13):3873-81. doi: 10.1016/j.bmc.2013.04.011.

Inoue, et al. "Synthesis and SAR study of new thiazole derivatives as vascular adhesion protein-1 (VAP-1) inhibitors for the treatment of diabetic macular edema." Bioorg Med Chem. Mar. 1, 2013;21(5):1219-33. doi: 10.1016/j.bmc.2012.12.025.

Foot, et al. "The discovery and development of selective 3-fluoro-4-aryloxyallylamine inhibitors of the amine oxidase activity of semicarbazide-sensitive amine oxidase/vascular adhesion protein-1 (SSAO/VAP-1)." Bioorg Med Chem Lett. Jun. 15, 2012;22(12):3935-40. doi: 10.1016/j.bmcl.2012.04.111.

Jakobsson, et al. "Structure of human semicarbazide-sensitive amine oxidase/vascular adhesion protein-1." Acta Crystallogr D Biol Crystallogr. Nov. 2005;61(Pt 11):1550-62. doi: 10.1107/S0907444905028805.

Nurminen, et al. "Novel hydrazine molecules as tools to understand the flexibility of vascular adhesion protein-1 ligand-binding site: toward more selective inhibitors." J Med Chem. Apr. 14, 2011;54(7):2143-54. doi: 10.1021/jm200059p.

Nurminen, et al. "Synthesis, in vitro activity, and three-dimensional quantitative structure-activity relationship of novel hydrazine inhibitors of human vascular adhesion protein-1." J Med Chem. Sep. 9, 2010;53(17):6301-15. doi: 10.1021/jm100337z.

Salmi and Jalkanen. "Vascular Adhesion Protein-1: a Cell Surface Amine Oxidase in Translation." Antioxid Redox Signal. Jan. 20, 2019;30(3):314-332. doi: 10.1089/ars.2017.7418.

Salter-Cid, et al. "Anti-inflammatory effects of inhibiting the amine oxidase activity of semicarbazide-sensitive amine oxidase." J Pharmacol Exp Ther. Nov. 2005;315(2):553-62. doi: 10.1124/jpet.105.089649.

Weston and Adams. "Hepatic consequences of vascular adhesion protein-1 expression." Neural Transm (Vienna). Jul. 2011;118(7):1055-64. doi: 10.1007/s00702-011-0647-0.

Yraola, et al. "New efficient substrates for semicarbazide-sensitive amine oxidase/VAP-1 enzyme: analysis by SARs and computational docking." J Med Chem. Oct. 19, 2006;49(21):6197-208. doi: 10.1021/jm051076e.

* cited by examiner

SSAO INHIBITORS AND USE THEREOF

RELATED APPLICATIONS

This application claims the benefit of and priority to International Application No. PCT/CN2019/113957, filed on Oct. 29, 2019, and International Application No. PCT/CN2020/087022, filed on Apr. 26, 2020, the entire contents of each of which are incorporated herein by reference in their entireties.

BACKGROUND

Semicarbazide-sensitive amino oxidase/vascular adhesion protein-1 (SSAO/VAP-1) exists both as a membrane-bound isoform and a plasma soluble isoform. It is predominantly expressed in endothelial cell surface, vascular smooth muscle, and adipose cells. Both the membrane-bound VAP-1 protein and the soluble SSAO enzyme have amine oxidase enzymatic activity. SSAO catalyzes oxidative deamination of primary amines and produces aldehyde, hydrogen peroxide and ammonium. SSAO protein and activities are involved in leukocyte adhesion and migration from blood to tissue, which is often upregulated during inflammation.

SSAO/VAP-1 participates in many cellular processes including glucose disposition, inflammation responses and the associated pain, and leukocyte recruitment. High activity levels of this enzyme are associated with diabetes, atherosclerosis, stroke and complications thereof, chronic kidney disease, and Alzheimer's disease, among other disorders. SSAO/VAP-1 has also been implicated in the pathogenesis of liver diseases such as the fatty liver disease.

Nonalcoholic fatty liver disease (NAFLD) has shown an increasing prevalence, along with a global increase in diabetes and metabolic syndrome. NAFLD, a continuum of liver abnormalities from nonalcoholic fatty liver (NAFL) to nonalcoholic steatohepatitis (NASH), can be characterized as ectopic accumulation of lipid, progressive lobular inflammation, hepatocyte degeneration and fibrosis in liver. It has a variable course but can lead to cirrhosis, liver cancer and other liver related morbidities. Therefore, there is a need for treatments for NAFLD and/or NASH.

An SSAO/VAP-1 inhibitor is believed to be able to reduce liver inflammation and fibrosis, and thereby provide a treatment for liver diseases, in particular, NAFLD and/or NASH. In addition, since activation of SSAO/VAP-1 has been implicated in inflammation and the associated pain, inhibition of SSAO/VAP-1 may also be useful in treating pain, and in particular, pain associated with osteoarthritis.

Currently, there is no approved drugs for the treatment for NASH, while the standard of care for NASH including diet control and/or life style changes often lacks effect once liver cell injury and inflammation are evident. In addition, the current standard of care for pain is dominated by nonsteroidal anti-inflammatory drugs (NSAIDS) and opioids, which are not recommended for chronic use due to adverse effect and abuse. Thus, there is a need for SSAO/VAP-1 inhibitors as therapeutic options for the treatment of chronic pain. The present application addresses the need.

SUMMARY

A first aspect of the application relates to a compound of Formula (I') or (I):

(I')

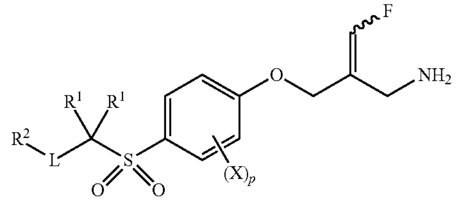

or (I)

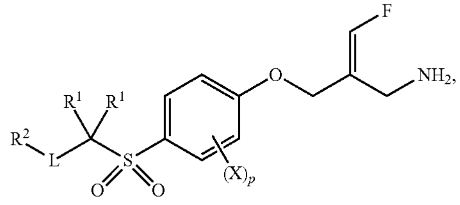

, or a pharmaceutically acceptable salt, solvate, prodrug, stereoisomer, or tautomer thereof, wherein $R^1$, $R^2$, L, X, and p are as described in detail below.

Another aspect of the application relates to a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating a SSAO-mediated disorder. The method comprises administering to a subject in need of a treatment for a disease or disorder associated with modulation of SSAO a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of reducing liver inflammation. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of reducing neuroinflammation. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of reducing liver fibrosis. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of reducing lung fibrosis. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating liver diseases. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating nonalcoholic fatty liver disease (NAFLD). The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating nonalcoholic steatohepatitis (NASH). The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating cardiovascular diseases. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating atherosclerosis. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating stroke and complications thereof. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating myocardial infarction. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating chronic kidney diseases. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating autoimmune diseases. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating metabolic diseases. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating inflammation. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating pain. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating pain associated with osteoarthritis. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of modulating (e.g., inhibiting) SSAO. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a compound of Formula (I') or (I), or a pharmaceutically acceptable salt, solvate, prodrug, stereoisomer, or tautomer thereof, or a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier, for use in a method of treating a SSAO-mediated disorder or of modulating (e.g., inhibiting) SSAO.

Another aspect of the application relates to use of a compound of Formula (I') or (I), or a pharmaceutically acceptable salt, solvate, prodrug, stereoisomer, or tautomer thereof, or a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier, in the manufacture of a medicament for treating a SSAO-mediated disorder or for modulating (e.g., inhibiting) SSAO.

The present application further provides methods of treating a disease or disorder associated with modulation of SSAO including, but not limited to, liver diseases, nonalcoholic steatohepatitis (NASH), cardiovascular diseases, metabolic diseases, inflammation, and pain, comprising administering to a subject suffering from at least one of the diseases or disorders a compound of Formula (I') or (I), or a pharmaceutically acceptable salt, solvate, prodrug, stereoisomer, or tautomer thereof.

The present application provides inhibitors of SSAO that are therapeutic agents in the treatment of diseases such as liver diseases, nonalcoholic steatohepatitis (NASH), cardiovascular diseases, metabolic diseases, inflammation, pain, and other disease associated with the modulation of SSAO.

The present application further provides compounds and compositions with an improved efficacy and safety profile relative to known SSAO inhibitors. The present application also provides agents with novel mechanisms of action toward SSAO in the treatment of various types of diseases including liver diseases, nonalcoholic steatohepatitis (NASH), cardiovascular diseases, metabolic diseases, inflammation, and pain. Ultimately the present application provides the medical community with a novel pharmacological strategy for the treatment of diseases and disorders associated with SSAO.

DETAILED DESCRIPTION

Compounds of the Application

The present application relates to compounds and compositions thereof that are capable of modulating the activity of semicarbazide-sensitive amino oxidase (SSAO). The application features methods of treating, preventing, or ameliorating a disease or disorder in which SSAO plays a role by administering to a subject in need thereof a therapeutically effective amount of a compound of Formula (I') or (I), or a pharmaceutically acceptable salt, solvate, prodrug, stereoisomer, or tautomer thereof. The compounds of the present application can be used in the treatment of a variety of SSAO-mediated diseases and disorders by inhibiting the activity of SSAO. Inhibition of SSAO provides treatment, prevention, or amelioration of diseases including, but not limited to, liver diseases, nonalcoholic steatohepatitis (NASH), cardiovascular diseases, metabolic diseases, inflammation, and pain.

In a first aspect of the application, a compound of Formula (I') or (I) is described:

(I')

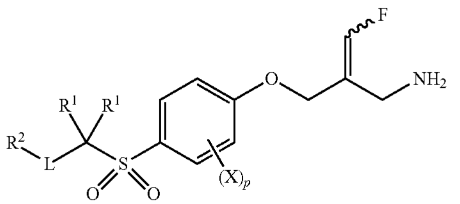

or (I)

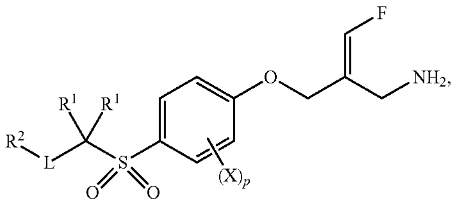

or a pharmaceutically acceptable salt, solvate, prodrug, stereoisomer, or tautomer thereof, wherein:

each X is independently Cl or F;

p is 0, 1, 2, or 3;

L is absent, —O—, ($C_1$-$C_4$) alkylene, substituted ($C_1$-$C_4$) alkylene, —O—($C_1$-$C_4$) alkylene, substituted —O—($C_1$-$C_4$) alkylene, ($C_1$-$C_4$) alkylene-O—, or substituted ($C_1$-$C_4$) alkylene-O—, wherein the substituted ($C_1$-$C_4$) alkylene, substituted —O—($C_1$-$C_4$) alkylene, or substituted ($C_1$-$C_4$) alkylene-O— is substituted with one or more $L^1$;

each $L^1$ is independently ($C_1$-$C_4$) alkyl, F, or $CF_3$; or two $L^1$, together with the atom to which they are attached, form a 3- to 5-membered cycloalkyl ring;

each $R^1$ is independently H, F, methyl, ethyl, or $CF_3$;

$R^2$ is ($C_1$-$C_4$) alkyl substituted with one or more ($C_1$-$C_4$) alkoxy, ($C_1$-$C_4$) alkoxy, $NR^3C(O)R^4$, $C(O)NR^3R^4$, phenyl, ($C_3$-$C_8$) cycloalkyl, heterocyclyl comprising one or two 3- to 6-membering rings and 1 to 3 heteroatoms selected from N and O, or heteroaryl comprising one or two 5- to 6-membered rings and 1 to 3 heteroatoms selected from N and O, wherein the phenyl, cycloalkyl, heterocyclyl, or heteroaryl is optionally substituted with one or more $R^5$;

$R^3$ is H, methyl, or ethyl;

$R^4$ is ($C_1$-$C_4$) alkyl or ($C_3$-$C_{10}$) cycloalkyl optionally substituted with one or more $R^8$; or $R^3$ and $R^4$, together with atom(s) to which they are attached, form a 3- to 6-membered ring optionally comprising one additional heteroatom selected from N and O and optionally substituted with one or more $R^5$;

each $R^5$ is independently ($C_1$-$C_4$) alkyl, ($C_1$-$C_4$) alkoxy, hydroxy, cyano, oxo, $C(O)R^7$, $C(O)NR^7R^{7'}$, $NR^3C(O)R^7$, $NR^3S(O)_2R^4$, $S(O)_2R^4$, ($C_1$-$C_4$) alkyl substituted with one or more hydroxy or $R^6$, ($C_3$-$C_{10}$) cycloalkyl optionally substituted with one or more hydroxy or $R^6$, or heterocyclyl comprising one or two 3- to 6-membering rings and 1 to 3 heteroatoms selected from N and O and optionally substituted with one or more hydroxy or $R^6$; or two $R^5$, together with the atom or atoms to which they are attached, form a 3- to 5-membered saturated or 5- or 6-membered aromatic ring optionally comprising 1 or 2 heteroatoms selected from N and O;

each $R^6$ is independently $NR^3C(O)R^7$ or $C(O)NR^3R^7$;

each $R^7$ is independently

OH, ($C_1$-$C_4$) alkoxy, ($C_1$-$C_6$) alkyl optionally substituted with one or more ($C_1$-$C_4$) alkoxy, $CF_3$, F, or ($C_3$-$C_{10}$) cycloalkyl, ($C_3$-$C_{10}$) cycloalkyl optionally substituted with one or more $R^8$, or phenyl optionally substituted with one or more $R^8$;

each $R^{7'}$ is independently H, methyl, or ethyl; or $R^7$ and $R^{7'}$, together with the atom to which they are attached, form a 3- to 6-membered ring optionally comprising one additional heteroatom selected from N and O and optionally substituted with one or more $R^8$; or $R^3$ and $R^7$, together with atom(s) to which they are attached, form a 3- to 6-membered ring optionally comprising one additional heteroatom selected from N and O and optionally substituted with one or more $R^8$; and each $R^8$ is independently ($C_1$-$C_4$) alkyl, ($C_1$-$C_4$) alkoxy, $CF_3$, OH, or F.

In some embodiments, in the compounds of Formula (I') or (I), each $R^7$ is independently ($C_1$-$C_4$) alkoxy, ($C_1$-$C_6$) alkyl optionally substituted with one or more ($C_1$-$C_4$) alkoxy, $CF_3$, F, or ($C_3$-$C_{10}$) cycloalkyl, ($C_3$-$C_{10}$) cycloalkyl optionally substituted with one or more $R^8$, or phenyl optionally substituted with one or more $R^8$.

In some embodiments, the compounds of Formula (I') or (I) have the structure of Formula (Ia), (Ia-0), (Ia'), (Ia'-0), (Ia1), (Ia1-0), (Ia1'), (Ia1'-0), (Ia2), (Ia2-O), (Ia2'), (Ia2'-0), (Ia3), (Ia3-0), (Ia3'), or (Ia3'-0):

(Ia)

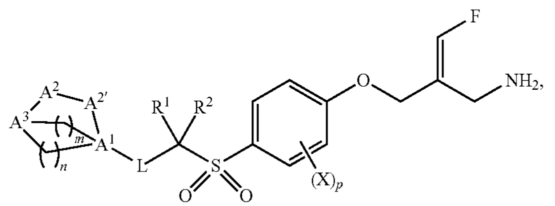

(Ia-0)

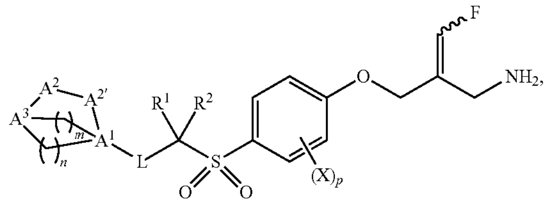

(Ia')

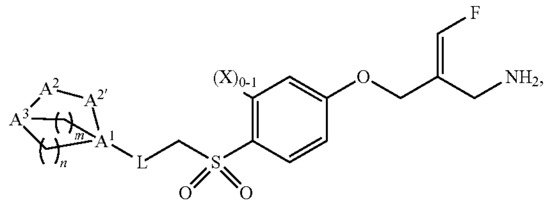

(Ia'-0)

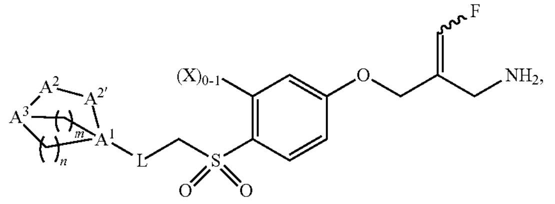

(Ia1)

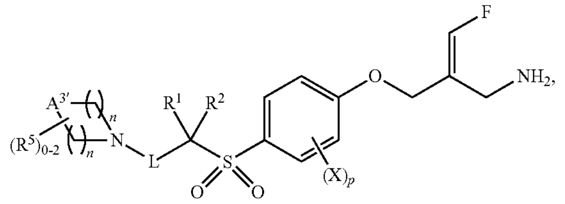

(Ia1-0)

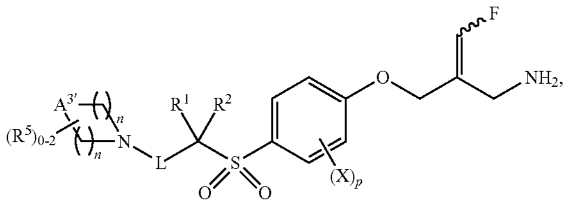

(Ia1')

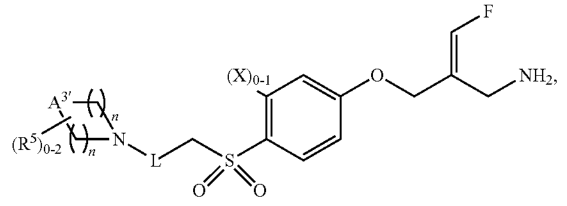

-continued (Ia1'-0)

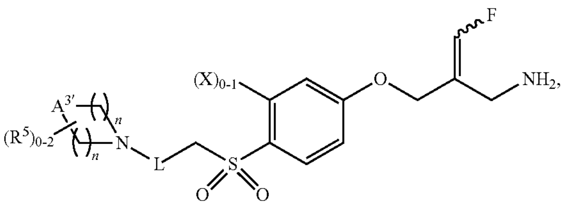

(Ia2)

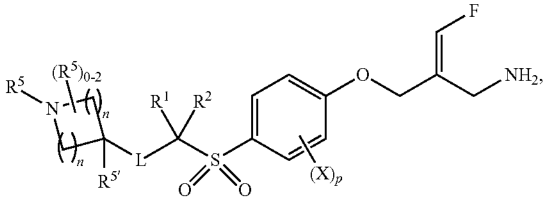

(Ia2-0)

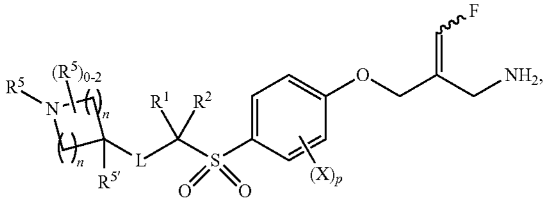

(Ia2')

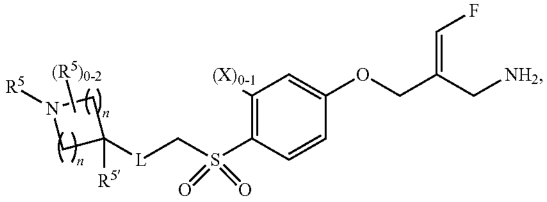

(Ia2'-0)

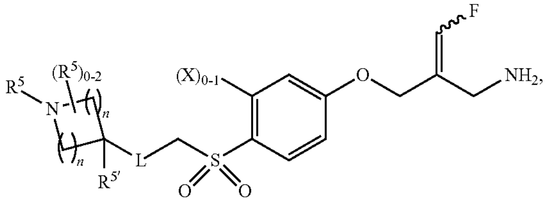

(Ia3)

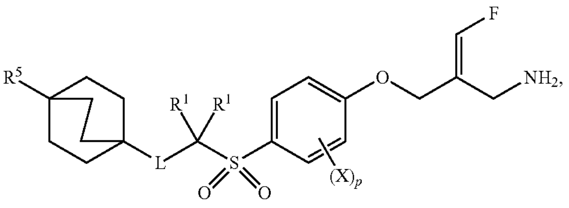

(Ia3-0)

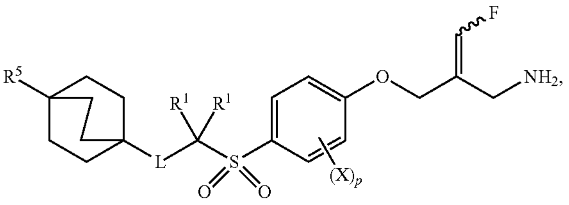

-continued (Ia3')

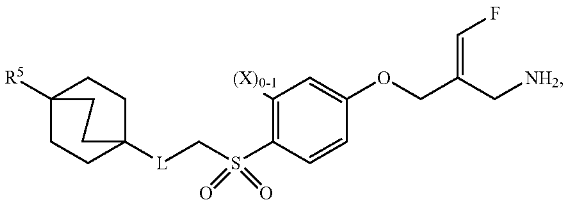

(Ia3'-0)

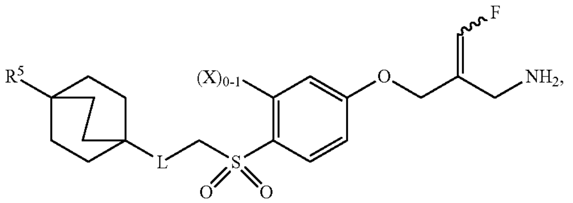

or a pharmaceutically acceptable salt, solvate, prodrug, stereoisomer, or tautomer thereof, wherein:

$A^1$ is N or $CR^{5'}$;

$R^{5'}$ is H, $(C_1-C_4)$ alkyl, $(C_1-C_4)$ alkoxy, hydroxy, or cyano;

$A^2$ and $A^2$ are each independently absent, $CH_2$, $CHR^5$, $C(R^5)_2$, NH, $NR^5$, or O, provided that at least one of $A^2$ and $A^{2'}$ is not absent and that $A^2$-$A^{2'}$ is not O—O, O—NH, O—$NR^5$, NH—O, NH—NH, NH—$NR^5$, $NR^5$—O, $NR^5$—NH, or $NR^5$—$NR^5$;

$A^3$ is $CH_2$, $CHR^5$, $C(R^5)_2$, NH, $NR^5$, or O when m is 0, or CH or $CR^5$ when m is 1 or 2, provided that $A^2$-$A^3$ is not O—O, O—NH, O—$NR^5$, NH—O, NH—NH, NH—$NR^5$, $NR^5$—O, $NR^5$—NH, or $NR^5$—$NR^5$;

$A^{3'}$ is $CH_2$, $CHR^5$, $C(R^5)_2$, NH, $NR^5$, or O;

m is 0, 1, or 2; and n is 1 or 2.

In some embodiments, the compounds of Formula (I') or (I) have the structure of Formula (Ib), (Ib-0), (Ib'), or (Ib'-0):

(Ib)

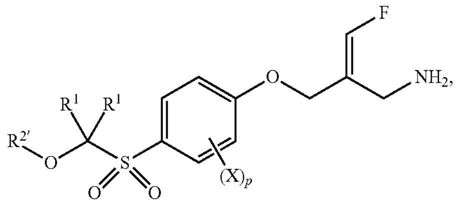

(Ib-0)

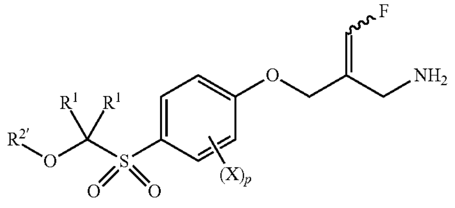

-continued (Ib')

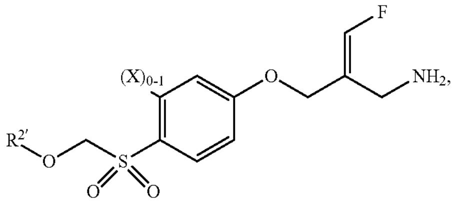

or (Ib'-0)

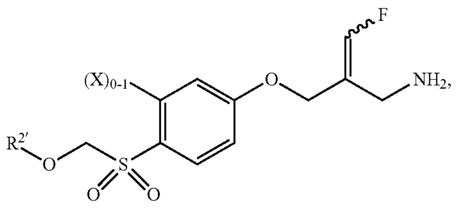

and pharmaceutically acceptable salts, solvates, prodrugs, stereoisomers, and tautomers thereof, wherein $R^{2'}$ is ($C_1$-$C_4$) alkyl substituted with one or more ($C_1$-$C_4$) alkoxy, ($C_1$-$C_4$) alkoxy, $NR^3C(O)R^4$, $C(O)NR^3R^4$, or heterocyclyl comprising one or two 3- to 6-membering rings and 1 to 3 heteroatoms selected from N and O, wherein the heterocyclyl is optionally substituted with one or more $R^5$.

In some embodiments, the compounds of Formula (I') or (I) have the structure of Formula (Ic), (Ic-0), (Ic'), or (Ic'-0):

(Ic)

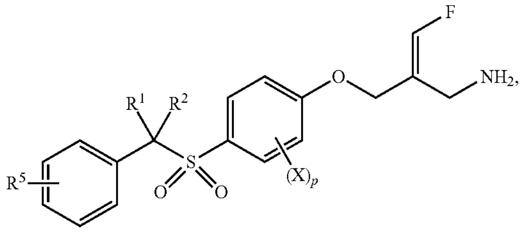

(Ic-0)

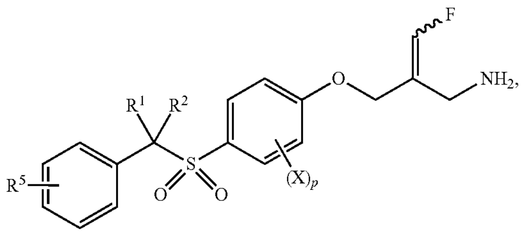

(Ic')

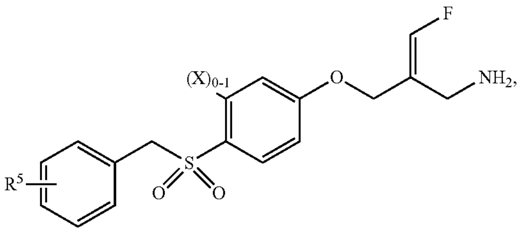

or

-continued (Ic'-0)

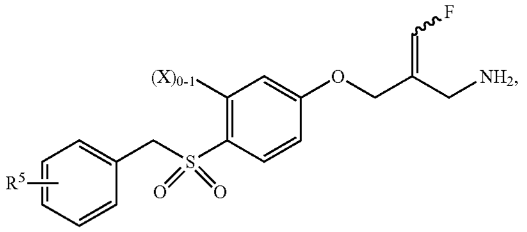

and pharmaceutically acceptable salts, solvates, prodrugs, stereoisomers, and tautomers thereof.

In some embodiments, the compounds of Formula (I') or (I) have the structure of Formula (Id1), (Id1-0), (Id1'), (Id1'-0), (Id2), (Id2-0), (Id2'), or (Id2'-0):

(Id1)

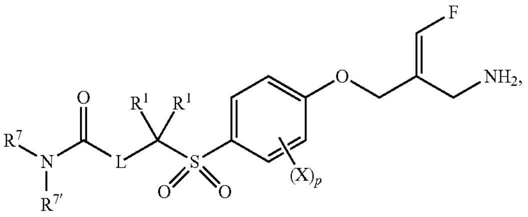

(Id1-0)

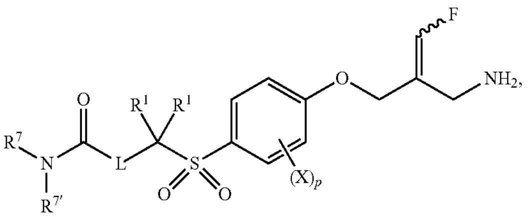

(Id1')

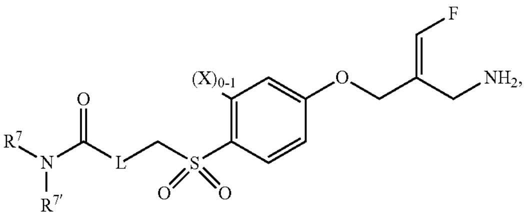

(Id1'-0)

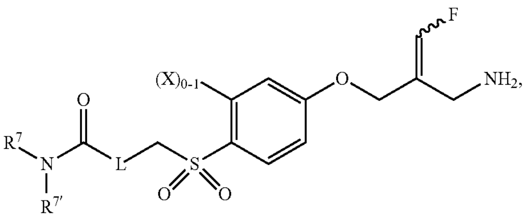

-continued (Id2)

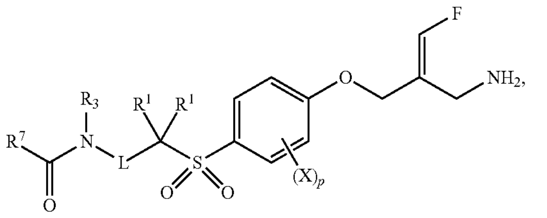

(Id2-0)

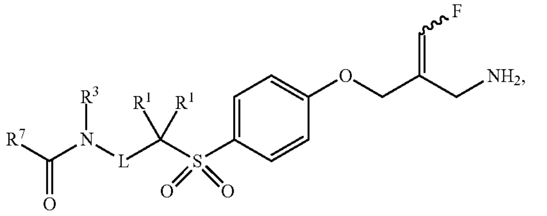

(Id2')

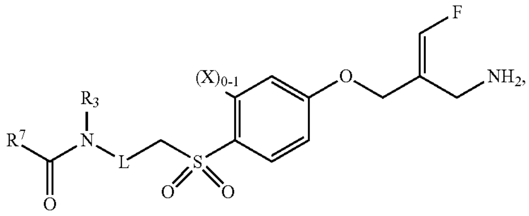

or (Id2'-0)

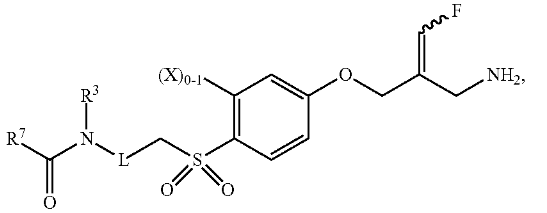

and pharmaceutically acceptable salts, solvates, prodrugs, stereoisomers, and tautomers thereof.

For the formulae above, where applicable:

In some embodiments, L is absent, —O—, ($C_1$-$C_4$) alkylene, substituted ($C_1$-$C_4$) alkylene, ($C_1$-$C_4$) alkylene-O—, or substituted ($C_1$-$C_4$) alkylene-O—.

In some embodiments, L is absent, —O—, ($C_1$-$C_2$) alkylene, substituted ($C_1$-$C_2$) alkylene, ($C_1$-$C_2$) alkylene-O—, or substituted ($C_1$-$C_2$) alkylene-O—.

In some embodiments, L is absent or —O—.

In some embodiments, L is absent.

In some embodiments, L is —O—.

In some embodiments, L is ($C_1$-$C_2$) alkylene substituted with one or more $L^1$.

In some embodiments, L is ($C_1$-$C_2$) alkylene-O— or ($C_1$-$C_2$) alkylene-O— substituted with one or more $L^1$.

In some embodiments, each $L^1$ is independently ($C_1$-$C_4$) alkyl, F, or $CF_3$.

In some embodiments, each $L^1$ is independently methyl, ethyl, F, or $CF_3$.

In some embodiments, each $L^1$ is independently methyl or ethyl.

In some embodiments, two $L^1$, together with the atom to which they are attached, form a cyclopropyl, cyclobutyl, or cyclopentyl ring.

In some embodiments, two $L^1$, together with the atom to which they are attached, form a cyclopropyl ring.

In some embodiments, each $R^1$ is H.

In some embodiments, each $R^1$ is independently F, methyl, ethyl, or $CF_3$.

In some embodiments, each $R^1$ is independently methyl or ethyl.

In some embodiments, each $R^1$ is independently methyl or $CF_3$.

In some embodiments, $R^2$ is ($C_1$-$C_4$) alkyl (i.e., methyl, ethyl, propyl, i-propyl, n-butyl, i-butyl, s-butyl, or t-butyl) substituted with one or more ($C_1$-$C_4$) alkoxy (i.e., methoxy, ethoxy, propoxy, i-propoxy, n-butoxy, i-butoxy, s-butoxy, or t-butoxy).

In some embodiments, $R^2$ is methyl or ethyl substituted with methoxy or ethoxy.

In some embodiments, $R^2$ is ($C_1$-$C_4$) alkoxy (i.e., methoxy, ethoxy, propoxy, i-propoxy, n-butoxy, i-butoxy, s-butoxy, or t-butoxy).

In some embodiments, $R^2$ is methoxy or ethoxy.

In some embodiments, $R^2$ is $NR^3C(O)R^4$ or $C(O)NR^3R^4$.

In some embodiments, $R^2$ is phenyl optionally substituted with one or more $R^5$.

In some embodiments, $R^2$ is ($C_3$-$C_8$) cycloalkyl (e.g., cyclopropyl, cyclobutyl, cyclopentyl, cyclohexyl, cycloheptyl, or cyclooctyl, or spiro-, bridged-, or fused cycloalkyl) optionally substituted with one or more $R^5$.

In some embodiments, $R^2$ is heterocyclyl (e.g., spiro-, bridged-, or fused-heterocyclyl) optionally substituted with one or more $R^5$.

In some embodiments, $R^2$ is a heterocyclyl selected from:

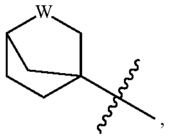

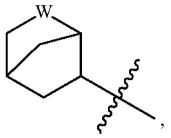

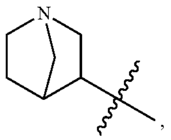

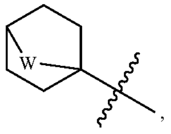

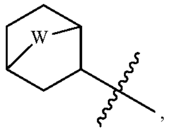

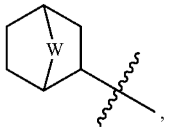

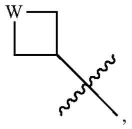

-continued
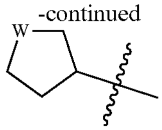,
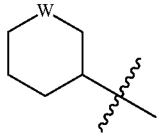,
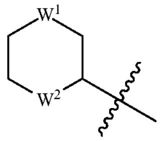,
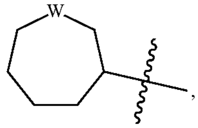,
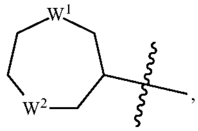,
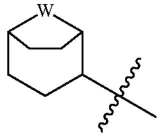,
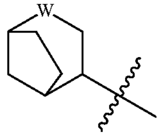,
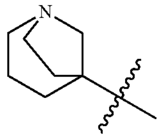,
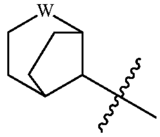,
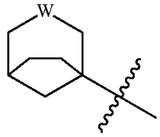,
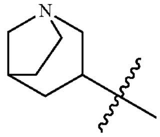,
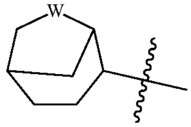,
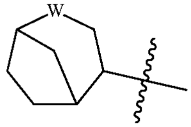,
-continued
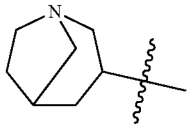,
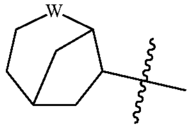,
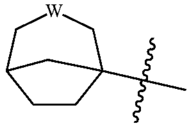,
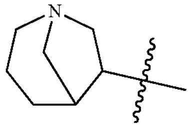,
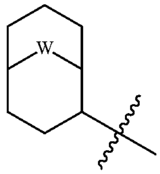,
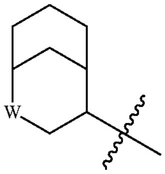,
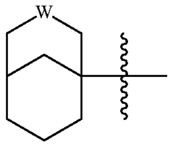,
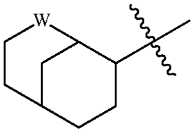,
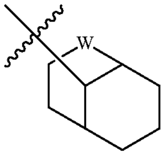,
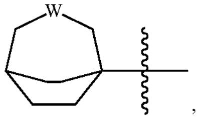,
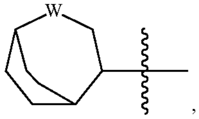,
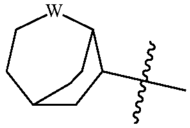, -continued

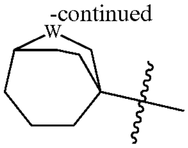,

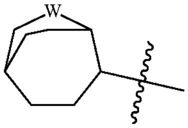,

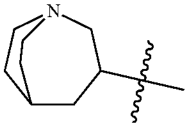,

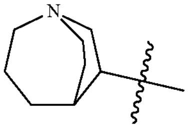,

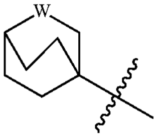,

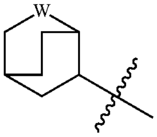, and

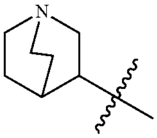, wherein W, $W^1$ and $W^2$ are each independently $CH_2$, $CHR^5$, $C(R^5)_2$, O, S, NH, or $NR^5$, each optionally substituted with one or more $R^5$.

In some embodiments, $R^2$ is heteroaryl optionally substituted with one or more $R^5$.

In some embodiments, $R^{2'}$ is ($C_1$-$C_4$) alkyl (i.e., methyl, ethyl, propyl, i-propyl, n-butyl, i-butyl, s-butyl, or t-butyl) substituted with one or more ($C_1$-$C_4$) alkoxy (i.e., methoxy, ethoxy, propoxy, i-propoxy, n-butoxy, i-butoxy, s-butoxy, or t-butoxy).

In some embodiments, $R^{2'}$ is methyl or ethyl substituted with methoxy or ethoxy.

In some embodiments, $R^{2'}$ is ($C_1$-$C_4$) alkoxy (i.e., methoxy, ethoxy, propoxy, i-propoxy, n-butoxy, i-butoxy, s-butoxy, or t-butoxy).

In some embodiments, $R^{2'}$ is methoxy or ethoxy.

In some embodiments, $R^{2'}$ is $NR^3C(O)R^4$ or $C(O)NR^3R^4$.

In some embodiments, $R^{2'}$ is heterocyclyl (e.g., spiro-, bridged-, or fused-heterocyclyl) optionally substituted with one or more $R^5$.

In some embodiments, $R^{2'}$ is a heterocyclyl selected from:

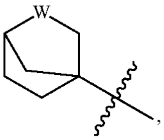, 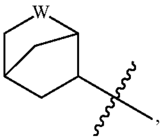, 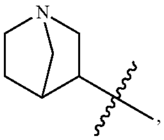,

-continued

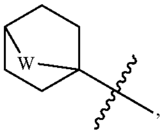, 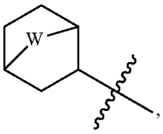, 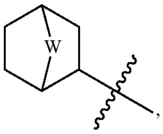,

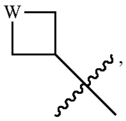, 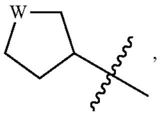, 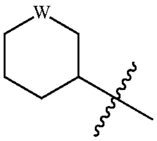,

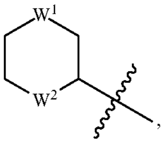, 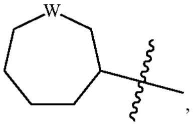,

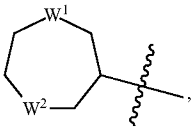, 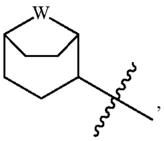, 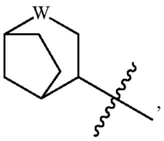,

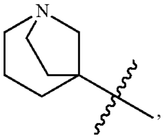, 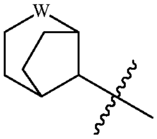, 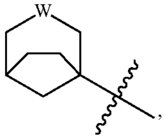,

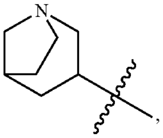, 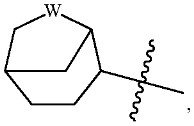,

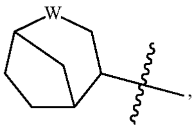, 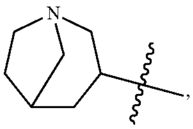,

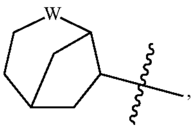, 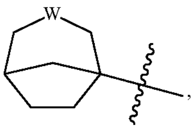,

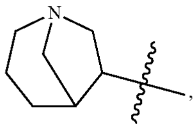, 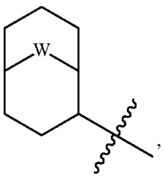, 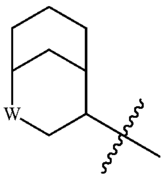,

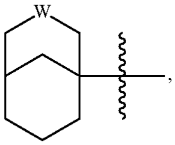, 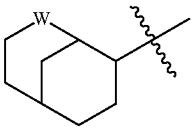,

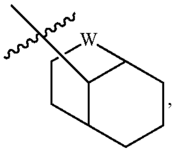, 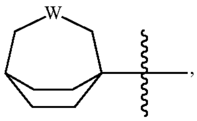,

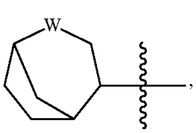, 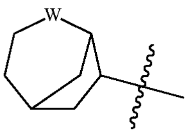,

-continued

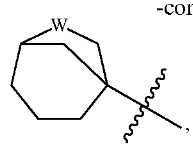,
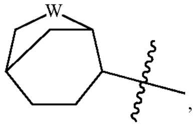,
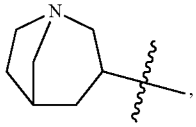,
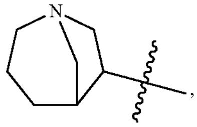,
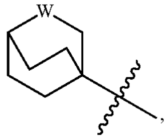,
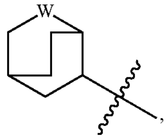, and
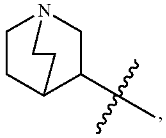, wherein W, $W^1$ and $W^2$ are each independently $CH_2$, $CHR^5$, $C(R^5)_2$, O, S, NH, or $NR^5$, each optionally substituted with one or more $R^5$.

In some embodiments, $R^3$ is H,

In some embodiments, $R^3$ is methyl or ethyl.

In some embodiments, $R^4$ is methyl, ethyl, propyl, i-propyl, n-butyl, i-butyl, s-butyl, or t-butyl.

In some embodiments, $R^4$ is methyl or ethyl.

In some embodiments, $R^4$ is $(C_3-C_{10})$ cycloalkyl (e.g., cyclopropyl, cyclobutyl, cyclopentyl, cyclohexyl, cycloheptyl, or cyclooctyl, or spiro-, bridged-, or fused cycloalkyl) optionally substituted with one or more $R^8$. In some embodiments, $R^4$ is $(C_3-C_6)$ cycloalkyl (e.g., cyclopropyl, cyclobutyl, cyclopentyl, or cyclohexyl, or spiro-, bridged-, or fused cycloalkyl) optionally substituted with one or more $R^8$. In some embodiments, $R^4$ is cyclopropyl or cyclobutyl optionally substituted with one or more $R^8$.

In some embodiments, $R^3$ and $R^4$, together with atom(s) to which they are attached, form a 3- to 6-membered ring optionally comprising one additional heteroatom selected from N and O and optionally substituted with one or more $R^5$. In some embodiments, each $R^5$ is independently selected from methyl, ethyl, cyclopentyl, and phenyl.

In some embodiments, $R^3$ and $R^4$, together with atom(s) to which they are attached, form a 4- to 6-membered ring optionally comprising one additional heteroatom selected from N and O and optionally substituted with one or more $R^5$. In some embodiments, each $R^5$ is independently selected from methyl, ethyl, cyclopentyl, and phenyl.

In some embodiments, $R^3$ and $R^4$, together with atom(s) to which they are attached, form a 3-membered ring optionally comprising one additional heteroatom selected from N and O and optionally substituted with one or more $R^5$. In some embodiments, each $R^5$ is independently selected from methyl, ethyl, cyclopentyl, and phenyl.

In some embodiments, $R^3$ and $R^4$, together with atom(s) to which they are attached, form a 4-membered ring optionally comprising one additional heteroatom selected from N and O and optionally substituted with one or more $R^5$. In some embodiments, each $R^5$ is independently selected from methyl, ethyl, cyclopentyl, and phenyl.

In some embodiments, $R^3$ and $R^4$, together with atom(s) to which they are attached, form a 5-membered ring optionally comprising one additional heteroatom selected from N and O and optionally substituted with one or more $R^5$. In some embodiments, each $R^5$ is independently selected from methyl, ethyl, cyclopentyl, and phenyl.

In some embodiments, $R^3$ and $R^4$, together with atom(s) to which they are attached, form a 6-membered ring optionally comprising one additional heteroatom selected from N and O and optionally substituted with one or more $R^5$. In some embodiments, each $R^5$ is independently selected from methyl, ethyl, cyclopentyl, and phenyl.

In some embodiments, at least one $R^5$ is $(C_1-C_4)$ alkyl (i.e., methyl, ethyl, propyl, i-propyl, n-butyl, i-butyl, s-butyl, or t-butyl), $(C_1-C_4)$ alkoxy (i.e., methoxy, ethoxy, propoxy, i-propoxy, n-butoxy, i-butoxy, s-butoxy, or t-butoxy), hydroxy, cyano, oxo, $C(O)R^7$, $C(O)NR^7R^{7'}$, $NR^3C(O)R^7$, $NR^3S(O)_2R^4$, $S(O)_2R^4$, or $(C_1-C_4)$ alkyl ((i.e., methyl, ethyl, propyl, i-propyl, n-butyl, i-butyl, s-butyl, or t-butyl)) substituted with one or more hydroxy or $R^6$.

In some embodiments, at least one $R^5$ is $(C_1-C_4)$ alkyl (i.e., methyl, ethyl, propyl, i-propyl, n-butyl, i-butyl, s-butyl, or t-butyl), $(C_1-C_4)$ alkoxy ((i.e., methoxy, ethoxy, propoxy, i-propoxy, n-butoxy, i-butoxy, s-butoxy, or t-butoxy)), hydroxy, cyano, oxo, or $(C_1-C_4)$ alkyl ((i.e., methyl, ethyl, propyl, i-propyl, n-butyl, i-butyl, s-butyl, or t-butyl)) substituted with one or more hydroxy or $R^6$.

In some embodiments, at least one $R^5$ is methyl, methoxy, hydroxy, or cyano.

In some embodiments, at least one $R^5$ is $C(O)R^7$, $C(O)NR^7R^{7'}$, $NR^3C(O)R^7$, $NR^3S(O)_2R^4$, or $S(O)_2R^4$.

In some embodiments, at least one $R^5$ is $C(O)R^7$, $C(O)NR^7R^{7'}$, or $NR^3C(O)R^7$.

In some embodiments, at least one $R^5$ is $(C_3-C_{10})$ cycloalkyl (e.g., cyclopropyl, cyclobutyl, cyclopentyl, cyclohexyl, cycloheptyl, or cyclooctyl, or spiro-, bridged-, or fused cycloalkyl) optionally substituted with one or more hydroxy or $R^6$. In some embodiments, at least one $R^5$ is $(C_3-C_6)$ cycloalkyl (e.g., cyclopropyl, cyclobutyl, cyclopentyl, or cyclohexyl, or spiro-, bridged-, or fused cycloalkyl) optionally substituted with one or more hydroxy or $R^6$. In some embodiments, at least one $R^5$ is cyclopropyl or cyclobutyl optionally substituted with one or more hydroxy or $R^6$.

In some embodiments, at least one $R^5$ is heterocyclyl comprising one or two 3- to 6-membering rings and 1 to 3 heteroatoms selected from N and O and optionally substituted with one or more hydroxy or $R^6$. In some embodiments, at least one $R^5$ is heterocyclyl comprising one 3- to 6-membering ring and 1 to 3 heteroatoms selected from N and O and optionally substituted with one or more hydroxy or $R^6$. In some embodiments, at least one $R^5$ is heterocyclyl comprising one 3- to 6-membering ring and 1 to 2 heteroatoms selected from N and O and optionally substituted with one or more hydroxy or $R^6$. In some embodiments, at least one $R^5$ is heterocyclyl comprising one 3- to 6-membering ring and 1 heteroatom selected from N and O and optionally substituted with one or more hydroxy or $R^6$. In some embodiments, at least one $R^5$ is heterocyclyl comprising two 3- to 6-membering rings and 1 to 3 heteroatoms selected from N and O and optionally substituted with one or more hydroxy or $R^6$. In some embodiments, at least one $R^5$ is heterocyclyl comprising two 3- to 6-membering rings and 1 to 2 heteroatoms selected from N and O and optionally substituted with one or more hydroxy or $R^6$.

In some embodiments, at least two $R^5$, together with the atom or atoms to which they are attached, form a 3- to 5-membered saturated or 5- or 6-membered aromatic ring optionally comprising 1 or 2 heteroatoms selected from N and O.

In some embodiments, at least two $R^5$, together with the atom or atoms to which they are attached, form a phenyl ring.

In some embodiments, at least two $R^5$, together with the atom or atoms to which they are attached, form a 3- to 5-membered saturated ring optionally comprising 1 or 2 heteroatoms selected from N and O.

In some embodiments, at least one $R^5$ is $(C_1-C_4)$ alkyl (i.e., methyl, ethyl, propyl, i-propyl, n-butyl, i-butyl, s-butyl, or t-butyl), $(C_1-C_4)$ alkoxy (i.e., methoxy, ethoxy, propoxy, i-propoxy, n-butoxy, i-butoxy, s-butoxy, or t-butoxy), hydroxy, cyano, oxo, or $(C_1-C_4)$ alkyl substituted with one or more hydroxy or $R^6$.

In some embodiments, $R^{5'}$ is H.

In some embodiments, $R^{5'}$ is $(C_1-C_4)$ alkyl (i.e., methyl, ethyl, propyl, i-propyl, n-butyl, i-butyl, s-butyl, or t-butyl), $(C_1-C_4)$ alkoxy (i.e., methoxy, ethoxy, propoxy, i-propoxy, n-butoxy, i-butoxy, s-butoxy, or t-butoxy), hydroxy, or cyano.

In some embodiments, $R^{5'}$ is methyl, methoxy, hydroxy, or cyano.

In some embodiments, at least one $R^6$ is $NR^3C(O)R^7$.

In some embodiments, at least one $R^6$ is $C(O)NR^3R^7$.

In some embodiments, each $R^7$ is independently $(C_1-C_4)$ alkoxy, $(C_1-C_6)$ alkyl optionally substituted with one or more $(C_1-C_4)$ alkoxy, $CF_3$, F, or $(C_3-C_{10})$ cycloalkyl, $(C_3-C_{10})$ cycloalkyl optionally substituted with one or more $R^8$, or phenyl optionally substituted with one or more $R^8$.

In some embodiments, at least one $R^7$ is $(C_1-C_4)$ alkoxy (i.e., methoxy, ethoxy, propoxy, i-propoxy, n-butoxy, i-butoxy, s-butoxy, or t-butoxy), $(C_1-C_6)$ alkyl (e.g., methyl, ethyl, propyl, i-propyl, n-butyl, i-butyl, s-butyl, t-butyl, pentyl, or hexyl) optionally substituted with one or more $(C_1-C_4)$ alkoxy (i.e., methoxy, ethoxy, propoxy, i-propoxy, n-butoxy, i-butoxy, s-butoxy, or t-butoxy), $CF_3$, F, or $(C_3-C_{10})$ cycloalkyl (e.g., cyclopropyl, cyclobutyl, cyclopentyl, cyclohexyl, cycloheptyl, or cyclooctyl).

In some embodiments, at least one $R^7$ is $(C_1-C_6)$ alkyl (e.g., methyl, ethyl, propyl, i-propyl, n-butyl, i-butyl, s-butyl, t-butyl, pentyl, or hexyl) or $(C_1-C_6)$ alkyl (e.g., methyl, ethyl, propyl, i-propyl, n-butyl, i-butyl, s-butyl, t-butyl, pentyl, or hexyl) substituted with one or more $(C_1-C_4)$ alkoxy (i.e., methoxy, ethoxy, propoxy, i-propoxy, n-butoxy, i-butoxy, s-butoxy, or t-butoxy), $CF_3$, F, or $(C_3-C_{10})$ cycloalkyl (e.g., cyclopropyl, cyclobutyl, cyclopentyl, cyclohexyl, cycloheptyl, or cyclooctyl, or spiro-, bridged-, or fused cycloalkyl).

In some embodiments, at least one $R^7$ is $(C_1-C_6)$ alkyl (e.g., methyl, ethyl, propyl, i-propyl, n-butyl, i-butyl, s-butyl, t-butyl, pentyl, or hexyl) or $(C_1-C_6)$ alkyl (e.g., methyl, ethyl, propyl, i-propyl, n-butyl, i-butyl, s-butyl, t-butyl, pentyl, or hexyl) substituted with one or more $(C_1-C_4)$ alkoxy (i.e., methoxy, ethoxy, propoxy, i-propoxy, n-butoxy, i-butoxy, s-butoxy, or t-butoxy), $CF_3$, F, or $(C_3-C_6)$ cycloalkyl (e.g., cyclopropyl, cyclobutyl, cyclopentyl, or cyclohexyl, or spiro-, bridged-, or fused cycloalkyl).

In some embodiments, at least one $R^7$ is methyl or ethyl.

In some embodiments, at least one $R^7$ is $(C_3-C_{10})$ cycloalkyl (e.g., cyclopropyl, cyclobutyl, cyclopentyl, cyclohexyl, cycloheptyl, or cyclooctyl, or spiro-, bridged-, or fused cycloalkyl) optionally substituted with one or more $R^8$.

In some embodiments, at least one $R^7$ is phenyl optionally substituted with one or more $R^8$.

In some embodiments, each $R^{7'}$ is H,

In some embodiments, at least one $R^{7'}$ is methyl or ethyl.

In some embodiments, $R^7$ and $R^{7'}$, together with atom(s) to which they are attached, form a 3- to 6-membered ring optionally comprising one additional heteroatom selected from N and O and optionally substituted with one or more $R^8$.

In some embodiments, $R^7$ and $R^{7'}$, together with atom(s) to which they are attached, form a 4- to 6-membered ring optionally comprising one additional heteroatom selected from N and O and optionally substituted with one or more $R^8$.

In some embodiments, $R^7$ and $R^{7'}$, together with atom(s) to which they are attached, form a 3- or 4-membered ring optionally comprising one additional heteroatom selected from N and O and optionally substituted with one or more $R^8$.

In some embodiments, $R^7$ and $R^{7'}$, together with atom(s) to which they are attached, form a 3-membered ring optionally comprising one additional heteroatom selected from N and O and optionally substituted with one or more $R^8$.

In some embodiments, $R^7$ and $R^{7'}$, together with atom(s) to which they are attached, form a 4-membered ring optionally comprising one additional heteroatom selected from N and O and optionally substituted with one or more $R^8$.

In some embodiments, $R^7$ and $R^{7'}$, together with atom(s) to which they are attached, form a 5-membered ring optionally comprising one additional heteroatom selected from N and O and optionally substituted with one or more $R^8$.

In some embodiments, $R^7$ and $R^{7'}$, together with atom(s) to which they are attached, form a 6-membered ring optionally comprising one additional heteroatom selected from N and O and optionally substituted with one or more $R^8$.

In some embodiments, $R^3$ and $R^7$, together with atom(s) to which they are attached, form a 3- to 6-membered ring optionally comprising one additional heteroatom selected from N and O and optionally substituted with one or more $R^8$.

In some embodiments, $R^3$ and $R^7$, together with atom(s) to which they are attached, form a 4- to 6-membered ring optionally comprising one additional heteroatom selected from N and O and optionally substituted with one or more $R^8$.

In some embodiments, $R^3$ and $R^7$, together with atom(s) to which they are attached, form a 3- or 4-membered ring optionally comprising one additional heteroatom selected from N and O and optionally substituted with one or more $R^8$.

In some embodiments, $R^3$ and $R^7$, together with atom(s) to which they are attached, form a 3-membered ring optionally comprising one additional heteroatom selected from N and O and optionally substituted with one or more $R^8$.

In some embodiments, $R^3$ and $R^7$, together with atom(s) to which they are attached, form a 4-membered ring optionally comprising one additional heteroatom selected from N and O and optionally substituted with one or more $R^8$.

In some embodiments, $R^3$ and $R^7$, together with atom(s) to which they are attached, form a 5-membered ring optionally comprising one additional heteroatom selected from N and O and optionally substituted with one or more $R^8$.

In some embodiments, $R^3$ and $R^7$, together with atom(s) to which they are attached, form a 6-membered ring optionally comprising one additional heteroatom selected from N and O and optionally substituted with one or more $R^8$.

In some embodiments, at least one $R^8$ is $(C_1-C_4)$ alkyl (i.e., methyl, ethyl, propyl, i-propyl, n-butyl, i-butyl, s-butyl, or t-butyl) or $(C_1-C_4)$ alkoxy (i.e., methoxy, ethoxy, propoxy, i-propoxy, n-butoxy, i-butoxy, s-butoxy, or t-butoxy).

In some embodiments, at least one $R^8$ is methyl or methoxy.

In some embodiments, at least one $R^8$ is $CF_3$ or F.

In some embodiments, p is 0.

In some embodiments, p is 1.

In some embodiments, X is F.

In some embodiments, X is Cl.

In some embodiments, m is 0.

In some embodiments, m is 1.

In some embodiments, m is 2.

In some embodiments, n is 1.

In some embodiments, n is 2.

Any of the moieties described herein for any one of $R^1$, $R^2$, $R^{2'}$, $R^3$, $R^4$, $R^5$, $R^{5'}$, $R^6$, $R^7$, $R^{7'}$, $R^8$, $A^1$, $A^2$, $A^{2'}$, $A^3$, $A^3$, X, L, $L^1$, m, n, and p can be combined with any of the moieties described herein for one or more of the remainder of $R^1$, $R^2$, $R^{2'}$, $R^3$, $R^4$, $R^5$, $R^{5'}$, $R^6$, $R^7$, $R^{7'}$, $R^8$, $A^1$, $A^2$, $A^{2'}$, $A^3$, $A^{3'}$, X, L, $L^1$, m, n, and p.

Non-limiting illustrative compounds of the application include those in Table 1.

TABLE 1

| Cmpd No. | Structure | Chemical name |
|---|---|---|
| 1 | 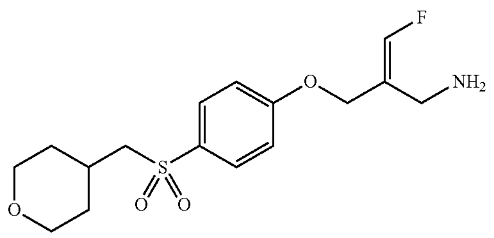 [SMILES: NC/C(=C\F)COc1ccc(S(=O)(=O)CC2CCOCC2)cc1] | (E)-3-fluoro-2-((4-(((tetrahydro-2H-pyran-4-yl)methyl)sulfonyl) phenoxy)methyl)prop-2-en-1-amine |
| 2 | 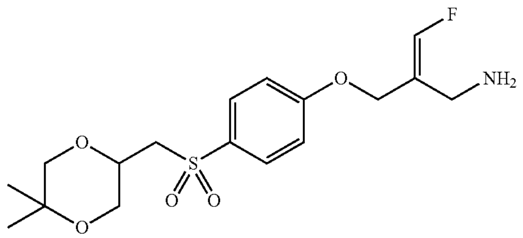 [SMILES: CC1(C)COC(CS(=O)(=O)c2ccc(OC/C(=C/F)CN)cc2)CO1] | (E)-2-((4-(((5,5-dimethyl-1,4-dioxan-2-yl)methyl)sulfonyl)phenoxy)methyl)-3-fluoroprop-2-en-1-amine |
| 3 | 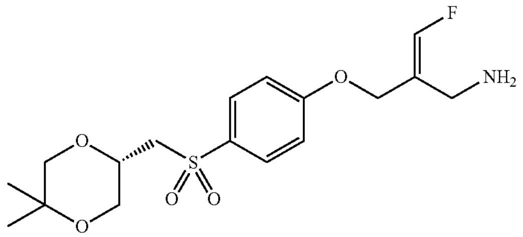 [SMILES: CC1(C)CO[C@H](CS(=O)(=O)c2ccc(OC/C(=C/F)CN)cc2)CO1] | (S,E)-2-((4-(((5,5-dimethyl-1,4-dioxan-2-yl)methyl)sulfonyl)phenoxy)methyl)-3-fluoroprop-2-en-1-amine |
| 4 | 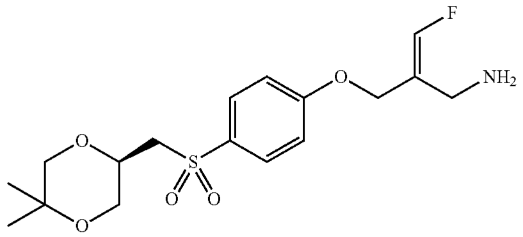 [SMILES: CC1(C)CO[C@@H](CS(=O)(=O)c2ccc(OC/C(=C/F)CN)cc2)CO1] | (R,E)-2-((4-(((5,5-dimethyl-1,4-dioxan-2-yl)methyl)sulfonyl)phenoxy)methyl)-3-fluoroprop-2-en-1-amine |
| 5 | 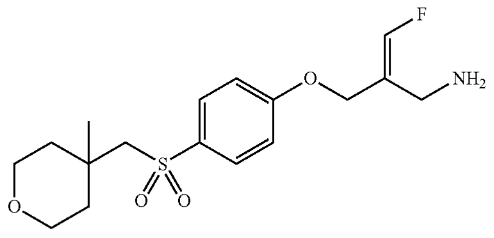 [SMILES: CC1(CS(=O)(=O)c2ccc(OC/C(=C/F)CN)cc2)CCOCC1] | (E)-3-fluoro-2-((4-(((4-methyltetrahydro-2H-pyran-4-yl)methyl)sulfonyl)phenoxy)methyl) prop-2-en-1-amine |

TABLE 1-continued

| Cmpd No. | Structure | Chemical name |
| --- | --- | --- |
| 6 | 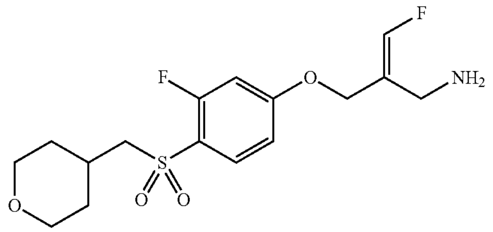 [SMILES: NC/C(=C\F)COc1ccc(S(=O)(=O)CC2CCOCC2)c(F)c1] | (E)-3-fluoro-2-((3-fluoro-4-(((tetrahydro-2H-pyran-4-yl)methyl)sulfonyl)phenoxy)methyl)prop-2-en-1-amine |
| 7 | 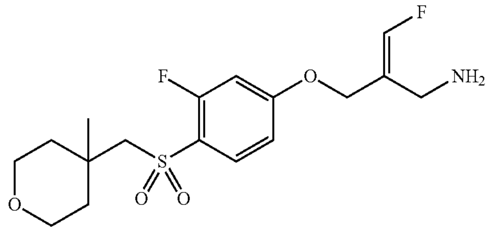 [SMILES: CC1(CS(=O)(=O)c2ccc(OC/C(=C/F)CN)cc2F)CCOCC1] | (E)-3-fluoro-2-((3-fluoro-4-(((4-methyltetrahydro-2H-pyran-4-yl)methyl)sulfonyl)phenoxy)methyl)prop-2-en-1-amine |
| 8 | 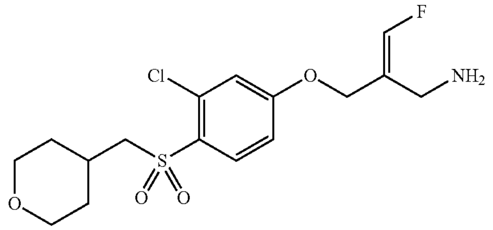 [SMILES: NC/C(=C\F)COc1ccc(S(=O)(=O)CC2CCOCC2)c(Cl)c1] | (E)-2-((3-chloro-4-(((tetrahydro-2H-pyran-4-yl)methyl)sulfonyl)phenoxy)methyl)-3-fluoroprop-2-en-1-amine |
| 9 | 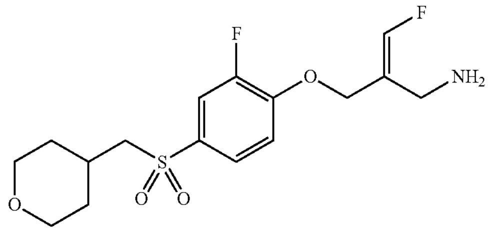 [SMILES: NC/C(=C\F)COc1ccc(S(=O)(=O)CC2CCOCC2)cc1F] | (E)-3-fluoro-2-((2-fluoro-4-(((tetrahydro-2H-pyran-4-yl)methyl)sulfonyl)phenoxy)methyl)prop-2-en-1-amine |
| 10 | 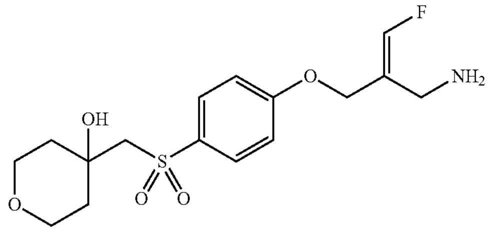 | (E)-4-(((4-((2-(aminomethyl)-3-fluoroallyl)oxy)phenyl)sulfonyl)methyl)tetrahydro-2H-pyran-4-ol |
| 11 | 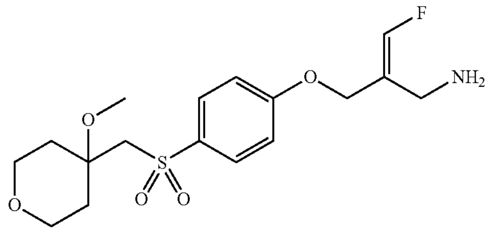 [SMILES: COC1(CS(=O)(=O)c2ccc(OC/C(=C/F)CN)cc2)CCOCC1] | (E)-3-fluoro-2-((4-(((4-methoxytetrahydro-2H-pyran-4-yl)methyl)sulfonyl)phenoxy)methyl)prop-2-en-1-amine |

TABLE 1-continued

| Cmpd No. | Structure | Chemical name |
| --- | --- | --- |
| 12 | 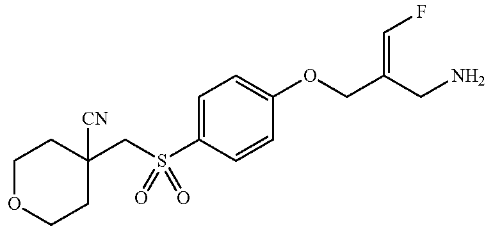 [SMILES: N#CC1(CS(=O)(=O)c2ccc(OC/C(=C/F)CN)cc2)CCOCC1] | (E)-4-(((4-((2-(aminomethyl)-3-fluoroallyl)oxy)phenyl)sulfonyl) methyl)tetrahydro-2H-pyran-4-carbonitrile |
| 13 | 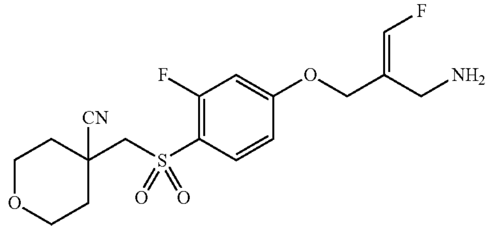 [SMILES: N#CC1(CS(=O)(=O)c2ccc(OC/C(=C/F)CN)cc2F)CCOCC1] | (E)-4-(((4-((2-(aminomethyl)-3-fluoroallyl)oxy)-2-fluorophenyl)sulfonyl)methyl) tetrahydro-2H-pyran-4-carbonitrile |
| 14 | 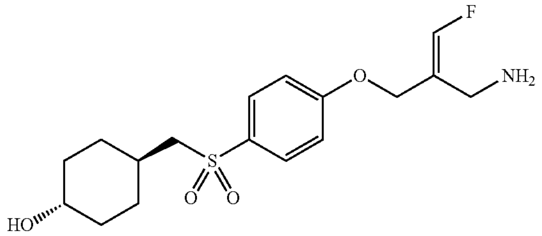 [SMILES: NC/C(=C\F)COc1ccc(S(=O)(=O)C[C@H]2CC[C@H](O)CC2)cc1] | (1r,4r)-4-(((4-(((E)-2-(aminomethyl)-3-fluoroallyl)oxy)phenyl)sulfonyl) methyl)cyclohexan-1-ol |
| 15 | 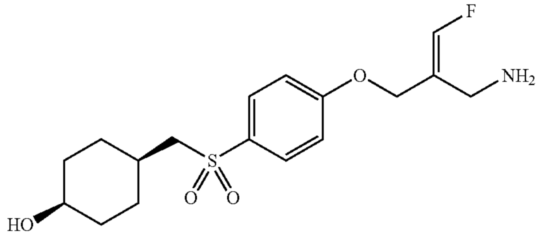 [SMILES: NC/C(=C\F)COc1ccc(S(=O)(=O)C[C@H]2CC[C@@H](O)CC2)cc1] | (1s,4s)-4-(((4-(((E)-2-(aminomethyl)-3-fluoroallyl)oxy)phenyl)sulfonyl) methyl)cyclohexan-1-ol |
| 16 | 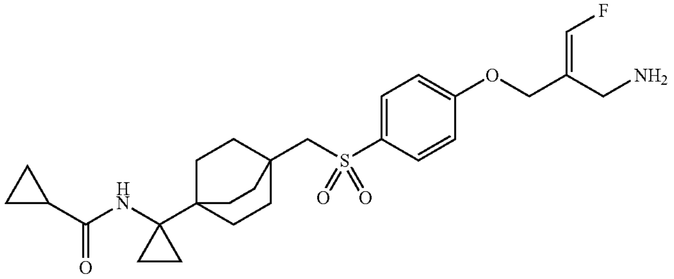 [SMILES: NC/C(=C\F)COc1ccc(S(=O)(=O)CC23CCC(C4(NC(=O)C5CC5)CC4)(CC2)CC3)cc1] | (E)-N-(1-(4-(((4-((2-(aminomethyl)-3-fluoroallyl)oxy)phenyl)sulfonyl) methyl)bicyclo[2.2.2]octan-1-yl)cyclopropyl) cyclopropanecarboxamide |
| 17 | 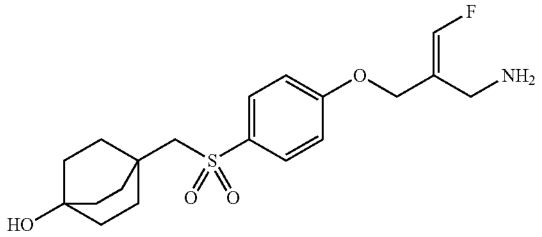 [SMILES: NC/C(=C\F)COc1ccc(S(=O)(=O)CC23CCC(O)(CC2)CC3)cc1] | (E)-4-(((4-((2-(aminomethyl)-3-fluoroallyl)oxy)phenyl)sulfonyl) methyl)bicyclo[2.2.2]octan-1-ol |

TABLE 1-continued

| Cmpd No. | Structure | Chemical name |
| --- | --- | --- |
| 18 | 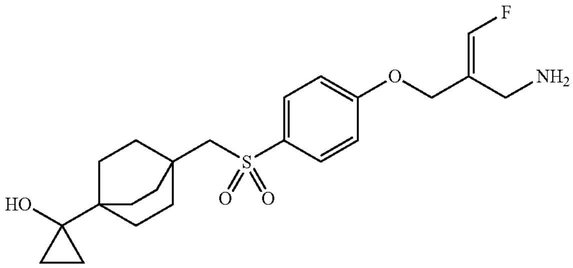 [SMILES: NC/C(=C\F)COc1ccc(S(=O)(=O)CC23CCC(C4(O)CC4)(CC2)CC3)cc1] | (E)-1-(4-(((4-((2-(aminomethyl)-3-fluoroallyl)oxy)phenyl)sulfonyl)methyl)bicyclo[2.2.2]octan-1-yl)cyclopropan-1-ol |
| 19 | 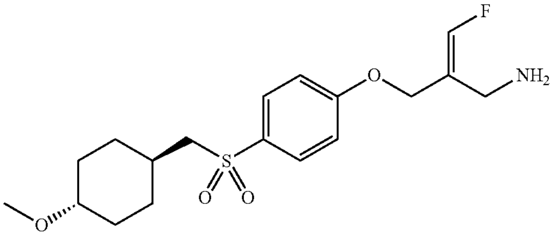 [SMILES: CO[C@H]1CC[C@H](CS(=O)(=O)c2ccc(OC/C(=C/F)CN)cc2)CC1] | (E)-3-fluoro-2-((4-((((1r,4r)-4-methoxycyclohexyl)methyl)sulfonyl)phenoxy)methyl)prop-2-en-1-amine |
| 20 | 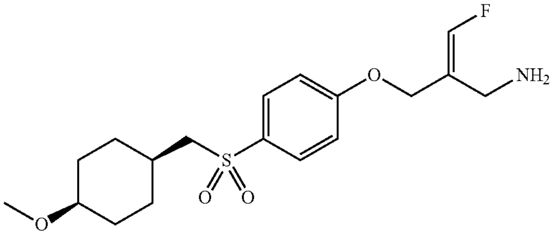 [SMILES: CO[C@H]1CC[C@@H](CS(=O)(=O)c2ccc(OC/C(=C/F)CN)cc2)CC1] | (E)-3-fluoro-2-((4-((((1s,4s)-4-methoxycyclohexyl)methyl)sulfonyl)phenoxy)methyl)prop-2-en-1-amine |
| 21 | 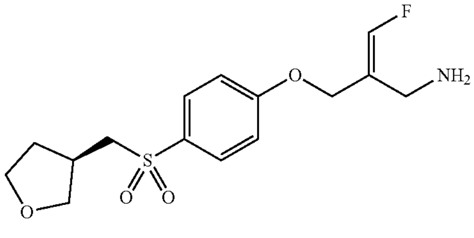 [SMILES: NC/C(=C\F)COc1ccc(S(=O)(=O)C[C@@H]2CCOC2)cc1] | (R,E)-3-fluoro-2-((4-(((tetrahydrofuran-3-yl)methyl)sulfonyl)phenoxy)methyl)prop-2-en-1-amine |
| 22 | 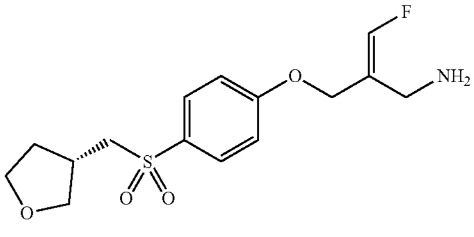 [SMILES: NC/C(=C\F)COc1ccc(S(=O)(=O)C[C@H]2CCOC2)cc1] | (S,E)-3-fluoro-2-((4-(((tetrahydrofuran-3-yl)methyl)sulfonyl)phenoxy)methyl)prop-2-en-1-amine |
| 23 | 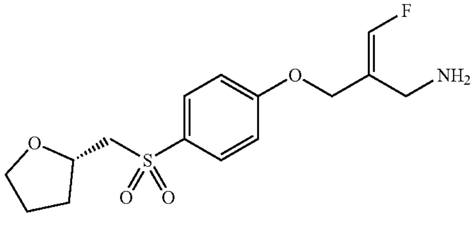 [SMILES: NC/C(=C\F)COc1ccc(S(=O)(=O)C[C@@H]2CCCO2)cc1] | (S,E)-3-fluoro-2-((4-(((tetrahydrofuran-2-yl)methyl)sulfonyl)phenoxy)methyl)prop-2-en-1-amine |

TABLE 1-continued

| Cmpd No. | Structure | Chemical name |
|---|---|---|
| 24 | 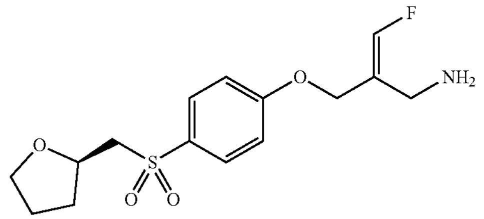 [SMILES: NC/C(=C\F)COc1ccc(S(=O)(=O)C[C@H]2CCCO2)cc1] | (R,E)-3-fluoro-2-((4-(((tetrahydrofuran-2-yl)methyl)sulfonyl)phenoxy)methyl)prop-2-en-1-amine |
| 25 | 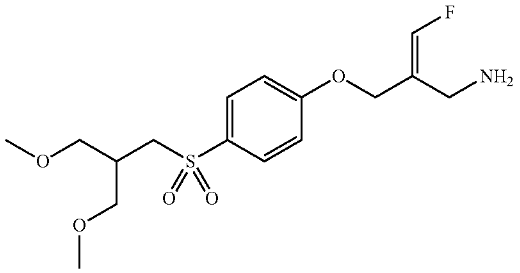 [SMILES: COCC(COC)CS(=O)(=O)c1ccc(OC/C(=C/F)CN)cc1] | (E)-3-fluoro-2-((4-((3-methoxy-2-(methoxymethyl)propyl)sulfonyl)phenoxy)methyl)prop-2-en-1-amine |
| 26 | 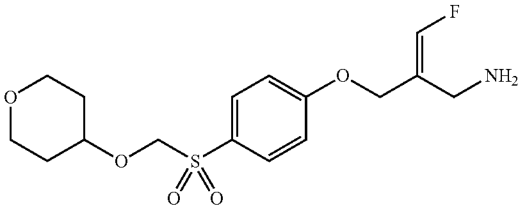 [SMILES: NC/C(=C\F)COc1ccc(S(=O)(=O)COC2CCOCC2)cc1] | (E)-3-fluoro-2-((4-((((tetrahydro-2H-pyran-4-yl)oxy)methyl)sulfonyl)phenoxy)methyl)prop-2-en-1-amine |
| 27 | 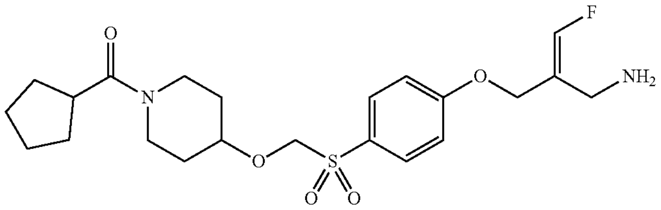 [SMILES: NC/C(=C\F)COc1ccc(S(=O)(=O)COC2CCN(C(=O)C3CCCC3)CC2)cc1] | (E)-(4-(((4-((2-(aminomethyl)-3-fluoroallyl)oxy)phenyl)sulfonyl)methoxy)piperidin-1-yl)(cyclopentyl)methanone |
| 28 | 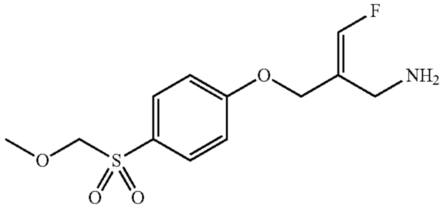 [SMILES: COCS(=O)(=O)c1ccc(OC/C(=C/F)CN)cc1] | (E)-3-fluoro-2-((4-((methoxymethyl)sulfonyl)phenoxy)methyl)prop-2-en-1-amine |
| 29 | 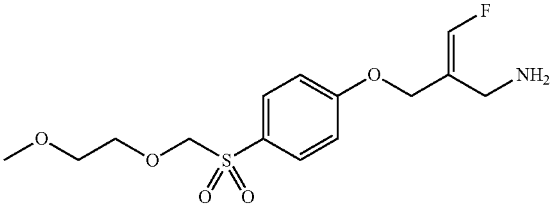 [SMILES: COCCOCS(=O)(=O)c1ccc(OC/C(=C/F)CN)cc1] | (E)-3-fluoro-2-((4-(((2-methoxyethoxy)methyl)sulfonyl)phenoxy)methyl)prop-2-en-1-amine |

TABLE 1-continued

| Cmpd No. | Structure | Chemical name |
|---|---|---|
| 30 | 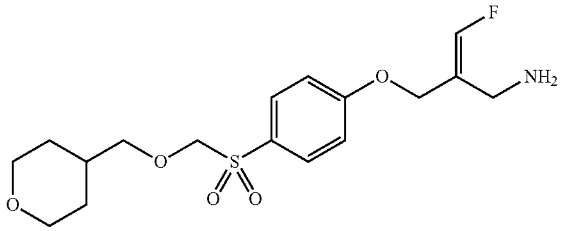 [SMILES: NC/C(=C\F)COc1ccc(S(=O)(=O)COCC2CCOCC2)cc1] | (E)-3-fluoro-2-((4-(((tetrahydro-2H-pyran-4-yl)methoxy)methyl)sulfonyl)phenoxy) methyl)prop-2-en-1-amine |
| 31 | 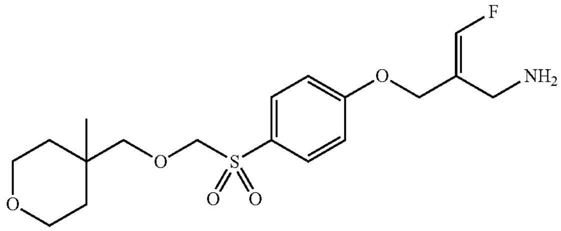 [SMILES: CC1(COCS(=O)(=O)c2ccc(OC/C(=C/F)CN)cc2)CCOCC1] | (E)-3-fluoro-2-((4-((((4-methyltetrahydro-2H-pyran-4-yl)methoxy)methyl)sulfonyl)phenoxy) methyl)prop-2-en-1-amine |
| 32 | 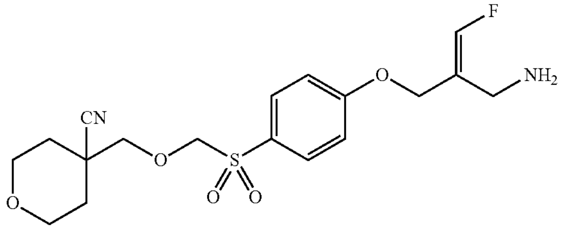 [SMILES: N#CC1(COCS(=O)(=O)c2ccc(OC/C(=C/F)CN)cc2)CCOCC1] | (E)-4-((((4-((2-(aminomethyl)-3-fluoroallyl)oxy)phenyl)sulfonyl) methoxy)methyl)tetrahydro-2H-pyran-4-carbonitrile |
| 33 | 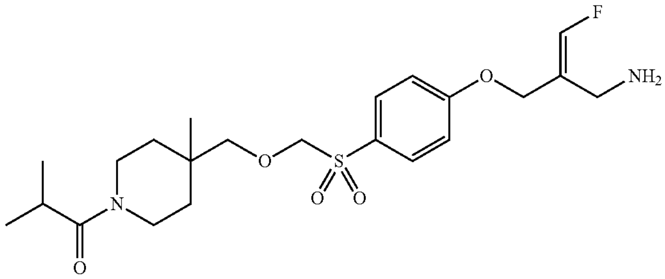 [SMILES: CC(C)C(=O)N1CCC(C)(COCS(=O)(=O)c2ccc(OC/C(=C/F)CN)cc2)CC1] | (E)-1-(4-((((4-((2-(aminomethyl)-3-fluoroallyl)oxy)phenyl)sulfonyl) methoxy)methyl)-4-methylpiperidin-1-yl)-2-methylpropan-1-one |
| 34 | 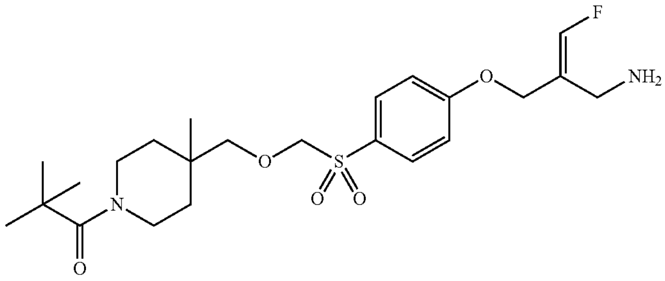 [SMILES: CC1(COCS(=O)(=O)c2ccc(OC/C(=C/F)CN)cc2)CCN(C(=O)C(C)(C)C)CC1] | (E)-1-(4-((((4-((2-(aminomethyl)-3-fluoroallyl)oxy)phenyl)sulfonyl) methoxy)methyl)-4-methylpiperidin-1-yl)-2,2-dimethylpropan-1-one |
| 35 | 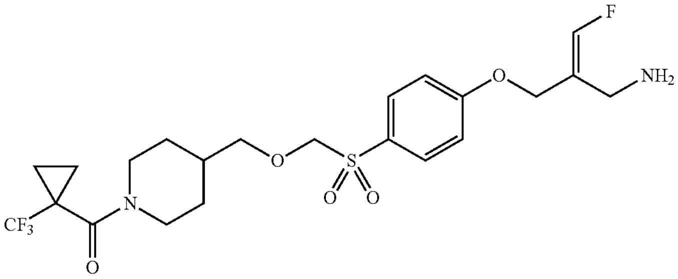 [SMILES: NC/C(=C\F)COc1ccc(S(=O)(=O)COCC2CCN(C(=O)C3(C(F)(F)F)CC3)CC2)cc1] | (E)-(4-((((4-((2-(aminomethyl)-3-fluoroallyl)oxy)phenyl)sulfonyl) methoxy)methyl)piperidin-1-yl)(1-(trifluoromethyl)cyclopropyl)methanone |

TABLE 1-continued

| Cmpd No. | Structure | Chemical name |
|---|---|---|
| 36 | 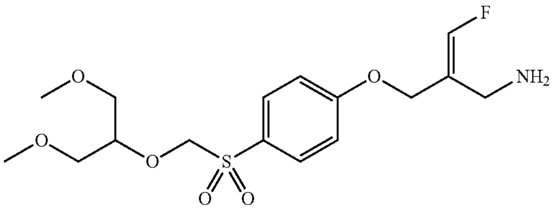 [SMILES: COCC(COC)OCS(=O)(=O)c1ccc(OC/C(=C/F)CN)cc1] | (E)-2-((4-((((1,3-dimethoxypropan-2-yl)oxy)methyl)sulfonyl)phenoxy)methyl)-3-fluoroprop-2-en-1-amine |
| 37 | 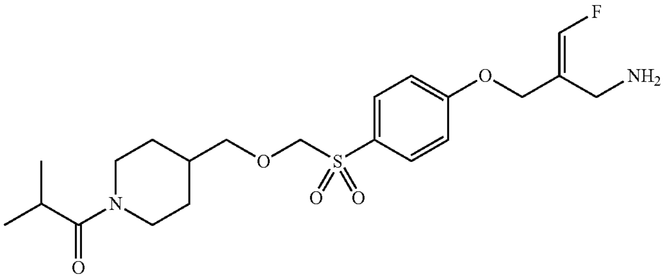 [SMILES: CC(C)C(=O)N1CCC(COCS(=O)(=O)c2ccc(OC/C(=C/F)CN)cc2)CC1] | (E)-1-(4-(((4-((2-(aminomethyl)-3-fluoroallyl)oxy)phenyl)sulfonyl)methyl)piperidin-1-yl)-2-methylpropan-1-one |
| 38 | 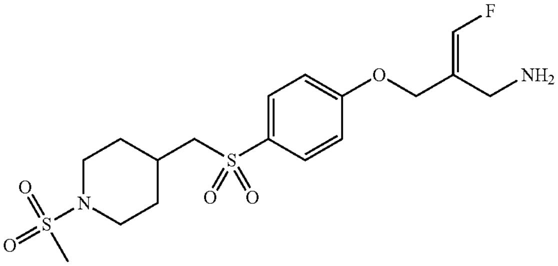 [SMILES: CS(=O)(=O)N1CCC(CS(=O)(=O)c2ccc(OC/C(=C/F)CN)cc2)CC1] | (E)-3-fluoro-2-((4-(((1-(methylsulfonyl)piperidin-4-yl)methyl)sulfonyl)phenoxy)methyl)prop-2-en-1-amine |
| 39 | 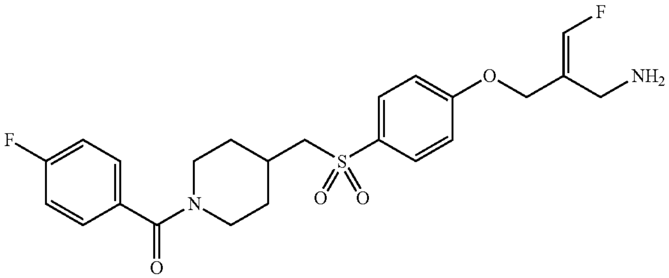 [SMILES: NC/C(=C\F)COc1ccc(S(=O)(=O)CC2CCN(C(=O)c3ccc(F)cc3)CC2)cc1] | (E)-(4-(((4-((2-(aminomethyl)-3-fluoroallyl)oxy)phenyl)sulfonyl)methyl)piperidin-1-yl)(4-fluorophenyl)methanone |
| 40 | 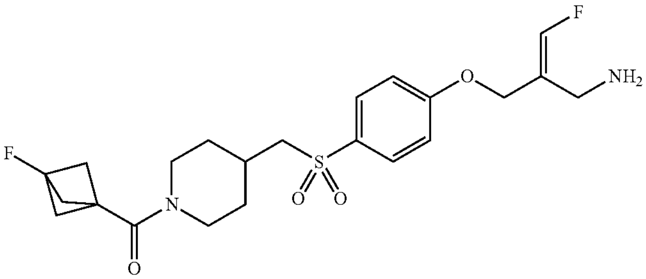 [SMILES: NC/C(=C\F)COc1ccc(S(=O)(=O)CC2CCN(C(=O)C34CC(F)(C3)C4)CC2)cc1] | (E)-(4-(((4-((2-(aminomethyl)-3-fluoroallyl)oxy)phenyl)sulfonyl)methyl)piperidin-1-yl)(3-fluorobicyclo[1.1.1]pentan-1-yl)methanone |

TABLE 1-continued

| Cmpd No. | Structure | Chemical name |
|---|---|---|
| 41 | 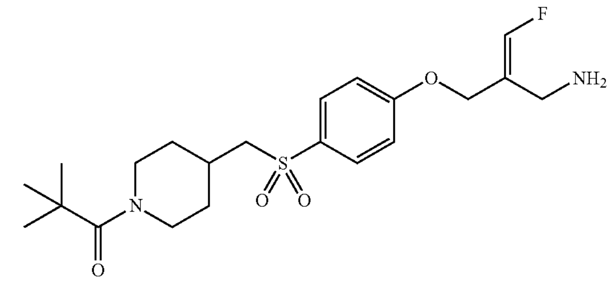 [SMILES: CC(C)(C)C(=O)N1CCC(CS(=O)(=O)c2ccc(OC/C(=C/F)CN)cc2)CC1] | (E)-1-(4-(((4-((2-(aminomethyl)-3-fluoroallyl)oxy)phenyl)sulfonyl)methyl)piperidin-1-yl)-2,2-dimethylpropan-1-one |
| 42 | 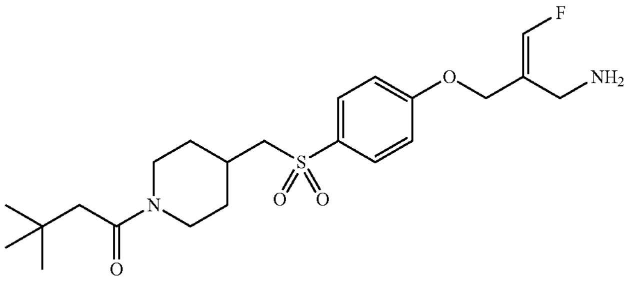 [SMILES: CC(C)(C)CC(=O)N1CCC(CS(=O)(=O)c2ccc(OC/C(=C/F)CN)cc2)CC1] | (E)-1-(4-(((4-((2-(aminomethyl)-3-fluoroallyl)oxy)phenyl)sulfonyl)methyl)piperidin-1-yl)-3,3-dimethylbutan-1-one |
| 43 | 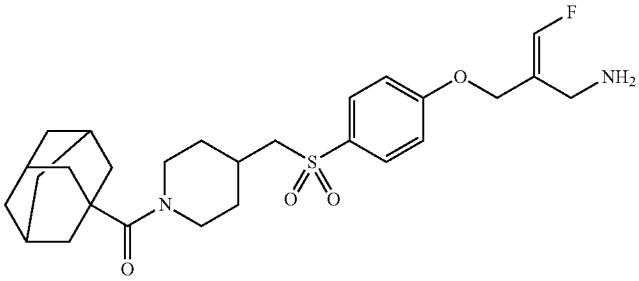 [SMILES: NC/C(=C\F)COc1ccc(S(=O)(=O)CC2CCN(C(=O)C34CC5CC(CC(C5)C3)C4)CC2)cc1] | (E)-adamantan-1-yl(4-(((4-((2-(aminomethyl)-3-fluoroallyl)oxy)phenyl)sulfonyl)methyl)piperidin-1-yl)methanone |
| 44 | 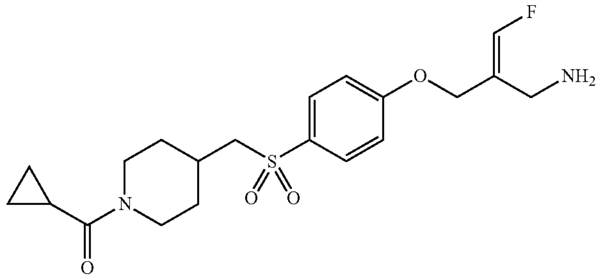 [SMILES: NC/C(=C\F)COc1ccc(S(=O)(=O)CC2CCN(C(=O)C3CC3)CC2)cc1] | (E)-(4-(((4-((2-(aminomethyl)-3-fluoroallyl)oxy)phenyl)sulfonyl)methyl)piperidin-1-yl)(cyclopropyl)methanone |
| 45 | 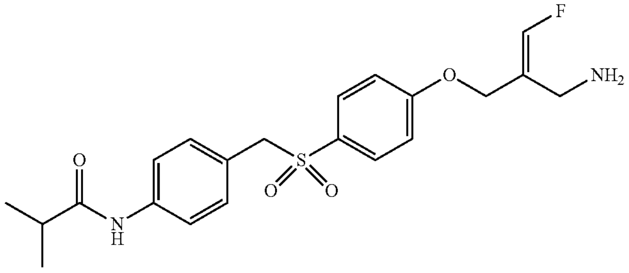 [SMILES: CC(C)C(=O)Nc1ccc(CS(=O)(=O)c2ccc(OC/C(=C/F)CN)cc2)cc1] | (E)-N-(4-(((4-((2-(aminomethyl)-3-fluoroallyl)oxy)phenyl)sulfonyl)methyl)phenyl)isobutyramide |

TABLE 1-continued

| Cmpd No. | Structure | Chemical name |
|---|---|---|
| 46 | 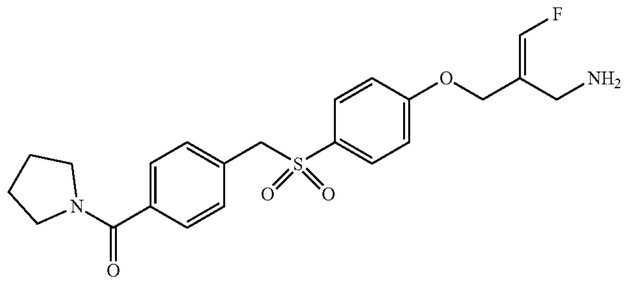 [SMILES: NC/C(=C\F)COc1ccc(S(=O)(=O)Cc2ccc(C(=O)N3CCCC3)cc2)cc1] | (E)-4-(((4-((2-(aminomethyl)-3-fluoroallyl)oxy)phenyl)sulfonyl)methyl)phenyl)(pyrrolidin-1-yl)methanone |
| 47 | 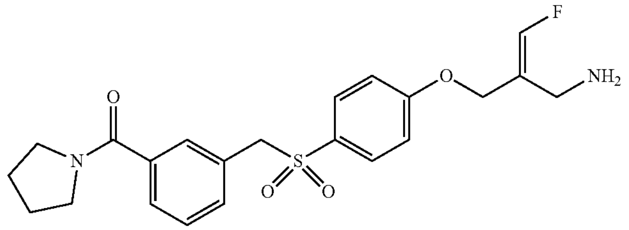 [SMILES: NC/C(=C\F)COc1ccc(S(=O)(=O)Cc2cccc(C(=O)N3CCCC3)c2)cc1] | (E)-(3-(((4-((2-(aminomethyl)-3-fluoroallyl)oxy)phenyl)sulfonyl)methyl)phenyl)(pyrrolidin-1-yl)methanone |
| 48 | 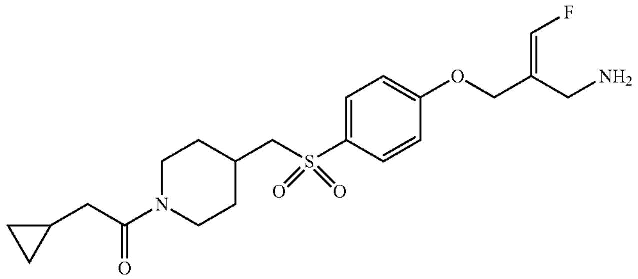 [SMILES: NC/C(=C\F)COc1ccc(S(=O)(=O)CC2CCN(C(=O)CC3CC3)CC2)cc1] | (E)-1-(4-(((4-((2-(aminomethyl)-3-fluoroallyl)oxy)phenyl)sulfonyl)methyl)piperidin-1-yl)-2-cyclopropylethan-1-one |
| 49 | 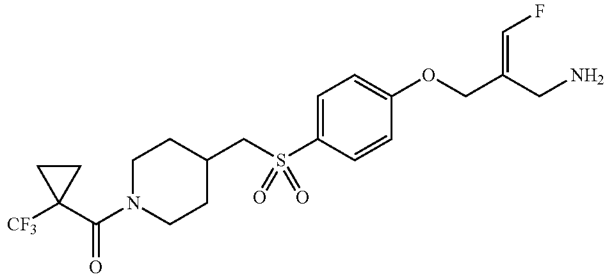 [SMILES: NC/C(=C\F)COc1ccc(S(=O)(=O)CC2CCN(C(=O)C3(C(F)(F)F)CC3)CC2)cc1] | (E)-(4-(((4-((2-(aminomethyl)-3-fluoroallyl)oxy)phenyl)sulfonyl)methyl)piperidin-1-yl)(1-(trifluoromethyl)cyclopropyl)methanone |
| 50 | 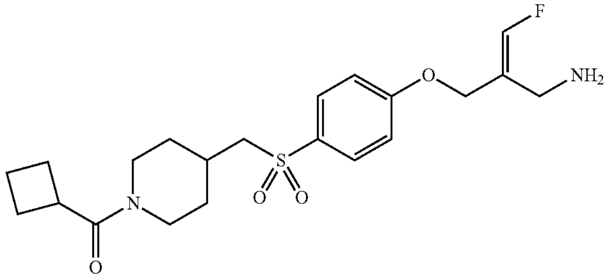 [SMILES: NC/C(=C\F)COc1ccc(S(=O)(=O)CC2CCN(C(=O)C3CCC3)CC2)cc1] | (E)-(4-(((4-((2-(aminomethyl)-3-fluoroallyl)oxy)phenyl)sulfonyl)methyl)piperidin-1-yl)(cyclobutyl)methanone |

TABLE 1-continued

| Cmpd No. | Structure | Chemical name |
| --- | --- | --- |
| 51 | 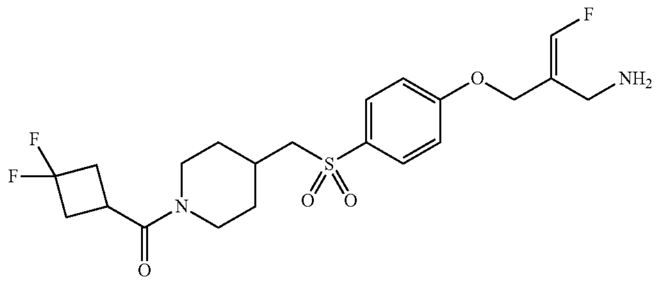 [SMILES: NC/C(=C\F)COc1ccc(S(=O)(=O)CC2CCN(C(=O)C3CC(F)(F)C3)CC2)cc1] | (E)-(4-(((4-((2-(aminomethyl)-3-fluoroallyl)oxy)phenyl)sulfonyl) methyl)piperidin-1-yl)(3,3-difluorocyclobutyl)methanone |
| 52 | 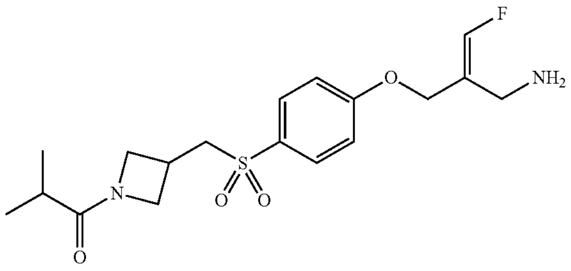 [SMILES: CC(C)C(=O)N1CC(CS(=O)(=O)c2ccc(OC/C(=C/F)CN)cc2)C1] | (E)-1-(3-(((4-((2-(aminomethyl)-3-fluoroallyl)oxy)phenyl)sulfonyl) methyl)azetidin-1-yl)-2-methylpropan-1-one |
| 53 | 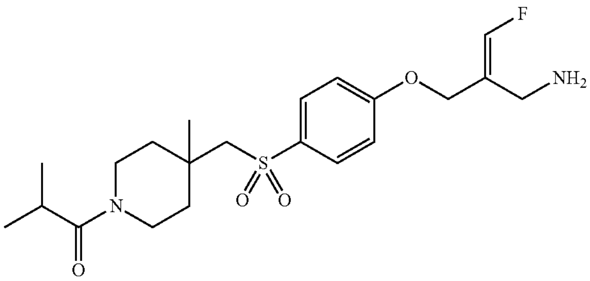 [SMILES: CC(C)C(=O)N1CCC(C)(CS(=O)(=O)c2ccc(OC/C(=C/F)CN)cc2)CC1] | (E)-1-(4-(((4-((2-(aminomethyl)-3-fluoroallyl)oxy)phenyl)sulfonyl) methyl)-4-methylpiperidin-1-yl)-2-methylpropan-1-one |
| 54 | 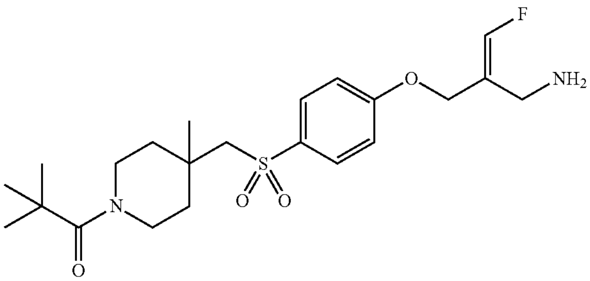 [SMILES: CC1(CS(=O)(=O)c2ccc(OC/C(=C/F)CN)cc2)CCN(C(=O)C(C)(C)C)CC1] | (E)-1-(4-(((4-((2-(aminomethyl)-3-fluoroallyl)oxy)phenyl)sulfonyl) methyl)-4-methylpiperidin-1-yl)-2,2-dimethylpropan-1-one |
| 55 | 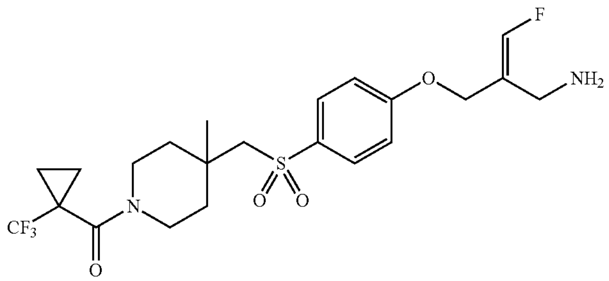 [SMILES: CC1(CS(=O)(=O)c2ccc(OC/C(=C/F)CN)cc2)CCN(C(=O)C2(C(F)(F)F)CC2)CC1] | (E)-(4-(((4-((2-(aminomethyl)-3-fluoroallyl)oxy)phenyl)sulfonyl) methyl)-4-methylpiperidin-1-yl)(1-(trifluoromethyl)cyclopropyl) methanone |

TABLE 1-continued

| Cmpd No. | Structure | Chemical name |
| --- | --- | --- |
| 56 | 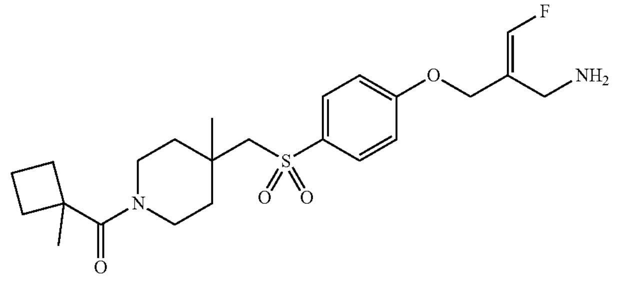 [SMILES: CC1(CS(=O)(=O)c2ccc(OC/C(=C/F)CN)cc2)CCN(C(=O)C2(C)CCC2)CC1] | (E)-(4-(((4-((2-(aminomethyl)-3-fluoroallyl)oxy)phenyl)sulfonyl) methyl)-4-methylpiperidin-1-yl)(1-methylcyclobutyl)methanone |
| 57 | 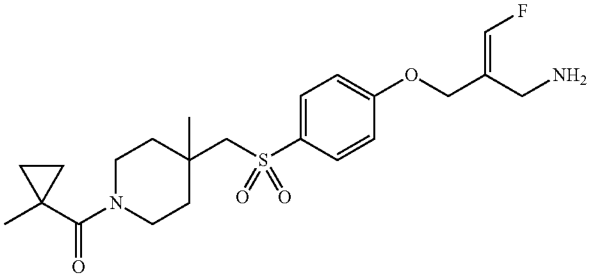 [SMILES: CC1(CS(=O)(=O)c2ccc(OC/C(=C/F)CN)cc2)CCN(C(=O)C2(C)CC2)CC1] | (E)-(4-(((4-((2-(aminomethyl)-3-fluoroallyl)oxy)phenyl)sulfonyl) methyl)-4-methylpiperidin-1-yl)(1-methylcyclopropyl)methanone |
| 58 | 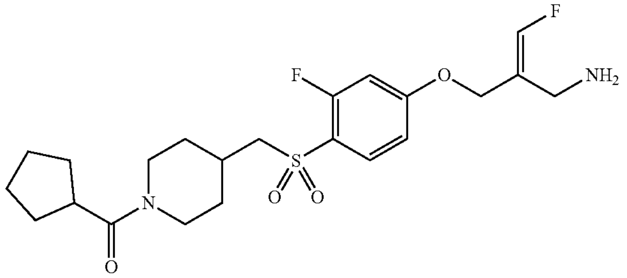 [SMILES: NC/C(=C\F)COc1ccc(S(=O)(=O)CC2CCN(C(=O)C3CCCC3)CC2)c(F)c1] | (E)-4-(((4-((2-(aminomethyl)-3-fluoroallyl)oxy)-2-fluorophenyl)sulfonyl)methyl) piperidin-1-yl)(cyclopentyl)methanone |
| 59 | 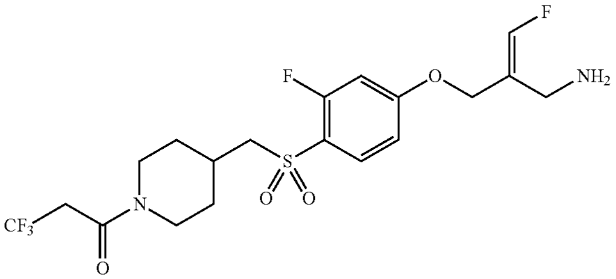 [SMILES: NC/C(=C\F)COc1ccc(S(=O)(=O)CC2CCN(C(=O)CC(F)(F)F)CC2)c(F)c1] | (E)-1-(4-(((4-((2-(aminomethyl)-3-fluoroallyl)oxy)-2-fluorophenyl)sulfonyl)methyl) piperidin-1-yl)-3,3,3-trifluoropropan-1-one |
| 60 | 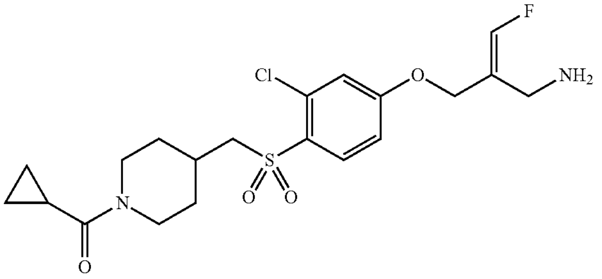 [SMILES: NC/C(=C\F)COc1ccc(S(=O)(=O)CC2CCN(C(=O)C3CC3)CC2)c(Cl)c1] | (E)-(4-(((4-((2-(aminomethyl)-3-fluoroallyl)oxy)-2-chlorophenyl)sulfonyl)methyl) piperidin-1-yl)(cyclopropyl)methanone |

TABLE 1-continued

| Cmpd No. | Structure | Chemical name |
|---|---|---|
| 61 | 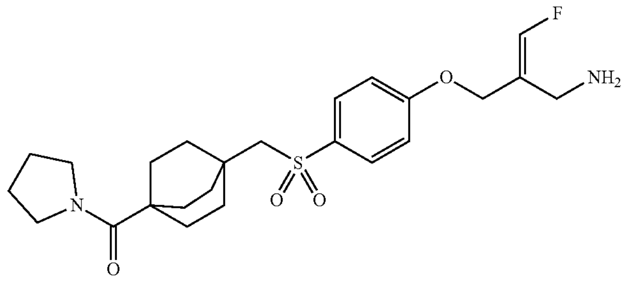 [SMILES: NC/C(=C\F)COc1ccc(S(=O)(=O)CC23CCC(C(=O)N4CCCC4)(CC2)CC3)cc1] | (E)-(4-(((4-((2-(aminomethyl)-3-fluoroallyl)oxy)phenyl)sulfonyl)methyl)bicyclo[2.2.2]octan-1-yl)(pyrrolidin-1-yl)methanone |
| 62 | 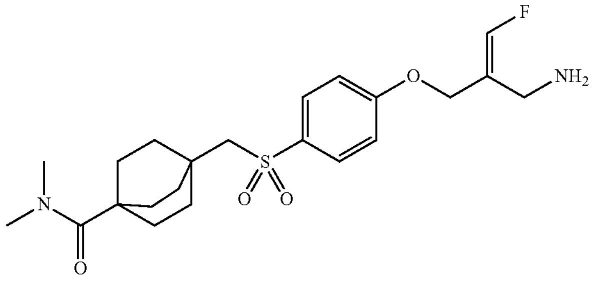 [SMILES: CN(C)C(=O)C12CCC(CS(=O)(=O)c3ccc(OC/C(=C/F)CN)cc3)(CC1)CC2] | (E)-4-(((4-((2-(aminomethyl)-3-fluoroallyl)oxy)phenyl)sulfonyl)methyl)-N,N-dimethylbicyclo[2.2.2]octane-1-carboxamide |
| 63 | 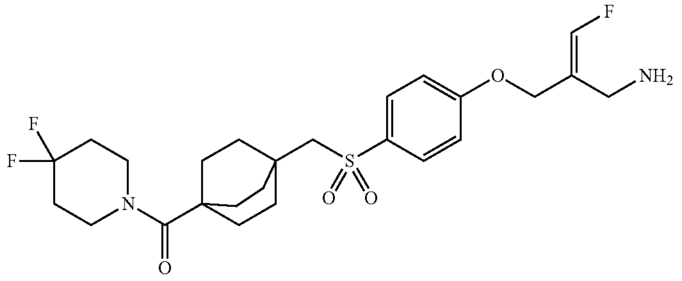 [SMILES: NC/C(=C\F)COc1ccc(S(=O)(=O)CC23CCC(C(=O)N4CCC(F)(F)CC4)(CC2)CC3)cc1] | (E)-(4-(((4-((2-(aminomethyl)-3-fluoroallyl)oxy)phenyl)sulfonyl)methyl)bicyclo[2.2.2]octan-1-yl)(4,4-difluoropiperidin-1-yl)methanone |
| 64 | 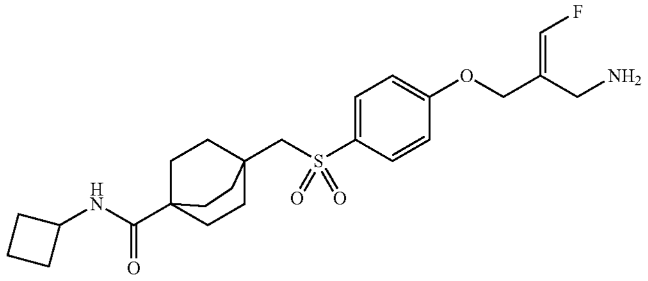 [SMILES: NC/C(=C\F)COc1ccc(S(=O)(=O)CC23CCC(C(=O)NC4CCC4)(CC2)CC3)cc1] | (E)-4-(((4-((2-(aminomethyl)-3-fluoroallyl)oxy)phenyl)sulfonyl)methyl)-N-cyclobutylbicyclo[2.2.2]octane-1-carboxamide |
| 65 | 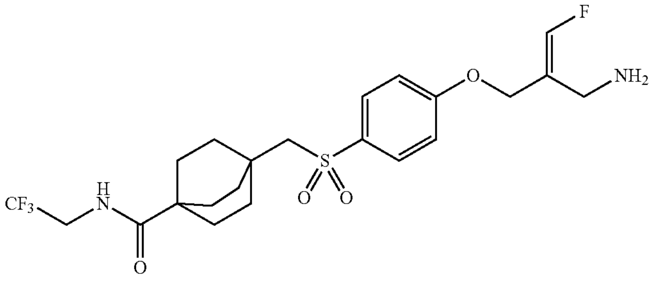 [SMILES: NC/C(=C\F)COc1ccc(S(=O)(=O)CC23CCC(C(=O)NCC(F)(F)F)(CC2)CC3)cc1] | (E)-4-(((4-((2-(aminomethyl)-3-fluoroallyl)oxy)phenyl)sulfonyl)methyl)-N-(2,2,2-trifluoroethyl)bicyclo[2.2.2]octane-1-carboxamide |

TABLE 1-continued

| Cmpd No. | Structure | Chemical name |
| --- | --- | --- |
| 66 | 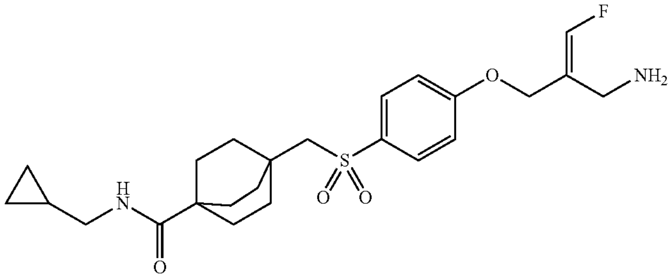 [SMILES: NC/C(=C\F)COc1ccc(S(=O)(=O)CC23CCC(C(=O)NCC4CC4)(CC2)CC3)cc1] | (E)-4-(((4-((2-(aminomethyl)-3-fluoroallyl)oxy)phenyl)sulfonyl) methyl)-N-(cyclopropylmethyl)bicyclo [2.2.2]octane-1-carboxamide |
| 67 | 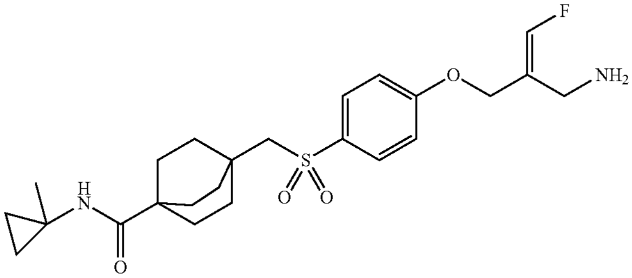 [SMILES: CC1(NC(=O)C23CCC(CS(=O)(=O)c4ccc(OC/C(=C/F)CN)cc4)(CC2)CC3)CC1] | (E)-4-(((4-((2-(aminomethyl)-3-fluoroallyl)oxy)phenyl)sulfonyl) methyl)-N-(1-methylcyclopropyl)bicyclo[2.2.2] octane-1-carboxamide |
| 68 | 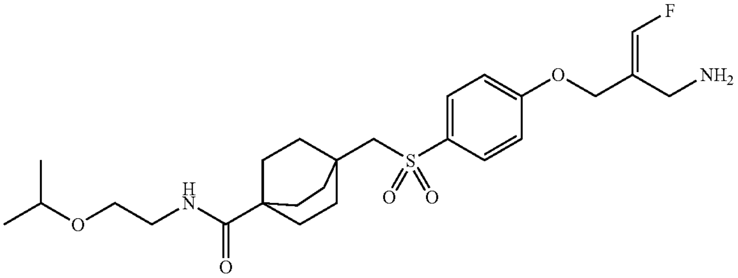 [SMILES: CC(C)OCCNC(=O)C12CCC(CS(=O)(=O)c3ccc(OC/C(=C/F)CN)cc3)(CC1)CC2] | (E)-4-(((4-((2-(aminomethyl)-3-fluoroallyl)oxy)phenyl)sulfonyl) methyl)-N-(2-isopropoxyethyl)bicyclo[2.2.2] octane-1-carboxamide |
| 69 | 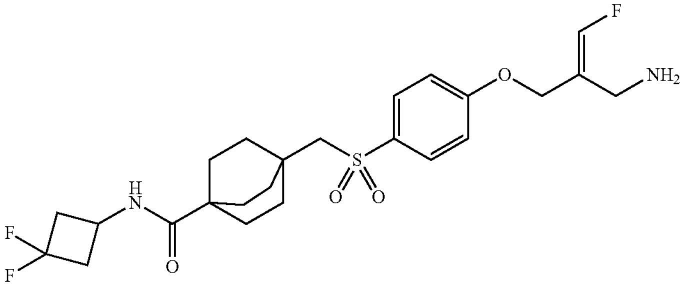 [SMILES: NC/C(=C\F)COc1ccc(S(=O)(=O)CC23CCC(C(=O)NC4CC(F)(F)C4)(CC2)CC3)cc1] | (E)-4-(((4-((2-(aminomethyl)-3-fluoroallyl)oxy)phenyl)sulfonyl) methyl)-N-(3,3-difluorocyclobutyl)bicyclo[2.2.2] octane-1-carboxamide |
| 70 | 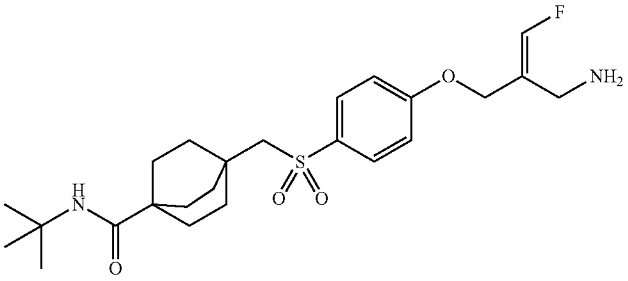 [SMILES: CC(C)(C)NC(=O)C12CCC(CS(=O)(=O)c3ccc(OC/C(=C/F)CN)cc3)(CC1)CC2] | (E)-4-(((4-((2-(aminomethyl)-3-fluoroallyl)oxy)phenyl)sulfonyl) methyl)-N-(tert-butyl)bicyclo[2.2.2]octane-1-carboxamide |

TABLE 1-continued

| Cmpd No. | Structure | Chemical name |
|---|---|---|
| 71 | 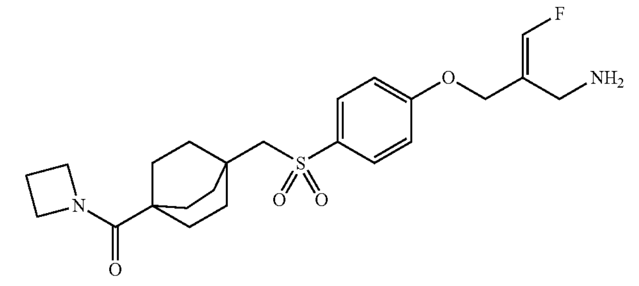 [SMILES: NC/C(=C\F)COc1ccc(S(=O)(=O)CC23CCC(C(=O)N4CCC4)(CC2)CC3)cc1] | (E)-4-(((4-((2-(aminomethyl)-3-fluoroallyl)oxy)phenyl)sulfonyl)methyl)bicyclo[2.2.2]octan-1-yl)(azetidin-1-yl)methanone |
| 72 | 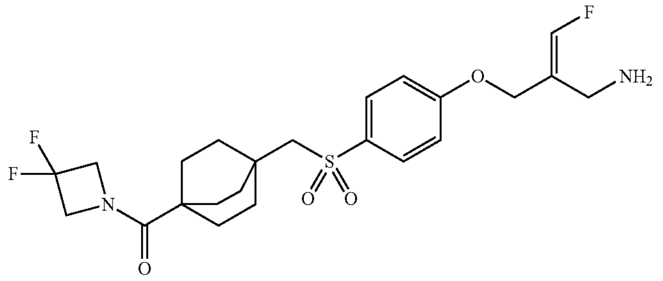 [SMILES: NC/C(=C\F)COc1ccc(S(=O)(=O)CC23CCC(C(=O)N4CC(F)(F)C4)(CC2)CC3)cc1] | (E)-4-(((4-((2-(aminomethyl)-3-fluoroallyl)oxy)phenyl)sulfonyl)methyl)bicyclo[2.2.2]octan-1-yl)(3,3-difluoroazetidin-1-yl)methanone |
| 73 | 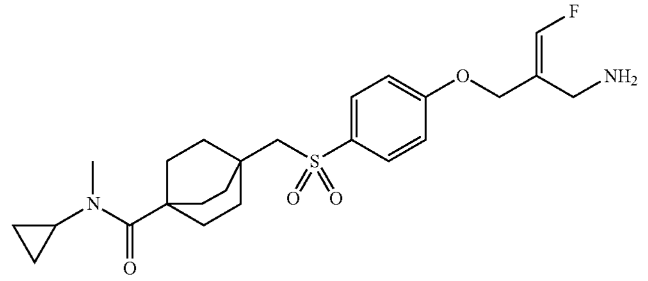 [SMILES: CN(C(=O)C12CCC(CS(=O)(=O)c3ccc(OC/C(=C/F)CN)cc3)(CC1)CC2)C1CC1] | (E)-4-(((4-((2-(aminomethyl)-3-fluoroallyl)oxy)phenyl)sulfonyl)methyl)-N-cyclopropyl-N-methylbicyclo[2.2.2]octane-1-carboxamide |
| 74 | 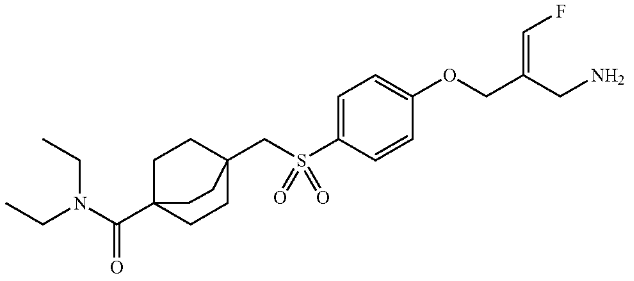 [SMILES: CCN(CC)C(=O)C12CCC(CS(=O)(=O)c3ccc(OC/C(=C/F)CN)cc3)(CC1)CC2] | (E)-4-(((4-((2-(aminomethyl)-3-fluoroallyl)oxy)phenyl)sulfonyl)methyl)-N,N-diethylbicyclo[2.2.2]octane-1-carboxamide |
| 75 | 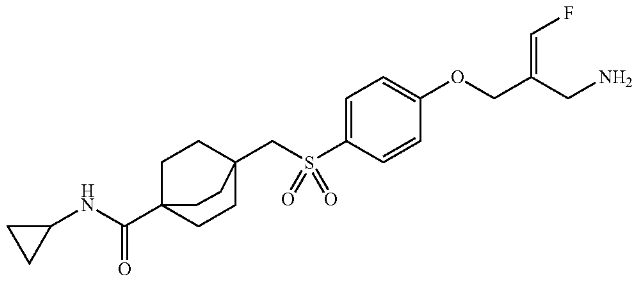 | (E)-4-(((4-((2-(aminomethyl)-3-fluoroallyl)oxy)phenyl)sulfonyl)methyl)-N-cyclopropylbicyclo[2.2.2]octane-1-carboxamide |

TABLE 1-continued

| Cmpd No. | Structure | Chemical name |
| --- | --- | --- |
| 76 | 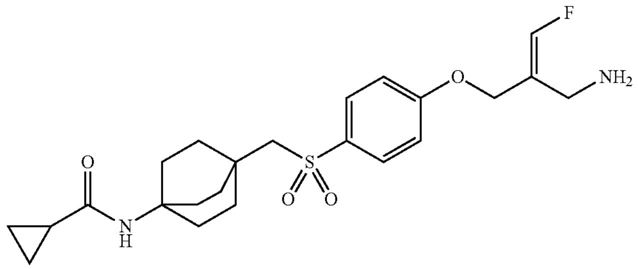 [SMILES: NC/C(=C\F)COc1ccc(S(=O)(=O)CC23CCC(NC(=O)C4CC4)(CC2)CC3)cc1] | (E)-N-(4-(((4-((2-(aminomethyl)-3-fluoroallyl)oxy)phenyl)sulfonyl) methyl)bicyclo[2.2.2]octan-1-yl)cyclopropanecarboxamide |
| 77 | 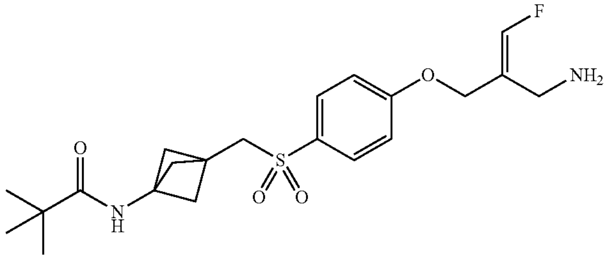 [SMILES: CC(C)(C)C(=O)NC12CC(CS(=O)(=O)c3ccc(OC/C(=C/F)CN)cc3)(C1)C2] | (E)-N-(3-(((4-((2-(aminomethyl)-3-fluoroallyl)oxy)phenyl)sulfonyl) methyl)bicyclo[1.1.1]pentan-1-yl)pivalamide |
| 78 | 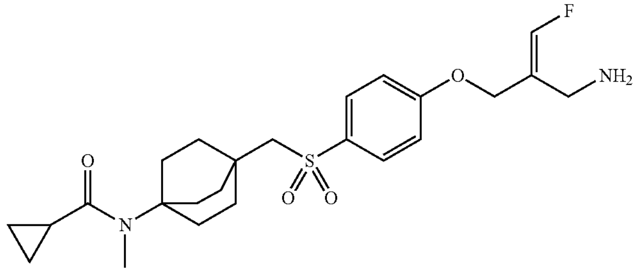 [SMILES: CN(C(=O)C1CC1)C12CCC(CS(=O)(=O)c3ccc(OC/C(=C/F)CN)cc3)(CC1)CC2] | (E)-N-(4-(((4-((2-(aminomethyl)-3-fluoroallyl)oxy)phenyl)sulfonyl) methyl)bicyclo[2.2.2]octan-1-yl)-N-methylcyclopropanecarboxamide |
| 79 | 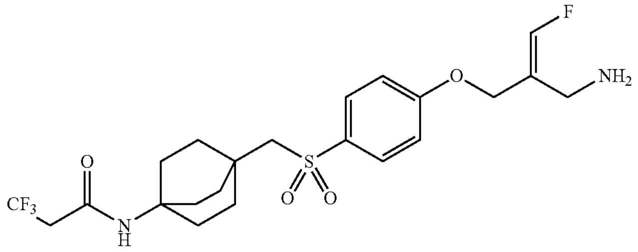 [SMILES: NC/C(=C\F)COc1ccc(S(=O)(=O)CC23CCC(NC(=O)CC(F)(F)F)(CC2)CC3)cc1] | (E)-N-(4-(((4-((2-(aminomethyl)-3-fluoroallyl)oxy)phenyl)sulfonyl) methyl)bicyclo[2.2.2]octan-1-yl)-3,3,3-trifluoropropanamide |
| 80 | 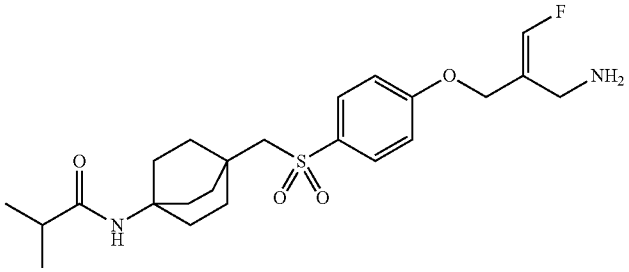 [SMILES: CC(C)C(=O)NC12CCC(CS(=O)(=O)c3ccc(OC/C(=C/F)CN)cc3)(CC1)CC2] | (E)-N-(4-(((4-((2-(aminomethyl)-3-fluoroallyl)oxy)phenyl)sulfonyl) methyl)bicyclo[2.2.2]octan-1-yl)isobutyramide |

TABLE 1-continued

| Cmpd No. | Structure | Chemical name |
|---|---|---|
| 81 | 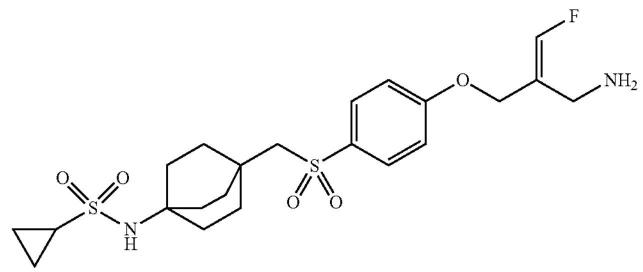 [SMILES: NC/C(=C\F)COc1ccc(S(=O)(=O)CC23CCC(NS(=O)(=O)C4CC4)(CC2)CC3)cc1] | (E)-N-(4-(((4-((2-(aminomethyl)-3-fluoroallyl)oxy)phenyl)sulfonyl) methyl)bicyclo[2.2.2]octan-1-yl)cyclopropanesulfonamide |
| 82 | 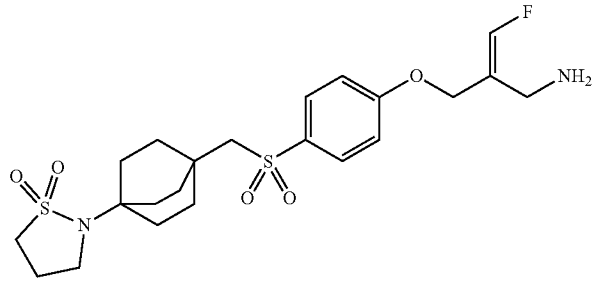 [SMILES: NC/C(=C\F)COc1ccc(S(=O)(=O)CC23CCC(N4CCCS4(=O)=O)(CC2)CC3)cc1] | (E)-2-(4-(((4-((2-(aminomethyl)-3-fluoroallyl)oxy)phenyl)sulfonyl) methyl)bicyclo[2.2.2]octan-1-yl)isothiazolidine 1,1-dioxide |
| 83 | 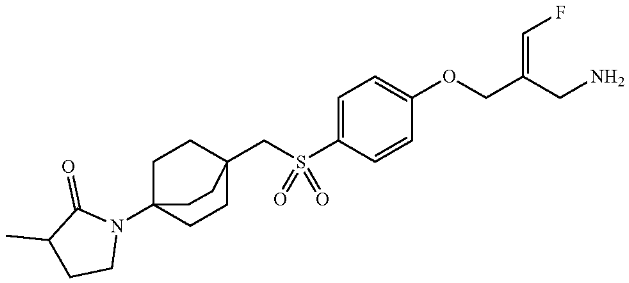 [SMILES: CC1CCN(C23CCC(CS(=O)(=O)c4ccc(OC/C(=C/F)CN)cc4)(CC2)CC3)C1=O] | (E)-1-(4-(((4-((2-(aminomethyl)-3-fluoroallyl)oxy)phenyl) sulfonyl)methyl)bicyclo[2.2.2]octan-1-yl)-3-methylpyrrolidin-2-one |
| 84 | 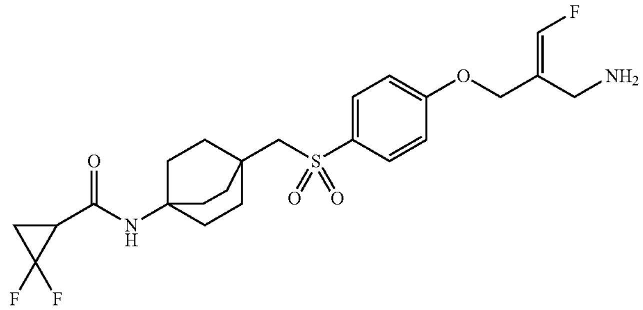 [SMILES: NC/C(=C\F)COc1ccc(S(=O)(=O)CC23CCC(NC(=O)C4CC4(F)F)(CC2)CC3)cc1] | (E)-N-(4-(((4-((2-(aminomethyl)-3-fluoroallyl)oxy)phenyl)sulfonyl) methyl)bicyclo[2.2.2]octan-1-yl)-2,2-difluorocyclopropane-1-carboxamide |
| 85 | 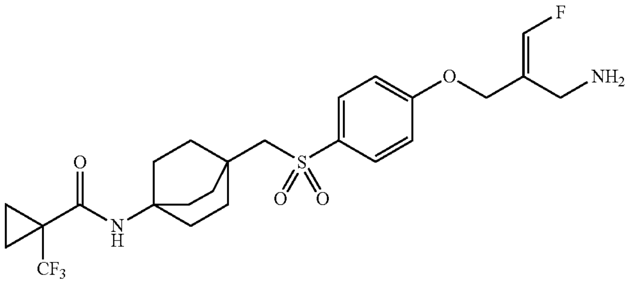 [SMILES: NC/C(=C\F)COc1ccc(S(=O)(=O)CC23CCC(NC(=O)C4(C(F)(F)F)CC4)(CC2)CC3)cc1] | (E)-N-(4-(((4-((2-(aminomethyl)-3-fluoroallyl)oxy)phenyl)sulfonyl) methyl)bicyclo[2.2.2]octan-1-yl)-1-(trifluoromethyl)cyclopropane-1-carboxamide |

TABLE 1-continued

| Cmpd No. | Structure | Chemical name |
| --- | --- | --- |
| 86 | 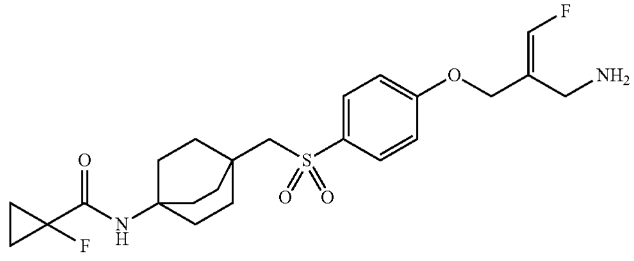 [SMILES: NC/C(=C\F)COc1ccc(S(=O)(=O)CC23CCC(NC(=O)C4(F)CC4)(CC2)CC3)cc1] | (E)-N-(4-(((4-((2-(aminomethyl)-3-fluoroallyl)oxy)phenyl)sulfonyl)methyl)bicyclo[2.2.2]octan-1-yl)-1-fluorocyclopropane-1-carboxamide |
| 87 | 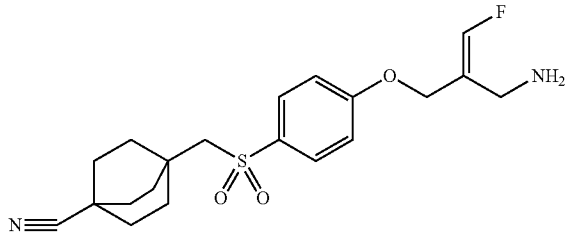 [SMILES: N#CC12CCC(CS(=O)(=O)c3ccc(OC/C(=C/F)CN)cc3)(CC1)CC2] | (E)-4-(((4-((2-(aminomethyl)-3-fluoroallyl)oxy)phenyl)sulfonyl)methyl)bicyclo[2.2.2]octane-1-carbonitrile |
| 88 | 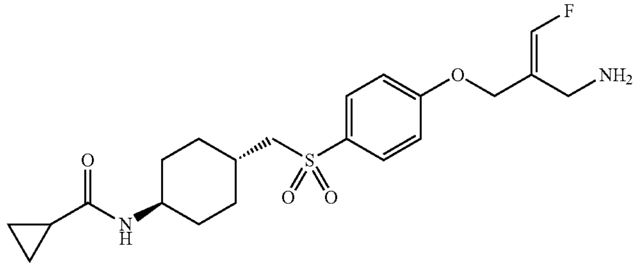 [SMILES: NC/C(=C\F)COc1ccc(S(=O)(=O)C[C@H]2CC[C@H](NC(=O)C3CC3)CC2)cc1] | N-((1r,4r)-4-(((4-(((E)-2-(aminomethyl)-3-fluoroallyl)oxy)phenyl)sulfonyl)methyl)cyclohexyl)cyclopropanecarboxamide |
| 89 | 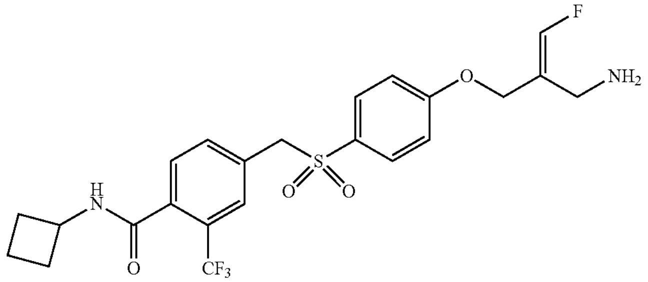 [SMILES: NC/C(=C\F)COc1ccc(S(=O)(=O)Cc2ccc(C(=O)NC3CCC3)c(C(F)(F)F)c2)cc1] | (E)-4-(((4-((2-(aminomethyl)-3-fluoroallyl)oxy)phenyl)sulfonyl)methyl)-N-cyclobutyl-2-(trifluoromethyl)benzamide |
| 90 | 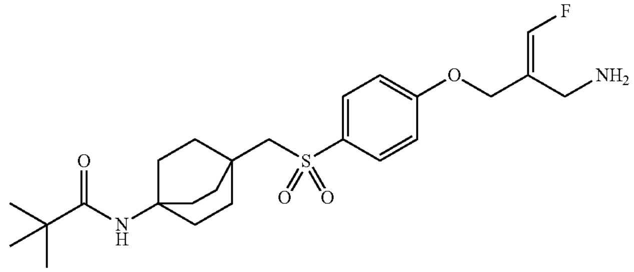 [SMILES: CC(C)(C)C(=O)NC12CCC(CS(=O)(=O)c3ccc(OC/C(=C/F)CN)cc3)(CC1)CC2] | (E)-N-(4-(((4-((2-(aminomethyl)-3-fluoroallyl)oxy)phenyl)sulfonyl)methyl)bicyclo[2.2.2]octan-1-yl)pivalamide |

TABLE 1-continued

| Cmpd No. | Structure | Chemical name |
|---|---|---|
| 91 | 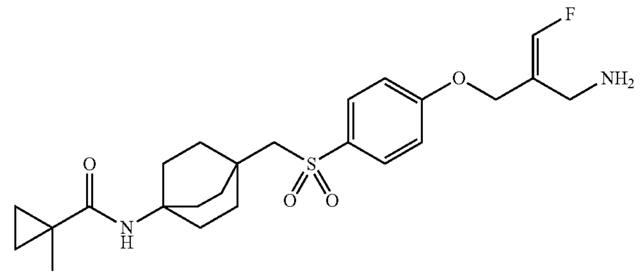 [SMILES: CC1(C(=O)NC23CCC(CS(=O)(=O)c4ccc(OC/C(=C/F)CN)cc4)(CC2)CC3)CC1] | (E)-N-(4-(((4-((2-(aminomethyl)-3-fluoroallyl)oxy)phenyl)sulfonyl)methyl)bicyclo[2.2.2]octan-1-yl)-1-methylcyclopropane-1-carboxamide |
| 92 | 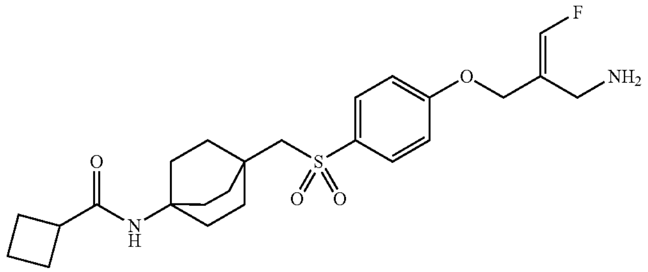 [SMILES: NC/C(=C\F)COc1ccc(S(=O)(=O)CC23CCC(NC(=O)C4CCC4)(CC2)CC3)cc1] | (E)-N-(4-(((4-((2-(aminomethyl)-3-fluoroallyl)oxy)phenyl)sulfonyl)methyl)bicyclo[2.2.2]octan-1-yl)cyclobutanecarboxamide |
| 93 | 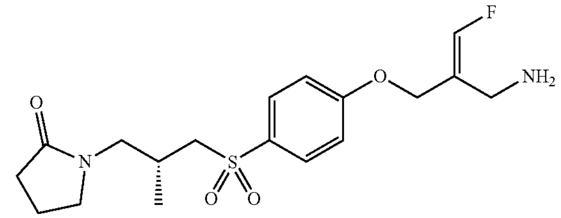 [SMILES: C[C@H](CN1CCCC1=O)CS(=O)(=O)c1ccc(OC/C(=C/F)CN)cc1] | (R,E)-1-(3-((4-((2-(aminomethyl)-3-fluoroallyl)oxy)phenyl)sulfonyl)-2-methylpropyl)pyrrolidin-2-one |
| 94 | 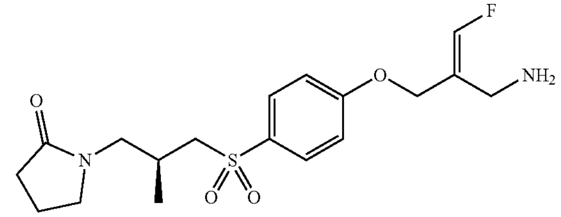 [SMILES: C[C@@H](CN1CCCC1=O)CS(=O)(=O)c1ccc(OC/C(=C/F)CN)cc1] | (S,E)-1-(3-((4-((2-(aminomethyl)-3-fluoroallyl)oxy)phenyl)sulfonyl)-2-methylpropyl)pyrrolidin-2-one |
| 95 | 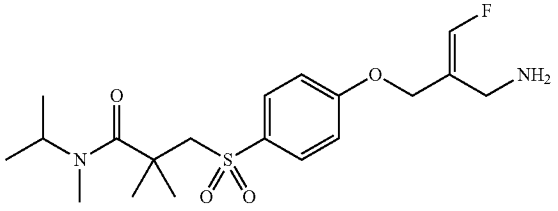 [SMILES: CC(C)N(C)C(=O)C(C)(C)CS(=O)(=O)c1ccc(OC/C(=C/F)CN)cc1] | (E)-3-((4-((2-(aminomethyl)-3-fluoroallyl)oxy)phenyl)sulfonyl)-N-isopropyl-N,2,2-trimethylpropanamide |
| 96 | 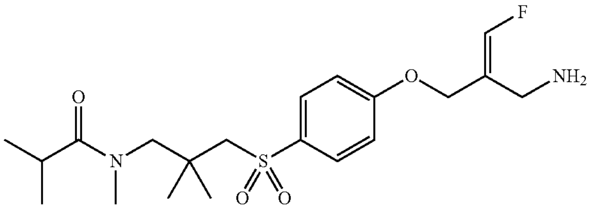 [SMILES: CC(C)C(=O)N(C)CC(C)(C)CS(=O)(=O)c1ccc(OC/C(=C/F)CN)cc1] | (E)-N-(3-((4-((2-(aminomethyl)-3-fluoroallyl)oxy)phenyl)sulfonyl)-2,2-dimethylpropyl)-N-methylisobutyramide |

TABLE 1-continued

| Cmpd No. | Structure | Chemical name |
| --- | --- | --- |
| 97 | 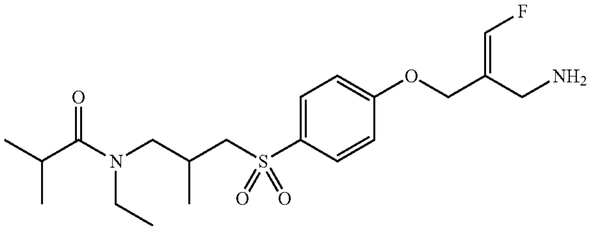 [SMILES: CCN(CC(C)CS(=O)(=O)c1ccc(OC/C(=C/F)CN)cc1)C(=O)C(C)C] | (E)-N-(3-((4-((2-(aminomethyl)-3-fluoroallyl)oxy)phenyl)sulfonyl)-2-methylpropyl)-N-ethylisobutyramide |
| 98 | 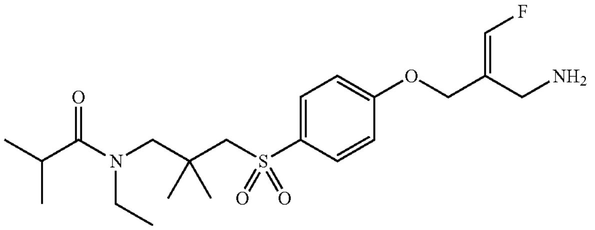 [SMILES: CCN(CC(C)(C)CS(=O)(=O)c1ccc(OC/C(=C/F)CN)cc1)C(=O)C(C)C] | (E)-N-(3-((4-((2-(aminomethyl)-3-fluoroallyl)oxy)phenyl)sulfonyl)-2,2-dimethylpropyl)-N-ethylisobutyramide |
| 99 | 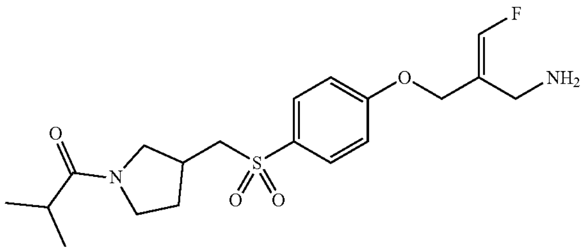 [SMILES: CC(C)C(=O)N1CCC(CS(=O)(=O)c2ccc(OC/C(=C/F)CN)cc2)C1] | (E)-1-(3-(((4-((2-(aminomethyl)-3-fluoroallyl)oxy)phenyl)sulfonyl)methyl)pyrrolidin-1-yl)-2-methylpropan-1-one |
| 100 | 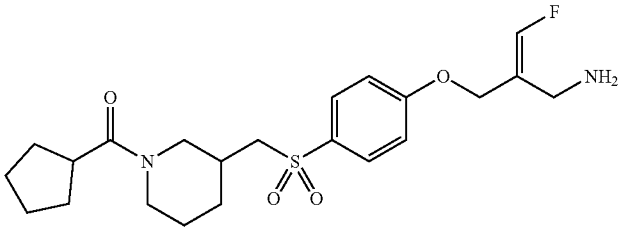 [SMILES: NC/C(=C\F)COc1ccc(S(=O)(=O)CC2CCCN(C(=O)C3CCCC3)C2)cc1] | (E)-3-(((4-((2-(aminomethyl)-3-fluoroallyl)oxy)phenyl)sulfonyl)methyl)piperidin-1-yl)(cyclopentyl)methanone |
| 101 | 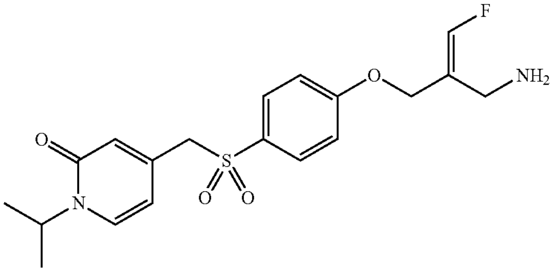 [SMILES: CC(C)n1ccc(CS(=O)(=O)c2ccc(OC/C(=C/F)CN)cc2)cc1=O] | (E)-4-(((4-((2-(aminomethyl)-3-fluoroallyl)oxy)phenyl)sulfonyl)methyl)-1-isopropylpyridin-2(1H)-one |
| 102 | 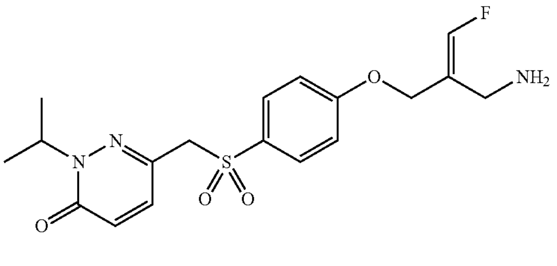 [SMILES: CC(C)n1nc(CS(=O)(=O)c2ccc(OC/C(=C/F)CN)cc2)ccc1=O] | (E)-6-(((4-((2-(aminomethyl)-3-fluoroallyl)oxy)phenyl)sulfonyl)methyl)-2-isopropylpyridazin-3(2H)-one |

TABLE 1-continued

| Cmpd No. | Structure | Chemical name |
|---|---|---|
| 103 | 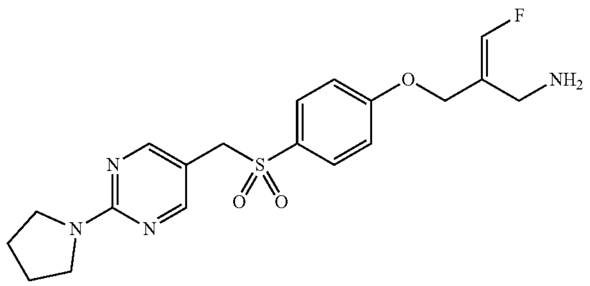 [SMILES: NC/C(=C\F)COc1ccc(S(=O)(=O)Cc2cnc(N3CCCC3)nc2)cc1] | (E)-3-fluoro-2-((4-(((2-(pyrrolidin-1-yl)pyrimidin-5-yl)methyl)sulfonyl)phenoxy)methyl)prop-2-en-1-amine |
| 104 | 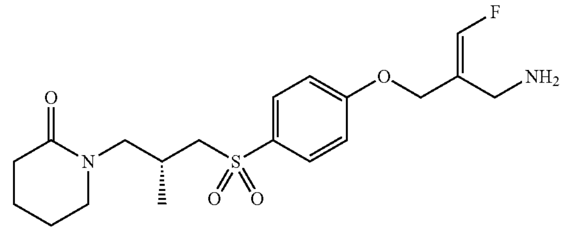 [SMILES: C[C@H](CN1CCCCC1=O)CS(=O)(=O)c1ccc(OC/C(=C/F)CN)cc1] | (R,E)-1-(3-((4-((2-(aminomethyl)-3-fluoroallyl)oxy)phenyl)sulfonyl)-2-methylpropyl)piperidin-2-one |
| 105 | 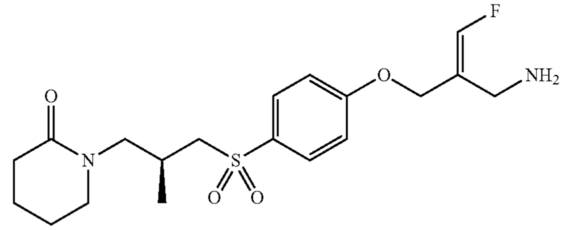 [SMILES: C[C@@H](CN1CCCCC1=O)CS(=O)(=O)c1ccc(OC/C(=C/F)CN)cc1] | (S,E)-1-(3-((4-((2-(aminomethyl)-3-fluoroallyl)oxy)phenyl)sulfonyl)-2-methylpropyl)piperidin-2-one |
| 106 | 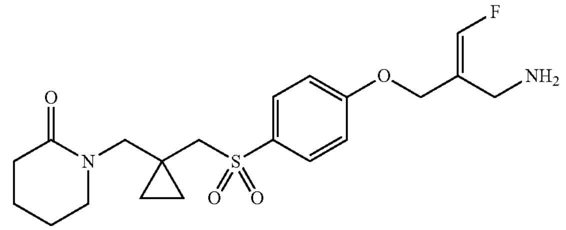 [SMILES: NC/C(=C\F)COc1ccc(S(=O)(=O)CC2(CN3CCCCC3=O)CC2)cc1] | (E)-1-((1-(((4-((2-(aminomethyl)-3-fluoroallyl)oxy)phenyl)sulfonyl)methyl)cyclopropyl)methyl)piperidin-2-one |
| 107 | 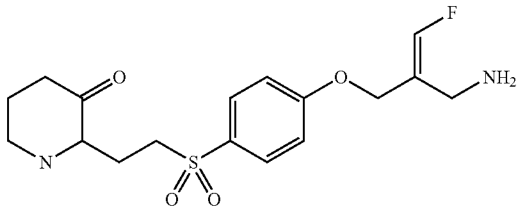 [SMILES: NC/C(=C\F)COc1ccc(S(=O)(=O)CCC2NCCCC2=O)cc1] | (E)-1-(2-((4-((2-(aminomethyl)-3-fluoroallyl)oxy)phenyl)sulfonyl)ethyl)piperidin-2-one |
| 108 | 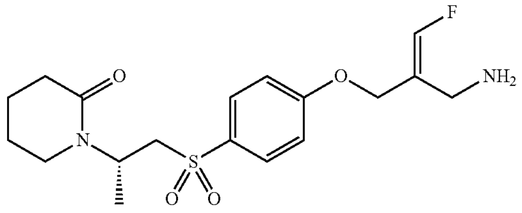 [SMILES: C[C@@H](CS(=O)(=O)c1ccc(OC/C(=C/F)CN)cc1)N1CCCCC1=O] | (S,E)-1-(1-((4-((2-(aminomethyl)-3-fluoroallyl)oxy)phenyl)sulfonyl)propan-2-yl)piperidin-2-one |

TABLE 1-continued

| Cmpd No. | Structure | Chemical name |
| --- | --- | --- |
| 109 | 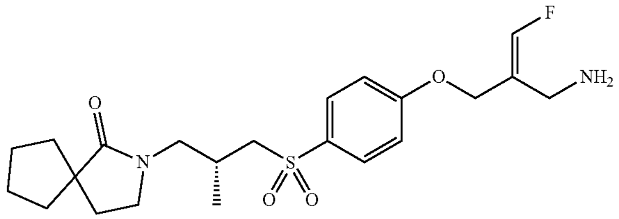 [SMILES: C[C@H](CN1CCC2(CCCC2)C1=O)CS(=O)(=O)c1ccc(OC/C(=C/F)CN)cc1] | (R,E)-2-(3-((4-((2-(aminomethyl)-3-fluoroallyl)oxy)phenyl)sulfonyl)-2-methylpropyl)-2-azaspiro[4.4]nonan-1-one |
| 110 | 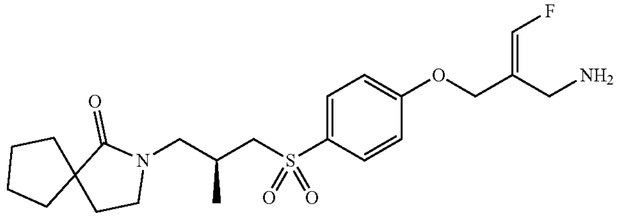 [SMILES: C[C@@H](CN1CCC2(CCCC2)C1=O)CS(=O)(=O)c1ccc(OC/C(=C/F)CN)cc1] | (S,E)-2-(3-((4-((2-(aminomethyl)-3-fluoroallyl)oxy)phenyl)sulfonyl)-2-methylpropyl)-2-azaspiro[4.4]nonan-1-one |
| 111 | 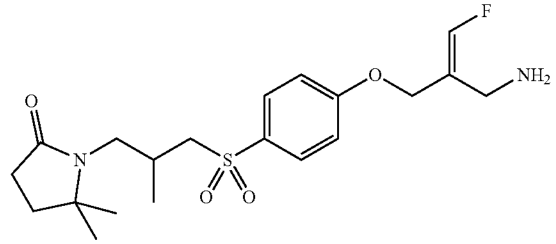 [SMILES: CC(CN1C(=O)CCC1(C)C)CS(=O)(=O)c1ccc(OC/C(=C/F)CN)cc1] | (E)-1-(3-((4-((2-(aminomethyl)-3-fluoroallyl)oxy)phenyl)sulfonyl)-2-methylpropyl)-5,5-dimethylpyrrolidin-2-one |
| 112 | 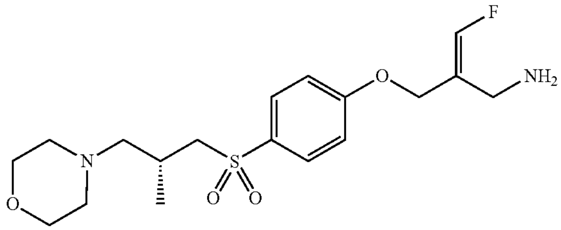 [SMILES: C[C@H](CN1CCOCC1)CS(=O)(=O)c1ccc(OC/C(=C/F)CN)cc1] | (R,E)-3-fluoro-2-((4-((2-methyl-3-morpholinopropyl)sulfonyl)phenoxy)methyl)prop-2-en-1-amine |
| 113 | 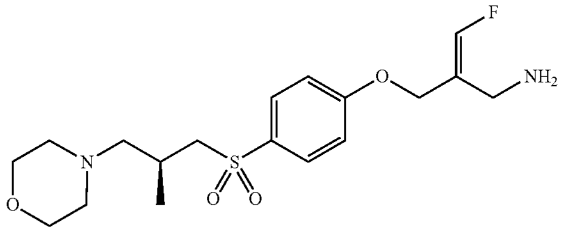 [SMILES: C[C@@H](CN1CCOCC1)CS(=O)(=O)c1ccc(OC/C(=C/F)CN)cc1] | (S,E)-3-fluoro-2-((4-((2-methyl-3-morpholinopropyl)sulfonyl)phenoxy)methyl)prop-2-en-1-amine |
| 114 | 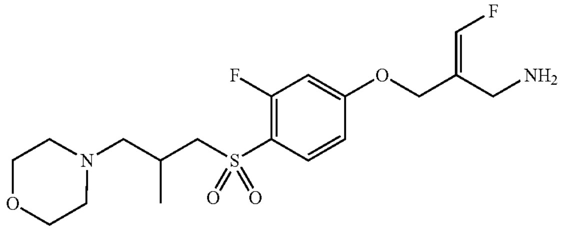 [SMILES: CC(CN1CCOCC1)CS(=O)(=O)c1ccc(OC/C(=C/F)CN)cc1F] | (E)-3-fluoro-2-((3-fluoro-4-((2-methyl-3-morpholinopropyl)sulfonyl)phenoxy)methyl)prop-2-en-1-amine |

TABLE 1-continued

| Cmpd No. | Structure | Chemical name |
|---|---|---|
| 115 | 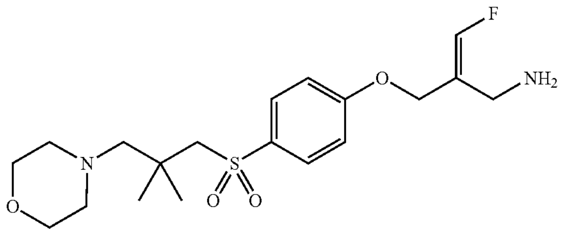 [SMILES: CC(C)(CN1CCOCC1)CS(=O)(=O)c1ccc(OC/C(=C/F)CN)cc1] | (E)-2-((4-((2,2-dimethyl-3-morpholinopropyl)sulfonyl)phenoxy)methyl)-3-fluoroprop-2-en-1-amine |
| 116 | 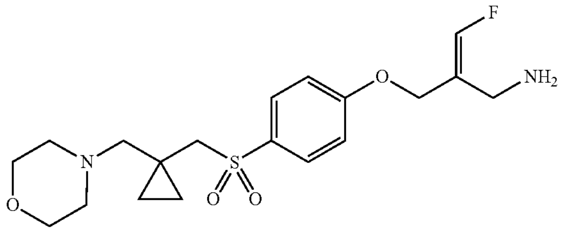 [SMILES: NC/C(=C\F)COc1ccc(S(=O)(=O)CC2(CN3CCOCC3)CC2)cc1] | (E)-3-fluoro-2-((4-(((1-(morpholinomethyl)cyclopropyl)methyl)sulfonyl)phenoxy)methyl)prop-2-en-1-amine |
| 117 | 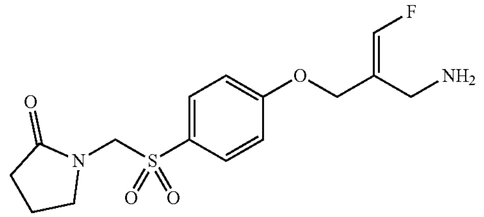 [SMILES: NC/C(=C\F)COc1ccc(S(=O)(=O)CN2CCCC2=O)cc1] | (E)-1-(((4-((2-(aminomethyl)-3-fluoroallyl)oxy)phenyl)sulfonyl)methyl)pyrrolidin-2-one |
| 118 | 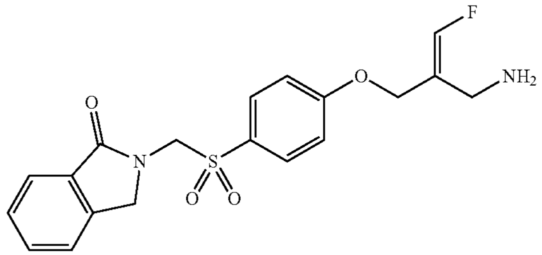 [SMILES: NC/C(=C\F)COc1ccc(S(=O)(=O)CN2Cc3ccccc3C2=O)cc1] | (E)-2-(((4-((2-(aminomethyl)-3-fluoroallyl)oxy)phenyl)sulfonyl)methyl)isoindolin-1-one |
| 119 | 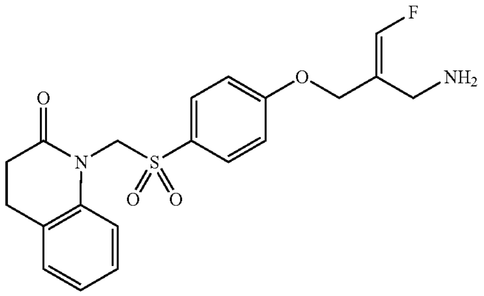 [SMILES: NC/C(=C\F)COc1ccc(S(=O)(=O)CN2C(=O)CCc3ccccc32)cc1] | (E)-1-(((4-((2-(aminomethyl)-3-fluoroallyl)oxy)phenyl)sulfonyl)methyl)-3,4-dihydroquinolin-2(1H)-one |
| 120 | 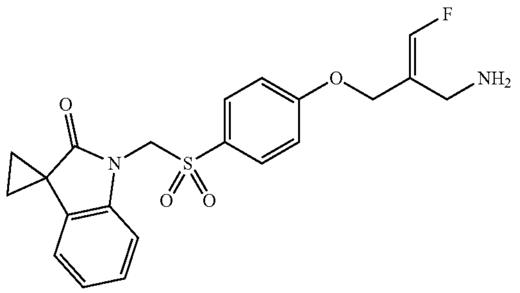 [SMILES: NC/C(=C\F)COc1ccc(S(=O)(=O)CN2C(=O)C3(CC3)c3ccccc32)cc1] | (E)-1'-(((4-((2-(aminomethyl)-3-fluoroallyl)oxy)phenyl)sulfonyl)methyl)spiro[cyclopropane-1,3'-indolin]-2'one |

TABLE 1-continued

| Cmpd No. | Structure | Chemical name |
|---|---|---|
| 121 | 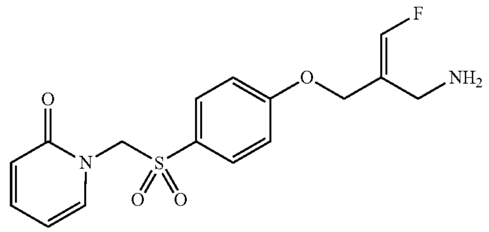 [SMILES: NC/C(=C\F)COc1ccc(S(=O)(=O)Cn2ccccc2=O)cc1] | (E)-1-(((4-((2-(aminomethyl)-3-fluoroallyl)oxy)phenyl)sulfonyl)methyl)pyridin-2(1H)-one |
| 122 | 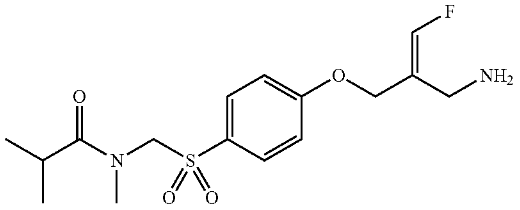 [SMILES: CC(C)C(=O)N(C)CS(=O)(=O)c1ccc(OC/C(=C/F)CN)cc1] | (E)-N-(((4-((2-(aminomethyl)-3-fluoroallyl)oxy)phenyl)sulfonyl)methyl)-N-methylisobutyramide |
| 123 | 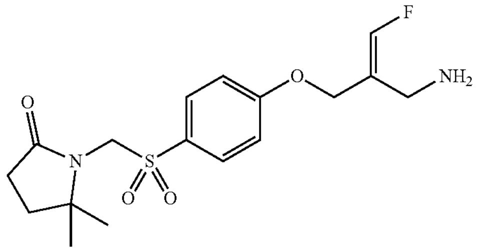 [SMILES: CC1(C)CCC(=O)N1CS(=O)(=O)c1ccc(OC/C(=C/F)CN)cc1] | (E)-1-(((4-((2-(aminomethyl)-3-fluoroallyl)oxy)phenyl)sulfonyl)methyl)-5,5-dimethylpyrrolidin-2-one |
| 124 | 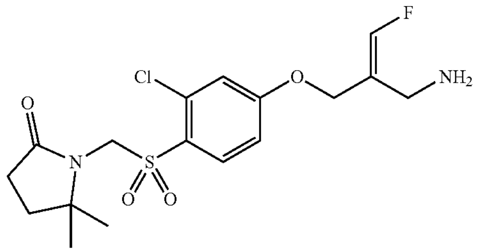 [SMILES: CC1(C)CCC(=O)N1CS(=O)(=O)c1ccc(OC/C(=C/F)CN)cc1Cl] | (E)-1-(((4-((2-(aminomethyl)-3-fluoroallyl)oxy)-2-chlorophenyl)sulfonyl)methyl)-5,5-dimethylpyrrolidin-2-one |
| 125 | 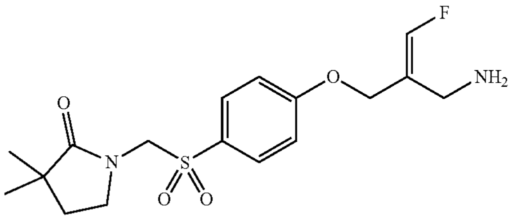 [SMILES: CC1(C)CCN(CS(=O)(=O)c2ccc(OC/C(=C/F)CN)cc2)C1=O] | (E)-1-(((4-((2-(aminomethyl)-3-fluoroallyl)oxy)phenyl)sulfonyl)methyl)-3,3-dimethylpyrrolidin-2-one |
| 126 | 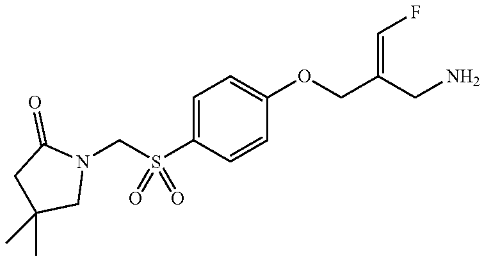 [SMILES: CC1(C)CC(=O)N(CS(=O)(=O)c2ccc(OC/C(=C/F)CN)cc2)C1] | (E)-1-(((4-((2-(aminomethyl)-3-fluoroallyl)oxy)phenyl)sulfonyl)methyl)-4,4-dimethylpyrrolidin-2-one |

TABLE 1-continued

| Cmpd No. | Structure | Chemical name |
|---|---|---|
| 127 | 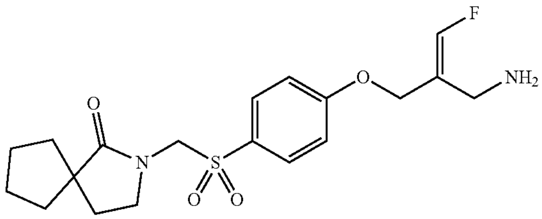 [SMILES: NC/C(=C\F)COc1ccc(S(=O)(=O)CN2CCC3(CCCC3)C2=O)cc1] | (E)-2-(((4-((2-(aminomethyl)-3-fluoroallyl)oxy)phenyl)sulfonyl)methyl)-2-azaspiro[4.4]nonan-1-one |
| 128 | 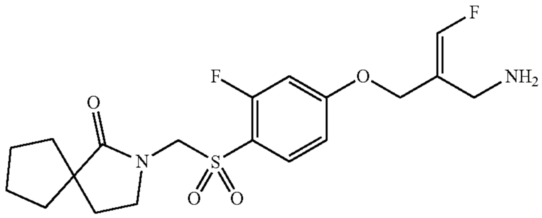 [SMILES: NC/C(=C\F)COc1ccc(S(=O)(=O)CN2CCC3(CCCC3)C2=O)c(F)c1] | (E)-2-(((4-((2-(aminomethyl)-3-fluoroallyl)oxy)-2-fluorophenyl)sulfonyl)methyl)-2-azaspiro[4.4]nonan-1-one |
| 129 | 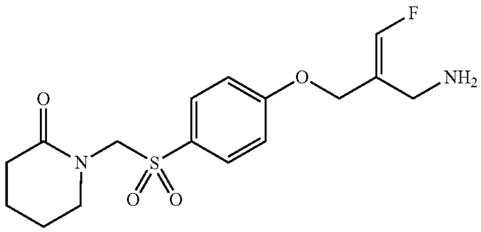 [SMILES: NC/C(=C\F)COc1ccc(S(=O)(=O)CN2CCCCC2=O)cc1] | (E)-1-(((4-((2-(aminomethyl)-3-fluoroallyl)oxy)phenyl)sulfonyl)methyl)piperidin-2-one |
| 130 | 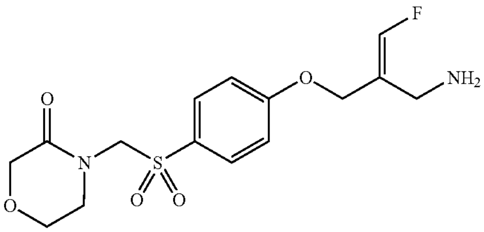 [SMILES: NC/C(=C\F)COc1ccc(S(=O)(=O)CN2CCOCC2=O)cc1] | (E)-4-(((4-((2-(aminomethyl)-3-fluoroallyl)oxy)phenyl)sulfonyl)methyl)morpholin-3-one |
| 131 | 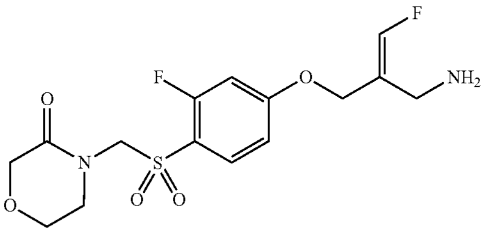 [SMILES: NC/C(=C\F)COc1ccc(S(=O)(=O)CN2CCOCC2=O)c(F)c1] | (E)-4-(((4-((2-(aminomethyl)-3-fluoroallyl)oxy)-2-fluorophenyl)sulfonyl)methyl)morpholin-3-one |
| 132 | 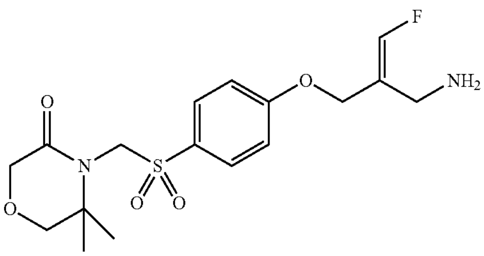 [SMILES: CC1(C)COCC(=O)N1CS(=O)(=O)c1ccc(OC/C(=C/F)CN)cc1] | (E)-4-(((4-((2-(aminomethyl)-3-fluoroallyl)oxy)phenyl)sulfonyl)methyl)-5,5-dimethylmorpholin-3-one |

TABLE 1-continued

| Cmpd No. | Structure | Chemical name |
|---|---|---|
| 133 | 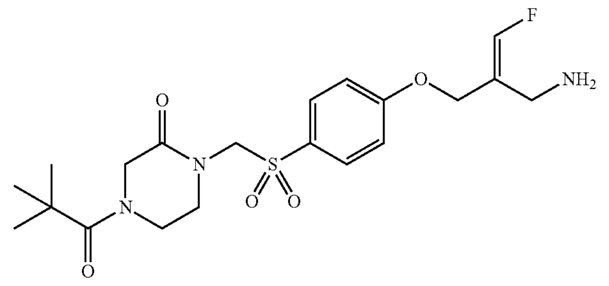 [SMILES: CC(C)(C)C(=O)N1CCN(CS(=O)(=O)c2ccc(OC/C(=C/F)CN)cc2)C(=O)C1] | (E)-1-(((4-((2-(aminomethyl)-3-fluoroallyl)oxy)phenyl)sulfonyl)methyl)-4-pivaloylpiperazin-2-one |
| 134 | 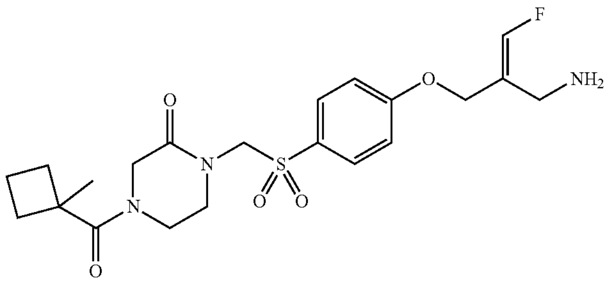 [SMILES: CC1(C(=O)N2CCN(CS(=O)(=O)c3ccc(OC/C(=C/F)CN)cc3)C(=O)C2)CCC1] | (E)-1-(((4-((2-(aminomethyl)-3-fluoroallyl)oxy)phenyl)sulfonyl)methyl)-4-(1-methylcyclobutane-1-carbonyl)piperazin-2-one |
| 135 | 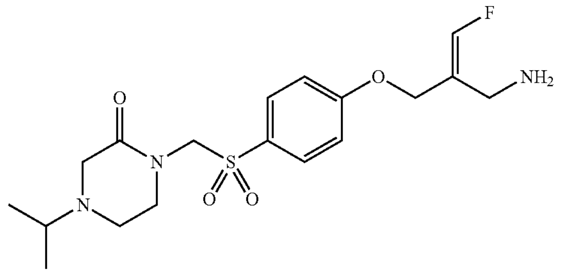 [SMILES: CC(C)N1CCN(CS(=O)(=O)c2ccc(OC/C(=C/F)CN)cc2)C(=O)C1] | (E)-1-(((4-((2-(aminomethyl)-3-fluoroallyl)oxy)phenyl)sulfonyl)methyl)-4-isopropylpiperazin-2-one |
| 136 | 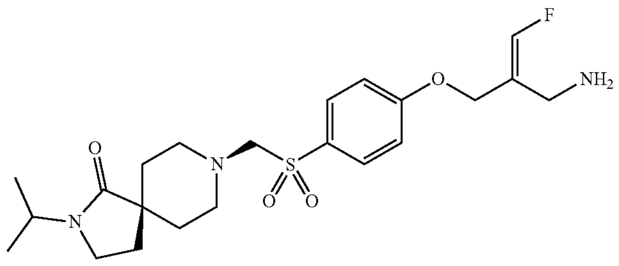 | (5r,8r)-8-(((4-(((E)-2-(aminomethyl)-3-fluoroallyl)oxy)phenyl)sulfonyl)methyl)-2-isopropyl-2-azaspiro[4.5]decan-1-one |
| 137 | 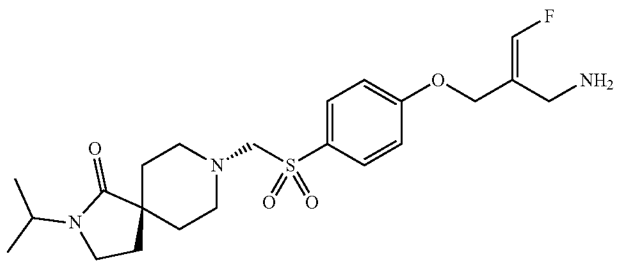 | (5s,8s)-8-(((4-(((E)-2-(aminomethyl)-3-fluoroallyl)oxy)phenyl)sulfonyl)methyl)-2-isopropyl-2-azaspiro[4.5]decan-1-one |

TABLE 1-continued

| Cmpd No. | Structure | Chemical name |
| --- | --- | --- |
| 138 | 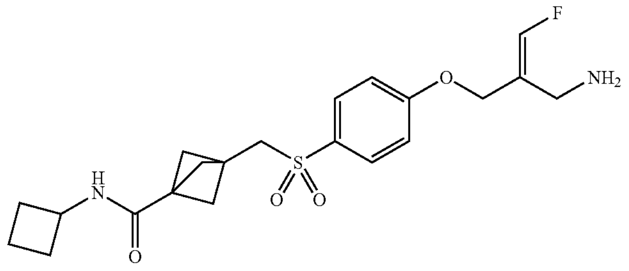 [SMILES: NC/C(=C\F)COc1ccc(S(=O)(=O)CC23CC(C(=O)NC4CCC4)(C2)C3)cc1] | (E)-3-(((4-((2-(aminomethyl)-3-fluoroallyl)oxy)phenyl)sulfonyl)methyl)-N-cyclobutylbicyclo[1.1.1]pentane-1-carboxamide |
| 139 | 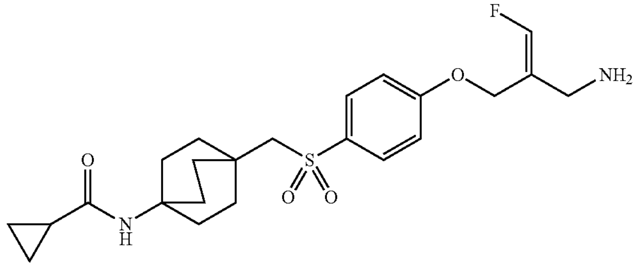 [SMILES: NC/C(=C/F)COc1ccc(S(=O)(=O)CC23CCC(NC(=O)C4CC4)(CC2)CC3)cc1] | (Z)-N-(4-(((4-((2-(aminomethyl)-3-fluoroallyl)oxy)phenyl)sulfonyl)methyl)bicyclo[2.2.2]octan-1-yl)cyclopropanecarboxamide |
| 140 | 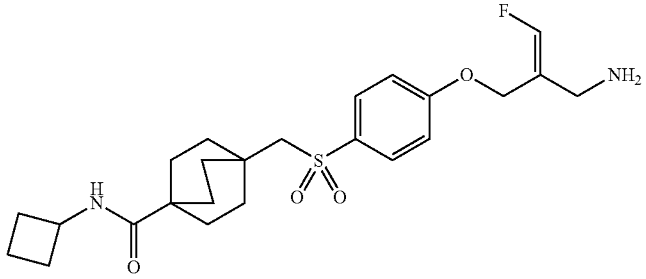 [SMILES: NC/C(=C/F)COc1ccc(S(=O)(=O)CC23CCC(C(=O)NC4CCC4)(CC2)CC3)cc1] | (Z)-4-(((4-((2-(aminomethyl)-3-fluoroallyl)oxy)phenyl)sulfonyl)methyl)-N-cyclobicyclo[2.2.2]octane-1-carboxamide |
| 141 | 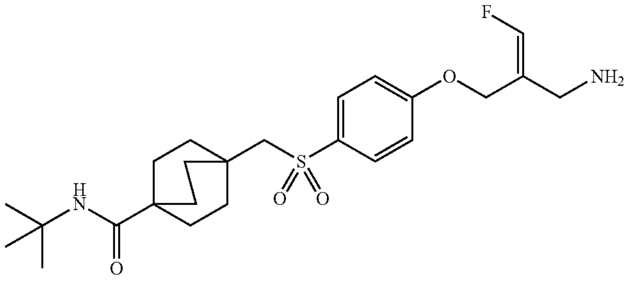 [SMILES: CC(C)(C)NC(=O)C12CCC(CS(=O)(=O)c3ccc(OC/C(=C\F)CN)cc3)(CC1)CC2] | (Z)-4-(((4-((2-(aminomethyl)-3-fluoroallyl)oxy)phenyl)sulfonyl)methyl)-N-(tert-butyl)bicyclo[2.2.2]octane-1-carboxamide |
| 142 | 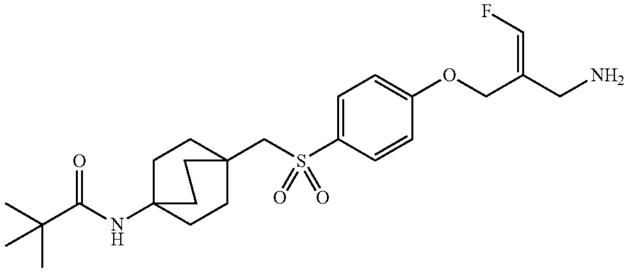 [SMILES: CC(C)(C)C(=O)NC12CCC(CS(=O)(=O)c3ccc(OC/C(=C\F)CN)cc3)(CC1)CC2] | (Z)-N-(4-(((4-((2-(aminomethyl)-3-fluoroallyl)oxy)phenyl)sulfonyl)methyl)bicyclo[2.2.2]octan-1-yl)pivalamide |

TABLE 1-continued

| Cmpd No. | Structure | Chemical name |
|---|---|---|
| 143 | 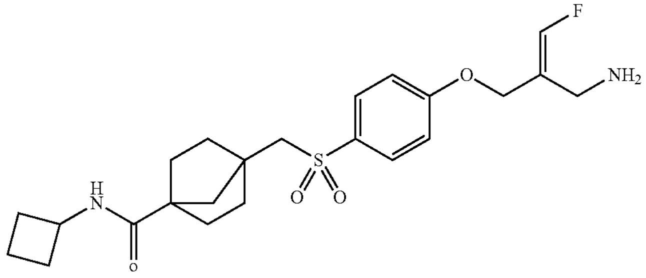 | (E)-4-(((4-((2-(aminomethyl)-3-fluoroallyl)oxy)phenyl)sulfonyl) methyl)-N-cyclobutylbicyclo[2.2.1]heptane-1-carboxamide |
| 144 | 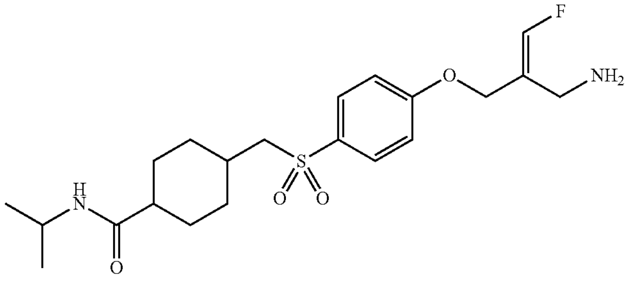 [SMILES: CC(C)NC(=O)C1CCC(CS(=O)(=O)c2ccc(OC/C(=C/F)CN)cc2)CC1] | (E)-4-(((4-((2-(aminomethyl)-3-fluoroallyl)oxy)phenyl)sulfonyl) methyl)-N-isopropylcyclohexane-1-carboxamide |
| 145 | 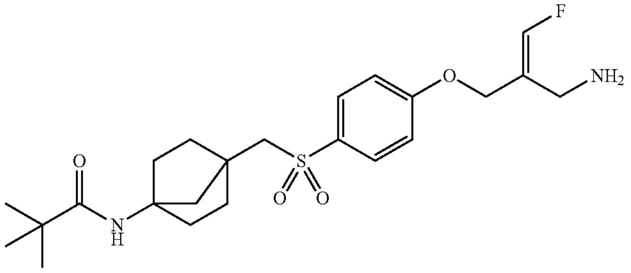 [SMILES: CC(C)(C)C(=O)NC12CCC(CS(=O)(=O)c3ccc(OC/C(=C/F)CN)cc3)(CC1)C2] | (E)-N-(4-(((4-((2-(aminomethyl)-3-fluoroallyl)oxy)phenyl)sulfonyl) methyl)bicyclo[2.2.1]heptan-1-yl)pivalamide |
| 146 | 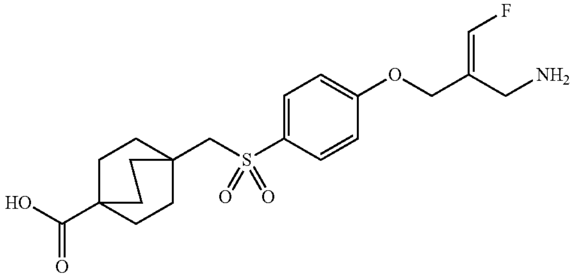 [SMILES: NC/C(=C\F)COc1ccc(S(=O)(=O)CC23CCC(C(=O)O)(CC2)CC3)cc1] | (E)-4-(((4-((2-(aminomethyl)-3-fluoroallyl)oxy)phenyl)sulfonyl) methyl)bicyclo[2.2.2.]octane-1-carboxylic acid |

Due to the existence of double bonds, the compounds of the present application may be in cis or trans, or Z or E, configuration. It is understood that although one configuration may be depicted in the structure of the compounds or formulae of the present application, the present application also encompasses the other configuration. For example, the compounds or formulae of the present application may be depicted with the group “ 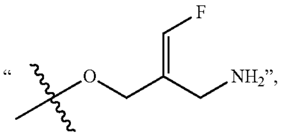 ”, the present application also encompasses the compounds or formulae with the other configuration which has the group “ 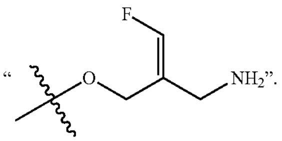 ”.

In some instances, the compounds or formulae of the present application may be depicted with the group

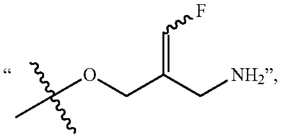

which means that the compounds or formulae may be in cis or trans, or Z or E, configuration.

In one embodiment, a compound of the present application (e.g., a compound of any of the formulae or any individual compounds disclosed herein) is a pharmaceutically acceptable salt. In another embodiment, a compound of the present application (e.g., a compound of any of the formulae or any individual compounds disclosed herein) is a solvate. In another embodiment, a compound of the present application (e.g., a compound of any of the formulae or any individual compounds disclosed herein) is a hydrate.

The details of the application are set forth in the accompanying description below. Although methods and materials similar or equivalent to those described herein can be used in the practice or testing of the present application, illustrative methods and materials are now described. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

Definitions

The articles "a" and "an" are used in this application to refer to one or more than one (i.e., at least one) of the grammatical object of the article. By way of example, "an element" means one element or more than one element.

The term "and/or" is used in this application to mean either "and" or "or" unless indicated otherwise.

The application also includes pharmaceutical compositions comprising an effective amount of a compound of the present application (e.g., a compound of any of the formulae or any individual compounds disclosed herein) and a pharmaceutically acceptable carrier.

The term "alkyl," as used herein, refers to saturated, straight or branched-chain hydrocarbon radicals containing, in certain embodiments, between one and six carbon atoms. Examples of $C_1$-$C_8$ alkyl radicals include, but are not limited to, methyl, ethyl, propyl, isopropyl, n-butyl, tert-butyl, neopentyl, n-hexyl, n-heptyl, and n-octyl radicals. Examples of $C_1$-$C_6$ alkyl radicals include, but are not limited to, methyl, ethyl, propyl, isopropyl, n-butyl, tert-butyl, neopentyl, and n-hexyl radicals.

The term "alkenyl," as used herein, denotes a monovalent group derived from a hydrocarbon moiety containing, in certain embodiments, from two to six carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl and the like.

The term "alkoxy" refers to an —O-alkyl radical.

The terms "hal," "halo," and "halogen," as used herein, refer to an atom selected from fluorine, chlorine, bromine and iodine.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound (fused, bridged, or spiro rings). Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1]heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl" as used herein, refers to an alkyl residue attached to a heteroaryl ring. Examples include, but are not limited to, pyridinylmethyl, pyrimidinylethyl and the like.

The term "heterocyclyl" or "heterocycloalkyl," as used herein, refers to a saturated or unsaturated non-aromatic 3-, 4-, 5-, 6-, 7-, or 8-membered monocyclic, 7-, 8-, 9-, 10-, 11-, or 12-membered bicyclic (fused, bridged, or spiro rings), or 11-, 12, 13, or 14-membered tricyclic ring system (fused, bridged, or spiro rings), where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocycloalkyl groups include, but are not limited to, [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, thiiranyl, 2-oxa-5-azabicyclo[2.2.1]heptanyl, 2,5-diazabicyclo[2.2.1] heptanyl, 2-oxa-6-azaspiro[3.3]heptanyl, 2,6-diazaspiro

[3.3]heptanyl, 1,4-dioxa-8-azaspiro[4.5]decanyl, 2-azaspiro[3.3]heptan-5-amine, 1-azaspiro[3.3]heptan-5-amine, 1-oxa-6-azaspiro[3.3]heptan-3-amine, 2-azaspiro[3.3]heptan-6-amine, 1-azaspiro[3.3]heptan-6-amine, 6-azaspiro[3.4]octan-2-amine, 5-azaspiro[3.4]octan-2-amine, 6-azaspiro[3.4]octan-1-amine, 5-azaspiro[3.4]octan-1-amine, 5-oxa-2-azaspiro[3.4]octan-7-amine, 7-amino-5-thia-2-azaspiro[3.4]octane 5,5-dioxide, 5-oxa-2-azaspiro[3.4]octan-8-amine, 8-amino-5-thia-2-azaspiro[3.4]octane 5,5-dioxide, and the like.

The term "alkylamino" refers to a group having the structure, e.g., $NH(C_1-C_6$ alkyl), where $C_1-C_6$ alkyl is as previously defined.

The term "dialkylamino" refers to a group having the structure, e.g., $N(C_1-C_6$ alkyl$)_2$, where $C_1-C_6$ alkyl is as previously defined.

In accordance with the application, any of the aryls, substituted aryls, heteroaryls and substituted heteroaryls described herein, can be any aromatic group. Aromatic groups can be substituted or unsubstituted.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted alkenyl," "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocyclyl," and any other optionally substituted group as used herein, refer to groups that are substituted or unsubstituted by independent replacement of one, two, or three or more of the hydrogen atoms thereon with substituents including, but not limited to: —F, —Cl, —Br, —I, —OH, protected hydroxy, $—NO_2$, —CN, $—NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_2$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, $—CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, $—OCO_2$—$C_1$-$C_{12}$-alkyl, $—OCO_2$—$C_2$-$C_{12}$-alkenyl, $—OCO_2$—$C_2$-$C_{12}$-alkenyl, $—OCO_2$—$C_3$-$C_{12}$-cycloalkyl, $—OCO_2$-aryl, $—OCO_2$-heteroaryl, $—OCO_2$-heterocycloalkyl, $—OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, $—NHCO_2$—$C_1$-$C_{12}$-alkyl, $—NHCO_2$—$C_2$-$C_{12}$-alkenyl, $—NHCO_2$—$C_2$-$C_{12}$-alkenyl, $—NHCO_2$—$C_3$-$C_{12}$-cycloalkyl, $—NHCO_2$-aryl, $—NHCO_2$-heteroaryl, $—NHCO_2$-heterocycloalkyl, $—NHC(O)NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, NHC(O)NH-heterocycloalkyl, $—NHC(S)NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, $—NHC(NH)NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NHheterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, C(NH)NH—$C_3$-$C_{12}$-cycloalkyl, —C(NH)NH-aryl, —C(NH)NH-heteroaryl, —C(NH)NHheterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-$SO_2NH_2$, $—SO_2NH$—$C_1$-$C_{12}$-alkyl, $—SO_2NH$—$C_2$-$C_{12}$-alkenyl, $—SO_2NH$—$C_2$-$C_{12}$-alkenyl, $—SO_2NH$—$C_3$-$C_{12}$-cycloalkyl, $—SO_2NH$-aryl, $—SO_2NH$-heteroaryl, $—SO_2NH$-heterocycloalkyl, $—NHSO_2$—$C_1$-$C_{12}$-alkyl, $—NHSO_2$—$C_2$-$C_{12}$-alkenyl, $—NHSO_2$—$C_2$-$C_{12}$-alkenyl, $—NHSO_2$—$C_3$-$C_{12}$-cycloalkyl, $—NHSO_2$-aryl, $—NHSO_2$-heteroaryl, $—NHSO_2$-heterocycloalkyl, $—CH_2NH_2$, $—CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "carrier", as used in this application, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The compounds of the present application may form salts which are also within the scope of this application. Reference to a compound of the Formulae herein is understood to include reference to salts thereof, unless otherwise indicated.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The compounds of the present application, for example, including the pharmaceutically acceptable salts, solvates, prodrugs, stereoisomers, or tautomers of the compounds, can exist in a solvated form with other solvent molecules or in an unsolvated form.

"Solvate" means solvent addition forms that contain either stoichiometric or non stoichiometric amounts of solvent. Some compounds or salts have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this application, as are positional isomers (such as, for example, 4-pyridyl and 3-pyridyl). For example, if a compound of Formula (I) incorporates a double bond or a fused ring, both the cis- and trans-forms, as well as mixtures, are embraced within the scope of the application. Individual stereoisomers of the compound of the application may, for example, be substantially free of other isomers, or may be admixed, for example, as racemates or with all other, or other selected, stereoisomers. The chiral centers of the present application can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of the present application (e.g., a compound of any of the formulae or any individual compounds disclosed herein) may have one or more asymmetric carbon atom and may occur as racemates, racemic mixtures or as individual enantiomers or diastereomers.

In the present specification, the structural formula of the compound represents a certain isomer for convenience in some cases, but the present application includes all isomers, such as geometrical isomers, optical isomers based on an asymmetrical carbon, stereoisomers, tautomers, and the like.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

The compounds of the application may contain asymmetric or chiral centers, and, therefore, exist in different stereoisomeric forms. It is intended that all stereoisomeric forms of the compounds of the application as well as mixtures thereof, including racemic mixtures, form part of the present application. In addition, the present application embraces all geometric and positional isomers. For example, if a compound of the application incorporates a double bond or a fused ring, both the cis- and trans-forms, as well as mixtures, are embraced within the scope of the application. Each compound herein disclosed includes all the enantiomers that conform to the general structure of the compound. The compound may be in a racemic or enantiomerically pure form, or any other form in terms of stereochemistry. The assay results may reflect the data collected for the racemic form, the enantiomerically pure form, or any other form in terms of stereochemistry.

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

In another embodiment of the application, the compound of the present application (e.g., a compound of any of the formulae or any individual compounds disclosed herein) is an enantiomer. In some embodiments the compound is the (S)-enantiomer. In other embodiments the compound is the (R)-enantiomer. In yet other embodiments, the compounds of the present application (e.g., a compound of any of the formulae or any individual compounds disclosed herein) may be (+) or (−) enantiomers. The compound may contain more than one stereocenter.

In another embodiment of the application, the compounds of the present application (e.g., a compound of any of the formulae or any individual compounds disclosed herein) are diastereomers. In some embodiments, the compounds are the syn diastereomer. In other embodiments, the compounds are the anti diastereomer.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column.

It is also possible that the compounds of the application may exist in different tautomeric forms, and all such forms are embraced within the scope of the application. Also, for example, all keto-enol and imine-enamine forms of the compounds are included in the application.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-imine.

The present application relates to a compound of the present application (e.g., a compound of any of the formulae or any individual compounds disclosed herein) or pharmaceutically acceptable salts, solvates, prodrugs, stereoisomers, or tautomers thereof, capable of inhibiting SSAO, which are useful for the treatment of diseases and disorders associated with modulation of SSAO. The application further relates to compounds of the present application (e.g., a compound of any of the formulae or any individual compounds disclosed herein), or pharmaceutically acceptable salts, solvates, prodrugs, stereoisomers, or tautomers thereof, which are useful for inhibiting SSAO. In some embodiments, the SSAO is wild-type SSAO. In other embodiments, the SSAO is a mutant SSAO.

In some embodiments, the application provides a compound of the present application (e.g., a compound of any of the formulae or any individual compounds disclosed herein), wherein the compound possesses advantageous characteristics, such as decreased brain penetration, i.e., decreased penetration through the blood-brain-barrier, compared to one or more known SSAO inhibitors, including, but not limited to BI 1467335 (PXS-4728A).

In some embodiments, the application provides a compound of the present application (e.g., a compound of any of the formulae or any individual compounds disclosed herein), wherein the compound is at least as potent as one or more known SSAO inhibitors, including, but not limited to BI 1467335 (PXS-4728A), at inhibiting the activity of the SSAO, and possesses additional advantageous characteristics, such as decreased brain penetration, i.e., decreased penetration through the blood-brain-barrier, compared to one or more known SSAO inhibitors, including, but not limited to BI 1467335 (PXS-4728A).

In some embodiments, the application provides a compound of the present application (e.g., a compound of any of the formulae or any individual compounds disclosed herein), wherein the compound is more potent than one or more known SSAO inhibitors, including, but not limited to BI 1467335 (PXS-4728A), at inhibiting the activity of the SSAO.

In some embodiments, the application provides a compound of the present application (e.g., a compound of any of the formulae or any individual compounds disclosed herein), wherein the compound is more potent than one or more known SSAO inhibitors, including, but not limited to BI 1467335 (PXS-4728A), at inhibiting the activity of the SSAO, and possesses additional advantageous characteristics, such as decreased brain penetration, i.e., decreased penetration through the blood-brain-barrier, compared to one or more known SSAO inhibitors, including, but not limited to BI 1467335 (PXS-4728A).

Potency of the inhibitor can be determined by $IC_{50}$ value. A compound with a lower $IC_{50}$ value, as determined under substantially similar conditions, is a more potent inhibitor relative to a compound with a higher $IC_{50}$ value. Brain penetration property can be determined by Brain Kpuu value. A compound with a lower brain Kpuu value, as determined under substantially similar conditions, is less brain penetrable The compounds of the present application can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compounds as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

The term "prodrug," as used in this application, means a compound which is convertible in vivo by metabolic means (e.g., by hydrolysis) to a disclosed compound.

Since prodrugs are known to enhance numerous desirable qualities of pharmaceuticals (e.g., solubility, bioavailability, manufacturing, etc.) the compounds of the present application (e.g., a compound of any of the formulae or any individual compounds disclosed herein), or pharmaceutically acceptable salts, solvates, prodrugs, stereoisomers, or tautomers thereof can be delivered in prodrug form. Thus, the present application is intended to cover prodrugs of a compound of the present application (e.g., a compound of any of the formulae or any individual compounds disclosed herein), or a pharmaceutically acceptable salt, solvate, prodrug, stereoisomer, or tautomer thereof, methods of delivering the same and compositions containing the same. "Prodrugs" are intended to include any covalently bonded carriers that release an active parent drug of the present application in vivo when such prodrug is administered to a mammalian subject. Prodrugs are prepared by modifying functional groups present in the compound in such a way that the modifications are cleaved, either in routine manipulation or in vivo, to the parent compound. Prodrugs include compounds of the application wherein a hydroxyl or amino, group is bonded to any group that, when the prodrug of the present application is administered to a mammalian subject, it cleaves to form a free hydroxyl or free amino group, respectively. Examples of prodrugs include, but are not limited to, acetate, formate, and benzoate derivatives of alcohol and amine functional groups in the compounds of each of the formulae described herein or a pharmaceutically acceptable salt, solvate, prodrug, stereoisomer, or tautomer thereof.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate.

As used herein, the term "analog" refers to a compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

The application also comprehends isotopically-labeled compounds, which are identical to those recited in the each of the formulae described herein, but for the fact that one or more atoms are replaced by an atom having an atomic mass or mass number different from the atomic mass or mass number most commonly found in nature. Examples of isotopes that can be incorporated into compounds of the application include isotopes of hydrogen, carbon, nitrogen, fluorine, such as $^{3}H$, $^{11}C$, $^{14}C$, $^{2}H$ and $^{18}F$.

Compounds of the present application (e.g., a compound of any of the formulae or any individual compounds disclosed herein), or pharmaceutically acceptable salts, solvates, prodrugs, stereoisomers, or tautomers thereof, that contain the aforementioned isotopes and/or other isotopes of other atoms are within the scope of the present application. Isotopically-labeled compounds of the present application, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are useful for their ease of preparation and detectability. $^{11}C$ and $^{18}F$ isotopes are useful in PET (positron emission tomography). PET is useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances, isotopically labeled compounds of the present application (e.g., a compound of any of the formulae or any individual compounds disclosed herein), or pharmaceutically acceptable salts, solvates, prodrugs, stereoisomers, or tautomers thereof, can generally be prepared by carrying out the procedures disclosed in the Schemes and/or in the Examples described herein, by substituting a readily available isotopically labeled reagent for a non-isotopically labeled reagent. In one embodiment, the compound of the present application (e.g., a compound of any of the formulae or any individual compounds disclosed herein) or pharmaceutically acceptable salts, solvates, prodrugs, stereoisomers, or tautomers thereof, is not isotopically labelled.

The term "administer", "administering", or "administration" as used in this application refers to either directly administering a disclosed compound or pharmaceutically acceptable salt of the disclosed compound or a composition to a subject, or administering a prodrug, derivative or analog of the compound or pharmaceutically acceptable salt of the compound or a composition to the subject, which can form an equivalent amount of active compound within the subject's body.

A "patient" or "subject" is a mammal, e.g., a human, mouse, rat, guinea pig, dog, cat, horse, cow, pig, or nonhuman primate, such as a monkey, chimpanzee, baboon or rhesus.

An "effective amount" or "therapeutically effective amount" when used in connection with a compound or pharmaceutical composition is an amount effective for treating or preventing a disease in a subject as described herein.

The term "treating" with regard to a subject, refers to improving at least one symptom of the subject's disorder. Treating includes curing, improving, or at least partially ameliorating the disorder.

The compounds of the present application, or a pharmaceutically acceptable salt, solvate, prodrug, stereoisomer, or tautomer thereof, can also be used to prevent a disease, condition or disorder. As used herein, "preventing" or "prevent" describes reducing or eliminating the onset of the symptoms or complications of the disease, condition or disorder.

The term "disorder" is used in this application to mean, and is used interchangeably with, the terms disease, condition, or illness, unless otherwise indicated.

As used herein, the term "SSAO-mediated" diseases or disorders means any disease or other deleterious condition in which SSAO, or a mutant thereof, is known to play a role. Accordingly, another embodiment of the present application relates to treating or lessening the severity of one or more diseases in which SSAO, or a mutant thereof, is known to play a role. Specifically, the present application relates to a method of treating or lessening the severity of a disease or condition selected from a liver disease, liver inflammation, liver fibrosis, nonalcoholic fatty liver disease (NAFLD), nonalcoholic steatohepatitis (NASH), atherosclerosis, stroke and complications thereof, chronic kidney disease, Alzheimer's disease, cardiovascular disease, metabolic disease, inflammation, pain, and pain associated with osteoarthritis, neuroinflammation, wherein said method comprises administering to a subject in need thereof a compounds of the present application (e.g., a compound of any of the formulae or any individual compounds disclosed herein), or pharmaceutically acceptable salts, solvates, prodrugs, stereoisomers, or tautomers thereof, or a composition according to the present application.

Methods for Preparing the Compounds

The compounds of the present application may be made by a variety of methods, including standard chemistry. Suitable synthetic routes are depicted in the Schemes given below.

The compounds of the present application (e.g., a compound of any of the formulae or any individual compounds disclosed herein) may be prepared by methods known in the art of organic synthesis as set forth in part by the following synthetic schemes. In the scheme described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of the compounds of the present application.

Those skilled in the art will recognize if a stereocenter exists in the compounds of the present application (e.g., a compound of any of the formulae or any individual compounds disclosed herein). Accordingly, the present application includes both possible stereoisomers (unless specified in the synthesis) and includes not only racemic compound but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

The compounds of the present application can be prepared in a number of ways well known to those skilled in the art of organic synthesis. By way of example, the compounds of the present application can be synthesized using the methods described below, together with synthetic methods known in the art of synthetic organic chemistry, or variations thereon as appreciated by those skilled in the art. Preferred methods include but are not limited to those methods described below. The compounds of the present application (i.e., a compound of the present application (e.g., a compound of any of the formulae or any individual compounds disclosed herein)) can be synthesized by following the steps outlined in General Scheme 1. Starting materials are either commercially available or made by known procedures in the reported literature or as illustrated.

General Scheme 1

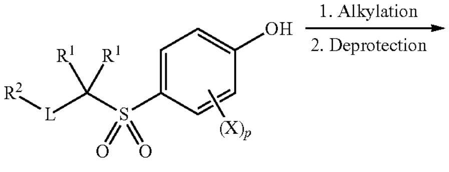

(I')-A

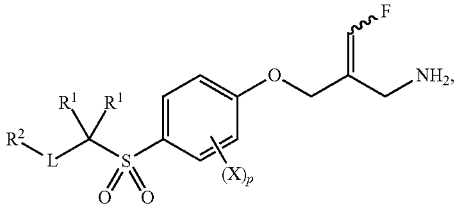

or (I')

-continued

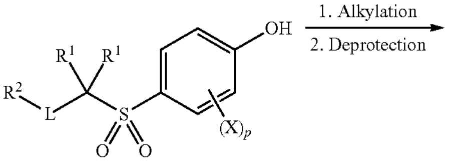

(I)-A

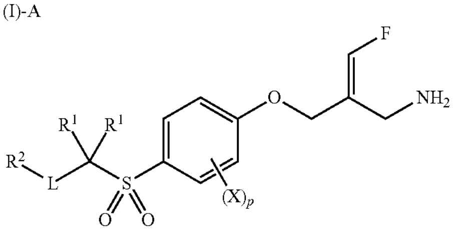

(I)

Scheme 1 depicts a generic synthesis of compounds of Formula (I') or (I). Specifically, the hydroxyl group of Compound (I)-A or Compound (I')-A can be alkylated with a suitably protected amine, typically under basic conditions, which can be deprotected to give compounds of Formula (I') or (I).

A mixture of enantiomers, diastereomers, cis/trans isomers resulting from the processes described above can be separated into their single components by chiral salt technique, chromatography using normal phase, reverse phase or chiral column, depending on the nature of the separation.

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 400 MHz. Spectra are given in ppm (δ) and coupling constants, J, are reported in Hertz. Tetramethylsilane (TMS) was used as an internal standard. Liquid chromatography-mass spectrometry (LC/MS) were collected using a SHIMADZU LCMS-2020EV or Agilent 1260-6125B LCMS. Purity and low resolution mass spectral data were measured using Agilent 1260-6125B LCMS system (with Diode Array Detector, and Agilent G6125BA Mass spectrometer) or using Waters Acquity UPLC system (with Diode Array Detector, and Waters 3100 Mass Detector). The purity was characterized by UV wavelength 214 nm, 220 nm, 254 nm and ESI. Column: poroshell 120 EC-C18 2.7 μm 4.6×100 mm; Flow rate 0.8 mL/min; Solvent A (100/0.1 water/formic acid), Solvent B (100 acetonitrile); gradient: hold 5% B to 0.3 min, 5-95% B from 0.3 to 2 min, hold 95% B to 4.8 min, 95-5% B from 4.8 to 5.4 min, then hold 5% B to 6.5 min. Or, column: Acquity UPLC BEH C18 1.7 μm 2.1×50 mm; Flow rate 0.5 mL/min; Solvent A (0.1% formic acid water), Solvent B (acetonitrile); gradient: hold 5% B for 0.2 min, 5-95% B from 0.2 to 2.0 min, hold 95% B to 3.1 min, then 5% B at 3.5 min.

Abbreviations used in the following examples and elsewhere herein are:

DIPEA N,N-diisopropylethylamine
DMF N,N-dimethylformamide
DMSO dimethylsulfoxide
IPA iso-propyl alcohol
IPE di-isopropyl ether
MeCN acetonitrile
AMMN Ammonia, 7.0 M solution in MeOH
THF tetrahydrofuran
m-CPBA 3-chlorobenzenecarboperoxoic acid FCC Flash column chromatography
DCM dichloromethane
LC/MS liquid chromatography-mass spectrometry
MeOH methanol
MS mass spectrometry
n-BuOH n-butyl alcohol
NMP N-methyl pyrrolidinone
NMR nuclear magnetic resonance
ppm parts per million
TEA triethylamine Biological Assays The biological activities of the compounds of the present application can be assessed with methods and assays known in the art. For example, the potency of the compounds of the present application can be evaluated with an SSAO Activity Assay. Briefly, compounds of the present application can be applied to recombinant hSSAO, hMAO-A, and hMAO-B isoforms and the amine oxidase activity of the enzymes are measured after the addition and subsequent oxidation of the luminogenic substrate (e.g., with the MAO-Glo assay kit from Promega). The $IC_{50}$ can be calculated, for example, by fitting the dose response curve using a 4-parameter non-linear regression routine.

In addition, the compounds of the preset application possess additional advantageous biological activities, such as decreased brain penetration, which can be evaluated with methods and assays known in the art. For example, Brain Kpuu assay composed of Blood-Brain-Barrier (BBB) assay and protein binding assay, can be utilized. The protein binding assay comprises equilibrium dialysis against brain lysate and plasma to calculate $f_{u(brain)}$ and $f_{u(plasma)}$, respectively. The BBB assay can be conducted in experimental animals at 1 mg/kg IV dosage. After dosing with the compounds of the present application, plasma and brain samples can be collected to analyze compound concentration ($C_{plasma}$ and $C_{brain}$). The Kpuu value of the tested compounds can be calculated by the equation:

$$Kpuu = \frac{c_{brain}}{c_{plasma}} \times \frac{f_{u(brain)}}{f_{u(plasma)}} \quad (1)$$

Methods of Using the Compounds

The compounds of the present invention are useful for modulating (e.g., inhibiting) an amine oxidase enzyme, such as membrane-bound SSAO/VAP-1 or soluble SSAO/VAP-1. The relative inhibitory potencies of the compounds can be determined by the amount needed to inhibit the amine oxidase activity of SSAO/VAP-1 in a variety of ways, e.g., in in vitro assays with recombinant human protein or with recombinant non-human enzyme, in cellular assays expressing normal enzyme, or in in vivo tests. Accordingly, the present application relates to methods of modulating (e.g., inhibiting) an amine oxidase enzyme, such as membrane-bound SSAO/VAP-1 or soluble SSAO/VAP-1, for the treatment of a disease or disorder.

The compounds of the present application are useful for the treatment of a disease or disorder associated with the SSAO (e.g., overexpression, dysregulation, or aberrant activity of SSAO). A disease or disorder associated with the SSAO includes, but is not limited to, inflammation or an inflammatory disease, fibrosis or a fibrotic disease, a liver disease, a cardiovascular disease, autoimmune disease, and a metabolic disease.

Inflammation or an inflammatory disease (e.g., inflammation or an inflammatory disease associated with the SSAO) includes, but is not limited to, arthritis, synovitis, Crohn's disease, ulcerative colitis, irritable bowel disease, asthma (e.g., eosinophilic asthma, severe asthma, virally exacerbated asthma), chronic pain, chronic pain from osteoarthritis, chronic pulmonary obstructive disease, cystic fibrosis, bronchiectasis, liver autoimmune disease, autoimmune hepatitis, primary biliary cirrhosis, sclerosing cholangitis, autoimmune cholangitis, alcoholic liver disease, NAFLD, NASH, neuroinflammation, cirrhosis, atherosclerosis, chronic heart failure, congestive heart failure, ischemic disease, stroke and complications thereof, myocardial infarction and complications thereof, inflammatory cell-mediated tissue destruction following stroke, psoriasis, contact dermatitis, inflammation due to diabetes, skin inflammation, pulmonary inflammation, liver inflammation, and the like.

Fibrosis or a fibrotic disease (e.g., a fibrotic disease associated with the SSAO) includes, but is not limited to, cystic fibrosis, pulmonary fibrosis (e.g., idiopathic pulmonary fibrosis), liver fibrosis, kidney fibrosis, lung fibrosis, fibrosis of other organs and tissues, radiation induced fibrosis, and other diseases where excessive fibrosis contributes to disease pathology, and the like.

A liver disease (e.g., a liver disease associated with the SSAO) includes, but is not limited to, liver inflammation, liver fibrosis, NASH, NAFLD, cirrhosis, liver autoimmune diseases, autoimmune hepatitis, primary biliary cirrhosis, sclerosing cholangitis, autoimmune cholangitis, and alcoholic liver disease.

A respiratory disease (e.g., a respiratory disease, associated with the SSAO) includes, but is not limited to, lung fibrosis, lung inflammation, asthma (e.g., eosinophilic asthma, severe asthma, virally exacerbated asthma), chronic pulmonary obstructive disease, cystic fibrosis, and bronchiectasis.

Another aspect of the application relates to a method of treating, preventing, inhibiting, or eliminating a disease or disorder associated with modulation of SSAO (e.g., inhibition of SSAO). The method comprises administering to a subject in need of a treatment for diseases or disorders associated with modulation of SSAO an effective amount a compound of the present application (e.g., a compound of any of the formulae or any individual compounds disclosed herein) or a pharmaceutically acceptable salt, solvate, prodrug, stereoisomer, or tautomer thereof or a pharmaceutical composition of a compound of the present application (e.g., a compound of any of the formulae or any individual compounds disclosed herein). In one embodiment, the SSAO-mediated disorder is a disease or disorder described herein. In some embodiments, the SSAO is wild-type SSAO. In other embodiments, the SSAO is mutant SSAO.

Another aspect of the application relates to a method of modulating SSAO, the method comprising administering to a subject in need thereof a therapeutically effective amount of a compound of the present application (e.g., a compound of any of the formulae or any individual compounds disclosed herein), or a pharmaceutically acceptable salt, solvate, prodrug, stereoisomer, or tautomer thereof, or a pharmaceutical composition of a compound of the present application (e.g., a compound of any of the formulae or any individual compounds disclosed herein). In one embodiment, modulating SSAO is inhibiting SSAO. In some embodiments, the SSAO is wild-type SSAO. In other embodiments, the SSAO is mutant SSAO.

Another aspect of the application relates to a compound of the present application (e.g., a compound of any of the formulae or any individual compounds disclosed herein), or a pharmaceutically acceptable salt, solvate, prodrug, stereoisomer, or tautomer thereof, for use in a method of treating a SSAO-mediated disorder. In one embodiment, the SSAO-mediated disorder is a disease or disorder described herein. In some embodiments, the SSAO is wild-type SSAO. In other embodiments, the SSAO is mutant SSAO.

In another aspect, the present application relates to a pharmaceutical composition of a compound of the present application (e.g., a compound of any of the formulae or any individual compounds disclosed herein), or a pharmaceutically acceptable salt, solvate, prodrug, stereoisomer, or tautomer thereof, for use in a method of treating a SSAO-mediated disorder. In one embodiment, the SSAO-mediated disorder is a disease or disorder described herein. In some embodiments, the SSAO is wild-type SSAO. In other embodiments, the SSAO is mutant SSAO.

Another aspect of the application relates to a compound of the present application (e.g., a compound of any of the formulae or any individual compounds disclosed herein), or a pharmaceutically acceptable salt, solvate, prodrug, stereoisomer, or tautomer thereof, for use in modulating SSAO. In one embodiment, modulating SSAO is inhibiting SSAO. In some embodiments, the SSAO is wild-type SSAO. In other embodiments, the SSAO is mutant SSAO.

In another aspect, the present application relates to a pharmaceutical composition of a compound of the present application (e.g., a compound of any of the formulae or any individual compounds disclosed herein), or a pharmaceutically acceptable salt, solvate, prodrug, stereoisomer, or tautomer thereof, for use in modulating SSAO. In one embodiment, modulating SSAO is inhibiting SSAO. In some embodiments, the SSAO is wild-type SSAO. In other embodiments, the SSAO is mutant SSAO.

Another aspect of the application relates to the use of a compound of the present application (e.g., a compound of any of the formulae or any individual compounds disclosed herein), or a pharmaceutically acceptable salt, solvate, prodrug, stereoisomer, or tautomer thereof, in the manufacture of a medicament for treating a SSAO-mediated disease or disorder. In one embodiment, the SSAO-mediated disorder is a disease or disorder described herein. In some embodiments, the SSAO is wild-type SSAO. In other embodiments, the SSAO is mutant SSAO.

In another aspect, the present application relates to the use of a pharmaceutical composition of a compound of the present application (e.g., a compound of any of the formulae or any individual compounds disclosed herein), or a pharmaceutically acceptable salt, solvate, prodrug, stereoisomer, or tautomer thereof, in the manufacture of a medicament for treating a SSAO-mediated disease or disorder. In one embodiment, the SSAO-mediated disorder is a disease or disorder described herein. In some embodiments, the SSAO is wild-type SSAO. In other embodiments, the SSAO is mutant SSAO.

Another aspect of the application relates to the use of a compound of the present application (e.g., a compound of any of the formulae or any individual compounds disclosed herein), or a pharmaceutically acceptable salt, solvate, prodrug, stereoisomer, or tautomer thereof, in the manufacture of a medicament for modulating SSAO. In one embodiment, modulating SSAO is inhibiting SSAO. In some embodiments, the SSAO is wild-type SSAO. In other embodiments, the SSAO is mutant SSAO.

In another aspect, the present application relates to the use of a pharmaceutical composition of a compound of the present application (e.g., a compound of any of the formulae or any individual compounds disclosed herein), or a pharmaceutically acceptable salt, solvate, prodrug, stereoisomer, or tautomer thereof, in the manufacture of a medicament for modulating SSAO. In one embodiment, modulating SSAO is inhibiting SSAO. In some embodiments, the SSAO is wild-type SSAO. In other embodiments, the SSAO is mutant SSAO.

The disclosed compound of the application can be administered in effective amounts to treat or prevent a disorder and/or prevent the development thereof in subjects.

The compound of the application can be administered in therapeutically effective amounts in a combinational therapy with one or more therapeutic agents (pharmaceutical combinations) or modalities, e.g., non-drug therapies. For example, synergistic effects can occur with other anti-proliferative, anti-cancer, immunomodulatory or anti-inflammatory substances. In some embodiments, a compound of the present application (e.g., a compound of any of the formulae or any individual compounds disclosed herein) is administered in combination with an additional therapeutic agent selected from an anti-inflammatory agent, an immunomodulatory agent, a chemotherapeutic agent, a neurotropic factor, an agent for treating cardiovascular disease, an agent for treating liver disease, an agent for treating lung disease, an agent for treating kidney disease, an agent for treating ocular disease, an agent for treating skin disease, an anti-viral agent, an agent for treating blood disorders, an agent for treating diabetes, and an agent for treating immunodeficiency disorders. Where the compound of the application is administered in conjunction with other therapies, dosages of the co-administered compounds will of course vary depending on the type of co-drug employed, on the specific drug employed, on the condition being treated and so forth.

Combination therapy includes the administration of the subject compound in further combination with other biologically active ingredients (such as, but not limited to, an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, an agent for treating immunodeficiency disorders, and an agent for treating pain) and non-drug therapies (such as, but not limited to, surgery or radiation treatment). For instance, the compound of the application can be used in combination with other pharmaceutically active compounds, preferably compounds that are able to enhance the effect of the compound of the application. The compound of the application can be administered simultaneously (as a single preparation or separate preparation) or sequentially to the other drug therapy or treatment modality. In general, a combination therapy envisions administration of two or more drugs during a single cycle or course of therapy.

Pharmaceutical Compositions

The present application also provides pharmaceutical compositions comprising a compound of the present application (e.g., a compound of any of the formulae or any individual compounds disclosed herein), or a pharmaceutically acceptable salt, solvate, prodrug, stereoisomer, or tautomer thereof, in combination with at least one pharmaceutically acceptable excipient or carrier.

A "pharmaceutical composition" is a formulation containing the compound of the present application in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or a pharmaceutically acceptable salt, solvate, prodrug, stereoisomer, or tautomer thereof thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical compositions of the application are formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the application can be administered to a subject in many of the well-known methods currently used for chemotherapeutic treatment. The dose chosen should be sufficient to constitute effective treatment but not as high as to cause unacceptable side effects. The state of the disease condition and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In one embodiment, the disease or disorder is a disease or disorder described herein.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compound (i.e., a compound of the present application (e.g., a compound of any of the formulae or any individual compounds disclosed herein)) of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compound into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compound is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound is formulated into ointments, salves, gels, or creams as generally known in the art.

The active compound can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the application are dictated by and directly dependent on the unique characteristics of the active compound and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Dosages can range from about 0.01 mg/kg per day to about 5000 mg/kg per day. An effective amount of a pharmaceutical agent is that which provides an objectively identifiable improvement as noted by the clinician or other qualified observer. As used herein, the term "dosage effective manner" refers to amount of an active compound to produce the desired biological effect in a subject or cell.

The pharmaceutical compositions can be included in a container, pack, or dispenser together with instructions for administration.

As used herein, "pharmaceutically acceptable salts" refer to derivatives of the compound of the present application wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compound of the present application can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compound of the present application can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compound of the present application can be delivered in prodrug form. Thus, the present application is intended to cover prodrugs of the presently claimed compound, methods of delivering the same and compositions containing the same. "Prodrugs" are intended to include any covalently bonded carriers that release an active parent drug of the present application in vivo when such prodrug is administered to a subject. Prodrugs in the present application are prepared by modifying functional groups present in the compound in such a way that the modifications are cleaved, either in routine manipulation or in vivo, to the parent compound. Prodrugs include the compound of the present application wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in the compound of the application, and the like, See Bundegaard, H., *Design of Prodrugs, p* 1-92, Elsevier, New York-Oxford (1985).

The compound, or pharmaceutically acceptable salts, tautomers, prodrugs, solvates, metabolites, polymorphs, analogs or derivatives thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound or a pharmaceutically acceptable salt, solvate, prodrug, stereoisomer, or tautomer thereof is administered orally. One skilled in the art will recognize the advantages of certain routes of administration.

The dosage regimen utilizing the compound is selected in accordance with a variety of factors including type, species, age, weight, sex and medical condition of the patient; the severity of the condition to be treated; the route of administration; the renal and hepatic function of the patient; and the particular compound or pharmaceutically acceptable salt, solvate, prodrug, stereoisomer, or tautomer thereof employed. An ordinarily skilled physician or veterinarian can readily determine and prescribe the effective amount of the drug required to prevent, counter or arrest the progress of the condition.

Techniques for formulation and administration of the disclosed compound of the application can be found in *Remington: the Science and Practice of Pharmacy,* $19^{th}$ edition, Mack Publishing Co., Easton, Pa. (1995). In an embodiment, the compound described herein, and the pharmaceutically acceptable salts, solvates, prodrugs, stereoisomers, or tautomers thereof, are used in pharmaceutical preparations in combination with a pharmaceutically acceptable carrier or diluent. Suitable pharmaceutically acceptable carriers include inert solid fillers or diluents and sterile aqueous or organic solutions. The compound or pharmaceutically acceptable salts, solvates, prodrugs, stereoisomers, or tautomers thereof will be present in such pharmaceutical compositions in amounts sufficient to provide the desired dosage amount in the range described herein.

All percentages and ratios used herein, unless otherwise indicated, are by weight. Other features and advantages of the present application are apparent from the different examples. The provided examples illustrate different components and methodology useful in practicing the present application. The examples do not limit the claimed application. Based on the present application the skilled artisan can identify and employ other components and methodology useful for practicing the present application.

EXAMPLES

The application is further illustrated by the following examples and synthesis schemes, which are not to be construed as limiting this application in scope or spirit to the specific procedures herein described. It is to be understood that the examples are provided to illustrate certain embodiments and that no limitation to the scope of the application is intended thereby. It is to be further understood that resort may be had to various other embodiments, modifications, and equivalents thereof which may suggest themselves to those skilled in the art without departing from the spirit of the present application and/or scope of the appended claims.

Example 1: Synthesis of Intermediate A

Intermediate A

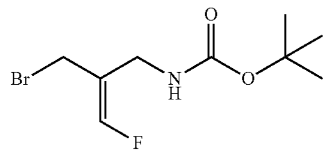

Intermediate A can be synthesized according to methods known in the art, such as the methods described in WO 2013/163675 A1.

Example 2: Synthesis of Intermediate B

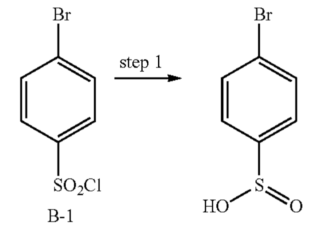

B-1

Intermediate B

Step 1: Intermediate B

A mixture of B-1 (1.5 g, 5.87 mmol), $NaHCO_3$ (902.48 mg, 10.74 mmol) and $Na_2SO_3$ (1.38 g, 10.92 mmol) in $H_2O$ (10 mL) was heated to 100° C. for 1 hr. After cooling to room temperature, the reaction mixture was diluted with $H_2O$ (30 ml) and acidized to pH=1 with con.HCl. The white solid was collected by filtration and washed with $H_2O$ to give Intermediate B (1.2 g, crude). The crude product was used for the next step without further purification. MS: m/z=219 (M−1).

Example 3: Synthesis of Intermediate C

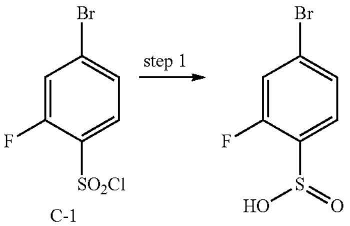

C-1

Intermediate C

Step 1: Intermediate C

A mixture of C-1 (1.5 g, 5.48 mmol), $NaHCO_3$ (843.12 mg, 10.04 mmol) and $Na_2SO_3$ (1.29 g, 10.26 mmol) in $H_2O$ (20 mL) was heated to 100° C. for 1 hr. After cooling to room temperature, the reaction mixture was diluted with $H_2O$ (30 ml) and acidized to pH=1 with con.HCl. The white solid was collected by filtration and washed with $H_2O$ to give Intermediate C (1.2 g, crude). The crude product was used for the next step without further purification. MS: m/z=237 (M−1).

Example 4: Synthesis of Intermediate D

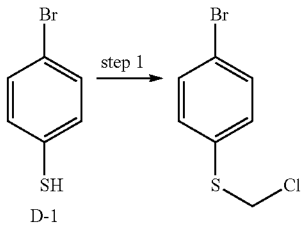

D-1

Intermediate D

Step 1: Intermediate D

To a mixture of D-1 (1.5 g, 7.93 mmol), 2,3,4,6,7,8,9,10-octahydropyrimido[1,2-a]azepine (1.21 g, 7.93 mmol, 1.18 mL) in toluene (30 mL) was added bromo(chloro)methane (20.53 g, 158.67 mmol) at 20° C. The reaction solution was stirred for 2 hr at 20° C. Then, the reaction mixture was filtered, and the filtrate was concentrated with a rotary evaporator. The crude product was purified by silica gel chromatography (ethyl acetate/petroleum ether 0 to 5%) to obtain Intermediate D (1.1 g, crude).

Example 5: Synthesis of Intermediate E

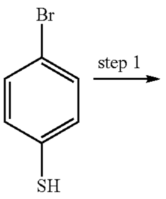

D-1

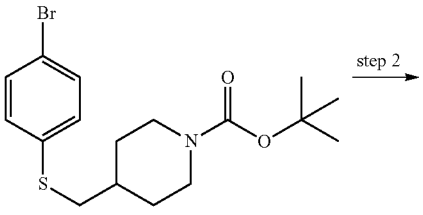

E-1

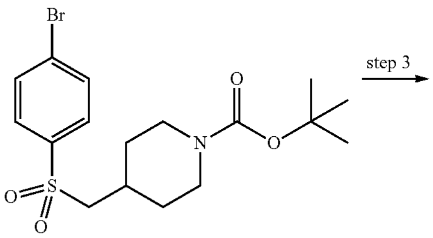

E-2

-continued

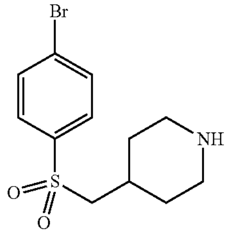

Intermediate E

Step 1: E-1

To a solution of D-1 (500 mg, 2.64 mmol) in DMF (10 mL) was added NaH (126.92 mg, 3.17 mmol, 60% purity) at 20° C. The reaction solution was stirred for 0.5 hr at 20° C. Then, tert-butyl 4-(bromomethyl)piperidine-1-carboxylate (882.79 mg, 3.17 mmol) was added. The reaction solution was stirred further for 18 hr at 20° C. Then, the solution was concentrated with a rotary evaporator. The crude product was purified by silica gel chromatography (ethyl acetate/petroleum ether 0 to 20%) to obtain E-1 (920 mg, 2.38 mmol, 90.05% yield). MS: m/z=386 (M+1).

Step 2: E-2

To a mixture of E-1 (450 mg, 1.16 mmol) in DCM (30 mL) was added 3-chlorobenzenecarboperoxoic acid (709.42 mg, 3.49 mmol, 85% purity) at 20° C. The mixture was stirred for 1 hr at 20° C. Then, the solution was washed with saturated aqueous $Na_2SO_3$ (10 mL), saturated aqueous $NaHCO_3$ (20 mL×2) and brine (15 mL), dried over $Na_2SO_4$ and concentrated with a rotary evaporator to obtain E-2 (450 mg, crude). The crude product was used for the next step without further purification. MS: m/z=418 (M+1).

Step 3: Intermediate E

To a solution of E-2 (450 mg, 1.08 mmol) in DCM (20 mL) was added HCl/Dioxane (4 M, 3 mL) at 20° C. and the reaction mixture was stirred at 20° C. for 1 hr. Then, the solution was concentrated with a rotary evaporator to obtain Intermediate E (380 mg, crude, HCl salt). The crude product was used for the next step without further purification. MS: m/z=318 (M+1).

Example 6: Synthesis of Intermediate F

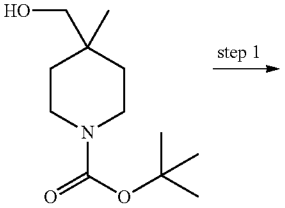

F-1

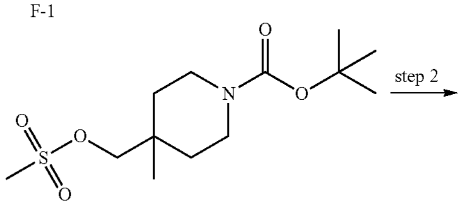

F-2

-continued

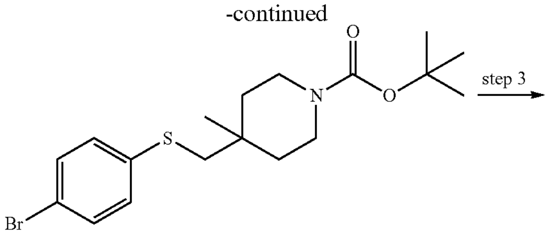

F-3

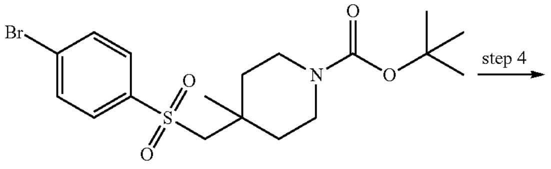

F-4

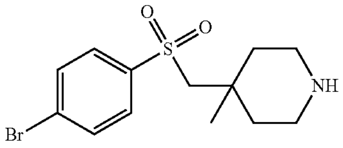

Intermediate F

Step 1: F-2

To a mixture of F-1 (2.0 g, 8.72 mmol), Et3N (2.65 g, 26.16 mmol) in DCM (30 mL) was added methanesulfonyl chloride (1.10 g, 9.59 mmol, 742.55 μL) at 20° C. The reaction solution was stirred for 1 hr at 20° C. Then, the mixture was concentrated with a rotary evaporator. The crude product was purified by silica gel chromatography (ethyl acetate/petroleum ether 0 to 50%) to obtain F-2 (2.5 g, 8.13 mmol, 93.25% yield). MS: m/z=308 (M+1).

Step 2: F-3

To a solution of 4-bromobenzenethiol (500 mg, 2.64 mmol) in DMF (15 mL) was added NaH (116.35 mg, 2.91 mmol, 60% purity) at 20° C. The reaction solution was stirred for 0.5 hr at 20° C. Then, F-2 (975.51 mg, 3.17 mmol) was added. The reaction solution was stirred further for 18 hr at 20° C. Then, the solution was concentrated with a rotary evaporator. The crude product was purified by silica gel chromatography (ethyl acetate/petroleum ether 0 to 10%) to obtain F-3 (150 mg, 374.65 μmol, 14.17% yield). MS: m/z=400 (M+1).

Step 3: F-4

To a mixture of F-3 (150 mg, 374.65 μmol) in DCM (20 mL) was added 3-chlorobenzenecarboperoxoic acid (228.19 mg, 1.12 mmol, 85% purity) at 20° C. The mixture was stirred for 1 hr at 20° C. Then, the solution was washed with saturated aqueous $Na_2SO_3$ (10 mL), saturated aqueous $NaHCO_3$ (20 mL×2) and brine (15 mL), dried over $Na_2SO_4$ and concentrated with a rotary evaporator to obtain F-4 (170 mg, crude). The crude product was used for the next step without further purification. MS: m/z=432 (M+1).

Step 4: Intermediate F

To a solution of F-4 (170 mg, 393.18 μmol) in DCM (15 mL) was added HCl/Dioxane (4 M, 2 mL) at 20° C. and the reaction mixture was stirred at 20° C. for 1 hr. Then, the solution was concentrated with a rotary evaporator to obtain Intermediate F (160 mg, crude, HCl salt). The crude product was used for the next step without further purification. MS: m/z=332 (M+1).

Example 7: Synthesis of Intermediate G

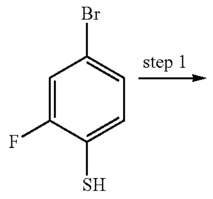

G-1

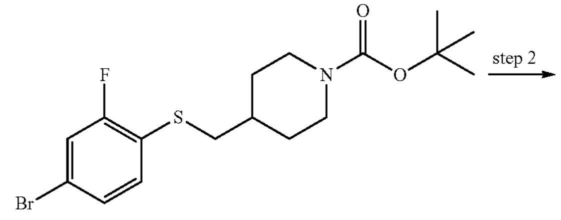

G-2

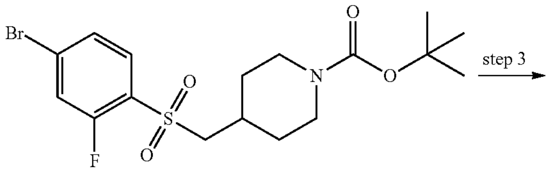

G-3

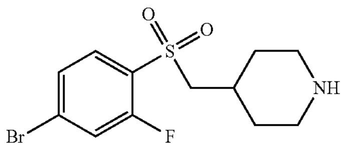

Intermediate G

Step 1: G-2

To a mixture of G-1 (1 g, 4.83 mmol), NaH (386.32 mg, 9.66 mmol, 60% purity) in DMF (20 mL) was added tert-butyl 4-methyl-4-(methylsulfonyloxymethyl)piperidine-1-carboxylate (1.61 g, 5.80 mmol) at 0° C. The reaction solution was stirred for 12 hr at 50° C. To the mixture, saturated aqueous ammonium chloride solution (50 mL) and ethyl acetate (100 mL) was added. The organic layer was separated and the aqueous layer was further extracted with ethyl acetate (50 mL×3). The combined organic extracts were dried over sodium sulfate. The solvent was evaporated under reduced pressure and the crude was purified by flash column chromatography (ethyl acetate/petroleum ether 10% to 80%) to give G-2 (1.3 g, 3.22 mmol, 66.57% yield). MS: m/z=404.3 (M+1).

Step 2: G-3

A mixture of G-2 (600 mg, 1.48 mmol) and m-CPBA (903.78 mg, 4.45 mmol, 85% purity) in DCM (20 mL) was stirred at 25° C. for 1 hr. $Na_2SO_3$ (14 g) was added to the mixture and stirred for 20 min. Then, the solution was filtered, concentrated and purified by silica gel chromatography (petroleum ether/ethylacetate=30/1-3/1, v/v) to obtain G-3 (500 mg, 1.15 mmol, 77.22% yield). MS: m/z=436.3 (M+1).

Step 3: Intermediate G

A mixture of G-3 (500 mg, 1.15 mmol) in HCl/Dioxane (4 M, 4.0 mL) at 20° C. and the reaction mixture was stirred at 30° C. for 1 hr. Then, the solution was concentrated with a rotary evaporator to obtain Intermediate G (600 mg, crude, HCl salt), which was used for the next step without further purification. MS: m/z=372.6 (M+1).

Example 8: Synthesis of Intermediate H

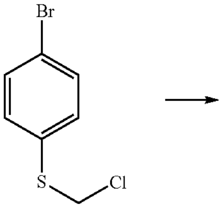

Intermediate D

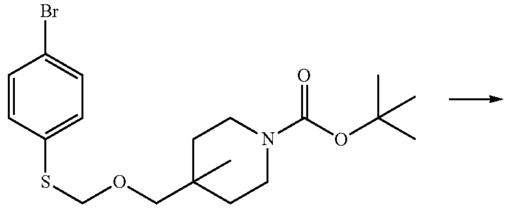

H-1

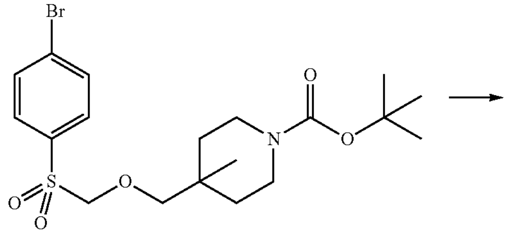

H-2

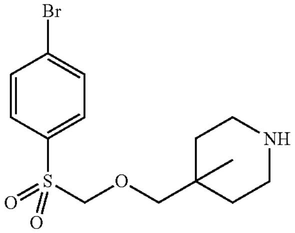

Intermediate H

Step 1: H-1

To a mixture of F-1 (1.74 g, 7.58 mmol) in DMF (15 mL) was added NaH (328.33 mg, 8.21 mmol, 60% purity) at 20° C. The reaction solution was stirred for 0.5 hr at 20° C. Then, Intermediate D (1.5 g, 6.31 mmol) was added. The reaction solution was stirred further for 18 hr at 20° C. Then, the solution was concentrated with a rotary evaporator. The crude product was purified by silica gel chromatography (ethyl acetate in petroleum ether, 0 to 10%) to obtain H-1 (420 mg, 975.84 μmol, 15.45% yield). MS: m/z=430 (M+1).

Step 2: H-2

To a mixture of H-2 (420 mg, 975.84 μmol) in DCM (30 mL) was added m-CPBA (594.34 mg, 2.93 mmol, 85% purity) at 20° C. The mixture was stirred for 1 hr at 20° C. Then, the solution was washed with saturated aqueous $Na_2SO_3$ (10 mL), saturated aqueous $NaHCO_3$ (20 mL×2) and brine (15 mL), dried over $Na_2SO_4$ and concentrated with a rotary evaporator to obtain H-3 (510 mg, crude). The crude product was used for the next step without further purification. MS: m/z=462 (M+1).

Step 3: Intermediate H

To a mixture of H-3 (510 mg, 1.10 mmol) in DCM (20 mL) was added HCl/Dioxane (4 M, 4 mL) at 20° C. and the reaction mixture was stirred at 20° C. for 1 hr. Then, the solution was concentrated with a rotary evaporator to obtain Intermediate H (450 mg, crude, HCl salt). The crude product was used for the next step without further purification. MS: m/z=362 (M+1).

Example 9: Synthesis of Intermediate I

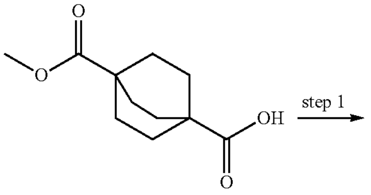

I-1

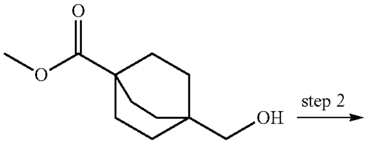

I-2

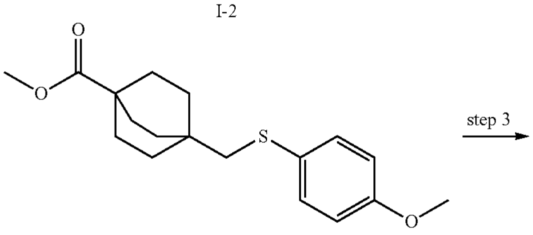

I-3

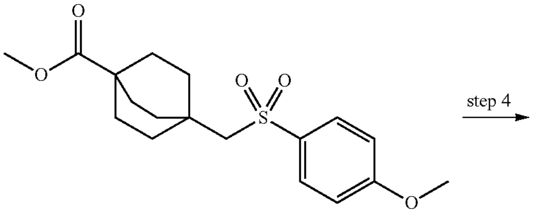

I-4

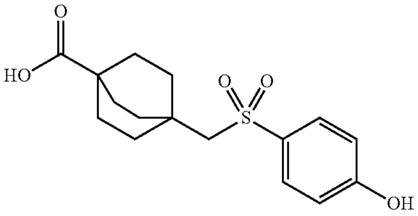

Intermediate I

Step 1: I-2

To a mixture of I-1 (5 g, 23.56 mmol) in anhydrous tetrahydrofuran (100 mL) at 0° C. was added a tetrahydrofuran solution of Borane-tetrahydrofuran complex (1 M, 47.12 mL) under nitrogen. The reaction mixture was stirred at 25° C. for 3 hr, then concentrated. The residue was partitioned between ethyl acetate and water. The organic layer was separated, washed with water, aqueous HCl solution, brine, dried over anhydrous magnesium sulfate, filtered and concentrated to give I-2 (4.5 g, crude). The crude product was used directly for the next step. LC/MS: m/z=199.2 (M+1).

Step 2: I-3

To a mixture of I-2 (1.78 g, 8.98 mmol) and 1-methoxy-4-[(4-methoxyphenyl)disulfanyl]benzene (3.00 g, 10.77 mmol) in acetonitrile (20 mL) was added tributylphosphine (2.54 g, 12.57 mmol, 3.1 mL) at 25° C. under the nitrogen atmosphere. The reaction mixture was stirred for 16 hr at 80° C. The mixture was concentrated. The residue was purified by silica gel chromatography (ethyl acetate in petroleum ether=0~10%, v/v) to afford I-3 (2.1 g, 6.55 mmol, 72.99% yield). LC/MS: m/z=321.1 (M+1).

Step 3: I-4

To a mixture of I-3 (2.1 g, 6.55 mmol) in DCM (10 mL) was added m-CPBA (3.39 g, 19.66 mmol) at 20° C. The mixture was stirred for 2 hr at 25° C. Then, the solution was washed with saturated aqueous sodium sulfite (10 mL), saturated aqueous sodium bicarbonate (20 mL×2) and brine (15 mL), dried over anhydrous sodium sulfate and concentrated with a rotary evaporator to give the crude product. The crude product was recrystallized by dichloromethane/petroleum ether to obtain I-4 (1.94 g, 5.50 mmol, 83.86% yield). LC/MS: m/z=353.1 (M+1).

Step 4: Intermediate I

A mixture of I-4 (1.9 g, 5.39 mmol) and boron tribromide (1 M in DCM, 20 mL) was stirred at 20° C. The mixture was poured into ice and warmed to 25° C. The mixture was filtered. The cake was washed by petroleum ether, dried under the vacuum to afford Intermediate I (1.74 g, 5.36 mmol, 99.50% yield). LC/MS: m/z=325.0 (M+1).

Example 10: Synthesis of Intermediate J

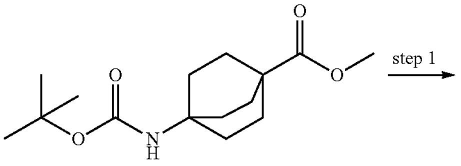

J-1

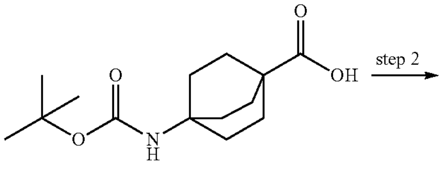

J-2

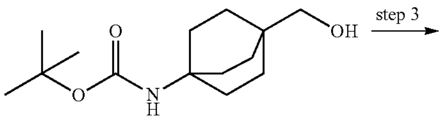

J-3

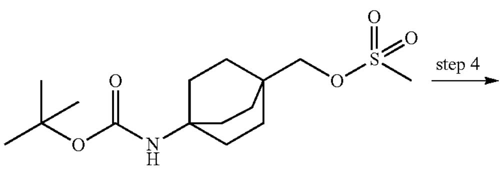

J-4

-continued

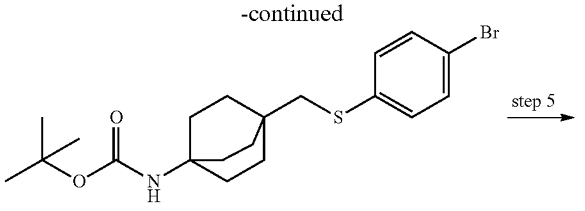

J-5

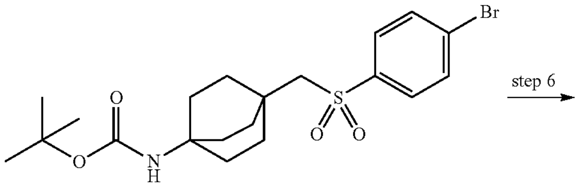

J-6

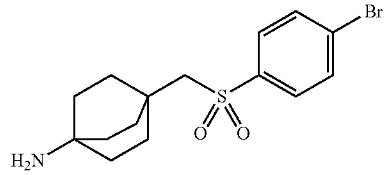

Intermediate J

Step 1: J-2

To a mixture of J-1 (5.9 g, 20.82 mmol) in tetrahydrofuran (30 mL) and water (30 mL) was added Lithium hydroxide monohydrate, 98% (4.37 g, 104.11 mmol) at 0° C. The reaction solution was stirred for 2 hr at 25° C. Then, the reaction mixture was adjusted to pH~6 by citric acid, extracted with ethyl acetate (50 mL×3). The combined organic layers washed with brine (100 mL), dried over anhydrous sodium sulfate, filtered and concentrated with a rotary evaporator to obtain J-2 (5.6 g, crude).

Step 2. J-3

To a mixture of J-2 (5.6 g, 20.79 mmol) in anhydrous tetrahydrofuran (50 mL) was dropwise added Borane-tetrahydrofuran complex (1 M in tetrahydrofuran, 62.38 mL) at 0° C. under the nitrogen atmosphere. The reaction mixture was stirred for 2 hr at 25° C. To the reaction mixture was dropwise added MeOH (20 mL) at 0~25° C. The reaction mixture was stirred at room temperature (~25° C.) for 0.5 hr. The reaction mixture was concentrated with a rotary evaporator to obtain crude J-3 (5.5 g, crude). The product was used in the next step directly without further purification.

Step 3: J-4

To a mixture of J-3 (5.5 g, 21.54 mmol), triethylamine (6.54 g, 64.62 mmol, 9.01 mL) in DCM (100 mL) was added Methanesulfonic anhydride (5.63 g, 32.31 mmol, 3.56 mL) at 0° C. The reaction solution was stirred for 2 hr at 25° C. Then, the solution was concentrated with a rotary evaporator. The crude product was purified by silica gel chromatography (ethyl acetate in petroleum ether=0~40%, v/v) to obtain J-4 (6.2 g, 18.59 mmol, 86.33% yield).

Step 4: J-5

To a mixture of 4-bromobenzenethiol (8.79 g, 46.48 mmol), cesium carbonate (18.17 g, 55.78 mmol) and potassium iodide (1.54 g, 9.30 mmol) in DMF (50 mL) was added J-4 (6.2 g, 18.59 mmol) under the nitrogen atmosphere. The reaction mixture was heated at 55° C. for 2 hr. Ethyl acetate (100 mL) and water (50 mL) were added, the organic layer was washed with brine (50 mL×4), dried over anhydrous sodium sulfate, filtered and concentrated, which was purified by column chromatography on silica gel (120 g, ethyl acetate in petroleum ether=0~15%, v/v) to give J-5 (6.9 g, 16.18 mmol, 87.03% yield).

Step 5: J-6

A mixture of J-5 (6.9 g, 16.18 mmol) and m-CPBA (9.85 g, 48.54 mmol, 85% purity) in DCM (100 mL) was stirred at 20° C. for 2 hr. Then, sodium sulfite (5 g) was added to the mixture and stirred for 20 min. Then, to the solution was added DCM (100 mL) and water (100 mL). The organic layer was washed with aqueous $NaHCO_3$ (50 mL×3), brine (50 mL×3), dried over anhydrous sodium sulfate, filtered, concentrated to give a crude, which was purified by column chromatography on silica gel (80 g, ethyl acetate in petroleum ether=0~20%, v/v) to give J-6 (7 g, 15.27 mmol, 94.38% yield).

Step 6: Intermediate J

To a mixture of J-6 (4 g, 8.73 mmol) in DCM (20 mL) was added HCl/Dioxane (15 mL, 4 M) at 20° C. and stirred at 20° C. for 1 hr. The reaction mixture was then concentrated to give Intermediate J (3.5 g, crude, HCl salt).

Example 11: Synthesis of Intermediate K

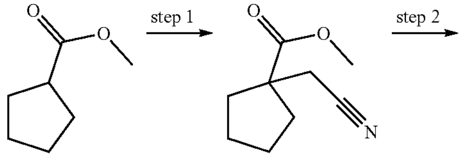

K-1 K-2

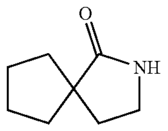

Intermediate K

Step 1: K-2

To a mixture of K-1 (10 g, 78.02 mmol) in tetrahydrofuran (100 mL) was added lithium diisopropylamide (2 M in THF, 78.02 mL) dropwise at −30° C. under argon. After stirred at −30° C. for 1 hr, 2-chloroacetonitrile (7.07 g, 93.63 mmol) was added into the mixture above at −30° C. The resulting mixture was stirred at −30° C. for 30 min, then warmed up to 25° C. and stirred for another 3 hr. After quenched with aqueous ammonia chloride (150 mL), the resulting mixture was poured into water (250 mL) and extracted with ethyl acetate (200 mL×3). The combined organic layers were dried over anhydrous sodium sulfate and concentrated under reduced pressure. The residue was purified by silica gel column (petroleum ether:ethyl acetate=4:1) to give K-2 (4.5 g, 34.49% yield). $^1H$ NMR (400 MHz, Chloroform-d) δ 3.82-3.74 (m, 3H), 2.67-2.62 (m, 2H), 1.90-1.59 (m, 8H).

Step 2: Intermediate K

To a mixture of K-2 (4.5 g, 26.91 mmol) in EtOH (50 mL) was added $NH_3.H_2O$ (5 mL) and Raney Nickel (1.5 g). The reaction mixture was stirred at 25° C. for 48 hr under the hydrogen atmosphere. The resulting mixture was filtered and the filtrate was concentrated under reduced pressure. The residue was purified by silica gel column (petroleum ether:ethyl acetate=2:1) to give Intermediate K (1.20 g, 32.03% yield). $^1H$ NMR (400 MHz, Chloroform-d) δ 5.96 (s, 1H), 3.23 (t, J=6.7 Hz, 2H), 1.99-1.81 (m, 4H), 1.79-1.68 (m, 2H), 1.64-1.55 (m, 2H), 1.48 (dd, J=11.1, 5.6 Hz, 2H).

Example 12: Synthesis of Compound 1

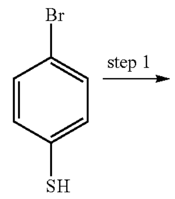

D-1

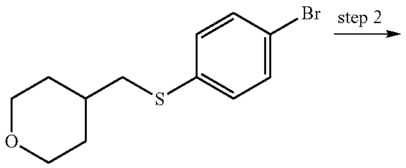

1-1

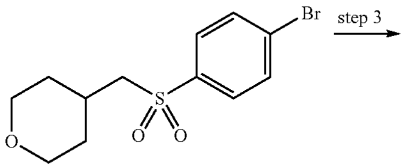

1-2

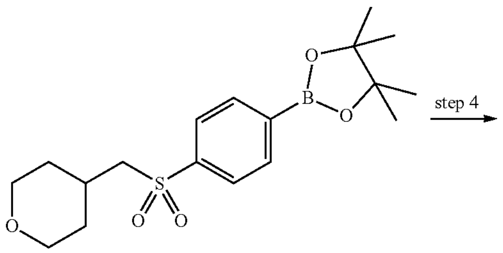

1-3

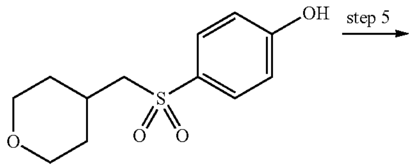

1-4

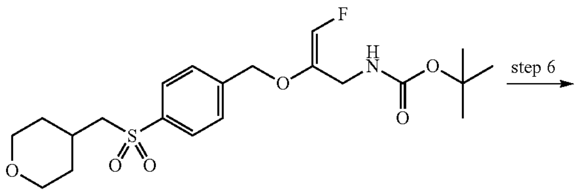

1-5

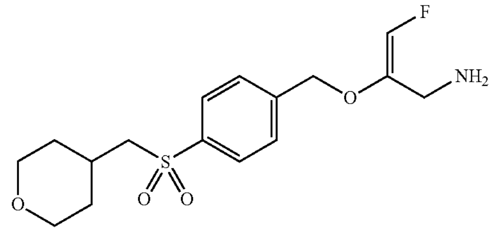

1

Step 1: 1-1

To a mixture of D-1 (959.96 mg, 5.08 mmol) in DMF (10 mL) was added NaH (243.68 mg, 6.09 mmol, 60% purity) at 20° C. The reaction solution was stirred for 0.5 hr at 20° C. Then, 4-(bromomethyl)tetrahydropyran (1.0 g, 5.58 mmol) was added. The reaction solution was stirred for further 18 hr at 20° C. Then, the solution was concentrated with a rotary evaporator. The crude product was purified by silica gel chromatography (ethyl acetate in petroleum ether, 0 to 10%) to obtain 1-1 (1.3 g, 4.53 mmol, 89.15% yield).

Step 2: 1-2

To a mixture of 1-1 (400 mg, 1.39 mmol) in DCM (30 mL) was added m-CPBA (848.24 mg, 4.18 mmol, 85% purity) at 20° C. The mixture was stirred for 2 hr at 20° C. Then, the solution was washed with saturated aqueous $Na_2SO_3$ (10 mL), saturated aqueous $NaHCO_3$ (20 ml×2) and brine (15 mL), dried over $Na_2SO_4$ and concentrated with a rotary evaporator to obtain 1-2 (400 mg, crude). The crude product was used for the next step without further purification.

Step 3: 1-3

To a mixture of 1-2 (300 mg, 939.81 μmol), 4,4,5,5-tetramethyl-2-(4,4,5,5-tetramethyl-1,3,2-dioxaborolan-2-yl)-1,3,2-dioxaborolane (286.38 mg, 1.13 mmol) and KOAc (276.70 mg, 2.82 mmol) in Dioxane (6 mL) was added Pd(dppf)$Cl_2$ (68.77 mg, 93.98 μmol) at 20° C. The reaction solution was heated to 120° C. for 0.667 hr under microwave. The mixture was filtered, and the filtrate was concentrated. The residual material was dissolved in DCM (15 mL), washed with $H_2O$ (15 mL) and brine (15 mL) and concentrated with a rotary evaporator to obtain 1-3 (410 mg, crude). The crude product was used for the next step without further purification.

Step 4: 1-4

To a mixture of 1-3 (410 mg, 1.12 mmol), acetic acid (525.00 mg, 8.74 mmol, 0.5 mL) in THF (15 mL) was added hydrogen peroxide (0.5 mL, 30% purity) at 20° C. The reaction solution was stirred for 1 hr at 20° C. Then, the solution was concentrated with a rotary evaporator to obtain 1-4 (300 mg, crude). The crude product was used for the next step without further purification. MS: m/z=255 (M-1).

Step 5: 1-5

To a mixture of 1-4 (300 mg, 1.17 mmol), Intermediate A (100 mg, 372.96 μmol) in MeCN (20 mL) was added $Cs_2CO_3$ (364.56 mg, 1.12 mmol) at 20° C. The reaction solution was stirred for 1 hr at 90° C. Then, the mixture was filtered, and the filtrate was concentrated with a rotary evaporator to obtain 1-5 (210 mg, crude). The crude product was used for the next step without further purification. MS: m/z=444 (M+1).

Step 6: Compound 1

To a mixture of 1-5 (210 mg, 473.48 μmol) in DCM (10 mL) was added HCl/Dioxane (4 M, 3 mL) at 20° C. and the reaction mixture was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to give Compound 1 (110 mg, 282.46 μmol, 59.66% yield, $HCO_2H$ salt). MS: m/z=344 (M+1). $^1H$ NMR (400 MHz, Methanol-$d_4$) δ 8.50 (s, 1H), 7.91-7.86 (m, 2H), 7.24-7.19 (m, 2H), 7.23 (d, J=81.1 Hz, 1H), 4.71 (dd, J=3.6, 1.1 Hz, 2H), 3.87-3.82 (m, 2H), 3.79 (d, J=2.3 Hz, 2H), 3.37 (td, J=11.8, 2.1 Hz, 2H), 3.15 (d, J=6.3 Hz, 2H), 2.11-2.05 (m, 1H), 1.75-1.71 (m, 2H), 1.40-1.37 (m, 2H). MS: m/z=344.00 (M+1, ESI+).

Example 13: Synthesis of Compound 2

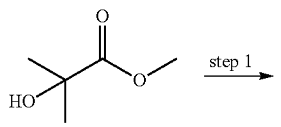

2-1

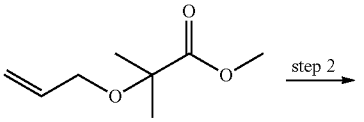

2-2

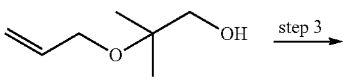

2-3

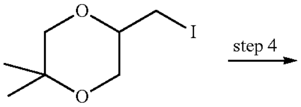

2-4

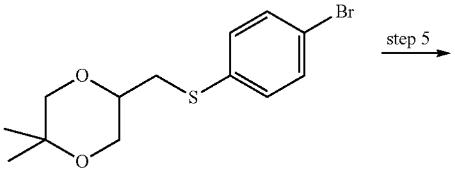

2-5

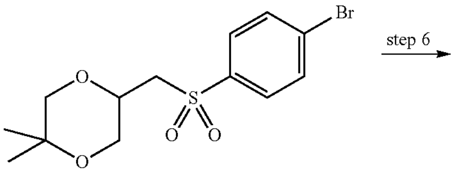

2-6

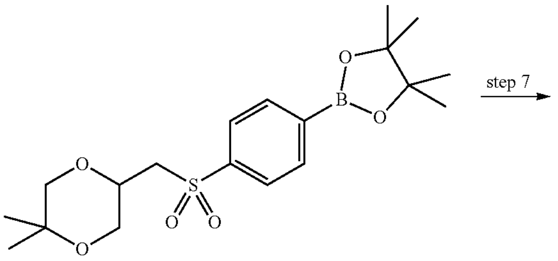

2-7

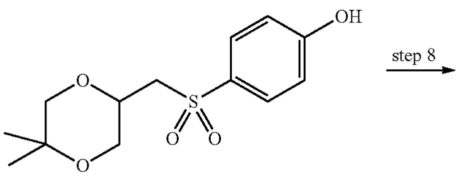

2-8

-continued

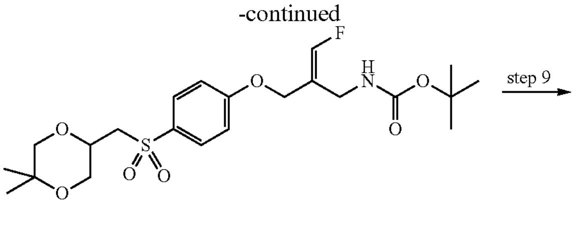

2-9

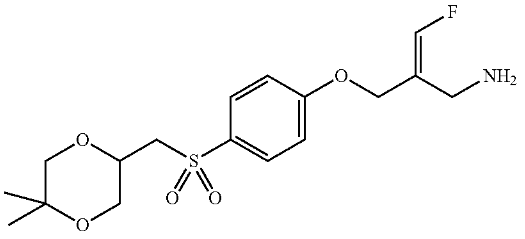

2

Step 1: 2-2

To a mixture of 2-1 (2.0 g, 16.93 mmol) in DMF (30 mL) was added NaH (713.59 mg, 17.84 mmol, 60% purity) at 20° C. The reaction solution was stirred for 0.5 hr at 20° C. Then, 3-bromoprop-1-ene (3.07 g, 25.40 mmol) was added. The reaction solution was stirred further for 18 hr at 20° C. Then, the solution was quenched with $H_2O$ (20 mL), and extracted by ethyl acetate (15 mL×2). The combined organic layers were washed with $H_2O$ (15 mL) and brine (15 mL), dried over $Na_2SO_4$ and concentrated with a rotary evaporator. The crude product was purified by silica gel chromatography (ethyl acetate in petroleum ether, 0 to 40%) to give 2-2 (2.3 g, 14.54 mmol, 85.88% yield). MS: m/z=159 (M+1).

Step 2: 2-3

To a mixture of 2-2 (2.3 g, 14.54 mmol) in THF (60 mL) was added $LiAlH_4$ (201.65 mg, 5.31 mmol) at 0° C. slowly over 0.5 hr. The reaction solution was stirred for 18 hr at 20° C. Then, the solution was cooled to 0° C. and quenched successively with $H_2O$ (1.1 mL), NaOH (1.1 mL, 15% aqueous solution) and $H_2O$ (3.3 mL). The mixture was stirred for 0.5 hr and then was filtered and concentrated with a rotary evaporator to obtain 2-3 (1.9 g, crude). The crude product was used for the next step without further purification. MS: m/z=131 (M+1).

Step 3: 2-4

To a mixture of 2-3 (1.9 g, 14.59 mmol) in MeCN (50 mL) was added $NaHCO_3$ (3.68 g, 43.78 mmol) and the mixture was cooled to 0° C. Molecular iodine (11.11 g, 43.78 mmol) was added and the reaction mixture was allowed to warm up to 25° C. and stirred for 6 hr. The reaction mixture was diluted with saturated aqueous sodium thiosulfate solution and concentrated under reduced pressure removing most of the organic solvent. The residue was extracted with ethyl acetate (30 mL×2) and the combined organic layers were dried over $Na_2SO_4$, filtered and concentrated under reduced pressure. The residue was purified by column chromatography (ethyl acetate in petroleum ether, 0 to 20%) to give 2-4 (2.3 g, 8.98 mmol, 61.54% yield). MS: m/z=257 (M+1).

Step 4: 2-5

To a mixture of 4-bromobenzenethiol (1.0 g, 5.29 mmol) in DMF (30 mL) was added NaH (250.0 mg, 6.25 mmol, 60% purity) at 20° C. The reaction solution was stirred for 0.5 hr at 20° C. Then, 2-4 (1.23 g, 4.81 mmol) was added. The reaction solution was stirred further for 18 hr at 20° C. Then, the solution was concentrated with a rotary evaporator. The crude product was purified by silica gel chromatography (ethyl acetate in petroleum ether, 0 to 30%) to obtain 2-5 (1.1 g, 3.47 mmol, 72.11% yield). MS: m/z=317 (M+1).

Step 5: 2-6

To a mixture of 2-5 (1.1 g, 3.47 mmol) in DCM (50 mL) was added m-CPBA (2.11 g, 10.40 mmol, 85% purity) at 20° C. The mixture was stirred for 1 hr at 20° C. Then, the solution was washed with saturated aqueous $Na_2SO_3$ (10 mL), saturated aqueous $NaHCO_3$ (20 mL×2) and brine (15 mL), dried over $Na_2SO_4$ and concentrated with a rotary evaporator to give 2-6 (440 mg, crude). The crude product was used for the next step without further purification. MS: m/z=349 (M+1).

Step 6: 2-7

To a mixture of 2-6 (440 mg, 1.26 mmol), 4,4,5,5-tetramethyl-2-(4,4,5,5-tetramethyl-1,3,2-dioxaborolan-2-yl)-1,3,2-dioxaborolane (383.92 mg, 1.51 mmol) and KOAc (363.32 mg, 3.78 mmol) in Dioxane (15 mL) was added $Pd(dppf)Cl_2$ (46.09 mg, 62.99 μmol) at 20° C. The reaction solution was heated to 120° C. for 0.667 hr under microwave. The mixture was filtered and evaporated to give 2-7 (550 mg, crude). The crude product was used for the next step without further purification. MS: m/z=397 (M+1).

Step 7: 2-8

To a mixture of 2-7 (550 mg, 1.39 mmol), acetic acid (1.05 g, 17.49 mmol, 1 mL) in THF (20 mL) was added hydrogen peroxide (1 mL, 30% purity) at 25° C. The reaction solution was stirred for 1 hr at 25° C. Then, the solution was quenched by $Na_2SO_3$, filtered and concentrated with a rotary evaporator to obtain 2-8 (450 mg, crude). The crude product was used for the next step without further purification. MS: m/z=287 (M+1).

Step 8: 2-9

To a mixture of 2-8 (450 mg, 1.57 mmol), Intermediate A (421.37 mg, 1.57 mmol) in MeCN (50 mL) was added $Cs_2CO_3$ (1.54 g, 4.71 mmol) at 20° C. The reaction solution was stirred for 1 hr at 90° C. Then, the mixture was filtered, and concentrated with a rotary evaporator. The crude product was purified by silica gel chromatography (ethyl acetate/petroleum ether 0 to 100%) to obtain 2-9 (330 mg, 696.86 μmol, 44.34% yield). MS: m/z=474 (M+1).

Step 9: Compound 2

To a mixture of 2-9 (330 mg, 696.86 μmol) in DCM (20 mL) was added HCl/Dioxane (4 M, 3 mL) at 25° C. and the reaction mixture was stirred at 25° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 2 (210 mg, 500.64 μmol, 71.84% yield, $HCO_2H$ salt). MS: m/z=374 (M+1). $^1H$ NMR (400 MHz, Methanol-$d_4$) δ 7.94-7.84 (m, 2H), 7.27-7.17 (m, 2H), 7.26 (d, J=81.0 Hz, 1H), 4.73 (dd, J=3.6, 1.0 Hz, 2H), 3.89-3.84 (m, 1H), 3.84 (d, J=2.2 Hz, 2H), 3.65-3.48 (m, 2H), 3.44-3.36 (m, 2H), 3.30-3.21 (m, 2H), 1.24 (s, 3H), 1.07 (s, 3H).

Example 14: Synthesis of Compound 3 & 4

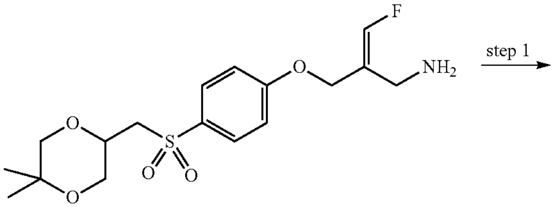

2

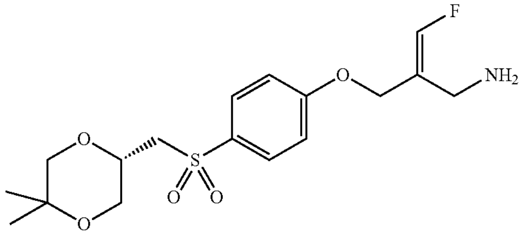

3

+

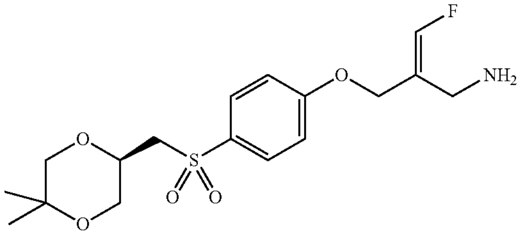

4

Step 1: Compound 3 & 4

Compound 2 (210 mg, 500.64 μmol) was separated by SFC to obtain Compound 3 & 4 (enantiomer 1, Rt=6.220 min, 67.4 mg, 180.48 μmol, 52.05% yield, Column: Chiralpak IG 250 mm*4.6 mm 5 μm, Mobile phase:MeCN:IPA:AMMN=80:20:0.2, F: 1 mL/min, T=30° C.) and (enantiomer 2, Rt=8.083 min, 53.2 mg, 142.46 μmol, 41.08% yield, Column: Chiralpak IG 250 mm*4.6 mm 5 μm, Mobile phase:MeCN:IPA:AMMN=80:20:0.2, F: 1 mL/min, T=30° C.). Enantiomer 1: $^1H$ NMR (400 MHz, Methanol-$d_4$) δ 7.91-7.81 (m, 2H), 7.23-7.15 (m, 2H), 6.96 (dt, J=83.2, 1.0 Hz, 1H), 4.68 (dd, J=3.6, 1.1 Hz, 2H), 3.86-3.83 (m, 1H), 3.63-3.51 (m, 2H), 3.49 (dd, J=2.4, 0.8 Hz, 2H), 3.44-3.36 (m, 2H), 3.31-3.23 (m, 2H), 1.24 (s, 3H), 1.07 (s, 3H). Enantiomer 2: $^1H$ NMR (400 MHz, Methanol-$d_4$) δ 7.89-7.85 (m, 2H), 7.19 (d, J=9.0 Hz, 2H), 6.97 (d, J=83.2 Hz, 1H), 4.68 (dd, J=3.6, 1.1 Hz, 2H), 3.86-3.83 (m, 1H), 3.63-3.51 (m, 2H), 3.52-3.48 (m, 2H), 3.46-3.35 (m, 2H), 3.29-3.24 (m, 2H), 1.24 (s, 3H), 1.07 (s, 3H).

Example 15: Synthesis of Compound 5

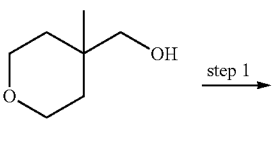

5-1

-continued

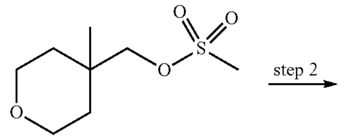

5-2

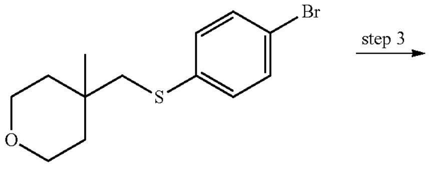

5-3

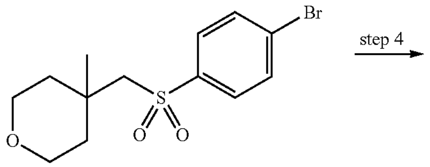

5-4

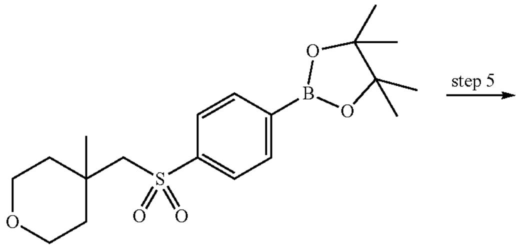

5-5

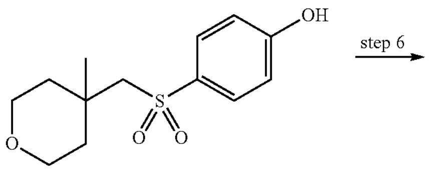

5-6

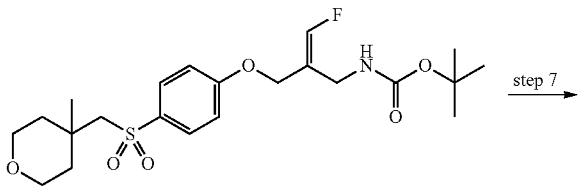

5-7

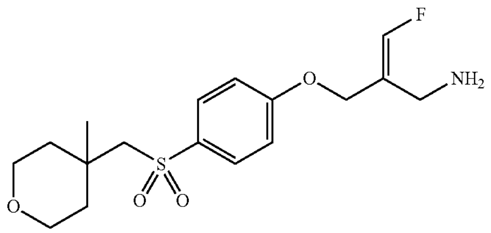

5

Step 1: 5-2

To a mixture of methanesulfonic anhydride (200 mg, 1.15 mmol) and TEA (582.96 mg, 5.76 mmol, 802.98 μL) in DCM (10 mL) was added 5-1 (250 mg, 1.92 mmol) at 0° C. The reaction solution was stirred for 2 hr at 0° C. $H_2O$ (5 mL) was added, the organic phase was separated, dried over $Na_2SO_4$ and concentrated to give 5-2 (300 mg, 1.44 mmol, 75.01% yield). MS: m/z=208.2 (M+1).

Step 2: 5-3

A mixture of 5-2 (300 mg, 1.44 mmol) and 4-bromobenzenethiol (326.81 mg, 1.73 mmol) in DMF (10 mL) was added $Cs_2CO_3$ (1.41 g, 4.32 mmol) at 20° C. The reaction solution was stirred for 8 hr at 100° C. Then, the solution was concentrated with a rotary evaporator. The crude product was purified by silica gel chromatography (petroleum ether/ethyl acetate=4/1, v/v) to obtain 5-3 (200 mg, 663.92 μmol, 46.09% yield). MS: m/z 301.2 (M+1).

Step 3: 5-4

A mixture of 5-3 (180 mg, 597.53 μmol) and m-CPBA (330.19 mg, 1.79 mmol, 85% purity) in DCM (20 mL) was stirred at 20° C. for 1 hr. $Na_2SO_3$ (4 g) was added to the mixture and stirred for 20 mi. Then, the solution was filtered, concentrated and purified by silica gel chromatography (petroleum ether/ethyl acetate=5/1-/1, v/v) to obtain 5-4 (180 mg, 540.15 μmol, 90.40% yield). MS: m/z=333.2 (M+1).

Step 4: 5-5

To a mixture of 4,4,5,5-tetramethyl-2-(4,4,5,5-tetramethyl-1,3,2-dioxaborolan-2-yl)-1,3,2-dioxaborolane (194.32 mg, 765.21 μmol), 5-4 (170 mg, 510.14 μmol) and cyclopentyl(diphenyl)phosphane; dichloropalladium; iron (37.33 mg, 51.01 μmol) in Dioxane (8 mL) was added KOAc (154.83 mg, 1.53 mmol) at 30° C. under the nitrogen atmosphere. The reaction solution was stirred for 2 hr at 100° C. Then, the solution was concentrated with a rotary evaporator. The crude product was purified by silica gel chromatography (petroleum ether/ethyl acetate=10/1-1/1, v/v) to obtain 5-5 (150 mg, 394.42 μmol, 77.32% yield). MS: m/z=380.3 (M+1).

Step 5: 5-6

A mixture of 5-5 (120 mg, 315.54 μmol) in THF (4 mL) and acetic acid (1 mL) was added $H_2O_2$ (315.54 μmol, 1 mL, 30% purity). The mixture was stirred at 25° C. for 0.5 hr. $Na_2SO_3$ (0.5 g) was added to the mixture and stirred for 20 min. The mixture was filtered and concentrated to give 5-6 (0.7 g, crude), which was used in the next step without purification. MS: m/z=270.3 (M+1).

Step 6: 5-7

A mixture of 5-6 (0.7 g) and Intermediate A (138.85 mg, 517.86 μmol) in MeCN (20 mL) was added $Cs_2CO_3$ (2.53 g, 7.77 mmol) at 20° C. The reaction solution was stirred for 1 hr at 80° C. Then, the solution was filtered and concentrated to obtain 5-7 (120 mg, crude), which was used in the next step without purification. MS: m/z=457.5 (M+1).

Step 7: Compound 5

A mixture of 5-7 (120 mg, 262.26 μmol) in HCl/Dioxane (4 M, 3 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 2-30% B; GT: 15 min; flow rate: 15 mL/min) to give Compound 5 (22 mg, 61.55 μmol, 23.47% yield).

$^1H$ NMR (400 MHz, Methanol-d4) δ 8.50 (s, 1H), 7.99 (d, J=8.0 Hz, 2H), 7.23 (d, J=80.0 Hz, 1H), 7.21 (d, J=8.0 Hz, 2H), 4.77-4.67 (m, 2H), 3.80 (d, J=2.4 Hz, 2H), 3.65 (dd, J=6.0, 4.6 Hz, 4H), 3.26 (s, 2H), 1.79-1.75 (m, 2H), 1.59-1.45 (m, 2H), 1.32 (s, 3H). ppm; MS: m/z=358.7 (M+1, ESI+).

Example 16: Synthesis of Compound 6

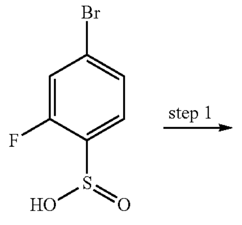

Intermediate C

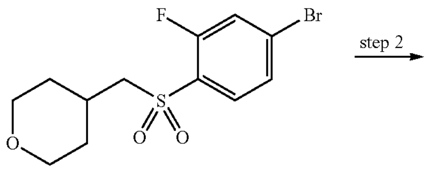

6-1

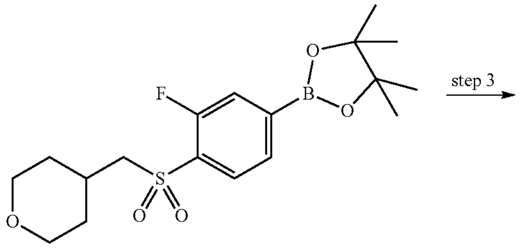

6-2

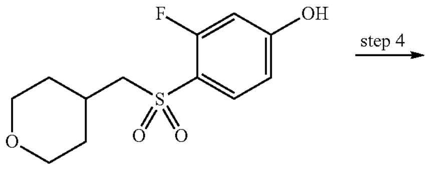

6-3

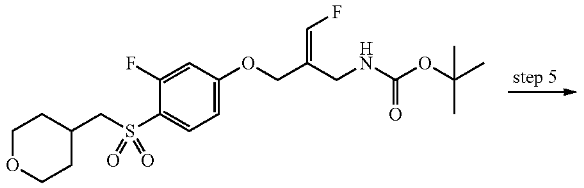

6-4

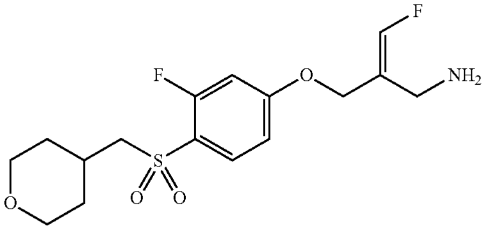

6

Step 1: 6-1

To a mixture of Intermediate C (1.0 g, 3.82 mmol) and 4-(bromomethyl)tetrahydropyran (751.61 mg, 4.20 mmol) in DMF (20 mL) was added $Na_2CO_3$ (1.21 g, 11.46 mmol). The reaction mixture was heated to 80° C. for 18 hr. Then, the solution was concentrated with a rotary evaporator. The crude product was purified by silica gel chromatography (petroleum ether in ethyl acetate, 0 to 40%) to obtain 6-1 (970 mg, 2.88 mmol, 75.38% yield).

Step 2: 6-2

To a mixture of 6-1 (500 mg, 1.48 mmol), 4,4,5,5-tetramethyl-2-(4,4,5,5-tetramethyl-1,3,2-dioxaborolan-2-yl)-1,3,2-dioxaborolane (451.84 mg, 1.78 mmol) and KOAc (436.57 mg, 4.45 mmol) in Dioxane (12 mL) was added Pd(dppf)$Cl_2$ (108.50 mg, 148.28 μmol) at 20° C. The reaction solution was heated to 120° C. for 0.667 hr under microwave. The mixture was filtered, and concentrated. The crude product was purified by silica gel chromatography (ethyl acetate in petroleum ether, 0 to 40%) to obtain 6-2 (350 mg, 910.82 μmol, 61.43% yield).

Step 3: 6-3

To a mixture of 6-2 (150 mg, 390.35 μmol), acetic acid (105.00 mg, 1.75 mmol, 0.1 mL) in THF (8 mL) was added hydrogen peroxide (0.2 mL, 30% purity) at 20° C. The reaction solution was stirred for 1 hr at 20° C. Then, the solution was concentrated with a rotary evaporator to obtain 6-3 (120 mg, crude). The crude product was used for the next step without further purification. MS: m/z=273 (M-1).

Step 4: 6-4

To a mixture of 6-3 (120 mg, 437.46 μmol), Intermediate A (60 mg, 223.78 μmol) in MeCN (20 mL) was added $Cs_2CO_3$ (218.73 mg, 671.33 μmol) at 20° C. The reaction solution was stirred for 1 hr at 90° C. Then, the mixture was filtered, and the filtrate was concentrated with a rotary evaporator to obtain 6-4 (110 mg, crude). The crude product was used for the next step without further purification. MS: m/z=462 (M+1).

Step 5: Compound 6

To a mixture of 6-4 (110 mg, 238.34 μmol) in DCM (15 mL) was added HCl/Dioxane (4 M, 2 mL) at 20° C. and the reaction mixture was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 6 (6.0 mg, 14.73 μmol, 6.18% yield, $HCO_2H$ salt). MS: m/z=362 (M+1). $^1H$ NMR (400 MHz, Methanol-$d_4$) δ 8.49 (s, 1H), 7.85 (t, J=8.7 Hz, 1H), 7.23 (d, J=80.9 Hz, 1H), 7.07-7.04 (m, 1H), 7.02 (d, J=2.6 Hz, 1H), 4.71 (dd, J=3.5, 1.0 Hz, 2H), 3.93-3.83 (m, 2H), 3.79 (d, J=2.3 Hz, 2H), 3.37-3.32 (m, 3H), 3.28 (d, J=6.4 Hz, 3H), 2.16 (dt, J=11.4, 6.5 Hz, 1H), 1.79-1.70 (m, 2H), 1.50-1.36 (m, 2H). MS: m/z=362.1 (M+1, ESI+).

Example 17: Synthesis of Compound 7

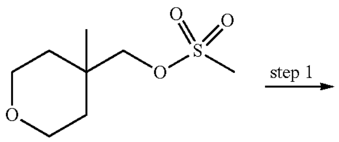

5-2

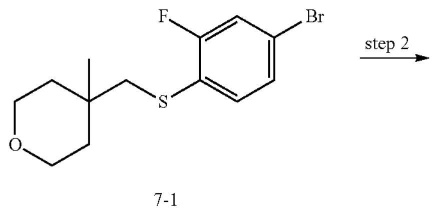

7-1

-continued

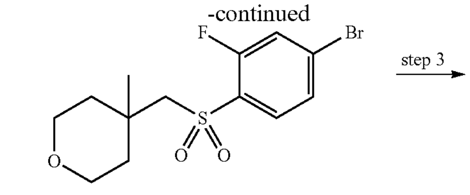

7-2

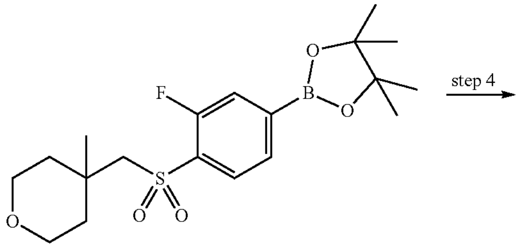

7-3

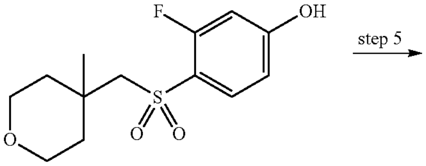

7-4

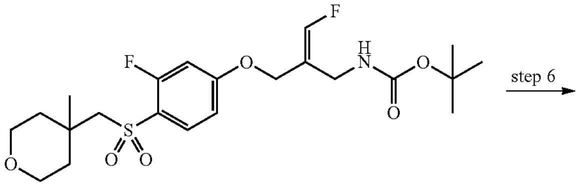

7-5

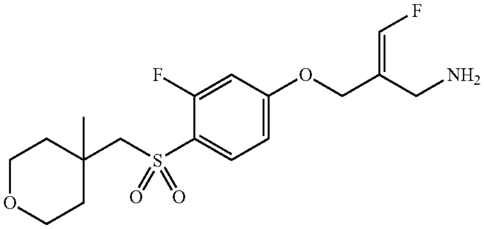

7

Step 1: 7-1

To a mixture of 4-bromo-2-fluoro-benzenethiol (547.57 mg, 2.64 mmol) and NaH (202.66 mg, 5.29 mmol, 60% purity) in DMF (20 mL) was added 5-2 (550.78 mg, 2.64 mmol) at 0° C. The reaction solution was stirred for 8 hr at 50° C. To the mixture was added saturated aqueous ammonium chloride solution (100 mL) and ethyl acetate (100 mL). The organic layer was separated and the aqueous layer was further extracted with ethyl acetate (80 mL×3). The combined organic extracts were dried over sodium sulfate. The solvent was evaporated under reduced pressure and the crude was purified by flash column chromatography (ethyl acetate in petroleum ether, 10% to 80%) to give 7-1 (189 mg, 592.05 μmol, 22.39% yield).

Step 2: 7-2

A mixture of 7-1 (150 mg, 469.88 μmol) and m-CPBA (286.18 mg, 1.41 mmol, 85% purity) in DCM (20 mL) was stirred at 20° C. for 1 hr. $Na_2SO_3$ (0.3 g) was added to the mixture and stirred for 20 min. Then, the solution was filtered, concentrated and purified by silica gel chromatography (petroleum ether/ethyl acetate=10/1-1/2, v/v) to obtain 7-2 (120 mg, 341.66 mol, 72.71% yield). MS: m/z=351.2 (M+1).

Step 3: 7-3

To a mixture of 4,4,5,5-tetramethyl-2-(4,4,5,5-tetramethyl-1,3,2-dioxaborolan-2-yl)-1,3,2-dioxaborolane (108.45 mg, 427.07 μmol), 7-2 (100 mg, 284.71 μmol) and cyclopentyl(diphenyl)phosphane; dichloropalladium; iron (20.83 mg, 28.47 μmol) in Dioxane (20 mL) was added KOAc (83.83 mg, 854.14 μmol) at 20° C. under the nitrogen atmosphere. The reaction solution was stirred for 4 hr at 100° C. Then, the solution was concentrated with a rotary evaporator and purified by column chromatography on silical gel (petroleum ether/ethyl acetate=1/10-1/1) to obtain 7-3 (80 mg, 200.86 μmol, 70.55% yield). MS: m/z=398.3 (M+1).

Step 4: 7-4

To a mixture of 7-3 (80 mg, 200.86 μmol) in THF (2 mL) and acetic acid (0.5 mL) was added $H_2O_2$ (0.5 mL, 30% purity). The mixture was stirred at 20° C. for 1 hr. $Na_2SO_3$ (0.2 g) was added to the mixture and stirred for 20 min. The mixture was filtered and concentrated to give 7-4 (300 mg, crude), which was used in the next step without purification. MS: m/z=288.3 (M+1).

Step 5: 7-5

To a mixture of Intermediate A (83.69 mg, 312.14 μmol) and 7-4 (300 mg) in MeCN (50 mL) was added $Cs_2CO_3$ (1.02 g, 3.12 mmol) at 20° C. The reaction solution was stirred for 1 hr at 80° C. Then, the solution was filtered and concentrated to obtain 7-5 (209 mg, crude). MS: m/z=475.5 (M+1).

Step 6: Compound 7

A mixture of 7-5 (200 mg, 408.52 μmol) in HCl/Dioxane (4 M, 5.0 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 7 (20 mg, 51.35 μmol, 12.57% yield). $^1H$ NMR (400 MHz, Methanol-d4) δ 8.50 (s, 1H), 7.84 (t, J=8.8 Hz, 1H), 7.22 (d, J=80.0 Hz, 1H), 7.04 (d, J=12.8 Hz, 2H), 4.71 (d, J=3.6 Hz, 2H), 3.77 (s, 2H), 3.66 (t, J=5.4 Hz, 4H), 3.39 (s, 2H), 1.87-1.73 (m, 2H), 1.54 (d, J=13.6 Hz, 2H), 1.32 (s, 3H). ppm; MS: m/z=376.5 (M+1, ESI+).

Example 18: Synthesis of Compound 8

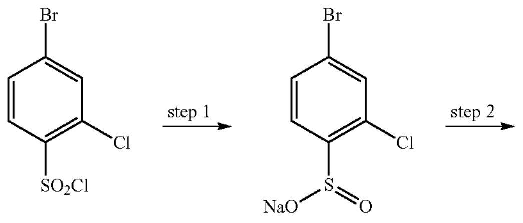

8-1

8-2

-continued

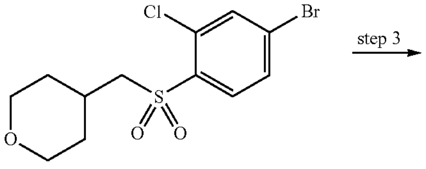

8-3

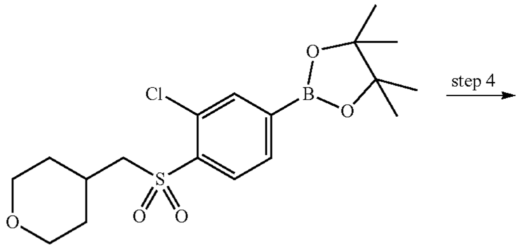

8-4

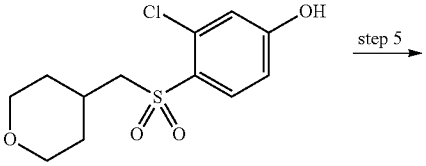

8-5

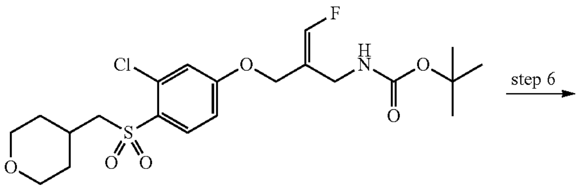

8-6

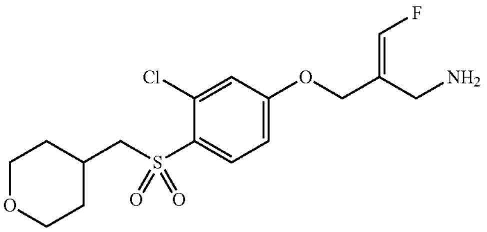

8

Step 1: 8-2

A mixture of 8-1 (1 g, 3.45 mmol), $Na_2SO_3$ (812.87 mg, 6.45 mmol) and $NaHCO_3$ (533.08 mg, 6.35 mmol) in $H_2O$ (20 mL) is heated at 100° C. for 1 hr. Then the mixture was concentrated to give 8-2 (2.5 g, crude). MS: m/z=277.5 (M+1).

Step 2: 8-3

A mixture of 8-2 (1 g, 3.82 mmol) and 4-(bromomethyl) tetrahydropyran (684.72 mg, 3.82 mmol) in DMF (20 mL) was stirred at 20° C. The reaction solution was stirred for 8 hr at 100° C. Then ethyl acetate (100 mL) and $H_2O$ (100 mL) were added, the organic was washed with brine (50 mL), dried over $Na_2SO_4$ and concentrated to give a residue, which was purified by column chromatography on silical gel (ethyl acetate/petroleum ether=1/10-1/1) to give 8-3 (300 mg, 848.27 μmol, 22.18% yield). MS: m/z=353.6 (M+1).

Step 3: 8-4

To a mixture of 8-3 (300.00 mg, 848.27 μmol), 4,4,5,5-tetramethyl-2-(4,4,5,5-tetramethyl-1,3,2-dioxaborolan-2-yl)-1,3,2-dioxaborolane (323.11 mg, 1.27 mmol) and cyclopentyl(diphenyl)phosphane; dichloropalladium; iron (62.07 mg, 84.83 mmol) in Dioxane (10 mL) was added KOAc (254.88 mg, 2.54 mmol) at 30° C. under the nitrogen atmosphere. The reaction solution was stirred for 2 hr at 100° C. Then, the solution was concentrated with a rotary evaporator. The crude product was purified by silica gel chromatography (petroleum ether/ethyl acetate=10/1-1:1, v/v) to obtain 8-4 (200 mg, 499.10 μmol, 58.84% yield). MS: m/z=400.7 (M+1).

Step 4: 8-5

To a mixture of 8-4 (150 mg, 344.69 μmol) in acetic acid (1 mL) and THF (4 mL) was added $H_2O_2$ (1 mL, 30% purity). The mixture was stirred at 20° C. for 1 hr. $Na_2SO_3$ (0.5 g) was added to the mixture and stirred for 20 min. The mixture was filtered and concentrated to give 8-5 (700 mg, crude), which was used in the next step without purification. MS: m/z=290.7 (M+1).

Step 5: 8-6

To a mixture of 8-5 (700 mg) and Intermediate A (193.65 mg, 722.24 μmol) in MeCN (30 mL) was added $Cs_2CO_3$ (705.96 mg, 2.17 mmol) at 20° C. The reaction solution was stirred for 1 hr at 80° C. Then, the solution was filtered and concentrated to obtain 8-6 (200 mg, crude), which was used in the next step without purification. MS: m/z=477.9 (M+1).

Step 6: Compound 8

A mixture of 8-6 (100 mg, 195.15 μmol) in HCl/Dioxane (4 M, 1.99 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-40% B; GT: 15 min; flow rate: 15 mL/min) to obtain Compound 8 (21 mg, 50.93 μmol, 26.10% yield). MS: m/z=377.8 (M+1, ESI+). $^1H$ NMR (400 MHz, Methanol-d4) δ 8.05 (d, J=8.8 Hz, 1H), 7.32 (d, J=2.4 Hz, 1H), 7.26 (d, J=80.0 Hz, 1H), 7.16 (d, J=3.2 Hz, 1H), 4.72 (d, J=3.6 Hz, 2H), 3.87 (d, J=11.6 Hz, 2H), 3.82 (s, 2H), 3.40-3.35 (m, 4H), 2.14 (s, 1H), 1.74 (d, J=13.2 Hz, 2H), 1.51-1.35 (m, 2H). ppm; MS: m/z=378.7 (M+1, ESI+).

Example 19: Synthesis of Compound 9

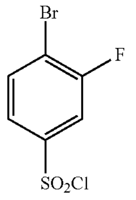

9-1

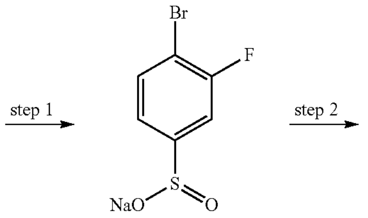

9-2

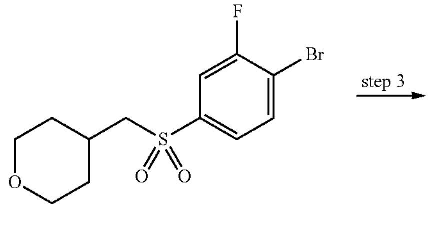

9-3

-continued

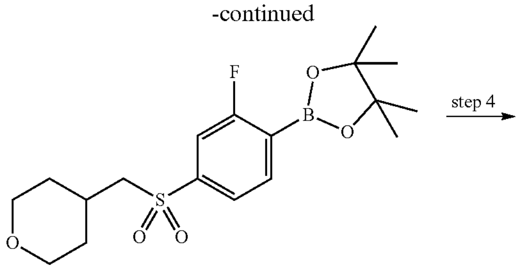

9-4

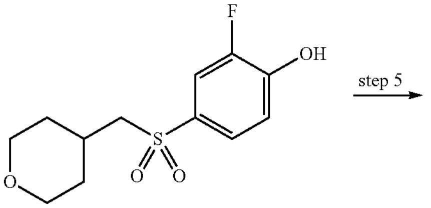

9-5

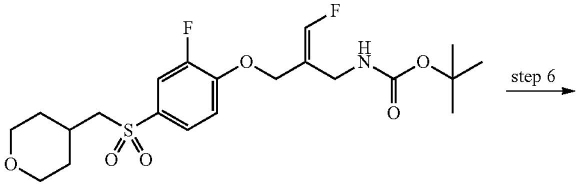

9-6

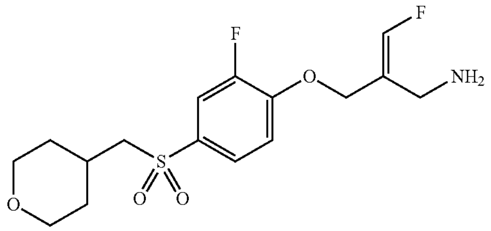

9

Step 1: 9-2

A mixture of 9-1 (1 g, 3.66 mmol), $Na_2SO_3$ (861.77 mg, 6.84 mmol), and $NaHCO_3$ (565.15 mg, 6.73 mmol) in $H_2O$ (30 mL) is heated at 100° C. for 1 hr. Then the mixture was concentrated to give 9-2 (4 g, crude). MS: m/z=261 (M+1).

Step 2: 9-3

A mixture of 9-2 (4 g, 15.32 mmol) and 4-(bromomethyl) tetrahydropyran (823.10 mg, 4.60 mmol) in DMF (50 mL) at 20° C. The reaction solution was stirred for 8 hr at 100° C. Then, the solution was concentrated with a rotary evaporator. The crude product was purified by silica gel chromatography (petroleum ether/ethyl acetate=10/1-3/1, v/v) to obtain 9-3 (400 mg, 1.19 mmol). MS: m/z=337 (M+1).

Step 3: 9-4

A mixture of 9-3 (273.22 mg, 810.24 μmol), 4,4,5,5-tetramethyl-2-(4,4,5,5-tetramethyl-1,3,2-dioxaborolan-2-yl)-1,3,2-dioxaborolane (246.90 mg, 972.29 μmol) in Dioxane (10 mL) was added KOAc (206.75 mg, 2.43 mmol) at 20° C. under the nitrogen atmosphere. The reaction solution was stirred for 4 hr at 100° C. Then, the solution was concentrated with a rotary evaporator and purified by column chromatography on silical gel(ethyl acetate/petroleum ether=1/10-1/1) to obtain 9-4 (200 mg, 520.47 μmol, 64.24% yield). MS: m/z=384 (M+1).

Step 4: 9-5

To a mixture of 9-4 (200 mg, 520.47 μmol) in acetic acid (0.5 mL) and THF (2 mL) was added $H_2O_2$ (1 mL, 30% purity). The mixture was stirred at 20° C. for 1 hr. $Na_2SO_3$ (0.5 g) was added to the mixture and stirred for 20 min. The mixture was filtered and concentrated to give 9-5 (0.8 g, crude), which was used in the next step without purification. MS: m/z=274 (M+1).

Step 5: 9-6

To a mixture of 9-5 (500 mg) and Intermediate A (146.62 mg, 546.83 μmol) in MeCN (80 mL) was added $Cs_2CO_3$ (1.78 g, 5.47 mmol) at 20° C. The reaction solution was stirred for 1 hr at 80° C. Then, the solution was filtered and concentrated to obtain 9-6 (200 mg, 433.35 μmol). MS: m/z=461 (M+1).

Step 6: Compound 9

A mixture of 9-6 (150 mg, 325.01 μmol) in HCl/Dioxane (4 M, 3 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 9 (23 mg, 63.64 μmol, 19.58% yield). $^1H$ NMR (400 MHz, Methanol-d4) δ 8.47 (s, 1H), 7.74 (t, J=8.4 Hz, 2H), 7.40 (t, J=8.4 Hz, 1H), 7.25 (d, J=80.0 Hz, 1H), 4.79 (d, J=3.6 Hz, 2H), 3.88 (d, J=11.2 Hz, 2H), 3.84-3.75 (m, 2H), 3.38 (t, J=11.6 Hz, 2H), 3.19 (d, J=6.4 Hz, 2H), 2.13 (s, 1H), 1.76 (d, J=13.2 Hz, 2H), 1.45-1.41 (m, 2H). ppm; MS: m/z=362.7 (M+1, ESI+).

Example 20: Synthesis of Compound 10

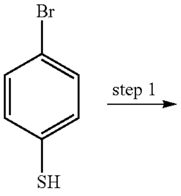

D-1

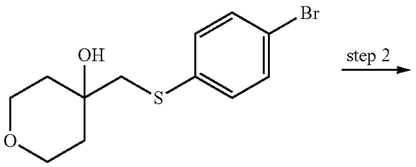

10-1

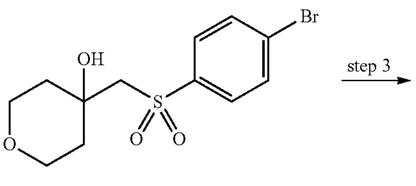

10-2

-continued

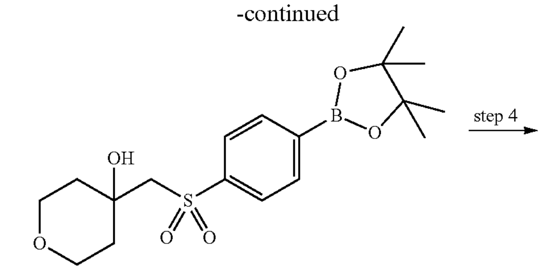

10-3

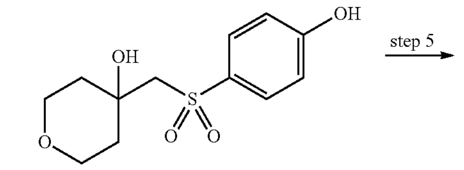

10-4

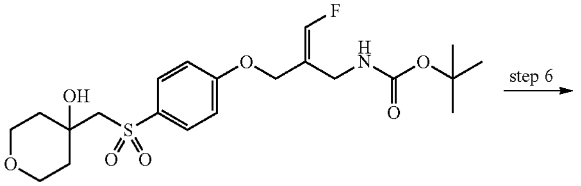

10-5

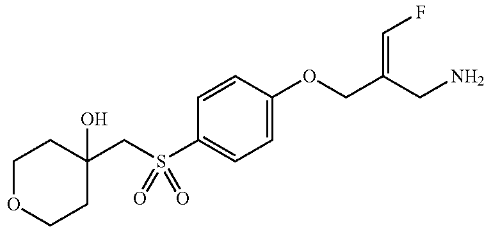

10

Step 1: 10-1

A mixture of D-1 (3 g, 15.87 mmol) and $Cs_2CO_3$ (7.75 g, 23.80 mmol) in MeCN (50 mL) was added 1,6-dioxaspiro [2.5]octane (1.81 g, 15.87 mmol) and the mixture was heated at 80° C. for 2 hr. After cooling to room temperature, the reaction mixture was filtered and concentrated to give a residue, which was purified by column chromatography on silical gel (ethyl acetate/petroleum ether=1/10-1/5, v/v) to give 10-1 (4 g, 13.19 mmol, 83.14% yield). MS: m/z=303 (M+1).

Step 2: 10-2

To a mixture of 10-1 (500 mg, 1.65 mmol) and m-CPBA (1.00 g, 4.95 mmol, 85% purity) in DCM (20 mL) was stirred at 20° C. for 1 hr. $Na_2SO_3$ (0.4 g) was added to the mixture and stirred for 20 min. Then, the solution was filtered, concentrated and purified by silica gel chromatography (petroleum ether/ethyl acetate=10/1-1/2, v/v) to obtain 10-2 (400 mg, 1.19 mmol, 72.36% yield). MS: m/z=335 (M+1).

Step 3: 10-3

To a mixture of 4,4,5,5-tetramethyl-2-(4,4,5,5-tetramethyl-1,3,2-dioxaborolan-2-yl)-1,3,2-dioxaborolane (454.52 mg, 1.79 mmol), 10-2 (400 mg, 1.19 mmol) in Dioxane (20 mL) was added cyclopentyl(diphenyl)phosphane; dichloropalladium; iron (87.31 mg, 119.33 μmol) and KOAc (351.33 mg, 3.58 mmol) at 20° C. under the nitrogen atmosphere. The reaction solution was stirred for 4 hr at 100° C. Then, the solution was concentrated with a rotary evaporator and purified by column chromatography on silical gel (ethyl acetate/petroleum ether=1/10-1/1) to obtain 10-3 (300 mg, 784.77 μmol, 65.77% yield). MS: m/z=382.2 (M+1).

Step 4: 10-4

A mixture of 10-3 (300 mg, 784.77 μmol) in THF (2 mL) and acetic acid (0.5 mL) was added $H_2O_2$ (0.5 mL, 30% purity). The mixture was stirred at 20° C. for 1 hr. $Na_2SO_3$ (0.3 g) was added to the mixture and stirred for 20 min. The mixture was filtered and concentrated to give 10-4 (0.6 g, crude), which was used in the next step without purification. MS: m/z=272 (M+1).

Step 5: 10-5

To a mixture of 10-4 (0.5 g) and Intermediate A (147.69 mg, 550.83 μmol) in MeCN (20 mL) was added $Cs_2CO_3$ (1.79 g, 5.51 mmol) at 20° C. The reaction solution was stirred for 1 hr at 80° C. Then, the solution was filtered and concentrated to obtain 10-5 (280 mg, crude). MS: m/z=459 (M+1).

Step 6: Compound 10

To a mixture of 10-5 (250 mg, 544.04 μmol) in HCl/Dioxane (4 M, 5 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-25% B; GT: 15 min; flow rate: 15 mL/min) to obtain Compound 10 (19 mg, 52.86 μmol). $^1H$ NMR (400 MHz, Methanol-d4) δ 7.89 (d, J=8.4 Hz, 2H), 7.23 (d, J=80.0 Hz, 1H), 7.20 (d, J=8.4 Hz, 2H), 4.71 (d, J=3.6 Hz, 2H), 3.84-3.79 (m, 2H), 3.78-3.71 (m, 2H), 3.69-3.65 (m, 2H), 3.40 (s, 2H), 1.95-1.84 (m, 2H), 1.72 (d, J=13.6 Hz, 2H). ppm; MS: m/z=360.6 (M+1, ESI+).

Example 21: Synthesis of Compound 11

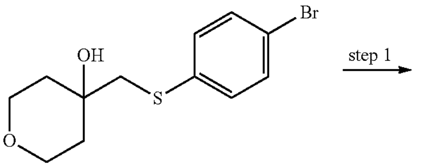

10-1

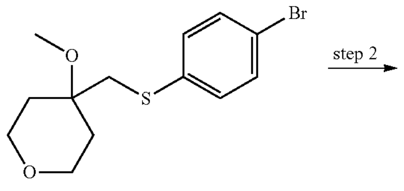

11-1

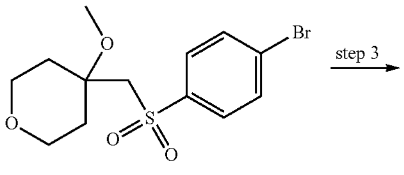

11-2

-continued

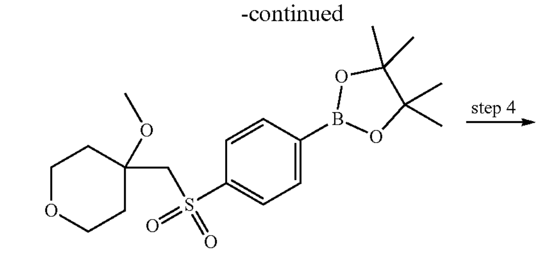

11-3

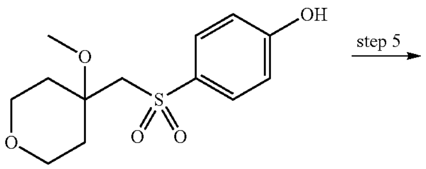

11-4

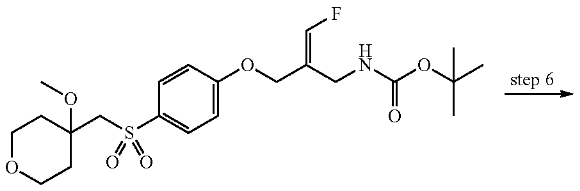

11-5

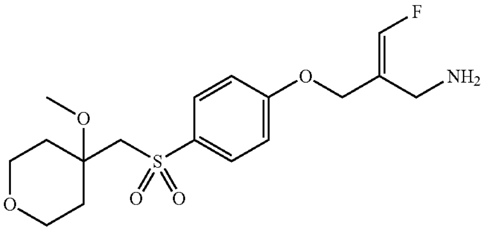

11

Step 1: 11-1

A mixture of 10-1 (1 g, 3.30 mmol) in DMF (10 mL) was added NaH (197.86 mg, 4.95 mmol, 60% purity) at 0° C. and stirred for 1 hr. MeI (936.22 mg, 6.60 mmol) was added. The reaction solution was stirred at 50° C. for 4 hr. To the mixture was added saturated aqueous ammonium chloride solution (150 mL) and ethyl acetate (100 mL). The organic layer was separated and the aqueous layer was further extracted with ethyl acetate (50 mL×3). The combined organic extracts were dried over sodium sulfate. The solvent was evaporated under reduced pressure and the crude was purified by flash column chromatography (ethyl acetate in petroleum ether, 10% to 80%) to give 11-1 (700 mg, 2.21 mmol, 66.91% yield). MS: m/z=317 (M+1).

Step 2: 11-2

A mixture of 11-1 (700 mg, 2.21 mmol) and m-CPBA (1.34 g, 6.62 mmol, 85% purity) in DCM (20 mL) was stirred at 20° C. for 1 hr. $Na_2SO_3$ (0.3 g) was added to the mixture and stirred for 20 min. Then, the solution was filtered, concentrated and purified by silica gel chromatography (petroleum ether/ethyl acetate=10/1-1/2, v/v) to obtain 11-2 (680 mg, 1.95 mmol, 88.24% yield). MS: m/z=349 (M+1).

Step 3: 11-3

To a mixture of 4,4,5,5-tetramethyl-2-(4,4,5,5-tetramethyl-1,3,2-dioxaborolan-2-yl)-1,3,2-dioxaborolane (327.20 mg, 1.29 mmol), 11-2 (300 mg, 859.01 μmol) in Dioxane (20 mL) was added cyclopentyl(diphenyl)phosphane; dichloropalladium; iron (62.85 mg, 85.90 mol) and KOAc (252.91 mg, 2.58 mmol) at 20° C. under the nitrogen atmosphere. The reaction solution was stirred for 4 hr at 100° C. Then, the solution was concentrated with a rotary evaporator and purified by column chromatography on silical gel (petroleum ether/ethylacetate=l/10-1/1) to obtain 11-3 (200 mg, 504.66 μmol, 58.75% yield). MS: m/z=396 (M+1).

Step 4: 11-4

A mixture of 11-3 (200 mg, 504.66 μmol) in THF (2 mL) and acetic acid (0.5 mL) was added $H_2O_2$ (0.5 mL, 30% purity). The mixture was stirred at 25° C. for 1 hr. $Na_2SO_3$ (0.3 g) was added to the mixture and stirred for 20 min. The mixture was filtered and concentrated to give 11-4 (0.6 g, crude), which was used in the next step without purification. MS: m/z=286 (M+1).

Step 5: 11-5

To a mixture of 11-4 (0.5 g) and Intermediate A (140.46 mg, 523.85 μmol) in MeCN (50 mL) was added $Cs_2CO_3$ (568.93 mg, 1.75 mmol) at 20° C. The reaction solution was stirred for 1 hr at 80° C. Then, the solution was filtered and concentrated to obtain 11-5 (200 mg, crude). MS: m/z=473 (M+1).

Step 6: Compound 11

A mixture of 11-5 (200 mg, 422.34 μmol) in HCl/Dioxane (4 M, 5 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 11 (25 mg, 66.95 μmol, 7.93% yield). $^1H$ NMR (400 MHz, Methanol-d4) δ 8.50 (s, 1H), 7.90 (d, J=8.4 Hz, 2H), 7.23 (d, J=80.0 Hz, 1H), 7.20 (d, J=8.4 Hz, 2H), 4.71 (d, J=3.6 Hz, 2H), 3.79 (d, J=2.4 Hz, 2H), 3.73-3.57 (m, 4H), 3.50 (s, 2H), 2.95 (s, 3H), 1.98 (d, J=14.0 Hz, 2H), 1.86-1.82 (m, 2H). ppm; MS: m/z=374.6 (M+1, ESI+).

Example 22: Synthesis of Compound 12

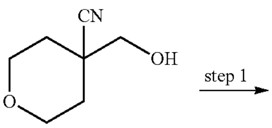

12-1

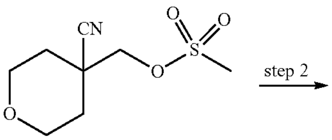

12-2

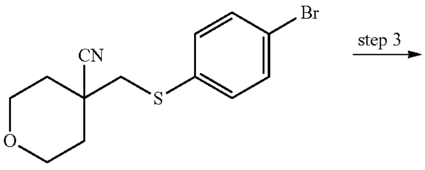

12-3

-continued

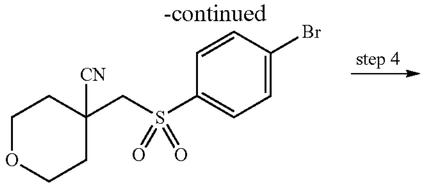

12-4

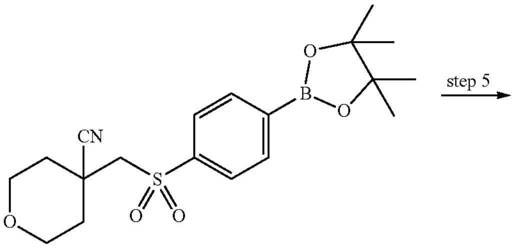

12-5

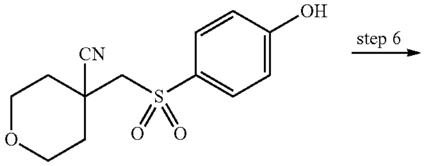

12-6

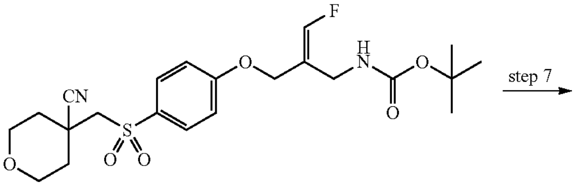

12-7

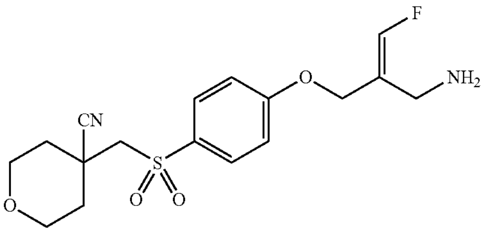

12

Step 1: 12-2

A mixture of 12-1 (1 g, 7.08 mmol), TEA (2.15 g, 21.25 mmol, 2.96 mL) in DCM (50 mL) was added MsCl (973.75 mg, 8.50 mmol) at 0° C. The reaction solution was stirred for 1 hr at 0° C. Then, the solution was concentrated with a rotary evaporator. The crude product was purified by silica gel chromatography (petroleum ether/ethyl acetate=4/1, v/v) to obtain 12-2 (1.4 g, 6.39 mmol, 90.14% yield).

Step 2: 12-3

A mixture of 4-bromobenzenethiol (689.87 mg, 3.65 mmol), NaH (87.56 mg, 3.65 mmol) in DMF (10 mL) was added 12-2 (400 mg, 1.82 mmol) at 0° C. The reaction solution was stirred for 12 hr at 50° C. To the mixture was added saturated aqueous ammonium chloride solution (100 mL) and ethyl acetate (120 mL). The organic layer was separated and the aqueous layer was further extracted with ethyl acetate (80 mL×3). The combined organic extracts were dried over sodium sulfate. The solvent was evaporated under reduced pressure and the crude was purified by flash column chromatography (petroleum ether in ethyl acetate, 10% to 80%) to give 12-3 (150 mg, 480.42 μmol, 26.33% yield). MS: m/z 312 (M+1).

Step 3: 12-4

A mixture of 12-3 (100 mg, 320.28 μmol) and m-CPBA (195.07 mg, 960.85 μmol, 85% purity) in DCM (20 mL) was stirred at 25° C. for 1 hr. $Na_2SO_3$ (14 g) was added to the mixture and stirred for 20 min. Then, the solution was filtered, concentrated and purified by silica gel chromatography (petroleum ether/ethyl acetate=30/1-3/1, v/v) to obtain 12-4 (80 mg, 232.41 μmol, 72.56% yield). MS: m/z=344 (M+1).

Step 4: 12-5

A 30 mL microwave reaction tube was charged with 12-4 (80 mg, 232.41 μmol), 4,4,5,5-tetramethyl-2-(4,4,5,5-tetramethyl-1,3,2-dioxaborolan-2-yl)-1,3,2-dioxaborolane (88.53 mg, 348.61 μmol), cyclopentyl(diphenyl)phosphane; dichloropalladium; iron (170.05 mg, 232.41 μmol) and KOAc (158.58 mg, 697.22 μmol) in Dioxane (10 mL). After $O_2$ was purged by bubbling $N_2$ into the reaction solution, the tube was sealed and heated at 120° C. for 0.5 hr in a Biotage microwave reactor. The reaction was cooled to room temperature, filtered and concentrated under reduced pressure. The resultant crude product was purified by flash chromatography (ethyl acetate in petroleum ether, 0-100%) to deliver 12-5 (75 mg, 191.67 μmol, 82.47% yield). MS: m/z=391 (M+1).

Step 5: 12-6

To a mixture of 12-5 (70 mg, 178.90 μmol) in THF (1 ml) and acetic acid (0.25 mL) was added $H_2O_2$ (0.5 mL, 30% purity). The mixture was stirred at 25° C. for 1 hr. $Na_2SO_3$ (0.3 g) was added to the mixture and stirred for 30 min. The reaction mixture was filtered and concentrated to give 12-6 (0.4 g, crude). MS: m/z=281 (M+1).

Step 6: 12-7

To a mixture of 12-6 (0.4 g) and Intermediate A (152.49 mg, 568.73 μmol) in MeCN (50 mL) was added $Cs_2CO_3$ (1.39 g, 4.27 mmol) at 20° C. The reaction solution was stirred for 1 hr at 80° C. Then, the solution was filtered, concentrated and purified by column chromatography on silical gel (ethyl acetate/petroleum ether=1/10-5/1) to obtain 12-7 (70 mg, 149.40 μmol, 10.51% yield). MS: m/z=468 (M+1).

Step 7: Compound 12

A mixture of 12-7 (70 mg, 149.40 μmol) in HCl/Dioxane (4 M, 4.0 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-35% B; GT: 15 min; flow rate: 15 mL/min) to obtain Compound 12 (12 mg, 32.57 μmol, 21.80% yield). $^1H$ NMR (400 MHz, Methanol-d4) δ 7.94 (d, J=8.4 Hz, 2H), 7.25 (d, J=80.0 Hz, 1H), 7.22 (d, J=8.4 Hz, 2H), 4.72 (d, J=3.6 Hz, 2H), 3.98-3.88 (m, 2H), 3.82 (d, J=2.4 Hz, 2H), 3.66 (d, J=13.9 Hz, 4H), 2.07 (d, J=13.6 Hz, 2H), 1.88-1.85 (m 2H). ppm; MS: m/z=369.5 (M+1, ESI+).

Example 23: Synthesis of Compound 13

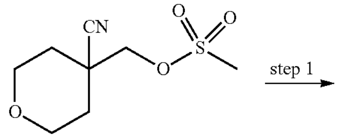

12-2

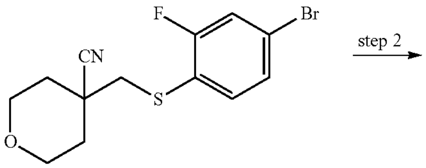

13-1

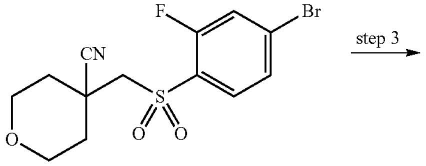

13-2

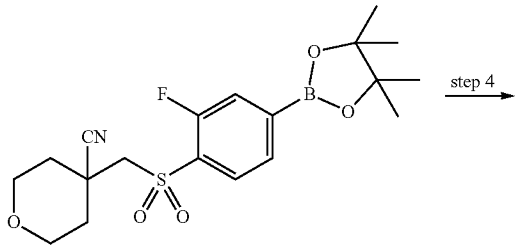

13-3

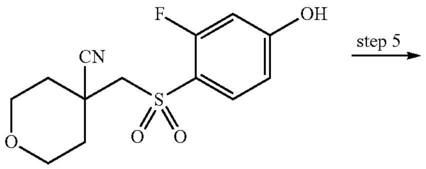

13-4

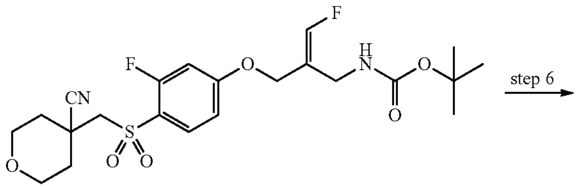

13-5

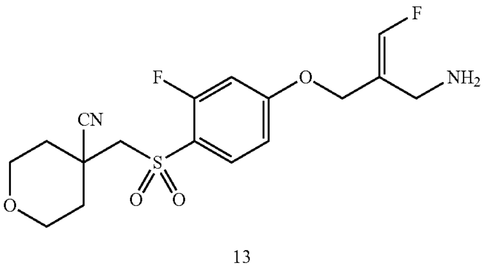

13

Step 1: 13-1

A mixture of 4-bromo-2-fluoro-benzenethiol (1 g, 4.83 mmol), NaH (370.10 mg, 9.66 mmol, 60% purity) in DMF (10 mL) was added 12-2 (423.56 mg, 1.93 mmol) at 0° C. The reaction solution was stirred for 12 hr at 50° C. To the mixture was added saturated aqueous ammonium chloride solution (100 mL) and ethyl acetate (100 ml). The organic layer was separated and the aqueous layer was further extracted with ethyl acetate (50 ml×3). The combined organic extracts were dried over sodium sulfate. The solvent was evaporated under reduced pressure and the crude was purified by flash column chromatography (ethyl acetate in petroleum ether, 10% to 80%) to give 13-1 (200 mg, 605.67 μmol, 12.54% yield). MS: m/z=330 (M+1).

Step 2: 13-2

To a mixture of 13-1 (200 mg, 605.67 μmol) and m-CPBA (368.88 mg, 1.82 mmol, 85% purity) in DCM (20 mL) was stirred at 25° C. for 1 hr. $Na_2SO_3$ (1 g) was added to the mixture and stirred for 20 min. Then, the solution was filtered, concentrated and purified by silica gel chromatography (petroleum ether/ethylacetate=30/1-10/1, v/v) to obtain 13-2 (120 mg, 331.30 μmol, 54.70% yield). MS: m/z=362 (M+1).

Step 3: 13-3

To a mixture of 13-2 (110 mg, 303.69 μmol), 4,4,5,5-tetramethyl-2-(4,4,5,5-tetramethyl-1,3,2-dioxaborolan-2-yl)-1,3,2-dioxaborolane (115.68 mg, 455.53 μmol) in Dioxane (4 mL) was added KOAc (158.58 mg, 911.06 μmol) at 20° C. under the nitrogen atmosphere. The reaction solution was stirred for 2 hr at 100° C. Then, the solution was concentrated with a rotary evaporator and purified by column chromatography on silical gel (petroleum ether/ethyl acetate=1/10-1/1) to obtain 13-3 (90 mg, 219.90 μmol, 72.41% yield). MS: m/z=409 (M+1).

Step 4: 13-4

A mixture of 13-3 (90 mg, 219.90 μmol) in THF (1 mL) and acetic acid (0.25 mL) was added $H_2O_2$ (0.5 mL, 30% purity). The mixture was stirred at 25° C. for 0.5 hr. $Na_2SO_3$ (0.35 g) was added to the mixture and stirred for 30 min. The reaction mixture was filtered and concentrated to give 13-4 (0.4 g, crude). MS: m/z=299 (M+1).

Step 5: 13-5

A mixture of 13-4 (0.4 g) and Intermediate A (143.33 mg, 534.55 μmol) in MeCN (5 mL) was added $Cs_2CO_3$ (1.31 g, 4.01 mmol) at 20° C. The reaction solution was stirred for 1 hr at 80° C. Then, the solution was filtered and concentrated and purified by column chromatography on silical gel (petroleum ether/ethyl acetate=1/10-5/1) to obtain 13-5 (60 mg, 123.32 μmol, 9.23% yield). MS: m/z=486 (M+1).

Step 6: Compound 13

A mixture of 13-5 (60 mg, 123.32 μmol) in HCl/Dioxane (4 M, 2.25 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 13 (5.3 mg, 13.72 μmol, 11.12% yield). $^1H$ NMR (400 MHz, Methanol-d4) δ 8.50 (s, 1H), 7.89 (t, J=8.8 Hz, 1H), 7.22 (d, J=80.0 Hz, 1H), 7.10-7.00 (m, 2H), 4.72 (d, J=3.6 Hz, 2H), 4.04-3.87 (m, 2H), 3.78 (d, J=2.4 Hz, 2H), 3.74 (s, 2H), 3.63 (t, J=12.4 Hz, 2H), 2.07 (d, J=13.6 Hz, 2H), 1.90-1.86 (m, 2H). ppm; MS: m/z=387.5 (M+1, ESI+).

Example 24: Synthesis of Compound 14 & 15

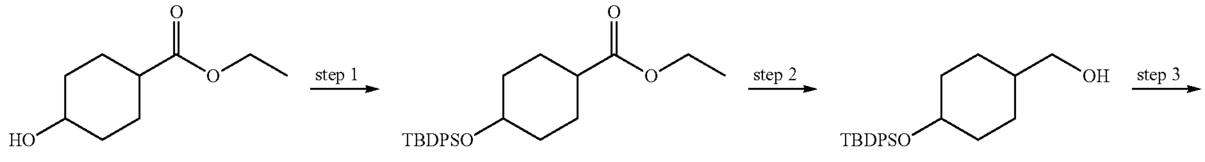

14-1 14-2 14-3

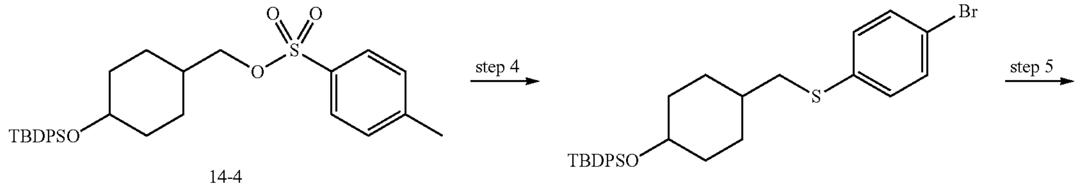

14-4 14-5

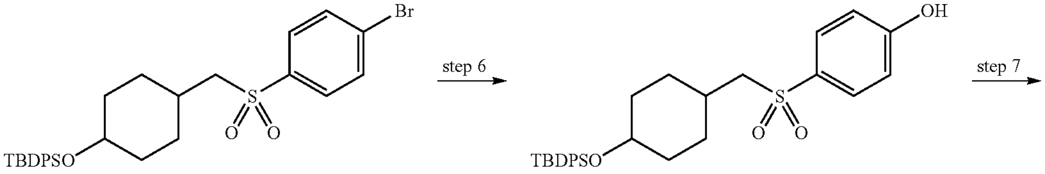

14-6 14-7

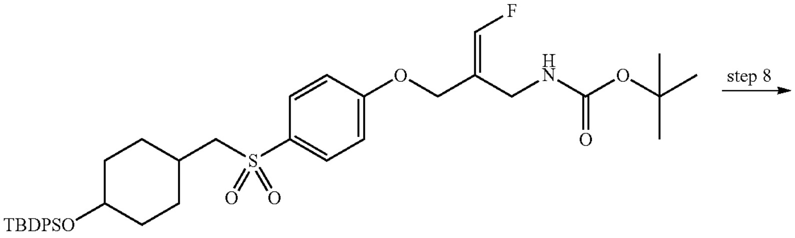

14-8

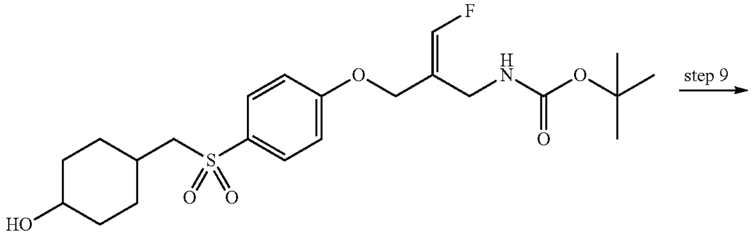

14-9

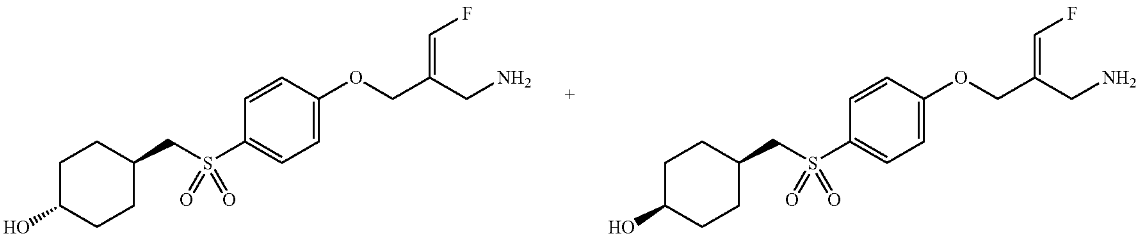

14 15

Step 1: 14-2

To a mixture of 14-1 (1.55 g, 9.00 mmol) in DCM (30 mL) was added tert-butylchlorodiphenylsilane (4.95 g, 18.0 mmol), Imidazole (1.53 g, 22.5 mmol). After stirred at 25° C. for 16 hr, the reaction mixture was poured into 50 mL water, extracted with DCM (50 mL×3). The combined organic layers were washed with water (50 mL) and brine (50 mL), dried over $Na_2SO_4$ and filtered. The filtrated was concentrated under reduced pressure. The residue was purified by silica gel column eluted with petroleum ether/ethyl acetate (20/1) to afford 14-2 (2.8 g, 75.77% yield).

Step 2: 14-3

To a mixture of 14-2 (2.8 g, 6.82 mmol) in THF (30 mL) was added $LiAlH_4$ (518.24 mg, 13.64 mmol) at 0° C. After addition, the mixture was warmed up to 25° C. and stirred at 25° C. for 2 hr. The resulting mixture was quenched with $Na_2SO_4.10H_2O$ (2.0 g) and ice-water (20 mL). The aqueous mixture was extracted with ethyl acetate (50 mL×3). The combined organic layers were washed with water (50 mL), brine (50 mL), dried over $Na_2SO_4$ and filtered. The filtrate was concentrated under reduced pressure. The residue was purified by silica gel column eluted with petroleum ether/ethyl acetate (10/1) to afford 14-3 (2.3 g, 91.51% yield).

Step 3: 14-4

To a mixture of 14-3 (2.3 g, 6.24 mmol) in DCM (30 mL) was added 4-methylbenzenesulfonyl chloride (1.78 g, 9.36 mmol) and TEA (1.26 g, 12.48 mmol). After stirred at 25° C. for 16 hr, the resulting mixture was poured into ice-water (30 mL) and extracted with DCM (50 mL×3). The combined organic layers were washed with water (50 mL), brine (50 mL), dried over $Na_2SO_4$ and filtered. The filtrate was concentrated under reduced pressure. The residue was purified by silica gel column eluted with petroleum ether/ethyl acetate (50/1) to afford 14-4 (3.2 g, 98.10% yield).

Step 4: 14-5

To a mixture of 14-4 (3.2 g, 6.12 mmol) in MeCN (30 mL) was added 4-Bromothiophenol (1.39 g, 7.35 mmol) and $K_2CO_3$ (1.69 g, 12.24 mmol). The resulting mixture was stirred at 80° C. for 3 hr. After cooling to 25° C., the reaction mixture was poured into ice-water (50 mL) and extracted with ethyl acetate (100 mL×3). The combined organic layers were washed with water (50 mL), brine (50 mL), dried over $Na_2SO_4$ and filtered. The filtrate was concentrated under reduced pressure. The residue was purified by silica gel column eluted with petroleum ether/ethyl acetate (50/1) to afford 14-5 (3.2 g, 96.87% yield).

Step 5: 14-6

To a mixture of 14-5 (2.0 g, 3.71 mmol) in MeOH/$H_2O$ (24 mL, 4/1) was added Oxone (4.56 g, 7.41 mmol). After stirred at 25° C. for 2 hr, the resulting mixture was poured into ice-water (50 mL) and extracted with ethyl acetate (50 mL×3). The combined organic layers were washed with water (50 mL), brine (50 mL), dried over $Na_2SO_4$ and filtered. The filtrate was concentrated under reduced pressure to afford 14-6 (2.05 g). which was used for next step directly without further purification.

Step 6: 14-7

To a mixture of 14-6 (2.05 g, 3.59 mmol) in Dioxane/$H_2O$ (30 mL, 1/1) was added t-Buxphos (304.57 mg, 0.72 mmol), $Pd_2(dba)_3$ (328.14 mg, 0.36 mmol) and KOH (603.66 mg, 10.76 mmol). The resulting mixture was stirred at 100° C. for 1 hr under argon. After cooling to 25° C., the reaction mixture was poured into ice-water (50 mL) and extracted with ethyl acetate (50 mL×3). The combined organic layers were washed with water (50 mL), brine (50 mL), dried over $Na_2SO_4$ and filtered. The filtrate was concentrated under reduced pressure. The residue was purified by silica gel column eluted with petroleum ether/ethyl acetate (5/1 to 2/1) to afford 14-7 (1.4 g, 76.74% yield). MS: m/z=509.3 (M+H, ESI+).

Step 7: 14-8

To a mixture of 14-7 (254 mg, 0.5 mmol) in DMF (5 mL) was added Intermediate A (160.64 mg, 0.6 mmol) and $K_2CO_3$ (275.60 mg, 2.00 mmol). The resulting mixture was stirred at 80° C. for 5 hr. After cooling to 25° C., the reaction mixture was poured into ice-water (50 mL) and extracted with ethyl acetate (50 mL×3). The combined organic layers were washed with water (50 mL), brine (50 mL), dried over $Na_2SO_4$ and filtered. The filtrate was concentrated under reduced pressure. The residue was purified by silica gel column eluted with petroleum ether/ethyl acetate (5/1) to afford 14-8 (330 mg, 94.97% yield). MS: m/z=696.5 (M+H, ESI+).

Step 8: 14-9

To a mixture of 14-8 (330 mg, 0.47 mmol) in THE (10 mL) was added TABF (1 M in THF, 0.95 mL). The resulting mixture was stirred at 40° C. for 6 hr. After cooling to 25° C., the reaction mixture was poured into ice-water (30 mL) and extracted with ethyl acetate (30 mL×3). The combined organic layers were washed with water (30 mL), brine (30 mL), dried over $Na_2SO_4$ and filtered. The filtrate was concentrated under reduced pressure. The residue was purified by silica gel column eluted with petroleum ether/ethyl acetate (1/1) to afford 14-9 (195 mg, 89.88% yield). MS: m/z=458.2 (M+H, ESI+).

Step 9: Compound 14 & 15

To a mixture of 14-9 (195 mg, 0.43 mmol) in DCM (10 mL) was added HCl (4 M in Dioxane, 2.13 mL). After stirred at 25° C. for 3 hr, the solvent was removed under reduced pressure. The residue was purified by prep-HPLC (column: Sunfire Prep C18 10 μm 19×250 mm; A: 0.05% HCl water, B: acetonitrile; gradient: 10-14% B; GT: 18 min; flow rate: 20 mL/min) to afford Compound 15 (35 mg, 22.98% yield) and Compound 14 (38 mg, 24.95% yield). Compound 15: $^1H$ NMR (400 MHz, DMSO-d6) δ 8.46 (br, 3H), 7.84-7.82 (m, 2H), 7.45 (s, 1H), 7.24-7.22 (m, 2H), 4.78 (s, 2H), 3.27-3.13 (m, 3H), 1.77-1.75 (m, 4H), 1.61-1.43 (m, 2H), 1.07-1.05 (m, 4H) ppm; MS: m/z=358.2 (M+H, ESI+).

Compound 14: $^1H$ NMR (400 MHz, DMSO-$d_6$) δ 8.49 (br, 3H), 7.84-7.83 (m, 2H), 7.44 (s, 1H), 7.23-7.21 (m, 2H), 4.78 (s, 2H), 3.64-3.59 (m, 3H), 3.16 (d, J=2.8 Hz, 2H), 1.78-1.36 (m, 9H) ppm; MS: m/z=358.2 (M+H, ESI+).

Example 25: Synthesis of Compound 16

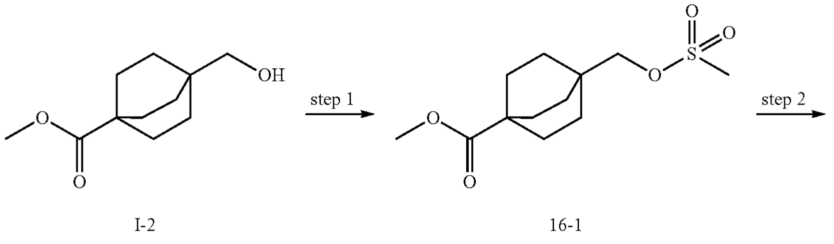

I-2 16-1

-continued
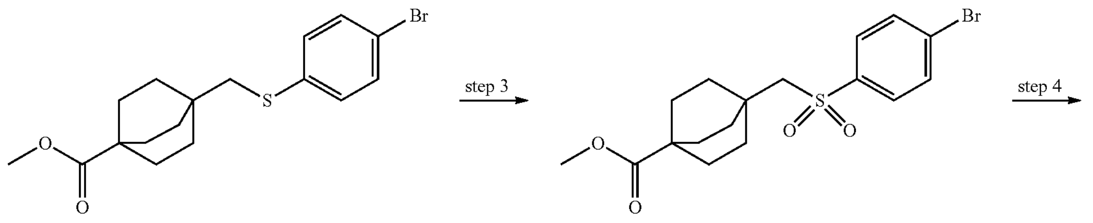
16-2 16-3
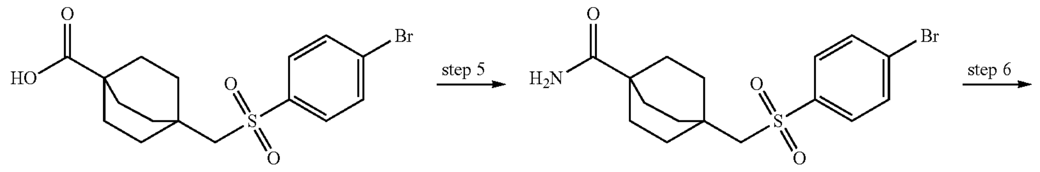
16-4 16-5
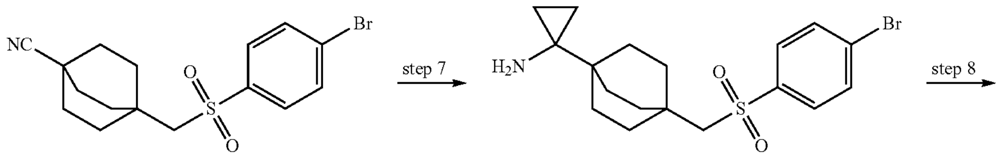
16-6 16-7
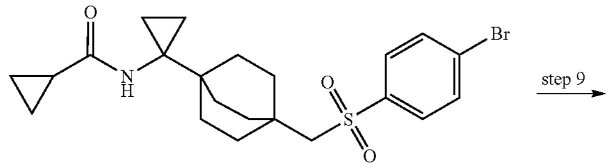
16-8
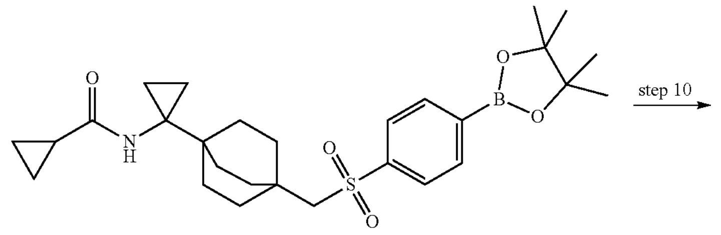
16-9
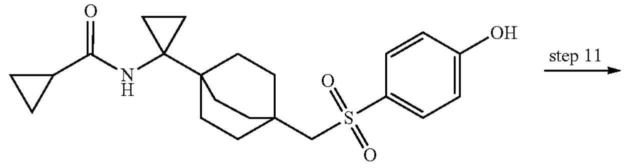
16-10
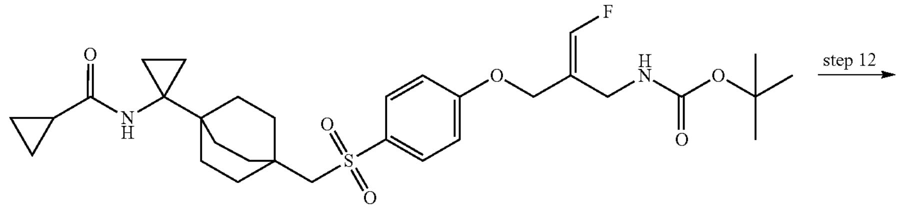
16-11

-continued

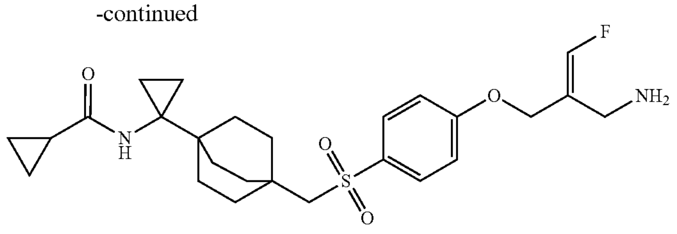

16

Step 1: 16-1

To a mixture of I-2 (4 g, 20.18 mmol), Triethylamine (6.12 g, 60.53 mmol, 8.44 mL) in DCM (40 mL) was added Methanesulfonic anhydride (5.27 g, 30.26 mmol, 3.34 mL) at 0° C. The reaction solution was stirred for 2 hr at 25° C. Then, the solution was concentrated with a rotary evaporator. The crude product was purified by silica gel chromatography (ethyl acetate in petroleum ether, 0~30%, v/v) to obtain 16-1 (4.9 g, 17.73 mmol, 87.88% yield).

Step 2: 16-2

To a mixture of 4-bromobenzenethiol (5.03 g, 26.60 mmol), Potassium iodide (1.47 g, 8.87 mmol, 471.70 uL) in DMF (30 mL) was added 16-1 (4.9 g, 17.73 mmol) under the nitrogen atmosphere. The reaction mixture was heated at 55° C. for 8 hr. Ethyl acetate (150 mL) and $H_2O$ (100 mL) were added, the organic layer was washed with brine (100 mL×3), dried over $Na_2SO_4$, filtered and concentrated to a residue, which was purified by column chromatography on silical gel (ethyl acetate in petroleum ether, 0-20%, v/v) to give 16-2 (5.5 g, 14.89 mmol, 83.99% yield).

Step 3: 16-3

To a mixture of 16-2 (5.5 g, 14.89 mmol) and m-CPBA (7.56 g, 37.23 mmol, 85% purity) in DCM (100 mL) was stirred at 20° C. for 2 hr. $Na_2SO_3$ (1 g) was added to the mixture and stirred for 20 min. Then, to the solution was added ethyl acetate (20 mL) and water (20 mL). The organic layer was washed with aq. $NaHCO_3$ (30 mL×3), brine (30 mL×3), dried over $Na_2SO_4$, filtered, concentrated to give crude, which was purified by column chromatography on silical gel (20 g, ethyl acetate in petroleum ether, 0-20%) to give 16-3 (4.5 g, 11.21 mmol, 75.29% yield).

Step 4: 16-4

A mixture of methyl 16-3 (1.5 g, 3.74 mmol) and lithium hydroxide monohydrate (784.24 mg, 18.69 mmol) in THF (10 mL) and water (10 mL) was stirred at 25° C. for 16 hr. Upon completion, the resulting mixture was concentrated to remove organic solvent. The residue was acidified with 1 M aqueous HCl to pH=5~6 and filtered to give the filter cake as 16-4 (1.1 g, 2.84 mmol, 75.99% yield). MS: m/z=387 (M+H)

Step 5: 16-5.

To a mixture of 16-4 (1.1 g, 2.84 mmol), ammonium chloride (1.52 g, 28.42 mmol, 993.62 uL) and HATU (1.62 g, 4.26 mmol) in DMF (10 mL) was added DIPEA (1.10 g, 8.52 mmol, 1.48 mL). After addition, the mixture was stirred at 25° C. for 16 hr. Upon completion, the resulting mixture was diluted with $H_2O$ (20 mL) and extracted with ethyl acetate (30 mL). The organic layer was washed with $H_2O$ (20 mL×3) and brine, dried over $Na_2SO_4$, filtered and concentrated to give 16-5 (1 g, 2.59 mmol, 91.14% yield). MS: m/z=386 (M+H)

Step 6: 16-6

A mixture of 16-5 (950 mg, 2.46 mmol) and Burgess Reagent (1.17 g, 4.92 mmol) in DCM (30 mL) was stirred at 25° C. for 3 hr. Upon completion, the resulting solution was concentrated. The residue was purified by FCC (silica gel, petroleum ether/ethyl acetate=3/1) to give 16-6 (900 mg, 2.44 mmol, 99.37% yield). MS: m/z=368 (M+H)

Step 7: 16-7

To a mixture of 16-6 (500 mg, 1.36 mmol) and $Ti(OiPr)_4$ (3.09 g, 10.86 mmol) in THE (10 mL) was added bromo (ethyl)magnesium (1 M in THF, 13.6 mL) dropwise at 25° C. After addition, the resulting mixture was stirred at 25° C. for 0.5 hr. Boron trifluoride diethyl etherate (805.0 mg, 5.67 mmol, 700 μL) was added at 25° C. After addition, the mixture was stirred at 25° C. for 0.5 hr. Upon completion, the resulting mixture was quenched with 10% aqueous NaOH and extracted with DCM (40 mL). The separated organic layer was washed with brine, dried over $Na_2SO_4$, filtered and concentrated. The residue was purified by FCC (silica gel, DCM/MeOH=100/1 to 20/1) to give 16-7 (170 mg, 426.75 μmol, 31.43% yield). MS: m/z=398 (M+H)

Step 8: 16-8

To a mixture of 16-7 (170 mg, 426.75 μmol), DIPEA (275.77 mg, 2.13 mmol, 371.66 μL) in DCM (10 mL) was added cyclopropanecarbonyl chloride (134 mg, 1.28 mmol, 116.52 μL). After addition, the mixture was stirred at 25° C. for 2 hr. Upon completion, the resulting solution was quenched with water. The separated organic layer was concentrated. The residue was purified by FCC (silica gel, DCM/MeOH=20/1) to give 16-8 (160 mg, 343.03 μmol, 80.38% yield). MS: m/z=466 (M+H)

Step 9: 16-9

A mixture of 16-8 (160 mg, 343.03 μmol), 4,4,5,5-tetramethyl-2-(4,4,5,5-tetramethyl-1,3,2-dioxaborolan-2-yl)-1,3,2-dioxaborolane (131 mg, 515.87 μmol), Pd(dppf) Cl2 (26 mg, 35.53 μmol) and KOAc (433 mg, 1.03 mmol) in Dioxane (5 mL) was microwaved at 120° C. for 30 min. Upon completion, the resulting mixture was cooled to room temperature, filtered and concentrated to give crude 16-9 (170 mg, 331.06 μmol, 96.51% yield).

Step 10: 16-10

A mixture of 16-9 (170 mg, 331.06 μmol), $H_2O_2$ (1 mL, 30% purity) and acetic acid (1 mL) in THF (4 mL) was stirred at 25° C. for 1 hr. Upon completion, the resulting solution was quenched with $Na_2SO_3$, filtered and concentrated. The residue was purified by FCC (silica gel, petroleum ether/ethyl acetate=1/1) to give 16-10 (120 mg, 297.37 μmol, 89.82% yield). MS: m/z=404 (M+H)

Step 11: 16-11

A mixture of 16-10 (120 mg, 297.37 μmol), Intermediate A (88 mg, 328.21 μmol) and $Cs_2CO_3$ (485 mg, 1.49 mmol) in MeCN (20 mL) was stirred at 95° C. for 1 hr. Upon completion, the resulting mixture was cooled to room temperature and filtered. The filtrate was concentrated. The residue was purified by FCC (silica gel, petroleum ether/ethyl acetate=1/1 to 1/4) to give 16-11 (130 mg, 220.06 μmol, 74.00% yield). MS: m/z=535 (M+H-56).

Step 12: Compound 16

A mixture of 16-11 (130 mg, 220.06 μmol) and HCl/Dioxane (4 M, 5.0 mL) in Dioxane (2 mL) was stirred at 25° C. for 1 hr. Upon completion, the resulting mixture was filtered to obtain the filter cake as Compound 16 (70 mg, 132.80 μmol, 60.35% yield, HCl salt). $^1$H NMR (500 MHz, Methanol-$d_4$) δ 7.77-7.72 (m, 2H), 7.24 (s, 0.5H), 7.12-7.09 (m, 2H), 7.08 (s, 0.5H), 4.62 (d, J=3.4 Hz, 2H), 3.74 (d, J=2.3 Hz, 2H), 2.94 (s, 2H), 1.60-1.50 (m, 6H), 1.43-1.30 (m, 7H), 0.74-0.64 (m, 4H), 0.58-0.53 (m, 2H), 0.51-0.40 (m, 2H). MS: m/z=491 (M+1, ESI+).

Example 26: Synthesis of Compound 17

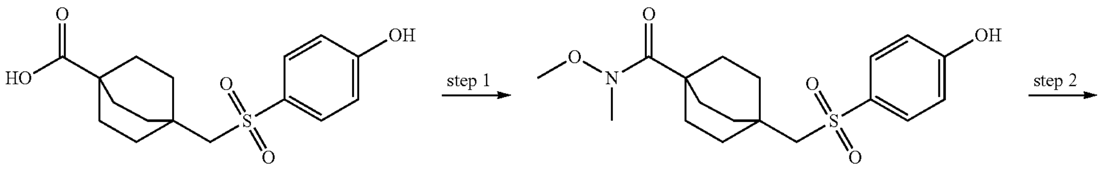

Intermediate I 17-1

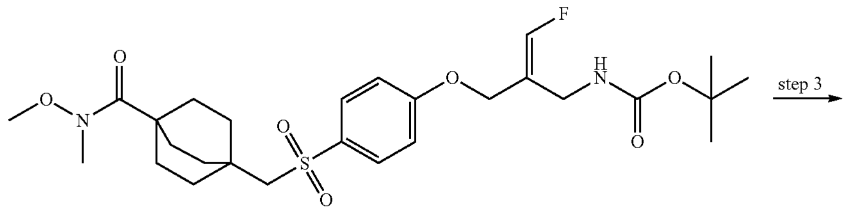

17-2

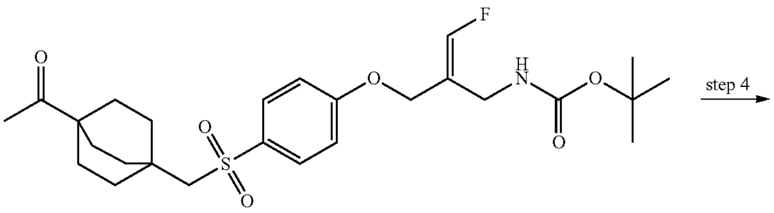

17-3

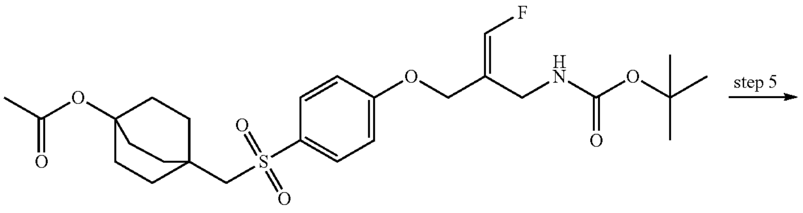

17-4

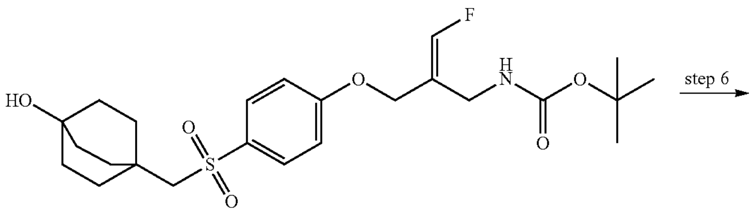

17-5

-continued

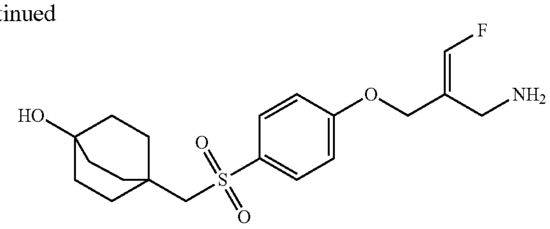

17

Step 1: 17-1

To a mixture of Intermediate I (900 mg, 2.77 mmol), N-methoxymethanamine (405.94 mg, 4.16 mmol, HCl salt) in DMF (10 mL) was added HATU (1.27 g, 3.33 mmol) and TEA (842.23 mg, 8.32 mmol, 1.16 mL) at 30° C. The reaction solution was stirred for 1 hr at 30° C. Then, ethyl acetate (100 mL) was added and the mixture reaction was washed with $H_2O$ (100 mL×3), the organic phases were dried over $Na_2SO_4$, filtered and concentrated. The crude product was purified by silica gel chromatography (petroleum ether/ethyl acetate=5/1-1/1, v/v) to obtain 17-1 (220 mg, 598.71 μmol, 21.58% yield).

Step 2: 17-2

To a mixture of 17-1 (200 mg, 544.28 μmol) and Intermediate A (145.93 mg, 544.28 μmol) in MeCN (40 mL) was added $Cs_2CO_3$ (532.01 mg, 1.63 mmol) at 20° C. The reaction solution was stirred for 1 hr at 80° C. Then, the solution was filtered and concentrated to give a residue, which was purified by column chromatography on silical (ethyl acetate/petroleum ether=5/1-1/1) to obtain 17-2 (220 mg, 396.63 μmol, 72.87% yield).

Step 3: 17-3

To a mixture of 17-2 (200 mg, 360.58 μmol) in THE (10 mL) was added bromo(methyl)magnesium (1 M in THF, 1.44 mL) at −40° C. The reaction solution was stirred for 2 hr at 25° C. Aq. $NH_4Cl$ (10 mL) and ethyl acetate (100 mL) were added, the organic phases were dried over $Na_2SO_4$, filtered and concentrated with a rotary evaporator. The crude product was purified by silica gel chromatography (petroleum ether/ethyl acetate=4/1-1/1, v/v) to obtain 17-3 (160 mg, 313.95 μmol, 87.07% yield).

Step 4: 17-4

A mixture of 17-3 (100 mg, 196.22 μmol) and m-CPBA (79.67 mg, 392.44 μmol, 85% purity) in DCM (5 mL) was stirred at 30° C. for 12 hr. $Na_2SO_3$ (4 g) was added to the mixture and stirred for 20 min. Then, the solution was filtered, concentrated and purified by silica gel chromatography (petroleum ether/ethylacetate=5/1-1/1, v/v) to obtain 17-4 (20 mg, 37.90 μmol, 19.32% yield). MS: m/z=348.4 (M+1).

Step 5: 17-5

To a mixture of 17-5 (20 mg, 37.90 μmol) in MeOH (5 mL) was added $K_2CO_3$ (15.72 mg, 113.71 μmol) at 25° C., and the reaction solution was stirred for 2 hr at 25° C. Then, the solution was concentrated with a rotary evaporator. The crude product was purified by silica gel chromatography (petroleum ether/ethyl acetate=4/1-1/1, v/v) to obtain 17-5 (18 mg, 37.07 mol, 97.79% yield). MS: m/z=334.4 (M+1).

Step 6: Compound 17

A mixture of 17-5 (18 mg, 37.07 μmol) in HCl/Dioxane (4 M, 3 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-95% B; GT: 25 min; flow rate: 15 mL/min) to obtain Compound 17 (4 mg, 9.27 μmol, 25.01% yield, $HCO_2H$ salt). $^1H$ NMR (400 MHz, Methanol-d4) δ 8.51 (s, 1H), 7.90-7.82 (m, 2H), 7.24 (d, J=80.0 Hz, 1H), 7.24-7.17 (m, 2H), 4.75-4.67 (m, 2H), 3.81 (d, J=2.4 Hz, 2H), 3.07 (s, 2H), 1.84-1.80 (m, 6H), 1.66-1.63 (m, 6H). ppm; MS: m/z=384.5 (M+1, ESI+).

Example 27: Synthesis of Compound 18

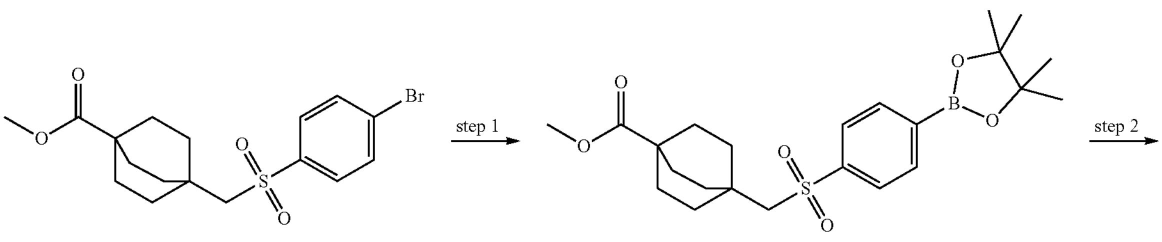

16-3

18-1

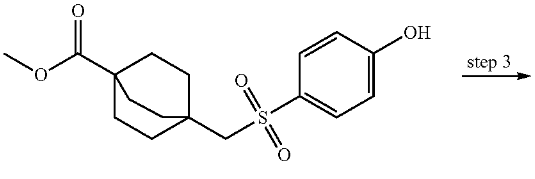

18-2

-continued

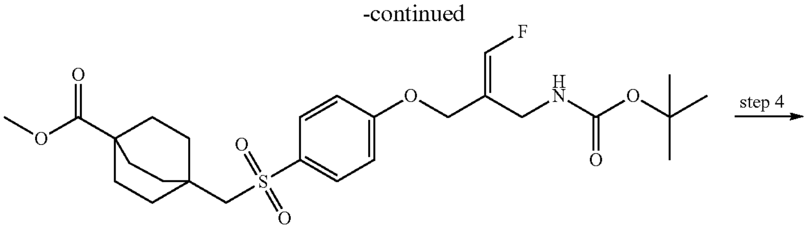

18-3

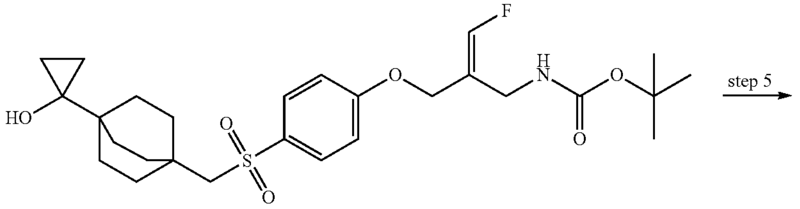

18-4

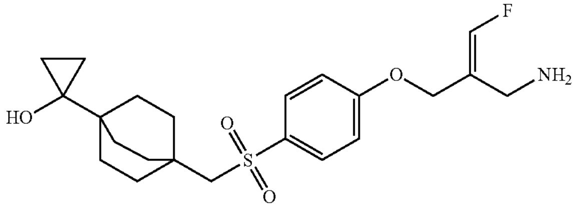

18

Step 1: 18-1

A mixture of 16-3 (590 mg, 1.47 mmol), 4,4,5,5-tetramethyl-2-(4,4,5,5-tetramethyl-1,3,2-dioxaborolan-2-yl)-1,3,2-dioxaborolane (560 mg, 2.21 mmol), Pd(dppf)$Cl_2$ (108 mg, 147.60 μmol) and KOAc (433 mg, 4.41 mmol) in Dioxane (5 mL) was microwaved at 120° C. for 30 min. The resulting mixture was cooled to room temperature, filtered and concentrated to give crude 18-1 (650 mg, 1.45 mmol, 98.61% yield. MS: m/z=448 (M+H)

Step 2: 18-2

A mixture of 18-1 (650 mg, 1.45 mmol), $H_2O_2$ (1 mL, 30% purity) and acetic acid (1.45 mmol, 1 mL) in THF (4 mL) was stirred at 25° C. for 1 hr. The resulting solution was quenched with $Na_2SO_3$, filtered and concentrated. The residue was purified by FCC (silica gel, petroleum ether/ethyl acetate=1/1) to give 18-2 (460 mg, 1.36 mmol, 93.76% yield). MS: m/z=339 (M+H)

Step 3: 18-3

A mixture of 18-2 (200 mg, 590.99 μmol) and $Cs_2CO_3$ (963 mg, 2.96 mmol) in MeCN (20 mL) was stirred at 95° C. for 1 hr. The resulting mixture was filtered. The filtrate was concentrated. The residue was purified by FCC (silica gel, petroleum ether/ethyl acetate=1/1-1/4) to give 18-3 (270 mg, 513.67 μmol, 86.92% yield). MS: m/z=470 (M+H-56).

Step 4: 18-4

To a mixture of 18-3 (270 mg, 513.67 gmol) and $Ti(OiPr)_4$ (1.17 g, 4.11 mmol) in THF (20 mL) was added bromo (ethyl)magnesium (1 M in THF, 5.14 mL) dropwise at 25° C. After addition, the resulting mixture was stirred at 25° C. for 2 hr. The resulting mixture was quenched with aqueous $NH_4Cl$ and extracted with DCM (40 mL). The separated organic layer was washed with brine, dried over $Na_2SO_4$, filtered and concentrated. The residue was purified by FCC (silica gel, petroleum ether/ethyl acetate=1/1) to give 18-4 (100 mg, 190.97 μmol, 37.18% yield). MS: m/z=468 (M+H-56)

Step 5: Compound 18

A mixture of 18-4 (100 mg, 190.97 μmol) and HCl/Dioxane (4 M, 3 mL) in Dioxane (1 mL) was stirred at 25° C. for 1 hr. The resulting mixture was concentrated and purified by prep. HPLC (gradient: 5-95% B, A: 0.2% $HCO_2H$, B: MeCN, GT: 18 min, flow rate: 15 mL/min) to give Compound 18 (20 mg, 42.59 μmol, 22.30% yield, $HCO_2H$ salt). $^1H$ NMR (400 MHz, Methanol-$d_4$) δ 8.53 (s, 1H), 7.90-7.82 (m, 2H), 7.31 (s, 0.5H), 7.24-7.14 (m, 2H), 7.11 (s, 0.5H), 4.71 (d, J=3.6 Hz, 2H), 3.78 (d, J=2.3 Hz, 2H), 3.06 (s, 2H), 1.68 (dd, J=10.1, 5.7 Hz, 6H), 1.47 (dd, J=10.0, 5.5 Hz, 6H), 0.58-0.50 (m, 2H), 0.50-0.41 (m, 2H). MS: m/z=424 (M+H, ESI+).

Example 28: Synthesis of Compound 19 & 20

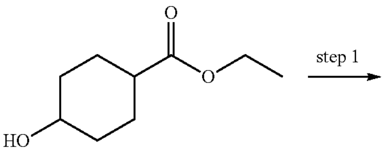

14-1

-continued

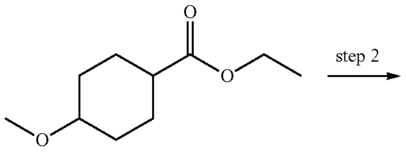

19-1

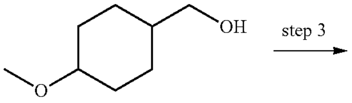

19-2

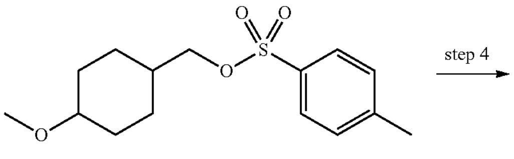

19-3

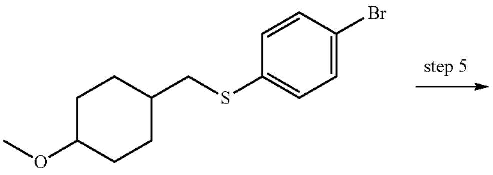

19-4

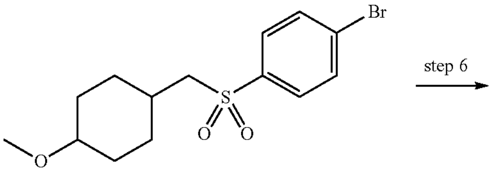

19-5

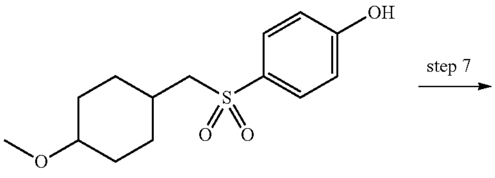

19-6

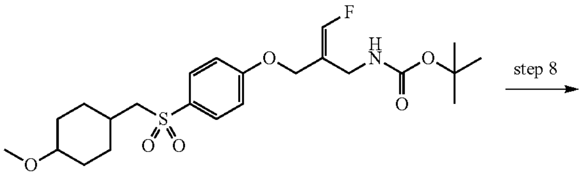

19-7

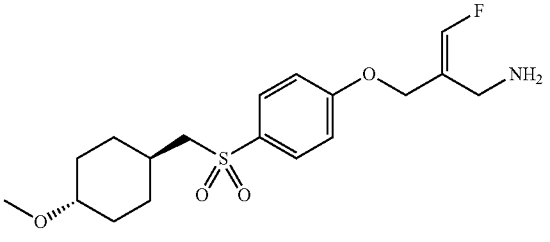

19

-continued

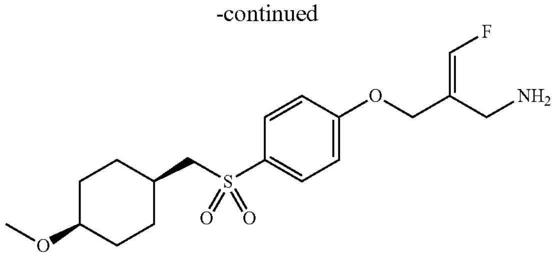

20

Step 1: 19-1

To a mixture of 14-1 (10 g, 58.06 mmol) in DMF (100 mL) was added NaH (4.64 g, 116.13 mmol, 60% purity) while the internal temperature was kept below 20° C. After addition, the resulting mixture was warmed up to 25° C. and stirred for 30 min, and then iodomethane (9.89 g, 69.68 mmol) was added. The reaction mixture was stirred at 25° C. for further 5 hr, poured into water (500 mL) and extracted with ethyl acetate (200 mL×3). The combined organic layers were dried over $Na_2SO_4$ and concentrated under reduced pressure. The residue was purified by silica gel column eluted with petroleum ether/ethyl acetate=3/1 to give 19-1 (3 g, 27.74% yield). $^1$H NMR (400 MHz, Chloroform-d) δ 4.12 (qd, J=7.1, 2.0 Hz, 2H), 3.33 (d, J=17.1 Hz, 3H), 3.13-3.09 (m, 1H), 2.25 (tt, J=11.7, 3.7 Hz, 1H), 2.15-2.06 (m, 1H), 2.06-1.96 (m, 2H), 1.95-1.77 (m, 2H), 1.65 (dq, J=14.3, 5.1 Hz, 1H), 1.57-1.40 (m, 2H), 1.25 (td, J=7.1, 4.7 Hz, 3H) ppm.

Step 2: 19-2

To a mixture of 19-1 (2.5 g, 13.42 mmol) in THF (25 mL) was added $LiAlH_4$ (1.53 g, 40.27 mmol) while the internal temperature was kept below 0° C. After addition, the resulting mixture was warmed up to 25° C. and stirred for 2 hr. The resulting mixture was quenched with ice water (300 mL) and filtered. The filtrate was extracted with ethyl acetate (100 mL×3) and the combined organic layers were dried over $Na_2SO_4$. After filtered, the filtrate was concentrated under reduced pressure and the residue was purified by silica gel column eluted with petroleum ether/ethyl acetate=2/1 to give 19-2 (1.5 g, 77.49% yield). $^1$H NMR (400 MHz, DMSO-$d_6$) δ 4.35 (dt, J=17.4, 5.3 Hz, 1H), 3.22 (s, 3H), 3.02-2.98 (m, 2H), 2.02-1.93 (m, 2H), 1.46-1.37 (m, 2H), 1.25-1.13 (m, 2H), 0.95-0.78 (m, 2H) ppm.

Step 3: 19-3

A mixture of 19-2 (500 mg, 3.47 mmol), 4-methylbenzenesulfonyl chloride (727.10 mg, 3.81 mmol) and TEA (701.68 mg, 6.93 mmol) in DCM (10 mL) was stirred at 25° C. for 5 hr. The resulting mixture was diluted with water (50 mL) and extracted with ethyl acetate (20 mL×3). The combined organic layers were dried over $Na_2SO_4$ and concentrated under reduced pressure. The residue was purified by silica gel column eluting with petroleum ether/ethyl acetate=3/1 to give 19-3 (760 mg, 70.52% yield). MS: m/z=299.1 (M+1, ESI+).

Step 4: 19-4

A mixture of 19-3 (750 mg, 2.51 mmol), 4-bromobenzenethiol (570.27 mg, 3.02 mmol) and $K_2CO_3$ (1.04 g, 7.54 mmol) in MeCN (15 mL) was stirred at 100° C. for 2 hr. After cooling down to 25° C., the resulting mixture was poured into water (100 mL) and extracted with ethyl acetate (30 mL×3). The combined organic layers were dried over $Na_2SO_4$ and concentrated under reduced pressure. The residue was purified by silica gel column (eluting with petroleum ether/ethyl acetate=10/1) to give 19-4 (590 mg, 72.97% yield). MS: m/z=316.03 (M+1, ESI+).

Step 5: 19-5

A mixture of 19-4 (590 mg, 1.83 mmol) and Oxone (2.25 g, 3.67 mmol) in MeOH/water (15 mL, 4/1) was stirred at 25° C. for 3 hr. The resulting mixture was diluted with water (100 mL) and extracted with ethyl acetate (30 mL×3). The combined organic layers were dried over $Na_2SO_4$ and concentrated under reduced pressure to give 19-5 (610 mg, 92.91% yield), which was used to next step without further purification. MS: m/z=347.02 (M+1, ESI+).

Step 6: 19-6

A mixture of 19-5 (600 mg, 1.68 mmol), $Pd_2(dba)_3$ (153.47 mg, 167.59 μmol), t-BuXPhos (142.33 mg, 335.19 μmol) and KOH (282.11 mg, 5.03 mmol) in Dioxane/water (12 mL, 1/1) was stirred at 100° C. for 2 hr under argon. After cooling down to 25° C., the resulting mixture was diluted with water (100 mL) and extracted with EA (30 mL×3). The combined organic layers were dried over $Na_2SO_4$ and concentrated under reduced pressure. The residue was purified by silica gel column (eluting with DCM/MeOH=20/1) to give 19-6 (500 mg, 92.91% yield). MS: m/z=285.1 (M+1, ESI+).

Step 7: 19-7

A mixture of 19-6 (300 mg, 1.05 mmol), Intermediate A (311.15 mg, 1.16 mmol) and $K_2CO_3$ (437.42 mg, 3.16 mmol) in DMF (6 mL) was stirred at 60° C. for 2 hr under argon. After cooling down to room temperature, the resulting mixture was diluted with water (100 mL) and extracted with eluting with ethyl acetate (30 mL×3). The combined organic layers were dried over $Na_2SO_4$ and concentrated under reduced pressure to give 19-7 (500 mg, 95.48% yield), which was used to next step without further purification. MS: m/z=472.2 (M+1, ESI+).

Step 8: Compound 19 & 20

To a mixture of 19-7 (500 mg, 954.24 μmol) in DCM (5 mL) was added HCl (3 M in ethyl acetate, 6.36 mL). After stirred at 25° C. for 3 hr, the excess of solvent was removed under reduced pressure. The residue was purified by prep-HPLC (column: Sunfire Prep C18 10 μm 19×250 mm; A: 0.05% HCl water, B: acetonitrile; gradient: 10-20% B; GT: 18 min; flow rate: 20 mL/min) to give Compound 19 (90 mg, 25.14% yield) and Compound 20 (100 mg, 27.65% yield). Compound 19: $^1H$ NMR (400 MHz, DMSO-$d_6$) δ 8.54 (s, 3H), 7.90-7.75 (m, 2H), 7.23 (d, J=9.0 Hz, 3H), 4.81 (d, J=3.6 Hz, 2H), 3.59 (d, J=2.1 Hz, 2H), 3.37 (s, 2H), 3.18 (s, 4H), 3.16 (s, 1H), 1.93-1.87 (m, 2H), 1.86-1.77 (m, 2H), 1.73-1.61 (m, 1H), 1.13-0.95 (m, 4H) ppm; MS: m/z=372.2 (M+1, ESI+). Compound 20: $^1H$ NMR (400 MHz, DMSO-$d_6$) δ 8.25 (s, 1H), 7.88-7.76 (m, 2H), 7.25-7.17 (m, 2H), 4.70 (d, J=3.4 Hz, 2H), 3.46 (d, J=2.3 Hz, 2H), 3.28-3.23 (m, 1H), 3.17 (d, J=4.7 Hz, 5H), 1.74 (dd, J=47.4, 7.8 Hz, 3H), 1.55-1.22 (m, 6H) ppm; MS: m/z=372.2 (M+1, ESI+).

Example 29: Synthesis of Compound 21 & 22

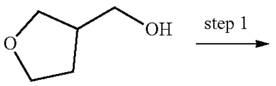

21-1

-continued

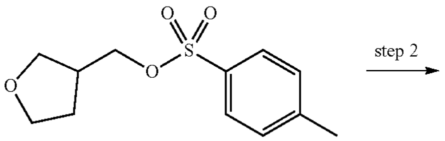

21-2

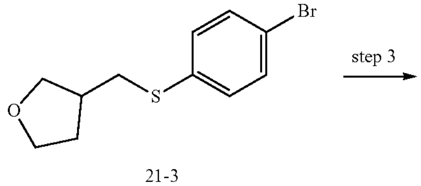

21-3

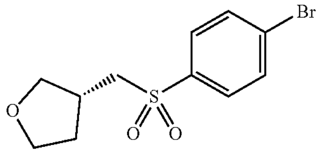

21-4

+

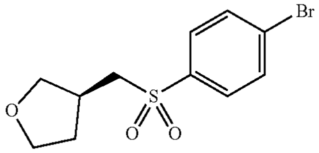

22-4

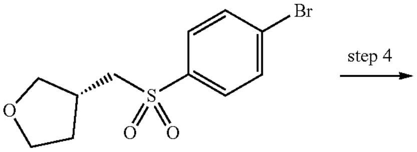

21-4

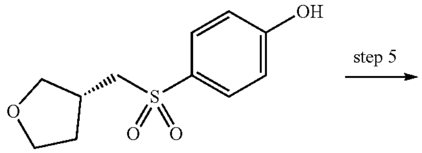

21-5

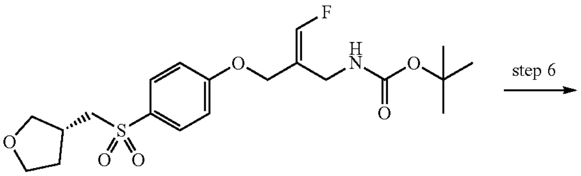

21-6

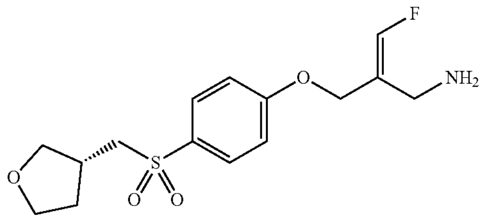

21

-continued

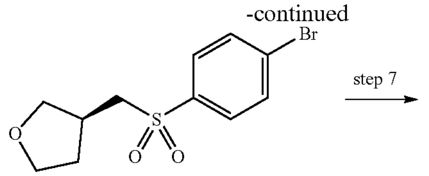

22-4

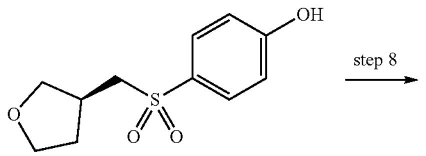

22-5

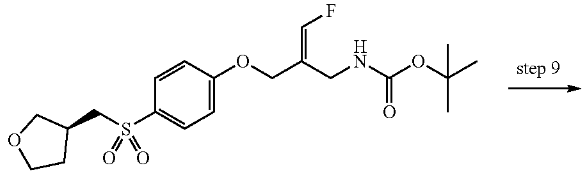

22-6

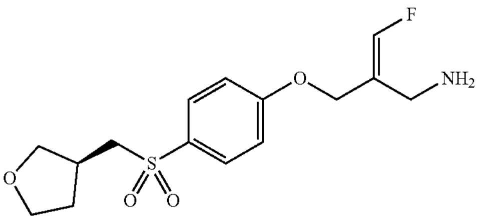

22

Step 1: 21-2

To a mixture of 21-1 (4.65 g, 45.53 mmol) and TEA (7.37 g, 72.85 mmol) in DCM (100 mL) was added 4-methylbenzenesulfonyl chloride (10.42 g, 54.64 mmol) at 0° C. After addition, the resulting mixture was warmed up to 10° C. and stirred for 18 hr. The reaction mixture was poured into ice water (100 mL) and extracted with DCM (100 mLx3). The combined organic layers were washed with brine (50 mLx3) and dried over anhydrous sodium sulfate. The solvent was removed under vacuum. The residue was purified by flash chromatography over silica gel eluting with ethyl acetate in petroleum ether (30%) to afford 21-2 (10.0 g, 85.69%). $^1$H NMR (400 MHz, $CDCl_3$) δ 7.75 (d, J=8.3 Hz, 2H), 7.32 (d, J=8.2 Hz, 2H), 3.91-3.88 (m, 2H), 3.77-3.61 (m, 3H), 3.46 (dd, J=9.1, 5.1 Hz, 1H), 2.60-2.49 (m, 1H), 2.42 (s, 3H), 2.01-1.90 (m, 1H), 1.57-1.46 (m, 1H) ppm.

Step 2: 21-3

To a mixture of 21-2 (3.1 g, 12.09 mmol) and 4-bromobenzenethiol (2.52 g, 13.30 mmol) in MeCN (50 mL) was added $K_2CO_3$ (5.01 g, 36.28 mmol). The resulting mixture was heated up to 100° C. and stirred for 4 hr. After that, the reaction mixture was cooled down to 10° C. and poured into water (100 mL). The aqueous mixture was extracted with DCM (100 mLx3). The combined organic layers were washed with brine (50 mLx3), dried over anhydrous sodium sulfate. The solvent was removed under reduced pressure. The residue was purified by silica gel column eluted with ethyl acetate in petroleum ether (8%) to afford 21-3 (3.0 g, 90.80%). $^1$H NMR (400 MHz, $CDCl_3$) δ 7.43-7.36 (m, 2H), 7.22-7.17 (m, 2H), 3.87-3.82 (m, 2H), 3.78-3.71 (m, 1H), 3.56 (dd, J=8.7, 5.8 Hz, 1H), 2.99-2.86 (m, 2H), 2.51-2.39 (m, 1H), 2.09-2.01 (m, 1H), 1.74-1.63 (m, 1H) ppm.

Step 3: 21-4 & 22-4

To a mixture of 21-3 (1.5 g, 5.49 mmol) in MeOH/$H_2O$ (35 mL, 4/1) was added Oxone (6.75 g, 10.98 mmol). After stirred at 10° C. for 2 hr, the reaction mixture was poured into water (100 mL) and the methanol was removed under reduced pressure. To the residue was added water (50 mL) and the aqueous mixture was extracted with ethyl acetate (100 mLx3). The combined organic layers were washed with brine (30 mLx3), dried over anhydrous sodium sulfate. The solvent was removed under reduced pressure to afford racemic mixture (1.5 g, 89.52%). $^1$H NMR (400 MHz, $CDCl_3$) δ 7.80-7.76 (m, 2H), 7.75-7.70 (m, 2H), 3.94 (dd, J=8.9, 7.1 Hz, 1H), 3.85 (td, J=8.4, 4.9 Hz, 1H), 3.73 (dd, J=16.0, 7.6 Hz, 1H), 3.50 (dd, J=8.9, 6.6 Hz, 1H), 3.23-3.09 (m, 2H), 2.68 (dt, J=14.3, 7.1 Hz, 1H), 2.18 (dtd, J=12.7, 7.7, 4.9 Hz, 1H), 1.68 (ddd, J=15.3, 12.7, 7.6 Hz, 1H) ppm. 300 mg of the racemic mixture was separated by SFC (column: Daicel chiralpak OD Prep C18 10 μm 25x250 mm; A: Supercritical $C_{02}$, B: EtOH; GT: 6 min; flow rate: 70 mL/min) to afford 21-4 or 22-4 (145 mg, 48.33%) and 22-4 or 21-4 (140 mg, 46.67%).

Step 4/7: 21-5 or 22-5

Procedure for one isomer was shown. To a mixture of 21-4 or 22-4 (145 mg, 475.12 μmol), $Pd_2(dba)_3$ (43.49 mg, 47.49 μmol) and t-BuXphos (40.50 mg, 95.02 μmol) in Dioxane/$H_2O$ (6 mL, 1/1) was added KOH (79.98 mg, 1.43 mmol). The resulting mixture was heated up to 100° C. and stirred for 1 hr under argon. After cooling down to 10° C., the solvent was removed under reduced pressure. To the aqueous residue was added water (50 mL). The pH value of aqueous mixture was adjusted to 3 with HCl (1 M in water). The aqueous mixture was extracted with ethyl acetate (50 mLx3). The combined organic layers were washed with brine (30 mLx3), dried over anhydrous sodium sulfate. The solvent was removed under vacuum. The residue was purified by flash chromatography over silica gel eluted with MeOH in DCM (5%) to afford 21-5 or 22-5 (110 mg, 95.56%). MS: m/z=243 (M+1, ESI+).

Step 5/8: 21-6 or 22-6

Procedure for one isomer was shown. To a mixture of 21-5 or 22-5 (55 mg, 227.0 mol) and Intermediate A (60.86 mg, 227.0 μmol) in MeCN (5 mL) was added $Cs_2CO_3$ (147.91 mg, 454.0 μmol). The resulting mixture was heated up to 80° C. and stirred for 15 hr. After cooling down to 10° C., the reaction mixture was poured into water (50 mL) and extracted with DCM (50 mLx3). The combined organic layers were washed with brine (30 mLx3), dried over anhydrous sodium sulfate. The solvent was removed under reduced pressure to afford 21-6 or 22-6 (80 mg, 82.05%), which was used to next step without further purification. MS: m/z=448 (M+18, ESI+).

Step 6/9: Compound 21 or 22

Procedure for one isomer was shown. To a mixture of 21-6 or 22-6 (80 mg, 186.26 μmol) in DCM (2 mL) was added HCl (2 mL, 3M in ethyl acetate). The resulting mixture was stirred at 10° C. for 1 hr. After that, the solvent was removed under reduced pressure. The residue was purified by prep-HPLC (column: Sunfire Prep C18 10 μm 19x250 mm; A: 0.05% HCl water, B: acetonitrile; gradient: 15-33% B; GT: 18 min; flow rate: 20 mL/min) to afford Compound 21 or 22 (30 mg, 44.02%). $^1$H NMR (400 MHz, DMSO-$d_6$) δ 8.43 (s, 3H), 7.85 (d, J=8.9 Hz, 2H), 7.47-7.20 (m, 3H), 4.78 (d, J=2.9 Hz, 2H), 3.74 (dd, J=8.5, 7.4 Hz, 1H), 3.67 (td, J=8.3, 5.0 Hz, 1H), 3.63-3.53 (m, 3H), 3.39 (tt, J=7.5, 5.7 Hz, 2H), 3.33-3.27 (m, 1H), 2.36 (dt, J=14.5, 7.4 Hz, 1H), 1.96 (dtd, J=12.4, 7.6, 4.9 Hz, 1H), 1.56-1.50 (m, 1H) ppm. MS: m/z=330 (M+1, ESI+). The other isomer, Compound 22 or 21 (35 mg) was obtained via the similar route. $^1$H NMR (400 MHz, DMSO) δ 8.32 (s, 3H), 7.88-7.82 (m, 2H), 7.46-7.20 (m, 3H), 4.76 (d, J=3.2 Hz, 2H), 3.75 (dd, J=8.5, 7.4 Hz, 1H), 3.67 (td, J=8.2, 4.9 Hz, 1H), 3.63-3.53 (m, 3H), 3.47-3.35 (m, 2H), 3.34-3.27 (m, 2H), 2.36 (dt, J=14.5, 7.4 Hz, 1H), 1.97-1.92 (m, 1H), 1.61-1.51 (m, 1H) ppm. MS: m/z=330 (M+1, ES+)

Example 30: Synthesis of Compound 23 & 24

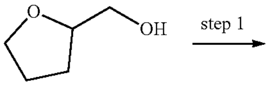

23-1

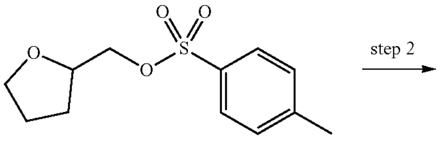

23-2

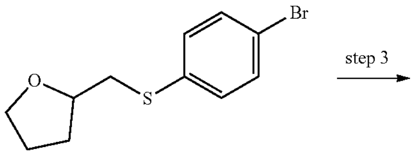

23-3

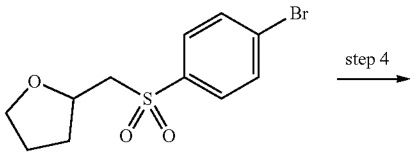

23-4

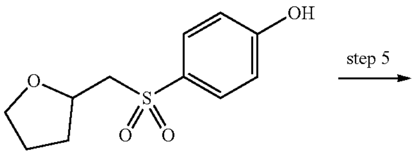

23-5

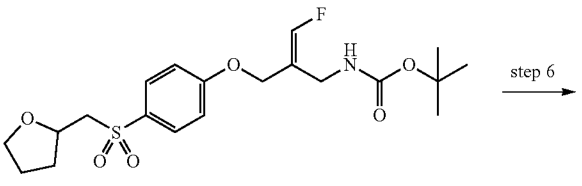

23-6

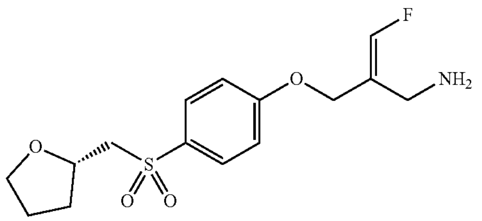

+

23

-continued

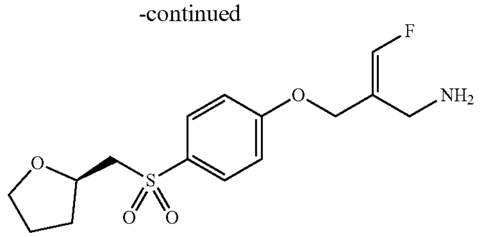

24

Step 1: 23-2

To a mixture of 23-1 (10 g, 97.91 mmol) in DCM (80 mL) was added TEA (24.77 g, 244.78 mmol) and 4-methylbenzenesulfonyl chloride (17.26 g, 244.78 mmol). After stirred at 25° C. for 6 hr, the resulting mixture was concentrated. To the residue was added water (500 mL) and the aqueous mixture was extracted with ethyl acetate (500 mL×2). The combined organic layers were washed with water (500 mL), brine (500 mL), dried over $Na_2SO_4$. The solvent was removed under reduced pressure. The residue was purified by silica gel column eluted with petroleum ether/ethyl acetate (4/1) to afford 23-2 (10 g, 39.85% yield). $^1$H NMR (400 MHz, $CDCl_3$) δ 7.72 (d, J=8.3 Hz, 2H), 7.25 (t, J=15.6 Hz, 2H), 4.06-3.83 (m, 3H), 3.68-3.63 (m, 2H), 2.37 (s, 3H), 1.99-1.71 (m, 3H), 1.70-1.46 (m, 1H) ppm.

Step 2: 23-3

A mixture of 23-2 (2.56 g, 9.99 mmol), 4-bromobenzenethiol (2.27 g, 11.99 mmol) and $K_2CO_3$ (2.07 g, 14.98 mmol) in DMF (40 mL) was stirred at 100° C. for 16 hr. After cooling down to room temperature, the resulting mixture was poured into water (200 mL) and extracted with ethyl acetate (200 mL×2). The combined organic layers were washed with water (200 mL), brine (100 mL), dried over $Na_2SO_4$. The solvent was removed under reduced pressure. The residue was purified by silica gel column eluted with petroleum ether/ethyl acetate (10/1) to afford 23-3 (1.5 g, 54.98% yield). MS: m/z=273 (M+1, ESI+).

Step 3: 23-4

To a mixture of 23-3 (1 g, 3.66 mmol) in MeOH and $H_2O$ (35 mL, 4:1) was added Oxone (4.50 g, 7.32 mmol). After stirred at 10° C. for 2 hr, the resulting mixture was poured into water (100 mL) and the methanol was removed under reduced pressure. To the residue was added water (50 mL) and the aqueous mixture was extracted with ethyl acetate (50 ml×3). The combined organic layers were washed with brine (30 mL×3), dried over anhydrous sodium sulfate. The solvent was removed under reduced pressure to afford 23-4 (1.1 g, 98.47%), which was used to the next step without further purification. $^1$H NMR (400 MHz, CDCl3) δ 7.82-7.77 (m, 2H), 7.72-7.67 (m, 2H), 4.26 (m, J=6.9, 5.4 Hz, 1H), 3.79-3.72 (m, 1H), 3.71-3.63 (m, 1H), 3.39 (dd, J=14.3, 6.9 Hz, 1H), 3.22 (dd, J=14.3, 5.3 Hz, 1H), 2.20-2.09 (m, 1H), 1.92-1.84 (m, 2H), 1.70-1.59 (m, 1H) ppm.

Step 4: 23-5

To a suspension of 23-4 (1.1 g, 3.60 mmol), t-BuXPhos (306.11 mg, 720.87 μmol) and $Pd_2(dba)_3$ (330.06 mg, 360.43 μmol) in Dioxane/$H_2O$ (20 mL, 1/1) was added KOH (202.24 mg, 3.60 mmol). The resulting mixture was heated up to 100° C. and stirred for 1 hr under argon. After cooling down to 10° C., the solvent was removed under reduced pressure. To the residue was added water (50 mL). The pH value of the resulting mixture was adjusted to 3 with HCl (1 M in water). The aqueous mixture was extracted with DCM (70 mL×3). The combined organic layers were washed with brine (30 mL×3), dried over anhydrous sodium sulfate. The solvent was removed under vacuum. The residue was purified by flash chromatography over silica gel eluted with MeOH in DCM (5%) to afford 23-5 (800 mg, 91.61%). MS: m/z=243 (M+1, ESI+).

Step 5: 23-6

To a mixture of 23-5 (215 mg, 887.36 μmol), Intermediate A (261.71 mg, 976.10 mol) in MeCN (5 mL) was added $Cs_2CO_3$ (722.80 mg, 2.22 mmol). The resulting mixture was heated up to 80° C. and stirred for 15 hr. After cooling down to 10° C., the resulting mixture was poured into water (30 mL) and extracted with DCM (30 mL×3). The combined organic layers were washed with brine (30 mL×3), dried over anhydrous sodium sulfate. The solvent was removed under reduced pressure. The residue was purified by silica gel column eluted with ethyl acetate in petroleum ether (10%) to afford 23-6 (300 mg, 78.71%). $^1H$ NMR (400 MHz, $CDCl_3$) δ 7.88-7.80 (m, 2H), 7.04-6.98 (m, 2H), 6.88-6.64 (m, 1H), 4.75 (s, 1H), 4.51 (d, J=3.2 Hz, 2H), 4.22 (p, J=6.4 Hz, 1H), 3.98 (t, J=10.5 Hz, 2H), 3.81-3.73 (m, 1H), 3.72-3.65 (m, 1H), 3.38 (dd, J=14.2, 6.3 Hz, 1H), 3.18 (dd, J=14.2, 5.9 Hz, 1H), 2.12 (m, 1H), 1.93-1.83 (m, 2H), 1.65-1.60 (m, 2H), 1.40 (s, 9H) ppm.

Step 6: Compound 23 & 24

To a mixture of 23-6 (300 mg, 698.48 μmol) in DCM (3 mL) was added HCl (3 mL, 3 M in ethyl acetate). After stirred at 10° C. for 4 hr, the solvent was removed under reduced pressure. The residue was purified by Prep-HPLC (column: Sunfire Prep C18 10 μm 19×250 mm; A: 0.05% HCl water, B: acetonitrile; gradient: 10-35% B; GT: 18 min; flow rate: 20 mL/min) and SFC (column: Daicel chiralpak OD Prep C18 10 μm 25×250 mm; A: Supercritical $CO_2$, B: EtOH; GT: 14 min; flow rate: 70 mL/min) to afford Compound 23 or 24 (41 mg, 16.04%). $^1H$ NMR (400 MHz, DMSO-d6) δ 8.09 (br, 3H), 7.84 (d, J=8.8 Hz, 2H), 7.36 (d, J=81.8 Hz, 1H), 7.20 (d, J=8.9 Hz, 2H), 4.71 (s, 2H), 4.04 (p, J=6.5 Hz, 1H), 3.60 (dd, J=14.3, 7.7 Hz, 3H), 3.55-3.43 (m, 3H), 1.94 (td, J=12.2, 7.5 Hz, 1H), 1.84-1.69 (m, 2H), 1.55-1.51 (m, 1H) ppm. MS: m/z=330 (M+1, ESI+). Compound 24 or 23 (46 mg, 18.00%). $^1H$ NMR (400 MHz, DMSO-d6) δ 8.29 (s, 3H), 7.83 (d, J=5.8 Hz, 2H), 7.35 (d, J=81.8 Hz, 1H), 7.21 (d, J=8.9 Hz, 2H), 4.75 (d, J=3.1 Hz, 2H), 4.04 (p, J=6.5 Hz, 1H), 3.60 (q, J=7.5 Hz, 3H), 3.55-3.50 (m, 1H), 3.47 (dd, J=6.0, 4.2 Hz, 2H), 2.01-1.89 (m, 1H), 1.84-1.67 (m, 2H), 1.55-1.50 (m, 1H) ppm. MS: m/z=330 (M+1, ESI+).

Example 31: Synthesis of Compound 25

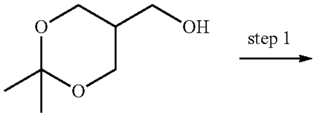

25-1

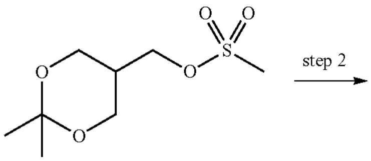

25-2

-continued

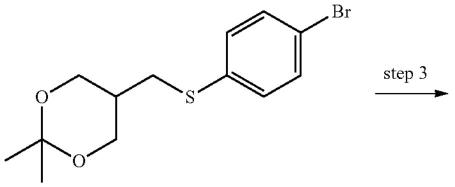

25-3

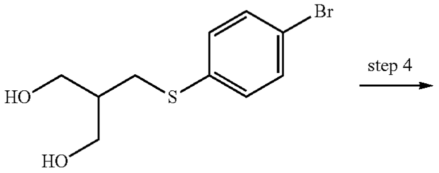

25-4

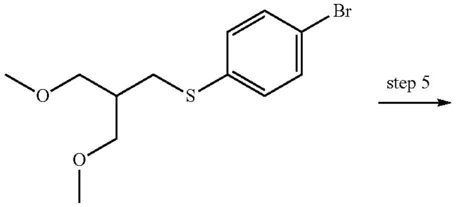

25-5

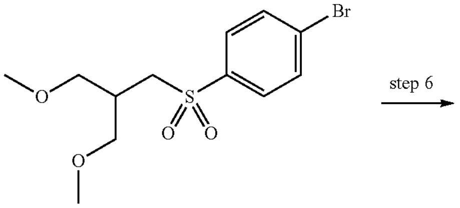

25-6

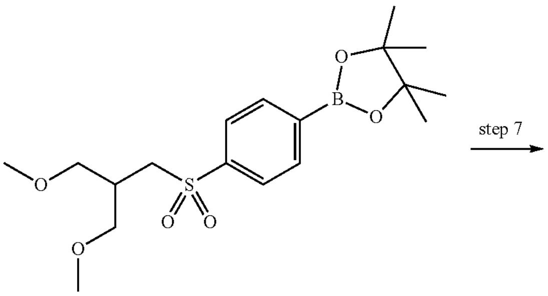

25-7

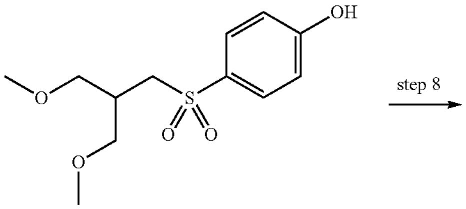

25-8

-continued

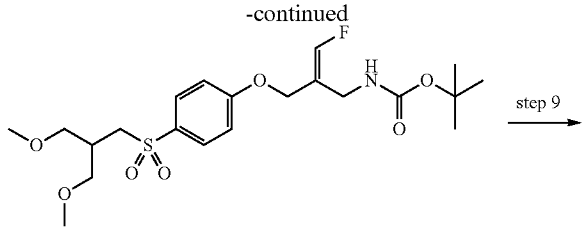

25-9

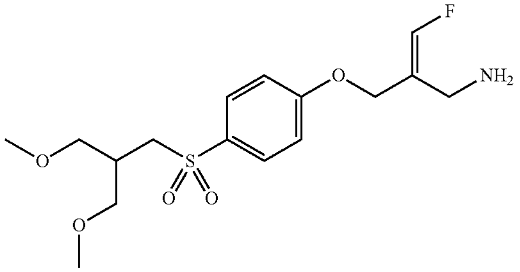

25

Step 1: 25-2

To a mixture of 25-1 (1.0 g, 6.84 mmol), $Et_3N$ (1.38 g, 13.68 mmol) in DCM (45 mL) was added methanesulfonyl chloride (861.97 mg, 7.52 mmol, 582.41 μL) at 25° C. The reaction solution was stirred for 1 hr at 25° C. Then, the solution was filtered and concentrated with a rotary evaporator. The crude product was purified by silica gel chromatography (ethyl acetate in petroleum ether, 0 to 50%, v/v) to obtain 25-2 (1.1 g, 4.90 mmol, 71.70% yield).

Step 2: 25-3

To a mixture of 4-bromobenzenethiol (400 mg, 2.12 mmol) in DMF (20 ml) was added NaH (110.0 mg, 2.75 mmol, 60% purity) at 25° C. The reaction solution was stirred for 0.5 hr at 25° C. Then, 25-2 (521.92 mg, 2.33 mmol) was added. The reaction solution was stirred for another 18 hr at 25° C. Then, the solution was concentrated with a rotary evaporator. The crude product was purified by silica gel chromatography (ethyl acetate in petroleum ether, 0 to 40%) to obtain 25-3 (410 mg, 1.29 mmol, 61.09% yield).

Step 3: 25-4

To a mixture of 25-3 (200 mg, 630.44 μmol) in MeOH (15 mL) was added HCl/Dioxane (4 M, 4 mL) at 25° C. and the reaction mixture was stirred at 25° C. for 2 hr. Then, the solution was concentrated with a rotary evaporator to obtain 25-4 (180 mg, crude).

Step 4: 25-5

To a mixture of 25-4 (180 mg, 649.40 μmol) in DMF (10 mL) was added NaH (64.93 mg, 1.62 mmol, 60% purity) at 25° C. The reaction solution was stirred for 0.5 hr at 25° C. Then, iodomethane (276.53 mg, 1.95 mmol, 121.28 μL) was added. The reaction solution was stirred further for 18 hr at 25° C. Then, the solution was concentrated with a rotary evaporator. The crude product was purified by silica gel chromatography (ethyl acetate in petroleum ether, 0 to 50%) to obtain 25-5 (180 mg, 589.72 μmol, 90.81% yield).

Step 5: 25-6

To a mixture of 25-5 (180 mg, 589.72 μmol) in DCM (20 mL) was added m-CPBA (119.73 mg, 589.72 μmol, 85% purity) at 25° C. The mixture was stirred for 1 hr at 25° C. Then, the solution was washed with saturated aqueous $Na_2SO_3$ (10 mL), saturated aqueous $NaHCO_3$ (20 mL×2) and brine (15 mL), dried over $Na_2SO_4$ and concentrated with a rotary evaporator to obtain 25-6 (210 mg, crude).

Step 6: 25-7

To a mixture of 25-6 (210 mg, 622.72 μmol), 4,4,5,5-tetramethyl-2-(4,4,5,5-tetramethyl-1,3,2-dioxaborolan-2-yl)-1,3,2-dioxaborolane (189.76 mg, 747.27 μmol) and KOAc (183.35 mg, 1.87 mmol) in Dioxane (10 mL) was added Pd(dppf)$Cl_2$ (45.56 mg, 62.27 μmol) at 25° C. The reaction solution was heated to 120° C. for 0.667 hr under microwave. The mixture was filtered and the filtrate was evaporated to obtain 25-7 (300 mg, crude).

Step 7: 25-8

To a mixture of 25-7 (300 mg, 780.65 μmol), acetic acid (0.4 mL) in THF (15 mL) was added $H_2O_2$ (0.3 mL, 30% purity) at 25° C. The reaction solution was stirred for 1 hr at 25° C. Then, to the solution was added $Na_2SO_3$ (0.5 g), filtered and concentrated with a rotary evaporator to obtain 25-8 (250 mg, crude). MS: m/z=273 (M-1).

Step 8: 25-9

To a mixture of 25-8 (250 mg, 911.30 μmol), Intermediate A (160 mg, 596.74 mol) in MeCN (30 mL) was added $Cs_2CO_3$ (890.76 mg, 2.73 mmol) at 25° C. The reaction solution was stirred for 1 hr at 90° C. Then, the mixture was filtered, and the filtrate was concentrated with a rotary evaporator to obtain 25-9 (230 mg, crude). The crude product was used for the next step without further purification. MS: m/z=462 (M+1).

Step 9: Compound 25

To a mixture of 25-9 (230 mg, 498.33 μmol) in DCM (15 mL) was added HCl/Dioxane (4 M, 4 mL) at 25° C. and the reaction mixture was stirred at 25° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 25 (67 mg, 164.44 μmol, 33.0% yield, $HCO_2H$ salt). MS: m/z=362 (M+1). $^1H$ NMR (400 MHz, Methanol-$d_4$) δ 7.90 (d, J=8.9 Hz, 2H), 7.29-7.21 (m, 2H), 7.28 (d, J=81.0 Hz, 1H), 4.74 (dd, J=3.6, 1.1 Hz, 2H), 3.92-3.81 (m, 2H), 3.47-3.37 (m, 4H), 3.26 (s, 6H), 3.25 (s, 2H), 2.34-2.31 (m, 1H).

Example 32: Synthesis of Compound 26

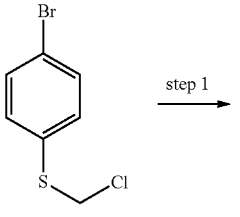

Intermediate D

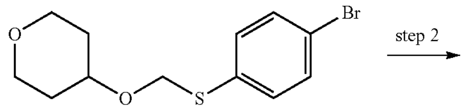

26-1

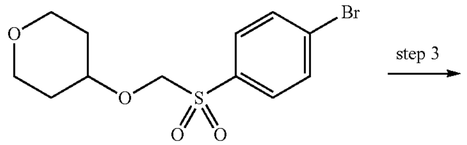

26-2

-continued

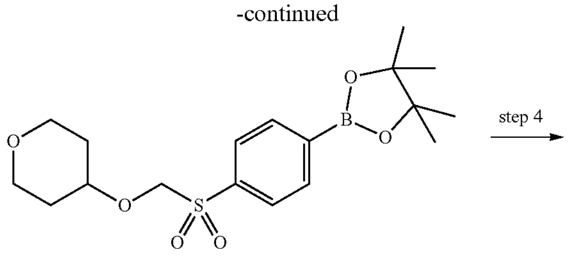

26-3

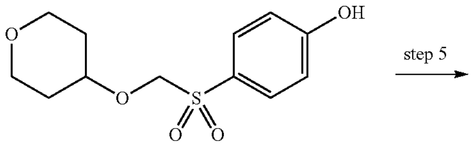

26-4

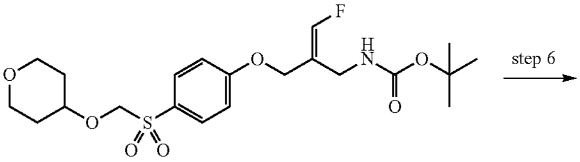

26-5

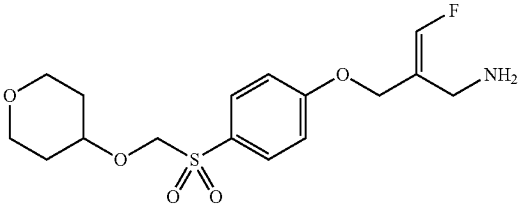

26

Step 1: 26-1

To a mixture of tetrahydropyran-4-ol (322.46 mg, 3.16 mmol) in DMF (10 mL) was added NaH (126.28 mg, 3.16 mmol, 60% purity) at 20° C. The reaction solution was stirred for 0.5 hr at 20° C. Then, Intermediate D (500 mg, 2.10 mmol) was added. The reaction solution was stirred further for 18 hr at 20° C. Then, the solution was concentrated with a rotary evaporator. The crude product was purified by silica gel chromatography (ethyl acetate in petroleum ether, 0 to 10%) to obtain 26-1 (300 mg, 989.40 μmol, 47.01% yield).

Step 2: 26-2

To a mixture of 26-1 (300 mg, 989.40 μmol) in DCM (20 mL) was added m-CPBA (602.60 mg, 2.97 mmol, 85% purity) at 20° C. The mixture was stirred for 1 hr at 20° C. Then, the solution was washed with saturated aqueous $Na_2SO_3$ (10 mL), saturated aqueous $NaHCO_3$ (20 mL×2) and brine (15 mL), dried over $Na_2SO_4$ and concentrated with a rotary evaporator to obtain 26-2 (350 mg, crude).

Step 3: 26-3

To a mixture of 26-2 (350 mg, 1.04 mmol), 4,4,5,5-tetramethyl-2-(4,4,5,5-tetramethyl-1,3,2-dioxaborolan-2-yl)-1,3,2-dioxaborolane (318.17 mg, 1.25 mmol) and KOAc (188.10 mg, 3.13 mmol) in Dioxane (10 mL) was added Pd(dppf)$Cl_2$ (76.40 mg, 104.41 μmol) at 20° C. The reaction solution was heated at 120° C. for 0.667 hr under microwave. The mixture was filtered, and the filtrate was concentrated. The residual material was dissolved in DCM (15 mL), washed with $H_2O$ (15 mL) and brine (15 mL) and concentrated with a rotary evaporator to obtain 26-3 (420 mg, crude).

Step 4: 26-4

To a mixture of 26-3 (420 mg, 1.10 mmol), acetic acid (0.3 mL) in THF (10 mL) was added hydrogen peroxide (0.5 mL, 30% purity) at 20° C. The reaction solution was stirred for 1 hr at 20° C. Then, the solution was concentrated with a rotary evaporator to obtain 26-4 (300 mg, crude). MS: m/z=271 (M-1).

Step 5: 26-5

To a mixture of 26-4 (300 mg, 1.10 mmol), Intermediate A (100 mg, 372.96 μmol) in MeCN (30 mL) was added $Cs_2CO_3$ (364.56 mg, 1.12 mmol) at 20° C. The reaction solution was stirred for 1 hr at 90° C. Then, the mixture was filtered, and the filtrate was concentrated with a rotary evaporator to obtain 26-5 (200 mg, crude). MS: m/z=460 (M+1).

Step 6: Compound 26

To a mixture of 26-5 (200 mg, 435.23 μmol) in DCM (15 mL) was added HCl/Dioxane (4 M, 3 mL) at 20° C. and the reaction mixture was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 10-40% B; GT: 15 min; flow rate: 15 mL/min) to obtain Compound 26 (13 mg, 36.17 mol, 8.31% yield). MS: m/z=360 (M+1). $^1H$ NMR (400 MHz, Methanol-$d_4$) δ 7.89-7.81 (m, 2H), 7.23-7.17 (m, 2H), 6.98 (d, J=82.9 Hz, 1H), 4.69 (s, 2H), 3.88 (m, 1H), 3.80 (m, 2H), 3.52 (d, J=2.4 Hz, 2H), 3.40 (m, 2H), 1.91-1.84 (m, 2H), 1.49 (m, 2H). MS: m/z=360.13 (M+1)

Example 33: Synthesis of Compound 27

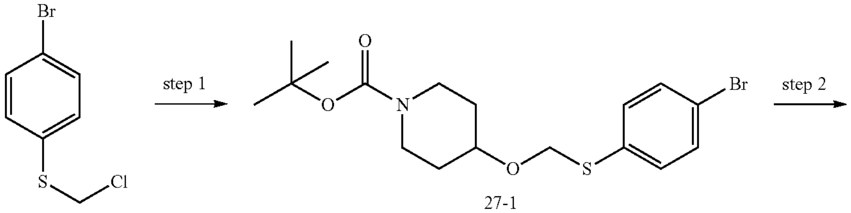

27-1

Intermediate D

-continued

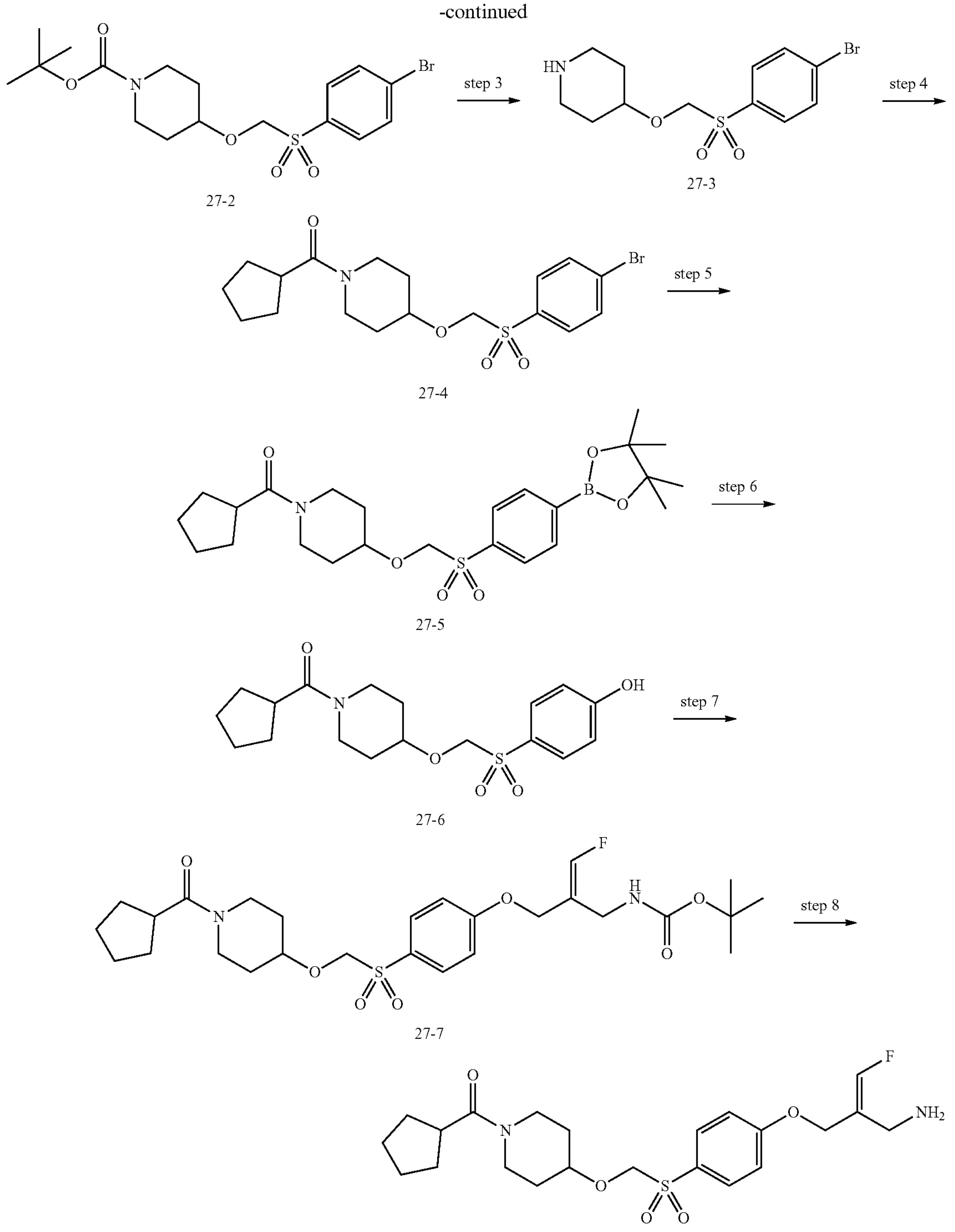

27-2

27-3

27-4

27-5

27-6

27-7

27

Step 1: 27-1

To a mixture of tert-butyl 4-hydroxypiperidine-1-carboxylate (651.74 mg, 3.24 mmol) in DMF (20 mL) was added NaH (194.28 mg, 4.86 mmol, 60% purity) at 25° C. The reaction solution was stirred for 0.5 hr at 25° C. Then, Intermediate D (1.0 g, 4.21 mmol) was added. The reaction solution was stirred for further 18 hr at 25° C. Then, the solution was concentrated with a rotary evaporator. The crude product was purified by silica gel chromatography (ethyl acetate in petroleum ether, 0 to 10%) to obtain 27-1 (800 mg, 1.99 mmol, 61.40% yield). MS: m/z=402 (M+1).

Step 2: 27-2

To a mixture of 27-1 (200 mg, 497.09 μmol) in DCM (20 mL) was added m-CPBA (403.68 mg, 1.99 mmol, 85% purity) at 25° C. The mixture was stirred for 1 hr at 25° C. Then, the solution was washed with saturated aqueous $Na_2SO_3$ (10 mL), saturated aqueous $NaHCO_3$ (20 mL×2)

and brine (15 mL), dried over $Na_2SO_4$ and concentrated with a rotary evaporator to obtain 27-2 (250 mg, crude). MS: m/z=434 (M+1).

Step 3: 27-3

To a mixture of 27-2 (250 mg, 575.58 μmol) in DCM (20 mL) was added HCl/Dioxane (4 M, 2 mL) at 25° C. and the reaction mixture was stirred at 25° C. for 1 hr. Then, the solution was concentrated with a rotary evaporator to obtain 27-3 (220 mg, crude, HCl salt). The crude product was used for the next step without further purification. MS: m/z=334 (M+1).

Step 4: 27-4

To a mixture of 27-3 (220 mg, 593.49 μmol), $Et_3N$ (180.16 mg, 1.78 mmol) in DCM (20 mL) was added cyclopentanecarbonyl chloride (86.56 mg, 652.84 μmol) at 25° C. The reaction solution was stirred for 1 hr at 25° C. Then, the solution was filtered and concentrated with a rotary evaporator. The crude product was purified by silica gel chromatography (ethyl acetate in petroleum ether, 0 to 60%, v/v) to obtain 27-4 (180 mg, 418.26 μmol, 70.47% yield). MS: m/z=430 (M+1).

Step 5: 27-5

To a mixture of 27-4 (180 mg, 418.26 μmol), 4,4,5,5-tetramethyl-2-(4,4,5,5-tetramethyl-1,3,2-dioxaborolan-2-yl)-1,3,2-dioxaborolane (127.45 mg, 501.91 μmol) and KOAc (123.15 mg, 1.25 mmol) in Dioxane (10 mL) was added $Pd(dppf)Cl_2$ (30.60 mg, 41.83 μmol) at 25° C. The reaction solution was heated to 120° C. for 0.667 hr under microwave. The mixture was filtered and the filtrate was evaporated to obtain 27-5 (220 mg, crude). MS: m/z=478 (M+1).

Step 6: 27-6

To a mixture of 27-5 (220 mg, 460.81 μmol), acetic acid (0.5 mL) in THF (10 mL) was added $H_2O_2$ (0.2 mL, 30% purity) at 25° C. The reaction solution was stirred for 1 hr at 25° C. Then, to the solution was added $Na_2SO_3$ (0.5 g), filtered and concentrated with a rotary evaporator to obtain 27-6 (230 mg, crude). MS: m/z=368 (M+1).

Step 7: 27-7

To a mixture of 27-6 (230 mg), Intermediate A (120 mg, 447.56 μmol) in MeCN (20 mL) was added $Cs_2CO_3$ (611.81 mg, 1.88 mmol) at 25° C. The reaction solution was stirred for 1 hr at 90° C. Then, the mixture was filtered, and the filtrate was concentrated with a rotary evaporator to obtain 27-7 (250 mg, crude). MS: m/z=555 (M+1).

Step 8: Compound 27

To a mixture of 27-7 (250 mg, 450.72 μmol) in DCM (15 mL) was added HCl/Dioxane (4 M, 3 mL) at 25° C. and the reaction mixture was stirred at 25° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, GT: 15 min; flow rate: 15 mL/min) to obtain Compound 27 (85 mg, 169.80 μmol, 37.67% yield, $HCO_2H$ salt). $^1H$ NMR (400 MHz, Methanol-d4) δ 7.91 (d, J=8.9 Hz, 2H), 7.29-7.22 (m, 2H), 7.27 (d, J=81.0 Hz, 1H), 4.75 (s, 4H), 4.00-3.95 (m, 1H), 3.85 (d, J=2.3 Hz, 2H), 3.78-3.64 (m, 3H), 3.40-3.32 (m, 2H), 3.10-2.98 (m, 1H), 2.00-1.40 (m, 12H). MS: m/z=455.74 (M+1, ESI+).

Example 34: Synthesis of Compound 28

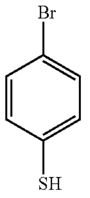

D-1

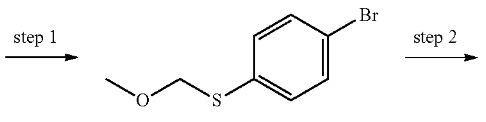

28-1

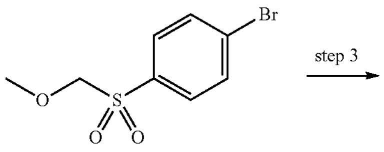

28-2

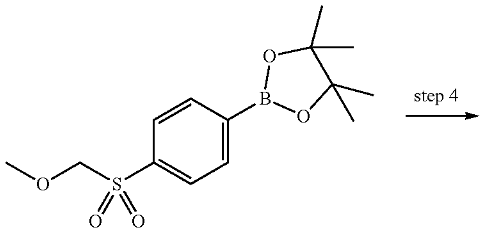

28-3

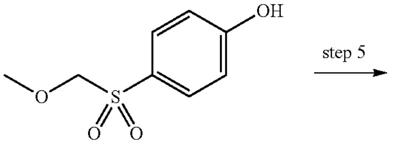

28-4

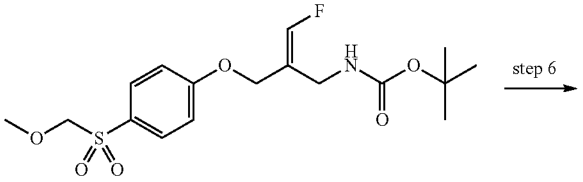

28-5

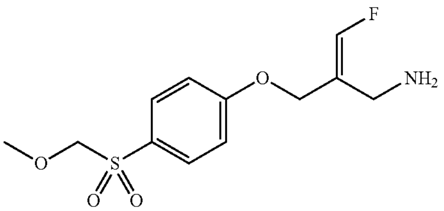

28

Step 1: 28-1

A mixture of D-1 (1 g, 5.29 mmol) and chloro(methoxy) methane (511.0 mg, 6.35 mmol) in MeCN (10 mL) was added $K_2CO_3$ (2.19 g, 15.87 mmol) at 20° C. The reaction solution was stirred for 1 hr at 40° C. Then, the solution was filtered and concentrated to obtain 28-1 (1 g, 4.29 mmol, 81.10% yield), which was used in the next step without purification.

Step 2: 28-2

A mixture of 28-1 (1 g, 4.29 mmol) and m-CPBA (2.37 g, 12.87 mmol, 85% purity) in DCM (50 mL) was stirred at 20° C. for 1 hr. $Na_2SO_3$ (6 g) was added to the mixture and stirred for 20 min. Then, the solution was filtered, concentrated and purified by silica gel chromatography (petroleum ether/ethyl acetate=5/1-1/1, v/v) to obtain 28-2 (800 mg, 3.02 mmol, 70.34% yield). MS: m/z=265 (M+1).

Step 3: 28-3

To a mixture of 28-2 (800 mg, 3.02 mmol), 4,4,4',4',5,5,5',5'-octamethyl-2,2'-bi(1,3,2-dioxaborolane) (919.50 mg, 3.62 mmol) and cyclopentyl(diphenyl)phosphane; dichloropalladium; iron (220.79 mg, 301.75 μmol) in Dioxane (10 mL) was added KOAc (888.42 mg, 9.05 mmol) at 20° C. under the nitrogen atmosphere. The reaction solution was stirred for 4 hr at 100° C. Then, the solution was concentrated with a rotary evaporator. The crude product was dissolved in ethyl acetate (60 mL), washed with $H_2O$ (100 mL×3), dried over $Na_2SO_4$, filtered and concentrated to obtain 28-3 (300 mg, 960.96 μmol, 31.85% yield). MS: m/z=312 (M+1).

Step 4: 28-4

To a mixture of 28-3 (300 mg, 960.96 μmol) in MeCN (4 mL) and acetic acid (1 mL) was added $H_2O_2$ (0.5 mL, 30% purity). The mixture was stirred at 25° C. for 1 hr. $Na_2SO_3$ (0.5 g) was added to the mixture and stirred for 20 min. The mixture was filtered and concentrated to give 28-4 (300 mg, crude). MS: m/z=202 (M+1, ESI+).

Step 5: 28-5

To a mixture of 28-4 (300 mg, 1.48 mmol) and Intermediate A (150 mg, 559.45 μmol) in MeCN (10 mL) was added $Cs_2CO_3$ (483.35 mg, 1.48 mmol) at 20° C. The reaction solution was stirred for 1 hr at 80° C. Then, the solution was filtered and concentrated to obtain 28-5 (400 mg, crude). MS: m/z=389 (M+1, ESI+).

Step 6: Compound 28

A mixture of 28-5 (200 mg, 513.56 μmol) in HCl/Dioxane (4 M, 4 mL) was stirred at 25° C. for 1 hr. Then, the solution was concentrated with a rotary evaporator. The crude product was purified by prep-HPLC (column: XBridge@ Prep C18 5 m 19×150 mm; A: 0.1% $HCO_2H$ water, B: acetonitrile; gradient: 2-30% B; GT: 15 min; flow rate: 15 mL/min) to obtain Compound 28 (80 mg, 238.56 μmol, 46.45% yield, $HCO_2H$ salt). $^1H$ NMR (400 MHz, Methanol-d4) δ 7.96 (d, J=8.0 Hz, 2H), 7.25 (d, J=80.0 Hz, 2H), 7.23 (d, J=8.0 Hz, 2H), 4.72 (dd, J=3.6, 1.0 Hz, 2H), 4.58 (s, 2H), 3.82 (d, J=2.3 Hz, 2H), 3.57 (s, 3H). ppm; MS: m/z=420.93 (M+1, ESI+).

Example 35: Synthesis of Compound 29

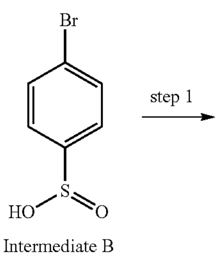

Intermediate B

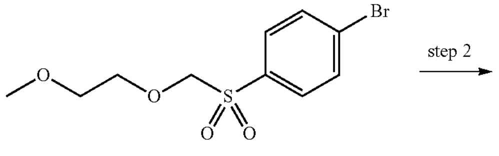

29-1

-continued

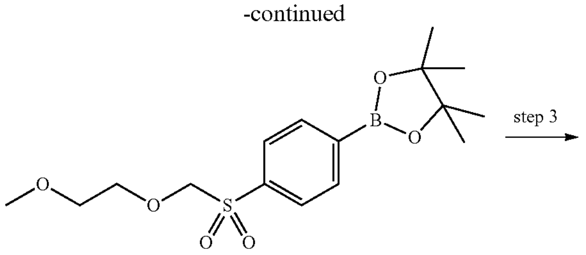

29-2

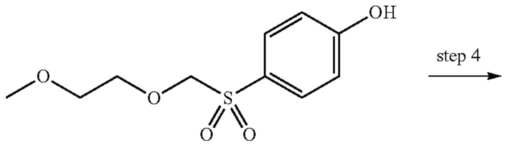

29-3

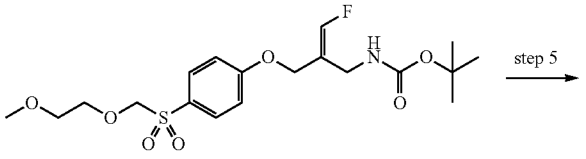

29-4

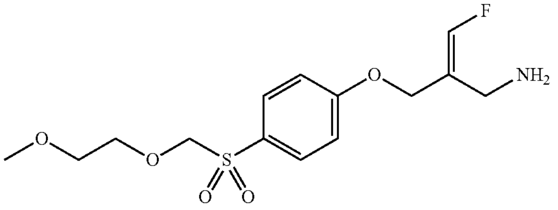

29

Step 1: 29-1

A mixture of Intermediate B (600 mg, 2.47 mmol) and 1-(chloromethoxy)-2-methoxy-ethane (369.0 mg, 2.96 mmol) in DMF (10 mL) was stirred at 20° C. The reaction solution was stirred for 8 hr at 100° C. Then ethyl acetate (100 mL) and $H_2O$ (100 mL) were added, the organic phase was washed with brine (50 mL), dried over $Na_2SO_4$ and concentrated to give a residue, which was purified by column chromatography on silical gel (ethyl acetate/petroleum ether=1/10-1/1) to give 29-1 (230 mg, 743.91 μmol, 30.14% yield).

Step 2: 29-2

A mixture of 29-1 (200 mg, 646.88 μmol), 4,4,5,5-tetramethyl-2-(4,4,5,5-tetramethyl-1,3,2-dioxaborolan-2-yl)-1,3,2-dioxaborolane (197.12 mg, 776.26 μmol) in Dioxane (13 mL) was added KOAc (194.37 mg, 1.94 mmol) at 20° C. under the nitrogen atmosphere. The reaction solution was stirred for 4 hr at 100° C. Then, the solution was concentrated with a rotary evaporator and purified by column chromatography on silical gel (ethyl acetate/petroleum ether=1/10-1/1) to obtain 29-2 (150 mg, 421.06 μmol, 65.09% yield). MS: m/z=309 (M+1).

Step 3: 29-3

A mixture of 29-2 (120 mg, 336.85 μmol) in THF (1 mL) and acetic acid (0.25 mL) was added $H_2O_2$ (0.5 mL, 30% purity). The mixture was stirred at 20° C. for 1 hr. $Na_2SO_3$ (0.2 g) was added to the mixture and stirred for 20 min. The mixture was filtered and concentrated to give 29-3 (350 mg, crude). MS: m/z=246 (M+1).

Step 4: 29-4

A mixture of 29-3 (350 mg, 1.42 mmol) and Intermediate A (114.31 mg, 426.34 μmol) in MeCN (50 mL) was added $Cs_2CO_3$ (1.39 g, 4.26 mmol) at 20° C. The reaction solution was stirred for 1 hr at 80° C. Then, the solution was filtered and concentrated to obtain 29-4 (230 mg, crude). MS: m/z=433 (M+1).

Step 5: Compound 29

A mixture of 29-4 (200 mg, 461.37 μmol) in HCl/Dioxane (4 M, 5 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 29 (42 mg, 125.98 μmol, 27.31% yield). $^1H$ NMR (400 MHz, Methanol-d4) δ 7.89 (d, J=8.4 Hz, 2H), 7.25 (d, J=80.0 Hz, 1H), 7.22 (d, J=8.4 Hz, 2H), 4.72 (d, J=3.6 Hz, 2H), 4.68 (s, 2H), 3.92 (t, J=4.4 Hz, 2H), 3.82 (d, J=2.4 Hz, 2H), 3.49 (t, J=4.4 Hz, 2H), 3.31 (s, 3H). ppm; MS: m/z=334.6 (M+1, ESI+).

Example 36: Synthesis of Compound 30

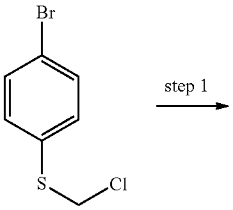

Intermediate D

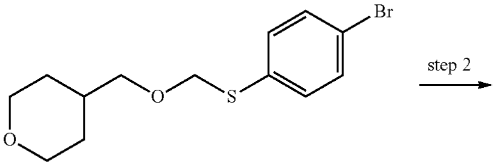

30-1

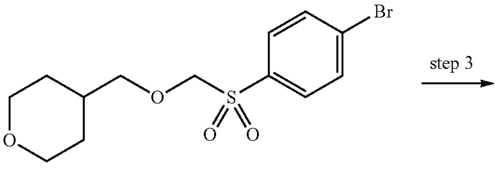

30-2

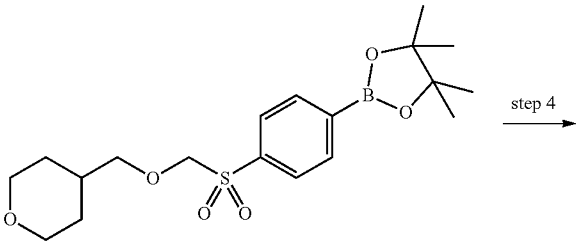

30-3

-continued

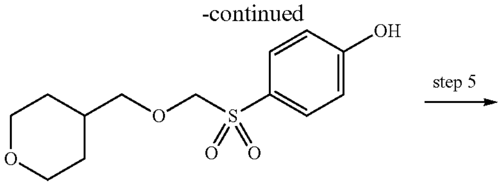

30-4

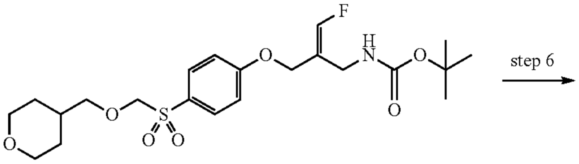

30-5

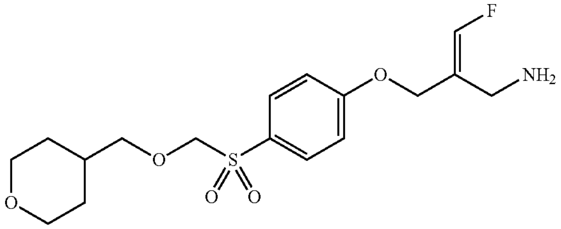

30

Step 1: 30-1

To a mixture of tetrahydropyran-4-ylmethanol (586.79 mg, 5.05 mmol) in DMF (15 mL) was added NaH (218.89 mg, 5.47 mmol, 60% purity) at 20° C. The reaction solution was stirred for 0.5 hr at 20° C. Then, Intermediate D (1.0 g, 4.21 mmol) was added. The reaction solution was stirred for further 18 hr at 20° C. Then, the solution was concentrated with a rotary evaporator. The crude product was purified by silica gel chromatography (ethyl acetate in petroleum ether, 0 to 10%) to obtain 30-1 (1.1 g, 3.47 mmol, 82.37% yield).

Step 2: 30-2

To a mixture of 30-1 (600 mg, 1.89 mmol) in DCM (20 mL) was added m-CPBA (1.15 g, 5.67 mmol, 85% purity) at 20° C. The mixture was stirred for 1 hr at 20° C. Then, the solution was washed with saturated aqueous $Na_2SO_3$ (10 mL), saturated aqueous $NaHCO_3$ (20 mL×2) and brine (15 mL), dried over $Na_2SO_4$ and concentrated with a rotary evaporator to obtain 30-2 (660 mg, crude).

Step 3: 30-3

To a mixture of 30-2 (660 mg, 1.89 mmol), 4,4,5,5-tetramethyl-2-(4,4,5,5-tetramethyl-1,3,2-dioxaborolan-2-yl)-1,3,2-dioxaborolane (575.87 mg, 2.27 mmol) and KOAc (556.41 mg, 5.67 mmol, 354.40 uL) in Dioxane (10 mL) was added Pd(dppf)$Cl_2$ (69.14 mg, 94.49 μmol) at 20° C. The reaction solution was heated at 120° C. for 0.667 hr under microwave. The mixture was filtered and concentrated to obtain 30-3 (760 mg, crude).

Step 4: 30-4

To a mixture of 30-3 (760 mg, 1.92 mmol), acetic acid (0.5 mL) in THF (10 mL) was added hydrogen peroxide (0.5 mL, 30% purity) at 20° C. The reaction solution was stirred for 0.5 hr at 20° C. Then, the solution was concentrated with a rotary evaporator to obtain 30-4 (600 mg, crude). MS: m/z=285 (M-1).

Step 5: 30-5

To a mixture of 30-4 (600 mg, 2.10 mmol), Intermediate A (250 mg, 932.41 μmol) in Acetonitrile (30 mL) was added $Cs_2CO_3$ (682.72 mg, 2.10 mmol) at 20° C. The reaction solution was stirred for 1 hr at 90° C. Then, the mixture was filtered, and the filtrate was concentrated with a rotary evaporator to obtain 30-5 (620 mg, crude). MS: m/z=474 (M+1).

Step 6: Compound 30

To a mixture of 30-5 (620 mg, 1.31 mmol) in DCM (15 mL) was added HCl/Dioxane (4 M, 4.00 mL) at 20° C. and the reaction mixture was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 30 (56 mg, 133.50 μmol, 10.20% yield, $HCO_2H$ salt). $^1H$ NMR (400 MHz, Methanol-d4) δ 8.51 (s, 1H), 7.89 (d, J=8.9 Hz, 2H), 7.27-7.23 (m, 2H), 7.27 (d, J=81.0 Hz, 1H), 4.75 (dd, J=3.6, 1.1 Hz, 2H), 4.67 (s, 2H), 3.92-3.87 (m, 2H), 3.84 (d, J=2.2 Hz, 2H), 3.65 (d, J=6.3 Hz, 2H), 3.39-3.31 (m, 3H), 1.81-1.78 (m, 1H), 1.61-1.51 (m, 3H), 1.28 (dtd, J=13.5, 11.8, 4.6 Hz, 3H). MS: m/z=374.6 (M+1, ESI+).

Example 37: Synthesis of Compound 31

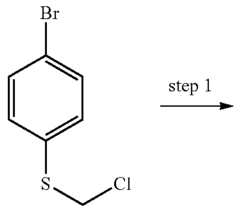

Intermediate D

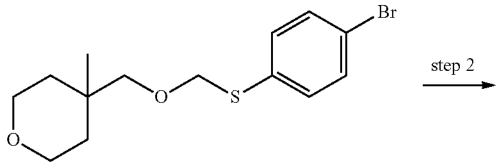

31-1

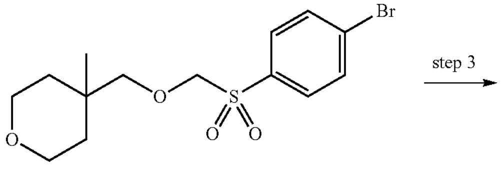

31-2

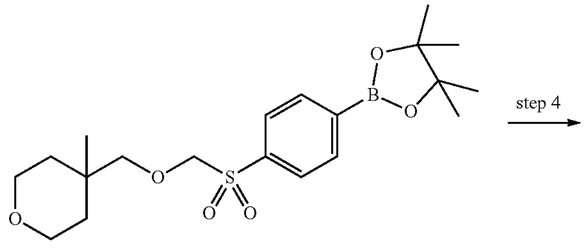

31-3

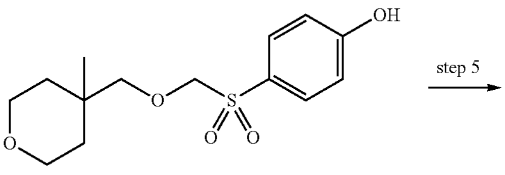

31-4

-continued

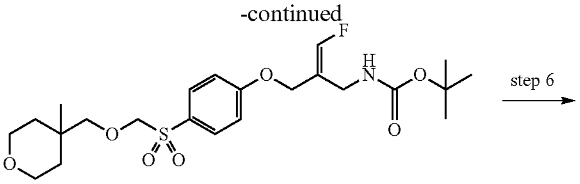

31-5

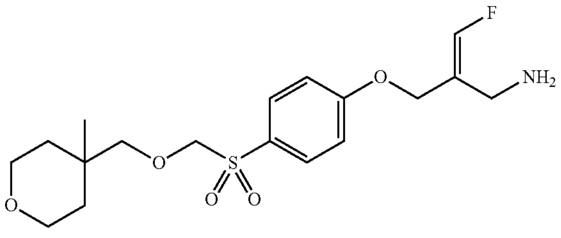

31

Step 1: 31-1

To a mixture of (4-methyltetrahydropyran-4-yl)methanol (822.06 mg, 6.31 mmol) in DMF (15 mL) was added NaH (269.40 mg, 6.74 mmol, 60% purity) at 20° C. The reaction solution was stirred for 0.5 hr at 20° C. Then, Intermediate D (1.0 g, 4.21 mmol) was added. The reaction solution was stirred for further 18 hr at 20° C. Then, the solution was concentrated with a rotary evaporator. The crude product was purified by silica gel chromatography (ethyl acetate in petroleum ether, 0 to 10%) to obtain 31-1 (410 mg, 1.24 mmol, 29.40% yield).

Step 2: 31-2

To a mixture of 31-1 (410 mg, 1.24 mmol) in DCM (20 mL) was added m-CPBA (1.01 g, 4.95 mmol, 85% purity) at 20° C. The mixture was stirred for 1 hr at 20° C. Then, the solution was washed with saturated aqueous $Na_2SO_3$ (10 mL), saturated aqueous $NaHCO_3$ (20 mL×2) and brine (15 mL), dried over $Na_2SO_4$ and concentrated with a rotary evaporator to obtain 31-2 (510 mg, crude).

Step 3: 31-3

To a mixture of 31-2 (510 mg, 1.40 mmol), 4,4,5,5-tetramethyl-2-(4,4,5,5-tetramethyl-1,3,2-dioxaborolan-2-yl)-1,3,2-dioxaborolane (427.81 mg, 1.68 mmol) and KOAc (413.35 mg, 4.21 mmol) in Dioxane (10 mL) was added $Pd(dppf)Cl_2$ (102.73 mg, 140.39 μmol) at 20° C. The reaction solution was heated at 120° C. for 0.667 hr under microwave. The mixture was filtered and concentrated to obtain 31-3 (320 mg, crude).

Step 4: 31-4

To a mixture of 31-3 (320 mg, 779.86 mol), acetic acid (0.4 mL) in THF (15 mL) was added $H_2O_2$ (0.3 mL, 30% purity) at 20° C. The reaction solution was stirred for 1 hr at 20° C. Then, to the solution was added $Na_2SO_3$ (0.5 g), filtered and concentrated with a rotary evaporator to obtain 31-4 (180 mg, crude). MS: m/z=299 (M-1).

Step 5: 31-5

To a mixture of 31-4 (180 mg, 599.26 μmol), Intermediate A (150 mg, 559.45 μmol) in MeCN (30 mL) was added $Cs_2CO_3$ (585.75 mg, 1.80 mmol) at 20° C. The reaction solution was stirred for 1 hr at 90° C. Then, the mixture was filtered, and the filtrate was concentrated with a rotary evaporator to obtain 31-5 (180 mg, crude). MS: m/z=488 (M+1).

Step 6: Compound 31

To a mixture of 31-5 (180 mg, 369.17 μmol) in DCM (15 mL) was added HCl/Dioxane (4 M, 3 mL) at 20° C. and the reaction mixture was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-35% B; GT: 15 min; flow rate: 15 mL/min) to obtain Compound 31 (43 mg, 99.19 μmol, 26.87% yield, $HCO_2H$ salt). $^1H$ NMR (400 MHz, Methanol-d4) δ 7.90 (d, J=8.9 Hz, 2H), 7.32-7.23 (m, 2H), 7.27 (d, J=80.9 Hz, 1H), 4.75 (d, J=3.5 Hz, 2H), 4.70 (s, 2H), 3.85 (d, J=2.2 Hz, 2H), 3.71-3.54 (m, 6H), 1.54 (ddd, J=13.6, 9.0, 4.5 Hz, 2H), 1.25-1.20 (m, 2H), 0.99 (s, 3H). MS: m/z=388.59 (M+1, ESI+).

Example 38: Synthesis of Compound 32

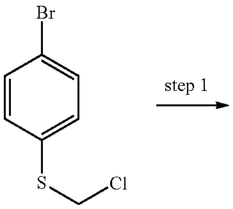

Intermediate D

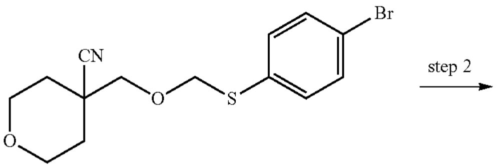

32-1

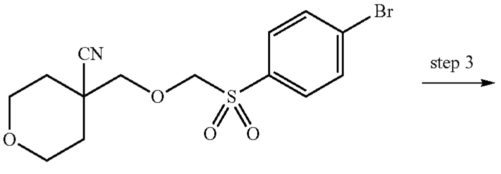

32-2

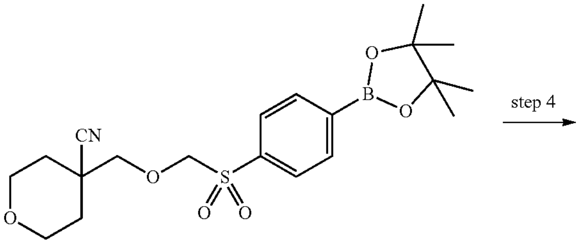

32-3

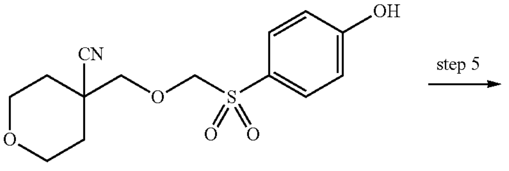

32-4

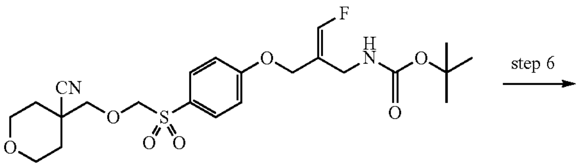

32-5

-continued

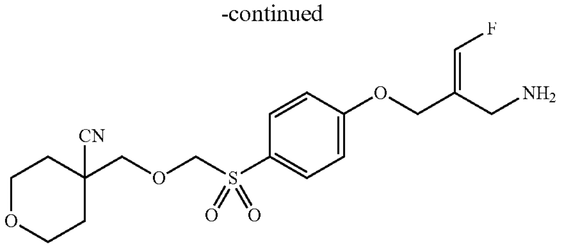

32

Step 1: 32-1

To a mixture of 4-(hydroxymethyl)tetrahydropyran-4-carbonitrile (800 mg, 5.67 mmol) in DMF (20 mL) was added NaH (252.56 mg, 6.31 mmol, 60% purity) at 20° C. The reaction solution was stirred for 0.5 hr at 20° C. Then, Intermediate D (1.0 g, 4.21 mmol) was added. The reaction solution was stirred further for 18 hr at 20° C. Then, the solution was concentrated with a rotary evaporator. The crude product was purified by silica gel chromatography (ethyl acetate in petroleum ether, 0 to 30%) to obtain 32-1 (810 mg, 2.37 mmol, 56.22% yield).

Step 2: 32-2

To a mixture of 32-1 (400 mg, 1.17 mmol) in DCM (30 mL) was added m-CPBA (949.10 mg, 4.67 mmol, 85% purity) at 20° C. The mixture was stirred for 1 hr at 20° C. Then, the solution was washed with saturated aqueous $Na_2SO_3$ (10 mL), saturated aqueous $NaHCO_3$ (20 mL×2) and brine (15 mL), dried over $Na_2SO_4$ and concentrated with a rotary evaporator to obtain 32-2 (460 mg, crude).

Step 3: 32-3

To a mixture of 32-2 (400 mg, 1.07 mmol), 4,4,5,5-tetramethyl-2-(4,4,5,5-tetramethyl-1,3,2-dioxaborolan-2-yl)-1,3,2-dioxaborolane (325.69 mg, 1.28 mmol) and KOAc (314.68 mg, 3.21 mmol) in Dioxane (10 mL) was added $Pd(dppf)Cl_2$ (78.20 mg, 106.88 μmol) at 20° C. The reaction solution was heated at 120° C. for 0.667 hr under microwave. The mixture was filtered and the filtrate was evaporated to obtain 32-3 (380 mg, crude).

Step 4: 32-4

To a mixture of 32-3 (380 mg, 901.94 μmol), acetic acid (0.4 mL) in THF (15 mL) was added $H_2O_2$ (0.3 mL, 30% purity) at 20° C. The reaction solution was stirred for 1 hr at 20° C. Then, to the solution was added $Na_2SO_3$ (0.5 g), filtered and concentrated with a rotary evaporator to obtain 32-4 (220 mg, crude). MS: m/z=310 (M-1).

Step 5: 32-5

To a mixture of 32-4 (220 mg, 706.59 μmol), Intermediate A (120 mg, 447.56 μmol) in MeCN (30 mL) was added $Cs_2CO_3$ (690.66 mg, 2.12 mmol) at 20° C. The reaction solution was stirred for 1 hr at 90° C. Then, the mixture was filtered, and the filtrate was concentrated with a rotary evaporator to obtain 32-5 (210 mg, crude). MS: m/z=499 (M+1).

Step 6: Compound 32

To a mixture of 32-5 (210 mg, 421.21 μmol) in DCM (15 mL) was added HCl/Dioxane (4 M, 3 mL) at 20° C. and the reaction mixture was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, GT: 15 min; flow rate: 15 mL/min) to obtain Compound 32 (86 mg, 193.49 μmol, 45.94% yield, $HCO_2H$ salt). $^1H$ NMR (400 MHz, Methanol-d4) δ 8.52 (s, 1H), 7.95 (d, J=9.0 Hz, 2H), 7.31-7.19 (m, 2H), 7.26 (d, J=81.1 Hz, 1H), 4.78 (s, 2H), 4.76-4.73 (m, 2H), 3.94 (d, J=10.0 Hz, 4H), 3.83 (d, J=2.2 Hz, 2H), 3.63 (td, J=12.1, 2.1 Hz, 2H), 1.93-1.76 (m, 2H), 1.66-1.60 (m, 2H), 1.22 (s, 2H). MS: m/z=399.59 (M+1, ESI+).
Example 39: Synthesis of Compound 33
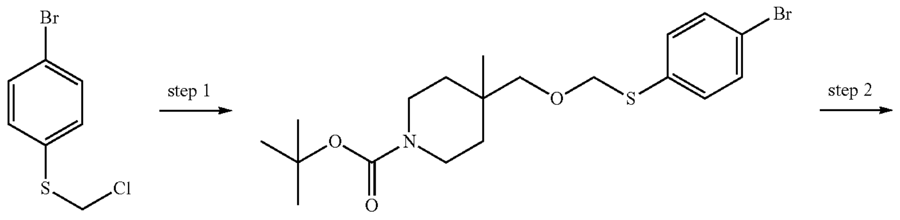
Intermediate D 33-1
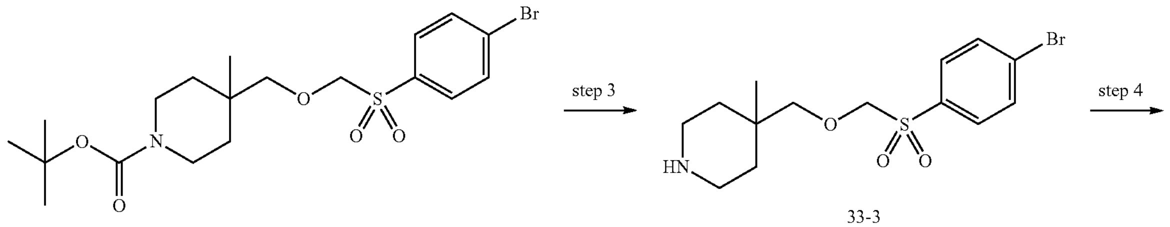
33-2 33-3
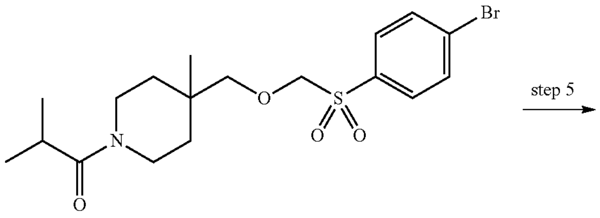
33-4
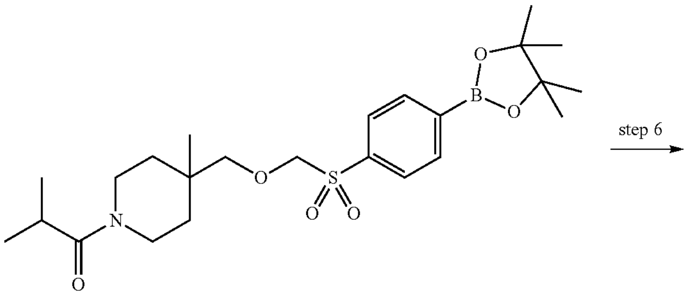
33-5
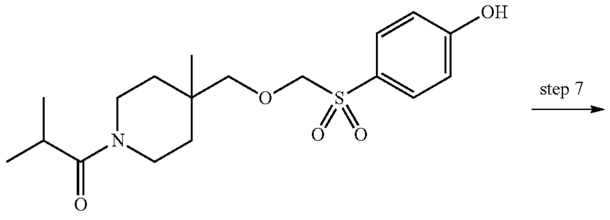
33-6

-continued

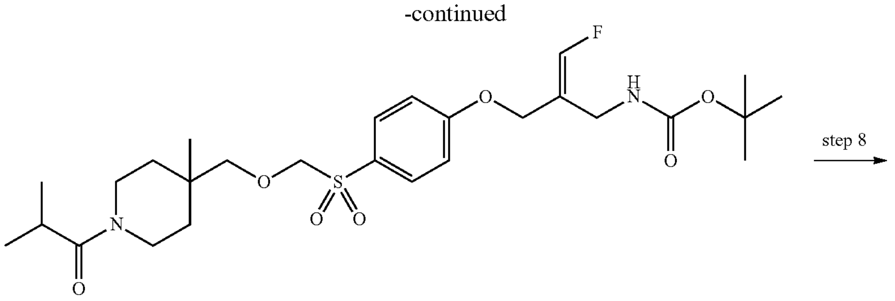

33-7

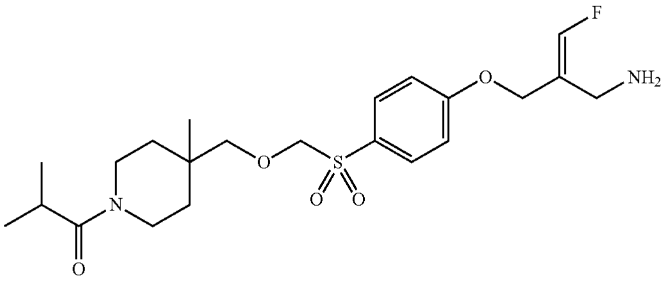

33

Step 1: 33-1

To a mixture of tert-butyl 4-(hydroxymethyl)-4-methyl-piperidine-1-carboxylate (1.74 g, 7.58 mmol) in DMF (15 mL) was added NaH (328.33 mg, 8.21 mmol, 60% purity) at 20° C. The reaction solution was stirred for 0.5 hr at 20° C. Then, Intermediate D (1.5 g, 6.31 mmol) was added. The reaction solution was stirred further for 18 hr at 20° C. Then, the solution was concentrated with a rotary evaporator. The crude product was purified by silica gel chromatography (ethyl acetate in petroleum ether, 0 to 10%) to obtain 33-1 (420 mg, 975.84 mol, 15.45% yield). MS: m/z=430 (M+1).

Step 2: 33-2

To a mixture of 33-1 (420 mg, 975.84 μmol) in DCM (30 mL) was added m-CPBA (594.34 mg, 2.93 mmol, 85% purity) at 20° C. The mixture was stirred for 1 hr at 20° C. Then, the solution was washed with saturated aqueous $Na_2SO_3$ (10 mL), saturated aqueous $NaHCO_3$ (20 mL×2) and brine (15 mL), dried over $Na_2SO_4$ and concentrated with a rotary evaporator to obtain 33-2 (510 mg, crude). The crude product was used for the next step without further purification. MS: m/z=462 (M+1).

Step 3: 33-3

To a mixture of 33-2 (510 mg, 1.10 mmol) in DCM (20 mL) was added HCl/Dioxane (4 M, 4 mL) at 20° C. and the reaction mixture was stirred at 20° C. for 1 hr. Then, the solution was concentrated with a rotary evaporator to obtain 33-3 (450 mg, crude, HCl salt). MS: m/z=362 (M+1).

Step 4: 33-4

To a mixture of 33-3 (200 mg, 501.58 μmol) and Et3N (152.26 mg, 1.50 mmol) in DCM (20 mL) was added 2-methylpropanoyl chloride (58.79 mg, 551.73 μmol, 57.63 μL) at 20° C. The reaction solution was stirred for 1 hr at 20° C. Then, the solution was washed with $H_2O$ (15 mL×2) and brine (15 mL), dried over $Na_2SO_4$ and concentrated with a rotary evaporator. The crude product was purified by silica gel chromatography (ethyl acetate in petroleum ether, 0 to 70%) to obtain 33-4 (180 mg, 416.31 μmol, 83.0% yield). MS: m/z=432 (M+1).

Step 5: 33-5

To a mixture of 33-4 (180 mg, 416.31 μmol), 4,4,5,5-tetramethyl-2-(4,4,5,5-tetramethyl-1,3,2-dioxaborolan-2-yl)-1,3,2-dioxaborolane (126.86 mg, 499.57 μmol) and KOAc (122.57 mg, 1.25 mmol) in Dioxane (10 mL) was added Pd(dppf)$Cl_2$ (30.46 mg, 41.63 μmol) at 20° C. The reaction solution was heated at 120° C. for 0.667 hr under microwave. The mixture was filtered and the filtrate was evaporated to obtain 33-5 (220 mg, crude). MS: m/z=480 (M+1).

Step 6: 33-6

To a mixture of 33-5 (220 mg, 458.87 μmol), acetic Acid (0.7 mL) in THF (20 mL) was added hydrogen peroxide (0.5 mL, 30% purity) at 20° C. The reaction solution was stirred for 1 hr at 20° C. Then, the solution was concentrated with a rotary evaporator to obtain 33-6 (260 mg, crude). MS: m/z=370 (M+1).

Step 7: 33-7

To a mixture of 33-6 260 mg, 703.70 μmol), Intermediate A (188.68 mg, 703.70 μmol) in MeCN (30 mL) was added $Cs_2CO_3$ (687.84 mg, 2.11 mmol) at 20° C. The reaction solution was stirred for 1 hr at 90° C. Then, the mixture was filtered, and the filtrate was concentrated with a rotary evaporator. The crude product was purified by silica gel chromatography (ethyl acetate in petroleum ether, 0 to 100%) to obtain 33-7 (220 mg, 395.20 mol, 56.16% yield). MS: m/z=557 (M+1).

Step 8: Compound 33

To a mixture of 33-7 (220 mg, 395.20 μmol) in DCM (15 mL) was added HCl/Dioxane (4 M, 4 mL) at 20° C. and the reaction mixture was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, GT: 15 min; flow rate: 15 mL/min) to obtain Compound 33 (23 mg, 45.76 μmol, 11.58% yield, $HCO_2H$ salt). $^1H$ NMR (400 MHz, Methanol-d4) δ 8.49 (s, 1H), 7.88 (dd, J=12.5, 8.8 Hz, 2H), 7.28 (d, J=81.0 Hz, 1H), 7.23 (dd, J=17.5, 8.8 Hz, 2H), 4.69 (d, J=5.3 Hz, 2H), 4.13 (s, 1H), 3.84 (d, J=2.2 Hz, 2H), 3.73-3.56 (m, 4H), 3.44 (t, J=12.1

Hz, 2H), 3.26 (d, J=10.1 Hz, 2H), 2.94-2.87 (m, 2H), 1.52 (d, J=9.8 Hz, 1H), 1.46-1.30 (m, 2H), 1.09 (dd, J=6.7, 1.1 Hz, 6H), 0.99 (s, 3H). MS: m/z=457.73 (M+1, ESI+).
Example 40: Synthesis of Compound 34
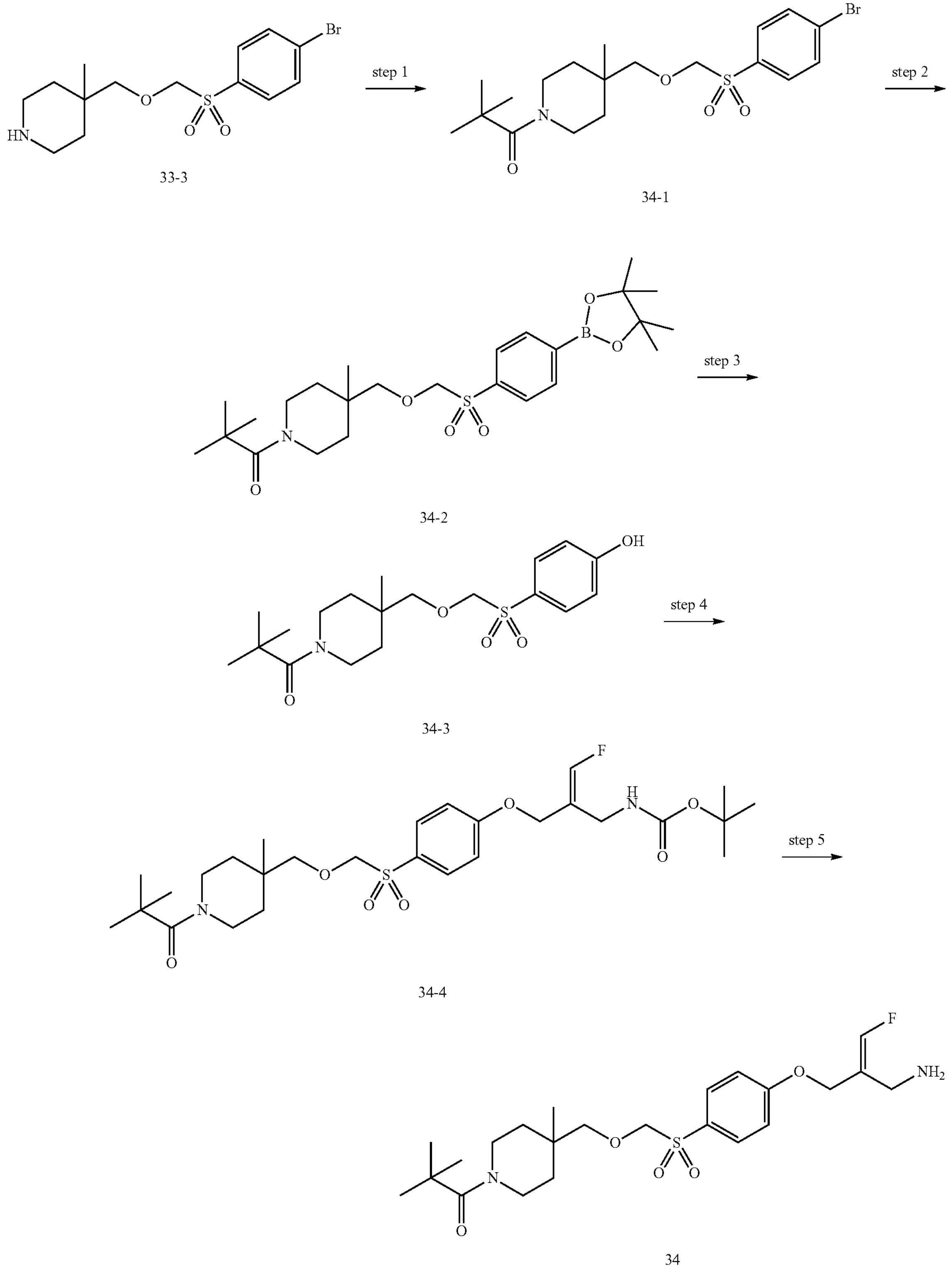
33-3
34-1
34-2
34-3
34-4
34

Step 1: 34-1

To a mixture of 33-3 (250 mg, 626.97 μmol) and Et3N (190.33 mg, 1.88 mmol) in DCM (20 mL) was added 2,2-dimethylpropanoyl chloride (83.16 mg, 689.67 μmol, 84.42 μL) at 20° C. The reaction solution was stirred for 1 hr at 20° C. Then, the solution was washed with $H_2O$ (15 mL×2) and brine (15 mL), dried over $Na_2SO_4$ and concentrated with a rotary evaporator. The crude product was purified by silica gel chromatography (ethyl acetate in petroleum ether, 0 to 70%) to obtain 34-1 (210 mg, 470.43 μmol, 75.03% yield). MS: m/z=446 (M+1).

Step 2: 34-2

To a mixture of 34-1 (210 mg, 470.43 μmol), 4,4,5,5-tetramethyl-2-(4,4,5,5-tetramethyl-1,3,2-dioxaborolan-2-yl)-1,3,2-dioxaborolane (143.35 mg, 564.52 μmol) and KOAc (138.51 mg, 1.41 mmol) in Dioxane (10 mL) was added Pd(dppf)$Cl_2$ (34.42 mg, 47.04 μmol) at 20° C. The reaction solution was heated at 120° C. for 0.667 hr under microwave. The mixture was filtered and the filtrate was evaporated to obtain 34-2 (300 mg, crude). MS: m/z=494 (M+1).

Step 3: 34-3

To a mixture of 34-2 (300 mg, 607.95 μmol), acetic acid (0.5 mL) in THF (15 mL) was added hydrogen peroxide (0.5 mL, 30% purity) at 20° C. The reaction solution was stirred for 1 hr at 20° C. Then, the solution was concentrated with a rotary evaporator to obtain 34-3 (320 mg, crude). MS: m/z=384 (M+1).

Step 4: 34-4

To a mixture of 34-3 (320 mg, 834.42 μmol), Intermediate A (223.73 mg, 834.42 mol) in MeCN (30 mL) was added $Cs_2CO_3$ (815.61 mg, 2.50 mmol) at 20° C. The reaction solution was stirred for 1 hr at 90° C. Then, the mixture was filtered, and the filtrate was concentrated with a rotary evaporator. The crude product was purified by silica gel chromatography (ethyl acetate in petroleum ether, 0 to 100%) to obtain 34-4 (230 mg, 403.01 μmol, 48.30% yield). MS: m/z=571 (M+1).

Step 5: Compound 34

To a mixture of 34-4 (230 mg, 403.01 μmol) in DCM (15 mL) was added HCl/Dioxane (4 M, 4 mL) at 20° C. and the reaction mixture was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 10-40% B; GT: 15 min; flow rate: 15 mL/min) to obtain Compound 34 (54 mg, 104.53 μmol, 25.94% yield, $HCO_2H$ salt). $^1H$ NMR (400 MHz, Methanol-d4) δ 8.50 (s, 1H), 7.90 (d, J=8.9 Hz, 2H), 7.28 (d, J=80.9 Hz, 1H), 7.25 (d, J=8.9 Hz, 2H), 4.75 (d, J=3.5 Hz, 1H), 4.70 (s, 2H), 4.12 (d, J=7.6 Hz, 1H), 3.84 (d, J=2.3 Hz, 3H), 3.61 (d, J=4.7 Hz, 2H), 1.54-1.42 (m, 2H), 1.28 (s, 9H), 0.99 (s, 3H). MS: m/z=471.68 (M+1, ESI+).

Example 41: Synthesis of Compound 35

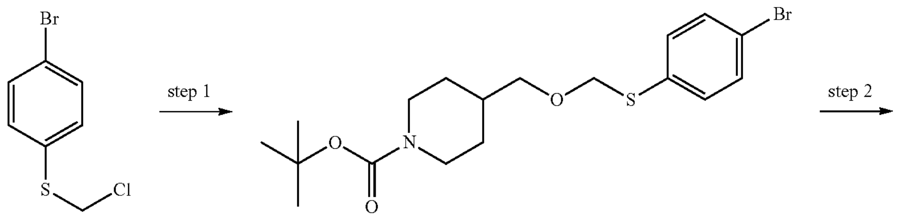

Intermediate D 35-1

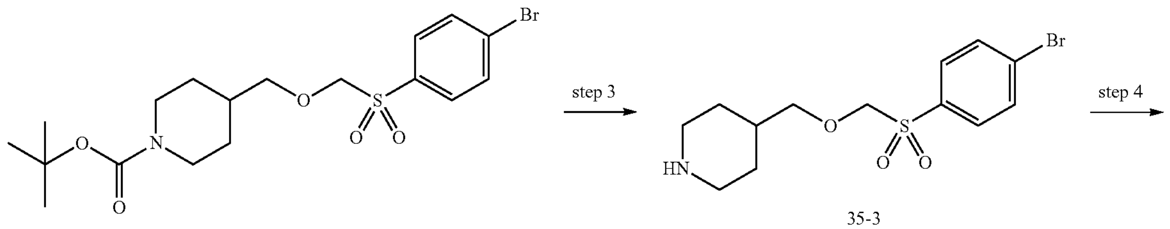

35-2

35-3

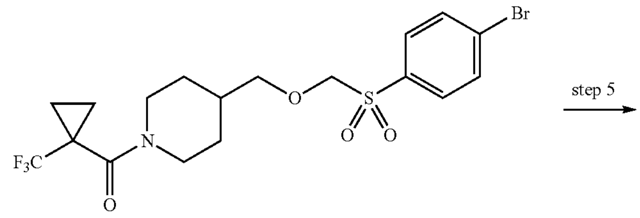

35-4

-continued

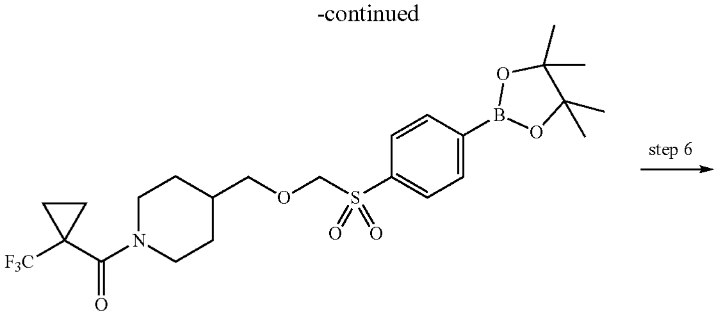

35-5

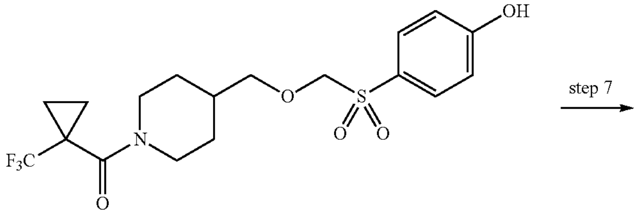

35-6

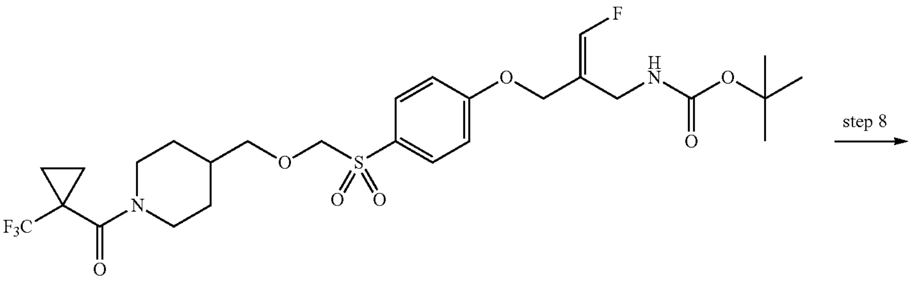

35-7

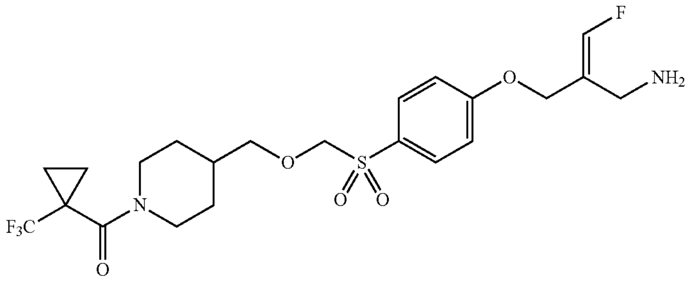

35

Step 1: 35-1

A mixture of Tert-butyl 4-(hydroxymethyl)piperidine-1-carboxylate (1.81 g, 8.42 mmol), NaH (241.95 mg, 6.31 mmol, 60% purity) in DMF (30 mL) was added Intermediate D (1 g, 4.21 mmol) at 0° C. The reaction solution was stirred for 18 hr at 30° C. To the mixture was added saturated aqueous ammonium chloride solution (20 mL) and ethyl acetate (20 mL). The organic layer was separated and the aqueous layer was further extracted with ethyl acetate (10 ml×3). The combined organic extracts were dried over sodium sulfate. The solvent was evaporated under reduced pressure and the crude was purified by flash column chromatography (ethyl acetate in petroleum ether, 10% to 80%) to give 35-1 (500 mg, 1.20 mmol, 28.53% yield).

Step 2: 35-2

A mixture of 35-1 (400 mg, 960.68 μmol) and m-CPBA (487.59 mg, 2.40 mmol, 85% purity) in DCM (50 mL) was stirred at 25° C. for 0.5 hr. $Na_2SO_3$ (14 g) was added to the mixture and stirred for 20 min. Then, the solution was filtered, concentrated and purified by silica gel chromatography (petroleum ether/ethylacetate=10/1-3/1, v/v) to obtain 35-2 (400 mg, 892.12 μmol, 92.86% yield).

Step 3: 35-3

A mixture of 35-2 (400 mg, 892.12 μmol) in HCl/Dioxane (4 M, 5.0 mL) was stirred at 25° C. for 1 hr. Then, the solution was concentrated with a rotary evaporator to obtain 35-3 (320 mg, crude).

Step 4: 35-4

A mixture of 35-3 (300 mg, 861.44 μmol), 1-(trifluoromethyl)cyclopropanecarboxylic acid (132.74 mg, 861.44 μmol) and TEA (261.51 mg, 2.58 mmol) in DCM (30 mL) was added HATU (491.32 mg, 1.29 mmol) at 20° C. The reaction solution was stirred for 1 hr at 20° C. Then, the solution was concentrated with a rotary evaporator. The crude product was dissolved in ethyl acetate (80 mL), washed with $H_2O$ (100 mL×3), dried over $Na_2SO_4$, filtered and concentrated to give 35-4 (280 mg, crude). MS: m/z=384 (M+1).

Step 5: 35-5

A 30 mL microwave reaction tube was charged with 35-4 (250 mg, 516.18 μmol), 4,4,5,5-tetramethyl-2-(4,4,5,5-tetramethyl-1,3,2-dioxaborolan-2-yl)-1,3,2-dioxaborolane (196.62 mg, 774.27 μmol) and cyclopentyl(diphenyl)phosphane; dichloropalladium; iron (37.77 mg, 51.62 μmol) and KOAc (151.98 mg, 1.55 mmol) in Dioxane (10 mL). After 02 was purged by bubbling N2 into the reaction solution, the tube was sealed and heated at 120° C. for 0.5 hr in a Biotage microwave reactor. The reaction was cooled to room temperature, filtered and concentrated under reduced pressure. The resultant crude product was purified by flash chromatography (ethyl acetate in petroleum ether, 0-100%) to deliver 35-5 (300 mg, crude). MS: m/z=531 (M+1).

Step 6: 35-6

To a mixture of 35-5 (300 mg, 564.56 μmol) in THF (25 ml) and acetic acid (1 mL) was added $H_2O_2$ (0.5 mL, 30% purity). The mixture was stirred at 25° C. for 0.5 hr. $Na_2SO_3$ (0.7 g) was added to the mixture and stirred for 30 min. The reaction mixture was filtered and concentrated to give 35-6 (1.2 g, crude). MS: m/z=421 (M+1).

Step 7: 35-7

A mixture of 35-6 (1 g, crude) and Intermediate A (254.49 mg, 949.15 μmol) in MeCN (50 mL) was added $Cs_2CO_3$ (2.32 g, 7.12 mmol) at 20° C. The reaction solution was stirred for 1 hr at 80° C. Then, the solution was filtered and concentrated to obtain 35-7 (300 mg, crude). MS: m/z=608 (M+1).

Step 8: Compound 35

A mixture of 35-7 (200 mg, 328.60 μmol) in HCl/Dioxane (4 M, 4 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, GT: 15 min; flow rate: 15 mL/min) to obtain Compound 35 (43.2 mg, 84.95 μmol, 25.85% yield). $^1H$ NMR (400 MHz, Methanol-d4) δ 8.52 (s, 1H), 7.87 (d, J=8.4 Hz, 2H), 7.21 (d, J=80.0 Hz, 1H), 7.22 (d, J=8.4 Hz, 2H), 4.72 (d, J=3.6 Hz, 2H), 4.65 (s, 2H), 4.36 (s, 2H), 3.78 (d, J=2.4 Hz, 2H), 3.67 (d, J=6.0 Hz, 2H), 3.10-3.06 (m, 2H), 1.84 (s, 1H), 1.70 (d, J=13.2 Hz, 2H), 1.34 (s, 2H), 1.20-1.17 (s, 4H). ppm; MS: m/z=509.5 (M+1, ESI+).

Example 42: Synthesis of Compound 36

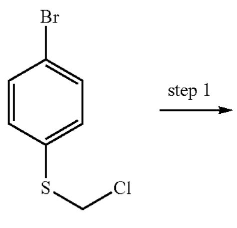

Intermediate D

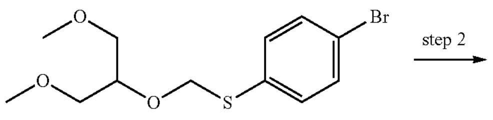

36-1

-continued

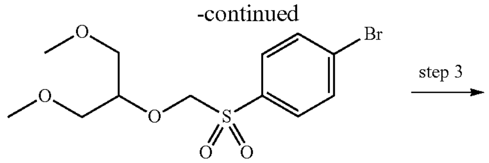

36-2

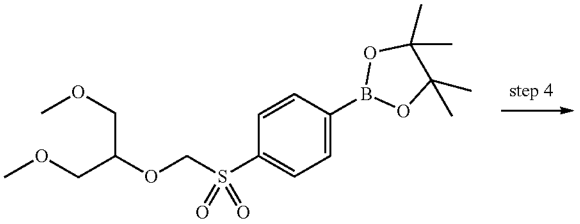

36-3

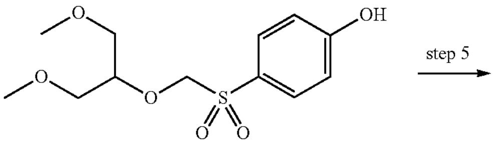

36-4

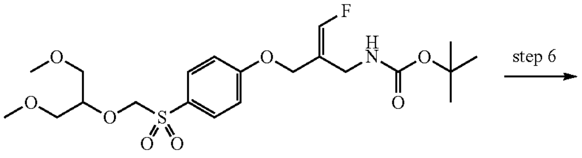

36-5

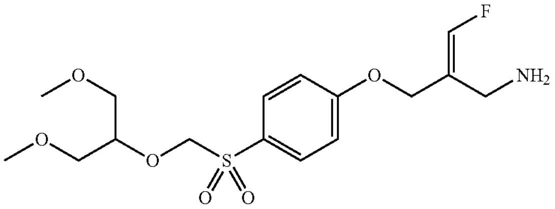

36

Step 1: 36-1

To a mixture of 1,3-dimethoxypropan-2-ol (400 mg, 3.33 mmol) in DMF (15 mL) was added NaH (159.79 mg, 4.00 mmol, 60% purity) at 25° C. The reaction solution was stirred for 0.5 hr at 25° C. Then, Intermediate D (790.84 mg, 3.33 mmol) was added. The reaction solution was stirred further for 18 hr at 25° C. Then, the solution was concentrated with a rotary evaporator. The crude product was purified by silica gel chromatography (ethyl acetate in petroleum ether, 0 to 40%) to obtain 36-1 (310 mg, 965.04 μmol, 28.99% yield).

Step 2: 36-2

To a mixture of 36-1 (310 mg, 965.04 μmol) in DCM (25 mL) was added m-CPBA (783.69 mg, 3.86 mmol, 85% purity) at 25° C. The mixture was stirred for 1 hr at 25° C. Then, the solution was washed with saturated aqueous $Na_2SO_3$ (10 mL), saturated aqueous $NaHCO_3$ (20 mL×2) and brine (15 mL), dried over $Na_2SO_4$ and concentrated with a rotary evaporator to obtain 36-2 (360 mg, crude).

Step 3: 36-3

To a mixture of 36-2 (360 mg, 1.02 mmol), 4,4,5,5-tetramethyl-2-(4,4,5,5-tetramethyl-1,3,2-dioxaborolan-2-yl)-1,3,2-dioxaborolane (310.57 mg, 1.22 mmol) and KOAc (300.07 mg, 3.06 mmol) in Dioxane (9 mL) was added $Pd(dppf)Cl_2$ (74.57 mg, 101.92 µmol) at 25° C. The reaction solution was heated at 120° C. for 0.667 hr under microwave. The mixture was filtered and the filtrate was evaporated to obtain 36-3 (360 mg, crude).

Step 4: 36-4

To a mixture of 36-3 (360 mg, 899.34 µmol), acetic acid (0.3 mL) in THF (20 mL) was added $H_2O_2$ (0.3 mL, 30% purity) at 25° C. The reaction solution was stirred for 1 hr at 25° C. Then, to the solution was added $Na_2SO_3$ (0.5 g), filtered and concentrated with a rotary evaporator to obtain 36-4 (330 mg, crude). MS: m/z=289 (M-1).

Step 5: 36-5

To a mixture of 36-4 (330 mg, 1.14 mmol), Intermediate A (180 mg, 671.33 µmol) in MeCN (30 mL) was added $Cs_2CO_3$ (1.11 g, 3.41 mmol) at 25° C. The reaction solution was stirred for 1 hr at 90° C. Then, the mixture was filtered, and the filtrate was concentrated with a rotary evaporator to obtain 36-5 (220 mg, crude). MS: m/z=478 (M+1).

Step 6: Compound 36

To a mixture of 36-5 (220 mg, 460.69 µmol) in DCM (20 mL) was added HCl/Dioxane (4 M, 3 mL) at 25° C. and the reaction mixture was stirred at 25° C. for 1 hr. Then, the solution was concentrated with a rotary evaporator. The crude product was purified by prep-HPLC (column: XBridge@ Prep C18 5 µm 19×150 mm; A: 0.1% $HCO_2H$ water, GT: 15 min; flow rate: 15 mL/min) to obtain Compound 36 (86 mg, 203.09 µmol, 44.08% yield, HF). $^1$H NMR (400 MHz, Methanol-d4) δ 7.93 (d, J=9.3 Hz, 2H), 7.26 (d, J=81.0 Hz, 1H), 7.24 (d, J=8.9 Hz, 2H), 4.83 (s, 2H), 4.75 (d, J=3.5 Hz, 1H), 4.19-3.98 (m, 2H), 3.83 (d, J=2.3 Hz, 2H), 3.53-3.39 (m, 7H), 3.33 (s, 6H). MS: m/z=378.63 (M+1, ESI+).

Example 43: Synthesis of Compound 37

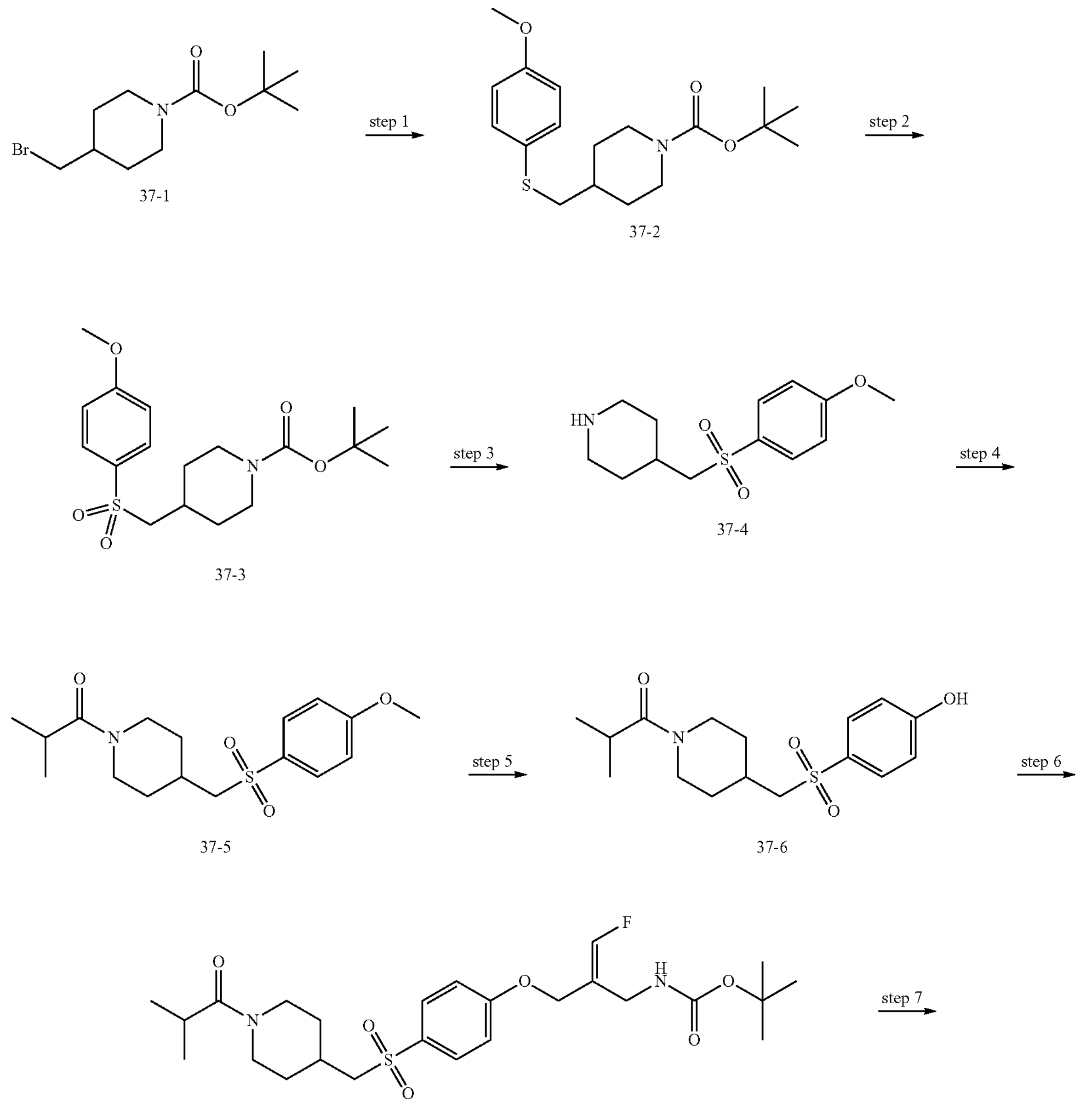

37-1, 37-2, 37-3, 37-4, 37-5, 37-6, 37-7

-continued

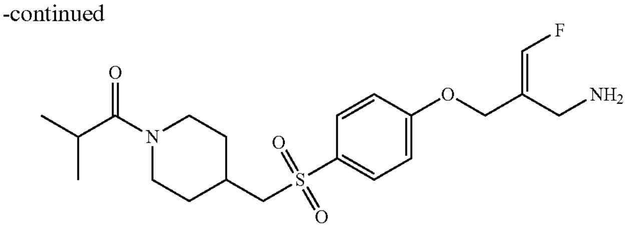

37

Step 1: 37-2

To a mixture of 4-methoxybenzenethiol (300 mg, 2.14 mmol, 263.16 uL) and 37-1 (595.25 mg, 2.14 mmol) in MeCN (10 mL) was added $Cs_2CO_3$ (1.39 g, 4.28 mmol) at 30° C. The reaction solution was stirred for 1 hr at 80° C. Then, the solution was filtered and concentrated to obtain 37-2 (700 mg, crude).

Step 2: 37-3

To a mixture of 37-2 (700 mg, 2.07 mmol) and m-CPBA (1.43 g, 8.30 mmol) in DCM (10 mL) was stirred at 20° C. for 1 hr. $Na_2SO_3$ (4 g) was added to the mixture and stirred for 20 min. Then, the solution was filtered, concentrated and purified by silica gel chromatography (petroleum ether/ethylacetate=5/1-1/1, v/v) to obtain 37-3 (300 mg, 811.96 μmol, 39.15% yield). MS: m/z=370 (M+1).

Step 3: 37-4

To a mixture of 37-3 (300 mg, 811.96 μmol) in HCl/Dioxane (4 M, 2.0 mL) was stirred at 20° C. for 1 hr. Then, the solution was concentrated with a rotary evaporated to obtain 37-4 (290 mg, 948.27 μmol, 116.79% yield, HCl salt). MS: m/z=270 (M+1).

Step 4: 37-5

To a mixture of 37-4 (200 mg, 742.50 μmol) and TEA (225.40 mg, 2.23 mmol) in DCM (5 mL) was added 2-methylpropanoyl chloride (94.94 mg, 891.00 μmol) at 0° C. The reaction solution was stirred for 1 hr at 20° C. Then, the solution was concentrated with a rotary evaporator. The crude product was dissolved in ethyl acetate (80 mL), washed with $H_2O$ (100 mL×3), dried over $Na_2SO_4$, filtered and concentrated to obtain 37-5 (200 mg, crude). MS: m/z=340 (M+1).

Step 5: 37-6

To a mixture of 37-5 (200 mg, 589.19 μmol) in DCM (10 mL) was added BBr3 (442.82 mg, 1.77 mmol) was stirred at 0° C. under the nitrogen atmosphere. The mixture was stirred at 40° C. for 1 hr. MeOH (4 mL) was added and stirred for 15 min. The reaction mixture was concentrated to give 37-6 (300 mg, crude, HBr salt), which was used in the next step without purification. MS: m/z=326 (M+1).

Step 6: 37-7

To a mixture of 37-6 (300 mg, 921.88 μmol) and Intermediate A (120 mg, 447.11 μmol) in MeCN (20 mL) was added $Cs_2CO_3$ (901.10 mg, 2.77 mmol) at 20° C. The reaction solution was stirred for 1 hr at 80° C. Then, the solution was filtered and concentrated to obtain 37-7 (300 mg, crude). MS: m/z=513 (M+1).

Step 7: Compound 37

To a mixture of 37-7 (200 mg, 384.15 μmol) in HCl/Dioxane (4 M, 2.0 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water; GT: 15 min; flow rate: 15 mL/min) to obtain Compound 37 (18 mg, 42.80 mol, 11.14% yield). $^1H$ NMR (400 MHz, Methanol-d4) S 8.49 (s, 1H), 7.89 (d, J=8.8 Hz, 2H), 7.23 (d, J=80.0 Hz, 1H), 7.22 (d, J=8.8 Hz, 2H), 4.71 (d, J=3.3 Hz, 2H), 4.44 (d, J=12.8 Hz, 1H), 4.01 (d, J=13.2 Hz, 1H), 3.80 (d, J=1.6 Hz, 2H), 3.17 (d, J=6.4 Hz, 2H), 3.09 (t, J=12.4 Hz, 1H), 2.91 (dt, J=13.2, 6.7 Hz, 1H), 2.62 (t, J=11.4 Hz, 1H), 2.16 (dd, J=12.8, 9.0 Hz, 1H), 1.98 (d, J=12.8 Hz, 1H), 1.83 (d, J=13.2 Hz, 1H), 1.40-1.14 (m, 2H), 1.06 (t, J=6.4 Hz, 6H) ppm; MS: m/z=413.20 (M+1, ESI+).

The compounds of Formula (I') or (I) in Table 2 below were made according to Example 43 of Compound 37.

TABLE 2

| Cmpd No. | $^1H$ NMR and/or LC/MS data |
|---|---|
| 38 | $^1H$ NMR (400 MHz, Methanol-d4) δ 7.89 (d, J = 8.0 Hz, 2H), 7.24 (d, J = 80.0 Hz, 1H), 7.22 (d, J = 8.0 Hz, 2H), 4.71 (d, J = 3.6 Hz, 2H), 3.81 (d, J = 2.4 Hz, 2H), 3.65 (dt, J = 12.4, 3.6 Hz, 2H), 3.19 (d, J = 6.3 Hz, 2H), 2.80 (s, 3H), 2.73 (td, J = 12.0, 2.4 Hz, 2H), 2.12-2.00 (m, 1H), 1.96 (d, J = 13.6 Hz, 2H), 1.47-1.37 (m, 2H) ppm; MS: m/z = 421.07 (M + 1, ESI+). |

Example 44: Synthesis of Compound 39

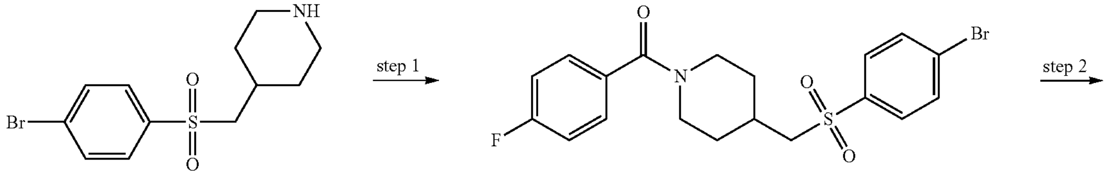

Intermediate E 39-1

-continued

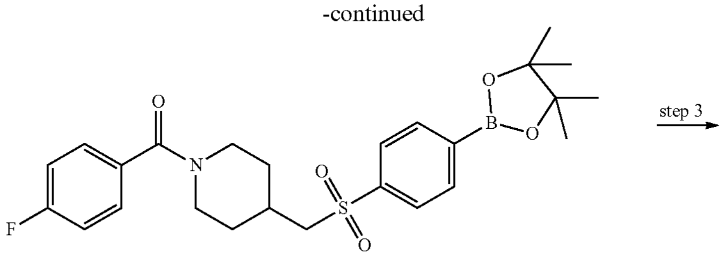

39-2

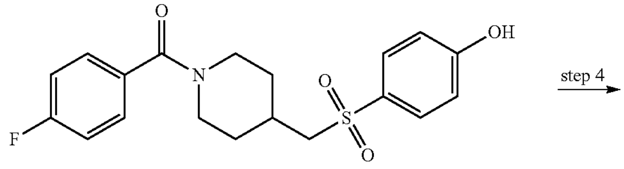

39-3

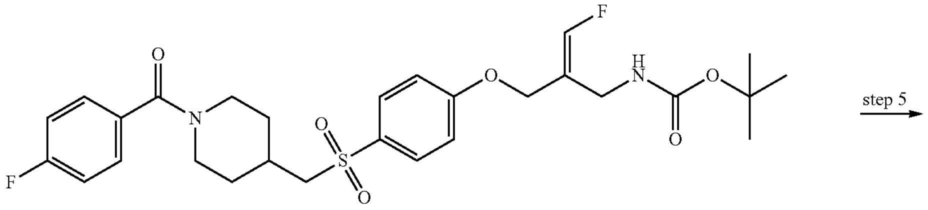

39-4

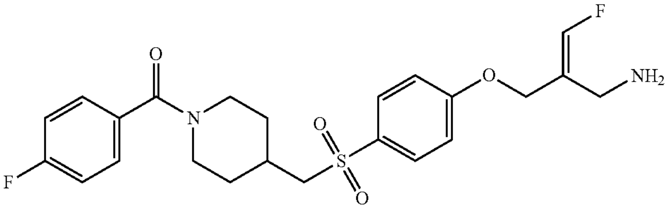

39

Step 1: 39-1

To a mixture of Intermediate E (380 mg, 1.07 mmol, HC), $Et_3N$ (433.64 mg, 4.29 mmol) in DCM (20 mL) was added 4-fluorobenzoyl chloride (169.87 mg, 1.07 mmol) at 20° C. The reaction solution was stirred for 1 hr at 20° C. Then, the solution was concentrated with a rotary evaporator. The crude product was purified by silica gel chromatography (ethyl acetate in petroleum ether, 0 to 60%) to obtain 39-1 (320 mg, 726.73 μmol, 67.83% yield). MS: m/z=441 (M+1).

Step 2: 39-2

To a mixture of 39-1 (320 mg, 726.73 μmol), 4,4,5,5-tetramethyl-2-(4,4,5,5-tetramethyl-1,3,2-dioxaborolan-2-yl)-1,3,2-dioxaborolane (221.45 mg, 872.08 μmol) and KOAc (213.97 mg, 2.18 mmol) in Dioxane (8 mL) was added Pd(dppf)$Cl_2$ (53.18 mg, 72.67 μmol) at 20° C. The reaction solution was heated to 120° C. for 0.667 hr under microwave. The mixture was filtered, and the filtrate was concentrated. The residual material was dissolved in DCM (15 mL), washed with $H_2O$ (15 mL) and brine (15 mL) and concentrated with a rotary evaporator to obtain 39-2 (410 mg, crude). MS: m/z=488 (M+1).

Step 3: 39-3

To a mixture of 39-2 (410 mg, 841.21 μmol), acetic acid (0.2 mL) in THF (7 mL) was added hydrogen peroxide (0.5 mL, 30% purity) at 20° C. The reaction solution was stirred for 1 hr at 20° C. Then, the solution was concentrated with a rotary evaporator to obtain 39-3 (420 mg, crude). MS: m/z=378 (M+1).

Step 4: 39-4

To a mixture of 39-3 (410 mg, 1.09 mmol), Intermediate A (100 mg, 372.96 μmol) in MeCN (20 mL) was added $Cs_2CO_3$ (364.56 mg, 1.12 mmol) at 20° C. The reaction solution was stirred for 1 hr at 90° C. Then, the mixture was filtered, and the filtrate was concentrated with a rotary evaporator to obtain 39-4 (220 mg, crude). MS: m/z=565 (M+1).

Step 5: Compound 39

To a mixture of 39-4 (220 mg, 389.63 μmol) in DCM (20 mL) was added HCl/Dioxane (4 M, 2 mL) at 20° C. and the reaction mixture was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 39 (35 mg, 68.55 mol, 17.59% yield, $HCO_2H$ salt). $^1H$ NMR (400 MHz, Methanol-d4) δ 8.50 (s, 1H), 7.88 (d, J=8.5 Hz, 2H), 7.49-7.39 (m, 2H), 7.26-7.14 (m, 4H), 7.22 (d, J=81.1 Hz, 1H), 4.72 (d, J=3.5 Hz, 2H), 4.51 (s, 1H), 3.80 (d, J=2.2 Hz, 2H), 3.66 (s, 1H), 3.30-3.25 (m, 1H), 3.20 (d, J=6.3 Hz, 2H), 3.11 (s, 1H), 2.96-2.79 (m, 1H), 2.19-2.14 (m, 1H), 1.89 (d, J=34.6 Hz, 2H), 1.34 (d, J=19.0 Hz, 2H). MS: m/z=464.90 (M+1, ESI+).

Example 45: Synthesis of Compound 40
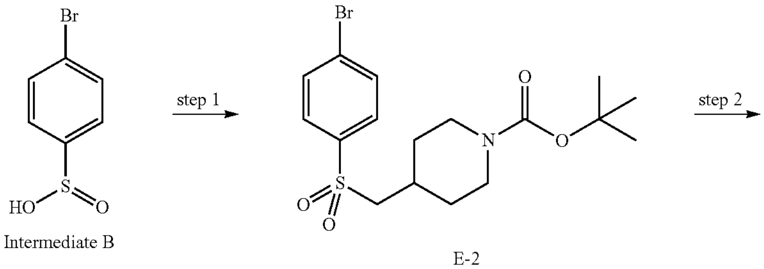
Intermediate B
E-2
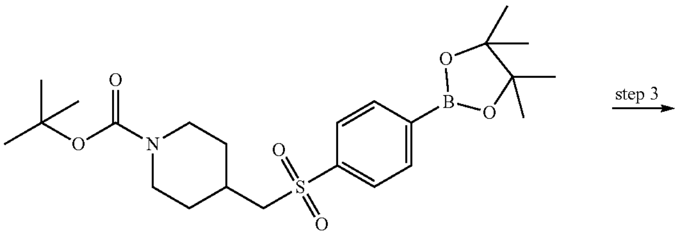
40-1
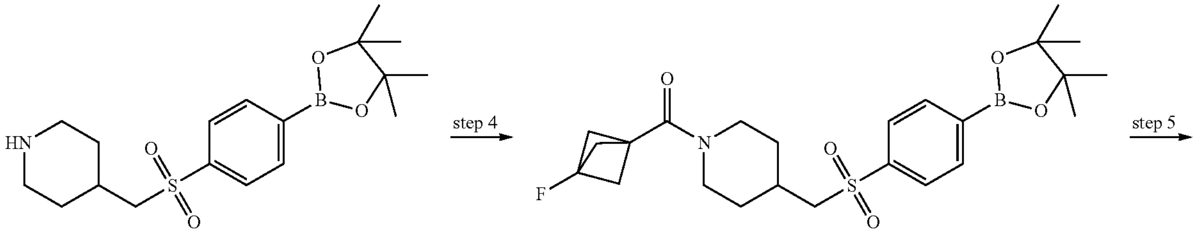
40-2
40-3
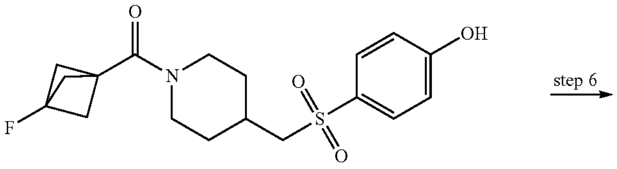
40-4
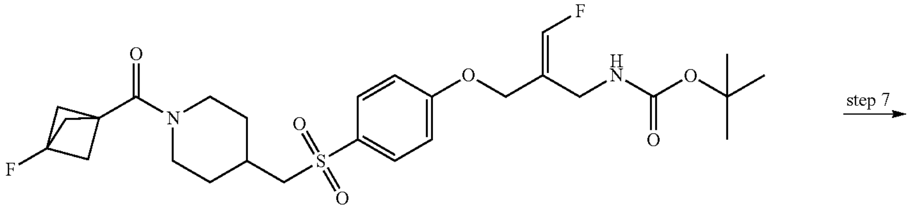
40-5
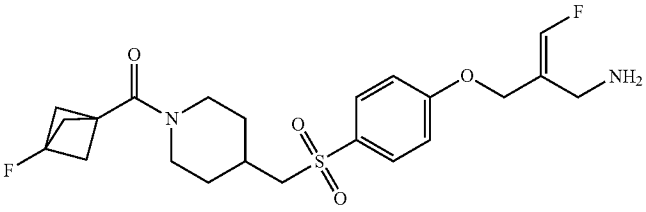
40

Step 1: E-2

To a mixture of Intermediate B (1 g, 4.52 mmol), tert-butyl 4-(bromomethyl)piperidine-1-carboxylate (1.51 g, 5.43 mmol) in MeCN (20 mL) was added $Cs_2CO_3$ (4.42 g, 13.57 mmol) at 20° C. The reaction solution was stirred for 4 hr at 80° C. Then, the solution was concentrated with a rotary evaporator. The crude product was purified by silica gel chromatography (petroleum ether/ethylacetate=4/1, v/v) to obtain E-2 (1.2 g, 2.87 mmol, 63.41% yield).

Step 2: 40-1

A 30 mL microwave reaction tube was charged with E-2 (1.2 g, 2.87 mmol), 4,4,5,5-tetramethyl-2-(4,4,5,5-tetramethyl-1,3,2-dioxaborolan-2-yl)-1,3,2-dioxaborolane (1.09 g, 4.30 mmol)cyclopentyl(diphenyl)phosphane; dichloropalladium; iron (209.89 mg, 286.84 µmol) and KOAc (844.55 mg, 8.61 mmol) in Dioxane (10 mL). After 02 was purged by bubbling N2 into the reaction solution, the tube was sealed and heated at 120° C. for 0.5 hr in a Biotage microwave reactor. The reaction was cooled to room temperature, filtered and concentrated under reduced pressure. The resultant crude product was purified by flash chromatography (ethyl acetate in petroleum ether, 0-100%) to give 40-1 (1 g, 2.15 mmol, 74.91% yield). MS: m/z=465 (M+1).

Step 3: 40-2

A mixture of 40-1 (1 g, 2.15 mmol) in HCl/Dioxane (4 M, 15 mL) was stirred at 25° C. for 1 hr. Then, the solution was concentrated to obtain 40-2 (800 mg, crude, HCl salt). MS: m/z=365 (M+1).

Step 4: 40-3

To a mixture of 40-2 (300 mg, 746.72 µmol), 3-fluorobicyclo[1.1.1]pentane-1-carboxylic acid (97.16 mg, 746.72 µmol) in DCM (10 mL) was added TEA (226.68 mg, 2.24 mmol) and HATU (425.89 mg, 1.12 mmol) at 30° C. The reaction solution was stirred for 1 hr at 30° C. Then, ethyl acetate (100 mL) was added and the mixture was washed with $H_2O$ (100 mL×3), dried over $Na_2SO_4$, filtered and concentrated. The crude product was purified by silica gel chromatography (petroleum ether/ethylacetate=5/1-1/1, v/v) to obtain 40-3 (200 mg, 418.94 µmol, 56.10% yield). MS: m/z=477 (M+1).

Step 5: 40-4

To a mixture of 40-3 (200 mg, 418.94 µmol) in THF (2 mL) and acetic acid (0.5 mL) was added $H_2O_2$ (1 mL, 30% purity). The mixture was stirred at 20° C. for 0.5 hr. $Na_2SO_3$ (0.3 g) was added to the mixture and stirred for 0.5 hr. The reaction mixture then filtered and concentrated to give 40-4 (0.5 g, crude). MS: m/z=367 (M+1).

Step 6: 40-5

A mixture of 40-4 (0.5 g, crude) and Intermediate A (437.83 mg, 1.63 mmol) in MeCN (30 mL) was added $Cs_2CO_3$ (886.74 mg, 2.72 mmol) at 20° C. The reaction solution was stirred for 1 hr at 80° C. Then, the solution was filtered and concentrated to obtain 40-5 (400 mg, crude). MS: m/z=554 (M+1).

Step 7: Compound 40

A mixture of 40-5 (400 mg, 721.18 µmol) in HCl/Dioxane (4 M, 8 mL) was stirred at 20° C. for 1 hr. Then, the solution was concentrated with a rotary evaporator. The crude product was purified by prep-HPLC (column: XBridge@ Prep C18 5 m 19×150 mm; A: 0.1% $HCO_2H$ water, GT: 15 min; flow rate: 15 mL/min) to obtain Compound 40 (60 mg, 132.0 µmol, 18.30% yield). $^1H$ NMR (400 MHz, Methanol-d4) δ 8.50 (s, 1H), 7.89 (d, J=8.5 Hz, 2H), 7.23 (d, J=80.0 Hz, 1H), 7.22 (d, J=8.5 Hz, 2H), 4.71 (d, J=3.6 Hz, 2H), 4.38 (d, J=13.6 Hz, 1H), 4.02 (d, J=13.6 Hz, 1H), 3.80 (s, 2H), 3.17 (d, J=6.0 Hz, 2H), 3.10 (t, J=12.8 Hz, 1H), 2.67 (t, J=12.8 Hz, 1H), 2.39 (t, J=3.2 Hz, 5H), 2.23-2.12 (m, 1H), 1.97 (d, J=13.6 Hz, 1H), 1.83 (d, J=13.6 Hz, 1H), 1.28-1.22 (m, 3H) ppm; MS: m/z=455.6 (M+1, ESI+).

Example 46: Synthesis of Compound 41

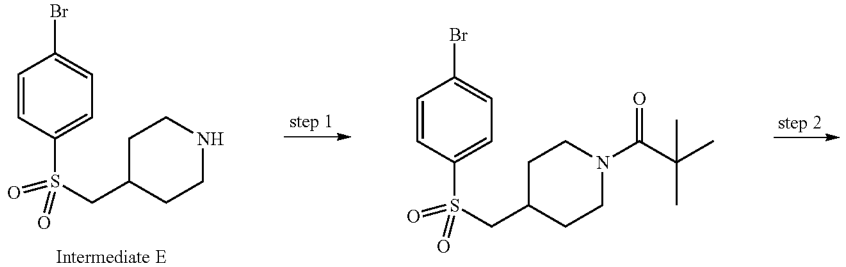

Intermediate E 41-1

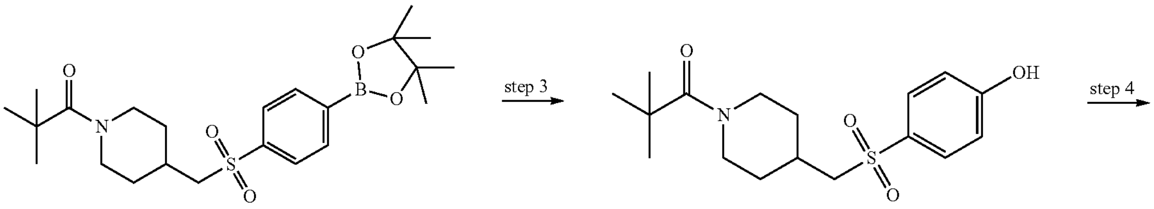

41-2

41-3

-continued

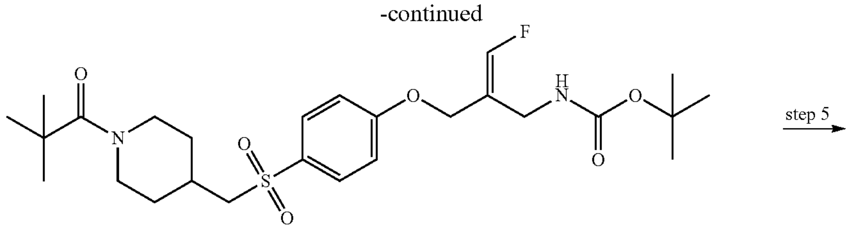

41-4

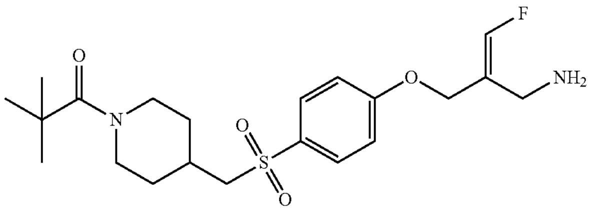

41

Step 1: 41-1

To a mixture of Intermediate E (340 mg, 1.07 mmol) and TEA (324.34 mg, 3.21 mmol, 446.75 μL) in DCM (10 mL) was added 2,2-dimethylpropanoyl chloride (167.47 mg, 1.39 mmol) at 0° C. The reaction solution was stirred for 1 hr at 20° C. Then, the solution was concentrated with a rotary evaporator. The crude product was dissolved in ethyl acetate (80 mL), washed with $H_2O$ (100 mL×3), dried over $Na_2SO_4$, filtered and concentrated to obtain 41-1 (300 mg, 745.63 μmol, 69.79% yield).

Step 2: 41-2

A mixture of 41-1 (300 mg, 745.63 μmol), 4,4,5,5-tetramethyl-2-(4,4,5,5-tetramethyl-1,3,2-dioxaborolan-2-yl)-1,3,2-dioxaborolane (227.21 mg, 894.75 μmol) and KOAc(351.22 mg, 2.24 mmol) in Dioxane (20 mL) was added cyclopentyl(diphenyl)phosphane; dichloropalladium; iron (54.56 mg, 74.56 μmol) at 20° C. under the nitrogen atmosphere. The reaction solution was stirred for 4 hr at 100° C. Then, the solution was concentrated with a rotary evaporator to give a residue, which was purified by column chromatography on silical gel (ethyl acetate/petroleum ether=1/10-1/0) to give 41-2 (200 mg, 445.03 μmol, 59.68% yield). MS: m/z=449 (M+1).

Step 3: 41-3

A mixture of 41-2 (200 mg, 445.03 μmol) in acetic acid (1 mL) and THF (5 mL) was added $H_2O_2$ (1 mL, 30% purity). The mixture was stirred at 25° C. for 1 hr. $Na_2SO_3$ (0.5 g) was added to the mixture and stirred for 20 min. The mixture was filtered concentrated to give 41-3 (152 mg, 447.78 μmol, 100.62% yield). MS: m/z=339 (M+1).

Step 4: 41-4

A mixture of 41-3 (120 mg, 353.51 μmol) and Intermediate A (94.79 mg, 353.51 μmol) in MeCN (10 mL) was added $Cs_2CO_3$ (345.55 mg, 1.06 mmol) at 20° C. The reaction solution was stirred for 1 hr at 80° C. Then, the solution was filtered and concentrated to obtain 41-4 (180 mg, crude). MS: m/z=526 (M+1).

Step 5: Compound 41

A mixture of 41-4 (150 mg, 284.81 μmol) in HCl/Dioxane (4 M, 4 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-40% B; GT: 15 min; flow rate: 15 mL/min) to obtain Compound 41 (20 mg, 46.89 μmol, 16.46% yield). $^1H$ NMR (400 MHz, Methanol-d4) δ 8.48 (s, 1H), 7.89 (d, J=8.6 Hz, 2H), 7.24 (d, J=80.0 Hz, 1H), 7.22 (d, J=8.6 Hz, 2H), 4.72 (d, J=3.6 Hz, 2H), 4.48 (d, J=13.2 Hz, 1H), 4.02 (d, J=14.4 Hz, 1H), 3.81 (d, J=2.4 Hz, 2H), 3.17 (d, J=6.4 Hz, 2H), 3.07 (d, J=13.2 Hz, 1H), 2.61 (t, J=12.4 Hz, 1H), 2.17-2.14 (m, 1H), 1.95 (d, J=13.2 Hz, 1H), 1.83 (d, J=13.2 Hz, 1H), 1.35-1.31 (m, 1H), 1.22-1.18 (m, 1H), 1.02 (s, 9H) ppm; MS: m/z=427.24 (M+1, ESI+).

The compounds of Formula (I') or (I) in Table 3 below were made according to Example 45 of Compound 40.

TABLE 3

| Cmpd No. | $^1H$ NMR and/or LC/MS data |
|---|---|
| 42 | $^1H$ NMR (400 MHz, Methanol-$d_4$) δ 8.50 (s, 1H), 7.91 (d, J = 8.9 Hz, 2H), 7.27 (d, J = 81.0 Hz, 1H), 7.25 (d, J = 8.9 Hz, 2H), 4.74 (d, J = 3.5 Hz, 2H), 4.51 (d, J = 13.4 Hz, 1H), 4.04 (d, J = 13.9 Hz, 1H), 3.84 (d, J = 2.2 Hz, 2H), 3.20 (dd, J = 6.3, 1.5 Hz, 3H), 3.11-3.03 (m, 2H), 2.64-2.59 (m, 1H), 2.44-2.25 (m, 3H), 2.17 (dd, J = 11.4, 6.3 Hz, 1H), 1.92 (dd, J = 46.2, 13.0 Hz, 3H), 1.40-1.15 (m, 3H), 1.04 (s, 9H). MS: m/z = 441.70 (M + 1, ESI+). |
| 43 | $^1H$ NMR (400 MHz, Methanol-$d_4$) δ 8.43 (s, 1H), 7.79 (d, J = 8.9 Hz, 2H), 7.12 (d, J = 8.8 Hz, 2H), 7.05 (d, J = 81.7 Hz, 1H), 4.61 (d, J = 3.5 Hz, 2H), 4.34 (d, J = 13.5 Hz, 3H), 3.61 (s, 2H), 3.07 (dd, J = 6.3, 4.1 Hz, 3H), 2.75 (t, J = 12.9 Hz, 3H), 2.14-2.00 (m, 2H), 1.92 (s, 5H), 1.88 (d, J = 2.9 Hz, 9H), 1.84-1.75 (m, 4H), 1.67 (d, J = 3.0 Hz, 10H), 1.16-1.12 (m, 4H). MS: m/z = 505.73 (M + 1, ESI+). |

The compounds of Formula (I') or (I) in Table 4 below were made according to Example 46 of Compound 41.
TABLE 4
| Cmpd No. | 1H NMR and/or LC/MS data |
|---|---|
| 44 | $^1$H NMR (400 MHz, Methanol-d4) δ 8.50 (s, 1H), 7.89 (d, J = 8.0 Hz, 2H), 7.23 (d, J = 80.0 Hz, 1H), 7.22 (d, J = 8.0 Hz, 2H), 4.71 (d, J = 3.6 Hz, 2H), 4.41-4.21 (m, 2H), 3.80 (d, J = 2.4 Hz, 2H), 3.18 (d, J = 6.4 Hz, 3H), 2.66 (t, J = 12.8 Hz, 1H), 2.19 (dd, J = 10.4, 5.2 Hz, 1H), 2.04-1.88 (m, 2H), 1.82 (d, J = 13.2 Hz, 1H), 1.36 (d, J = 12.8 Hz, 1H), 1.21 (d, J = 12.8 Hz, 1H), 0.86-0.70 (m, 4H) ppm; MS: m/z = 411.1 (M + 1, ESI+). |
Example 47: Synthesis of Compound 45
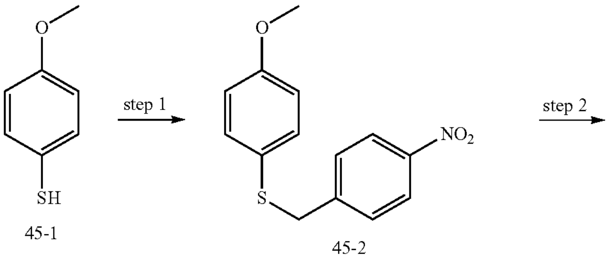
45-1
45-2
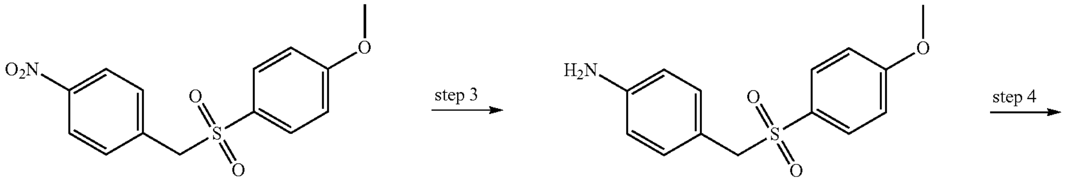
45-3
45-4
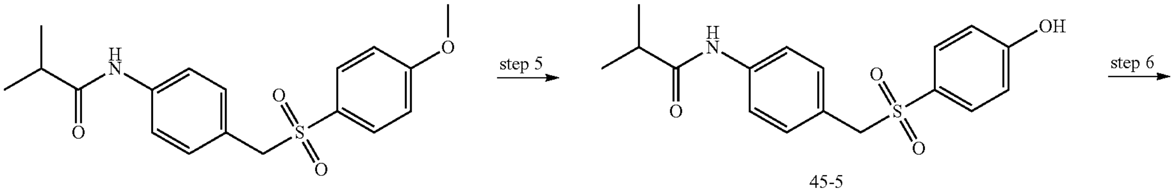
45-5
45-5
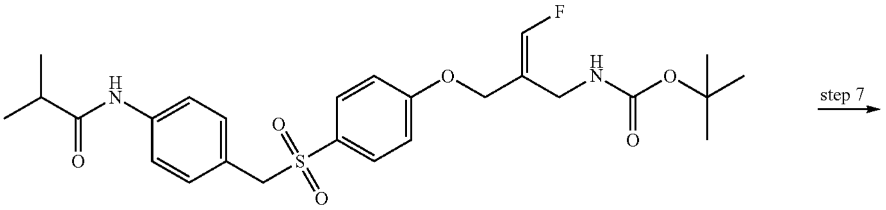
45-7
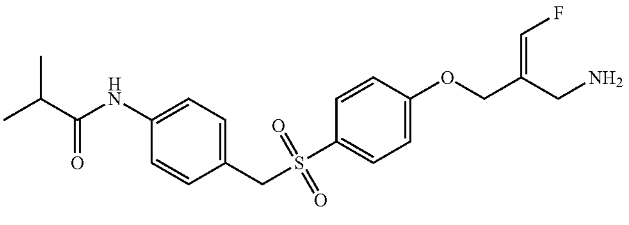
45

Step 1: 45-2

To a mixture of 45-1 (500 mg, 3.57 mmol) in DMF (10 mL) was added NaH (156.90 mg, 3.92 mmol, 60% purity) at 20° C. The reaction solution was stirred for 0.5 hr at 20° C. Then, 1-(bromomethyl)-4-nitro-benzene (785.83 mg, 3.64 mmol) was added. The reaction solution was stirred further for 18 hr at 20° C. Then, the solution was concentrated with a rotary evaporator. The crude product was purified by silica gel chromatography (ethyl acetate in petroleum ether, 0-10%) to give 45-2 (850 mg, 3.09 mmol, 86.57% yield).

Step 2: 45-3

To a mixture of 45-2 (500 mg, 1.82 mmol) in DCM (30 mL) was added m-CPBA (1.11 g, 5.45 mmol, 85% purity) at 20° C. The mixture was stirred for 2 hr at 20° C. Then, the solution was washed with saturated aqueous $Na_2SO_3$ (15 mL), saturated aqueous $NaHCO_3$ (20 mL×2) and brine (15 mL), dried over $Na_2SO_4$ and concentrated with a rotary evaporator to obtain 45-3 (550 mg, crude).

Step 3: 45-4

To a mixture of 45-3 (550 mg, 1.79 mmol) in MeOH (20 mL) was added Pd/C (217.35 mg, 178.97 μmol, 10% purity) at 20° C. The reaction solution was stirred for 18 hr at 20° C. under $H_2$ atmosphere. Then, the mixture was filtered, and the filtrate was concentrated with a rotary evaporator to obtain 45-4 (510 mg, crude). MS: m/z=278 (M+1).

Step 4: 45-5

To a mixture of 45-4 (510 mg, 1.84 mmol), $Et_3N$ (558.23 mg, 5.52 mmol) in DCM (40 mL) was added 2-methylpropanoyl chloride (195.94 mg, 1.84 mmol) at 20° C. The reaction solution was stirred for 2 hr at 20° C. Then, the solution was concentrated with a rotary evaporator. The crude product was purified by silica gel chromatography (ethyl acetate in petroleum ether, 0 to 60%) to obtain 45-5 (330 mg, 949.84 μmol, 51.65% yield). MS: m/z=348 (M+1).

Step 5: 45-6

To a mixture of 45-5 (330 mg, 949.84 μmol) in DCM (15 mL) was added $BBr_3$ (0.5 ml, 5.29 mmol) at 0° C. The reaction mixture was stirred for 1 hr at 20° C. Then, the solution was quenched with MeOH (20 mL) at 0° C., and stirred for 0.25 hr at 20° C. The solution was concentrated with a rotary evaporator to obtain 45-6 (330 mg, crude). MS: m/z=332 (M+1).

Step 6: 45-7

To a mixture of 45-6 (330 mg, 989.80 μmol), Intermediate A (100 mg, 372.96 mol) in MeCN (30 mL) was added $Cs_2CO_3$ (364.56 mg, 1.12 mmol) at 20° C. The reaction solution was stirred for 1 hr at 90° C. Then, the mixture was filtered, and the filtrate was concentrated with a rotary evaporator to obtain 45-7 (220 mg, crude). MS: m/z=521 (M+1).

Step 7: Compound 45

To a mixture of 45-7 (220 mg, 422.58 μmol) in DCM (20 mL) was added HCl/Dioxane (4 M, 3.0 mL) at 20° C. and the reaction mixture was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, GT: 15 min; flow rate: 15 mL/min) to obtain Compound 45 (44 mg, 94.32 μmol, 22.32% yield, $HCO_2H$ salt). $^1H$ NMR (400 MHz, Methanol-d4) δ 8.52 (s, 1H), 7.58 (d, J=8.7 Hz, 2H), 7.50-7.42 (m, 2H), 7.23 (d, J=81.1 Hz, 1H), 7.14-7.06 (m, 2H), 7.03 (d, J=8.4 Hz, 2H), 4.67 (d, J=3.5 Hz, 2H), 4.41 (s, 2H), 3.76 (d, J=2.2 Hz, 2H), 2.60-2.56 (m, 1H), 1.18 (d, J=6.8 Hz, 6H) ppm. MS: m/z=420.96 (M+1, ESI+).

Example 48: Synthesis of Compound 46

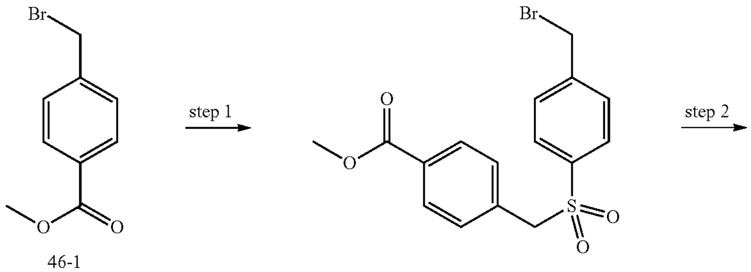

46-1

46-2

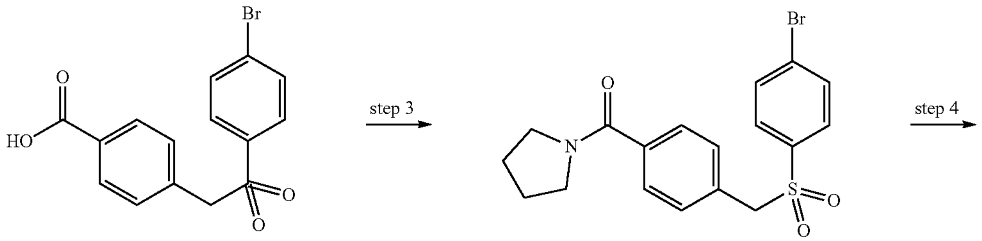

46-3

46-4

-continued

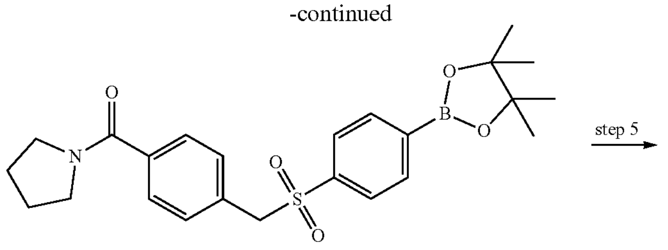

46-5

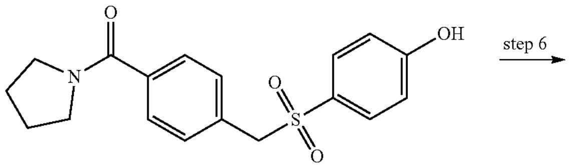

46-6

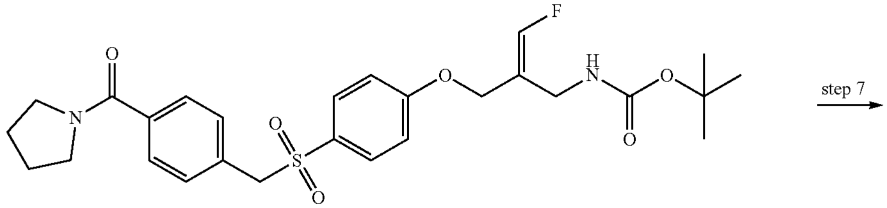

46-7

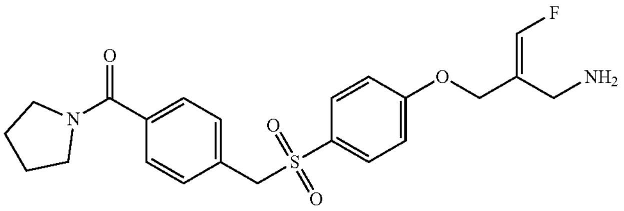

46

Step 1: 46-2

To a mixture of 46-1 (1.2 g, 5.24 mmol) and 4-bromobenzenesulfinic acid (1.51 g, 6.81 mmol) was added $K_2CO_3$ (1.45 g, 10.48 mmol) and stirred at 120° C. for 0.5 hr under microwave. Water (20 mL) was added, extracted with DCM (30 mL), the organic layer was washed with water, brine and dried with $Na_2SO_4$. The organic layer was concentrated and the residue was purified by column chromatography on silcal gel (ethyl acetate/petroleum ether=1/10-1/1, v/v) to give 46-2 (1.4 g, 3.79 mmol, 72.38% yield).

Step 2: 46-3

To a mixture of 46-2 (0.4 g, 1.08 mmol) in MeOH (5 mL) was added NaOH (4 M in water, 8.13 mL) and the mixture was stirred at 90° C. for 5 hr. HCl (1 M in water) was added to adjusted pH to 3. $H_2O$ (20 mL) was then added, and the mixture was extracted with ethyl acetate (150 mL), washed with $H_2O$, brine. The organic layer was dried over $Na_2SO_4$, concentrated and the residue was purified by column chromatography on silcal gel (ethyl acetate/petroleum ether=1/10-1/1, v/v) to give 46-3 (0.35 g, 985.35 μmol, 90.96% yield).

Step 3: 46-4

A mixture of 46-3 (0.35 g, 985.35 μmol), HATU (561.99 mg, 1.48 mmol), DIPEA (382.05 mg, 2.96 mmol, 514.89 μL) in DMF (8 mL) was added pyrrolidine (91.10 mg, 1.28 mmol, 106.43 μL) and stirred at 20° C. for 8 hr. $H_2O$ (30 mL) was added, and the mixture was extracted with ethyl acetate (100 mL), washed with $H_2O$, brine. The organic layer was dried over $Na_2SO_4$, concentrated and the residue was purified by column chromatography on silcal gel (ethyl acetate/petroleum ether=1/10-1/1, v/v) to give 46-4 (0.38 g, 930.67 μmol, 94.45% yield). MS: m/z=408.0 (M+1).

Step 4: 46-5

A mixture of 46-4 (0.38 g, 930.67 μmol), 4,4,5,5-tetramethyl-2-(4,4,5,5-tetramethyl-1,3,2-dioxaborolan-2-yl)-1,3,2-dioxaborolane (354.50 mg, 1.40 mmol), potassium acetate (182.68 mg, 1.86 mmol) and cyclopentyl(diphenyl)phosphane; dichloromethane; dichloropalladium; iron (38.0 mg, 46.53 μmol) in Dioxane (8 mL) was stirred at 120° C. for 0.7 hr under microwave. The reaction mixture was filtered, the filtrate was concentrated to give 46-4 (crude, 0.4 g). MS: m/z=456.2 (M+1).

Step 5: 46-6

To a mixture of 46-5 (0.4 g, 878.40 μmol) in THF (4 mL) and acetic acid (1 mL) was added $H_2O_2$ (0.5 mL, 30% purity). The reaction was stirred at 20° C. for 1 hr. $Na_2SO_3$ (1.0 g) was added to quench the reaction, and the reaction mixture was filtered and concentrated to give 46-6 (crude, 0.3 g). MS: m/z=346.1 (M+1).

Step 6: 46-7

To a mixture of 46-6 (0.3 g, 868.53 μmol) in MeCN (20 mL) was added $Cs_2CO_3$ (848.95 mg, 2.61 mmol) and Intermediate A (302.73 mg, 1.13 mmol). The mixture was stirred at 95° C. for 1 hr. The reaction mixture was concentrated and the residue was purified by flash chromatography on silcal gel (ethyl acetate/petroleum ether=1/10-5/1, v/v) to give 46-7 (0.3 g, 563.25 μmol, 64.85% yield). MS: m/z=533.2 (M+1).

Step 7: Compound 46

A mixture of 46-7 (0.3 g, 563.25 μmol) in HCl/Dioxane (4 M, 4.22 mL) was stirred at 20° C. for 0.5 hr. Then, the solution was concentrated and the residue was purified by Prep-HPLC (prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 46 (0.2 g, 417.94 μmol, 74.20% yield, $HCO_2H$ salt). $^1H$ NMR (400 MHz, Methanol-d4) δ 8.52 (s, 1H), 7.68-7.53 (m, 2H), 7.43 (d, J=8.2 Hz, 2H), 7.33 (s, 0.5H), 7.24 (d, J=8.2 Hz, 2H), 7.11 (d, J=9.0 Hz, 2.5H), 4.69 (d, J=3.4 Hz, 2H), 4.54 (s, 2H), 3.81 (d, J=2.1 Hz, 2H), 3.58 (t, J=6.9 Hz, 2H), 3.42 (t, J=6.6 Hz, 2H), 2.16-1.80 (m, 4H). MS: m/z=433.2 (M+1, ESI+).

The compounds of Formula (I') or (I) in Table 5 below were made according to Example 48 of Compound 46.

TABLE 5

| Cmpd No. | $^1H$ NMR and/or LC/MS data |
|---|---|
| 47 | $^1H$ NMR (400 MHz, Methanol-$d_4$) δ 8.52 (s, 1H), 7.65-7.54 (m, 2H), 7.47-7.45 (m, 1H), 7.44-7.34 (m, 1H), 7.33 (s, 0.5H), 7.28 (dd, J = 4.7, 2.8 Hz, 2H), 7.17-7.03 (m, 2.5H), 4.69 (d, J = 3.4 Hz, 2H), 4.55 (s, 2H), 3.82 (d, J = 2.2 Hz, 2H), 3.55 (t, J = 7.0 Hz, 2H), 3.29 (t, J = 7.0 Hz, 3H), 2.06-1.75 (m, 4H) ppm. MS: m/z = 433.2 (M + 1, ESI+). |

The compounds of Formula (I') or (I) in Table 6 below were made according to Example 44 of Compound 39.

TABLE 6

| Cmpd No. | $^1H$ NMR and/or LC/MS data |
|---|---|
| 48 | $^1H$ NMR (400 MHz, Methanol-$d_4$) δ 8.52 (s, 1H), 7.65-7.54 (m, 2H), 7.47-7.45 (m, 1H), 7.44-7.34 (m, 1H), 7.33 (s, 0.5H), 7.28 (dd, J = 4.7, 2.8 Hz, 2H), 7.17-7.03 (m, 2.5H), 4.69 (d, J = 3.4 Hz, 2H), 4.55 (s, 2H), 3.82 (d, J = 2.2 Hz, 2H), 3.55 (t, J = 7.0 Hz, 2H), 3.29 (t, J = 7.0 Hz, 3H), 2.06-1.75 (m, 4H) ppm. MS: m/z = 433.2 (M + 1, ESI+). |
| 49 | $^1H$ NMR (400 MHz, Methanol-$d_4$) δ 7.72 (d, J = 8.9 Hz, 2H), 7.05 (d, J = 8.9 Hz, 2H), 6.97 (s, 1H), 4.55 (d, J = 3.5 Hz, 2H), 4.32-4.22 (m, 2H), 3.79-3.69 (m, 2H), 3.65 (d, J = 2.3 Hz, 2H), 3.00 (t, J = 5.7 Hz, 3H), 2.97-2.85 (m, 2H), 2.46 (td, J = 12.8, 3.0 Hz, 2H), 2.12 (d, J = 6.8 Hz, 3H), 2.04-1.91 (m, 2H), 1.83-1.62 (m, 3H), 1.22-0.98 (m, 3H), 0.79-0.71 (m, 2H) ppm. MS: m/z = 425.67 (M + 1, ESI+). |
| 50 | $^1H$ NMR (400 MHz, Methanol-$d_4$) δ 8.51 (s, 1H), 7.92 (d, J = 8.9 Hz, 2H), 7.26 (d, J = 81.0 Hz, 1H), 7.25 (d, J = 8.9 Hz, 2H), 4.74 (d, J = 3.6 Hz, 2H), 4.66-4.58 (m, 1H), 4.35 (s, 3H), 4.13 (d, J = 2.4 Hz, 1H), 3.84 (d, J = 2.3 Hz, 2H), 3.20 (t, J = 5.8 Hz, 4H), 2.29-2.11 (m, 2H), 1.95 (d, J = 12.0 Hz, 3H), 1.40-1.24 (m, 6H), 1.21 (q, J = 2.7, 1.9 Hz, 3H) ppm. MS: m/z = 479.64 (M + 1, ESI+). |
| 51 | $^1H$ NMR (400 MHz, Methanol-$d_4$) δ 8.49 (s, 1H), 7.96-7.88 (m, 2H), 7.30-7.21 (m, 2H), 7.27 (d, J = 81.0 Hz, 1H), 4.74 (d, J = 3.5 Hz, 2H), 4.62 (dd, J = 3.6, 1.0 Hz, 1H), 4.42 (d, J = 13.7 Hz, 2H), 4.13 (d, J = 2.4 Hz, 1H), 3.84 (d, J = 2.3 Hz, 2H), 3.80 (s, 1H), 3.21-3.16 (m, 3H), 2.88-2.72 (m, 7H), 2.23-2.10 (m, 2H), 2.02-1.80 (m, 4H), 1.40-1.14 (m, 4H) ppm. MS: m/z = 461.72 (M + 1, ESI+). |

Example 49: Synthesis of Compound 52

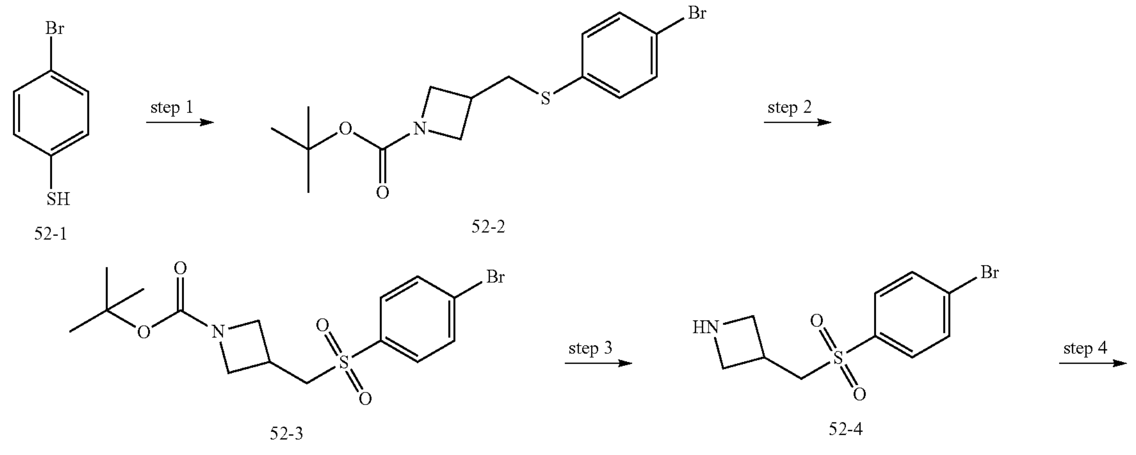

52-1 52-2 52-3 52-4

-continued

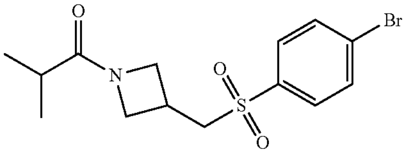

52-5 step 5

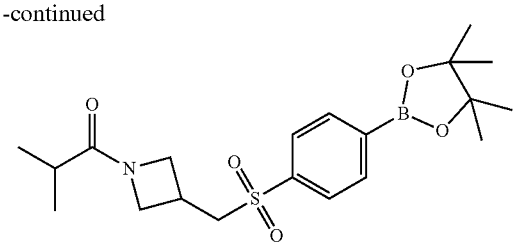

52-6 step 6

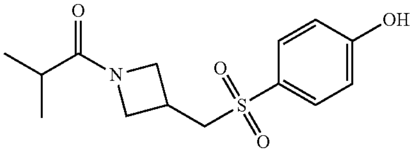

52-7 step 7

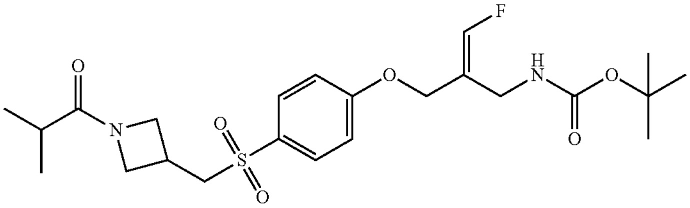

52-8 step 8

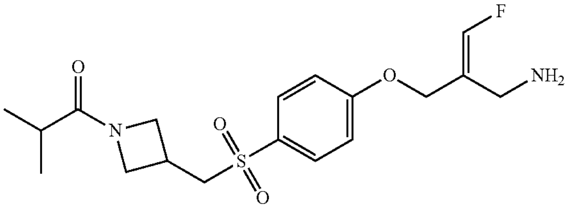

52

Step 1: 52-2

To a mixture of 52-1 (687.17 mg, 3.63 mmol) in DMF (15 mL) was added NaH (159.90 mg, 4.0 mmol, 60% purity) at 20° C. The reaction solution was stirred for 0.5 hr at 20° C. Then, tert-butyl 3-(bromomethyl)azetidine-1-carboxylate (1.0 g, 4.00 mmol) was added. The reaction solution was stirred further for 18 hr at 20° C. Then, the solution was concentrated with a rotary evaporator. The crude product was purified by silica gel chromatography (ethyl acetate in petroleum ether, 0 to 10%) to obtain 52-2 (1.1 g, 3.07 mmol, 84.47% yield). MS: m/z=358 (M+1).

Step 2: 52-3

To a mixture of 52-2 (1.1 g, 3.07 mmol) in DCM (40 mL) was added m-CPBA (2.49 g, 12.28 mmol, 85% purity) at 20° C. The mixture was stirred for 2 hr at 20° C. Then, the solution was washed with saturated aqueous $Na_2SO_3$ (10 mL), saturated aqueous $NaHCO_3$ (20 mL×2) and brine (15 mL), dried over $Na_2SO_4$ and concentrated with a rotary evaporator to obtain 52-3 (1.0 g, crude). MS: m/z=390 (M+1).

Step 3: 52-4

To a mixture of 52-3 (1.0 g, 2.56 mmol) in DCM (30 mL) was added HCl/Dioxane (4 M, 4 mL) at 20° C. and the reaction mixture was stirred at 20° C. for 1 hr. Then, the solution was concentrated with a rotary evaporator to obtain 52-4 (800 mg, crude, HCl salt). MS: m/z=290 (M+1).

Step 4: 52-5

To a mixture of 52-4 (400 mg, 1.22 mmol), $Et_3N$ (495.67 mg, 4.90 mmol) in DCM (30 mL) was added 2-methylpropanoyl chloride (143.53 mg, 1.35 mmol) at 20° C. The reaction solution was stirred for 1 hr at 20° C. Then, the solution was concentrated with a rotary evaporator. The crude product was purified by silica gel chromatography (ethyl acetate in petroleum ether, 0 to 60%) to obtain 52-5 (300 mg, 832.72 μmol, 68.00% yield). MS: m/z=360 (M+1).

Step 5: 52-6

To a mixture of 52-5 (300 mg, 832.72 μmol), 4,4,5,5-tetramethyl-2-(4,4,5,5-tetramethyl-1,3,2-dioxaborolan-2-yl)-1,3,2-dioxaborolane (253.75 mg, 999.26 μmol) and KOAc (245.17 mg, 2.50 mmol) in Dioxane (8 mL) was added Pd(dppf)$Cl_2$ (60.93 mg, 83.27 μmol) at 20° C. The reaction solution was stirred for 0.667 hr at 120° C. under microwave. The mixture was filtered and the filtrate was evaporated to 52-6 (330 mg, crude). MS: m/z=408 (M+1).

Step 6: 52-7

To a mixture of 52-6 (330 mg, 810.15 μmol), acetic acid (0.2 mL) in THF (10 mL) was added hydrogen peroxide (0.4 mL, 30% purity) at 20° C. The reaction solution was stirred for 1 hr at 20° C. Then, the solution was filtered and concentrated with a rotary evaporator to obtain 52-7 (200 mg, crude). MS: m/z=296 (M+1).

Step 7: 52-8

To a mixture of 52-7 (200 mg, 672.56 μmol), Intermediate A (100 mg, 372.96 μmol) in MeCN (20 mL) was added $Cs_2CO_3$ (364.56 mg, 1.12 mmol) at 20° C. The reaction solution was stirred for 1 hr at 90° C. Then, the mixture was filtered, and the filtrate was concentrated with a rotary evaporator to obtain 52-8 (150 mg, crude). MS: m/z=485 (M+1).

Step 8: Compound 52

To a mixture of 52-8 (150 mg, 309.55 μmol) in DCM (10 mL) was added HCl/Dioxane (4 M, 3 mL) at 20° C. and the reaction mixture was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 52 (22 mg, 51.10 μmol, 16.51% yield, $HCO_2H$ salt). $^1H$ NMR (400 MHz, Methanol-d4) δ 8.47 (s, 1H), 7.90 (d, J=8.9 Hz, 2H), 7.28 (d, J=81.1 Hz, 1H), 7.26 (d, J=8.9 Hz, 2H), 4.75 (d, J=3.5 Hz, 1H), 4.35 (q, J=8.5 Hz, 2H), 4.13 (d, J=2.4 Hz, 2H), 3.66 (dd, J=10.2, 6.0 Hz, 1H), 3.05-3.00 (m, 3H), 2.48 (p, J=6.8 Hz, 2H), 1.30-1.23 (m, 2H), 1.06 (d, J=1.8 Hz, 6H). MS: m/z=385.24 (M+1, ESI+).

Example 50: Synthesis of Compound 53

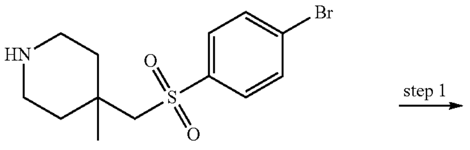

Intermediate F

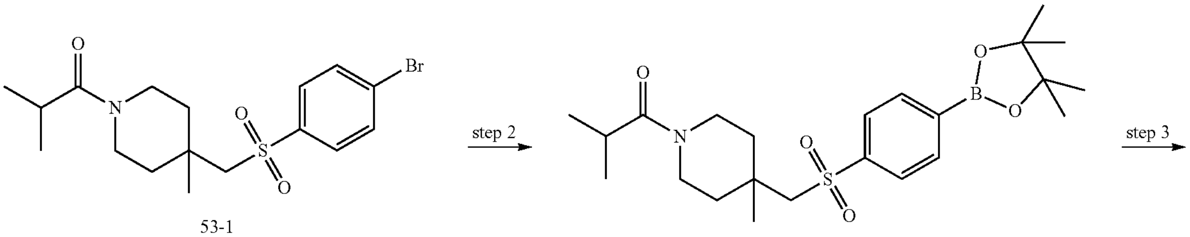

53-1

53-2

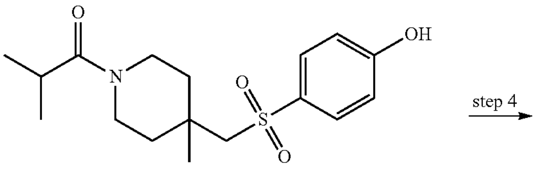

53-3

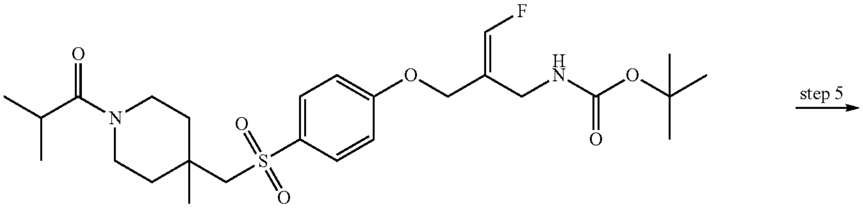

53-4

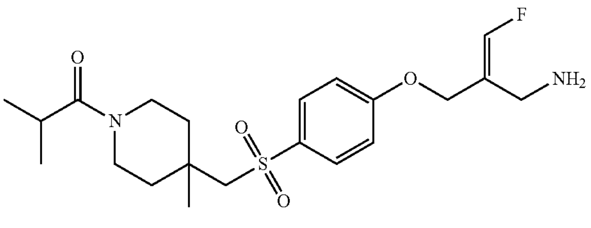

53

Step 1: 53-1

To a mixture of Intermediate F (80 mg, 216.97 μmol) and TEA (65.87 mg, 650.91 μmol) in DCM (10 mL) was added 2-methylpropanoyl chloride (46.24 mg, 433.94 μmol) at 0° C. The reaction solution was stirred for 1 hr at 20° C. Then, the solution was concentrated with a rotary evaporator. The crude product was dissolved in ethyl acetate (80 mL), washed with $H_2O$ (100 mL×3), dried over $Na_2SO_4$, filtered and concentrated to obtain 53-1 (80 mg, 198.83 μmol, 91.64% yield). MS: m/z=402 (M+1).

Step 2: 53-2

To a mixture of 53-1 (80 mg, 198.83 μmol), 4,4,5,5-tetramethyl-2-(4,4,5,5-tetramethyl-1,3,2-dioxaborolan-2-yl)-1,3,2-dioxaborolane (60.59 mg, 238.60 μmol) and cyclopentyl(diphenyl)phosphane; dichloropalladium; iron (145.49 mg, 198.83 μmol) in Dioxane (5 mL) was added KOAc (304.87 mg, 596.50 μmol) at 20° C. under the nitrogen atmosphere. The reaction solution was stirred for 4 hr at 100° C. Then, the solution was concentrated with a rotary evaporator and purified by column chromatography on silical gel (ethyl acetate/petroleum ether=1/10-1/1) to obtain 53-2 (60 mg, 133.51 μmol, 67.15% yield). MS: m/z=449 (M+1).

Step 3: 53-3

To a mixture of 53-2 (60 mg, 133.51 μmol) in THF (5 mL) and acetic acid (1 mL) was added $H_2O_2$ (1 mL, 30% purity). The mixture was stirred at 25° C. for 1 hr. $Na_2SO_3$ (0.5 g) was added to the mixture and stirred for 20 min. The mixture was filtered and concentrated to give 53-3 (600 mg, crude). MS: m/z=339 (M+1).

Step 4: 53-4

To a mixture of 53-3 (600 mg, crude) and Intermediate A (94.79 mg, 353.51 μmol) in MeCN (10 mL) was added $Cs_2CO_3$ (575.91 mg, 1.77 mmol) at 20° C. The reaction solution was stirred for 1 hr at 80° C. Then, the solution was filtered and concentrated to obtain 53-4 (60 mg, 113.93 μmol, 6.45% yield). MS: m/z=526 (M+1).

Step 5: Compound 53

A mixture of 53-4 (60 mg, 113.93 μmol) in HCl/Dioxane (4 M, 3 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 10-40% B; GT: 15 min; flow rate: 15 mL/min) to give Compound 53 (20 mg, 42.32 μmol, 37.15% yield, $HCO_2H$ salt). $^1H$ NMR (400 MHz, Methanol-d4) δ 8.50 (s, 1H), 7.90 (d, J=8.0 Hz, 2H), 7.22 (d, J=80.0 Hz, 1H), 7.21 (d, J=8.0 Hz, 2H), 4.71 (s, 2H), 3.33-3.29 (m, 2H), 3.66-3.62 (m, 2H), 3.56-3.37 (m, 2H), 3.28 (s, 2H), 2.99-2.85 (m, 1H), 1.86-1.82 (s, 1H), 1.67-1.61 (s, 2H), 1.52-1.45 (m, 1H), 1.32 (s, 3H), 1.07 (d, J=6.8 Hz, 6H) ppm; MS: m/z=427.27 (M+1, ESI+).

The compounds of Formula (I') or (I) in Table 7 below were made according to Example 50 of Compound 53.

TABLE 7

| Cmpd No. | $^1H$ NMR and/or LC/MS data |
|---|---|
| 54 | MS: m/z = 441.70 (M + 1, ESI+). |
| 55 | $^1H$ NMR (400 MHz, Methanol-d4) δ 8.51 (s, 1H), 7.90 (d, J = 8.4 Hz, 2H), 7.21 (d, J = 80.0 Hz, 1H), 7.20 (d, J = 8.4 Hz, 2H), 4.71 (d, J = 3.6 Hz, 2H), 3.85-3.69 (m, 4H), 3.61-3.57 (m, 2H), 1.79-1.76 (m, 2H), 1.62-1.56 (m, 2H), 1.33 (s, 5H), 1.19 (s, 2H) ppm; MS: m/z = 493.6 (M + 1, ESI+). |
| 56 | $^1H$ NMIR (400 MHz, Methanol-d4) δ 8.52 (s, 1H), 7.89 (d, J = 8.4 Hz, 2H), 7.20 (d, J = 80.0 Hz, 1H), 7.20 (d, J = 8.4 Hz, 2H), 4.71 (d, J = 3.6 Hz, 2H), 3.77 (d, J = 2.4 Hz, 2H), 3.39-3.34 (m, 4H), 3.27 (s, 2H), 2.49-2.44 (m, 2H), 2.04-1.94 (m, 1H), 1.88-1.84 (m, 3H), 1.69 (d, J = 10.4 Hz, 2H), 1.57-1.53 (m, 2H), 1.41 (s, 3H), 1.32 (s, 3H) ppm; MS: m/z = 453.7 (M + 1, ESI+). |

Example 51: Synthesis of Compound 57

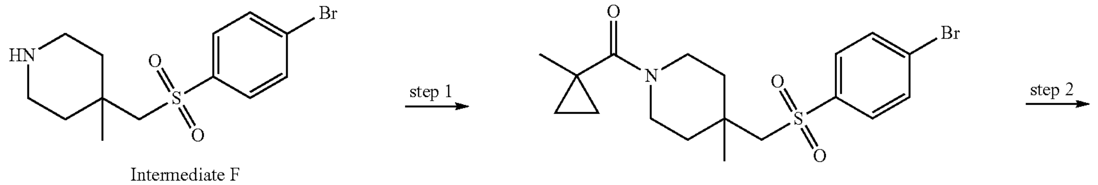

Intermediate F 57-1

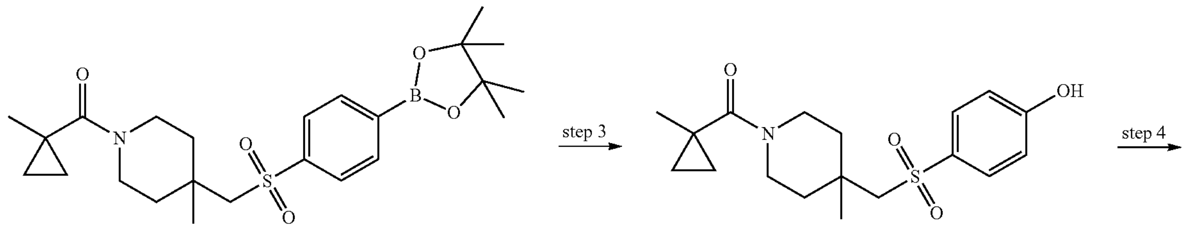

57-2

57-3

-continued

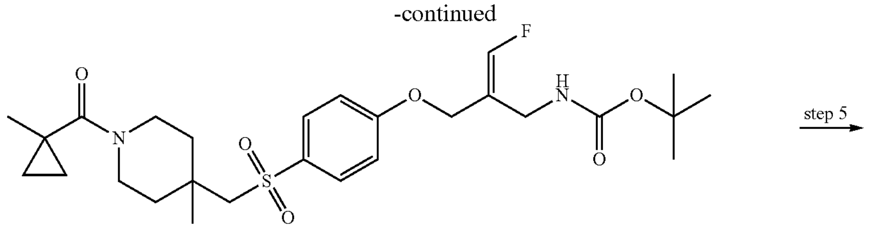

57-4

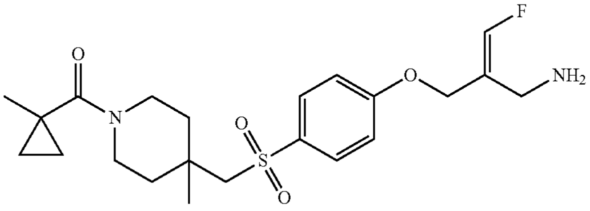

57

Step 1: 57-1

To a mixture of Intermediate F (50 mg, 150.49 μmol), 1-methylcyclopropanecarboxylic acid (18.08 mg, 180.58 μmol) in DCM (10 mL) was added TEA (45.68 mg, 451.46 μmol, 62.92 μL) and HATU (85.83 mg, 225.73 μmol) at 30° C. The reaction solution was stirred for 1 hr at 30° C. Then, ethyl acetate (100 mL) was added and the mixture reaction was washed with $H_2O$ (100 mL×3), dried over $Na_2SO_4$, filtered and concentrated. The crude product was purified by silica gel chromatography (petroleum ether/ethyl acetate=5/1-1/1, v/v) to obtain 57-1 (55 mg, 132.74 μmol, 88.20% yield).

Step 2: 57-2

A 30 mL microwave reaction tube was charged with 57-1 (55 mg, 132.74 μmol), 4,4,5,5-tetramethyl-2-(4,4,5,5-tetramethyl-1,3,2-dioxaborolan-2-yl)-1,3,2-dioxaborolane (50.56 mg, 199.10 μmol), cyclopentyl(diphenyl)phosphane; dichloropalladium; iron (9.71 mg, 13.27 mol) and KOAc (39.08 mg, 398.21 μmol) in Dioxane (5 mL). After 02 was purged by bubbling N2 into the reaction solution, the tube was sealed and heated at 120° C. for 0.5 hr in a Biotage microwave reactor. The reaction was cooled to room temperature, filtered and concentrated under reduced pressure. The resultant crude product was purified by flash chromatography (ethyl acetate in petroleum ether, 0-100%) to deliver 57-2 (40 mg, 86.69 μmol, 65.31% yield). MS: m/z=461 (M+1).

Step 3: 57-3

A mixture of 57-2 (40 mg, 86.69 μmol) in THF (1 ml) and $H_2O$ (0.25 mL) was added $H_2O_2$ (0.5 mL, 30% purity). The mixture was stirred at 25° C. for 0.5 hr. $Na_2SO_3$ (0.6 g) was added to the mixture and stirred for 30 min. The reaction mixture was filtered and concentrated in vacuo to give 57-3 (0.5 g, crude). MS: m/z=351 (M+1).

Step 4: 57-4

A mixture of 57-3 (0.5 g, crude) and Intermediate A (152.58 mg, 569.06 μmol) in MeCN (50 mL) was added $Cs_2CO_3$ (1.39 g, 4.27 mmol) at 20° C. The reaction solution was stirred for 1 hr at 80° C. Then, the solution was filtered and concentrated to obtain 57-4 (80 mg, crude). MS: m/z=538 (M+1).

Step 5: Compound 57

A mixture of 57-4 (80 mg, 148.51 μmol) in HCl/Dioxane (4 M, 3.26 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, GT: 15 min; flow rate: 15 mL/min) to afford Compound 57 (4.2 mg, 8.67 μmol, 5.84% yield, $HCO_2H$ salt). $^1H$ NMR (400 MHz, Methanol-d4) δ 8.51 (s, 1H), 7.90 (d, J=8.4 Hz, 2H), 7.32 (d, J=80.0 Hz, 1H), 7.21 (d, J=8.4 Hz, 2H), 4.71 (d, J=3.6 Hz, 2H), 3.93-3.78 (m, 2H), 3.75-3.70 (m, 2H), 3.58-3.54 (m, 2H), 3.31-3.28 (m, 2H), 1.78-1.74 (m, 2H), 1.58-1.54 (m, 2H), 1.33 (s, 3H), 1.28 (s, 3H), 0.86 (d, J=5.0 Hz, 2H), 0.61 (t, J=3.2 Hz, 2H) ppm; MS: m/z=439.6 (M+1, ESI+).

The compounds of Formula (I') or (I) in Table 8 below were made according to Example 51 (starting from Intermediate G) of Compound 57.

TABLE 8

| Cmpd No. | $^1H$ NMR and/or LC/MS data |
|---|---|
| 58 | $^1H$ NMR (400 MHz, Methanol-d4) δ 7.86 (t, J = 8.4 Hz, 1H), 7.25 (d, J = 80.0 Hz, 1H), 7.04 (d, J = 10.4 Hz, 2H), 4.72 (d, J = 3.6 Hz, 2H), 4.45 (d, J = 13.2 Hz, 1H), 4.05 (d, J = 14.0 Hz, 1H), 3.84-3.81 (m, 2H), 3.31-3.27 (m, 2H), 3.15-2.94 (m, 2H), 2.62 (t, J = 12.8 Hz, 1H), 2.22 (d, J = 12.4 Hz, 1H), 1.97 (d, J = 13.2 Hz, 1H), 1.84 (d, J = 13.2 Hz, 3H), 1.72-1.68 (m, 4H), 1.62-1.58 (m, 2H), 1.32 (t, J = 13.2 Hz, 1H), 1.26-1.22 (m, 1H) ppm; MS: m/z = 457.6 (M + 1, ESI+). |
| 59 | $^1H$ NMR (400 MHz, Methanol-d4) δ 8.48 (s, 1H), 7.86 (t, J = 8.8 Hz, 1H), 7.24 (d, J = 80.0 Hz, 1H), 7.09-6.92 (m, 2H), 4.71 (d, J = 3.2 Hz, 2H), 4.45 (d, J = 13.6 Hz, 1H), |

TABLE 8-continued
| Cmpd No. | $^1$H NMR and/or LC/MS data |
| --- | --- |
| | 3.88 (d, J = 14.0 Hz, 1H), 3.80 (s, 2H), 3.48-3.44 (m, 2H), 3.13 (t, J = 13.2 Hz, 1H), 2.68 (t, J = 12.8 Hz, 1H), 2.22 (s, 1H), 2.00-1.96 (m, 1H), 1.87 (d, J = 13.2 Hz, 1H), 1.40-1.16 (m, 3H) ppm; MS: m/z = 471.6 (M + 1, ESI+). |
Example 52: Synthesis of Compound 60
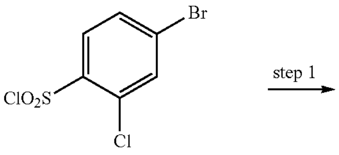
60-1
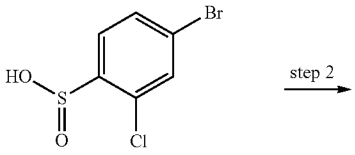
60-2
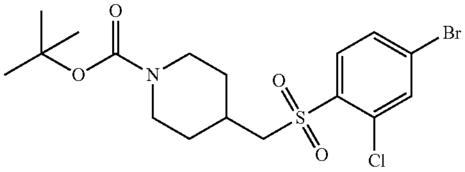
60-3
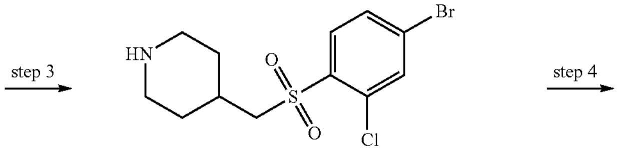
60-4
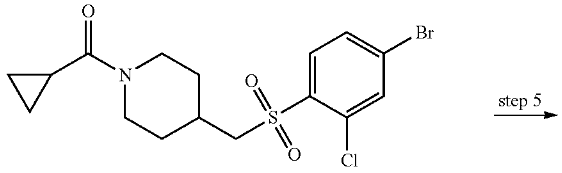
60-5
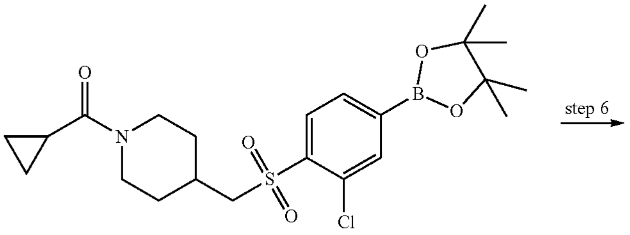
60-6
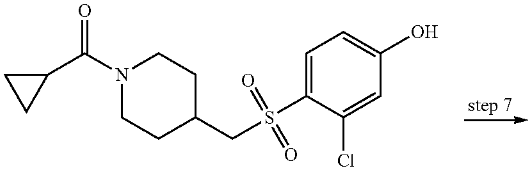
60-7
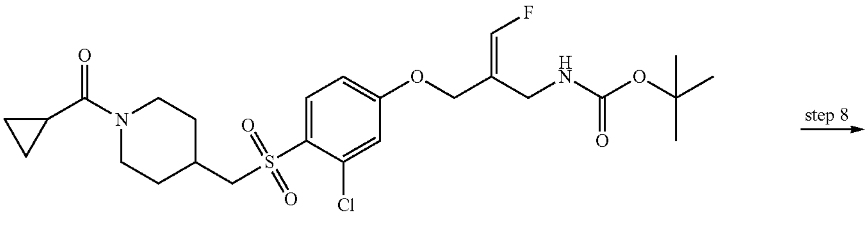
60-8
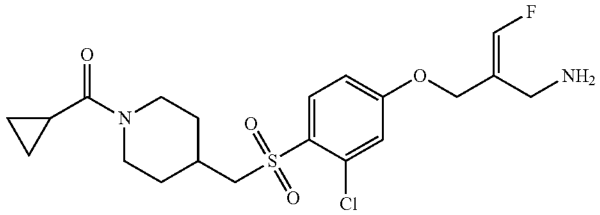
60

Step 1: 60-2

To a mixture of 60-1 (1.0 g, 3.08 mmol) in water (20 mL) was added $Na_2SO_3$ (777.07 mg, 6.17 mmol) and NaH $CO_3$ (517.91 mg, 6.17 mmol) in one portion, and the mixture was then stirred at 100° C. for 1 hr. After the temperature was cooled to 25° C., HCl (con.) was added to adjust the pH to 3. Then, the suspension was filtered, the cake was dried to give 60-2 (0.89 g, 3.07 mmol, 99.57% yield).

Step 2: 60-3

To a mixture of 60-2 (300 mg, 1.17 mmol), tert-butyl 4-(bromomethyl)piperidine-1-carboxylate (359.28 mg, 1.29 mmol) in DMF (15 mL) was added $Na_2CO_3$ (373.32 mg, 3.52 mmol) at 25° C. The reaction solution was stirred for 18 hr at 100° C. Then, the solution was quenched with $H_2O$ (20 mL), and extracted by ethyl acetate (15 mL×2). The combined organic layers were washed with $H_2O$ (15 mL) and brine (15 mL), dried over $Na_2SO_4$ and concentrated with a rotary evaporator. The crude product was purified by silica gel chromatography (ethyl acetate in petroleum ether, 0 to 80%) to obtain 60-3 (100 mg, 220.85 μmol, 18.815% yield).

Step 3: 60-4

To a mixture of 60-3 (100 mg, 220.85 mol) in DCM (15 mL) was added HC/Dioxane (4 M, 2 mL) at 25° C. and the reaction mixture was stirred at 25° C. for 1 hr. Then, the solution was concentrated with a rotary evaporator to obtain 60-4 (100 mg, crude, HC salt). MS: m/z=352 (M+1).

Step 4: 60-5

To a mixture of 60-4 (100 mg, 256.98 μmol), $Et_3N$ (78.01 mg, 770.94 μmol) in DCM (20 mL) was added cyclopropanecarbonyl chloride (29.55 mg, 282.68 μmol) at 25° C. The reaction solution was stirred for 1 hr at 25° C. Then, the solution was filtered and concentrated with a rotary evaporator. The crude product was purified by silica gel chromatography (ethyl acetate in petroleum ether, 0-60%, v/v) to obtain 60-5 (73 mg, 173.50 μmol, 67.52% yield). MS: m/z=420 (M+1).

Step 5: 60-6

To a mixture of 60-5 (73 mg, 173.50 μmol), 4,4,5,5-tetramethyl-2-(4,4,5,5-tetramethyl-1,3,2-dioxaborolan-2-yl)-1,3,2-dioxaborolane (52.87 mg, 208.20 μmol) and KOAc (51.08 mg, 520.50 μmol) in Dioxane (6 mL) was added $Pd(dppf)Cl_2$ (12.70 mg, 17.35 μmol) at 25° C. The reaction solution was heated to 120° C. for 0.667 hr under microwave. The mixture was filtered and the filtrate was evaporated to obtain 60-6 (100 mg, crude). MS: m/z=468 (M+1).

Step 6: 60-7

To a mixture of 60-6 (100 mg, 213.76 μmol), acetic acid (0.3 mL) in THF (10 mL) was added $H_2O_2$ (0.1 mL, 30% purity) at 25° C. The reaction solution was stirred for 1 hr at 25° C. Then, to the solution was added $Na_2SO_3$ (0.5 g) and then filtered and concentrated with a rotary evaporator to obtain 60-7 (110 mg, crude). MS: m/z=358 (M+1).

Step 7: 60-8

To a mixture of 60-7 (100 mg, 279.45 μmol), Intermediate A (74.93 mg, 279.45 μmol) in MeCN (20 mL) was added $Cs_2CO_3$ (273.15 mg, 838.34 μmol) at 25° C. The reaction solution was stirred for 1 hr at 90° C. Then, the mixture was filtered, and the filtrate was concentrated with a rotary evaporator to obtain 60-8 (160 mg, crude). MS: m/z=545 (M+1).

Step 8: Compound 60

To a mixture of 60-8 (100 mg, 183.47 μmol) in DCM (20 mL) was added HCl/Dioxane (4 M, 2 mL) at 20° C. and the reaction mixture was stirred at 25° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, GT: 15 min; flow rate: 15 mL/min) to obtain Compound 60 (25 mg, 50.92 μmol, 27.75% yield, $HCO_2H$ salt). $^1H$ NMR (400 MHz, Methanol-d4) δ 8.52 (s, 11H), 8.08 (d, J=8.9 Hz, 1H), 7.34 (d, J=2.5 Hz, 1H), 7.26 (d, J=80.9 Hz, 1H), 7.20 (dd, J=8.9, 2.5 Hz, 1H), 4.75 (d, J=3.4 Hz, 2H), 3.83 (d, J=2.2 Hz, 2H), 3.27-3.09 (m, 2H), 2.69 (t, J=13.0 Hz, 2H), 2.31-2.15 (m, 2H), 2.06-1.77 (m, 6H), 1.50-1.17 (m, 4H), 0.83-0.75 (m, 4H). MS: m/z=445.56 (M+1, ESI+).

Example 53: Synthesis of Compound 62

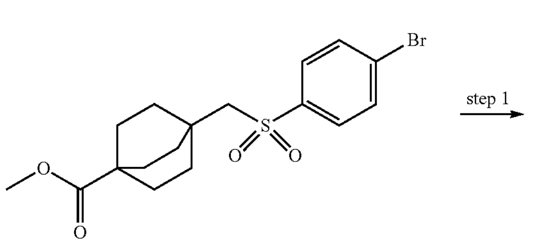

16-3

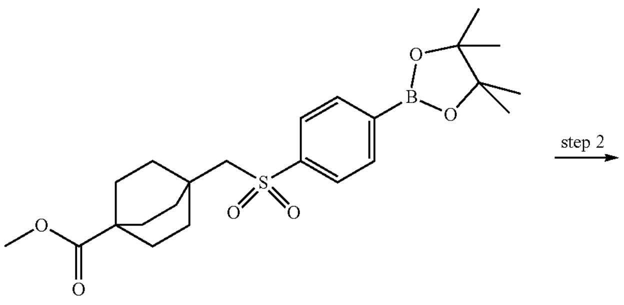

62-1

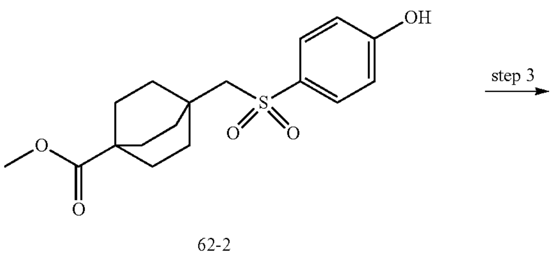

62-2

-continued

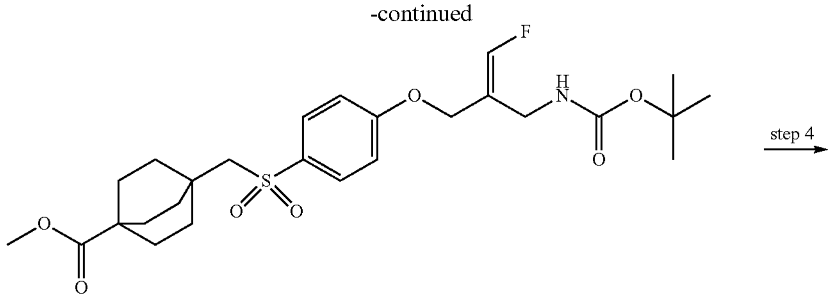

62-3

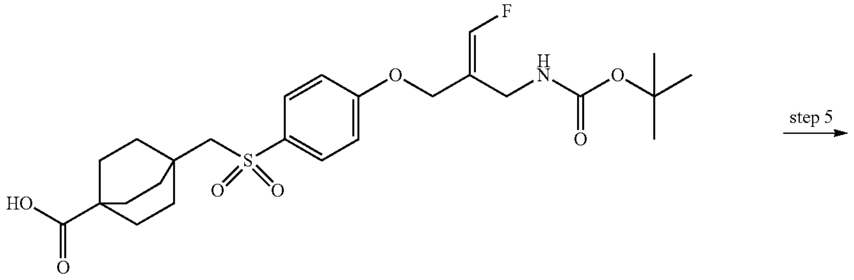

62-4

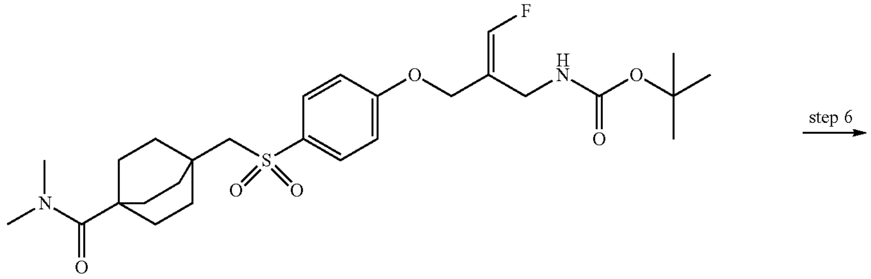

62-5

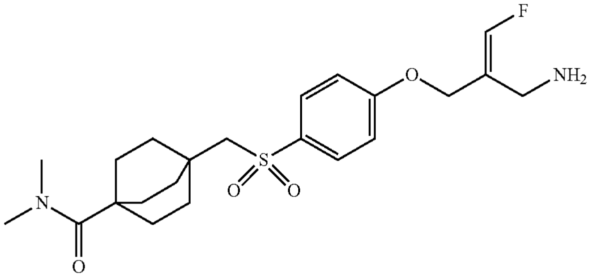

62

Step 1: 62-1

A 8 mL microwave reaction tube was charged with 16-3 (140 mg, 348.85 μmol), 4,4,5,5-tetramethyl-2-(4,4,5,5-tetramethyl-1,3,2-dioxaborolan-2-yl)-1,3,2-dioxaborolane (106.30 mg, 418.62 μmol), bis(diphenylphosphino)ferrocene]dichloropalladium(II) (25.50 mg, 34.85 μmol) and potassium acetate (102.71 mg, 1.05 mmol) in Dioxane (3 mL). After oxygen was purged by bubbling nitrogen into the reaction solution, the tube was sealed and heated at 120° C. for 0.5 hr in a Biotage microwave reactor. The reaction mixture was filtered and concentrated under reduced pressure to give 62-1 (300 mg, crude).

Step 2: 62-2

To a mixture of methyl 62-1 (300 mg, 669.08 μmol), acetate acid (669.08 μmol, 0.5 mL) in THF (2 mL) was added hydrogen peroxide (0.5 mL, 30% purity) at 20° C. The reaction solution was stirred for 0.5 hr at 20° C. Then, the solution was concentrated with a rotary evaporator to obtain a crude, which was purified by column chromatography on silica gel (20 g, ethyl acetate in petroleum ether, 0-65%) to 62-2 (120 mg, 354.59 μmol, 53.0% yield). $^{1}H$ NMR (400 MHz, Chloroform-d) δ 7.79-7.73 (m, 2H), 6.98-6.91 (m, 2H), 3.64 (s, 3H), 2.92 (s, 2H), 1.83-1.71 (m, 12H) ppm.

Step 3: 62-3

To a mixture of 62-2 (120 mg, 354.59 μmol), Intermediate A (114.09 mg, 425.51 μmol) in acetonitrile (10 mL) was added Cesium carbonate (346.60 mg, 1.06 mmol) at 20° C. The reaction solution was stirred for 1 hr at 95° C. Then, the mixture was filtered and the filtrate was concentrated with a rotary evaporator to obtain a crude, which was purified by column chromatography on silica gel (20 g, ethyl acetate in petroleum ether, 0-40%) to give 62-3 (120 mg, 228.30 μmol, 64.38% yield).

Step 4: 62-4

To a solution of 62-3 (120 mg, 228.30 μmol) in THF (4 mL) and water (2 mL) was added Lithium hydroxide monohydrate (95.79 mg, 2.28 mmol) at 20° C. The reaction solution was heated to 55° C. and stirred for 1 hr. Then, the mixture was adjusted to pH ~5 with 1 M HCl solution. The reaction mixture was extracted with ethyl acetate (20 mL×3). The combined organic layers were washed with brine (20 mL×2), dried over anhydrous sodium sulfate, filtered and concentrated with a rotary evaporator to give 62-4 (110 mg, 215.01 μmol, 94.18% yield).

Step 5: 62-5

To a mixture of N-methylmethanamine (20.72 mg, 254.10 μmol, HCl salt), 62-4 (100 mg, 195.46 μmol) in DCM (10 mL) was added TEA (59.34 mg, 586.39 μmol, 81.73 μL) and HATU (89.19 mg, 234.56 μmol) at 25° C. The reaction solution was stirred for 2 hr at 25° C. The crude product was purified by silica gel chromatography (12 g, ethyl acetate in petroleum ether, 0-100%, v/v) to obtain 62-5 (100 mg, 185.64 μmol, 94.97% yield).

Step 6: Compound 62

To a solution of 62-5 (100 mg, 185.64 μmol) in DCM (2 mL) was added HCl/Dioxane (2 mL, 4 M) at 20° C. and stirred at 20° C. for 1 hr. The reaction mixture was concentrated to give crude, which was slurried with acetonitrile (6 mL) for 15 minutes and filtered. The filter cake was dried by lyophilization (water:acetonitrile=4:1, 20 mL) to give Compound 62 (67.0 mg, 141.05 μmol, 75.98% yield, HCl salt). $^1$H NMR (400 MHz, Methanol-d4) δ 7.91-7.83 (m, 2H), 7.27 (d, J=84.0 Hz, 1H), 7.24-7.18 (m, 2H), 4.73 (dd, J=3.6, 1.1 Hz, 2H), 3.84 (d, J=2.2 Hz, 2H), 3.09 (s, 2H), 3.03 (s, 6H), 1.94-1.85 (m, 6H), 1.77-1.72 (m, 6H) ppm. MS: m/z=439.2 (M+1).

Example 54: Synthesis of Compound 63

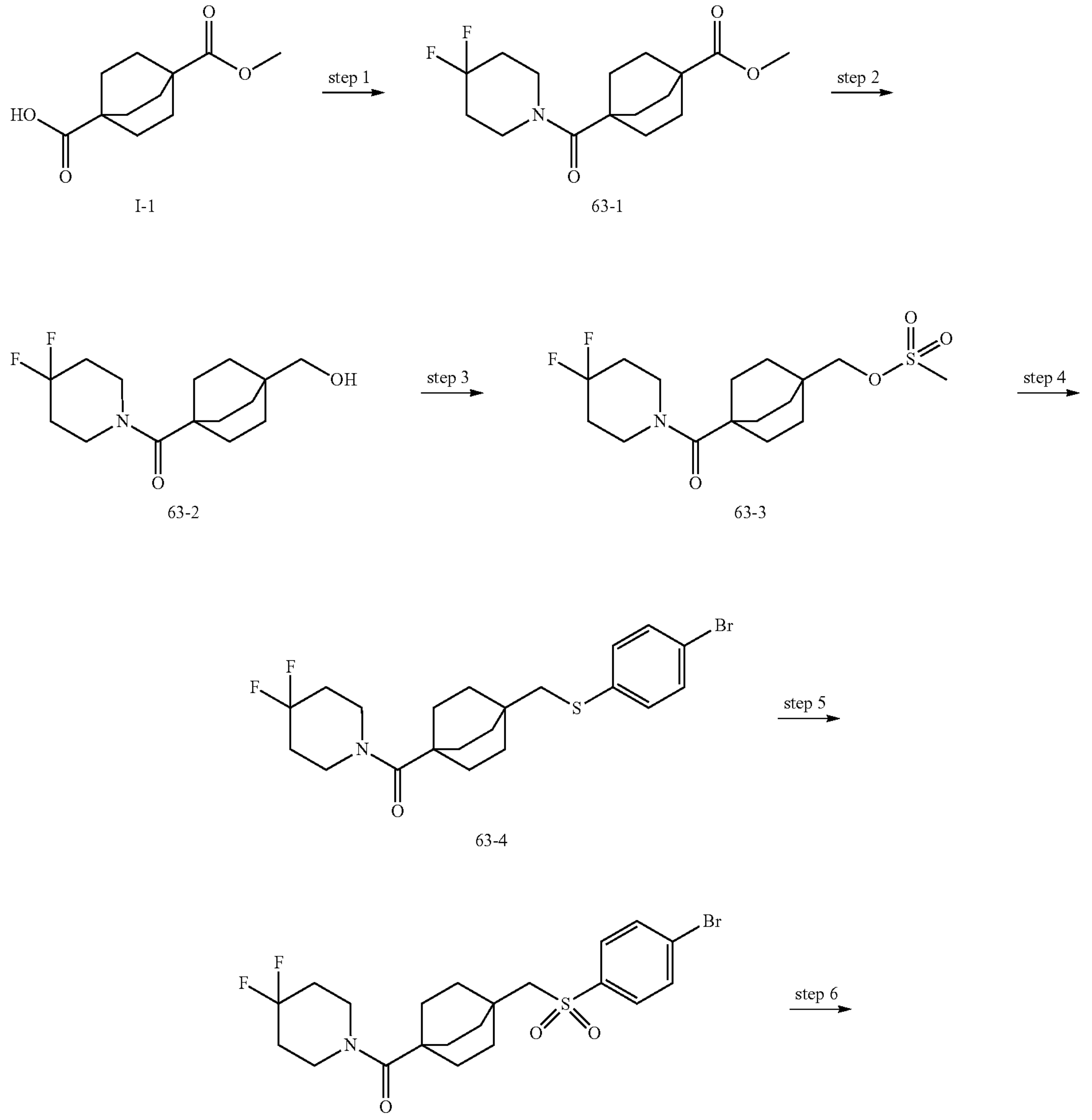

I-1

63-1

63-2

63-3

63-4

63-5

-continued

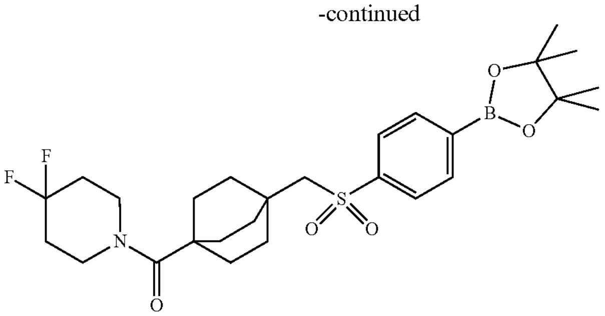

step 7

63-6

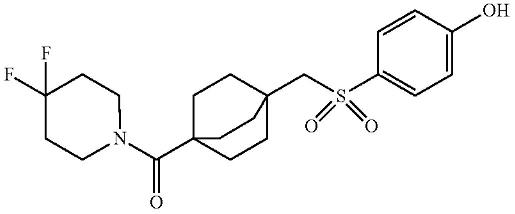

step 8

63-7

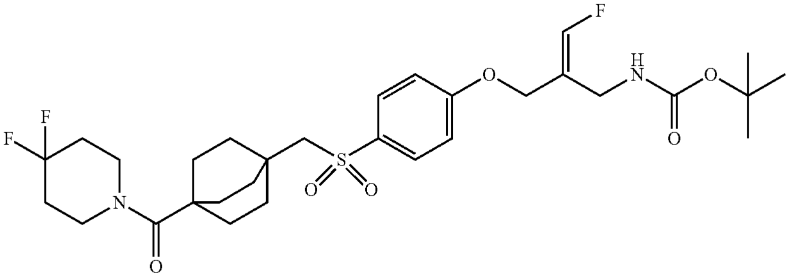

step 9

63-8

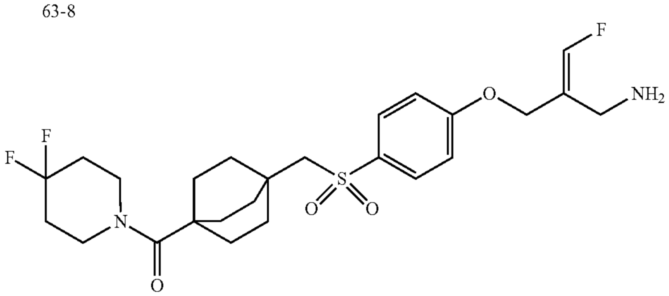

63

Step 1: 63-1

To a mixture of 4,4-difluoropiperidine (684.85 mg, 5.65 mmol), I-1 (1 g, 4.71 mmol) in DCM (20 mL) was added TEA (1.43 g, 14.13 mmol, 1.97 mL) and HATU (2.15 g, 5.65 mmol) at 25° C. The reaction solution was stirred for 2 hr at 25° C. The mixture was concentrated and crude product was purified by silica gel chromatography (12 g, ethyl acetate in petroleum ether, 0-35%, v/v) to obtain 63-1 (1.28 g, 4.06 mmol, 86.15% yield). $^1$H NMR (400 MHz, Chloroform-d) δ 3.75-3.70 (m, 4H), 3.66 (s, 3H), 2.02-1.80 (m, 16H).

Step 2: 63-2

To a mixture of 63-1 (473 mg, 1.5 mmol) in THF (10 mL) was added $LiAlH_4$ (45.79 mg, 1.21 mmol) at 0° C. The reaction solution was stirred for 2 hr at 0° C. Water (0.1 mL) was added and stirred for 15 minutes, the mixture was then dried over anhydrous sodium sulfate, filtered and concentrated to obtain 63-2 (370 mg, 1.29 mmol, 85.84% yield).

Step 3: 63-3

To a mixture of 63-2 (370 mg, 1.29 mmol), TEA (390.89 mg, 3.86 mmol, 538.42 μL) in DCM (5 mL) was added methanesulfonic anhydride (336.46 mg, 1.93 mmol) at 0° C. The reaction solution was stirred for 2 hr at 25° C. Then, the solution was concentrated with a rotary evaporator. The crude product was purified by silica gel chromatography (4 g, ethyl acetate in petroleum ether, 0-40%, v/v) to obtain 63-3 (390 mg, 1.07 mmol, 82.88% yield). $^1$H NMR (400 MHz, Chloroform-d) δ 3.88 (s, 2H), 3.73 (t, J=5.8 Hz, 4H), 3.00 (s, 3H), 2.01-1.87 (m, I0H), 1.57-1.53 (m, 6H) ppm.

Step 4: 63-4

To a solution of 4-bromobenzenethiol (504.46 mg, 2.67 mmol), cesium carbonate (1.04 g, 3.20 mmol) and potassium iodide (88.58 mg, 533.61 μmol) in DMF (3 mL) was added 63-3 (390 mg, 1.07 mmol) under the nitrogen atmosphere. The reaction mixture was heated at 55° C. for 2 hr. Ethyl acetate (60 mL) and water (50 mL) were added, the organic was washed with brine (50 mL×3), dried over anhydrous sodium sulfate, filtered and concentrated to a residue, which was purified by column chromatography on silica gel (ethyl acetate in petroleum ether, 0-25%, v/v) to give 63-4 (300 mg, 654.45 μmol, 61.32% yield). MS: m/z=458.1 (M+1).

Step 5: 63-5

To a mixture of 63-4 (300 mg, 654.45 μmol) and m-CPBA (398.60 mg, 1.96 mmol, 85% purity) in DCM (10 mL) was stirred at 20° C. for 2 hr. The sodium sulfite (1 g) was added to the mixture and stirred for 20 min. Then, to the solution was added ethyl acetate (20 mL) and water (20 mL). The organic layer was washed with aqueous $NaHCO_3$ (30 mL×3), brine (30 mL×3), dried over anhydrous sodium sulfate, filtered, concentrated to obtain 63-5 (270 mg, crude).

Step 6: 63-6

A 30 mL microwave reaction tube was charged with 63-5 (270 mg, 550.57 μmol), 4,4,5,5-tetramethyl-2-(4,4,5,5-tetramethyl-1,3,2-dioxaborolan-2-yl)-1,3,2-dioxaborolane (167.77 mg, 660.68 μmol), bis(diphenylphosphino)ferrocene]dichloropalladium(II) (40.29 mg, 55.06 mol) and potassium acetate (162.10 mg, 1.65 mmol) in Dioxane (10 mL). After oxygen was purged by bubbling nitrogen into the reaction solution, the tube was sealed and heated at 120° C. for 0.5 hr in a Biotage microwave reactor. The reaction mixture was filtered and concentrated under reduced pressure to give 63-6 (500 mg, crude).

Step 7: 63-7

To a mixture of 63-6 (500 mg, 930.29 μmol), acetate acid (930.29 μmol, 1 mL) in tetrahydrofuran (4 mL) was added hydrogen peroxide (1 mL, 30% purity) at 20° C. The reaction solution was stirred for 1 hr at 20° C. Then, the solution was concentrated with a rotary evaporator to obtain 63-7 (400 mg, crude).

Step 8: 63-8

To a mixture of 63-7 (200 mg, 467.83 μmol), Intermediate A (150.52 mg, 561.40 mol) in MeCN (20 mL) was added Cesium carbonate (457.29 mg, 1.40 mmol) at 20° C. The reaction solution was stirred for 1 hr at 95° C. Then, the mixture was filtered, and the filtrate was concentrated with a rotary evaporator to obtain a crude, which was purified by column chromatography on silica gel (20 g, ethyl acetate in petroleum ether, 0-65%, v/v) to give 63-8 (70 mg, 113.87 μmol, 24.34% yield).

Step 9: Compound 63

To a mixture of 63-8 (70 mg, 113.87 μmol) in Dioxane (4 mL) was added HCl/Dioxane (2 mL, 4 M) at 40° C. and stirred at 40° C. for 1 hr. The reaction mixture was concentrated with a rotary evaporator to give a crude, which was purified by prep-HPLC (column: XBridge@ Prep C18 5 μm 19×150 mm; A: 0.1% $HCO_2H$ water, B: acetonitrile; GT: 15 min; flow rate: 15 mL/min) to give Compound 63 (7.5 mg, 13.38 μmol, 11.75% yield, $HCO_2H$ salt). $^1H$ NMR (400 MHz, Methanol-d4) δ 8.54 (s, 1H), 7.89-7.83 (m, 2H), 7.27 (d, J=84.0 Hz, 1H), 7.22-7.18 (m, 2H), 4.70 (d, J=3.6 Hz, 2H), 3.79-3.70 (m, 6H), 3.09 (s, 2H), 2.00-1.86 (m, 10H), 1.80-1.74 (m, 6H) ppm. MS: m/z=515.2 (M+1).

The compounds of Formula (I') or (I) in Table 9 below were made according to Example 54 of Compound 63.

TABLE 9

| Cmpd No. | $^1H$ NMR and/or LC/MS data |
|---|---|
| 61 | $^1H$ NMR (400 MHz, Methanol-$d_4$) δ 7.89-7.82 (m, 2H), 7.26 (d, J = 80.0 Hz, 1H), 7.24-7.17 (m, 2H), 4.72 (dd, J = 3.5, 1.0 Hz, 2H), 3.83 (d, J = 2.2 Hz, 2H), 3.67-3.58 (m, 2H), 3.45-3.35 (m, 2H), 3.08 (s, 2H), 1.96-1.68 (m, 16H) ppm. MS: m/z = 465.2 (M + H). |

Example 55: Synthesis of Compound 64

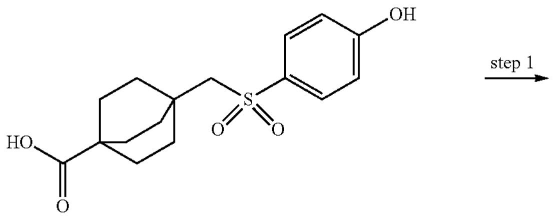

Intermediate I

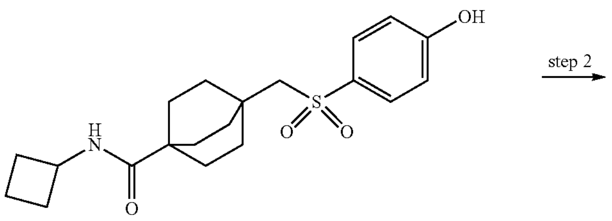

64-1

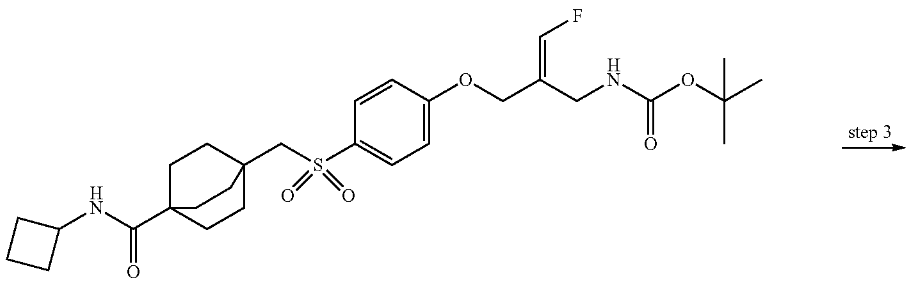

64-2

-continued

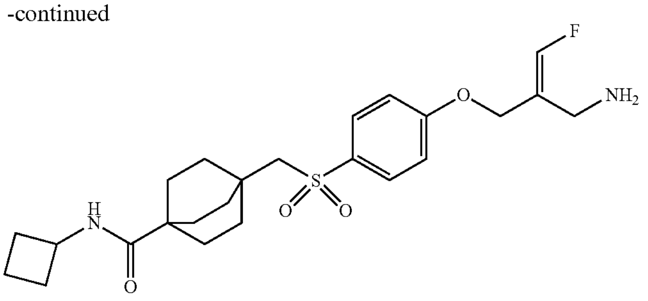

64

Step 1: 64-1

A mixture of Intermediate I (400 mg, 1.23 mmol), diisopropylethylamine (318.73 mg, 2.47 mmol, 429.55 μL), HATU (562.62 mg, 1.48 mmol), cyclobutanamine (105.24 mg, 1.48 mmol) in DMF (4 mL) was stirred at 20° C. for 16 hr. The mixture was poured into aqueous $NaHCO_3$ and filtered. The cake was dissolved with DCM/MeOH and concentrated to afford 64-1 (461 mg, 1.22 mmol, 99.04% yield). MS: m/z=378.1 (M+1).

Step 2: 64-2

To a mixture of 64-1 (461 mg, 1.22 mmol), Intermediate A (360.18 mg, 1.34 mmol) in MeCN (4 mL) was added Cesium carbonate (795.78 mg, 2.44 mmol) at 20° C. The reaction solution was heated to 94° C. and stirred for 1 hr at 94° C. The mixture was filtered and the filtrate was concentrated with a rotary evaporator. The residue was purified by column chromatography on silica gel (12 g, ethyl acetate in petroleum ether, 20-100%, v/v) to give 64-2 (578 mg, 1.02 mmol, 83.81% yield). MS: m/z=509.2 (M+1-56).

Step 3: Compound 64

A mixture of 64-2 (578 mg, 1.02 mmol) and Hydrochloric acid/Dioxane (4 M, 20 mL) was stirred for 1 hr at 20° C. The mixture was concentrated, slurried in acetonitrile and filtered. The cake was dissolved in water and freeze-dried to give Compound 64 (494 mg, 985.92 μmol, 96.32% yield, HCl salt). $^1$H NMR (400 MHz, DMSO-d6) δ 8.27 (s, 3H), 7.87-7.79 (m, 2H), 7.48-7.44 (m, 1H), 7.35 (d, J=72.0 Hz, 1H), 7.24-7.18 (m, 2H), 4.75 (d, J=3.4 Hz, 2H), 4.20-4.11 (m, 1H), 3.62 (d, J=5.8 Hz, 2H), 3.14 (s, 2H), 2.13-2.01 (m, 2H), 1.98-1.83 (m, 2H), 1.65-1.50 (m, 14H). MS: m/z=465.2 (M+1).

The compounds of Formula (I') or (I) in Table 10 below were made according to Example 55 of Compound 64.

TABLE 10

| Cmpd No. | $^1$H NMR and/or LC/MS data |
|---|---|
| 65 | $^1$H NMR (400 MHz, DMSO-$d_6$) δ 8.26 (s, 3H), 7.99 (t, J = 6.4 Hz, 1H), 7.86-7.79 (m, 2H), 7.34 (d, J = 80.0 Hz, 1H), 7.22-7.17 (m, 2H), 4.74 (d, J = 3.4 Hz, 2H), 3.80 (dd, J = 9.8, 6.3 Hz, 2H), 3.60 (s, 2H), 3.14 (s, 2H), 1.62 (s, 12H) ppm. MS: m/z = 493.1 (M + 1). |
| 66 | $^1$H NMR (400 MHz, Methanol-$d_4$) δ 7.87 (d, J = 8.9 Hz, 2 H), 7.26 (d, J = 80.9 Hz, 1H), 7.21 (d, J = 8.9 Hz, 2 H), 4.73 (d, J = 3.5 Hz, 2 H), 3.84 (s, 2 H), 3.09 (s, 2 H), 3.01 (d, J = 6.8 Hz, 2 H), 1.75 (s, 12 H), 1.06-0.83 (m, 1 H), 0.48-0.39 (m, 2 H), 0.20-0.15 (m, 2 H) ppm. MS: m/z = 465.2 (M + 1). |
| 67 | $^1$H NMR (400 MHz, DMSO-$d_6$) δ 8.18 (s, 3H), 7.78-7.74 (m, 2H), 7.41 (s, 1H), 7.28 (d, J = 80.0 Hz, 1H), 7.16-7.11 (m, 2H), 4.67 (d, J = 3.4 Hz, 2H), 3.55 (s, 2H), 3.05 (s, 2H), 1.49 (s, 12H), 1.13 (s, 3H), 0.49-0.35 (m, 4H) ppm. MS: m/z = 465.2 (M + 1). |
| 68 | $^1$H NMR (400 MHz, DMSO-$d_6$) δ 8.22 (s, 3H), 7.86-7.79 (m, 2H), 7.34 (d, J = 80.0 Hz, 1H), 7.30 (t, J = 5.7 Hz, 1H), 7.22-7.17 (m, 2H), 4.73 (d, J = 3.4 Hz, 2H), 3.61 (d, J = 2.1 Hz, 2H), 3.55-3.43 (m, 1H), 3.33-3.25 (m, 2H), 3.15-3.06 (m, 4H), 1.59 (s, 12H), 1.04 (d, J = 6.1 Hz, 6H) ppm. MS: m/z = 497.2 (M + 1). |
| 69 | $^1$H NMR (400 MHz, Methanol-$d_4$) δ 7.86 (d, J = 8.7 Hz, 2 H), 7.26 (d, J = 80.9 Hz, 1H), 7.21 (d, J = 8.6 Hz, 2 H), 4.72 (d, J = 3.5 Hz, 2 H), 4.07 (q, J = 7.3, 6.8 Hz, 1 H), 3.83 (d, J = 2.2 Hz, 2 H), 3.08 (s, 2 H), 2.90-2.78 (m, 2 H), 2.65-2.47 (m, 2 H), 1.74 (s, 12 H) ppm. MS: m/z = 501.2 (M + 1). |
| 70 | $^1$H NMR (400 MHz, Methanol-$d_4$) δ 8.55 (br, 1 H), 7.90 (d, J = 8.9 Hz, 2 H), 7.24 (d, J = 8.9 Hz, 2 H), 7.24 (d, J = 81.8 Hz, 1 H), 6.40 (s, 1 H), 4.75 (d, J = 3.5 Hz, 2 H) 3.74 (s, 2 H), 3.12 (s, 2 H), 1.74 (s, 12 H), 1.32 (s, 9 H) ppm. MS: m/z = 467.3 (M + 1). |
| 71 | $^1$H NMR (400 MHz, DMSO-$d_6$) δ 8.23 (s, 1H), 7.84-7.66 (m, 2H), 7.21-7.04 (m, 2H), 7.01 (d, J = 84.0 Hz, 1H), 4.60 (d, J = 3.4 Hz, 2H), 4.23 (s, 2H), 3.70 (s, 2H), 3.30 (d, J = 2.4 Hz, 2H), 3.05 (s, 2H), 2.15-1.98 (m, 2H), 1.63-1.43 (m, 12H) ppm. $^{19}$F NMR (376 MHz, DMSO-$d_6$) δ −129.62 ppm. MS: m/z = 451.3 (M + 1). |
| 72 | $^1$H NMR (400 MHz, Methanol-$d_4$) δ 8.44 (s, 1H), 7.75 (d, J = 8.9 Hz, 2H), 7.13-7.01 (m, 2H), 7.00 (d, J = 84.0 Hz, 1H), 4.59-4.11 (m, 6H), 3.54 (d, J = 2.7 Hz, 2H), 2.97 (s, 2H), 1.66 (t, J = 9.8 Hz, 12H) ppm. $^{19}$F NMR (376 MHz, Methanol-d4) δ −103.39 ppm. MS: m/z = 487.2 (M + 1). |
| 73 | $^1$H NMR (400 MHz, DMSO-$d_6$) δ 8.28 (s, 1H), 7.84-7.76 (m, 2H), 7.21-7.15 (m, 2H), 7.11 (d, J = 84.0 Hz, 1H), 4.67 (d, J = 3.5 Hz, 2H), 3.41 (s, 2H), 3.12 (s, 2H), 2.83 (s, 3H), 2.81-2.74 (m, 1H), 1.79 (dd, J = 10.1, 5.5 Hz, 6H), 1.61 (dd, J = 9.9, 5.5 Hz, 6H), 0.70-0.64 (m, 2H), 0.57 (dt, J = 7.1, 4.7 Hz, 2H) ppm. MS: m/z = 465.2 (M + 1). |

TABLE 10-continued
| Cmpd No. | $^1$H NMR and/or LC/MS data |
|---|---|
| 74 | $^1$H NMR (400 MHz, Methanol-$d_4$) δ 8.51 (s, 1 H), 7.86 (d, J = 8.9 Hz, 2H), 7.22 (d, J = 81.2 Hz, 1 H), 7.20 (d, J = 8.9 Hz, 2 H), 4.71 (d, J = 3.5 Hz, 2 H), 3.80 (d, J = 2.2 Hz, 2 H), 3.42 (br, 4 H), 3.08 (s, 2 H), 1.87 (dd, J = 10.1, 5.2 Hz, 6 H), 1.75 (dd, J = 10.0, 5.2 Hz, 6 H), 1.12 (br, 6 H) ppm. MS: m/z = 467.2 (M + 1). |
| 75 | $^1$H NMR (400 MHz, DMSO-$d_6$) δ 8.19 (s, 3H), 7.86-7.78 (m, 2H), 7.35 (d, J = 84.0 Hz, 1H), 7.29 (d, J = 4.0 Hz, 1H), 7.23-7.16 (m, 2H), 4.77-4.67 (m, 2H), 3.61 (d, J = 6.1 Hz, 3H), 3.13 (s, 2H), 2.60-2.53 (m, 1H), 1.57 (s, 12H), 0.53-0.48 (m, 2H), 0.41-0.32 (m, 2H) ppm. MS: m/z = 451.3 (M + 1). |
Example 56: Synthesis of Compound 76
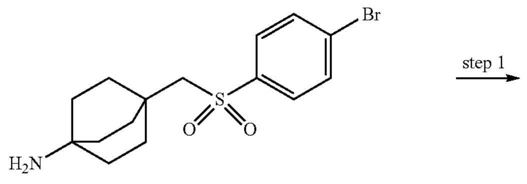
Intermediate J
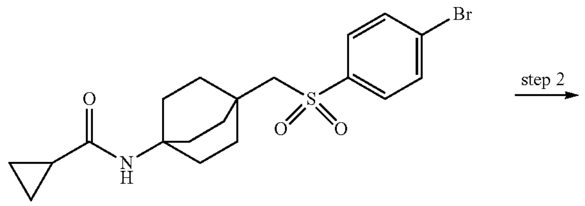
76-1
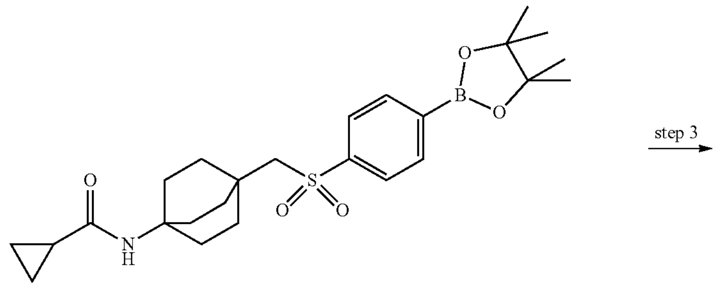
76-2
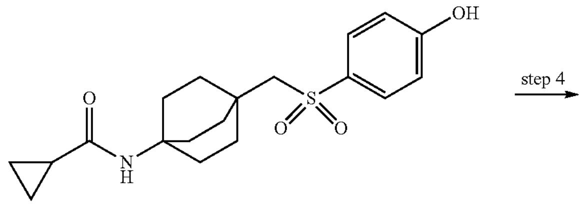
76-3

-continued

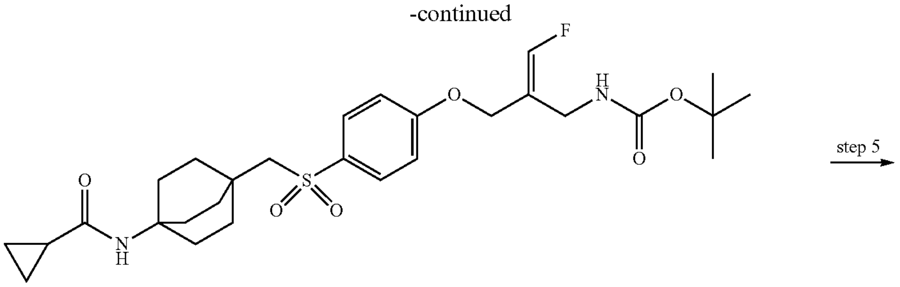

76-4

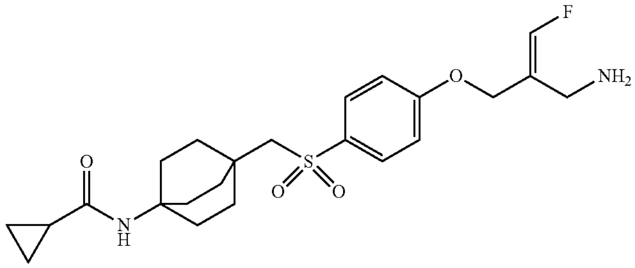

76

Step 1: 76-1

To a mixture of Intermediate J (700 mg, 1.77 mmol, HCl salt) and TEA (538.31 mg, 5.32 mmol, 741.47 μL) in DCM (30 mL) was added cyclopropanecarbonyl chloride (222.44 mg, 2.13 mmol, 193.43 μL) at 25° C. The reaction solution was stirred for 2 hr at 25° C. The mixture was concentrated and the crude product was purified by silica gel chromatography (12 g, ethyl acetate in petroleum ether, 0-35%, v/v) to obtain 76-1 (590 mg, 1.38 mmol, 78.04% yield).

Step 2: 76-2

A 30 mL microwave reaction tube was charged with 76-1 (590 mg, 1.38 mmol), 4,4,5,5-tetramethyl-2-(4,4,5,5-tetramethyl-1,3,2-dioxaborolan-2-yl)-1,3,2-dioxaborolane (421.67 mg, 1.66 mmol), bis(diphenylphosphino)ferrocene]dichloropalladium(II) (101.25 mg, 138.38 mol) and potassium acetate (407.41 mg, 4.15 mmol) in Dioxane (8 mL). After oxygen was purged by bubbling nitrogen into the reaction solution, the tube was sealed and heated at 120° C. for 0.5 hr in a Biotage microwave reactor. The reaction mixture was filtered and concentrated under reduced pressure to give 76-2 (1 g, crude).

Step 3: 76-3

To a mixture of 76-2 (1 g, 2.10 mmol), acetate acid (0.5 mL) in THF (4 mL) was added hydrogen peroxide (0.5 mL, 30% purity) at 20° C. The reaction solution was stirred for 0.5 hr at 20° C. Then, the solution was concentrated with a rotary evaporator to obtain a crude, which was purified by silica gel chromatography (12 g, ethyl acetate in petroleum ether, 0-65%, v/v) to obtain 76-3 (450 mg, 1.23 mmol, 58.54% yield).

Step 4: 76-4

To a mixture of 76-3 (450 mg, 1.24 mmol), Intermediate A (398.34 mg, 1.49 mmol) in MeCN (15 mL) was added Cesium carbonate (806.77 mg, 2.48 mmol) at 20° C. The reaction solution was stirred for 1 hr at 95° C. Then, the mixture was filtered and the filtrate was concentrated with a rotary evaporator to obtain a crude, which was purified by silica gel chromatography (12 g, ethyl acetate in petroleum ether, 0-65%, v/v) to obtain 76-4 (620 mg, 1.13 mmol, 90.94% yield).

Step 5: Compound 76

To a mixture of 76-4 (620 mg, 1.13 mmol) in DCM (10 mL) was added HCl/Dioxane (4 M, 10 mL) at 20° C. and stirred at 20° C. for 1 hr. The reaction mixture was filtered. The filter cake was slurried with acetonitrile (6 mL) for 15 minutes and filtered. The filter cake was dried by lyophilization (water:acetonitrile=4:1, 20 mL) to give Compound 76 (449.5 mg, 922.95 mol, 81.98% yield, HCl salt). $^1$H NMR (400 MHz, Methanol-d4) δ 7.90-7.84 (m, 2H), 7.27 (d, J=80.0 Hz, 1H) 7.25-7.19 (m, 2H), 4.75-4.71 (m, 2H), 3.84 (s, 2H), 3.07 (s, 2H), 1.93-1.86 (m, 6H), 1.82-1.74 (m, 6H), 1.55-1.49 (m, 1H), 0.74 (dt, J=4.6, 2.9 Hz, 2H), 0.66-0.61 (m, 2H) ppm. MS: m/z=451.2 (M+1).

The compounds of Formula (I') or (I) in Table 11 below were made according to Example 56 of Compound 76.

TABLE 11

| Cmpd No. | $^1$H NMR and/or LC/MS data |
|---|---|
| 77 | $^1$H NMR (400 MHz, Methanol-$d_4$) δ 7.95 (s, 1H), 7.91-7.86 (m, 2H), 7.27 (d, J = 80.0 Hz, 1H), 7.26-7.20 (m, 2H), 4.73 (d, J = 3.5 Hz, 2H), 3.84 (d, J = 2.3 Hz, 2H), 3.54 (s, 2H), 1.99 (s, 6H), 1.11 (s, 9H) ppm. MS: m/z = 425.2 (M +1). |
| 80 | $^1$H NMR (400 MHz, Methanol-$d_4$) δ 7.89-7.84 (m, 2H), 7.27 (d, J = 80.0 Hz, 1H), 7.24-7.19 (m, 2H), 4.73 (d, J = 3.6 Hz, 2H), 3.84 (d, J = 2.3 Hz, 2H), 3.07 (s, 2H), 2.38-2.32 (m, 1H), 1.93-1.84 (m, 6H), 1.82-1.74 (m, 6H), 1.03 (d, J = 6.8 Hz, 6H) ppm. MS: m/z = 453.2 (M + 1). |
| 81 | $^1$H NMR (400 MHz, Methanol-$d_4$) δ 8.52 (s, 1 H), 7.93-7.80 (m, 2 H), 7.28-7.18 (m, 2 H), 7.23 (d, J = 80.0 Hz, 1H), 4.72 (d, J = 3.6 Hz, 2 H), 3.80 (d, J = 2.2 Hz, |

TABLE 11-continued
| Cmpd No. | $^1$H NMR and/or LC/MS data |
|---|---|
| | 2 H), 3.07 (s, 2 H), 2.50-2.45 (m, 1 H), 1.95-1.74 (m, 12 H), 1.07-0.95 (m, 4 H) ppm. MS: m/z = 487.2 (M + H). |
| 90 | $^1$H NMR (400 MHz, Methanol-d$_4$) δ 7.90-7.83 (m, 2H), 7.27 (d, J = 80.0 Hz, 1H), 7.25-7.19 (m, 2H), 4.73 (d, J = 3.5 Hz, 2H), 3.84 (d, J = 2.2 Hz, 2H), 3.08 (s, 2H), 1.94-1.87 (m, 6H), 1.83-1.76 (m, 6H), 1.13 (s, 9H) ppm. MS: m/z = 467.3 (M + 1). |
Example 57: Synthesis of Compound 78
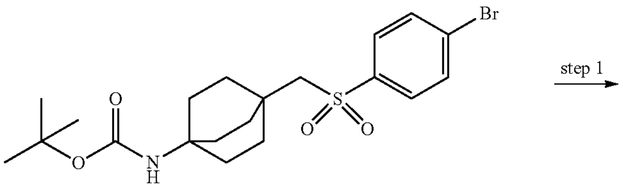
J-6
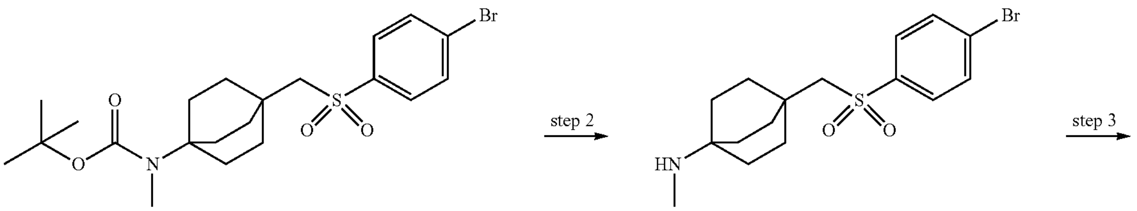
78-1 78-2
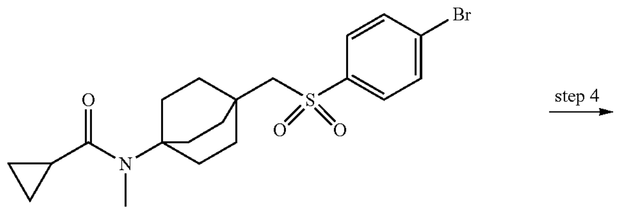
78-3
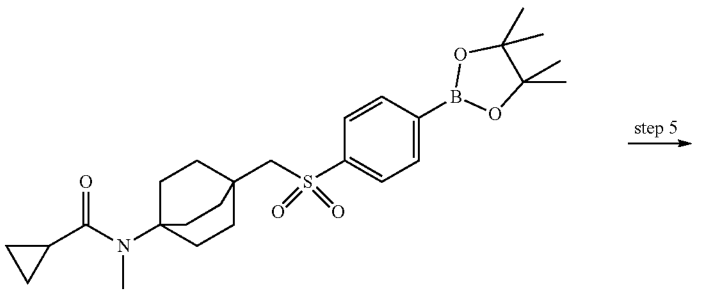
78-4
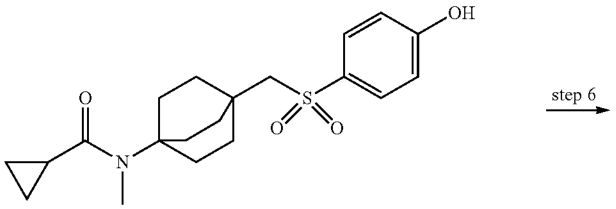
78-5

-continued

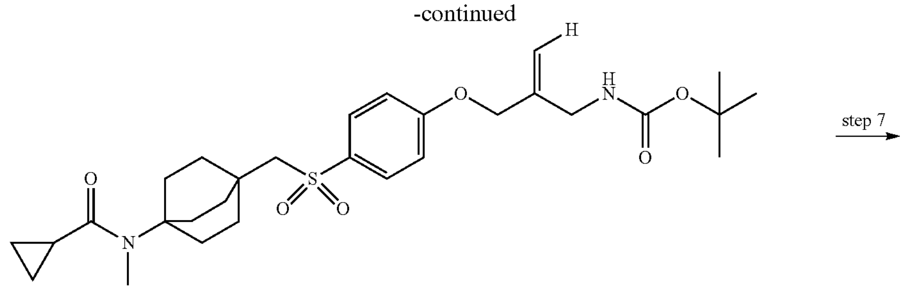

78-6

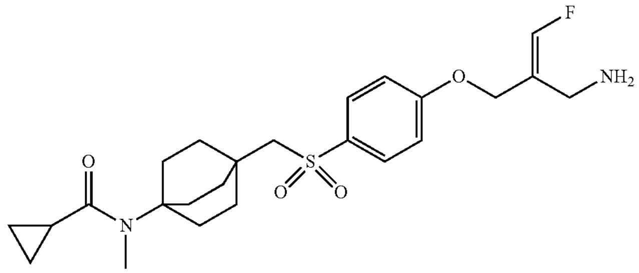

78

Step 1: 78-1

To a mixture of J-6 (300 mg, 654.44 μmol) in DMF (5 mL) was added NaH (34.03 mg, 850.77 μmol, 60% purity) at 0° C. and stirred at 0° C. for 30 min. Iodomethane (279 mg, 1.97 mmol, 122.37 μL) was added at 0° C. After addition, the mixture was stirred at 25° C. for 16 hr. Upon completion, the resulting mixture was quenched with water (20 mL) and extracted with ethyl acetate (30 mL). The separated organic layer was washed with water (20 mL×3) and brine, dried over anhydrous sodium sulfate, filtered and concentrated to give crude 78-1 (300 mg, 635.01 μmol, 97.03% yield). MS: m/z=416.0 (M+1-56).

Step 2: 78-2

A mixture of 78-1 (300 mg, 635.01 μmol) and HCl/Dioxane (4 M, 5 mL) in Dioxane (2 mL) was stirred at 25° C. for 1 hr. The resulting mixture was concentrated to give crude 78-2 (230 mg, 617.75 μmol, 97.28% yield, HCl salt). MS: m/z=372.1 (M+1)

Step 3: 78-3

To a mixture of 78-2 (230 mg, 617.75 μmol) and diisopropylethylamine (79.84 mg, 617.75 μmol, 107.60 μL) in DCM (20 mL) was added cyclopropanecarbonyl chloride (64.58 mg, 617.75 μmol, 56.15 μL) at 0° C. After addition, the solution was stirred at 25° C. for 1 hr. Upon completion, the resulting solution was washed with water (20 mL) and brine, dried over anhydrous sodium sulfate, filtered and concentrated. The residue was purified by silica gel chromatography (ethyl acetate in petroleum ether, 5-10%, v/v) to give 78-3 (200 mg, 454.14 mol, 73.52% yield). MS: m/z=440.1 (M+1)

Step 4: 78-4

A mixture of 78-3 (200 mg, 454.14 μmol), 4,4,5,5-tetramethyl-2-(4,4,5,5-tetramethyl-1,3,2-dioxaborolan-2-yl)-1,3,2-dioxaborolane (173 mg, 681.27 μmol), bis(diphenylphosphino)ferrocene]dichloropalladium(II) (33 mg, 45.10 μmol) and potassium acetate (82 mg, 1.37 mmol) in Dioxane (10 mL) was microwaved at 120° C. for 40 min. Upon completion, the resulting mixture was cooled to room temperature, filtered and concentrated to give crude 78-4 (220 mg, 451.32 μmol, 99.38% yield). MS: m/z=488.2 (M+1).

Step 5: 78-5

A mixture of 78-4 (220 mg, 451.32 μmol), hydrogen peroxide (1 mL, 30% purity) and acetate acid (1 mL) in THE (4 mL) was stirred at 25° C. for 1 hr. Upon completion, the resulting solution was quenched with sodium sulfite, filtered and concentrated to give crude 78-5 (170 mg, 450.34 μmol, 99.78% yield). MS: m/z=378.1 (M+1).

Step 6: 78-6

A mixture of 78-5 (170 mg, 450.34 μmol) and $Cs_2CO_3$ (733.64 mg, 2.25 mmol) in MeCN (20 mL) was stirred at 95° C. for 2 hr. Upon completion, the resulting mixture was filtered. The filtrate was concentrated. The residue was purified by silica gel chromatography (ethyl acetate in petroleum ether, 25-50%, v/v) to give 78-6 (180 mg, 318.75 μmol, 70.78% yield). MS: m/z=509.2 (M+1-56)

Step 7: Compound 78

A mixture of 78-6 (180 mg, 318.75 μmol) and HCl/Dioxane (4 M, 5 mL) in Dioxane (2 mL) was stirred at 25° C. for 1 hr. The resulting mixture was concentrated and purified by prep-HPLC (column: XBridge@ Prep C18 5 μm 19×150 mm; A: 0.2% $HCO_2H$ water, B: acetonitrile; gradient: 5-50% B; GT: 25 min; flow rate: 15 mL/min) to give Compound 78 (15 mg, 32.29 μmol, 10.13% yield, $HCO_2H$ salt). $^1H$ NMR (400 MHz, Methanol-d4) δ 8.43 (s, 1H), 7.84-7.70 (m, 2H), 7.17-7.07 (m, 2H), 7.14 (d, J=80.0 Hz, 1H), 4.63 (d, J=3.5 Hz, 2H), 3.72 (d, J=2.1 Hz, 2H), 3.00 (s, 3H), 2.98 (s, 2H), 1.97 (dd, J=9.9, 5.8 Hz, 6H), 1.76-1.63 (m, 7H), 0.67-0.61 (m, 4H) ppm. MS: m/z=465.2 (M+1).

Example 58: Synthesis of Compound 79

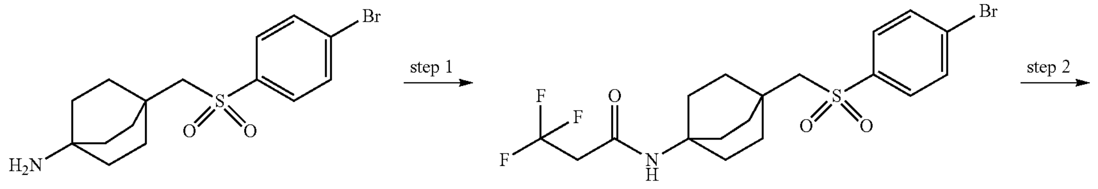

Intermediate J 79-1

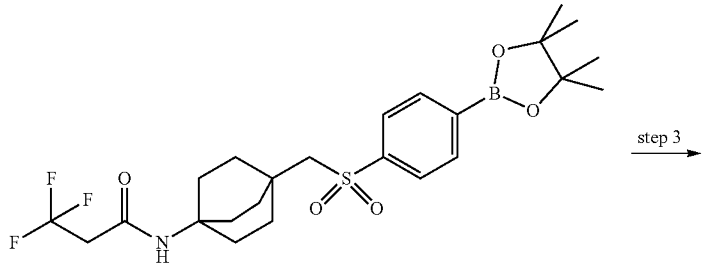

79-2

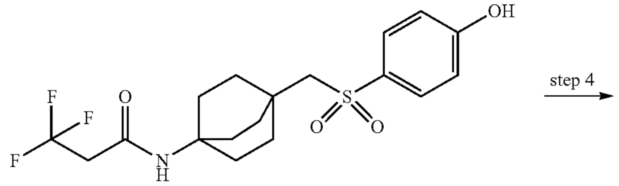

79-3

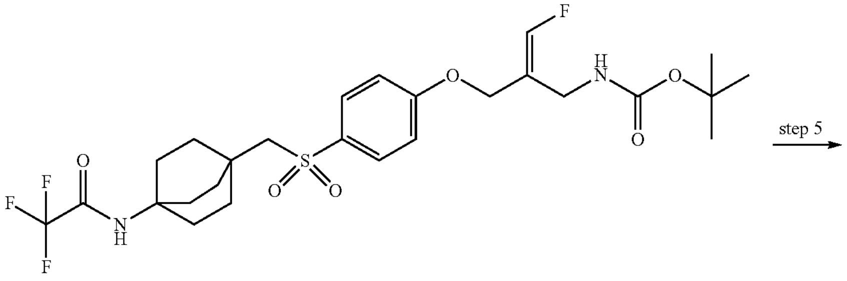

79-4

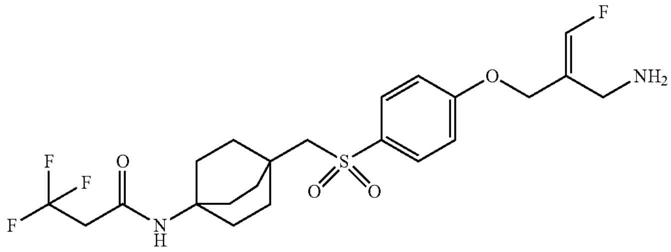

79

Step 1: 79-1

To a mixture of 3,3,3-trifluoropropanoic acid (71.36 mg, 557.31 μmol, 49.22 L), Intermediate J (200 mg, 506.64 μmol, HCl salt) in DCM (5 mL) was added TEA (153.80 mg, 1.52 mmol, 211.85 μL) and HATU (231.17 mg, 607.97 μmol) at 25° C. The reaction solution was stirred for 2 hr at 25° C. The crude product was purified by silica gel chromatography (12 g, ethyl acetate in petroleum ether, 0-35%, v/v) to obtain 79-1 (160 mg, 341.64 μmol, 67.43% yield).

Step 2: 79-2

A 30 mL microwave reaction tube was charged with 79-1 (160 mg, 341.64 μtmol), 4,4,5,5-tetramethyl-2-(4,4,5,5-tetramethyl-1,3,2-dioxaborolan-2-yl)-1,3,2-dioxaborolane (104.11 mg, 409.97 μmol), bis(diphenylphosphino)ferrocene]dichloropalladium(II) (25.0 mg, 34.16 μmol) and potassium acetate (100.59 mg, 1.02 mmol) in Dioxane (2 mL). After oxygen was purged by bubbling nitrogen into the reaction solution, the tube was sealed and heated at 120° C. for 0.5 hr in a Biotage microwave reactor. The reaction mixture was filtered and concentrated under reduced pressure to give 79-2 (300 mg, crude).

Step 3: 79-3

To a mixture of 79-2 (300 mg, 582.08 μmol), acetate acid (0.2 mL) in THF (1 mL) was added hydrogen peroxide (0.2 mL, 30% purity) at 20° C. The reaction solution was stirred for 0.5 hr at 20° C. Then, the solution was concentrated with a rotary evaporator to obtain a crude, which was purified by silica gel chromatography (12 g, ethyl acetate in petroleum ether, 0-65%, v/v) to obtain 79-3 (55 mg, 135.66 μmol, 23.31% yield).

Step 4: 79-4

To a mixture of 79-3 (55 mg, 135.66 μmol), Intermediate A (43.65 mg, 162.79 μmol) in MeCN (5 mL) was added Cesium carbonate (132.60 mg, 406.97 μmol) at 20° C. The reaction solution was stirred for 1 hr at 95° C. Then, the mixture was filtered and the filtrate was concentrated with a rotary evaporator to obtain a crude, which was purified by silica gel chromatography (ethyl acetate in petroleum ether, 0-65%, v/v) to obtain 79-4 (28 mg, 47.25 μmol, 34.83% yield).

Step 5: Compound 79

To a solution of 79-4 (28 mg, 47.25 μmol) in DCM (1 mL) was added HCl/Dioxane (4 M, 222.34 μL) at 20° C. and stirred at 20° C. for 1 hr. The reaction mixture was filtered. The filter cake was slurried with acetonitrile (3 mL) for 15 minutes and filtered. The filter cake was dried by lyophilization (water:acetonitrile=4:1, 20 mL) to give Compound 79 (7.5 mg, 14.18 μmol, 30.01% yield, HCl salt). $^1$H NMR (400 MHz, DMSO-d6) δ 8.25 (s, 3H), 7.86-7.81 (m, 2H), 7.78 (s, 1H), 7.35 (d, J=80.0 Hz, 1H), 7.22-7.19 (m, 2H), 4.74 (d, J=3.5 Hz, 2H), 3.62 (s, 2H), 3.59-3.56 (m, 1H), 3.17-3.14 m, 1H), 3.12 (s, 2H), 1.80-1.62 (m, 12H) ppm. MS: m/z=493.2 (M+1).

The compounds of Formula (I') or (I) in Table 12 below were made according to Example 58 of Compound 79.

TABLE 12

| Cmpd No. | $^1$H NMR and/or LC/MS data |
|---|---|
| 84 | $^1$H NMR (400 MHz, Methanol-d4) δ 7.91-7.81 (m, 2H), 7.27 (d, J = 80.0 Hz, 1H), 7.24-7.18 (m, 2H), 4.73 (d, J = 3.6 Hz, 2H), 3.84 (d, J = 2.2 Hz, 2H), 3.08 (s, 2H), 2.45-2.40 (m, 1H), 1.95-1.73 (m, 13H), 1.69-1.58 (m, 1H) ppm. MS: m/z = 487.2 (M + 1). |
| 85 | $^1$H NMR (400 MHz, Methanol-$d_4$) δ 7.91-7.83 (m, 2H), 7.27 (d, J = 80.0 Hz, 1H), 7.21 (d, J = 8.9 Hz, 2H), 6.98 (s, 1H), 4.73 (d, J = 3.6 Hz, 2H), 3.84 (d, J = 2.3 Hz, 2H), 3.08 (s, 2H), 1.90 (dd, J = 10.4, 5.1 Hz, 6H), 1.80 (dd, J = 10.5, 5.1 Hz, 6H), 1.19 (s, 4H) ppm. MS: m/z = 519.2 (M + 1). |
| 86 | $^1$H NMR (400 MHz, Methanol-$d_4$) δ 7.91-7.82 (m, 2H), 7.27 (d, J = 80.0 Hz, 1H), 7.24-7.20 (m, 2H), 4.73 (d, J = 3.5 Hz, 2H), 3.84 (d, J = 2.2 Hz, 2H), 3.09 (s, 2H), 1.98-1.92 (m, 6H), 1.85-1.78 (m, 6H), 1.28-1.17 (m, 4H) ppm. MS: m/z = 469.2 (M + 1). |
| 91 | $^1$H NMR (400 MHz, Methanol-$d_4$) δ 7.90-7.83 (m, 2H), 7.27 (d, J = 84.0 Hz, 1H), 7.24-7.17 (m, 2H), 6.38 (s, 0.5H), 4.72 (d, J = 3.5 Hz, 2H), 3.84 (d, J = 2.3 Hz, 2H), 3.07 (s, 2H), 1.94-1.86 (m, 6H), 1.82-1.74 (m, 6H), 1.27 (s, 3H), 0.99 (q, J = 3.8 Hz, 2H), 0.53 (q, J = 3.9 Hz, 2H) ppm. MS: m/z = 465.2 (M + 1). |
| 92 | $^1$H NMR (400 MHz, Methanol-d4) δ 7.88-7.84 (m, 2H), 7.27 (d, J = 84.0 Hz, 1H), 7.23-7.18 (m, 2H), 7.07 (s, 0.3H) 4.72 (d, J = 3.5 Hz, 2H), 3.84 (d, J = 2.2 Hz, 2H), 3.07 (s, 2H), 3.03-2.97 (m, 1H), 2.17-2.12 (m, 2H), 2.08-2.00 (m, 2H), 1.97-1.91 (m, 1H), 1.90-1.75 (m, 13H) ppm. MS: m/z = 465.2 (M + 1). |

Example 59: Synthesis of Compound 82

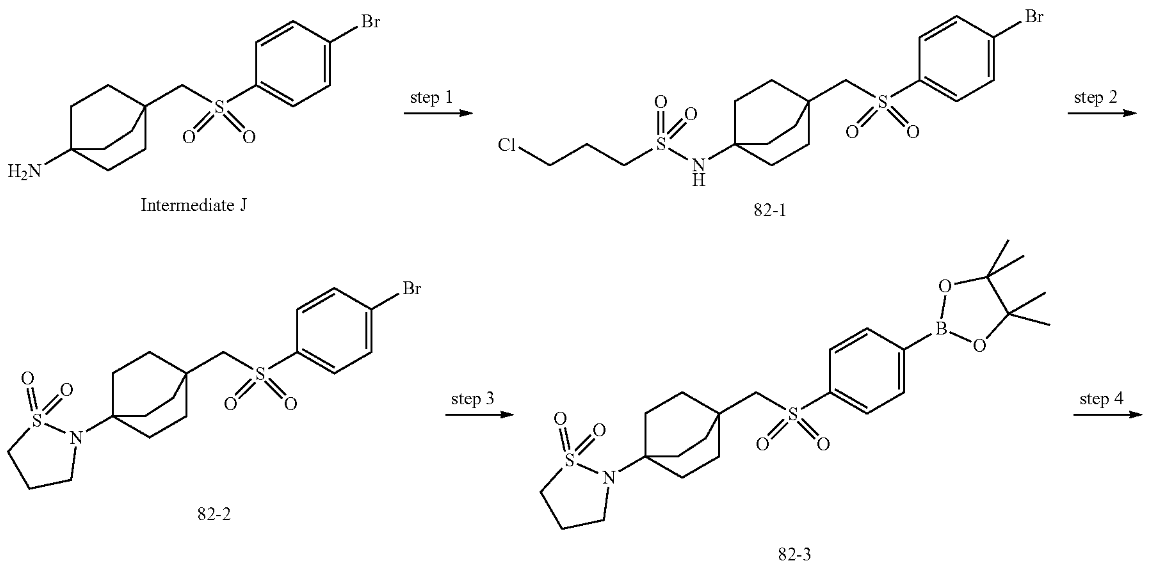

Intermediate J 82-1

82-2

82-3

-continued

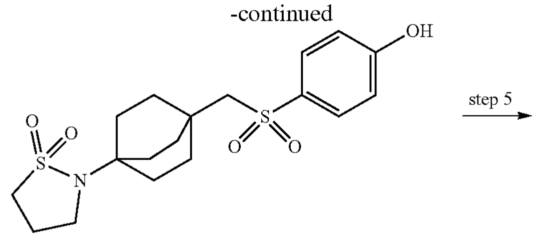

82-4

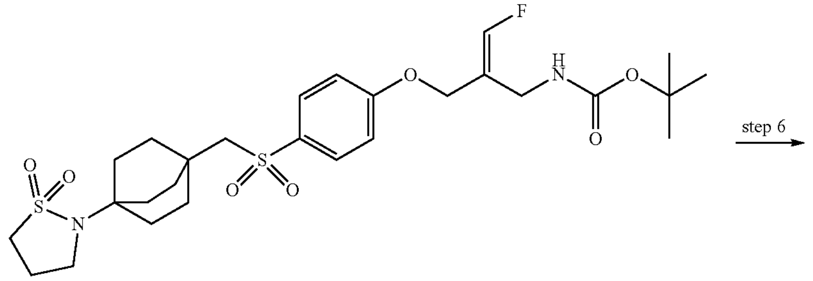

82-5

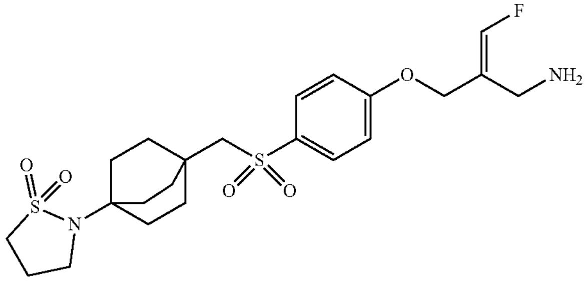

82

Step 1: 82-1

To a mixture of Intermediate J (300 mg, 759.97 μmol, HCl salt) and DIPEA (294.65 mg, 2.28 mmol, 397.11 μL) in DMF (4 mL) was added 3-chloropropane-1-sulfonyl chloride (269.10 mg, 1.52 mmol, 185.59 μL) at 25° C. The reaction solution was stirred for 2 hr at 25° C. The mixture was added ethyl acetate (50 mL) and washed with brine (50 mL). The organic layer was concentrated with a rotary evaporator to obtain crude product, which was purified by silica gel chromatography (4 g, ethyl acetate in petroleum ether, 0-35%, v/v) to obtain 82-1 (80 mg, 160.36 μmol, 21.10% yield).

Step 2: 82-2

To a mixture of 82-1 (80 mg, 160.36 μmol) in DMF (2 mL) was added Cesium carbonate (156.74 mg, 481.08 μmol) at 30° C. The reaction solution was stirred for 0.5 hr at 30° C. The mixture was added ethyl acetate (50 mL) and washed with brine (50 mL). The organic layer was concentrated with a rotary evaporator to obtain 82-2 (75 mg, crude). MS: m/z=462.0 (M+1).

Step 3: 82-3

A 30 mL microwave reaction tube was charged with 82-2 (75 mg, 162.19 μmol), 4,4,5,5-tetramethyl-2-(4,4,5,5-tetramethyl-1,3,2-dioxaborolan-2-yl)-1,3,2-dioxaborolane (49.42 mg, 194.63 μmol), bis(diphenylphosphino)ferrocene] dichloropalladium(II) (11.87 mg, 16.22 μmol) and potassium acetate (47.75 mg, 486.57 μmol) in Dioxane (4 mL). After oxygen was purged by bubbling nitrogen into the reaction solution, the tube was sealed and heated at 120° C. for 0.5 hr in a Biotage microwave reactor. The reaction mixture was filtered and concentrated under reduced pressure to give 82-3 (120 mg, crude).

Step 4: 82-4

To a mixture of 82-3 (120 mg, 235.53 μmol), acetate acid (0.1 mL) in THF (2 mL) was added hydrogen peroxide (0.1 mL, 30% purity) at 20° C. The reaction solution was stirred for 0.5 hr at 20° C. Then, the solution was concentrated with a rotary evaporator to obtain a crude, which was purified by silica gel chromatography (4 g, ethyl acetate in petroleum ether, 0-80%, v/v) to obtain 82-4 (50 mg, 125.15 μmol, 53.13% yield).

Step 5: 82-5

To a mixture of 82-4 (50 mg, 125.15 μmol), Intermediate A (40.27 mg, 150.18 mol) in MeCN (3 mL) was added Cesium carbonate (81.55 mg, 250.30 μmol) at 20° C. The reaction solution was stirred for 1 hr at 95° C. Then, the mixture was filtered and the filtrate was concentrated with a rotary evaporator to obtain a crude, which was purified by silica gel chromatography (12 g, ethyl acetate in petroleum ether, 0-65%, v/v) to obtain 82-5 (45 mg, 76.70 μmol, 61.28% yield).

Step 6: Compound 82

To a mixture of 82-5 (45 mg, 76.70 μmol) in DCM (1 mL) was added HCl/Dioxane (4 M, 1 mL) at 20° C. and stirred at 20° C. for 1 hr. The reaction mixture was concentrated to give crude. The crude was added dichloromethane (20 mL) and washed with saturated $NaHCO_3$ solution (15 mL×3) and water (15 mL). The organic layer was concentrated and dried by lyophilization (water:acetonitrile=4:1, 10 mL) to give Compound 82 (8 mg, 16.44 μmol, 21.44% yield). $^1$H NMR (400 MHz, Methanol-d4) δ 7.86-7.80 (m, 2H), 7.20-7.14 (m, 2H), 6.94 (d, J=84.0 Hz, 1H), 4.66 (dd, J=3.6, 1.2 Hz, 2H), 3.46 (d, J=2.5 Hz, 2H), 3.34 (d, J=6.5 Hz, 2H), 3.16 (t, J=7.5 Hz, 2H), 3.06 (s, 2H), 2.26-2.18 (m, 2H), 2.01-1.94 (m, 6H), 1.84-1.77 (m, 6H) ppm. MS: m/z=487.2 (M+1).
Example 60: Synthesis of Compound 83
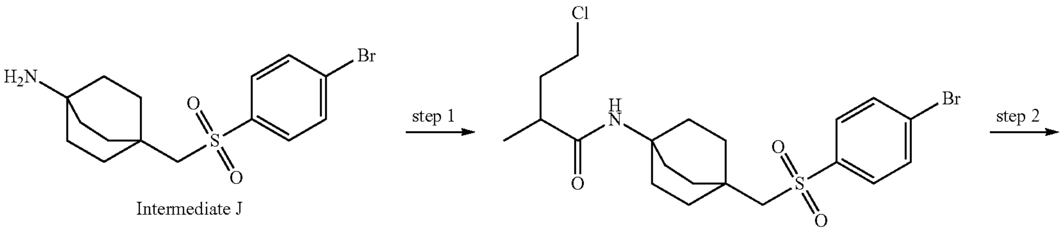
Intermediate J
83-1
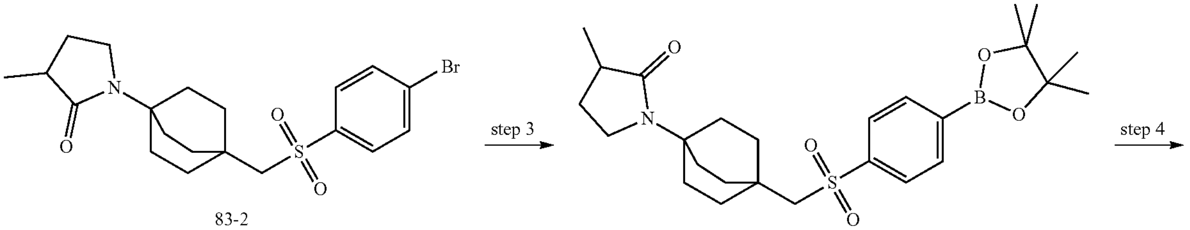
83-2
83-3
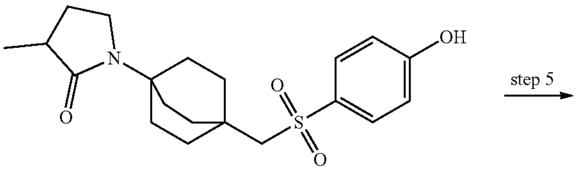
83-4
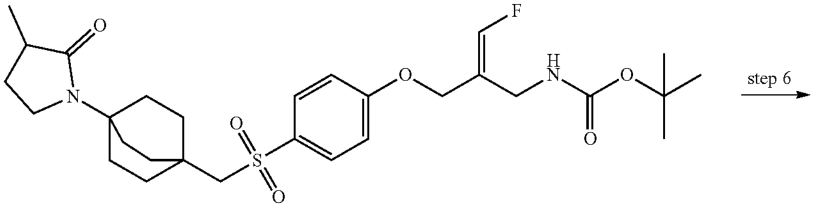
83-5
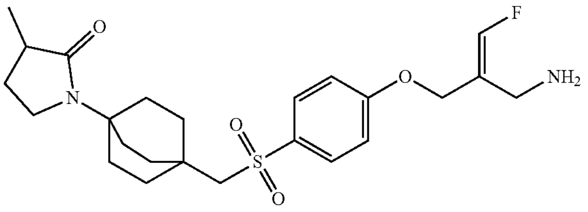
83

Step 1: 83-1

To a mixture of Intermediate J (700.27 mg, 1.77 mmol, HCl salt), DIPEA (625.28 mg, 4.84 mmol, 842.69 μL) in DCM (15 mL) was added 4-chloro-2-methyl-butanoyl chloride (250 mg, 1.61 mmol, 103.62 μL). After addition, the mixture was stirred at 25° C. for 16 hr. Upon completion, the resulting solution was concentrated. The residue was purified by silica gel chromatography (petroleum ether:ethyl acetate=3:1) to give 83-1 (700 mg, 1.47 mmol, 91.03% yield). MS: m/z=476.1 (M+1).

Step 2: 83-2

A mixture of 83-1 (400 mg, 838.83 μmol) and t-BuOK (188 mg, 1.68 mmol) in DMSO (10 mL) was stirred at 25° C. for 1 hr. Upon completion, the resulting mixture was diluted with water and extracted with DCM. The separated organic layer was washed with water for three times and brine, dried over anhydrous sodium sulfate, filtered and concentrated. The residue was purified by silica gel chromatography (petroleum ether:ethyl acetate=1:1) to give 83-2 (250 mg, 567.67 μmol, 67.67% yield). MS: m/z=440.1 (M+1).

Step 3: 83-3

A mixture of 83-2 (250 mg, 567.67 μmol), 4,4,5,5-tetramethyl-2-(4,4,5,5-tetramethyl-1,3,2-dioxaborolan-2-yl)-1,3,2-dioxaborolane (216 mg, 850.60 μmol), bis(diphenylphosphino)ferrocene]dichloropalladium(II) (42 mg, 57.40 μmol) and potassium acetate (433 mg, 1.70 mmol) in Dioxane (5 mL) was microwaved at 120° C. for 30 min. Upon completion, the resulting mixture was cooled to room temperature, filtered and concentrated to give 83-3 (crude, 250 mg).

Step 4: 83-4

A mixture of 83-3 (250 mg, 512.86 μmol), hydrogen peroxide (1 mL, 30% purity) and acetate acid (1 mL) in THF (4 mL) was stirred at 25° C. for 1 hr. Upon completion, the resulting solution was quenched with sodium sulfite, filtered and concentrated. The residue was purified by silica gel chromatography (petroleum ether:ethyl acetate=1:1) to give 83-4 (120 mg, 317.88 μmol, 61.98% yield). MS: m/z=378.2 (M+1).

Step 5: 83-5

A mixture of 83-4 (120 mg, 317.88 μmol), Intermediate A (94 mg, 350.59 μmol) and cesium carbonate (517.86 mg, 1.59 mmol) in MeCN (20 mL) was stirred at 95° C. for 1 hr. Upon completion, the resulting mixture was cooled to room temperature and filtered. The filtrate was concentrated. The residue was purified by silica gel chromatography (ethyl acetate in petroleum ether, 20-50%, v/v) to give 83-5 (130 mg, 230.21 μmol, 72.42% yield). MS: m/z=509.2 (M+1-56).

Step 6: Compound 83

A mixture of 83-5 (130 mg, 230.21 μmol) and HCl/Dioxane (4 M, 5 mL) in Dioxane (4 mL) was stirred at 25° C. for 1 hr. Upon completion, the resulting mixture was filtered to obtain the filter cake as Compound 83 (80 mg, 159.66 μmol, 69.36% yield, HCl salt). $^1$H NMR (500 MHz, Methanol-d4) δ 7.79-7.73 (m, 2H), 7.20 (d, J=64.0 Hz, 1H), 7.14-7.10 (m, 2H), 4.63 (d, J=3.4 Hz, 2H), 3.74 (d, J=2.1 Hz, 2H), 3.35-3.30 (m, 1H), 3.29-3.23 (m, 1H), 2.97 (s, 2H), 2.27-2.21 (m, 1H), 2.05-2.02 (m, 1H), 2.01-1.88 (m, 6H), 1.70 (t, J=7.9 Hz, 6H), 1.41-1.38 (m, 1H), 0.99 (d, J=7.1 Hz, 3H) ppm. MS: m/z=465.2 (M+1).

Example 61: Synthesis of Compound 87

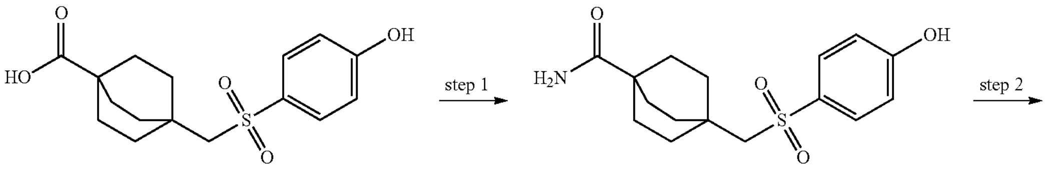

Intermediate I 87-1

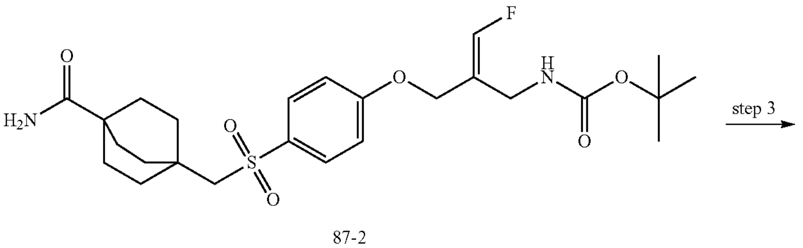

87-2

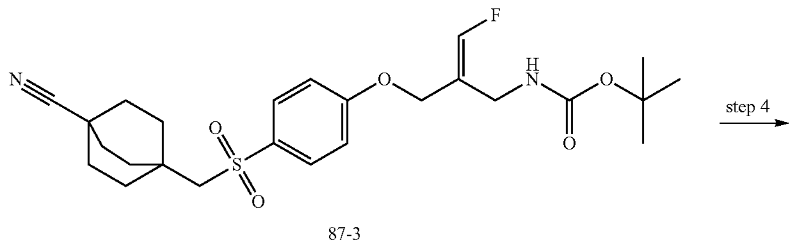

87-3

-continued

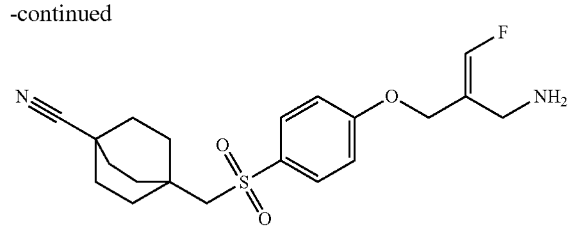

87-4

Step 1: 87-1

To a mixture of Intermediate I (200 mg, 616.54 μmol), Ammonium chloride (989.39 mg, 18.50 mmol) and HATU (352 mg, 925.76 μmol) in DMF (10 mL) was added DIPEA (239 mg, 1.85 mmol, 322.10 μL). After addition, the mixture was stirred at 25° C. for 16 hr. Upon completion, the resulting mixture was diluted with water (20 mL) and extracted with ethyl acetate (30 mL). The separated organic layer was washed with water (20 mL×3) and brine, dried over anhydrous sodium sulfate, filtered and concentrated to 87-1 (180 mg, 556.58 μmol, 90.27% yield). MS: m/z=324.1 (M+1).

Step 2: 87-2

A mixture of 87-1 (180 mg, 556.58 μmol), Intermediate A (179.08 mg, 667.89 μmol) and cesium carbonate (906.72 mg, 2.78 mmol) in MeCN (30 mL) was stirred at 95° C. for 1 hr. The resulting mixture was filtered and concentrated to give 87-2 (280 mg, 548.36 μmol, 98.52% yield). MS: m/z=455.1 (M+1-56).

Step 3: 87-3

A mixture of 87-2 (280 mg, 548.36 μmol) and Burgess Reagent (392 mg, 1.64 mmol) in DCM (10 mL) was stirred at 25° C. for 1 hr. The resulting solution was concentrated. The residue was purified by silica gel chromatography (petroleum ether/ethyl acetate=5/1, v/v) to give 87-3 (200 mg, 406.01 μmol, 74.04% yield). MS: m/z=437.1 (M+1-56).

Step 4: Compound 87

A mixture of 87-3 (200 mg, 406.01 μmol) and HCl/Dioxane (4 M, 5 mL) in Dioxane (2 mL) was stirred at 25° C. for 1 hr. Upon completion, the resulting mixture was filtered to give the filter cake as Compound 87 (120 mg, 279.75 μmol, 68.90% yield, HCl salt). $^1$H NMR (400 MHz, Methanol-d4) δ 7.91-7.83 (m, 2H), 7.27 (d, J=80.0 Hz, 1H), 7.25-7.18 (m, 2H), 4.73 (d, J=3.5 Hz, 2H), 3.84 (d, J=2.3 Hz, 2H), 3.09 (s, 2H), 1.99-1.90 (m, 6H), 1.80 (dd, J=10.4, 5.5 Hz, 6H). MS: m/z=393.1 (M+1).

Example 62: Synthesis of Compound 88

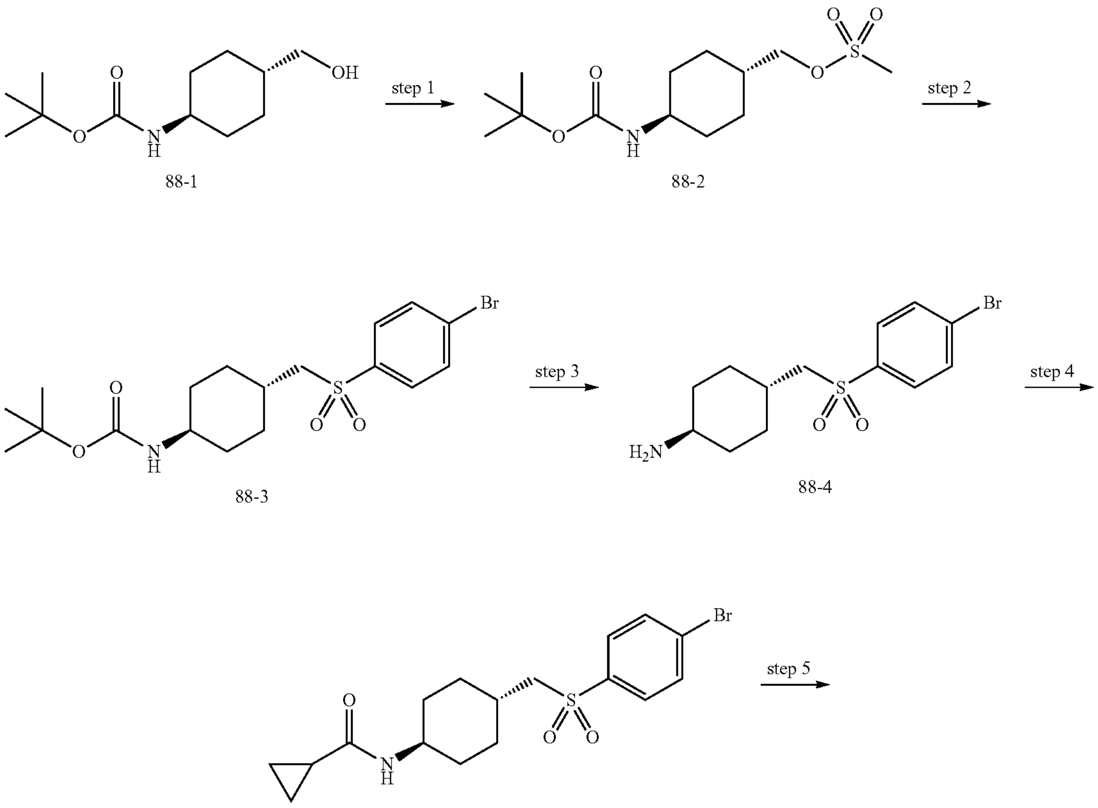

88-1 88-2 88-3 88-4 88-5

-continued

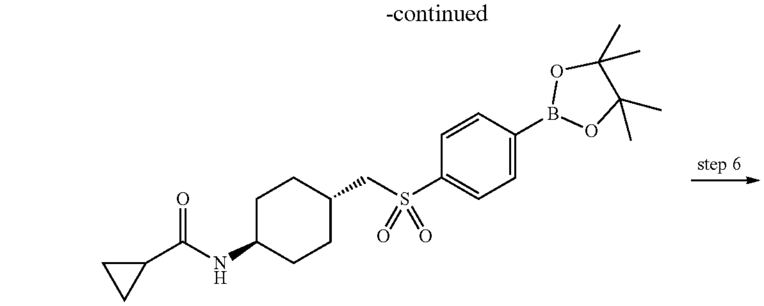

88-6

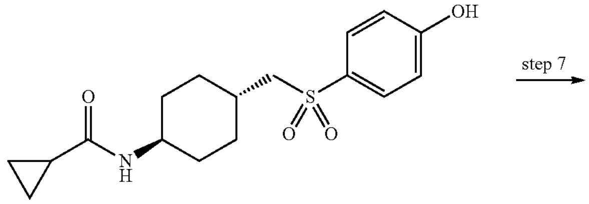

88-7

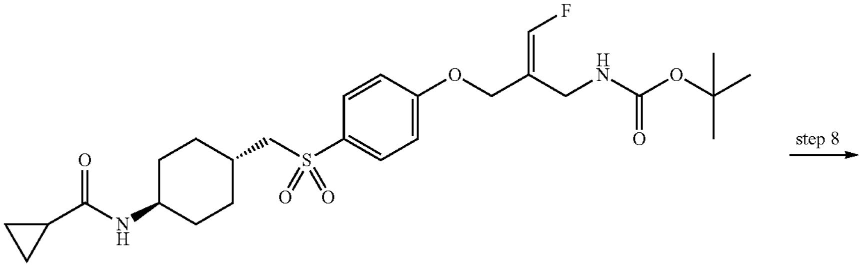

88-8

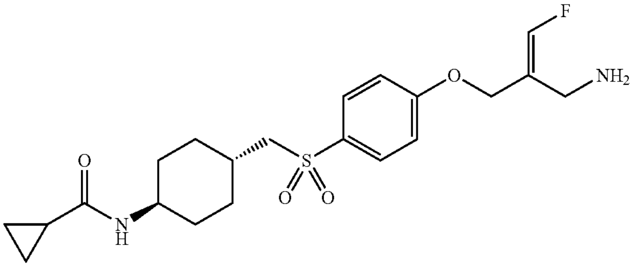

88

Step 1: 88-2

A mixture of 88-1 (1 g, 4.36 mmol), TEA (1.32 g, 13.08 mmol, 1.82 mL) in DCM (20 mL) was added methanesulfonic acid anhydride (911.56 mg, 5.23 mmol) in one portion at 0° C. The reaction mixture was stirred at 20° C. for 1 hr. Water (30 mL) was added, and the mixture was extracted with DCM (150 mL), washed with water and brine, dried over anhydrous sodium sulfate. Then, the organic phases were concentrated to obtain 88-2 (1.3 g, 4.23 mmol, 96.98% yield).

Step 2: 88-3

A mixture of 88-2 (1.3 g, 4.23 mmol), 4-bromobenzenesulfinic acid (1.22 g, 5.50 mmol) and Cesium carbonate (4.13 g, 12.69 mmol) in DMF (10 mL) was heated to 120° C. and stirred at 120° C. for 1 hr. Water (30 mL) was added, and the mixture was extracted with ethyl acetate (150 mL), washed with water and brine, dried over anhydrous sodium sulfate. Then, the solution was concentrated with a rotary evaporator, the crude product was purified by silica gel chromatography (ethyl acetate in petroleum ether, 10-50%, v/v) to obtain 88-3 (1.2 g, 2.78 mmol, 65.61% yield).

Step 3: 88-4

A mixture of 88-3 (0.35 g, 809.49 μmol) in HCl/Dioxane (4 M, 6.07 mL) was stirred at 30° C. for 1 hr. The reaction mixture was concentrated to obtain 88-4 (0.29 g, 786.51 μmol, 97.16% yield, HCl salt). MS: m/z=332.0 (M+1).

Step 4: 88-5

To a mixture of 88-4 (0.29 g, 786.51 μmol, HCl salt), TEA (397.94 mg, 3.93 mmol, 548.12 μL) in DCM (10 mL) was added cyclopropanecarbonyl chloride (246.65 mg, 2.36 mmol, 214.48 μL) dropwise at 0° C. for 0.2 hr and stirred at 30° C. for 0.8 hr. Water (20 mL) was added, and the mixture was extracted with DCM (30 mL), washed with brine, dried over anhydrous sodium sulfate. The organic phases were concentrated to obtain 88-5 (300 mg, 749.38 μmol, 95.28% yield). MS: m/z=400.0 (M+1).

Step 5: 88-6

A mixture of 88-5 (300 mg, 749.38 μmol), 4,4,5,5-tetramethyl-2-(4,4,5,5-tetramethyl-1,3,2-dioxaborolan-2-yl)-1,3,2-dioxaborolane (228.36 mg, 899.26 μmol), bis(di-phenylphosphino)ferrocene]dichloropalladium(II) (27.42 mg, 37.47 μmol), potassium acetate (227.66 mg, 2.25 mmol) in Dioxane (15 mL) was stirred at 120° C. under microwave for 0.7 hr. The reaction mixture was filtered and concentrated to give 88-6 (335 mg, 748.78 μmol, 99.92% yield).

Step 6: 88-7

To a mixture of 88-6 (335 mg, 748.78 μmol) in acetate acid (1 mL) and THF (4 mL) was added hydrogen peroxide (0.25 mL, 30% purity) dropwise at 20° C. and stirred for 1 hr. Sodium sulfite (1.0 g) was added, and the mixture was filtered and concentrated to give 88-7 (200 mg, 592.71 μmol, 79.16% yield).

Step 7: 88-8

To a mixture of 88-7 (200 mg, 592.71 μmol) in MeCN (30 mL) was added Cesium carbonate (579.35 mg, 1.78 mmol), Intermediate A (190.70 mg, 711.25 μmol) and stirred at 95° C. for 0.8 hr. The reaction mixture was concentrated and the residue was purified by flash chromatography on silica gel (ethyl acetate in petroleum ether, 10-30%, v/v) to give 88-8 (145 mg, 276.38 μmol, 46.63% yield).

Step 8: Compound 88

A mixture of 88-8 (145 mg, 276.38 μmol) in HCl/Dioxane (4 M, 2.07 mL) was stirred at 30° C. for 1 hr. Then, the solution was concentrated and the residue was purified by prep-HPLC (column: XBridge@ Prep C18 5 μm 19×150 mm; A: 0.2% $HCO_2H$ water, B: acetonitrile; gradient: 5-95% B; GT: 25 min; flow rate: 15 mL/min) to obtain Compound 88 (5.6 mg, 11.90 μmol, 4.31% yield, $HCO_2H$ salt). $^1H$ NMR (400 MHz, Methanol-d4) δ 8.44 (s, 1H), 7.91-7.69 (m, 2H), 7.12 (d, J=80.0 Hz, 1H), 7.20-7.08 (m, 2H), 4.63 (d, J=3.5 Hz, 2H), 3.69 (d, J=2.3 Hz, 2H), 3.52-3.44 (m, 1H), 3.28 (d, J=6.4 Hz, 1H), 3.03 (d, J=6.0 Hz, 2H), 1.80 (d, J=14.9 Hz, 4H), 1.45-1.39 (m, 1H), 1.12 (q, J=10.6 Hz, 4H), 0.73 (td, J=4.7, 2.1 Hz, 2H), 0.62-0.58 (m, 2H) ppm. MS: m/z=425.1 (M+1).

Example 63: Synthesis of Compound 89

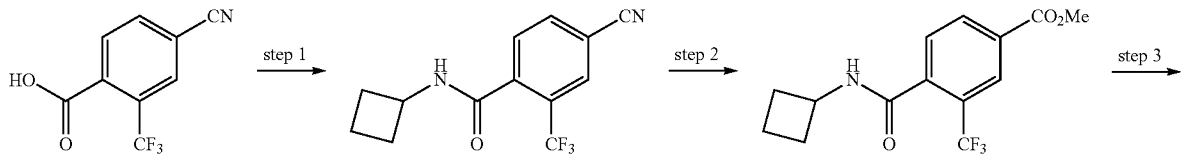

89-1 89-2 89-3

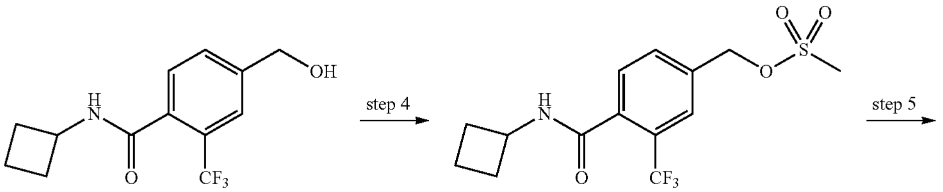

89-4 89-5

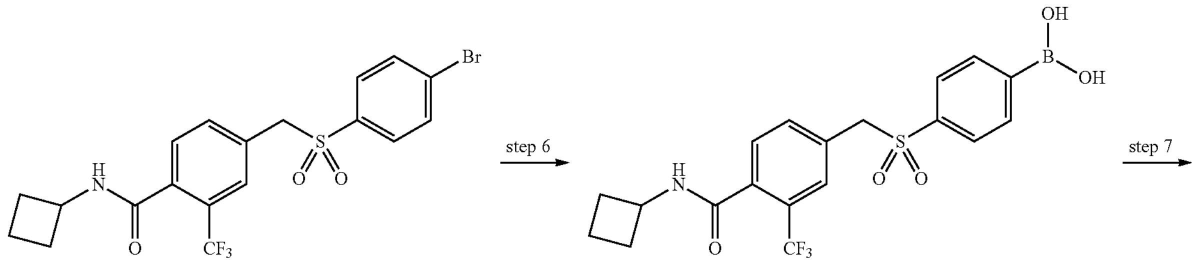

89-6 89-7

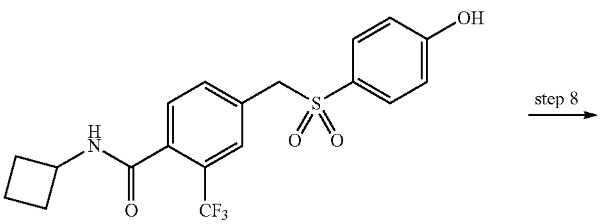

89-8

-continued

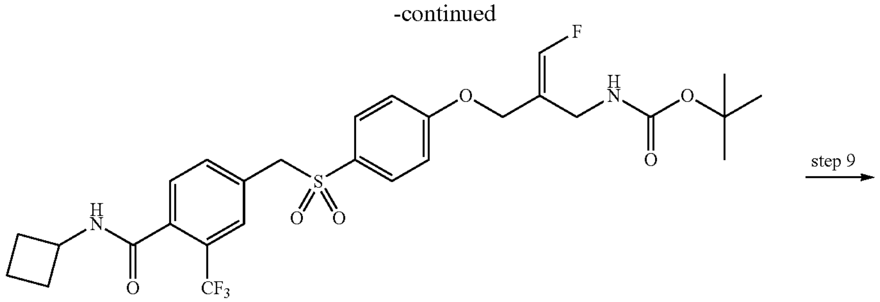

89-9

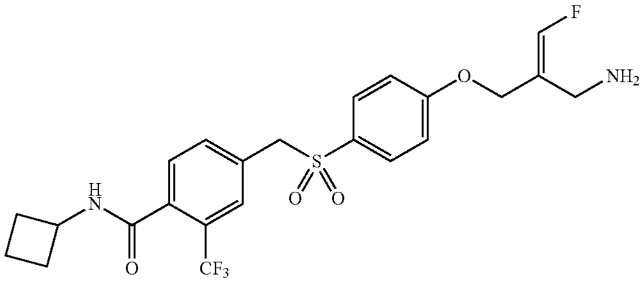

89

Step 1: 89-2

A mixture of 89-1 (1.1 g, 5.11 mmol), cyclobutanamine (400.02 mg, 5.62 mmol, 480.22 μL), HATU (2.92 g, 7.67 mmol), DIPEA (1.98 g, 15.34 mmol, 2.67 mL) in DMF (10 mL) was stirred at 30° C. for 3 hr. Water (50 mL) was added, and the mixture was extracted with ethyl acetate (150 mL), washed with brine, dried over anhydrous sodium sulfate, the organic phases were concentrated and purified by silica gel chromatography (ethyl acetate in petroleum ether, 10-50%, v/v) to 89-2 (1.3 g, 4.85 mmol, 94.78% yield). MS: m/z=269.0 (M+1).

Step 2: 89-3

A mixture of 89-2 (1 g, 3.73 mmol) in HCl in methanol (4 M, 46.60 mL) was heated to 90° C. and stirred at 90° C. for 2 hr. The reaction mixture was concentrated and purified by flash chromatography on silica gel (ethyl acetate in petroleum ether, 5-50%, v/v) to give 89-3 (0.5 g, 1.66 mmol, 44.52% yield). MS: m/z=302.1 (M+1).

Step 3: 89-4

A mixture of 89-3 (several batches, 1 g, 3.32 mmol) in THF (30 mL) was added DIBAL-H in hexane (1 M, 13.28 mL) dropwise and stirred at 0° C. for 1 hr. Water (5 mL) was added, the mixture was filtered, the filtrate was concentrated and purified by silica gel chromatography (ethyl acetate in petroleum ether, 10-50%, v/v) to obtain 89-4 (700 mg, 2.56 mmol, 77.18% yield). MS: m/z=274.1 (M+1).

Step 4: 89-5

To a mixture of 89-4 (0.5 g, 1.83 mmol), TEA (555.48 mg, 5.49 mmol, 765.12 μL) in DCM (20 mL) was added methanesulfonic acid anhydride (382.50 mg, 2.20 mmol) in portions at 0° C. and stirred for 1 hr. Water (20 mL) was added, and the mixture was extracted with DCM (60 mL), washed with brine, dried over anhydrous sodium sulfate. The organic phases were concentrated to obtain 89-5 (600 mg, 1.71 mmol, 93.33% yield). MS: m/z=352.1 (M+1).

Step 5: 89-6

A mixture of 89-5 (0.3 g, 853.87 μmol), Cesium carbonate (556.42 mg, 1.71 mmol), 4-bromobenzenesulfinic acid (245.40 mg, 1.11 mmol) in DMF (10 mL) was stirred at 120° C. under microwave for 1 hr. Water (20 mL) was added, and the mixture was extracted with ethyl acetate (100 mL), washed with brine, dried over anhydrous sodium sulfate. The organic phases were concentrated and purified by silica gel chromatography (ethyl acetate in petroleum ether, 10-90%, v/v) to obtain 89-6 (260 mg, 545.87 μmol, 63.93% yield). MS: m/z=476.0 (M+1).

Step 6: 89-7

A mixture of 89-6 (260 mg, 545.87 μmol), 4,4,5,5-tetramethyl-2-(4,4,5,5-tetramethyl-1,3,2-dioxaborolan-2-yl)-1,3,2-dioxaborolane (207.93 mg, 818.80 μmol), bis(di-phenylphosphino)ferrocene]dichloropalladium(II) (19.97 mg, 27.29 μmol), potassium acetate (160.72 mg, 1.64 mmol) in Dioxane (10 mL) was stirred at 120° C. for 1 hr. The reaction mixture was filtered and the filtrate was concentrated to obtain 89-7 (240 mg, 543.94 μmol, 99.65% yield). MS: m/z=442.1 (M+1).

Step 7: 89-8

A mixture of 89-7 (240 mg, 543.94 μmol) in THF (4 mL), acetate acid (1 mL) was added hydrogen peroxide (0.18 mL, 30% purity) dropwise and stirred at 30° C. for 1 hr. Sodium sulfite (1.0 g) was added, filtered and concentrated to get crude product 89-8 (224 mg, 541.83 mol, 99.61% yield). MS: m/z=414.1 (M+1).

Step 8: 89-9

A mixture of 89-8 (224 mg, 541.83 μmol), Intermediate A (188.86 mg, 704.39 μmol), Cesium carbonate (529.62 mg, 1.63 mmol) in MeCN (20 mL) was heated to 95° C. and stirred at 95° C. for 1 hr. The reaction mixture was filtered, the filtrate was concentrated and purified by silica gel chromatography (ethyl acetate in petroleum ether, 10-30%, v/v) to obtain 89-9 (145 mg, 241.42 μmol, 44.56% yield). MS: m/z=501.2 (M+1-100).

Step 9: Compound 89

A mixture of 89-9 (145 mg, 241.42 μmol) in HCl/Dioxane (4 M, 6.04 mL) was stirred at 30° C. for 1 hr. Then, the solution was concentrated and the residue was purified by prep-HPLC (column: XBridge@ Prep C18 5 m 19×150 mm; A: 0.2% $HCO_2H$ water, B: acetonitrile; gradient: 5-90% B;

GT: 25 min; flow rate: 15 mL/min) to obtain Compound 89 (25 mg, 46.56 mol, 19.29% yield, $HCO_2H$ salt). $^1H$ NMR (400 MHz, Methanol-d4) δ 8.54 (s, 1H), 7.68-7.57 (m, 2H), 7.52 (d, J=7.5 Hz, 1H), 7.47-7.34 (m, 2H), 7.17 (d, J=84.0 Hz, 1H), 7.18-7.10 (m, 2H), 4.76-4.67 (m, 2H), 4.63 (s, 2H), 4.44 (p, J=8.2 Hz, 1H), 3.72 (d, J=2.3 Hz, 2H), 2.47-2.22 (m, 2H), 2.04-2.00 (m, 2H), 1.80-1.78 (m, 2H) ppm. MS: m/z=501.2 (M+1).

Example 64: Synthesis of Compounds 93 & 94

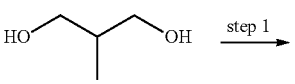

93-1

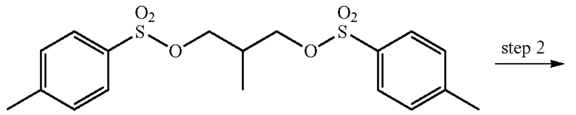

93-2

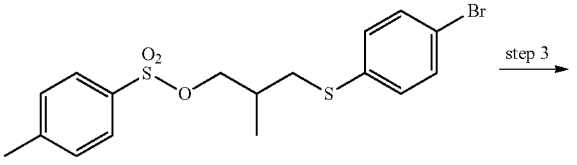

93-3

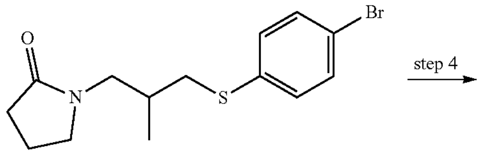

93-4

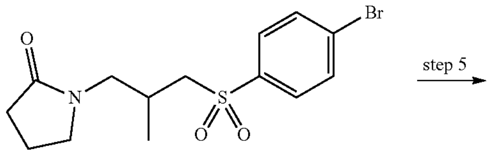

93-5

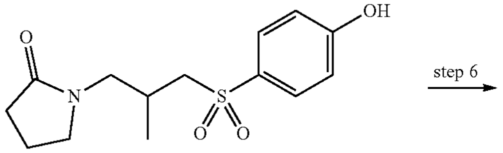

93-6

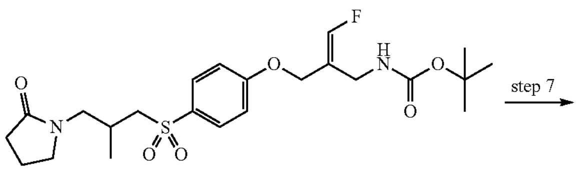

93-7

-continued

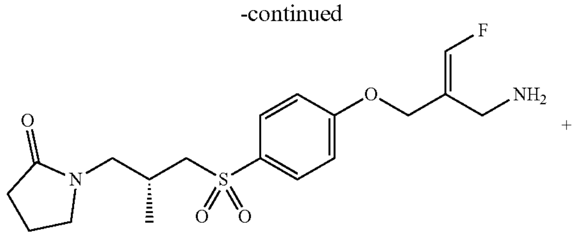

93

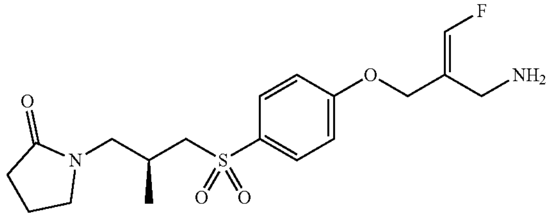

94

Step 1: 93-2

To a mixture of 93-1 (10.0 g, 110.96 mmol) and TEA (33.68 g, 332.89 mmol) in DCM (250 mL) was added tosyl chloride (52.85 g, 277.41 mmol) in portions while the internal temperature was kept below 10° C. After addition, the resulting mixture was warmed up to 25° C. and stirred for 5 hr. The reaction mixture was poured into water (300 mL) and the organic layer was separated. The aqueous phase was extracted with DCM (200 mL×3). The combined organic layers were dried over anhydrous sodium sulfate and concentrated under reduced pressure. The residue was purified by silica gel column eluted with petroleum ether:ethyl acetate=4:1 to give 93-2 (43.0 g, 97.25% yield). $^1H$ NMR (400 MHz, Chloroform-d) δ 7.67 (d, J=8.3 Hz, 4H), 7.28 (d, J=8.1 Hz, 4H), 3.90-3.74 (m, 4H), 2.39 (s, 6H), 2.15-2.01 (m, 1H), 0.84 (d, J=7.0 Hz, 3H) ppm.

Step 2: 93-3

To a mixture of 93-2 (10 g, 25.09 mmol) and potassium acetate (10.39 g, 75.28 mmol) in MeCN (80 mL) was added 4-bromobenzenethiol (4.74 g, 25.09 mmol) in portions while the internal temperature was kept below 25° C. After stirred at 50° C. for 3 hr, the reaction mixture was poured into water (300 mL) and the organic layer was separated. The aqueous phase was extracted with dichloromethane (200 mL×3). The combined organic layers were dried over anhydrous sodium sulfate and concentrated under reduced pressure. The residue was purified by silica gel column eluted with petroleum ether:ethyl acetate=4:1 to give 93-3 (3.5 g, 33.58% yield). $^1H$ NMR (400 MHz, Chloroform-d) δ 7.74 (dd, J=17.1, 10.4 Hz, 2H), 7.35 (dd, J=15.9, 8.3 Hz, 4H), 7.16-7.07 (m, 2H), 4.06-3.95 (m, 2H), 2.93 (dd, J=13.3, 6.6 Hz, 1H), 2.74 (dd, J=13.3, 6.8 Hz, 1H), 2.45 (d, J=3.9 Hz, 3H), 2.06-1.95 (m, 1H), 1.00 (t, J=13.0 Hz, 3H) ppm.

Step 3: 93-4

To a mixture of pyrrolidin-2-one (245.87 mg, 2.89 mmol) in DMF (50 mL) was added t-BuOK (808.93 mg, 7.22 mmol) and 93-3 (1.0 g, 2.41 mmol) at 25° C. After stirred at 25° C. for 3 hr, the reaction mixture was poured into water (200 mL) and extracted with DCM (150 mL×3). The combined organic layers were dried over anhydrous sodium sulfate and concentrated under reduced pressure. The residue was purified by silica gel column (petroleum ether:ethyl acetate=3:1) to give 93-4 (600 mg, 75.92% yield). MS: m/z=328 (M+1).

Step 4: 93-5

To a mixture of 93-4 (550 mg, 1.68 mmol) in water/methanol (25 mL, 1/4) was added Oxone (2.06 g, 3.35 mmol) at 25° C. After stirred at 25° C. for 3 hr, the reaction mixture was poured into water (60 mL) and extracted with ethyl acetate (40 mL×3). The combined organic layers were dried over anhydrous sodium sulfate and concentrated under reduced pressure to give 93-5 (530 mg, 87.80% yield). MS: m/z=360 (M+1).

Step 5: 93-6

To a mixture of 93-5 (300 mg, 832.73 μmol) in Dioxane/water (30 mL, 4/1) was added t-BuXPhos (70.62 mg, 166.55 μmol), KOH (140.18 mg, 2.51 mmol) and $Pd_2(dba)_3$ (76.20 mg, 83.27 μmol). The resulting mixture was stirred at 100° C. for 3 hr under argon atmosphere. After cooling down to room temperature, the reaction mixture was filtered and the filter cake was washed with ethyl acetate (150 mL). The filtrate was washed with brine (50 mL×3), dried over anhydrous sodium sulfate and concentrated under reduced pressure. The residue was purified by silica gel column (dichloromethane:ethyl acetate=2:1) to give 93-6 (240 mg, 96.92% yield). MS: m/z=298 (M+1).

Step 6: 93-7

To a mixture of 93-6 (240 mg, 807.08 μmol) and potassium carbonate (348.05 mg, 2.52 mmol) in MeCN (15 mL) was added Intermediate A (225.41 mg, 840.71 μmol). The resulting mixture was stirred at 80° C. for 3 hr. After cooling down to room temperature, the reaction mixture was poured into water (50 mL) and extracted with ethyl acetate (40 mL×3). The combined organic layers were dried over anhydrous sodium sulfate and concentrated under reduced pressure. The residue was purified by chromatography column (dichloromethane:methanol=10:1) to give 93-7 (329 mg, 84.12% yield). MS: m/z=485 (M+1).

Step 7: Compound 93 & 94

To a mixture of 93-7 (329 mg, 678.94 μmol) in DCM (5 mL) was added HCl (3 M in ethyl acetate, 5 mL). After stirred at 25° C. for 1 hr, the excess solvent was removed under reduced pressure. The residue was purified by prep-HPLC ($HCO_2H$) and SFC (column: Daicel chiralpak AD Prep C18 10 μm 25×250 mm; A: Supercritical $CO_2$, B: EtOH; GT: 12 min; flow rate: 70 g/min) and prep-HPLC (column: Sunfire Prep C18 10 μm 19×250 mm; A: 0.05% HCl water, B: acetonitrile; gradient: 15-35% B; GT: 18 min; flow rate: 20 mL/min) to give Enantiomer 1 (Compound 93 or 94) (50 mg, 17.50% yield, HCl salt) and Enantiomer 2 (Compound 94 or 93) (50 mg, 17.50% yield, HCl salt). Enantiomer 1: $^1$H NMR (400 MHz, DMSO-d6) δ 8.30 (s, 3H), 7.89-7.82 (m, 2H), 7.29 (dd, J=48.7, 41.7 Hz, 3H), 4.76 (d, J=3.2 Hz, 2H), 3.61 (d, J=4.5 Hz, 2H), 3.27-3.12 (m, 4H), 3.09-2.91 (m, 2H), 2.20 (dd, J=16.8, 9.0 Hz, 2H), 2.14-2.04 (m, 1H), 1.95-1.73 (m, 2H), 0.92 (d, J=6.7 Hz, 3H). MS: m/z=385.2 (M+1). Enantiomer 2: $^1$H NMR (400 MHz, DMSO-d6) δ 8.35 (s, 3H), 7.85 (t, J=5.9 Hz, 2H), 7.32 (dd, J=59.8, 29.5 Hz, 3H), 4.77 (d, J=3.1 Hz, 2H), 3.61 (d, J=4.8 Hz, 2H), 3.26-3.11 (m, 4H), 3.09-2.91 (m, 2H), 2.19 (t, J=8.3 Hz, 2H), 2.09 (dt, J=14.1, 6.9 Hz, 1H), 1.91-1.75 (m, 2H), 0.92 (d, J=6.7 Hz, 3H). MS: m/z=385.2 (M+1).

The compounds of Formula (I') or (I) in Table 13 below were made according to Example 64 of Compound 93 & 94.

TABLE 13

| Cmpd No. | $^1$H NMR and/or LC/MS data |
|---|---|
| 104 or 105 | $^1$H NMR (400 MHz, DMSO-$d_6$) δ 8.30 (s, 3H), 7.85 (d, J = 8.9 Hz, 2H), 7.46-7.23 (m, 3H), 4.76 (d, J = 3.1 Hz, 2H), 3.61 (d, J = 5.4 Hz, 2H), 3.40 (dd, J = 13.3, 8.2 Hz, 1H), 3.21-3.06 (m, 3H), 3.03-2.90 (m, 2H), 2.18 (t, J = 5.6 Hz, 3H), 1.75-1.51 (m, 4H), 0.92 (d, J = 6.7 Hz, 3H) ppm. MS: m/z = 399.2 (M + 1). |
| 105 or 104 | $^1$H NMR (400 MHz, DMSO-$d_6$) δ 8.30 (s, 3H), 7.85 (d, J = 8.9 Hz, 2H), 7.45-7.22 (m, 3H), 4.76 (d, J = 3.1 Hz, 2H), 3.61 (d, J = 5.4 Hz, 2H), 3.40 (dd, J = 13.3, 8.2 Hz, 1H), 3.21-3.06 (m, 3H), 3.03-2.90 (m, 2H), 2.18 (t, J = 5.6 Hz, 3H), 1.75-1.51 (m, 4H), 0.92 (d, J = 6.7 Hz, 3H) ppm. MS: m/z = 399.2 (M + 1). |
| 112 or 113 | $^1$H NMR (400 MHz, DMSO-$d_6$) δ 11.21 (s, 1H), 8.38 (s, 3H), 7.94-7.91 (d, J = 8.8 Hz, 2H), 7.45-7.23 (m, 3H), 4.78 (d, J = 2.8 Hz, 2H), 4.03-3.87 (m, 5H), 3.61-3.59 (d, J = 4.8 Hz, 2H), 3.35-3.31 (d, J = 12.4 Hz, 1H), 3.25-3.14 (m, 3H), 3.06-2.97 (m, 3H), 2.45 (s, 1H), 1.13-1.12 (d, J = 6.4 Hz, 3H) ppm. MS: m/z = 387.2 (M + 1). |
| 113 or 112 | $^1$H NMR (400 MHz, DMSO-$d_6$) 611.21 (s, 1H), 8.46 (s, 3H), 7.94-7.91 (d, J = 8.8 Hz, 2H), 7.45-7.23 (m, 3H), 4.80 (s, 2H), 3.96-3.87 (m, 5H), 3.60-3.59 (d, J = 4.8 Hz, 2H), 3.34-3.02 (m, 7H), 2.45 (s, 1H), 1.14-1.12 (d, J = 6.8 Hz, 3H) ppm. MS: m/z = 387.2 (M + 1). |
| 109 or 110 | Intermediate K was used. $^1$H NMR (400 MHz, DMSO-$d_6$) δ 8.33 (s, 3H), 7.83 (dd, J = 9.4, 2.4 Hz, 2H), 7.47-7.19 (m, 3H), 4.76 (d, J = 3.1 Hz, 2H), 3.61 (d, J = 4.6 Hz, 2H), 3.20 (dd, J = 8.6, 5.0 Hz, 2H), 3.15-2.93 (m, 4H), 2.24-2.09 (m, 1H), 1.85-1.72 (m, 2H), 1.70-1.55 (m, 6H), 1.50-1.38 (m, 2H), 0.91 (d, J = 6.7 Hz, 3H) ppm. MS: m/z = 439.3 (M + 1). |
| 110 or 109 | Intermediate K was used. $^1$H NMR (400 MHz, DMSO-$d_6$) δ 8.34(s, 3H), 7.84 (d, J = 8.9 Hz, 2H), 7.47-7.21 (m, 3H), 4.77 (d, J = 3.1 Hz, 2H), 3.61 (d, J = 4.6 Hz, 2H), 3.20 (dd, J = 8.5, 5.1 Hz, 2H), 3.14-2.94 (m, 4H), 2.23-2.10 (m, 1H), 1.85-1.72 (m, 2H), 1.70-1.53 (m, 6H), 1.46 (d, J = 6.7 Hz, 2H), 0.91 (d, J = 6.7 Hz, 3H) ppm. MS: m/z = 439.3 (M + 1). |

Example 65: Synthesis of Compound 95

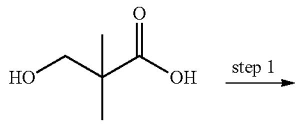

95-1

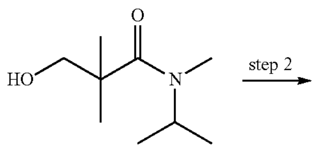

95-2

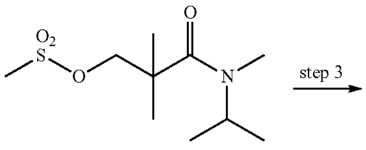

95-3

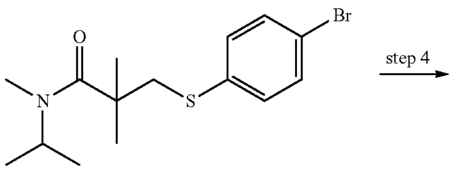

95-4

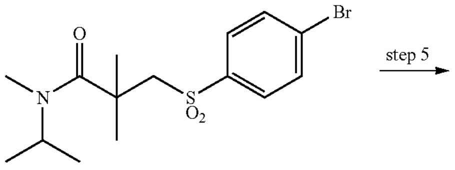

95-5

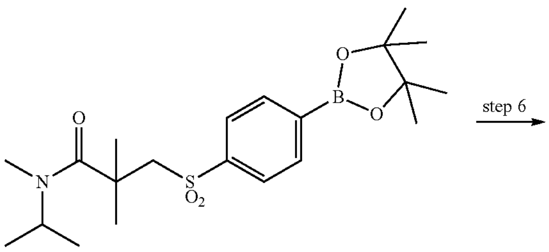

95-6

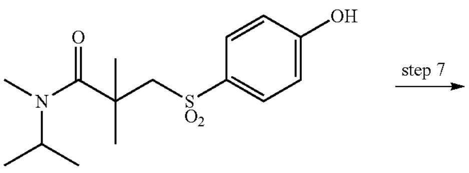

95-7

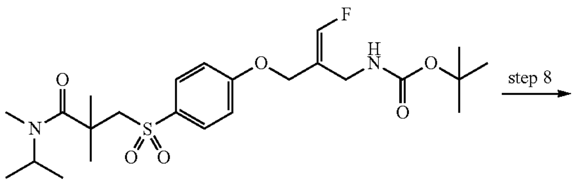

95-8

-continued

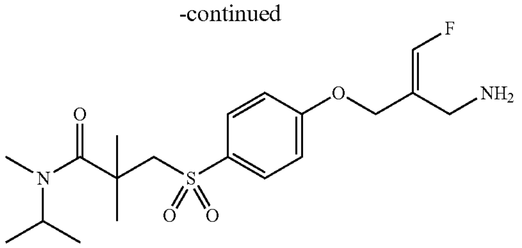

95

Step 1: 95-2

To a mixture of 95-1 (500 mg, 4.23 mmol) and N-methylpropan-2-amine (928.67 mg, 12.70 mmol, 1.32 mL) in DCM (20 mL) was added HATU (1.93 g, 5.08 mmol) and TEA (1.28 g, 12.70 mmol, 1.77 mL) at 30° C. The reaction solution was stirred for 1 hr at 30° C. Then, ethyl acetate (100 mL) was added and the mixture reaction was washed with water (100 mL×3), dried over anhydrous sodium sulfate, filtered and concentrated to obtain 95-2 (500 mg, crude). MS: m/z=173.2 (M+1).

Step 2: 95-3

To a mixture of 95-2 (500 mg, 2.89 mmol), TEA (876.09 mg, 8.66 mmol, 1.21 mL) in DCM (10 mL) was added methanesulfonic acid anhydride (502.72 mg, 2.89 mmol) at 0° C. The reaction solution was stirred for 2 hr at 0° C. Water (5 mL) was added, the organic was dried over anhydrous sodium sulfate and concentrated to give 95-3 (400 mg, crude). MS: m/z=251.3 (M+1).

Step 3: 95-4

To a mixture of 95-3 (400 mg, 1.59 mmol) and 4-bromobenzenethiol (361.08 mg, 1.91 mmol) in MeCN (20 mL) was added Cesium carbonate (1.56 g, 4.77 mmol) at 20° C. The reaction solution was stirred for 24 hr at 80° C. Then, the solution was concentrated with a rotary evaporator. The crude product was purified by silica gel chromatography (petroleum ether:ethylacetate=4:1, v/v) to obtain 95-4 (120 mg, 348.52 μmol, 21.90% yield). MS: m/z=344.3 (M+1).

Step 4: 95-5

A mixture of 95-4 (120 mg, 348.52 μmol) and m-CPBA (153.23 mg, 1.05 mmol, 85% purity) in DCM (10 mL) was stirred at 20° C. for 1 hr. The sodium sulfite (6 g) was added to the mixture and stirred for 20 min. Then, the solution was filtered, concentrated and purified by silica gel chromatography (ethyl acetate in petroleum ether, 15-50%, v/v) to obtain 95-5 (100 mg, 265.74 μmol, 76.25% yield). MS: m/z=376.3 (M+1).

Step 5: 95-6

To a mixture of 95-5 (80 mg, 212.59 μmol), 4,4,5,5-tetramethyl-2-(4,4,5,5-tetramethyl-1,3,2-dioxaborolan-2-yl)-1,3,2-dioxaborolane (64.78 mg, 255.11 μmol) in Dioxane (3 mL) was added potassium acetate (63.88 mg, 637.78 μmol) and bis(diphenylphosphino)ferrocene]dichloropalladium(II) (15.56 mg, 21.26 μmol) at 20° C. under nitrogen atmosphere. The reaction solution was stirred for 4 hr at 100° C. Then, the solution was concentrated with a rotary evaporator and purified by column chromatography on silical gel (ethyl acetate in petroleum ether, 10-50%, v/v) to obtain 95-6 (60 mg, 141.72 μmol, 66.66% yield). MS: m/z=423.3 (M+1).

Step 6: 95-7

To a mixture of 95-6 (60 mg, 141.72 μmol) in THF (4 mL) was added acetate acid (1 mL) and hydrogen peroxide (1 mL, 30% purity). The mixture was stirred at 25° C. for 30 min. The sodium sulfite (1 g) was added to the mixture. The reaction mixture was filtered and concentrated to give 95-7 (100 mg, crude). MS: m/z=313.4 (M+1).

Step 7: 95-8

To a mixture of 95-7 (100 mg, 319.07 μmol) and Intermediate A (94.79 mg, 353.51 mol) in MeCN (10 mL) was added Cesium carbonate (345.55 mg, 1.06 mmol) at 20° C. The reaction solution was stirred for 1 hr at 86° C. Then, the solution was filtered and concentrated to obtain 95-8 (130 mg, crude).

Step 8: Compound 95

A mixture of 95-8 (120 mg, 239.70 μmol) in HCl/Dioxane (4 M, 3 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-40% B; GT: 15 min; flow rate: 15 mL/min) to obtain Compound 95 (20 mg, 44.79 μmol, 18.69% yield, $HCO_2H$ salt). $^1H$ NMR (400 MHz, Methanol-$d_4$) δ 8.50 (s, 1H), 7.88 (d, J=8.6 Hz, 2H), 7.23 (d, J=80.0 Hz, 1H), 7.19 (d, J=8.6 Hz, 2H), 4.71 (d, J=3.6 Hz, 2H), 3.80 (d, J=2.4 Hz, 2H), 3.65 (s, 2H), 2.88 (s, 3H), 2.58-2.52 (m, 1H), 1.45 (s, 6H), 1.17 (d, J=6.8 Hz, 6H) ppm. MS: m/z=401.49 (M+1).

Example 66: Synthesis of Compound 96

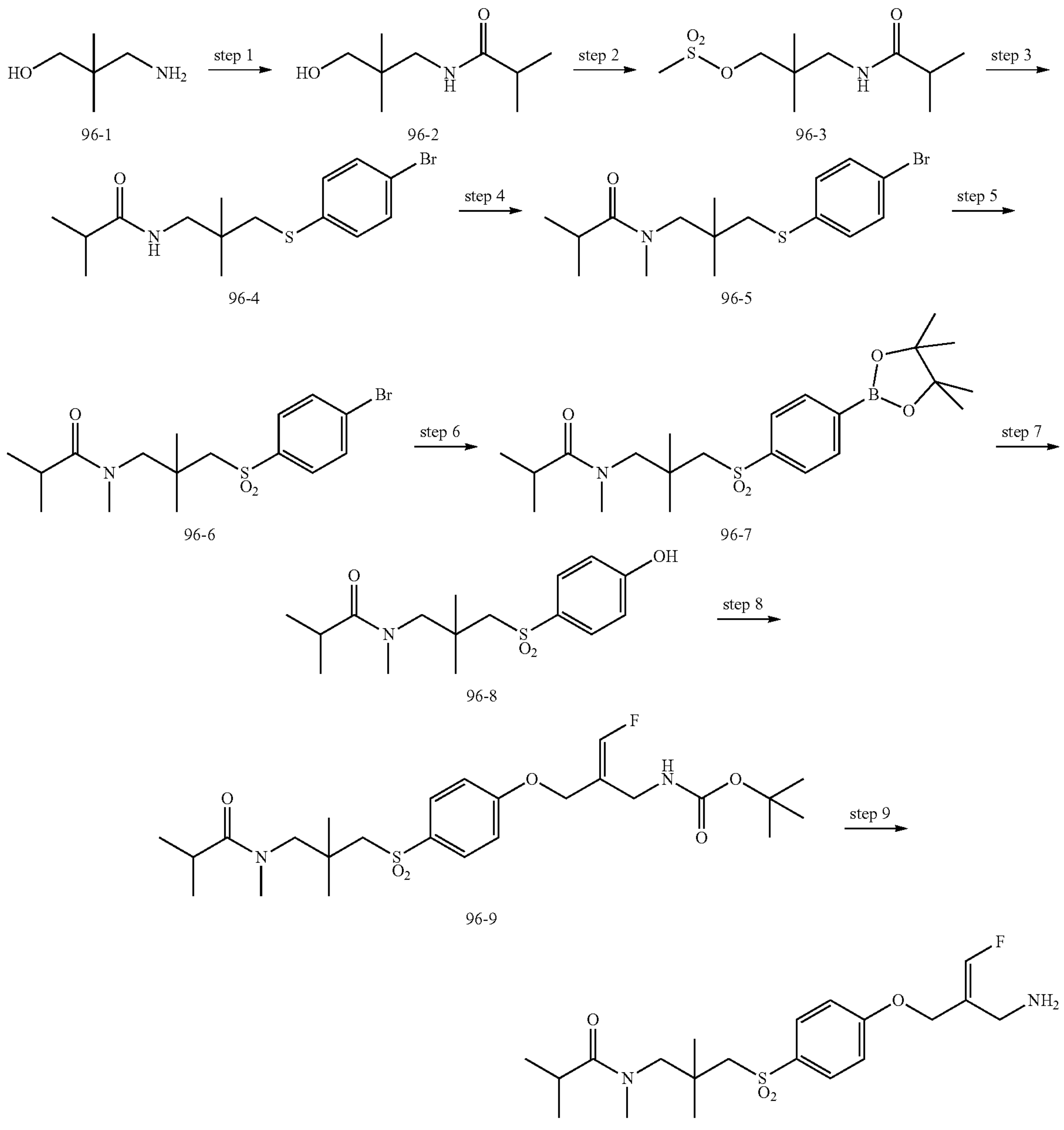

96-1, 96-2, 96-3, 96-4, 96-5, 96-6, 96-7, 96-8, 96-9, 96

Step 1: 96-2

To a mixture of 96-1 (500 mg, 4.85 mmol), TEA (1.47 g, 14.54 mmol, 2.03 mL) in DCM (10 mL) was added 2-methylpropanoyl chloride (309.85 mg, 2.91 mmol, 303.78 μL) at 0° C. The reaction solution was stirred for 1 hr at 0° C. Then, water (20 mL) was added, dried over anhydrous sodium sulfate and concentrated to obtain 96-2 (600 mg, 3.46 mmol, 71.45% yield). MS: m/z=173.2 (M+1).

Step 2: 96-3

To a mixture of 96-2 (600 mg, 3.46 mmol), TEA (1.05 g, 10.39 mmol, 1.45 mL) in DCM (10 mL) was added methanesulfonic acid anhydride (723.92 mg, 4.16 mmol) at 0° C. The reaction solution was stirred for 2 hr at 0° C. Water (5 mL) was added, the organic was dried over anhydrous sodium sulfate and concentrated to give 96-3 (670 mg, crude). MS: m/z=334.4 (M+1).

Step 3: 96-4

A 30 mL microwave reaction tube was charged with 96-3 (0.6 g, 2.39 mmol), 4-bromobenzenethiol (496.49 mg, 2.63 mmol), Cesium carbonate (2.33 g, 7.16 mmol) in acetonitrile (20 mL). After oxygen was purged by bubbling nitrogen into the reaction solution, the tube was sealed and heated at 100° C. for 30 min in a Biotage microwave reactor. The reaction was cooled to room temperature, filtered and concentrated under reduced pressure. The resultant crude product was purified by flash chromatography (ethyl acetate in petroleum ether, 0-100%, v/v) to deliver 96-4 (300 mg, 871.31 µmol, 36.50% yield). MS: m/z=344.3 (M+1).

Step 4: 96-5

To a mixture of 96-4 (300 mg, 871.31 µmol) and NaH (66.77 mg, 1.67 mmol, 60% purity) in DMF (20 mL) was added iodomethane (247.34 mg, 1.74 mmol, 108.48 µL) at 0° C. The reaction solution was stirred for 2 hr at 20° C. Water (50 mL) was added and the mixture was extracted with ethyl acetate (100 mL), the organic layer was dried over anhydrous sodium sulfate, filtered and concentrated to give 96-5 (250 mg, crude). MS: m/z=358.3 (M+1).

Step 5: 96-6

A mixture of 96-5 (200 mg, 558.14 µmol) and m-CPBA (308.42 mg, 1.67 mmol, 85% purity) in DCM (10 mL) was stirred at 20° C. for 1 hr. The sodium sulfite (4 g) was added to the mixture and stirred for 20 min. Then, the solution was filtered, concentrated and purified by silica gel chromatography (ethyl acetate in petroleum ether, 15-50%, v/v) to obtain 96-6 (180 mg, 461.14 µmol, 82.62% yield). MS: m/z=390.3 (M+1).

Step 6: 96-7

To a mixture of 96-6 (180 mg, 461.14 µmol), 4,4,5,5-tetramethyl-2-(4,4,5,5-tetramethyl-1,3,2-dioxaborolan-2-yl)-1,3,2-dioxaborolane (175.65 mg, 691.71 µmol) in Dioxane (10 mL) was added bis(diphenylphosphino)ferrocene]dichloropalladium(II) (33.74 mg, 46.11 µmol) at 30° C. under the nitrogen atmosphere. The reaction solution was stirred for 2 hr at 100° C. Then, the solution was concentrated with a rotary evaporator. The crude product was purified by silica gel chromatography (ethyl acetate in petroleum ether, 10-50%, v/v) to obtain 96-7 (120 mg, 274.35 µmol, 59.49% yield). MS: m/z=437.4 (M+1).

Step 7: 96-8

To a mixture of 96-7 (120 mg, 274.35 µmol) in THF (4 mL) and acetate acid (1 mL) was added hydrogen peroxide (1 mL, 30% purity). The mixture was stirred at 25° C. for 0.5 hr. The sodium sulfite (0.5 g) was added to the mixture and stirred for 20 min. The mixture was filtered and concentrated to give 96-8 (0.7 g, crude). MS: m/z=327.4 (M+1).

Step 8: 96-9

To a mixture of 96-8 (0.7 g, 2.14 mmol) and Intermediate A (114.64 mg, 427.56 µmol) in MeCN (20 mL) was added Cesium carbonate (2.09 g, 6.41 mmol) at 20° C. The reaction solution was stirred for 1 hr at 80° C. Then, the solution was filtered and concentrated to obtain 96-9 (200 mg, crude).

Step 9: Compound 96

A mixture of 96-9 (190.59 mg, 391.68 µmol) in HCl/Dioxane (4 M, 4 mL) was stirred at 20° C. for 1 hr. Then, the solution was concentrated with a rotary evaporator. The crude product was purified by prep-HPLC (column: XBridge@ Prep C18 5 µm 19×150 mm; A: 0.1% $HCO_2H_4$ water, B: acetonitrile; gradient: 10-40% B; GT: 15 min; flow rate: 15 mL/min) to obtain Compound 96 (20 mg, 48.25 µmol, 12.32% yield, $HCO_2H$ salt). MS: m/z=415.81 (M+1).

Example 67: Synthesis of Compound 97

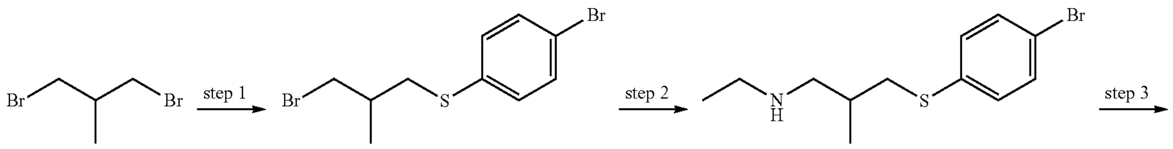

97-1 97-2 97-3

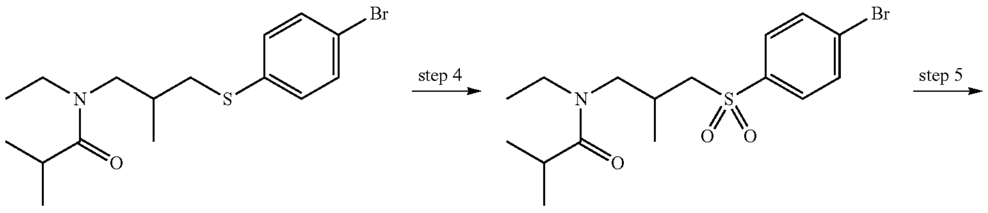

97-4 97-5

-continued

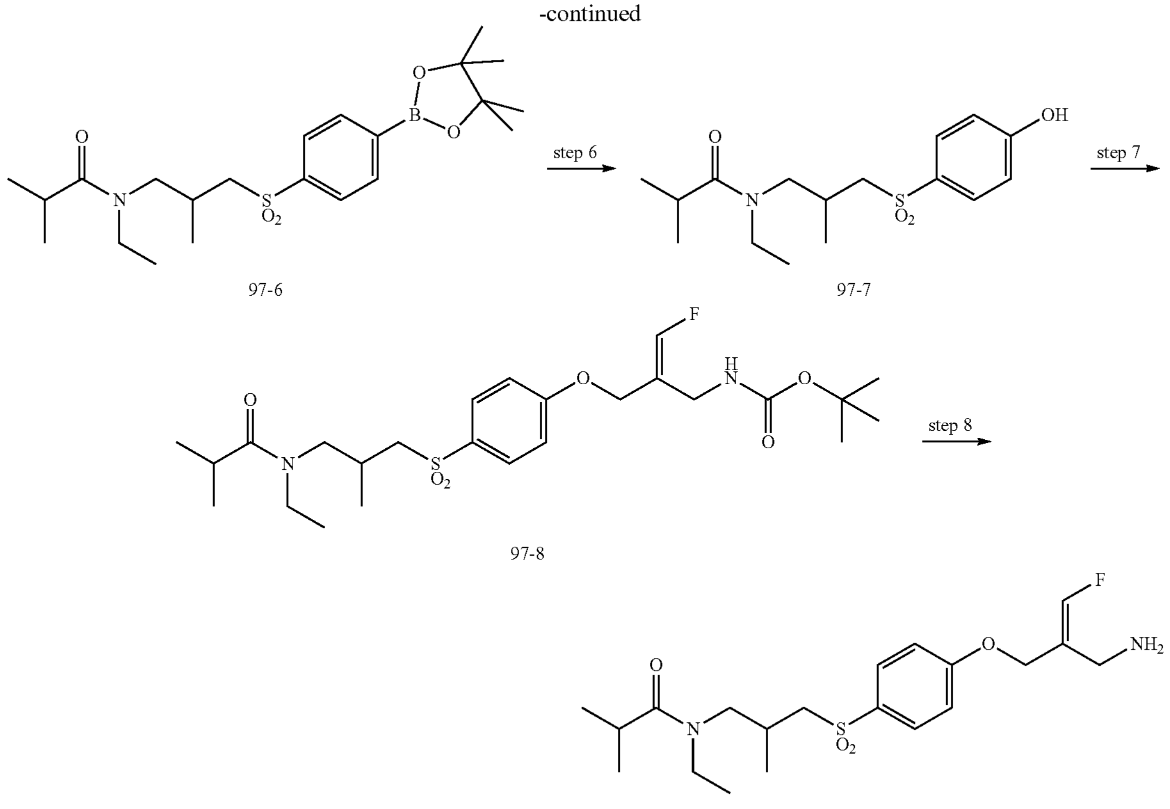

97-6 97-7 97-8 97

Step 1: 97-2

To a mixture of 97-1 (1.03 g, 4.76 mmol), potassium iodide (66 mg, 397.59 μmol, 21.15 μL), Cesium carbonate (2.58 g, 7.93 mmol) in MeCN (15 mL) was added 4-bromobenzenethiol (750 mg, 3.97 mmol) in MeCN (5 mL). After addition, the mixture was stirred at 25° C. for 1 hr. Upon completion, the resulting mixture was filtered. The filtrate was concentrated to give 97-2 (1.20 g, 3.70 mmol, 93.35% yield).

Step 2: 97-3

A mixture of 97-2 (1.20 g, 3.70 mmol), ethanamine (906 mg, 11.11 mmol, HCl salt) and DIPEA (2.39 g, 18.51 mmol, 3.22 mL) in MeCN (10 mL) was microwaved at 120° C. for 1 hr. Upon completion, the resulting mixture was cooled down to room temperature and filtered. The filtrate was concentrated and purified by silica gel chromatography (dichloromethane:methanol=20:1) to give 97-3 (770 mg, 2.67 mmol, 72.14% yield). MS: m/z=288.1 (M+1).

Step 3: 97-4

To a mixture of 97-3 (770 mg, 2.67 mmol) and TEA (810.94 mg, 8.01 mmol, 1.12 mL) in DCM (20 mL) was added 2-methylpropanoyl chloride (1.42 g, 13.36 mmol, 1.40 mL) dropwise. After addition, the solution was stirred at 25° C. for 1 hr. Upon completion, the resulting solution was quenched with water (20 mL). The separated organic layer was concentrated. The residue was purified by silica gel chromatography (petroleum ether:ethyl acetate=5:1) to give 97-4 (160 mg, 446.51 μmol, 16.71% yield). MS: m/z=358.1 (M+1).

Step 4: 97-5

To a mixture of 97-4 (160 mg, 446.51 μmol) in DCM (10 mL) was added m-CPBA (226.62 mg, 1.12 mmol, 85% purity). After addition, the solution was stirred at 25° C. for 1 hr. Upon completion, the resulting solution was quenched with aqueous sodium sulfite. The separated organic layer was washed with aqueous $NaHCO_3$ and brine, dried over anhydrous sodium sulfate, filtered and concentrated to give 97-5 (170 mg, 435.52 μmol, 97.54% yield). MS: m/z=390.1 (M+1).

Step 5: 97-6

A mixture of 97-5 (170 mg, 435.52 μmol), 4,4,5,5-tetramethyl-2-(4,4,5,5-tetramethyl-1,3,2-dioxaborolan-2-yl)-1,3,2-dioxaborolane (166 mg, 653.70 μmol), Pd(dppf)$Cl_2$-dichloromethane (36 mg, 44.08 μmol) and potassium acetate (128 mg, 1.30 mmol) in Dioxane (10 mL) was microwaved at 120° C. for 1 hr. Upon completion, the resulting mixture was cooled down to room temperature and filtered. The filtrate was concentrated to give 97-6 (190 mg, 434.39 μmol, 99.74% yield).

Step 6: 97-7

A mixture of 97-6 (190 mg, 434.39 μmol), hydrogen peroxide (0.5 mL, 30% purity) and acetic acid (0.5 mL) in THF (2 mL) was stirred at 25° C. for 1 hr. Upon completion, the resulting solution was quenched with sodium sulfite, filtered and concentrated to give 97-7 (140 mg, 427.56 μmol, 98.43% yield).

Step 7: 97-8

A mixture of 97-7 (140 mg, 427.56 μmol), Intermediate A (140 mg, 522.15 μmol) and Cesium carbonate (700 mg, 2.15 mmol) in MeCN (20 mL) was stirred at 95° C. for 2 hr. Upon completion, the resulting mixture was cooled down to room temperature and filtered. The filtrate was concentrated. The residue was purified by silica gel chromatography (petroleum ether:ethyl acetate=2:1) to give 97-8 (140 mg, 272.03 μmol, 63.62% yield). MS: m/z=515.3 (M+1).

Step 8: Compound 97

To a mixture of 97-8 (140 mg, 272.03 μmol) in DCM (4 mL) was added trifluoroacetic acid (2.96 g, 25.96 mmol, 2 mL). After addition, the solution was stirred at 25° C. for 1 hr. Upon completion, the resulting solution was concentrated. The residue was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to give Compound 97 (92 mg, 197.76 μmol, 72.70% yield, $HCO_2H$ salt). $^1H$ NMR (400 MHz, Methanol-d4) δ 8.51 (s, 0.3H), 7.93-7.84 (m, 2H), 7.25 (d, J=80.0 Hz, 1H), 7.27-7.20 (m, 2H), 4.72 (d, J=3.3 Hz, 2H), 3.82 (d, J=2.2 Hz, 2H), 3.58-3.44 (m, 1H), 3.45-3.36 (m, 1H), 3.31-2.96 (m, 4H), 2.96-2.78 (m, 1H), 2.46-2.26 (m, 1H), 1.17 (t, J=7.1 Hz, 2H), 1.13-0.99 (m, 10H). MS: m/z=415.7 (M+1).

Example 68: Synthesis of Compound 98

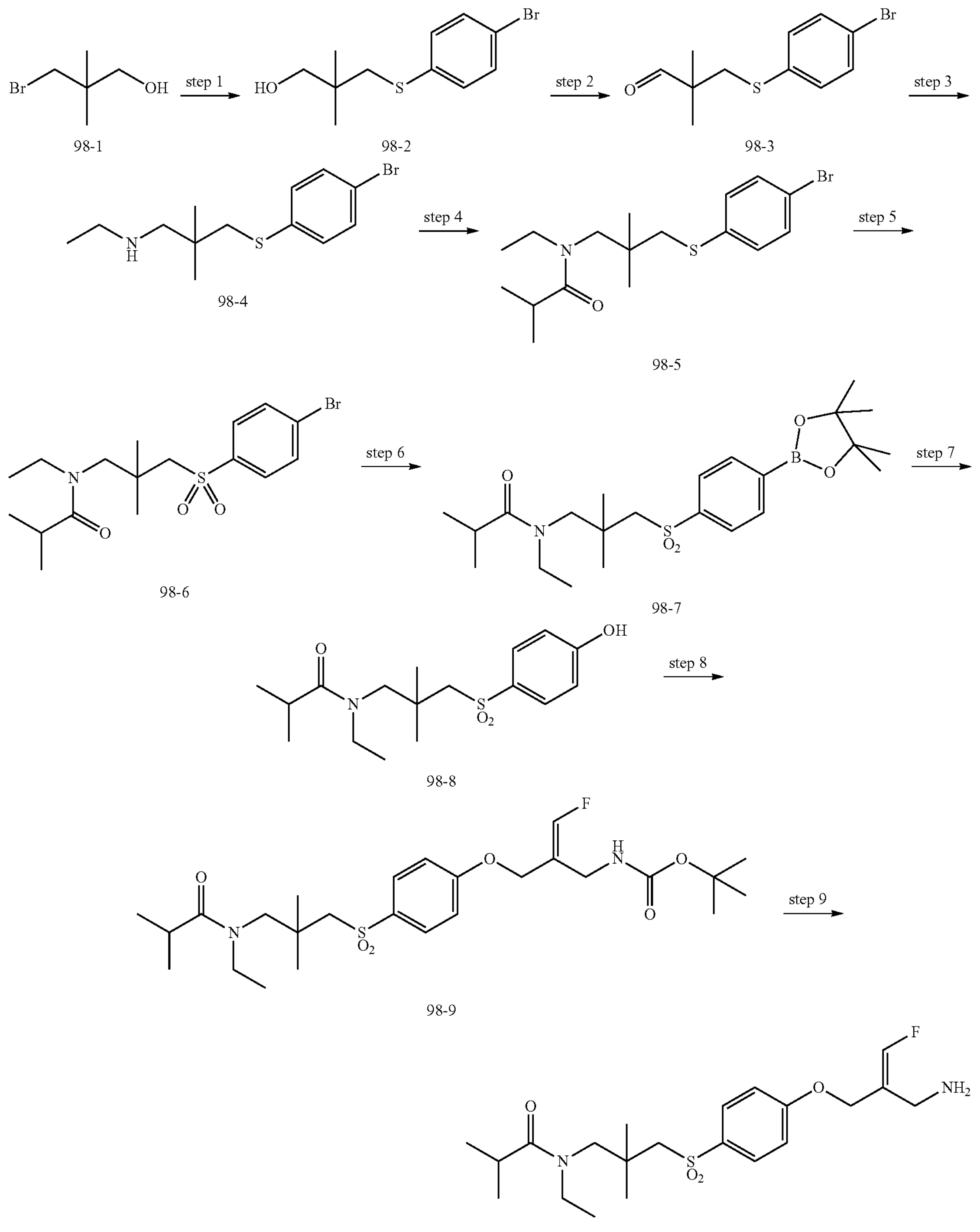

98-1, 98-2, 98-3, 98-4, 98-5, 98-6, 98-7, 98-8, 98-9, 98

Step 1: 98-2

A mixture of 4-bromobenzenethiol (4 g, 21.16 mmol), 98-1 (4.59 g, 27.50 mmol), Cesium carbonate (13.79 g, 42.31 mmol), potassium iodide (352.00 mg, 2.12 mmol) in MeCN (20 mL) was microwaved at 120° C. for 1 hr. Upon completion, the resulting mixture was cooled to room temperature and filtered. The filtrate was concentrated to give 98-2 (5.8 g, 21.08 mmol, 99.62% yield).

Step 2: 98-3

To a mixture of 98-2 (1 g, 3.63 mmol) DCM (20 mL) was added Dess-Martin Periodinane (2.31 g, 5.45 mmol) at 0° C. After addition, the mixture was stirred at 25° C. for 1 hr. Upon completion, the resulting mixture was quenched with aqueous $Na_2S_2O_3$. The separated organic layer was concentrated. The residue was purified by silica gel chromatography (ethyl acetate in petroleum ether, 10-20%) to give 98-3 (700 mg, 2.56 mmol, 70.52% yield).

Step 3: 98-4

To a mixture of 98-3 (500 mg, 1.83 mmol) and ethanamine (448 mg, 5.49 mmol, HCl salt) in methanol (15 mL) was added acetate acid (275 mg, 4.58 mmol) and $NaBH_3CN$ (230 mg, 3.66 mmol). After addition, the mixture was stirred at 25° C. for 2 hr. Upon completion, the resulting mixture was washed with saturated aqueous $NaHCO_3$ and extracted with ethyl acetate (30 mL). The separated organic layer was washed with brine, dried over anhydrous sodium sulfate, filtered and concentrated. The residue was purified by silica gel chromatography (dichloromethane:methanol=20:1) to give 98-4 (240 mg, 793.98 μmol, 43.38% yield). MS: m/z=302.1 (M+1).

Step 4: 98-5

To a mixture of 98-4 (240 mg, 793.98 μmol) and DIPEA (513 mg, 3.97 mmol, 691.37 μL) in DCM (20 mL) was added 2-methylpropanoyl chloride (423.00 mg, 3.97 mmol, 414.71 μL) at 0° C. After addition, the solution was stirred at 25° C. for 1 hr. Upon completion, the resulting solution was washed with water (20 mL) and brine, dried over anhydrous sodium sulfate, filtered and concentrated. The residue was purified by silica gel chromatography (ethyl acetate in petroleum ether, 5-10%, v/v) to give 98-5 (200 mg, 537.11 μmol, 67.65% yield). MS: m/z=372.1 (M+1).

Step 5: 98-6

To a mixture of 98-5 (200 mg, 537.11 μmol) in DCM (15 mL) was added m-CPBA (327 mg, 1.61 mmol, 85% purity). After addition, the solution was stirred at 25° C. for 1 hr. Upon completion, the resulting solution was washed with saturated aqueous $NaHCO_3$ and saturated aqueous sodium sulfite. The separated organic layer was dried over anhydrous sodium sulfate, filtered and concentrated to give 98-6 (210 mg, 519.34 μmol, 96.69% yield). MS: m/z=404.1 (M+1).

Step 6: 98-7

A mixture of 98-6 (210 mg, 519.34 μmol), 4,4,5,5-tetramethyl-2-(4,4,5,5-tetramethyl-1,3,2-dioxaborolan-2-yl)-1,3,2-dioxaborolane (198 mg, 779.72 μmol), bis(diphenylphosphino)ferrocene]dichloropalladium(II) (38.00 mg, 51.93 μmol) and potassium acetate (153 mg, 1.56 mmol) in Dioxane (10 mL) was microwaved at 120° C. for 40 min. Upon completion, the resulting mixture was cooled down to room temperature, filtered and concentrated to give 98-7 (230 mg, 509.50 μmol, 98.11% yield). MS: m/z=452.3 (M+1).

Step 7: 98-8

A mixture of 98-7 (230 mg, 509.50 μmol), hydrogen peroxide (1 mL, 30% purity) and acetate acid (1 mL) in THF (4 mL) was stirred at 25° C. for 1 hr. Upon completion, the resulting solution was quenched with sodium sulfite, filtered and concentrated to give 98-8 (170 mg, 497.86 μmol, 97.72% yield). MS: m/z=342.2 (M+1).

Step 8: 98-9

A mixture of 98-8 (170 mg, 497.86 μmol), Intermediate A (160 mg, 596.74 μmol) and Cesium carbonate (811 mg, 2.49 mmol) in MeCN (20 mL) was stirred at 95° C. for 2 hr. Upon completion, the resulting mixture was cooled down to room temperature and filtered. The filtrate was concentrated. The residue was purified by silica gel chromatography (ethyl acetate in petroleum ether, 20-50%) to give 98-9 (160 mg, 302.64 μmol, 60.79% yield). MS: m/z=529.3 (M+1).

Step 9: Compound 98

To a mixture of 98-9 (160 mg, 302.64 μmol) in Dioxane (3 mL) was added Dioxane/HCl (4 M, 2.5 mL). After addition, the mixture was stirred at 25° C. for 2 hr. Upon completion, the resulting mixture was concentrated and purified by prep-HPLC (column: XBridge@ Prep C18 5 μm 19×150 mm; A: 0.1% $HCO_2H$ water, B: acetonitrile; GT: 15 min; flow rate: 15 mL/min) to give Compound 98 (74 mg, 155.93 μmol, 51.52% yield, $HCO_2H$ salt). $^1H$ NMR (400 MHz, Methanol-d4) δ 8.41 (s, 1H), 7.85-7.73 (m, 2H), 7.16 (d, J=80.0 Hz, 1H), 7.17-7.08 (m, 2H), 4.63 (d, J=3.7 Hz, 2H), 3.73 (d, J=2.2 Hz, 2H), 3.43 (q, J=7.1 Hz, 2H), 3.32 (s, 2H), 3.10 (s, 2H), 2.86 (p, J=6.7 Hz, 1H), 1.15-1.04 (m, 9H), 1.03-0.95 (m, 6H) ppm. MS: m/z=429.2 (M+1).

Example 69: Synthesis of Compound 99

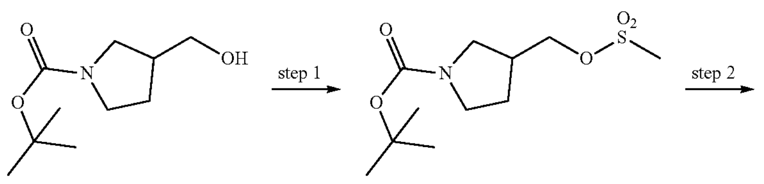

99-1 99-2

-continued

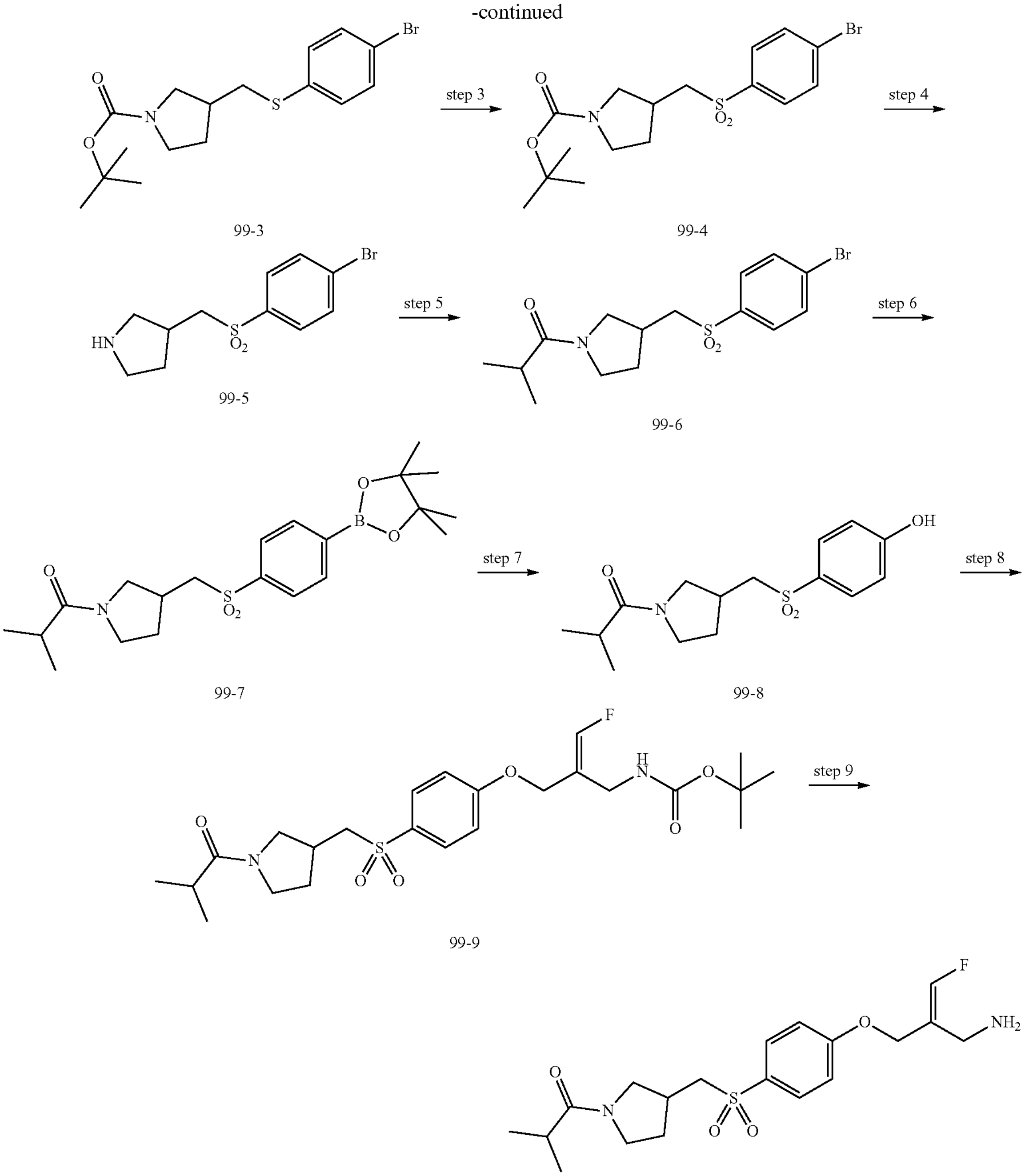

99-3 99-4 99-5 99-6 99-7 99-8 99-9 99

Step 1: 99-2

To a mixture of 99-1 (1 g, 4.97 mmol) and TEA (1.51 g, 14.91 mmol, 2.08 mL) in DCM (20 mL) was added methyl sulfonyl chloride (683.00 mg, 5.96 mmol) at 0° C. The reaction solution was stirred for 2 hr at 0° C. Water (5 mL) was added, the organic was dried over anhydrous sodium sulfate and concentrated to give 99-2 (1.1 g, 3.94 mmol, 79.25% yield). MS: m/z=348.4 (M+1).

Step 2: 99-3

A mixture of 4-bromobenzenethiol (744.51 mg, 3.94 mmol) and 99-2 (1 g, 3.58 mmol) in MeCN (20 mL) was added Cesium carbonate (3.50 g, 10.74 mmol) at 30° C. The reaction solution was stirred for 4 hr at 80° C. Then, the solution was filtered, concentrated and purified by column chromatography on silica gel (ethyl acetate in petroleum ether, 10-50%, v/v) to obtain 99-3 (1 g, 2.69 mmol, 75.03% yield). MS: m/z=372.3 (M+1).

Step 3: 99-4

A mixture of 99-3 (0.5 g, 1.34 mmol) and m-CPBA (681.60 mg, 3.36 mmol, 85% purity) in DCM (20 mL) was stirred at 20° C. for 1 hr. The sodium sulfite (1 g) was added to the mixture and stirred for 20 min. Then, the solution was filtered, concentrated and purified by silica gel chromatography (ethyl acetate in petroleum ether, 10-25%, v/v) to obtain 99-4 (400 mg, 989.32 μmol, 73.67% yield). MS: m/z=404.3 (M+1).

Step 4: 99-5

A mixture of 99-4 (400 mg, 989.32 μmol) in HCl/Dioxane (4 M, 5 mL) was stirred at 25° C. for 1 hr. Then, the solution was concentrated with a rotary evaporator to obtain 99-5 (337 mg, 989.25 μmol, 99.99% yield, HCl salt). MS: m/z=340.6 (M+1).

Step 5: 99-6

To a mixture of 99-5 (300 mg, 986.18 μmol) and TEA (299.38 mg, 2.96 mmol, 412.36 μL) in DCM (20 mL) was added 2-methylpropanoyl chloride (157.62 mg, 1.48 mmol, 154.53 μL) at 0° C. The reaction solution was stirred for 1 hr at 20° C. Then, the solution was concentrated with a rotary evaporator. The crude product was dissolved in ethyl acetate (80 mL), washed with water (100 mL×3), dried over anhydrous sodium sulfate, filtered and concentrated to obtain 99-6 (300 mg, 801.51 μmol, 81.27% yield). MS: m/z=374.2 (M+1).

Step 6: 99-7

A 30 mL microwave reaction tube was charged with 99-6 (300 mg, 801.51 μmol), 4,4,5,5-tetramethyl-2-(4,4,5,5-tetramethyl-1,3,2-dioxaborolan-2-yl)-1,3,2-dioxaborolane (305.30 mg, 1.20 mmol), bis(diphenylphosphino)ferrocene] dichloropalladium(II) (58.65 mg, 80.15 μmol) and potassium acetate (235.99 mg, 2.40 mmol) in Dioxane (8 mL). After oxygen was purged by bubbling nitrogen into the reaction solution, the tube was sealed and heated at 120° C. for 0.5 hr in a Biotage microwave reactor. The reaction was cooled to room temperature, filtered and concentrated under reduced pressure. The resultant crude product was purified by flash chromatography (ethyl acetate in petroleum ether, 0-100%, v/v) to deliver 99-7 (270 mg, 640.79 μmol, 79.95% yield). MS: m/z=421.3 (M+1).

Step 7: 99-8

To a mixture of 99-7 (270 mg, 640.79 μmol) in THF (25 mL) and acetate acid (0.5 mL) was added hydrogen peroxide (1 mL, 30% purity). The mixture was stirred at 20° C. for 1 hr. The sodium sulfite (0.5 g) was added to the mixture and stirred for 30 min. The reaction mixture was filtered and concentrated to give 99-8 (0.7 g, crude). MS: m/z=311.4 (M+1).

Step 8: 99-9

To a mixture of 99-8 (0.7 g, 2.25 mmol) and Intermediate A (241.09 mg, 899.18 mol) in MeCN (50 mL) was added Cesium carbonate (2.20 g, 6.74 mmol) at 20° C. The reaction solution was stirred for 1 hr at 80° C. Then, the solution was filtered and concentrated to obtain 99-9 (340 mg, 681.90 μmol, 30.33% yield). MS: m/z=499.6 (M+1).

Step 9: Compound 99

A mixture of 99-9 (300 mg, 601.68 μmol) in HCl/Dioxane (4 M, 4 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 99 (16.3 mg, 40.90 μmol, 6.80% yield). $^1H$ NMR (400 MHz, Methanol-d4) δ 7.86-7.73 (m, 2H), 7.16-7.11 (m, 2H), 7.01 (d, J=80.0 Hz, 1H), 4.60 (dd, J=3.6, 1.1 Hz, 2H), 3.58-3.53 (m, 2H), 3.48-3.22 (m, 4H), 2.98-2.86 (m, 1H), 2.66-2.38 (m, 2H), 2.15-1.96 (m, 1H), 1.77-1.50 (m, 1H), 1.19 (t, J=7.2 Hz, 1H), 1.02-0.90 (m, 6H) ppm. MS: m/z=399.64 (M+1).

Example 70: Synthesis of Compound 100

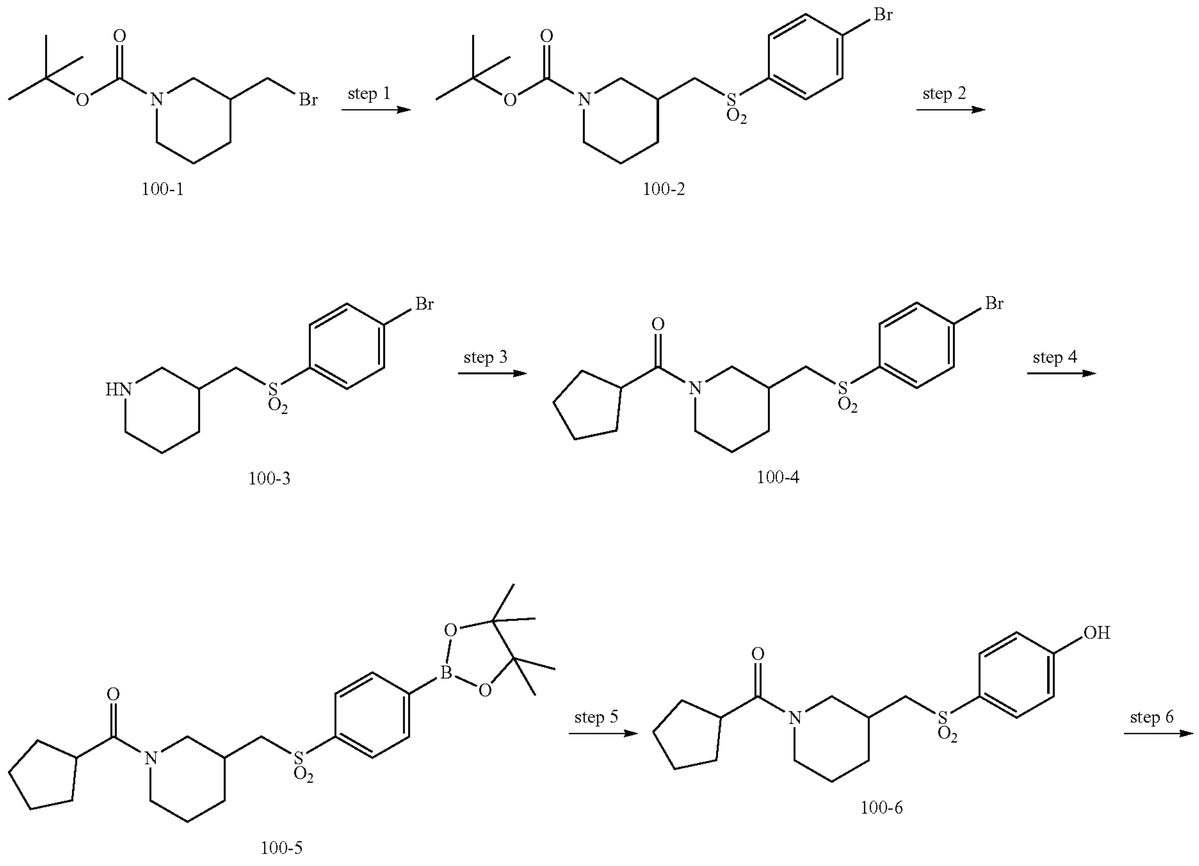

100-1 100-2 100-3 100-4 100-5 100-6

-continued

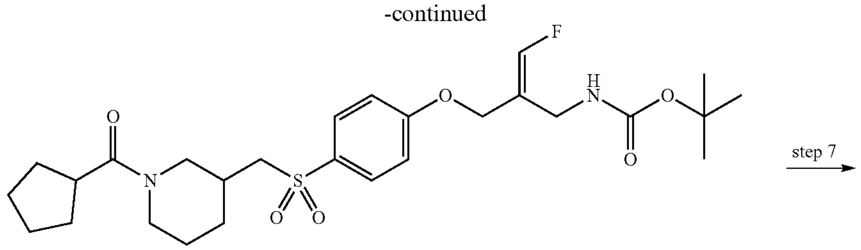

100-7

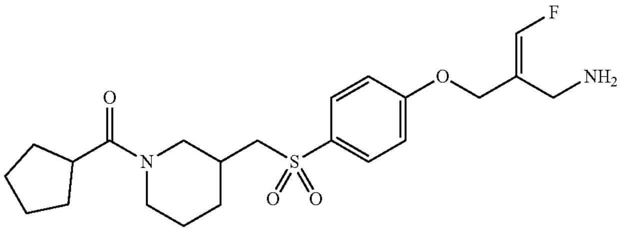

100

Step 1: 100-2

To a mixture of 4-bromobenzenesulfinic acid (400 mg, 1.81 mmol) and 100-1 (503.34 mg, 1.81 mmol) in DMF (10 mL) was added sodium carbonate (383.55 mg, 3.62 mmol) at 25° C. The reaction solution was stirred 100° C. for 16 hr. Then, the solution was quenched with water (30 mL), and extracted by ethyl acetate (30 mL×2). The combined organic layers were washed with water (20 mL) and brine (20 mL), dried over anhydrous sodium sulfate, filtered and concentrated with a rotary evaporator to obtain 100-2 (900 mg).

Step 2: 100-3

To a mixture of 100-2 (900 mg, 2.15 mmol) in DCM (10 mL) was added HCl/Dioxane (4 M, 1.08 mL) at 25° C. and the reaction mixture was stirred at 25° C. for 4 hr. Then, the solution was concentrated with a rotary evaporator to obtain 100-3 (720 mg). MS: m/z=319 (M+1).

Step 3: 100-4

To a mixture of cyclopentanecarboxylic acid (138.09 mg, 1.21 mmol, 131.52 L), HATU (627.29 mg, 1.65 mmol) and TEA (333.88 mg, 3.30 mmol, 459.89 μL) in DCM (10 mL) was added 100-3 (350 mg, 1.10 mmol) at 25° C. The reaction solution was stirred for 4 hr at 25° C. Then, the solution was quenched with water (20 mL), and extracted by DCM (20 mL×2). The combined organic layers were washed with water (20 mL) and brine (20 mL), dried over anhydrous sodium sulfate and concentrated with a rotary evaporator to obtain the crude product. The crude product was purified by silica gel chromatography (ethyl acetate in petroleum ether, 0-50%, v/v) to obtain 100-4 (140 mg, 337.87 μmol, 30.72% yield). MS: m/z=415 (M+1).

Step 4: 100-5

To a mixture of 100-4 (100 mg, 241.34 μmol), 4,4,5,5-tetramethyl-2-(4,4,5,5-tetramethyl-1,3,2-dioxaborolan-2-yl)-1,3,2-dioxaborolane (73.54 mg, 289.61 μmol) and potassium acetate (71.06 mg, 724.01 μmol) in Dioxane (5 ml) was added 1,1'-Bis(diphenylphosphino)ferrocene-palladiμm(II) dichloride dichloromethane complex (19.71 mg, 24.13 μmol) at 30° C. under the nitrogen atmosphere. The reaction solution was stirred at 120° C. for 0.5 hr in a Biotage microwave reactor. The solution was concentrated with a rotary evaporator. The residue was quenched with water (20 mL), and extracted by ethyl acetate (20 mL×2). The combined organic layers were washed with water (15 mL) and brine (15 mL), dried over anhydrous sodium sulfate and concentrated with a rotary evaporator to obtain 100-5 (150 mg).

Step 5: 100-6

To a mixture of 100-5 (150 mg, 327.89 μmol) in THF (5 mL) was added acetic acid (0.5 mL) and hydrogen peroxide (0.5 mL, 30% purity) at 25° C. The reaction solution was stirred for 1 hr at 25° C. Then sodium sulfite (0.5 g) and water (15 mL) was added to the mixture and extracted with ethyl acetate (20 mL×2). The combined organic layers were washed with water (20 mL) and brine (20 mL), dried over anhydrous sodium sulfate and concentrated with a rotary evaporator to obtain 100-6 (120 mg).

Step 6: 100-7

To a mixture of 100-7 (120 mg, 341.43 μmol) and Intermediate A (91.55 mg, 341.43 μmol) in MeCN (5 mL) was added Cesium carbonate (333.74 mg, 1.02 mmol) at 25° C. The reaction solution was stirred for 1 hr at 90° C. Then, the solution was concentrated with a rotary evaporator. The residue was quenched with water (20 mL) and extracted by ethyl acetate (20 mL×2). The combined organic layers were washed with water (20 mL) and brine (20 mL), dried over anhydrous sodium sulfate and concentrated with a rotary evaporator to obtain the crude product. The crude product was purified by Silica gel chromatography (petroleum ether: ethyl acetate=1:2) to obtain 100-7 (50 mg, 92.82 μmol, 27.19% yield). MS: m/z=539 (M+1).

Step 7: Compound 100

To a mixture of 100-7 (50 mg, 92.82 μmol) in DCM (5 mL) was added trifluoroacetate acid (740.0 mg, 6.49 mmol, 0.5 mL) at 25° C. and the reaction mixture was stirred at 25° C. for 2 hr. Then, the solution was concentrated with a rotary evaporator to obtain the crude product. The crude product was purified by prep-HPLC (column: XBridge@ Prep C18 5 μm 19×150 mm; A: 0.1% $HCO_2H$ water, B: acetonitrile; gradient: 5-35% B; GT: 15 min; flow rate: 15 mL/min) to obtain Compound 100 (19 mg, 43.32 μmol, 46.67% yield, $HCO_2H$ salt). $^1H$ NMR (400 MHz, Methanol-d4): δ 8.53 (s, 1H), 7.95-7.88 (m, 2H), 7.23 (d, J=84.0 Hz, 1H), 7.28-7.19 (m, 2H), 4.73 (dd, J=3.5, 1.1 Hz, 2H), 4.26 (t, J=14.8 Hz, 1H), 3.79 (dd, J=4.2, 2.2 Hz, 2H), 3.27-3.09 (m, 3H), 3.07-2.92 (m, 1H), 2.76-2.63 (m, 1H), 2.02-1.80 (m, 4H), 1.78-1.55 (m, 8H), 1.43-1.39 (m, 2H) ppm. MS: m/z=439.66 (M+1).
Example 71: Synthesis of Compound 101
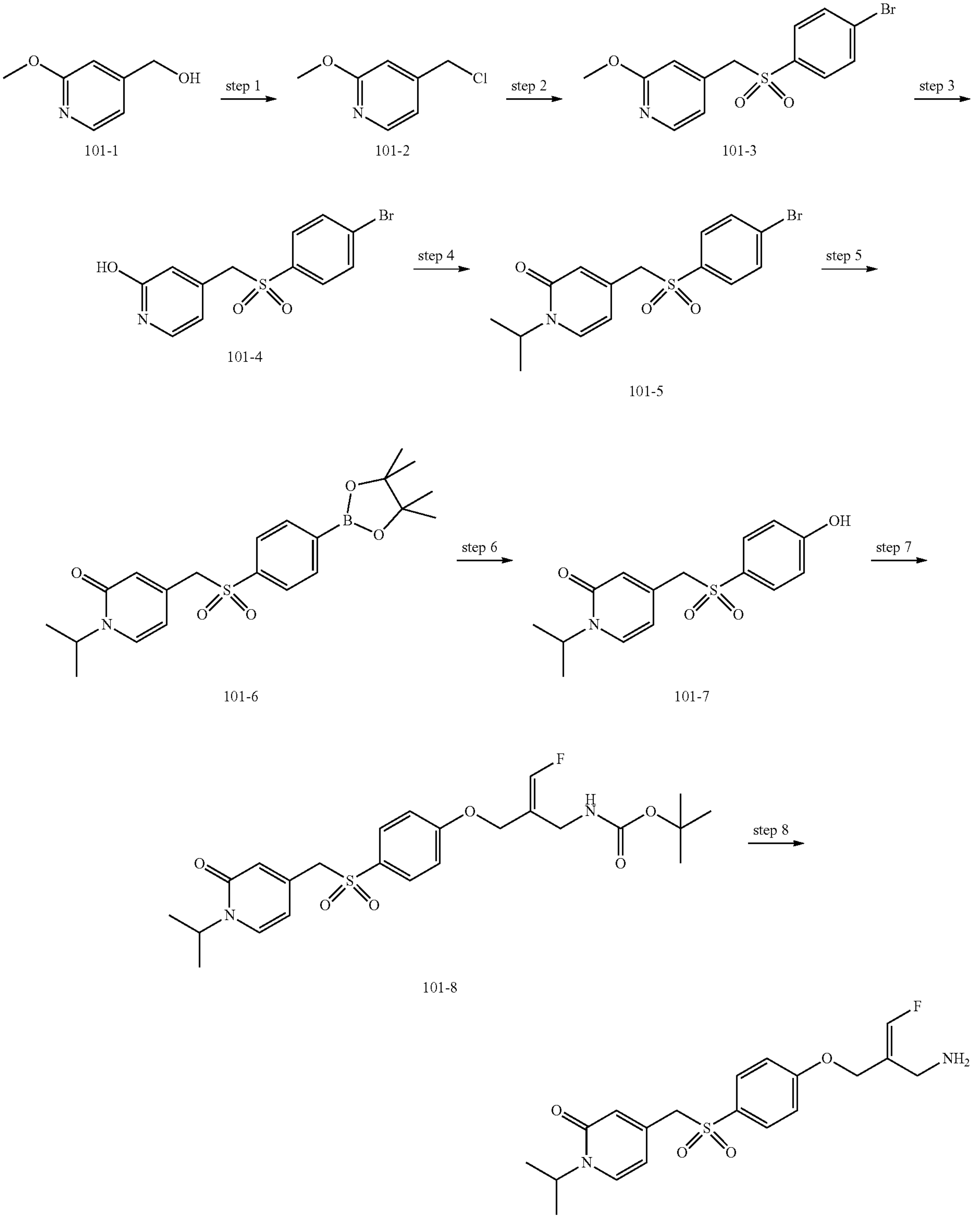
101-1 101-2 101-3 101-4 101-5 101-6 101-7 101-8 101

Step 1: 101-2

To a mixture of 101-1 (500 mg, 3.59 mmol) in DCM (10 mL) was added SOC12 (2.14 g, 17.97 mmol) at 0° C. The reaction solution was stirred for 1 hr at 60° C. The mixture was concentrated to give 102-2 (600 mg, crude, HCl salt). MS: m/z=194.06 (M+1).

Step 2: 101-3

To a mixture of (4-bromophenyl)sulfinyloxysodium (1 g, 4.11 mmol) and 101-2 (600.0 mg, 3.81 mmol) in DMF (20 mL) was stirred at 20° C. The reaction solution was stirred for 1 hr at 70° C. Then ethyl acetate (100 mL) were added, the organic phase was washed with $H_2O$ (100 mL×3) and brine (50 mL), dried over $Na_2SO_4$ and concentrated to obtain 101-3 (800 mg, 2.34 mmol, 56.82% yield).

Step 3: 101-4

A mixture of 101-3 (780 mg, 2.28 mmol) and TMSI (2.28 mmol, 2 mL) in MeCN (10 mL) was stirred at 80° C. for 1 hr. Then, the solution was concentrated with a rotary evaporator to obtain 101-4 (800 mg, crude). MS: m/z=328.18 (M+1).

Step 4: 101-5

To a mixture of 101-4 (800 mg, 2.44 mmol) and 2-iodopropane (1.24 g, 7.31 mmol, 731.27 µL) in MeCN (20 mL) was added Cesium carbonate (2.38 g, 7.31 mmol) at 20° C. The reaction solution was stirred for 4 hr at 80° C. Then, the solution was filtered and concentrated and purified by column chromatography on silica gel (ethyl acetate in petroleum ether, 10-20%, v/v) to obtain 101-5 (120 mg, 324.10 µmol, 13.30% yield). MS: m/z=370.26 (M+1).

Step 5: 101-6

To a mixture of 101-5 (110 mg, 297.09 µmol), 4,4,5,5-tetramethyl-2-(4,4,5,5-tetramethyl-1,3,2-dioxaborolan-2-yl)-1,3,2-dioxaborolane (75.44 mg, 297.09 µmol) in Dioxane (5 mL) was added potassium acetate (87.47 mg, 891.26 µmol) and bis(diphenylphosphino)ferrocene]dichloropalladium(II) (260.86 mg, 356.51 µmol) at 20° C. under the nitrogen atmosphere. The reaction solution was stirred for 4 hr at 100° C. Then, the solution was concentrated with a rotary evaporator and purified by column chromatography on silica gel (ethyl acetate in petroleum ether, 10-50%, v/v) to obtain 101-6 (80 mg, 191.70 µmol, 64.53% yield). MS: m/z=417.33 (M+1).

Step 6: 101-7

To a mixture of 101-6 (80 mg, 191.70 µmol) in acetate acid (0.5 mL) and THF (2 mL) was added hydrogen peroxide (1 mL, 30% purity). The mixture was stirred at 20° C. for 1 hr. The sodium sulfite (0.5 g) was added to the mixture and stirred for 20 min. The mixture was filtered and concentrated to give 101-7 (60 mg, crude).

Step 7: 101-8

To a mixture of 101-7 (60 mg, 195.21 µmol) and Intermediate A (52.34 mg, 195.21 µmol) in MeCN (10 mL) was added Cesium carbonate (190.81 mg, 585.62 µmol) at 20° C. The reaction solution was stirred for 1 hr at 80° C. Then, the solution was filtered and concentrated to obtain 101-8 (100 mg, crude).

Step 8: Compound 101

A mixture of 101-8 (90 mg, 181.97 µmol) in HCl/Dioxane (4 M, 4.0 mL) was stirred at 20° C. for 1 hr. Then, the solution was concentrated with a rotary evaporator. The crude product was purified by prep-HPLC (column: XBridge@ Prep C18 5 µm 19×150 mm; A: 0.1% $HCO_2H$ water, B: acetonitrile; gradient: 5-30% B; GT: 15 min; flow rate: 15 mL/min) to obtain Compound 101 (20 mg, 45.40 µmol, 24.95% yield, $HCO_2H$ salt). $^1H$ NMR (400 MHz, Methanol-d4) δ 8.51 (s, 1H), 7.74 (d, J=8.0 Hz, 2H), 7.66 (d, J=7.2 Hz, 1H), 7.18 (d, J=80.0 Hz, 1H), 7.16 (d, J=8.0 Hz, 2H), 6.42 (dd, J=7.2, 2.4 Hz, 1H), 6.11 (d, J=2.4 Hz, 1H), 5.13-5.06 (m, 1H), 4.93-4.88 (m, 2H), 4.69 (d, J=3.6 Hz, 2H), 3.79 (d, J=2.4 Hz, 2H), 1.35 (d, J=6.8 Hz, 6H) ppm. MS: m/z=395.13 (M+1).

Example 72: Synthesis of Compound 102

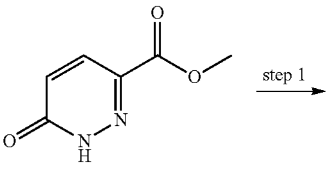

102-1

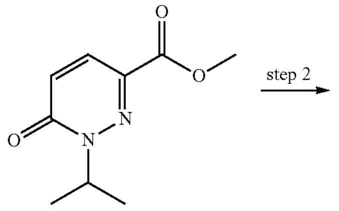

102-2

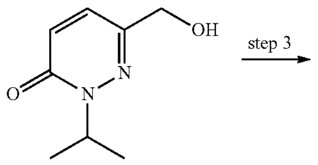

102-3

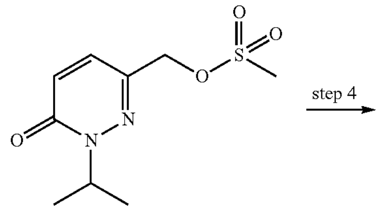

102-4

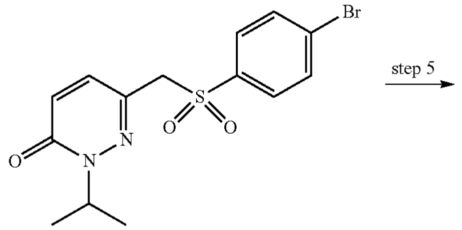

102-5

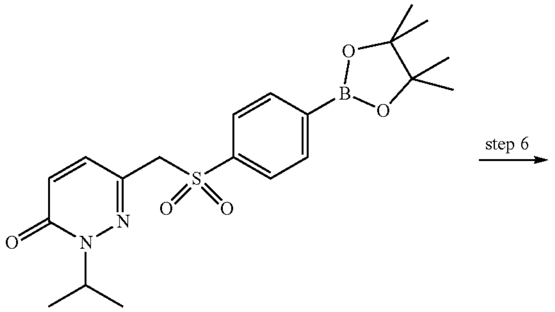

102-6

-continued

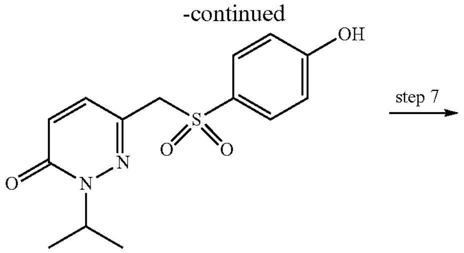

102-7

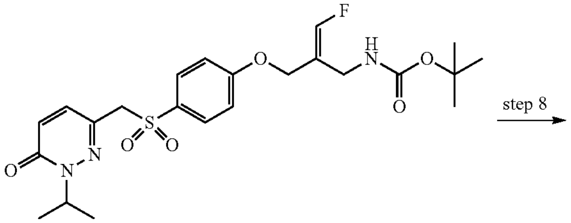

102-8

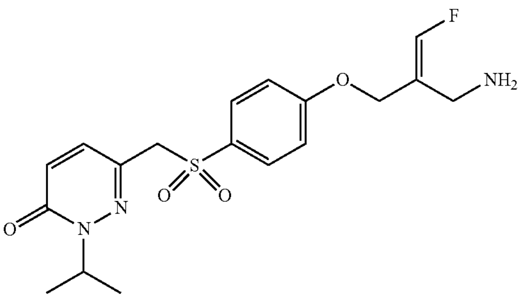

102

Step 1: 102-2

To a mixture of 102-1 (1.5 g, 9.73 mmol) in DMF (20 mL) was added NaH (409.35 mg, 10.23 mmol, 60% purity) at 0° C. The reaction solution was stirred for 0.5 hr at 60° C. Then, 2-iodopropane (1.87 g, 11.00 mmol, 1.10 mL) was added. The reaction solution was stirred for further 4 hr at 60° C. Then, the solution was poured into water (50 mL), extracted with ethyl acetate (20 mL×3), dried over anhydrous sodium sulfate, and concentrated under reduced pressure. The crude product was purified by silica gel chromatography (ethyl acetate in petroleum ether, 0-30%) to obtain 102-2 (1.7 g, 8.66 mmol, 89.03% yield). MS: m/z=197 (M+1).

Step 2: 102-3

To a mixture of 102-2 (500 mg, 2.55 mmol) in THF (10 mL) was added $LiBH_4$ (2 M in THF, 3.82 mL) at 0° C. The reaction mixture was stirred for 2 hr at 25° C. Then, the solution was quenched with MeOH (20 mL) at 0° C. and stirred for 0.25 hr at 20° C. The solution was concentrated with a rotary evaporator. The crude product was purified by silica gel chromatography (ethyl acetate in petroleum ether, 0-100%) to obtain 102-3 (400 mg, 2.38 mmol, 93.32% yield). MS: m/z=169 (M+1).

Step 3: 102-4

To a mixture of 102-3 (400 mg, 2.38 mmol), TEA (721.95 mg, 7.13 mmol) in DCM (20 mL) was added methane sulfonyl chloride (299.67 mg, 2.62 mmol) at 25° C. The reaction solution was stirred for 1 hr at 25° C. Then, the solution was filtered and concentrated with a rotary evaporator. The crude product was purified by silica gel chromatography (ethyl acetate in petroleum ether, 0-50%) to obtain 102-4 (600 mg, crude). MS: m/z=247 (M+1).

Step 4: 102-5

To a mixture of 102-4 (600 mg, 2.44 mmol), 4-bromobenzenesulfinic acid (807.87 mg, 3.65 mmol) in DMF (20 mL) was added potassium carbonate (1.01 g, 7.31 mmol) at 25° C. The reaction solution was stirred for 18 hr at 90° C. Then, the solution was quenched with water (20 mL), and extracted by ethyl acetate (15 mL×2). The combined organic layers were washed with water (15 mL) and brine (15 mL), dried over anhydrous sodium sulfate and concentrated with a rotary evaporator to obtain 102-5 (860 mg, crude). MS: m/z=372 (M+1).

Step 5: 102-6

To a mixture of 102-5 (220 mg, 592.59 μmol), 4,4,5,5-tetramethyl-2-(4,4,5,5-tetramethyl-1,3,2-dioxaborolan-2-yl)-1,3,2-dioxaborolane (180.58 mg, 711.11 μmol) and potassium acetate (174.48 mg, 1.78 mmol) in Dioxane (10 mL) was added bis(diphenylphosphino)ferrocene]dichloropalladium(II) (43.36 mg, 59.26 μmol) at 25° C. The reaction solution was heated at 120° C. for 0.667 hr under microwave. The mixture was filtered and the filtrate was evaporated to obtain 102-6 (310 mg, crude). MS: m/z=419 (M+1).

Step 6: 102-7

To a mixture of 102-6 (310 mg, 741.07 μmol), acetate acid (0.5 mL) in THF (20 mL) was added hydrogen peroxide (0.3 mL, 30% purity) at 25° C. The reaction solution was stirred for 1 hr at 25° C. Then, to the solution was added sodium sulfite (0.3 g), filtered and concentrated with a rotary evaporator to obtain 102-7 (250 mg, crude). MS: m/z=309 (M+1).

Step 7: 102-8

To a mixture of 102-7 (250 mg, 810.76 μmol), Intermediate A (200 mg, 745.93 mol) in MeCN (30 mL) was added Cesium carbonate (792.48 mg, 2.43 mmol) at 25° C. The reaction solution was stirred for 1 hr at 90° C. Then, the mixture was filtered, and the filtrate was concentrated with a rotary evaporator to obtain 102-8 (310 mg, crude). MS: m/z=496 (M+1).

Step 8: Compound 102

To a mixture of 102-8 (310 mg, 625.55 μmol) in DCM (15 mL) was added HCl/Dioxane (4 M, 3 mL) at 25° C. and the reaction mixture was stirred at 25° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 102 (110 mg, 249.17 μmol, 39.83% yield, $HCO_2H$ salt). $^1H$ NMR (400 MHz, Methanol-d4) δ 8.51 (s, 1H), 7.74-7.64 (m, 2H), 7.50 (d, J=9.5 Hz, 1H), 7.23 (d, J=81.0 Hz, 1H), 7.22-7.13 (m, 2H), 6.93 (d, J=9.5 Hz, 1H), 5.10 (p, J=6.6 Hz, 1H), 4.70 (dd, J=3.7, 1.0 Hz, 2H), 4.56 (s, 2H), 3.79 (d, J=2.3 Hz, 2H), 1.08 (d, J=6.7 Hz, 6H) ppm. MS: m/z=396.1 (M+1).

Example 73: Synthesis of Compound 103

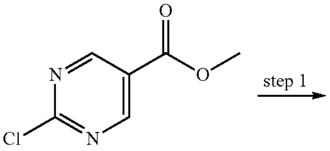

103-1

-continued

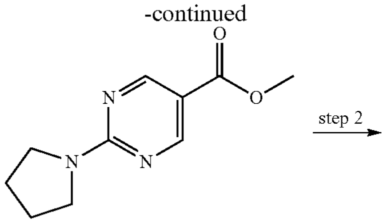

103-2

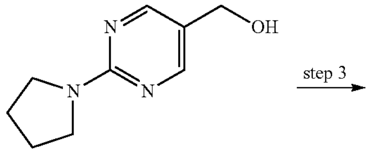

103-3

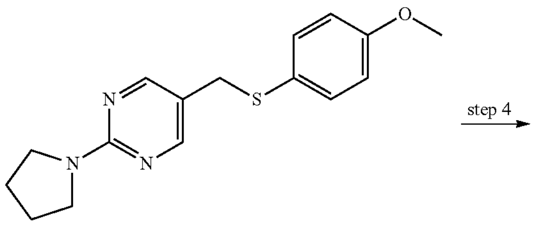

103-4

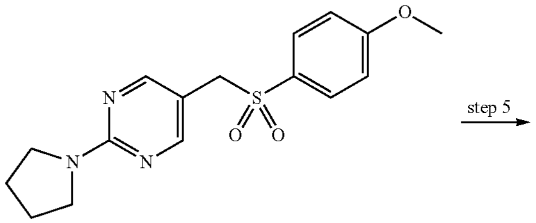

103-5

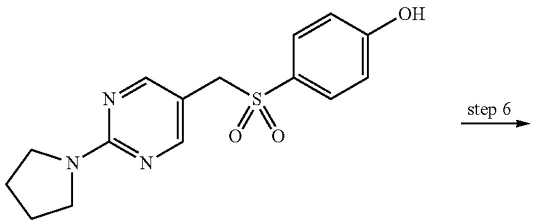

103-6

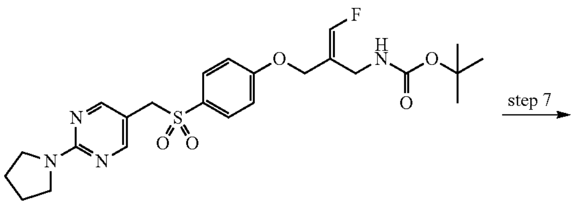

103-7

-continued

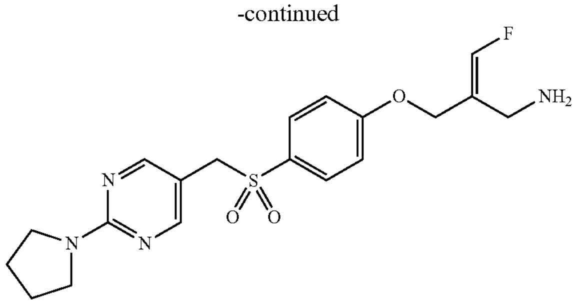

103

Step 1: 103-2

To a mixture of 103-1 (1.0 g, 5.79 mmol), TEA (1.76 g, 17.38 mmol) in THF (20 mL) was added pyrrolidine (824.26 mg, 11.59 mmol, 962.92 μL) at 25° C. The reaction solution was stirred for 2 hr at 25° C. Then, the solution was concentrated with a rotary evaporator. The crude product was purified by silica gel chromatography (ethyl acetate in petroleum ether, 0-50%, v/v) to obtain 103-2 (1.1 g, 5.31 mol, 91.60% yield). MS: m/z 208.1 (M+1).

Step 2: 103-3

To a mixture of 103-2 (70 mg, 3.38 mmol) in TH (15 mL) was added $LiBH_4$ (2 M in THF, 6.76 mL) at 0° C. The reaction mixture was stirred for 2 hr at 25° C. Then, the solution was quenched with methanol (20 mL) at 0° C. and stirred for 0.25 hr at 20° C. The solution was concentrated with a rotary evaporator. The crude product was purified by silica gel chromatography (methanol in dichloromethane, 0-10%) to obtain 103-3 (410 mg, 2.29 mmol, 67.73% yield). MS: m/z=180.1 (M+1).

Step 3: 103-4

To a mixture of 103-3 (410 mg, 2.29 mmol) and 1-methoxy-4-[(4-methoxyphenyl)disulfanyl]benzene (764.25 mg, 2.75 mmol) in MeCN (20 mL) was added tributylphosphane (647.99 mg, 3.20 mmol, 790.23 μL) at 25° C. The reaction mixture was stirred for 16 hr at 80° C. Then, the solution was concentrated with a rotary evaporator. The crude product was purified by silica gel chromatography (ethyl acetate in petroleum ether, 0-50%) to obtain 103-4 (510 mg, 1.69 mmol, 73.96% yield). MS: m/z=302.1 (M+1).

Step 4: 103-5

To a mixture of 103-4 (510 mg, 1.69 mmol) in DCM (20 mL) was added m-CPBA (1.03 g, 5.08 mmol, 85% purity) at 20° C. The mixture was stirred for 1 hr at 20° C. Then, the solution was washed with saturated aqueous sodium sulfite (10 mL), saturated aqueous $NaHCO_3$ (20 mL×2) and brine (15 mL), dried over anhydrous sodium sulfate and concentrated with a rotary evaporator to obtain 103-5 (500 mg, crude). MS: m/z=334.1 (M+1).

Step 5: 103-6

To a solution of 103-5 (500 mg, 1.50 mmol) in DCM (25 mL) was added boron tribromide (1.13 g, 4.50 mmol) at 0° C. The reaction mixture was stirred for 1 hr at 25° C. Then, the solution was quenched with methanol (20 mL) at 0° C. and stirred for 0.25 hr at 20° C. The solution was filtered and concentrated with a rotary evaporator to obtain 103-6 (310 mg, crude). MS: m/z=320.1 (M+1).

Step 6: 103-7

To a mixture of 103-6 (310 mg, 774.44 μmol), Intermediate A (160 mg, 596.74 μmol) in MeCN (30 mL) was added cesium carbonate (756.98 mg, 2.32 mmol) at 20° C. The reaction solution was stirred for 1 hr at 90° C. Then, the mixture was filtered, and the filtrate was concentrated with a rotary evaporator. The crude product was purified by silica gel chromatography (ethyl acetate in petroleum ether, 0-100%) to obtain 103-7 (110 mg, 217.14 μmol, 28.04% yield). MS: m/z=507.2 (M+1).

Step 7: Compound 103

To a solution of 103-7 (110 mg, 217.14 μmol) in DCM (20 mL) was added HCl/Dioxane (4 M, 2 mL) at 25° C. and the reaction mixture was stirred at 25° C. for 1 hr. Then, the solution was concentrated with a rotary evaporator. The crude product was purified by prep-HPLC (column: XBridge@ Prep C18 5 μm 19×150 mm; A: 0.2% $HCO_2H$ water, B: acetonitrile; gradient: 5-50% B; GT: 25 min; flow rate: 15 mL/min) to obtain Compound 103 (25 mg, 55.25 mol, 25.44% yield, $HCO_2H$ salt). $^1H$ NMR (400 MHz, Methanol-d4) δ 8.52 (s, 1H), 7.64-7.60 (m, 2H), 7.44-7.42 (m, 1H), 7.25 (d, J=1.9 Hz, 1H), 7.23 (d, J=81.0 Hz, 1H), 7.11 (d, J=9.0 Hz, 2H), 4.69 (d, J=3.5 Hz, 2H), 4.54 (s, 2H), 3.81 (d, J=2.2 Hz, 2H), 3.58 (t, J=6.9 Hz, 2H), 3.42 (t, J=6.6 Hz, 2H), 2.02-1.87 (m, 4H) ppm. MS: m/z=407.1 (M+1).

Example 74: Synthesis of Compound 106

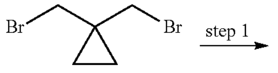

106-1

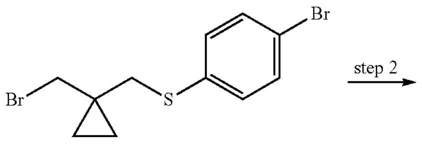

106-2

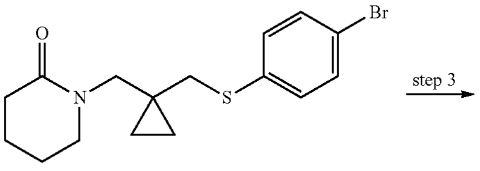

106-3

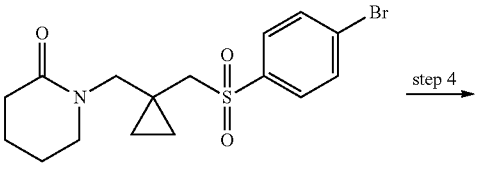

106-4

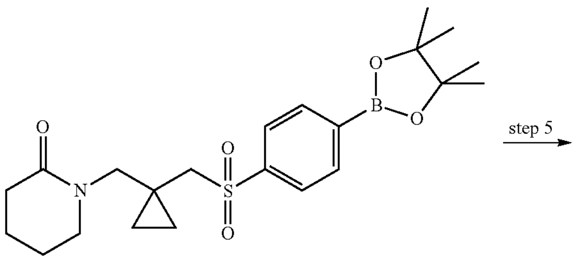

106-5

-continued

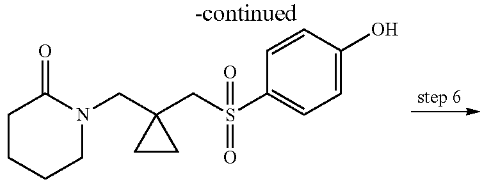

106-6

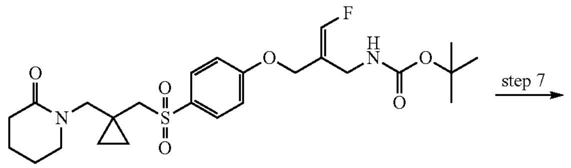

106-7

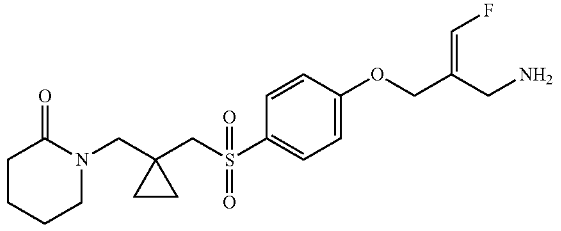

106

Step 1: 106-2

To a mixture of 106-1 (2.41 g, 10.58 mmol), 4-bromothiophenol (1 g, 5.29 mmol) in MeCN (60 mL) was added Cesium carbonate (3.45 g, 10.58 mmol) at 0° C. The reaction solution was stirred for 1 hr at 25° C. Then, the solution was concentrated with a rotary evaporator. The crude product was purified by silica gel chromatography (ethyl acetate in petroleum ether, 1-10%, v/v) to obtain 106-2 (1 g, 2.98 mmol, 56.26% yield). MS: m/z=336.0 (M+1).

Step 2: 106-3

A mixture of Piperidin-2-one (294.96 mg, 2.98 mmol) and potassium; 2-methylpropan-2-olate (667.76 mg, 5.95 mmol) in DMSO (10 mL) was stirred at 50° C. for 1 hr. 106-2 (500 mg, 1.49 mmol) was added at 50° C. and stirred at 50° C. for 3 hr. Water (100 mL) was added and the mixture was extracted with ethyl acetate (100 mL), the organic layer was separated, dried over anhydrous sodium sulfate, filtered and concentrated to give 106-3 (200 mg, 564.49 μmol, 37.94% yield). MS: m/z=354.3 (M+1).

Step 3: 106-4

A mixture of 106-3 (200 mg, 564.49 μmol) and m-CPBA (343.80 mg, 1.69 mmol, 85% purity) in DCM (20 mL) was stirred at 20° C. for 1 hr. The sodium sulfite (0.3 g) was added to the mixture and stirred for 20 min. Then, the solution was filtered, concentrated and purified by silica gel chromatography (ethyl acetate in petroleum ether, 10-50%, v/v) to obtain 106-4 (150 mg, 388.30 μmol, 68.79% yield). MS: m/z=386.3 (M+1).

Step 4: 106-5

To a mixture of 4,4,5,5-tetramethyl-2-(4,4,5,5-tetramethyl-1,3,2-dioxaborolan-2-yl)-1,3,2-dioxaborolane (118.32 mg, 465.96 μmol), 106-4 (120 mg, 310.64 μmol) and bis(diphenylphosphino)ferrocene]dichloropalladium(II) (22.73 mg, 31.06 μmol) in Dioxane (20 mL) was added potassium acetate (91.46 mg, 931.91 μmol) at 20° C. under the nitrogen atmosphere. The reaction solution was stirred for 4 hr at 100° C. Then, the solution was concentrated with a rotary evaporator and purified by column chromatography on silica gel (ethyl acetate in petroleum ether, 10-50%) to obtain 106-5 (90 mg, 207.68 μmol, 66.85% yield). MS: m/z=433.3 (M+1).

Step 5: 106-6

To a mixture of 106-5 (90 mg, 207.68 μmol) in THF (2 mL) and acetate acid (0.5 mL) was added hydrogen peroxide (0.5 mL, 30% purity). The mixture was stirred at 20° C. for 1 hr. The sodium sulfite (0.3 g) was added to the mixture and stirred for 20 min. The mixture was filtered and concentrated to give 106-6 (0.5 g, crude). MS: m/z=323.4 (M+1).

Step 6: 106-7

To a mixture of 106-6 (0.5 g, 1.55 mmol) and Intermediate A (124.36 mg, 463.81 μmol) in MeCN (50 mL) was added Cesium carbonate (1.51 g, 4.64 mmol) at 20° C. The reaction solution was stirred for 1 hr at 80° C. Then, the solution was filtered and concentrated and purified by column chromatography on silica gel (ethyl acetate in petroleum ether, 10-20%) to obtain 106-7 (160 mg, 313.35 μmol, 20.27% yield).

Step 7: Compound 106

A mixture of 106-7 (160 mg, 313.35 μmol) in HCl/Dioxane (4 M, 3.0 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 106 (5 mg, 12.18 μmol, 1.55% yield, $HCO_2H$ salt). $^1H$ NMR (400 MHz, Methanol-d4) δ 8.49 (s, 1H), 7.88 (d, J=8.4 Hz, 2H), 7.23 (d, J=80.0 Hz, 1H), 7.20 (d, J=8.4 Hz, 2H), 4.71 (d, J=3.6 Hz, 2H), 3.80 (s, 2H), 3.48 (s, 2H), 3.43 (d, J=6.0 Hz, 2H), 3.35-3.30 (m, 2H), 2.35 (s, 2H), 1.82 (s, 4H), 0.73-0.57 (m, 4H) ppm. MS: m/z=411.68 (M+1).

The compounds of Formula (I') or (I) in Table 14 below were made according to Example 74 of Compound 106.

TABLE 14

| Cmpd No. | $^1H$ NMR and/or LC/MS data |
|---|---|
| 107 | $^1H$ NMR (400 MHz, Methanol-$d_4$) δ 8.48 (s, 1H), 7.89 (d, J = 8.4 Hz, 2H), 7.24 (d, J = 80.0 Hz, 1H), 7.22 (d, J = 8.4 Hz, 2H), 4.72 (d, J = 3.6 Hz, 2H), 3.81 (d, J = 2.4 Hz, 2H), 3.65 (t, J = 7.2 Hz, 2H), 3.48-3.85 (m, 2H), 3.36 (t, J = 5.6 Hz, 2H), 2.24 (t, J = 6.4 Hz, 2H), 1.73 (d, J = 13.6 Hz, 4H) ppm. MS: m/z = 371.61 (M + 1). |
| 111 | $^1H$ NMR (400 MHz, Methanol-$d_4$) δ 8.51 (s, 1H), 7.92-7.84 (m, 2H), 7.25 (d, J = 80.0 Hz, 1H), 7.28-7.20 (m, 2H), 4.75-4.71 (m, 2H), 3.81 (d, J = 2.4 Hz, 2H), 3.31-3.22 (m, 2H), 3.09-2.95 (m, 2H), 2.40-2.28 (m, 3H), 1.91-1.78 (m, 2H), 1.23 (s, 3H), 1.19 (s, 3H), 1.06 (d, J = 7.0 Hz, 3H) ppm. MS: m/z = 413.68 (M + 1). |
| 114 | $^1H$ NMR (400 MHz, Methanol-$d_4$) δ 8.43 (s, 1H), 7.90-7.83 (m, 1H), 7.27 (d, J = 80.0 Hz, 1H), 7.11-7.03 (m, 2H), 4.73 (d, J = 3.6 Hz, 2H), 3.90-3.79 (m, 3H), 3.64-3.60 (m, 4H), 3.04-3.01 (m, 1H), 2.37-2.24 (m, 4H), 2.22-2.13 (m, 3H), 1.06 (d, J = 6.0 Hz, 3H) ppm. MS: m/z = 405.66 (M + 1). |
| 116 | $^1H$ NMR (400 MHz, Methanol-$d_4$) δ 7.86 (d, J = 8.4 Hz, 2H), 7.19 (d, J = 8.4 Hz, 2H), 6.76 (d, J = 80.0 Hz, 1H), 4.67 (d, J = 3.6 Hz, 2H), 3.64 (t, J = 4.4 Hz, 4H), 3.49 (s, 2H), 3.38 (s, 2H), 2.31 (s, 4H), 2.11 (s, 2H), 0.55 (s, 2H), 0.35 (s, 2H) ppm. MS: m/z = 399.64 (M + 1). |

Example 75: Synthesis of Compound 108

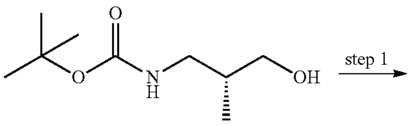

108-1

-continued

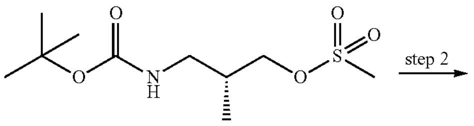

108-2

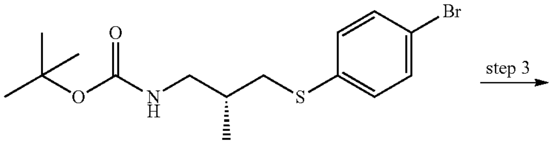

108-3

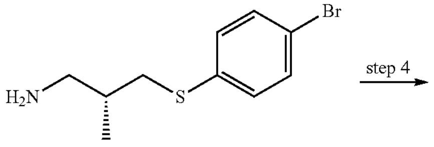

108-4

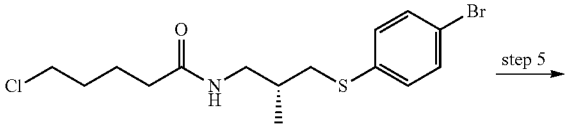

108-5

-continued

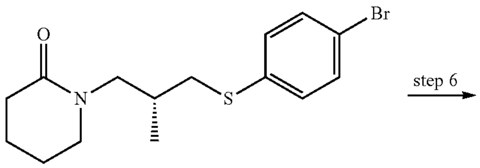

108-6

-continued

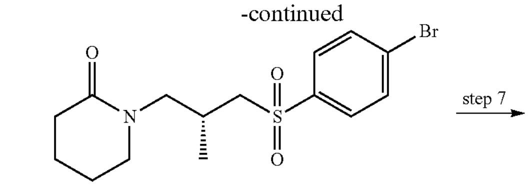

108-7

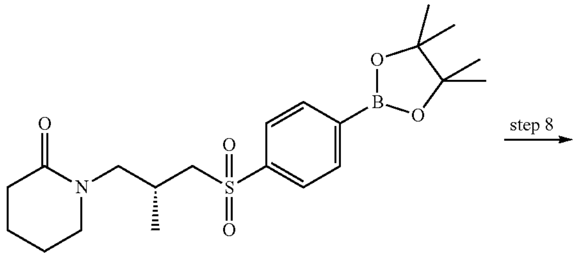

108-8

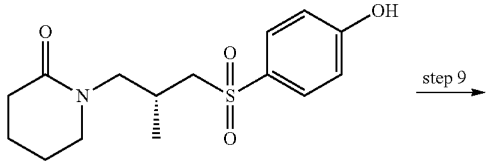

108-9

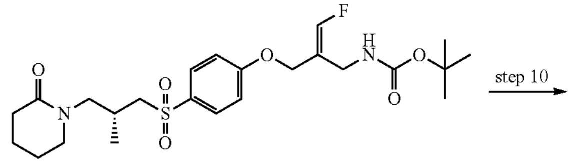

108-10

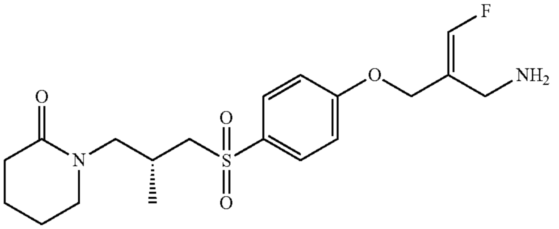

108

Step 1: 108-2

To a mixture of 108-1 (1 g, 5.71 mmol) and methylsulfonyl chloride (784.49 mg, 6.85 mmol) in DCM (30 mL) was added TEA (577.49 mg, 5.71 mmol, 795.44 μL) at 0'° C. The reaction was stirred for 1 hr at 0'° C. DCM (50 mL) and water (100 mL) were added, the organic phase was separated and dried over anhydrous sodium sulfate, filtered and concentrated to give 108-2 (1.4 g, 5.53 mmol, 96.84% yield).

Step 2: 108-3

To a mixture of 4-bromobenzenethiol (500 mg, 2.64 mmol), NaH (101.33 mg, 2.64 mmol, 60% purity) in DMF (20 mL) was added 108-2 (401.93 mg, 1.59 mmol) at 0° C. The reaction solution was stirred for 4 hr at 30° C. To the mixture was added saturated aqueous ammonium chloride solution (100 mL) and ethyl acetate (100 mL). The organic layer was separated and the aqueous layer was further extracted with ethyl acetate (50 mL×3). The combined organic extracts were dried over anhydrous sodium sulfate. The solvent was evaporated under reduced pressure and the crude product was purified by flash column chromatography (ethyl acetate in petroleum ether, 10-80%) to give 108-3 (300 mg, 866.35 μmol, 65.52% yield). MS: m/z=346.2 (M+1).

Step 3: 108-4

A mixture of 108-3 (300 mg, 866.35 μmol) in HCl/Dioxane (4 M, 5.0 mL) was stirred at 25° C. for 1 hr. Then, the solution was concentrated with a rotary evaporator to obtain 108-4 (251 mg, crude, HCl salt). MS: m/z=282.6 (M+1).

Step 4: 108-5

To a mixture of 5-chloropentanoyl chloride (157.97 mg, 1.02 mmol, 131.64 μL) and TEA (257.78 mg, 2.55 mmol, 355.07 μL) in DCM (20 mL) was added 108-4 (240 mg, 849.17 mol, HCl salt) at 0° C. The reaction solution was stirred for 1 hr at 20° C. Then, the solution was concentrated with a rotary evaporator. The crude product was dissolved in ethyl acetate (80 mL), washed with water (100 mL×3), dried over anhydrous sodium sulfate, filtered and concentrated to obtain 108-5 (300 mg, crude). MS: m/z=364.7 (M+1).

Step 5: 108-6

A mixture of 108-5 (300 mg, 822.53 μmol) and potassium; 2-methylpropan-2-olate (369.19 mg, 3.29 mmol) in DMSO (10 mL) was stirred at 50° C. for 2 hr. Water (100 mL) was added and extracted with ethyl acetate (100 mL), the organic layer was separated, dried over anhydrous sodium sulfate, filtered and concentrated to give 108-6 (150 mg, 456.94 μmol, 55.55% yield). MS: m/z=328.2 (M+1).

Step 6: 108-7

A mixture of 108-6 (150 mg, 456.94 μmol) and m-CPBA (278.30 mg, 1.37 mmol, 85% purity) in DCM (20 mL) was stirred at 20° C. for 1 hr. The sodium sulfite (0.3 g) was added to the mixture and stirred for 20 min. Then, the solution was filtered, concentrated and purified by silica gel chromatography (ethyl acetate in petroleum ether, 10-50%, v/v) to obtain 108-7 (120 mg, 333.09 μmol, 72.89% yield). MS: m/z=360.2 (M+1).

Step 7: 108-8

To a mixture of 4,4,5,5-tetramethyl-2-(4,4,5,5-tetramethyl-1,3,2-dioxaborolan-2-yl)-1,3,2-dioxaborolane (126.88 mg, 499.63 μmol), 108-7 (120 mg, 333.09 μmol) and bis(diphenylphosphino)ferrocene]dichloropalladium(II) (24.37 mg, 33.31 μmol) in Dioxane (20 mL) was added potassium acetate (98.07 mg, 999.26 μmol) at 20° C. under the nitrogen atmosphere. The reaction solution was stirred for 4 hr at 100° C. Then, the solution was concentrated with a rotary evaporator and purified by column chromatography on silica gel (ethyl acetate in petroleum ether, 10-50%) to obtain 108-8 (110 mg, 270.05 μmol, 81.08% yield). MS: m/z=407.3 (M+1).

Step 8: 108-9

To a mixture of 108-8 (110 mg, 270.05 μmol) in THF (2 mL) and acetate acid (0.5 mL) was added hydrogen peroxide (0.5 mL, 30% purity). The mixture was stirred at 20° C. for 1 hr. The sodium sulfite (0.3 g) was added to the mixture and stirred for 20 min. The mixture was filtered and concentrated to give 108-9 (400 mg, crude). MS: m/z=297.3 (M+1).

Step 9: 108-10

To a mixture of 108-9 (0.4 g, 1.35 mmol) and Intermediate A (108.20 mg, 403.54 mol) in MeCN (50 mL) was added Cesium carbonate (1.31 g, 4.04 mmol) at 20° C. The reaction solution was stirred for 1 hr at 80° C. Then, the solution was filtered and concentrated and purified by column chromatography on silica gel (ethyl acetate in petroleum ether, 10-20%) to obtain 108-10 (90 mg, 185.73 μmol, 13.81% yield).

Step 10: Compound 108

A mixture of 108-10 (90 mg, 185.73 μmol) in HCl/Dioxane (4 M, 4 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 108 (5 mg, 13.01 μmol, 7.0% yield, $HCO_2H$ salt). $^1H$ NMR (400 MHz, Methanol-d4) δ 7.86 (d, J=8.4 Hz, 2H), 7.23 (d, J=80.0 Hz, 1H), 7.20 (d, J=8.4 Hz, 2H), 4.73-4.69 (m, 2H), 3.79-3.75 (m, 2H), 3.25-3.22 (m, 2H), 2.22-2.18 (m, 1H), 1.69 (s, 4H), 1.23 (d, J=6.6 Hz, 4H), 1.19 (s, 3H) ppm. MS: m/z=385.65 (M+1).

Example 76: Synthesis of Compound 115

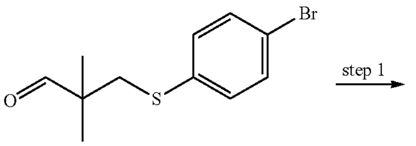

98-3

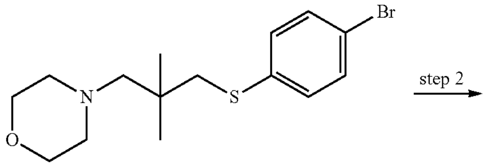

115-1

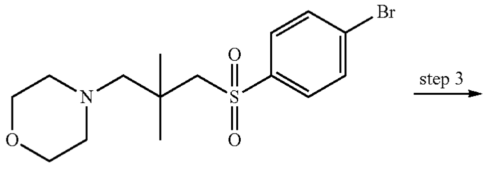

115-2

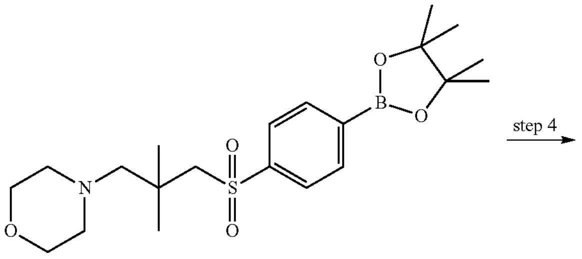

115-3

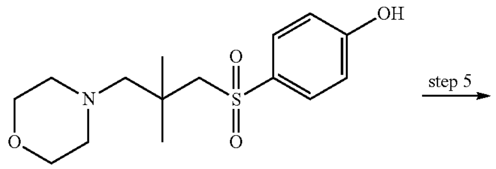

115-4

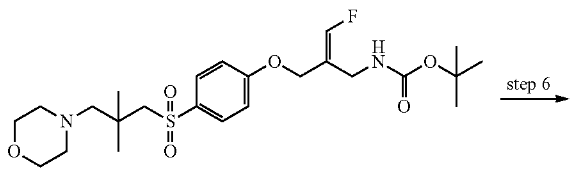

115-5

-continued

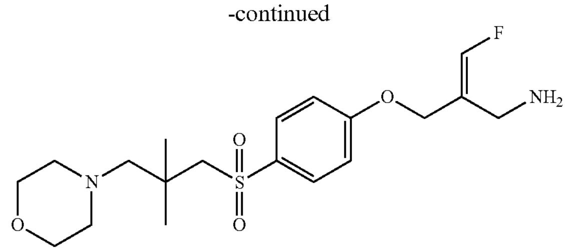

115

Step 1: 115-1

To a mixture of 98-3 (600 mg, 2.20 mmol), morpholine (382.68 mg, 4.39 mmol, 384.22 μL) in DCM (20 mL) was added $NaBH(OAc)_3$ (1.40 g, 6.59 mmol) at 0° C. The reaction solution was stirred for 4 hr at 25° C. Then, the solution was concentrated with a rotary evaporator. The crude product was purified by silica gel chromatography (ethyl acetate in petroleum ether, 10-50%, v/v) to obtain 115-1 (600 mg, 1.74 mmol, 79.34% yield). MS: m/z=344.3 (M+1).

Step 2: 115-2

A mixture of 115-1 (600 mg, 1.74 mmol) and m-CPBA (1.06 g, 5.23 mmol, 85% purity) in DCM (50 mL) was stirred at 25° C. for 0.5 hr. The sodium sulfite (14 g) was added to the mixture and stirred for 20 min. Then, the solution was filtered, concentrated and purified by silica gel chromatography (ethyl acetate in petroleum ether, 3-25%, v/v) to obtain 115-2 (540 mg, 1.43 mmol, 82.35% yield). MS: m/z=376.3 (M+1).

Step 3: 115-3

A 30 mL microwave reaction tube was charged with 115-2 (540 mg, 1.43 mmol), 4,4,5,5-tetramethyl-2-(4,4,5,5-tetramethyl-1,3,2-dioxaborolan-2-yl)-1,3,2-dioxaborolane (506.11 mg, 1.99 mmol), bis(diphenylphosphino)ferrocene]dichloropalladium(II) (97.22 mg, 132.87 μmol) and potassium acetate (391.20 mg, 3.99 mmol) in Dioxane (15 mL). After oxygen was purged by bubbling nitrogen into the reaction solution, the tube was sealed and heated at 120° C. for 0.5 hr in a Biotage microwave reactor. The reaction was cooled to room temperature, filtered and concentrated under reduced pressure. The resultant crude product was purified by flash chromatography (ethyl acetate in petroleum ether, 0-100%) to deliver 115-3 (580 mg, crude). MS: m/z=423.3 (M+1).

Step 4: 115-4

A mixture of 115-3 (500 mg, 1.18 mmol) in THF (25 mL) and acetate acid (0.5 mL) was added hydrogen peroxide (1 mL, 30% purity). The mixture was stirred at 25° C. for 1 hr. The sodium sulfite (0.6 g) was added to the mixture and stirred for 30 min. The reaction mixture was filtered and concentrated to give 115-4 (1.1 g, crude). MS: m/z=313.4 (M+1).

Step 5: 115-5

To a mixture of 115-4 (1 g, 3.19 mmol) and Intermediate A (342.20 mg, 1.28 mmol) in MeCN (50 mL) was added Cesium carbonate (3.12 g, 9.57 mmol) at 20° C. The reaction solution was stirred for 1 hr at 80° C. Then, the solution was filtered and concentrated to obtain 115-5 (400 mg, crude).

Step 6: Compound 115

A mixture of 115-5 (400 mg, 799.01 μmol) in HCl/Dioxane (4 M, 4 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 115 (26.3 mg, 58.90 μmol, 7.37% yield, $HCO_2H$ salt). $^1H$ NMR (400 MHz, Methanol-d4) δ 8.27 (s, 1H), 7.86 (d, J=8.6 Hz, 2H), 7.25 (d, J=80.0 Hz, 1H), 7.21 (d, J=8.5 Hz, 2H), 4.72 (d, J=3.6 Hz, 2H), 3.83 (d, J=2.4 Hz, 2H), 3.64 (t, J=4.4 Hz, 4H), 3.26 (d, J=4.4 Hz, 2H), 2.58 (t, J=4.4 Hz, 4H), 2.38 (s, 2H), 1.10 (s, 6H) ppm. MS: m/z=401.63 (M+1).

Example 77: Synthesis of Compound 117

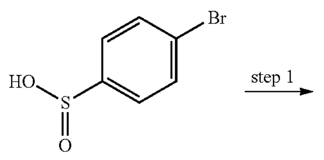

Intermediate B

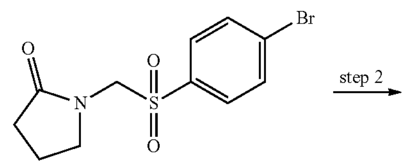

117-1

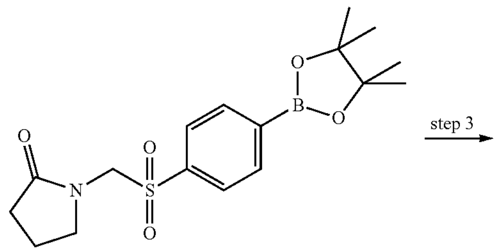

117-2

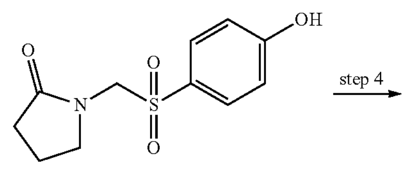

117-3

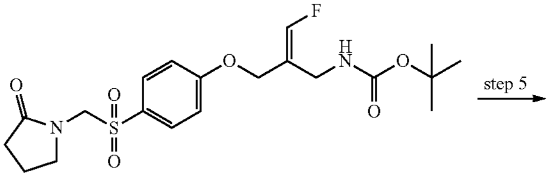

117-4

-continued

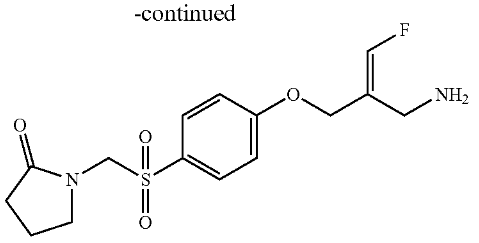

117

Step 1: 117-1

A mixture of Intermediate B (300 mg, 1.36 mmol), pyrrolidin-2-one (577.44 mg, 6.79 mmol) and polyformaldehyde (407.46 mg, 13.57 mmol) in $HCO_2H$ (4 mL) and water (1 mL) was heated to 100° C. and stirred for 1 hr. After cooling to room temperature, the white solid was collected by filtration and washed with water (40 mL) to give 117-1 (200 mg, 628.56 μmol, 46.32% yield). MS: m/z=318.1 (M+1).

Step 2: 117-2

To a mixture of 117-1 (200 mg, 628.56 μmol), 4,4,5,5-tetramethyl-2-(4,4,5,5-tetramethyl-1,3,2-dioxaborolan-2-yl)-1,3,2-dioxaborolane (191.54 mg, 754.27 μmol) and bis (diphenylphosphino)ferrocene]dichloropalladium(II) (45.99 mg, 62.86 μmol) in Dioxane (10 mL) was added potassium acetate (185.07 mg, 1.89 mmol) at 20° C. under the nitrogen atmosphere. The reaction solution was stirred for 4 hr at 100° C. Then, the solution was concentrated with a rotary evaporator. The crude product was dissolved in ethyl acetate (60 mL), washed with water (100 mL×3), dried over anhydrous sodium sulfate, filtered and concentrated to obtain 117-2 (200 mg, crude). MS: m/z=365.2 (M+1).

Step 3: 117-3

To a mixture of 117-2 (200 mg, 547.57 μmol) in THF (4 mL) and acetate acid (1 mL) was added hydrogen peroxide (1 mL, 30% purity). The mixture was stirred at 20° C. for 1 hr. Sodium sulfite (0.5 g) was added to the mixture and stirred for 20 min. The mixture was filtered and concentrated to give 117-3 (180 mg, crude). MS: m/z=255.2 (M+1).

Step 4: 117-4

To a mixture of 117-3 (180 mg, 705.08 μmol) and Intermediate A (150 mg, 559.45 mol) in MeCN (10 mL) was added Cesium carbonate (689.19 mg, 2.12 mmol) at 20° C. The reaction solution was stirred for 1 hr at 80° C. Then, the solution was filtered and concentrated to obtain 117-4 (80 mg, 180.79 μmol, 25.64% yield). MS: m/z=442.5 (M+1).

Step 5: Compound 117

A mixture of 117-4 (80 mg, 180.79 μmol) in HCl/Dioxane (4 M, 4.00 mL) was stirred at 25° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 2-30% B; GT: 15 min; flow rate: 15 mL/min) to obtain Compound 117 (15 mg, 38.62 μmol, 21.36% yield, $HCO_2H$ salt). $^1H$ NMR (400 MHz, Methanol-d4) δ 8.52 (s, 1H), 7.83 (d, J=8.0 Hz, 2H), 7.18 (d, J=8.0 Hz, 2H), 7.21 (d, J=80 Hz, 1H), 4.70 (d, J=4.0 Hz, 2H), 3.79 (s, 2H), 3.71-3.68 (m, 2H), 3.32-3.29 (m, 2H), 3.23-3.19 (m, 2H), 2.08-2.02 (m, 2H) ppm. MS: m/z=343.0 (M+1, ESI+).

The compounds of Formula (I') or (I) in Table 15 below were made according to Example 77 of Compound 117.

TABLE 15

| Cmpd No. | $^1$H NMR and/or LC/MS data |
|---|---|
| 118 | $^1$H NMR (400 MHz, Methanol-$d_4$) δ 8.51 (s, 1H), 7.77 (d, J = 8.0 Hz, 2H), 7.68-7.59 (m, 3H), 7.48 (t, J = 7.4 Hz, 1H), 7.18 (d, J = 80.0 Hz, 1H), 7.11 (d, J = 8.8 Hz, 2H), 5.07 (s, 2H), 4.83 (s, 2H), 4.66 (d, J = 3.6 Hz, 2H), 3.76 (d, J = 2.4 Hz, 2H) ppm. MS: m/z = 390.71 (M + 1). |
| 119 | $^1$H NMR (400 MHz, Methanol-$d_4$) δ 8.53 (s, 1H), 7.66-7.59 (m, 2H), 7.21 (d, J = 80.0 Hz, 1H), 7.16-7.12 (m, 2H), 6.98 (d, J = 2.0 Hz, 1H), 6.95-6.83 (m, 2H), 6.75 (d, J = 8.1 Hz, 1H), 4.74-4.67(m, 2H), 4.41 (s, 2H), 3.77 (d, J = 2.4 Hz, 2H), 2.90-2.84 (m, 2H), 2.55 (dd, J = 8.6, 6.4 Hz, 2H) ppm. MS: m/z = 405.3 (M + 1). |
| 120 | $^1$H NMR (400 MHz, Methanol-$d_4$) δ 7.64-7.58 (m, 2H), 7.19-7.10 (m, 2H), 7.05-7.02 (m, 2H), 7.14 (d, J = 80.0 Hz, 1H), 7.01-6.98 (m, 1H), 6.89-6.84 (m, 1H), 5.21 (s, 2H), 4.60 (d, J = 3.6, Hz, 2H), 3.69 (d, J = 2.4 Hz, 2H), 1.49 (q, J = 4.0, 3.6 Hz, 2H), 1.42-1.31 (m, 2H) ppm. MS: m/z = 417.2 (M + 1). |
| 122 | $^1$H NMR (400 MHz, Methanol-$d_4$) δ 7.82 (d, J = 8.0 Hz, 2H), 7.24 (d, J = 80.0 Hz, 1H), 7.14 (d, J = 8.0 Hz, 2H), 4.89 (s, 2H), 4.70 (d, J = 3.6 Hz, 2H), 3.81 (d, J = 2.4 Hz, 2H), 3.29 (s, 3H), 2.87-2.81 (m, 1H), 0.91 (d, J = 6.8 Hz, 6H) ppm. MS: m/z = 358.8 (M + 1). |
| 123 | $^1$H NMR (400 MHz, Methanol-$d_4$) δ 8.51 (s, 1H), 7.87 (d, J = 8.4 Hz, 2H), 7.23 (d, J = 80.0 Hz, 1H), 7.19 (d, J = 8.4 Hz, 2H), 4.71 (d, J = 3.2 Hz, 4H), 3.80 (d, J = 2.4 Hz, 2H), 2.35 (t, J = 8.0 Hz, 2H), 1.96 (t, J = 8.0 Hz, 2H), 1.35 (s, 6H) ppm. MS: m/z = 371.6 (M + 1). |
| 124 | $^1$H NMR (400 MHz, Methanol-$d_4$) δ 8.17 (s, 1H), 7.98-7.91 (m, 1H), 7.28 (dd, J = 15.1, 2.4 Hz, 1H), 7.28 (d,J = 80.9 Hz, 1H), 7.15-7.05 (m, 1H), 4.79 (d, J = 1.6 Hz, 2H), 4.73 (d, J = 3.5 Hz, 1H), 4.65-4.61 (m, 1H), 4.15-4.07 (m, 1H), 3.84 (dd, J = 8.2, 2.4 Hz, 1H), 2.48-2.39 (m, 2H), 1.92 (t, J = 7.9 Hz, 2H), 1.35 (s, 6H) ppm. MS: m/z = 405.57 (M + 1). |
| 125 | $^1$H NMR (400 MHz, Methanol-$d_4$) δ 8.50 (s, 1H), 7.84 (d, J = 8.4 Hz, 2H), 7.23 (d, J = 80.0 Hz, 1H), 7.19 (d, J = 8.5 Hz, 2H), 4.78-4.67 (m, 4H), 3.80 (d, J = 2.4 Hz, 2H), 3.62 (t, J = 7.0 Hz, 2H), 1.90 (t, J = 7.0 Hz, 2H), 0.98 (s, 6H) ppm. MS: m/z = 371.6 (M + 1). |
| 126 | $^1$H NMR (400 MHz, Methanol-$d_4$) δ 8.52 (s, 1H), 7.92-7.82 (m, 2H), 7.25 (d, J = 80.0 Hz, 1H), 7.27-7.19 (m, 2H), 4.75 (s, 2H), 4.72 (d, J = 3.6 Hz, 2H), 3.82 (d, J = 2.4 Hz, 2H), 3.44 (s, 2H), 2.08 (s, 2H), 1.15 (s, 6H) ppm. MS: m/z = 371.6 (M + 1). |
| 127 | $^1$H NMR (400 MHz, Methanol-$d_4$) δ 7.83 (d, J = 8.4 Hz, 2H), 7.25 (d, J = 80.0 Hz, 1H), 7.18 (d, J = 8.4 Hz, 2H), 4.74 (s, 2H), 4.71 (d, J = 3.6 Hz, 2H), 3.82 (d, J = 2.4 Hz, 2H), 3.63 (t, J = 7.0 Hz, 2H), 1.94 (t, J = 7.0 Hz, 2H), 1.68-1.49 (m, 8H) ppm. MS: m/z = 397.6 (M + 1). |
| 128 | MS: m/z = 415.5 (M + 1). |
| 129 | $^1$H NMR (400 MHz, Methanol-$d_4$) δ 8.51 (s, 1H), 7.83 (d, J = 8.9 Hz, 2H), 7.23 (d, J = 81.1 Hz, 1H), 7.21-7.15 (m, 2H), 4.74-4.67 (m, 2H), 3.80 (d, J = 2.3 Hz, 2H), 3.65 (t, J = 5.9 Hz, 2H), 3.31 (s, 2H), 2.17 (t, J = 6.6 Hz, 2H), 1.91-1.72 (m, 4H). MS: m/z = 357.00 (M + 1). |
| 130 | $^1$H NMR (400 MHz, Methanol-$d_4$) δ 8.28 (s, 3H), 7.82 (d, J = 8.0 Hz, 2H), 7.36 (d, J = 80.0 Hz, 1H), 7.22 (d, J = 8.0 Hz, 2H), 4.97 (s, 2H), 4.75 (d, J = 3.6 Hz, 2H), 3.94 (s, 2H), 3.84 (dd, J = 6.4, 4.0 Hz, 2H), 3.62 (dd, J = 6.4, 4.0 Hz, 4H) ppm. MS: m/z = 359.2 (M + 1). |
| 131 | $^1$H NMR (400 MHz, Methanol-$d_4$) δ 7.80 (t, J = 8.4 Hz, 1H), 7.25 (d, J = 80.0 Hz, 1H), 6.99 (d, J = 9.6 Hz, 2H), 5.01 (s, 2H), 4.70 (d, J = 3.6 Hz, 2H), 3.95 (s, 2H), 3.92-3.85 (m, 2H), 3.84-3.79 (m, 2H), 3.76 (t, J = 5.0 Hz, 2H) ppm. MS: m/z = 377.5 (M + 1). |
| 132 | $^1$H NMR (400 MHz, Methanol-$d_4$) δ 8.52 (s, 1H), 7.82 (d, J = 8.4 Hz, 2H), 7.21 (d, J = 80.0 Hz, 1H), 7.17 (d, J = 8.4 Hz, 2H), 4.70 (d, J = 3.6 Hz, 2H), 4.03 (s, 2H), 3.96 (t, J = 5.2 Hz, 2H), 3.77 (d, J = 6.4 Hz, 4H), 1.29 (s, 6H) ppm. MS: m/z = 387.5 (M + 1). |

Example 78: Synthesis of Compound 121

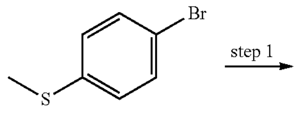

121-1

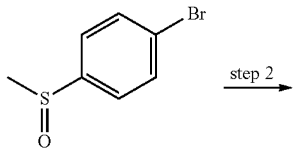

121-2

-continued

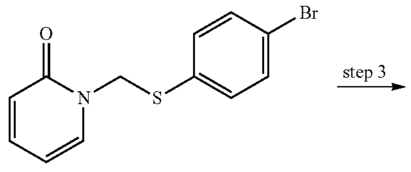

121-3

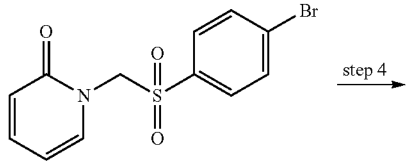

121-4

-continued

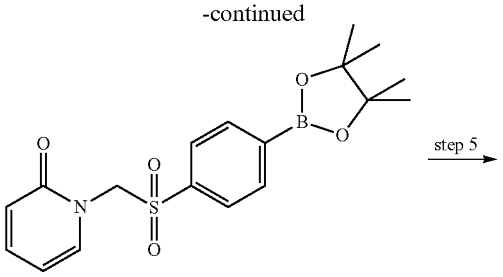

121-5

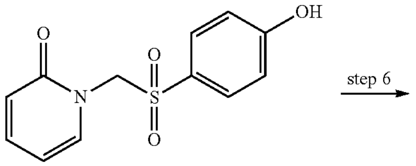

121-6

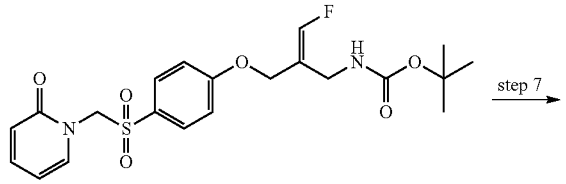

121-7

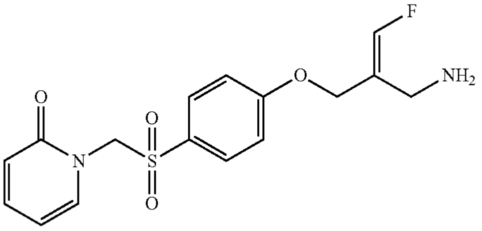

121

Step 1: 121-2

To a mixture of 121-1 (2 g, 9.85 mmol) in DCM (50 mL) was added m-CPBA (2.10 g, 10.34 mmol, 85% purity) at 20° C. The mixture was stirred for 1 hr at 20° C. Then, the solution was washed with saturated aqueous sodium sulfite (10 mL), saturated aqueous $NaHCO_3$ (20 mL×2) and brine (15 mL), dried over anhydrous sodium sulfate and concentrated with a rotary evaporator. The crude product was purified by silica gel chromatography (ethyl acetate in petroleum ether, 0-60%) to obtain 121-2 (2.0 g, 9.13 mmol, 92.70% yield). MS: m/z=220 (M+1).

Step 2: 121-3

To a mixture of 121-2 (1.0 g, 4.56 mmol), 2-fluoropyridine (1.06 g, 10.95 mmol) in DCM (20 mL) was added trifluoromethanesulfonic anhydride (1.55 g, 5.48 mmol, 919.80 μL) dropwise at −50° C. The reaction solution was stirred for 18 hr at 20° C. Then, the solution was quenched with saturated aqueous $NaHCO_3$ (5 mL), stirred vigorously for about 10 minutes, diluted with water (10 mL), extracted with DCM (15 mL). The organic phase was dried over anhydrous sodium sulfate and concentrated with a rotary evaporator. The crude product was purified by silica gel chromatography (ethyl acetate in petroleum ether, 0-40%) to obtain 121-3 (980 mg, 3.31 mmol, 72.49% yield). MS: m/z=297 (M+1).

Step 3: 121-4

To a mixture of 121-3 (350 mg, 1.18 mmol) in DCM (25 mL) was added m-CPBA (839.70 mg, 4.14 mmol, 85% purity) at 20° C. The mixture was stirred for 4 hr at 20° C. Then, the solution was washed with saturated aqueous sodium sulfate (10 mL), saturated aqueous $NaHCO_3$ (20 mL×2) and brine (15 mL). The organic phase was dried over anhydrous sodium sulfate and concentrated with a rotary evaporator to obtain 121-4 (370 mg, crude). MS: m/z=328 (M+1).

Step 4: 121-5

To a mixture of 121-4 (370 mg, 1.13 mmol), 4,4,5,5-tetramethyl-2-(4,4,5,5-tetramethyl-1,3,2-dioxaborolan-2-yl)-1,3,2-dioxaborolane (343.55 mg, 1.35 mmol) and potassium acetate (331.94 mg, 3.38 mmol) in Dioxane (10 mL) was added bis(diphenylphosphino)ferrocene]dichloropalladium(II) (82.49 mg, 112.74 μmol) at 20° C. The reaction solution was heated to 120° C. for 0.667 hr under microwave. The mixture was filtered and the filtrate was concentrated. The residual material was dissolved in DCM (15 mL), washed with water (15 mL) and brine (15 mL), the organic phase was then concentrated with a rotary evaporator to obtain 121-5 (440 mg, crude). MS: m/z=376 (M+1).

Step 5: 121-6

To a mixture of 121-5 (440 mg, 1.17 mmol), acetate acid (0.3 mL) in THF (10 mL) was added hydrogen peroxide (0.5 mL, 30% purity) at 20° C. The reaction solution was stirred for 1 hr at 20° C. Then, the solution was concentrated with a rotary evaporator to obtain 121-6 (350 mg, crude). MS: m/z=264 (M-1).

Step 6: 121-7

To a mixture of 121-6 (350 mg, 1.32 mmol), Intermediate A (100 mg, 372.96 μmol) in MeCN (30 mL) was added Cesium carbonate (364.56 mg, 1.12 mmol) at 20° C. The reaction solution was stirred for 1 hr at 90° C. Then, the mixture was filtered, and the filtrate was concentrated with a rotary evaporator to obtain 121-7 (180 mg, crude). MS: m/z=453 (M+1).

Step 7: Compound 121

To a mixture of 121-7 (180 mg, 397.79 μmol) in DCM (20 mL) was added HCl/Dioxane (4 M, 3 mL) at 20° C. and the reaction mixture was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 121 (38 mg, 95.38 mol, 23.98% yield, $HCO_2H$ salt). $^1H$ NMR (400 MHz, Methanol-d4) δ 8.51 (s, 1H), 7.70-7.62 (m, 3H), 7.47 (td, J=6.8, 3.3 Hz, 1H), 7.23 (d, J=81.1 Hz, 1H), 7.12 (d, J=8.9 Hz, 2H), 6.39 (td, J=6.8, 1.4 Hz, 1H), 6.30 (d, J=9.2 Hz, 1H), 5.48 (s, 2H), 4.69 (d, J=3.6 Hz, 2H), 3.79 (d, J=2.4 Hz, 2H) ppm. MS: m/z=352.78 (M+1).

Example 79: Synthesis of Compound 133

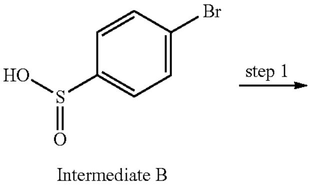

Intermediate B

-continued

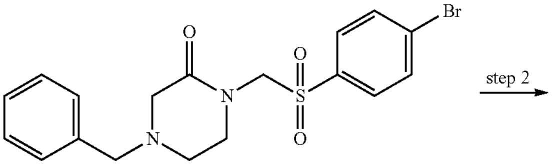

133-1

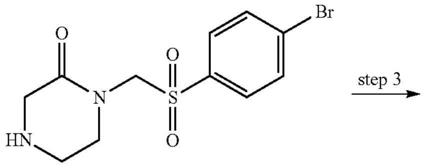

133-2

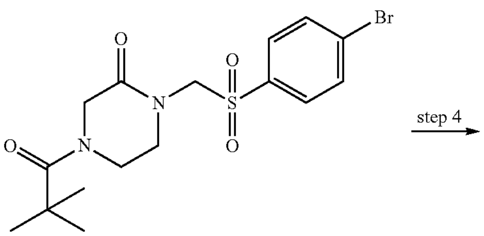

133-3

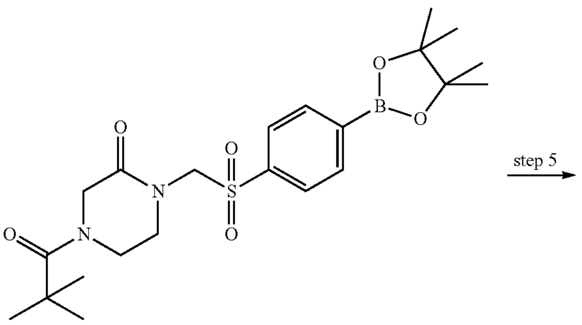

133-4

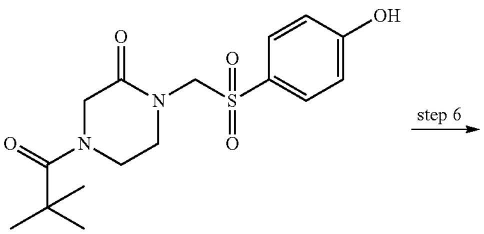

133-5

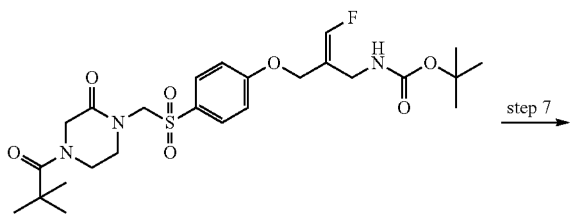

133-6

-continued

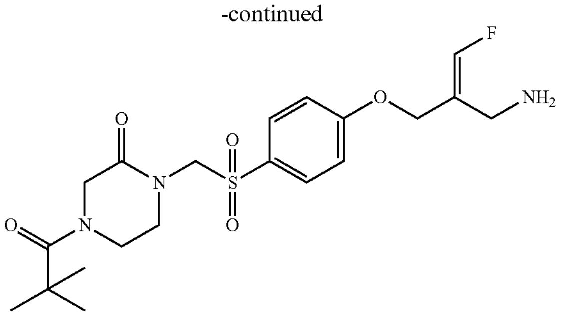

133

Step 1: 133-1

A mixture of 4-benzylpiperazin-2-one (6.45 g, 33.93 mmol), Intermediate A (5 g, 22.62 mmol) and polyformaldehyde (2.04 g, 67.85 mmol) in $HCO_2H$ (20 mL) was heated to 100° C. and stirred at 100° C. for 1 hr. After cooling to room temperature, the reaction was concentrated and purified by column chromatography on silica gel (ethyl acetate in petroleum ether, 10-50%) to give 133-1 (5 g, 11.81 mmol, 52.22% yield). MS: m/z=423.3 (M+1).

Step 2: 133-2

To a mixture of 133-1 (5 g, 11.81 mmol) in DCM (20 mL) was added 1-chloroethyl carbonochloridate (3.38 g, 23.62 mmol, 2.58 mL) at 0° C. The reaction solution was stirred for 8 hr at 90° C. Then, MeOH (50 mL) was added and the solution was concentrated with a rotary evaporator. The crude product was purified by silica gel chromatography (petroleum ether:ethyl acetate=4:1, v/v) to obtain 133-2 (1 g, 3.0 mmol, 25.41% yield). MS: m/z=333.2 (M+1).

Step 3: 133-3

To a mixture of 133-2 (100 mg, 300.12 μmol), 2,2-dimethylpropanoyl chloride (72.37 mg, 600.24 μmol) in DCM (10 mL) was added TEA (91.11 mg, 900.36 μmol, 125.49 ptL) at 0° C. The reaction solution was stirred for 2 hr at 25° C. Then, the solution was concentrated with a rotary evaporator. The crude product was purified by silica gel chromatography (petroleum ether:ethyl acetate=4:1, v/v) to obtain 133-3 (100 mg, 239.63 μmol, 79.84% yield). MS: m/z=317.3 (M+1).

Step 4: 133-4

A 30 mL microwave reaction tube was charged with 4,4,5,5-tetramethyl-2-(4,4,5,5-tetramethyl-1,3,2-dioxaborolan-2-yl)-1,3,2-dioxaborolane (91.28 mg, 359.44 μmol), 133-3 (100 mg, 239.63 μmol), bis(diphenylphosphino)ferrocene]dichloropalladium(II) (17.53 mg, 23.96 μmol) and potassium acetate (70.55 mg, 718.88 μmol) in Dioxane (5 mL). After oxygen was purged by bubbling nitrogen into the reaction solution, the tube was sealed and heated at 120° C. for 0.5 hr in a Biotage microwave reactor. The reaction was cooled to room temperature, filtered and concentrated under reduced pressure. The resultant crude product was purified by flash chromatography (ethyl acetate in petroleum ether, 0-100%) to deliver 133-4 (80 mg, 172.27 μmol, 71.89% yield). MS: m/z=464.3 (M+1).

Step 5: 133-5

To a mixture of 133-4 (80 mg, 172.27 μmol) in THE (1 mL) and acetate acid (0.25 mL) was added hydrogen peroxide (0.5 mL, 30% purity). The mixture was stirred at 25° C. for 0.5 hr. Sodium sulfite (0.6 g) was added to the mixture and stirred for 30 min. The reaction mixture was filtered and concentrated to give 133-5 (0.5 g, crude). MS: m/z=354.4 (M+1).

Step 6: 133-6

To a mixture of 133-6 (0.5 g, 1.41 mmol) and Intermediate A (151.30 mg, 564.30 μmol) in MeCN (50 mL) was added Cesium carbonate (1.38 g, 4.23 mmol) at 20° C. The reaction was stirred for 1 hr at 80° C. Then, the solution was filtered and concentrated to obtain 133-6 (75 mg, crude). MS: m/z=541.6 (M+1).

Step 7: Compound 133

A mixture of 133-6 (75 mg, 138.47 μmol) in HCl/Dioxane (4 M, 3 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 133 (6 mg, 12.31 μmol, 8.89% yield, $HCO_2H$ salf). $^1H$ NMR (400 MHz, Methanol-d4) δ 8.52 (s, 1H), 7.82 (d, J=8.4 Hz, 2H), 7.21 (d, J=80.0 Hz, 1H), 7.17 (d, J=8.6 Hz, 2H), 4.91 (s, 2H), 4.70 (d, J=3.6 Hz, 2H), 4.03 (s, 2H), 3.96 (t, J=5.2 Hz, 2H), 3.77 (d, J=6.4 Hz, 4H), 1.29 (s, 9H) ppm. MS: m/z=541.6 (M+1).

Example 80: Synthesis of Compound 134

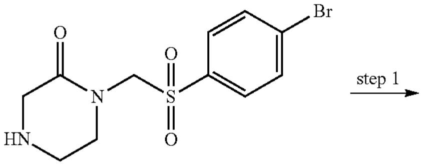

133-2

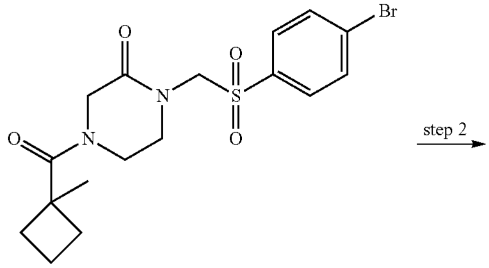

134-1

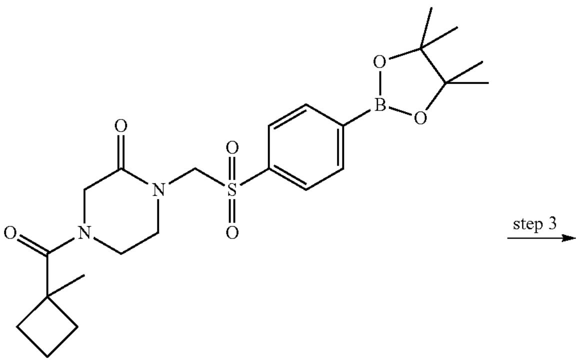

134-2

-continued

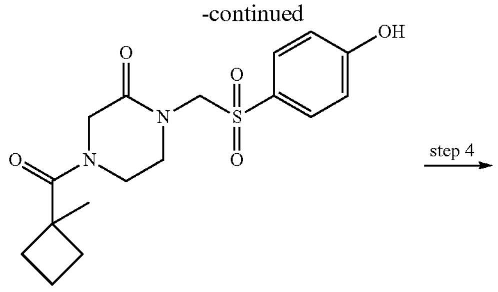

134-3

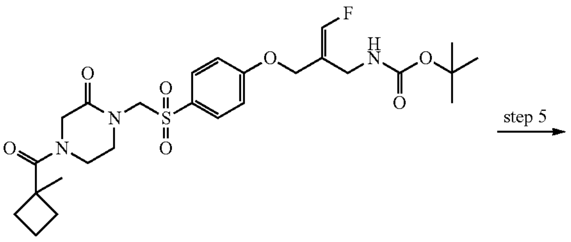

134-4

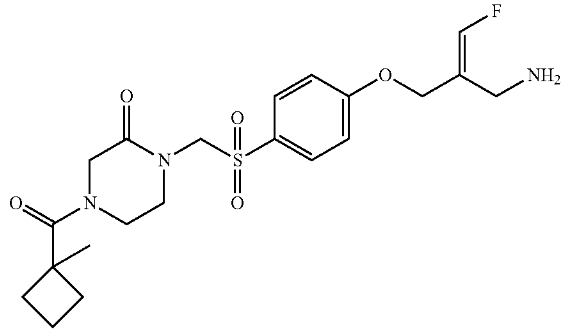

134

Step 1: 134-1

To a mixture of 133-2 (120 mg, 360.14 μmol), 1-methylcyclobutanecarboxylic acid (49.33 mg, 432.17 μmol) and TEA (109.33 mg, 1.08 mmol, 150.59 μL) in DCM (10 mL) was added HATU (205.41 mg, 540.21 μmol) at 0° C. The reaction solution was stirred for 2 hr at 25° C. Then, the solution was concentrated with a rotary evaporator. The crude product was purified by silica gel chromatography (ethyl acetate in petroleum ether, 12-50%, v/v) to obtain 134-1 (100 mg, 232.92 μmol, 64.67% yield). MS: m/z=429.3 (M+1).

Step 2: 134-2

A 30 mL microwave reaction tube was charged with 4,4,5,5-tetramethyl-2-(4,4,5,5-tetramethyl-1,3,2-dioxaborolan-2-yl)-1,3,2-dioxaborolane (88.72 mg, 349.38 μmol), 134-1 (100 mg, 232.92 μmol), bis(diphenylphosphino)ferrocene]dichloropalladium(II) (17.04 mg, 23.29 μmol) and potassium acetate (68.58 mg, 698.77 μmol) in Dioxane (10 mL). After oxygen was purged by bubbling nitrogen into the reaction solution, the tube was sealed and heated at 120° C. for 0.5 hr in a Biotage microwave reactor. The reaction was cooled to room temperature, filtered and concentrated under reduced pressure. The resultant crude product was purified by flash chromatography (ethyl acetate in petroleμme ether, 0-100%) to deliver 134-2 (60 mg, 125.95 μmol, 54.07% yield). MS: m/z=476.3 (M+1).

Step 3: 134-3

To a mixture of 134-2 (60 mg, 125.95 μmol) in THF (1 ml) and acetate acid (0.25 mL) was added hydrogen peroxide (0.5 mL, 30% purity). The mixture was stirred at 25° C. for 0.5 hr. The sodium sulfite (0.6 g) was added to the mixture and stirred for 30 min. The reaction mixture was filtered and concentrated to give 134-3 (0.5 g, crude). MS: m/z=366.4 (M+1).

Step 4: 134-4

To a mixture of 134-3 (0.5 g, 1.36 mmol) and Intermediate A (146.34 mg, 545.81 μmol) in MeCN (50 mL) was added Cesium carbonate (1.33 g, 4.09 mmol) at 20° C. The reaction was stirred for 1 hr at 80° C. Then, the solution was filtered and concentrated to obtain 134-4 (90 mg, crude).

Step 5: Compound 134

A mixture of 134-4 (90 mg, 162.56 μmol) in HCl/Dioxane (4 M, 3 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-35% B; GT: 15 min; flow rate: 15 mL/min) to obtain Compound 134 (9 mg, 18.02 μmol, 11.08% yield, $HCO_2H$ salt). $^1H$ NMR (400 MHz, Methanol-$d_4$) δ 8.50 (s, 1H), 7.82 (d, J=8.4 Hz, 2H), 7.24 (d, J=80.0 Hz, 1H), 7.18 (d, J=8.4 Hz, 2H), 4.73-4.69 (m, 2H), 4.60-4.57 (m, 2H), 3.94-3.89 (m, 2H), 3.84-3.80 (m, 2H), 3.73 (d, J=3.2 Hz, 4H), 2.53-2.49 (m, 2H), 2.06-2.03 (m, 1H), 1.95-1.90 (m, 2H), 1.79-1.76 (m, 1H), 1.43 (s, 3H) ppm. MS: m/z=454.6 (M+1).

Example 81: Synthesis of Compound 135

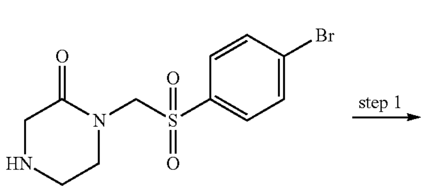

133-2

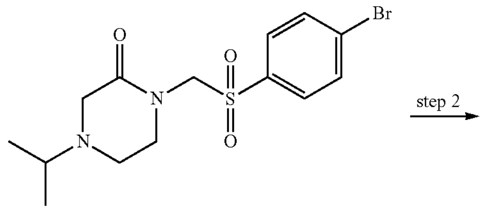

135-1

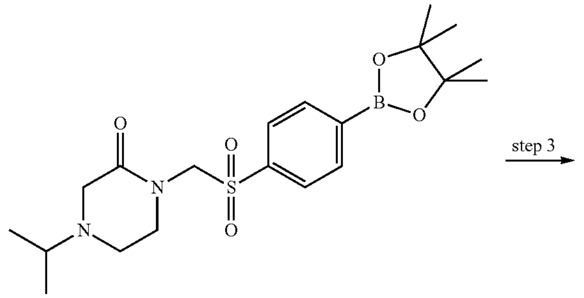

135-2

-continued

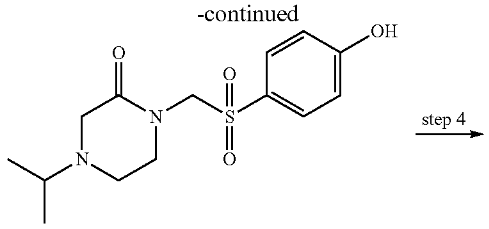

135-3

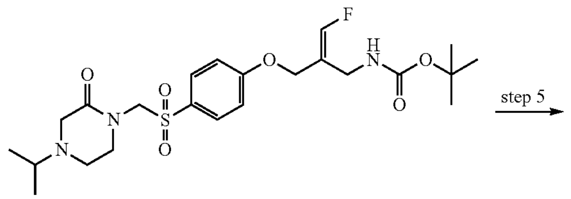

135-4

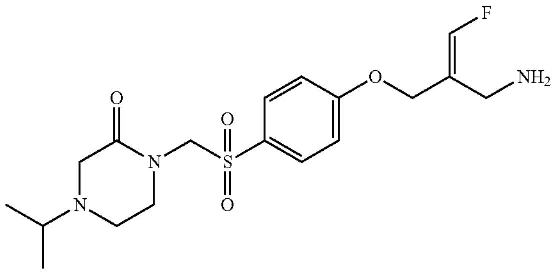

135

Step 1: 135-1

To a mixture of 2-iodopropane (459.16 mg, 2.70 mmol, 270.09 μL), 133-2 (300 mg, 900.36 μmol) in MeCN (10 mL) was added TEA (273.32 mg, 2.70 mmol, 376.48 μL) at 20° C. The reaction solution was stirred for 6 hr at 80° C. Then, the solution was concentrated with a rotary evaporator. The crude product was purified by silica gel chromatography (ethyl acetate in petroleum ether, 20-50%, v/v) to obtain 135-1 (100 mg, 266.47 μmol, 29.60% yield). MS: m/z=375.2 (M+1).

Step 2: 135-2

To a mixture of 4,4,5,5-tetramethyl-2-(4,4,5,5-tetramethyl-1,3,2-dioxaborolan-2-yl)-1,3,2-dioxaborolane (101.50 mg, 399.70 μmol), 135-1 (100 mg, 266.47 μmol) and bis(diphenylphosphino)ferrocene]dichloropalladium(II) (19.50 mg, 26.65 μmol) in Dioxane (5 mL) was added potassium acetate (80.07 mg, 799.40 μmol) at 20° C. under the nitrogen atmosphere. The reaction solution was stirred for 4 hr at 100° C. Then, the solution was concentrated with a rotary evaporator and purified by column chromatography on silica gel (ethyl acetate in petroleum ether, 10-50%, v/v) to obtain 135-2 (80 mg, 189.42 μmol, 71.09% yield). MS: m/z=422.3 (M+1).

Step 3: 135-3

To a mixture of 135-2 (80 mg, 189.42 μmol) in THF (2 mL) and acetate acid (0.5 mL) was added hydrogen peroxide (1 mL, 30% purity). The mixture was stirred at 25° C. for 0.5 hr. Sodium sulfite (0.3 g) was added to the mixture and stirred for 0.5 hr. The reaction mixture was filtered and concentrated to give 135-3 (400 mg, crude). MS: m/z=312.3 (M+1).

Step 4: 135-4

To a mixture of 135-3 (400 mg, 1.28 mmol) and Intermediate A (137.33 mg, 512.19 mol) in MeCN (20 mL) was added Cesium carbonate (834.41 mg, 2.56 mmol) at 20° C. The reaction was stirred for 1 hr at 80° C. Then, the solution was filtered and concentrated to obtain 135-4 (60 mg, 120.10 μmol, 9.38% yield). MS: m/z=499.5 (M+1).

Step 5: Compound 135

A mixture of 135-4 (60 mg, 120.10 μmol) in HCl/Dioxane (4 M, 3 mL) was stirred at 20° C. for 1 hr. Then, the solution was concentrated with a rotary evaporator. The crude product was purified by prep-HPLC (column: XBridge@ Prep C18 5 μm 19×150 mm; A: 0.1% $HCO_2H$ water, B: acetonitrile; gradient: 5-30% B; GT: 15 min; flow rate: 15 mL/min) to obtain Compound 135 (3 mg, 7.51 μmol, 6.25% yield, $HCO_2H$ salt). $^1H$ NMR (400 MHz, Methanol-d4) δ 8.54 (s, 1H), 7.91-7.85 (m, 2H), 7.21 (d, J=80.0 Hz, 1H), 7.19 (d, J=9.0 Hz, 2H), 4.72 (d, J=3.6 Hz, 2H), 4.61 (d, J=6.7 Hz, 2H), 3.91-3.85 (m, 2H), 3.77 (d, J=2.4 Hz, 2H), 3.61-3.55 (m, 2H), 3.49 (s, 1H), 3.14 (s, 1H), 2.23-2.16 (m, 1H), 1.22-1.18 (d, J=8.0 Hz, 6H) ppm. MS: m/z=400.1 (M+1).

Example 82: Synthesis of Compound 136 & 137

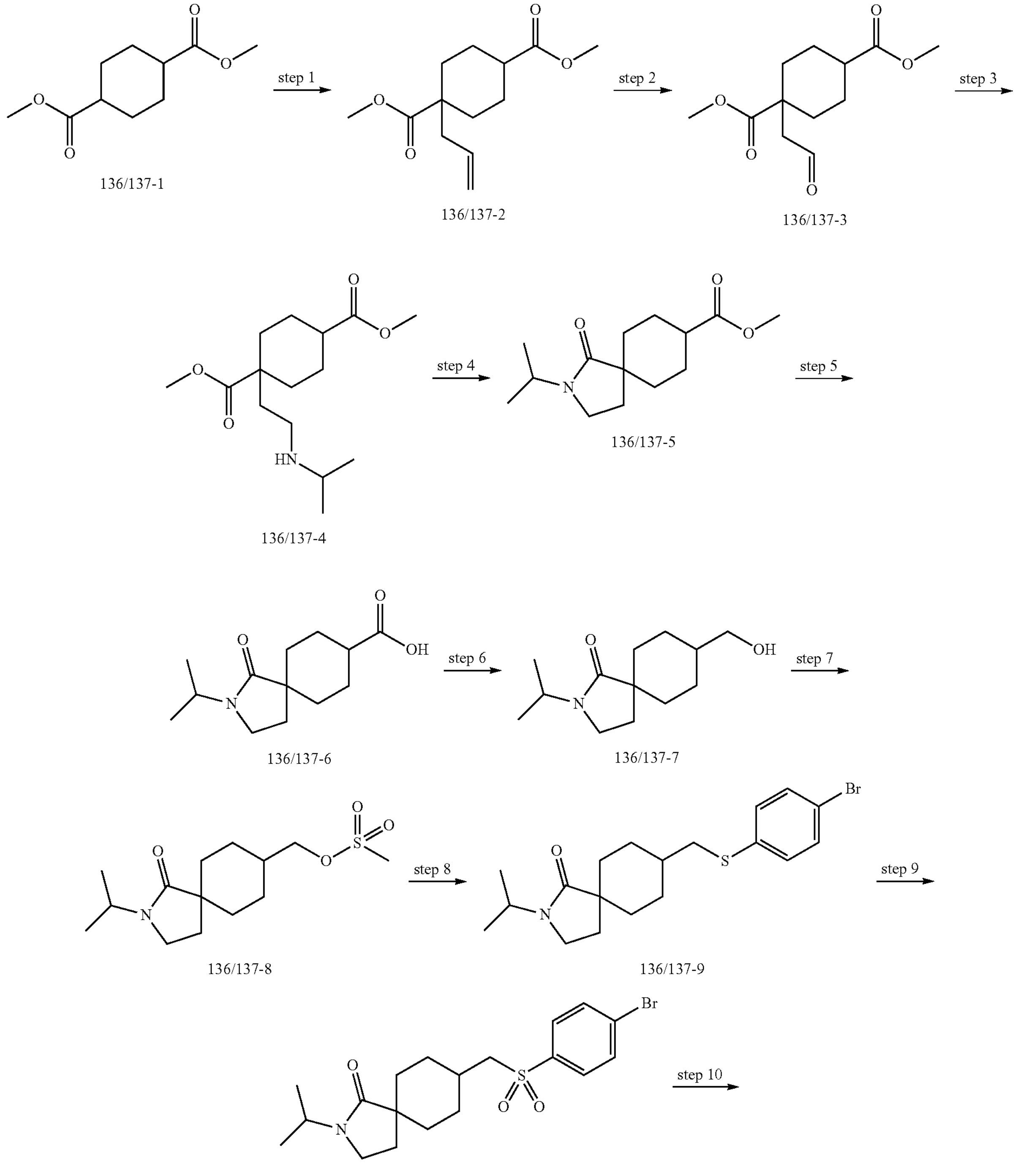

136/137-1 136/137-2 136/137-3

136/137-4 136/137-5

136/137-6 136/137-7

136/137-8 136/137-9

136/137-10

-continued
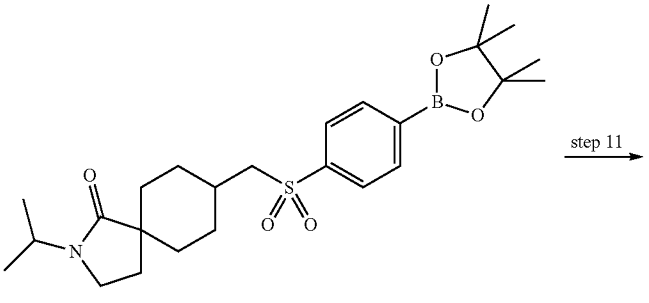
136/137-11
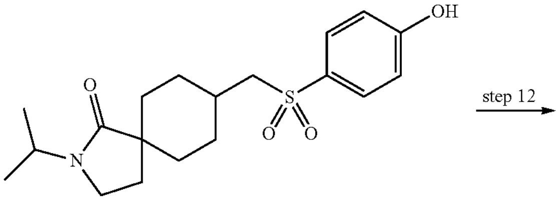
136/137-12
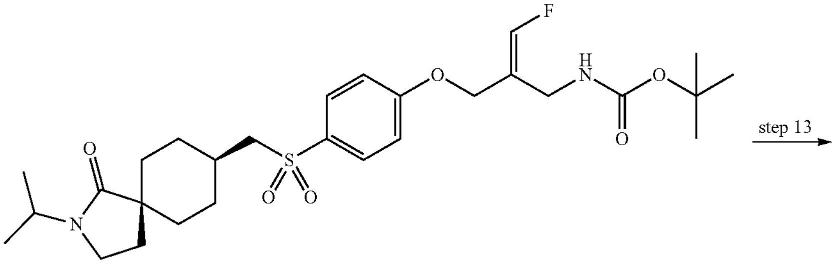
136-13
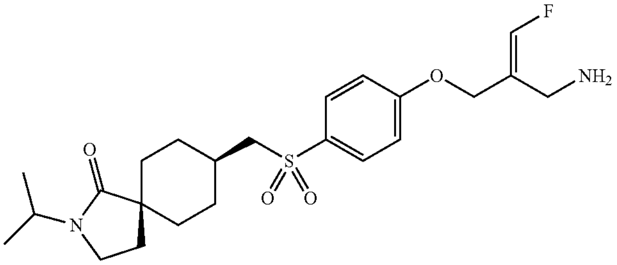
136
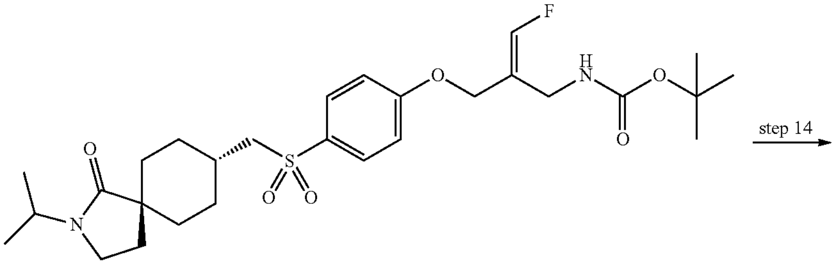
137-13

-continued

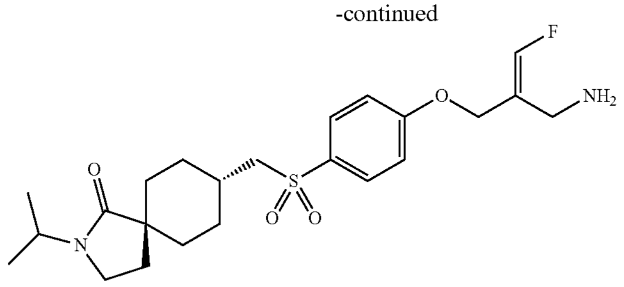

137

Step 1: 136/137-2

To a mixture of N-isopropylpropan-2-amine (606.44 mg, 5.99 mmol, 844.62 μL) in THF (30 mL) was added butyl lithium (2.5 M, 2.40 mL) under the $N_2$ atmosphere at −78° C. The solution was stirred for 15 minutes, warmed up to 0° C. and stirred for an additional 1 hr, then re-cooled to −78° C. Then, 136/137-1 (1 g, 4.99 mmol, 900.90 μL) in THF (2 mL) was added and the reaction mixture was stirred at −78° C. for 1 hr followed by the additional of a mixture of HMPA (671.22 mg, 3.75 mmol, 651.67 μL) and 3-iodoprop-1-ene (1.01 g, 5.99 mmol, 547.12 μL). The reaction solution was stirred for 1 hr at −78° C. Then, the dry ice bath was removed and the stirring was continued to allow the reaction mixture to warm to room temperature (~25° C.) over 1 hr. The reaction mixture was poured into ice-water (20 mL) and ethyl acetate (30 mL). The two layers were separated and the aqueous layer was extracted with ethyl acetate (50 mL×3). The combined organic layers were washed with brine (50 mL×3), dried over anhydrous sodium sulfate, filtered and concentrated with a rotary evaporator to obtain crude 136/137-2 (1.2 g, 4.99 mmol, 99.99% yield). The crude was used in the next step directly without further purification. $^1H$ NMR (400 MHz, Chloroform-d) δ 5.71-5.62 (m, 1H), 5.07-4.97 (m, 2H), 3.68 (s, 3H), 3.64 (s, 3H), 2.36-2.22 (m, 3H), 2.21-2.19 (m, 2H), 1.94-1.84 (m, 2H), 1.58-1.42 (m, 2H), 1.22-1.14 (m, 2H) ppm.

Step 2: 136/137-3

To a mixture of 136/137-2 (1.2 g, 4.99 mmol) in water (15 mL) and 2-propanol (30 mL) was added an aqueous solution of sodium periodate (2.67 g, 12.48 mmol) in water (15 mL), followed by addition of potassium osmate(VI) dihydrate (184.0 mg, 499.39 μmol). The reaction mixture was stirred at 25° C. for 2 hr. The reaction mixture was poured into ice-water (20 mL) and ethyl acetate (30 mL). The two layers were separated and the aqueous layer was extracted with ethyl acetate (50 mL×3). The combined organic layers were washed with brine (50 mL×3), dried over anhydrous sodium sulfate, filtered and concentrated with a rotary evaporator to obtain crude 136/137-3 (0.9 g, 3.71 mmol, 74.39% yield). MS: m/z=243.1 (M+1).

Step 3: 136/137-4

To a mixture of 136/137-3 (0.9 g, 3.71 mmol) in MeOH (30 mL) was added propan-2-amine (263.50 mg, 4.46 mmol, 381.34 μL). The reaction mixture was stirred at 25° C. for 0.5 hr, followed by addition of Sodium Cyanoborohydride (350.17 mg, 5.57 mmol). The reaction mixture was stirred at 25° C. for 2 hr. The reaction mixture was poured into ice-water (20 mL) and ethyl acetate (30 mL). The two layers were separated and the aqueous layer was extracted with ethyl acetate (50 mL×3). The combined organic layers were washed with brine (50 mL×3), dried over anhydrous sodium sulfate, filtered and concentrated with a rotary evaporator to obtain a crude, which was purified by silica gel chromatography (ethyl acetate in petroleum ether: 0~20%, v/v) to give 136/137-4 (1.2 g, crude). MS: m/z=286.2 (M+1).

Step 4: 136/137-5

To a mixture of 136/137-4 (1.2 g, 4.20 mmol) in methanol (20 mL) was added potassium carbonate (1.16 g, 8.41 mmol). The reaction mixture was heated to 80° C. and stirred for 16 hr. The reaction mixture was filtered and concentrated with a rotary evaporator to obtain a crude, which was purified by silica gel chromatography (ethyl acetate in petroleum ether: 0~30%, v/v) to give 136/137-5 (200 mg, 789.46 μmol, 18.77% yield). MS: m/z=254.2 (M+1).

Step 5: 136/137-6

To a mixture of 136/137-5 (200 mg, 789.46 μmol) in water (5 mL) and THF (5 mL) was added Lithium hydroxide, monohydrate (165.63 mg, 3.95 mmol). The reaction mixture was stirred at 25° C. for 3 hr. Then pH of the reaction mixture was adjusted to ~5 with 1 M HCl and the mixture was extracted with ethyl acetate (20 mL×3). The combined organic layers were washed with brine (20 mL×3), dried over sodium sulfate, filtered and concentrated with a rotary evaporator to obtain 136/137-6 (180 mg, 752.16 μmol, 95.28% yield). MS: m/z=240.2 (M+1).

Step 6: 136/137-7

To a mixture of 136/137-6 (180 mg, 752.16 μmol) in THF (5 mL) was added Borane-tetrahydrofuran complex (1 M, 1.13 mL) at 0° C. under the nitrogen atmosphere dropwise. The reaction mixture was stirred for 2 hr at 25° C. Then, to the reaction mixture was added MeOH (20 mL) at 0~25° C. dropwise. The reaction mixture was stirred at room temperature for 0.5 hr, and concentrated with a rotary evaporator to obtain 136/137-7 (180 mg, crude). MS: m/z=226.2 (M+1).

Step 7: 136/137-8

To a mixture of crude 136/137-7 (180 mg, 798.84 μmol), Triethylamine (242.50 mg, 2.40 mmol, 334.03 μL) in DCM (15 mL) was added Methanesulfonic anhydride (208.74 mg, 1.20 mmol) at 0° C. The reaction solution was stirred for 2 hr at 25° C. Then, the solution was concentrated with a rotary evaporator to obtain 136/137-8 (250 mg, crude). MS: m/z=304.2 (M+1).

Step 8: 136/137-9

To a mixture of crude 136/137-8 (250 mg, 823.95 μmol), Cesium carbonate (671.15 mg, 2.06 mmol) and Potassium iodide (68.39 mg, 411.97 μmol) in DMF (10 mL) was added 4-bromobenzenethiol (311.57 mg, 1.65 mmol) under the nitrogen atmosphere. The reaction mixture was heated at 65° C. for 4 hr. Ethyl acetate (50 mL) and water (50 mL) were added, the organic layer was washed with brine (50 mL×4), dried over $Na_2SO_4$, filtered and concentrated to give a crude, which was purified by column chromatography (ethyl acetate in petroleum ether: 0~25%, v/v) to give 136/137-9 (200 mg, 504.56 μmol, 61.24% yield). MS: m/z=396.1 (M+1).

Step 9: 136/137-10

To a mixture of 136/137-9 (200 mg, 504.56 μmol) and m-CPBA (307.31 mg, 1.51 mmol, 85% purity) in DCM (20 mL) was stirred at 20° C. for 2 hr. $Na_2SO_3$ (5 g) was added to the mixture and stirred for 20 minutes. Then, to the solution was added DCM (50 mL) and water (50 mL). The organic layer was washed with aqueous $NaHCO_3$ (50 mL×3), brine (50 mL×3), dried over $Na_2SO_4$, filtered, and concentrated to give a crude, which was purified by column chromatography (ethyl acetate in petroleum ether: 0-35%, v/v) to give 136/137-10 (190 mg, 443.53 μmol, 87.90% yield). MS: m/z=428.1 (M+1).

Step 10: 136/137-11

A mixture of 4,4,5,5-tetramethyl-2-(4,4,5-trimethyl-1,3, 2-dioxaborolan-2-yl)-1,3,2-dioxaborolane (127.69 mg, 532.23 μmol), 136/137-10 (190 mg, 443.53 μmol), bis (diphenylphosphino)ferrocene]dichloropalladium(II) (32.45 mg, 44.35 μmol) and Potassium acetate (130.58 mg, 1.33 mmol) in Dioxane (5 mL) was heated at 80° C. for 2 hr under the nitrogen atmosphere. The reaction was cooled to room temperature, filtered and concentrated under reduced pressure to give 136/137-11 (250 mg, crude).

Step 11: 136/137-12

To a mixture of crude 136/137-11 (250 mg, 525.82 μmol), Acetate acid (630.98 mol, 0.3 mL) in THF (5 mL) was added Hydrogen peroxide (330.0 mg, 2.91 mmol, 0.3 mL, 30% purity) at 20° C. The reaction solution was stirred for 0.5 hr at 20° C. Then, the solution was concentrated with a rotary evaporator to obtain a crude, which was purified by column chromatography (MeOH in DCM: 0~15%, v/v) to obtain 136/137-12 (144 mg, 394.0 μmol, 74.93% yield).

Step 12: 136/137-13

To a mixture of 136/137-12 (144 mg, 394.0 μmol), Intermediate A (114.09 mg, 425.52 μmol) in Acetonitrile (8 mL) was added potassium carbonate (108.91 mg, 787.99 μmol) at 20° C. The reaction solution was stirred for 1 hr at 90° C. Then, the mixture was filtered and concentrated with a rotary evaporator to obtain a crude, which was purified by prep-TLC (petroleum ether:ethyl acetate=1:1) to give 136-13 (or 137-13, 100 mg, 180.93 μmol, 45.92% yield) and 137-13 (or 136-13, 50 mg, 90.47 μmol, 22.96% yield). MS: m/z=497.2 (M+1-56).

Step 13: Compound 136 or 137

To a mixture of 136-13 (or 137-13, 100 mg, 180.93 μmol) in DCM (5 mL) was added HCl/dioxane (4 M, 2 mL) at 20° C. and stirred for 1 hr. The reaction mixture was filtered. The filter cake was slurried with acetonitrile (3 mL) for 15 minutes and filtered. The solid was dried by lyophilization (water:acetonitrile=4:1, 20 mL) to give Compound 136 or Compound 137 (68.1 mg, 139.04 μmol, 76.85% yield, HCl salt). $^1H$ NMR (400 MHz, Methanol-d4) δ 7.88 (d, J=8.6 Hz, 2H), 7.27 (d, J=80.0 Hz, 1H), 7.23 (d, J=8.6 Hz, 2H), 4.73 (d, J=3.5 Hz, 2H), 4.24-4.15 (m, 1H), 3.86-3.81 (m, 2H), 3.30-3.21 (m, 4H), 2.12 (dd, J=8.8, 4.2 Hz, 1H), 1.86 (t, J=6.9 Hz, 2H), 1.79-1.62 (m, 6H), 1.31-1.25 (m, 2H), 1.12 (d, J=6.8 Hz, 6H) ppm. MS: m/z=453.3 (M+1).

Step 14: Compound 137 or 136

To a mixture of 137-13 (or 136-13, 50 mg, 90.47 μmol) in DCM (5 mL) was added HCl/Dioxane (4 M, 2.0 mL) at 20° C. and stirred for 1 hr. The reaction mixture was filtered. The filter cake was slurried with acetonitrile (3 mL) for 15 minutes and filtered. The solid was dried by lyophilization (water:acetonitrile=4:1, 20 mL) to give Compound 137 or Compound 136 (32 mg, 65.43 μmol, 72.3% yield, HCl salt). $^1H$ NMR (400 MHz, Methanol-d4) δ 7.92-7.86 (m, 2H), 7.28 (s, J=80.0 Hz, 1H), 7.28-7.21 (m, 2H), 4.74 (d, J=3.5 Hz, 2H), 4.24-4.18 (m, 1H), 3.85 (d, J=2.3 Hz, 2H), 3.30 (d, J=5.6 Hz, 2H), 3.13 (d, J=6.0 Hz, 2H), 1.93 (t, J=6.9 Hz, 2H), 1.88-1.80 (m, 2H), 1.78-1.72 (m, 1H), 1.59-1.51 (m, 2H), 1.47-1.37 (m, 2H), 1.30-1.25 (m, 1H), 1.25-1.19 (m, 1H), 1.13 (d, J=6.8 Hz, 6H) ppm. MS: m/z=453.2 (M+1).

Example 83: Synthesis of Compound 138

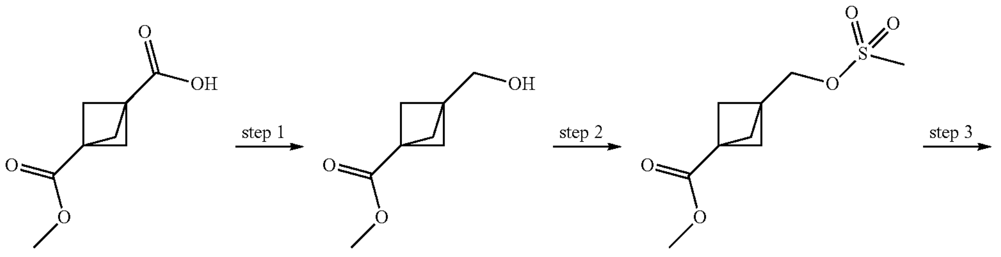

138-1 138-2 138-3

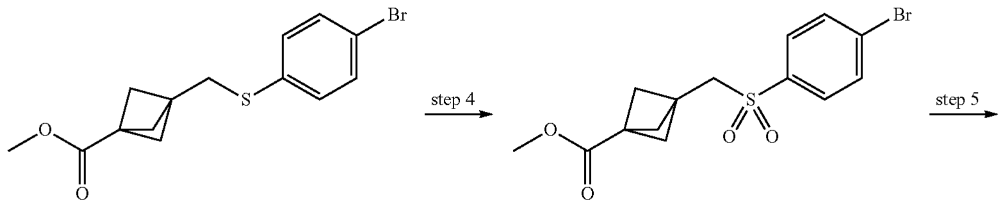

138-4 138-5

-continued
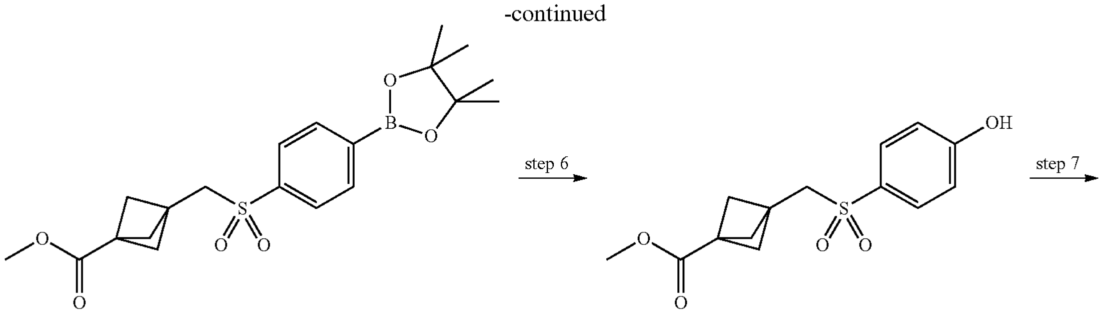
138-6 138-7
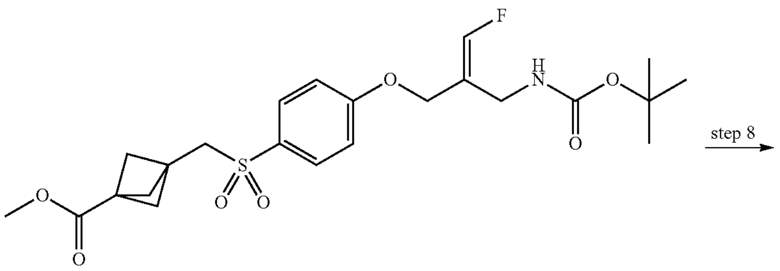
138-8
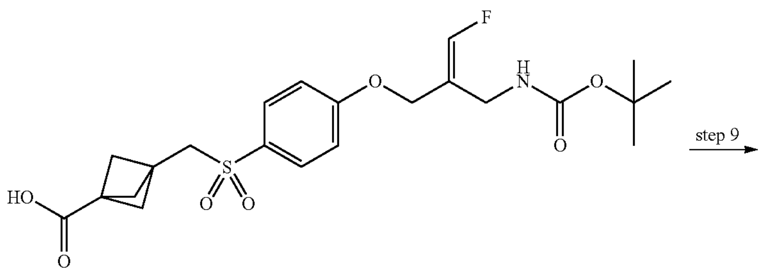
138-9
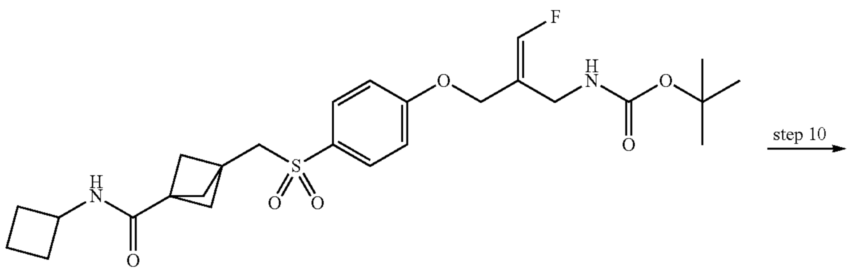
138-10
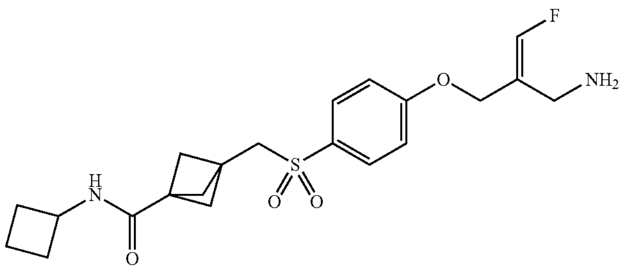
138

Step 1: 138-2

To a mixture of 138-1 (1 g, 5.88 mmol) in THF (20 mL) was added Borane-tetrahydrofuran complex (1 M, 17.63 mL) at 0° C. under the nitrogen atmosphere dropwise. The reaction mixture was stirred for 2 hr at 25° C. Then, to the reaction mixture was added MeOH (20 mL) at 0-25° C. dropwise. The reaction mixture was stirred at room temperature (~25° C.) for 0.5 hr and concentrated with a rotary evaporator to obtain crude 138-2 (900 mg, 5.76 mmol, 98.06% yield).

Step 2: 138-3

To a mixture of 138-2 (900 mg, 5.76 mmol), Triethylamine (1.75 g, 17.29 mmol, 2.41 mL) in DCM (20 mL) was added Methanesulfonic anhydride (1.51 g, 8.64 mmol) at 0° C. The reaction solution was stirred for 2 hr at 25° C. Then, the solution was concentrated and purified by column chromatography (ethyl acetate in petroleum ether: 0~40%, v/v) to obtain 138-3 (1.25 g, 5.34 mmol, 92.59% yield).

Step 3: 138-4

To a solution of 4-bromobenzenethiol (2.52 g, 13.34 mmol), Cesium carbonate (5.22 g, 16.01 mmol) and Potassium iodide (442.87 mg, 2.67 mmol) in DMF (10 mL) was added 138-3 (1.25 g, 5.34 mmol) under the nitrogen atmosphere. The reaction mixture was heated at 55° C. for 3 hr. Ethyl acetate (100 mL) and $H_2O$ (50 mL) were added, the organic layer was washed with brine (50 mL×4), dried over $Na_2SO_4$, filtered and concentrated to a crude, which was purified by column chromatography (ethyl acetate in petroleum ether, 0~15%) to give 138-4 (1.2 g, 3.67 mmol, 68.73% yield).

Step 4: 138-5

To a mixture of 138-4 (1.2 g, 3.67 mmol) and m-CPBA (2.23 g, 11.00 mmol, 85% purity) in DCM (20 mL) was stirred at 20° C. for 2 hr. $Na_2SO_3$ (5 g) was added to the mixture and stirred for 20 minutes. Then, to the solution was added DCM (100 mL) and water (100 mL). The organic layer was washed with aqueous $NaHCO_3$ (50 mL×3), brine (50 mL×3), dried over $Na_2SO_4$, filtered, concentrated to give a crude, which was purified by column chromatography (ethyl acetate in petroleum ether: 0~40%) to give 138-5 (920 mg, 2.56 mmol, 69.84% yield).

Step 5: 138-6

A 30 mL microwave reaction tube was charged with 138-5 (920 mg, 2.56 mmol), 4,4,5,5-tetramethyl-2-(4,4,5,5-tetramethyl-1,3,2-dioxaborolan-2-yl)-1,3,2-dioxaborolane (780.40 mg, 3.07 mmol), bis(diphenylphosphino)ferrocene] dichloropalladium(II) (187.39 mg, 256.10 mol) and Potassium Acetate (754.01 mg, 7.68 mmol) in Dioxane (10 mL). After $O_2$ was purged by bubbling $N_2$ into the reaction solution, the tube was sealed and heated at 120° C. for 0.5 hr in a Biotage microwave reactor. The reaction was cooled to room temperature, filtered and concentrated under reduced pressure to give 138-6 (1.5 g, crude). The crude product was used into the next step directly without further purification.

Step 6: 138-7

To a mixture of crude 138-6 (1.5 g, 3.69 mmol) and Acetate acid (3.69 mmol, 0.4 mL) in THF (3 mL) was added Hydrogen peroxide (440.0 mg, 3.88 mmol, 0.4 mL, 30% purity) at 20° C. The reaction solution was stirred for 0.5 hr at 20° C. Then, the solution was concentrated with a rotary evaporator to obtain a crude, which was purified by column chromatography (ethyl acetate in petroleum ether: 0~ 65%) to give 138-7 (600 mg, 2.02 mmol, 54.84% yield).

Step 7: 138-8

To a mixture of 138-7 (600 mg, 2.02 mmol), Intermediate A (651.45 mg, 2.43 mmol) in Acetonitrile (5 mL) was added Cesium carbonate (1.32 g, 4.05 mmol) at 20° C. The reaction solution was stirred for 1 hr at 95° C. Then, the mixture was filtered and the filtrate was concentrated with a rotary evaporator to obtain a crude, which was purified by column chromatography (ethyl acetate in petroleum ether: 0~45%, v/v) to obtain 138-8 (430 mg, 889.26 μmol, 43.92% yield).

Step 8: 138-9

To a mixture of 138-8 (430 mg, 889.26 μmol) in Water (6 mL) and THF (6 mL) was added Lithium hydroxide monohydrate (373.13 mg, 8.89 mmol) at 20° C. The reaction solution was heated to 55° C. and stirred for 8 hr. Then, pH of the mixture was adjusted to ~5 with 1 M HCl. The reaction mixture was extracted with ethyl acetate (20 mL×3). The combined organic layers were washed with brine (20 mL×2), dried over sodium sulfate, filtered and concentrated to give 138-9 (350 mg, 745.44 μmol, 83.83% yield).

Step 9: 138-10

To a mixture of cyclobutanamine (63.62 mg, 894.52 μmol, 76.37 lL), 138-9 (350 mg, 745.44 μmol) in DCM (10 mL) was added HATU (340.13 mg, 894.52 μmol) and Triethylamine (226.29 mg, 2.24 mmol, 311.7 μL) at 25° C. The reaction solution was stirred for 2 hr at 25° C. The reaction mixture was concentrated to give a crude, which was purified by column chromatography (ethyl acetate in petroleum ether: 0~ 100%, v/v) to obtain 138-10 (300 mg, 574.02 μmol, 77.0% yield).

Step 10: Compound 138

A mixture of 138-10 (300 mg, 574.02 μmol) and Hydrochloric acid/dioxane (4 M, 1 mL) was stirred for 1 hr at 20° C. The mixture was concentrated, slurried in $CH_3CN$ (6 mL) and filtered. The cake was dissolved in water and freeze-dried to give Compound 138 (147.9 mg, 322.24 μmol, 56.14% yield, HCl salt). $^1H$ NMR (400 MHz, Methanol-$d_4$) δ 7.92-7.85 (m, 2H), 7.28 (d, J=84.0 Hz, 1H), 7.27-7.20 (m, 2H), 4.73 (dd, J=3.6, 1.0 Hz, 2H), 4.30-4.20 (m, 1H), 3.84 (d, J=2.3 Hz, 2H), 3.49 (s, 2H), 2.25-2.15 (m, 2H), 2.04-1.93 (m, 8H), 1.75-1.62 (m, 2H) ppm. MS: m/z=423.3 (M+1).

The compounds of Formula (I') or (I) in Table 16 below were made according to Example 83 of Compound 138 (using 139-1 instead of intermediate A)

TABLE 16

| Cmpd No. | $^1H$ NMR and/or LC/MS data |
|---|---|
| 140 | $^1H$ NMR (400 MHz, Methanol-$d_4$) δ 8.54 (s, 1H), 7.88 (d, J = 8.9 Hz, 2H), 7.23 (d, J = 8.9 Hz, 2H), 7.11 (d, J = 84.0 Hz, 1H), 4.90(s, 2H), 4.30-4.26 (m, 1H), 3.64 (d, J = 3.0 Hz, 2H), 3.10 (s, 2H), 2.29-2.20 (m, 2H), 2.04-1.93 (m, 2H), 1.84-1.66 (m, 14H) ppm. MS: m/z = 465.3 (M + 1). |
| 141 | $^1H$ NMR (400 MHz, Methanol-$d_4$) δ 8.55 (s, 1H), 7.88 (d, J = 8.8 Hz, 2H), 7.23 (d, J = 8.8 Hz, 2H), 7.11 (d, J = 84.0 Hz, 1H), 6.41 (s, 1H), 4.90 (s, 2H), 3.63 (d, J = 3.0 Hz, 2H), 3.09 (s, 2H), 1.78-1.74 (m, 12H), 1.32 (s, 9H) ppm. MS: m/z = 467.3 (M + 1). |

Example 84: Synthesis of Compound 139

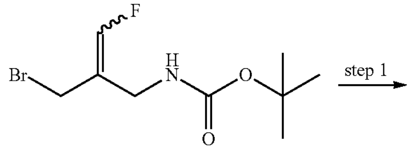

139-1

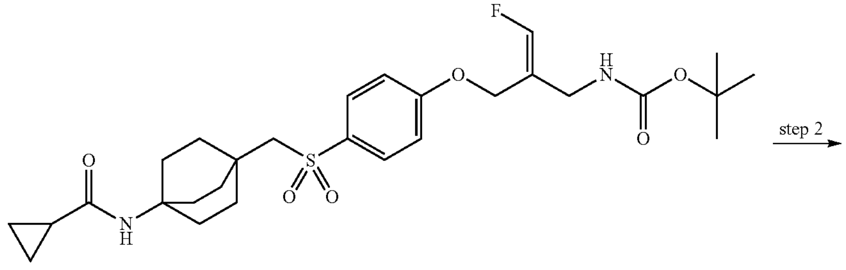

139-2

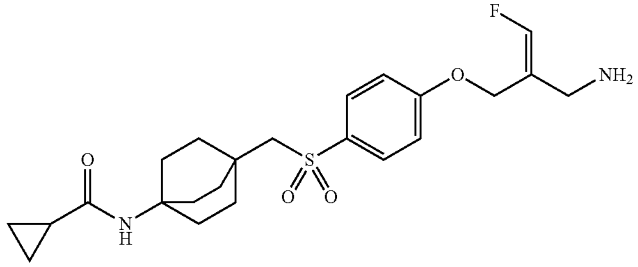

139

Step 1: 139-2

To a mixture of 76-3 (60 mg, 165.08 μmol), 139-1 (57.54 mg, 214.60 μmol, Z/E=1/1, synthesized according to methods known in the art, such as the methods described in WO 2013/163675 A1) in Acetonitrile (10 mL) was added Cesium carbonate (161.36 mg, 495.24 μmol) at 25° C. The reaction solution was stirred for 1 hr at 90° C. Then, the mixture was filtered and the filtrate was concentrated with a rotary evaporator to obtain a crude, which was purified by column chromatography (petroleum ether:ethyl acetate=1:2) to obtain 139-2 (32 mg, 58.11 μmol, 35.2% yield).

Step 2: Compound 139

To a mixture of 139-2 (32 mg, 58.11 μmol) in dichloromethane (10 mL) was added HCl/Dioxane (4 M, 1 mL) at 25° C. and stirred for 2 hr. Then, the solution was concentrated to obtain a crude, which was purified by prep-HPLC (column: XBridge@ Prep C18 5 μm 19×150 mm; A: 0.2% $HCO_2H$ water, B: acetonitrile; gradient: 5-75% B; GT: 18 min; flow rate: 15 mL/min) to obtain Compound 139 (15.3 mg, 33.96 μmol, 58.44% yield, HCOOH salt). $^1$H NMR (400 MHz, Methanol-d4) δ 8.52 (s, 1H), 7.93-7.85 (m, 2H), 7.29-7.20 (m, 2H), 7.12 (d, J=80.0 Hz, 1H), 4.93 (s, 2H), 3.68 (d, J=3.1 Hz, 2H), 3.08 (s, 2H), 1.98-1.87 (m, 6H), 1.84-1.74 (m, 6H), 1.53 (td, J=8.1, 4.0 Hz, 1H), 0.75 (dt, J=4.7, 3.0 Hz, 2H), 0.70-0.63 (m, 2H) ppm. MS: m/z=451.2 (M+1).

The compounds of Formula (I') or (I) in Table 17 below were made according to Example 84 of Compound 139

TABLE 17

| Cmpd No. | $^1$H NMR and/or LC/MS data |
|---|---|
| 142 | $^1$H NMR (400 MHz, Methanol-$d_4$) δ 8.51 (s, 1H), 7.92-7.85 (m, 2H), 7.26-7.20 (m, 2H), 7.12 (d, J = 80.0 Hz, 1H), 6.33 (s, 1H), 4.92 (d, J = 2.9 Hz, 2H), 3.68 (d, J = 2.9 Hz, 2H), 3.09 (s, 2H), 1.93-1.88 (m, 6H), 1.81-1.74 (m, 6H), 1.14 (s, 9H) ppm. MS: m/z = 467.3 (M + 1). |

Example 85: Synthesis of Compound 143

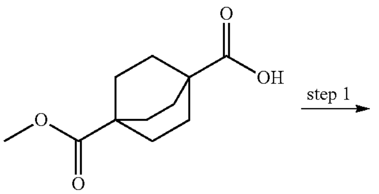

143-1

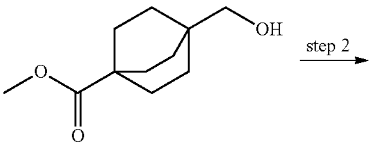

143-2

-continued
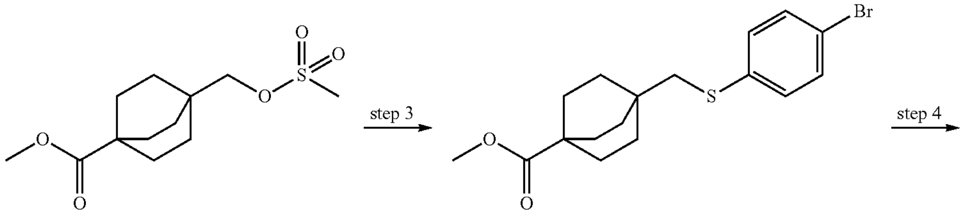
143-3 143-4
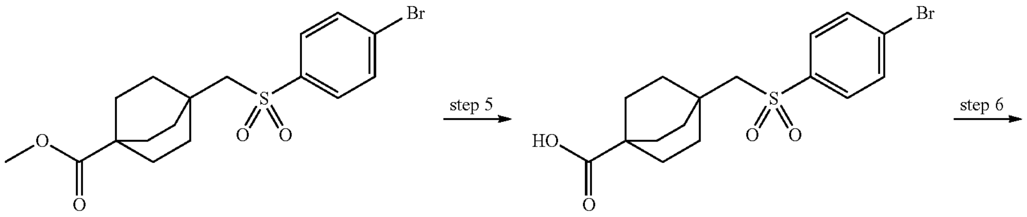
143-5 143-6
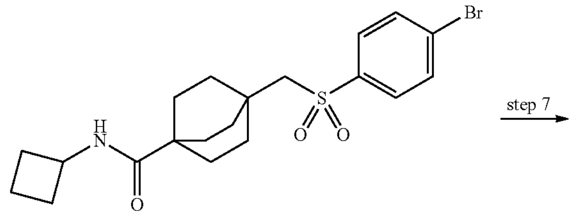
143-7
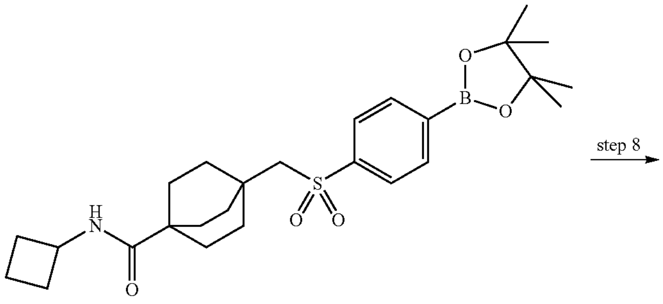
143-8
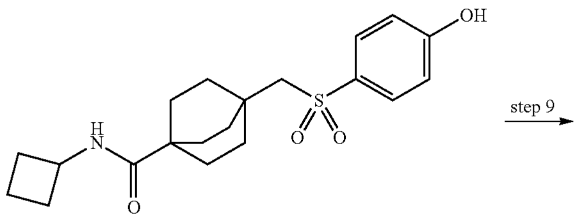
143-9
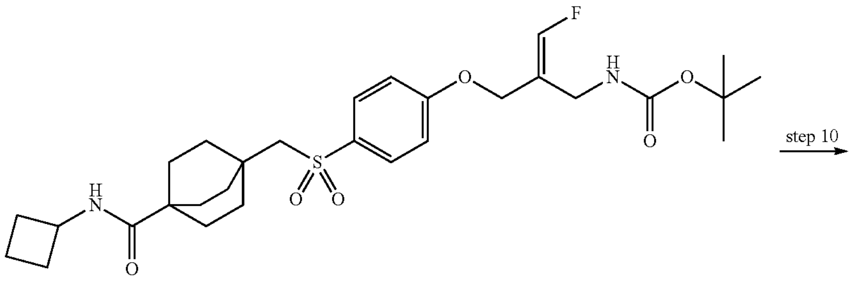
143-10

-continued

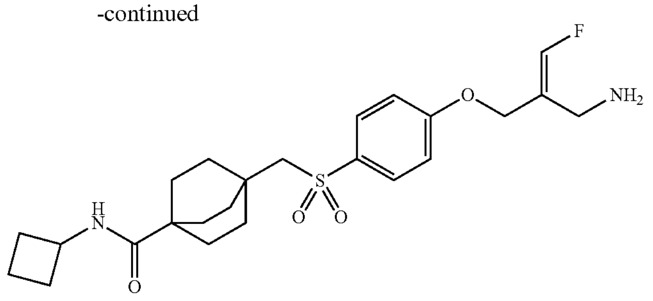

143

Step 1: 143-2

To a mixture of 143-1 (480 mg, 2.42 mmol) in THF (10 mL) was added Borane-tetrahydrofuran complex (1 M, 3.63 mL) at 0° C. under the nitrogen atmosphere dropwise. The reaction mixture was stirred for 2 hr at 25° C. Them, to the reaction mixture was added MeOH (20 mL) at 0~25° C. dropwise. The reaction mixture was stirred at room temperature (~25° C.) for 0.5 hr and concentrated with a rotary evaporator to obtain crude 143-2 (450 mg).

Step 2: 143-3

To a mixture of crude 143-2 (450 mg, 2.44 mmol), Triethylamine (741.49 mg, 7.33 mmol, 1.02 mL) in DCM (15 mL) was added Methanesulfonic anhydride (638.24 mg, 3.66 mmol) at 0'° C. The reaction solution was stirred for 2 hr at 25° C. Then, the solution was concentrated with a rotary evaporator to obtain 143-3 (660 mg, crude).

Step 3: 143-4

To a solution of 4-bromobenzenethiol (951.41 mg, 5.03 mmol), Cesium carbonate (2.05 g, 6.29 mmol) and Potassium iodide (208.83 mg, 1.26 mmol) in DMF (10 mL) was added crude 143-3 (660 mg, 2.52 mmol) under the nitrogen atmosphere. The reaction mixture was heated at 65° C. for 4 hr. Ethyl acetate (50 mL) and $H_2O$ (50 mL) were added, the organic layer was washed with brine (50 mL×4), dried over $Na_2SO_4$, filtered and concentrated to a residue, which was purified by column chromatography (ethyl acetate in petroleum ether: 0~8%, v/v) to give 143-4 (540 mg, 1.52 mmol, 60.41% yield).

Step 4: 143-5

To a mixture of 143-4 (540 mg, 1.52 mmol) and m-CPBA (925.72 mg, 4.56 mmol, 85% purity) in DCM (20 mL) was stirred at 20° C. for 2 hr. $Na_2SO_3$ (5 g) was added to the mixture and stirred for 20 minutes. Then, to the solution was added DCM (50 mL) and water (50 mL). The organic layer was washed with aqueous $NaHCO_3$ (50 mL×3), brine (50 mL×3), dried over $Na_2SO_4$, filtered, concentrated to give crude, which was purified by column chromatography (ethyl acetate in petroleum ether: 0~20%, v/v) to give 143-5 (530 mg, 1.37 mmol, 90.04% yield).

Step 5: 143-6

To a mixture of 143-5 (530 mg, 1.37 mmol) in THF (20 mL) and water (20 mL) was added Lithium hydroxide monohydrate (574.22 mg, 13.68 mmol) at 20° C. The reaction solution was heated at 55° C. for 8 hr. Then, pH of the mixture was adjusted to ~5 with 1 M HCl. The reaction mixture was extracted with ethyl acetate (20 mL×3). The combined organic layers were washed with brine (20 mL×2), dried over sodium sulfate, filtered and concentrated to give 143-6 (500 mg, 1.34 mmol, 97.88% yield).

Step 6: 143-7

A mixture of 143-6 (200 mg, 535.82 μmol), diisopropylethylamine (138.50 mg, 1.07 mmol, 186.66 μL), HATU (244.48 mg, 642.98 μmol), cyclobutanamine (57.16 mg, 803.73 μmol, 68.62 μL) and DCM (20 mL) was stirred at 20° C. for 16 hr. Then, the mixture was concentrated with a rotary evaporator to obtain a crude, which was purified by silica gel chromatography (ethyl acetate in petroleum ether: 0~60%, v/v) to give 143-7 (200 mg, 469.08 μmol, 87.54% yield).

Step 7: 143-8

A mixture of 143-7 (200 mg, 469.08 μmol), 4,4,5,5-tetramethyl-2-(4,4,5,5-tetramethyl-1,3,2-dioxaborolan-2-yl)-1,3,2-dioxaborolane (142.94 mg, 562.90 μmol), bis(diphenylphosphino)ferrocene]dichloropalladium(II) (34.32 mg, 46.91 μmol) and Potassium Acetate (138.11 mg, 1.41 mmol) in Dioxane (5 mL) was heated at 80° C. for 2 hr under the nitrogen atmosphere. The reaction was cooled to room temperature, filtered and concentrated to give 143-8 (240 mg, crude).

Step 8: 143-9

To a mixture of 143-8 (240 mg, 506.94 μmol) and Acetate acid (608.32 μmol, 0.2 mL) in THF (5 mL) was added Hydrogen peroxide (220.0 mg, 1.94 mmol, 0.2 mL, 30% purity) at 20° C. The reaction solution was stirred for 0.5 hr at 20° C. Then, the solution was concentrated to obtain a crude, which was purified by column chromatography (MeOH in DCM: 0~15%, v/v) to obtain 143-9 (150 mg, 412.69 μmol, 81.41% yield).

Step 9: 143-10

To a mixture of 143-9 (150 mg, 412.69 μmol), Intermediate A (119.50 mg, 445.70 μmol) in acetonitrile (8 mL) was added potassium carbonate (114.08 mg, 825.38 μmol) at 20° C. The reaction solution was stirred for 1 hr at 70° C. Then, the mixture was filtered and the filtrate was concentrated to obtain a crude, which was purified by column chromatography (ethyl acetate in petroleum ether: 0~70%, v/v) to give 143-10 (170 mg, 308.71 μmol, 74.80% yield).

Step 10: Compound 143

To a solution of 143-10 (170 mg, 308.71 μmol) in DCM (5 mL) was added HCl/dioxane (4 M, 2 mL) at 20° C. and stirred for 1 hr. The reaction mixture was filtered. The filter cake was slurried with acetonitrile (3 mL) for 15 minutes and filtered. The filter cake was dried under the reduced pressure by oil pump for 8 hr at 45° C. to give Compound 143 (150 mg, 307.99 μmol, 99.77% yield, HCl salt). $^1H$ NMR (400 MHz, Methanol-d4) δ 7.94-7.84 (m, 2H), 7.27 (d, J=80.0 Hz, 1H), 7.28-7.20 (m, 2H), 4.74 (d, J=3.5 Hz, 2H), 4.30 (t, J=8.3 Hz, 1H), 3.84 (d, J=2.3 Hz, 2H), 3.51 (s, 2H), 2.29-2.17 (m, 2H), 2.08-1.93 (m, 2H), 1.88-1.57 (m, 12H) ppm. MS: m/z=451.2 (M+1).

The compounds of Formula (I') or (I) in Table 18 below were made according to Example 85 of Compound 143
TABLE 18
| Cmpd No. | $^1$H NMR and/or LC/MS data |
|---|---|
| 144 | $^1$H NMR (400 MHz, Methanol-$d_4$) δ 7.91-7.85 (m, 2H), 7.27 (d, J = 80.0 Hz, 1H), 7.26-7.20 (m, 2H), 4.77-4.71 (m, 2H), 3.95-3.89 (m, 1H), 3.87-3.82 (m, 2H), 3.27 (d, J = 6.4 Hz, 2H), 2.22 (d, J = 8.6 Hz, 2H), 1.74-1.48 (m, 8H), 1.11 (d, J = 6.6 Hz, 6H) ppm. MS: m/z = 427.3 (M + H). (Cis and trans mixture) |
Example 86: Synthesis of Compound 145
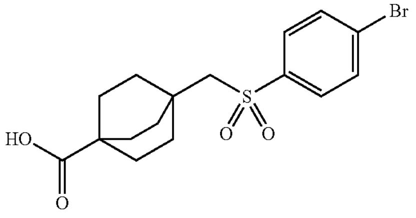
143-6
step 1
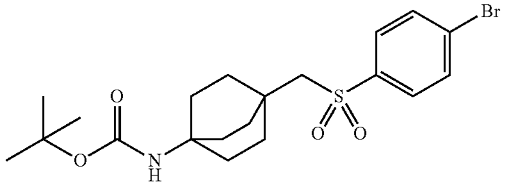
145-1
step 2
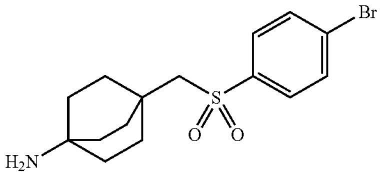
145-2
step 3
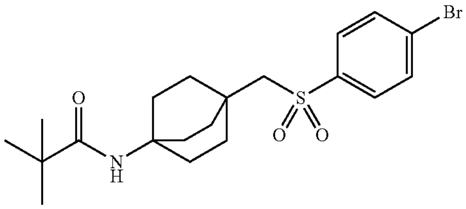
145-3
step 4
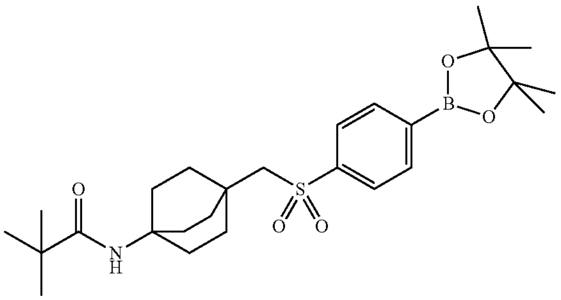
145-4
step 5
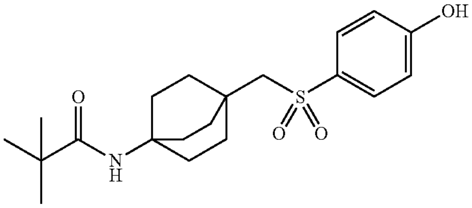
145-5
step 6
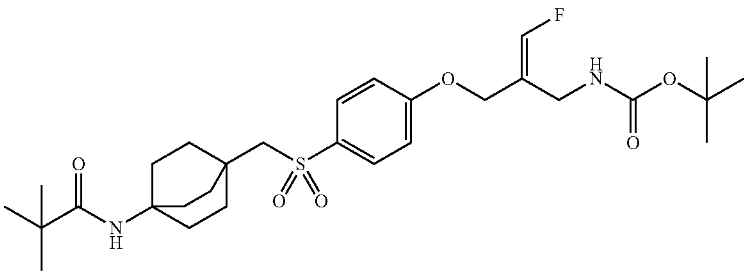
145-6
step 7

-continued

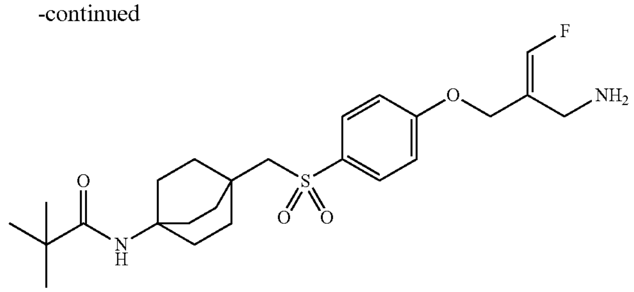

145

Step 1: 145-1

To a solution of 143-6 (300 mg, 803.73 μmol) in toluene (5 mL) and t-BuOH (0.2 mL) was added Triethylamine (105.73 mg, 1.04 mmol, 145.63 μL) and DPPA (254.11 mg, 1.04 mmol, 198.52 μL) at 20° C. under the nitrogen atmosphere. The reaction solution was heated to 70° C. and stirred for 3 hr. The reaction mixture was concentrated to give a crude, which was purified by column chromatography (ethyl acetate in petroleum ether: 0~20%, v/v) to obtain 145-1 (200 mg, 450.06 μmol, 56.0% yield). MS: m/z=388.2 (M+1-56).

Step 2: 145-2

To a mixture of 145-1 (200 mg, 450.06 μmol) in DCM (10 mL) was added HCl/dioxane (4 M, 4 mL) at 20° C. and stirred for 1 hr. The reaction mixture was concentrated to give 145-2 (180 mg, crude, HCl salt). MS: m/z=344.2 (M+1).

Step 3: 145-3

To a mixture of 145-2 (180 mg, 472.78 μmol, HCl salt) and Triethylamine (143.52 mg, 1.42 mmol, 197.69 μL) in DCM (10 mL) was added 2,2-dimethylpropanoyl chloride (114.01 mg, 945.56 μmol, 115.75 μL) at 25° C. The reaction solution was stirred for 2 hr at 25° C. The mixture was concentrated and purified by column chromatography (ethyl acetate in petroleum ether: 0~45%, v/v) to obtain 145-3 (170 mg, 396.84 μmol, 83.94% yield).

Step 4: 145-4

A mixture of 145-3 (170 mg, 396.84 μmol), 4,4,5,5-tetramethyl-2-(4,4,5,5-tetramethyl-1,3,2-dioxaborolan-2-yl)-1,3,2-dioxaborolane (120.93 mg, 476.21 μmol), bis(diphenylphosphino)ferrocene]dichloropalladium(II) (29.04 mg, 39.68 μmol) and Potassium acetate (116.84 mg, 1.19 mmol) in Dioxane (8 mL) was heated at 80° C. for 2 hr under the nitrogen atmosphere. The reaction was cooled to room temperature, filtered and concentrated to give 145-4 (200 mg, crude).

Step 5: 145-5

To a mixture of 145-4 (200 mg, 420.66 μmol) and Acetate acid (504.79 μmol, 0.2 mL) in THF (5 mL) was added Hydrogen peroxide (220.0 mg, 1.94 mmol, 0.2 mL, 30% purity) at 20° C. The reaction solution was stirred for 0.5 hr at 20° C. Then, the solution was concentrated to obtain a crude, which was purified by column chromatography (MeOH in DCM: 0~15%, v/v) to obtain 145-5 (110 mg, 300.97 μmol, 71.55% yield). MS: m/z=366.2 (M+1).

Step 6: 145-6

To a mixture of 145-5 (110 mg, 300.97 μmol), Intermediate A (87.15 mg, 325.05 μmol) in Acetonitrile (8 mL) was added potassium carbonate (83.19 mg, 601.94 μmol) at 20° C. The reaction solution was stirred for 1 hr at 90° C. Then, the mixture was filtered and the filtrate was concentrated to obtain a crude, which was purified by column chromatography (ethyl acetate in petroleum ether: 0~70%, v/v) to give 145-6 (20 mg, 36.19 μmol, 12.02% yield).

Step 7: Compound 145

To a mixture of 145-6 (20 mg, 36.19 μmol) in DCM (5 mL) was added HCl/dioxane (4 M, 266.67 μL) at 20° C. and stirred for 1 hr. The reaction mixture was filtered. The filter cake was slurried with acetonitrile (3 mL) for 15 minutes and filtered. The filter cake was dried under the reduced pressure by oil pump for 8 hr at 45° C. to give Compound 145 (2.1 mg, 4.29 μmol, 11.87% yield, HCl salt). $^1$H NMR (400 MHz, Methanol-d4) δ 7.93-7.86 (m, 2H), 7.27 (d, J=80.0 Hz, 1H), 7.26 (s, 1H), 7.25-7.20 (m, 2H), 4.73 (dd, J=3.6, 1.1 Hz, 2H), 3.84 (d, J=2.2 Hz, 2H), 3.48 (s, 2H), 1.86-1.73 (m, 8H), 1.66-1.58 (m, 2H), 1.15 (s, 9H) ppm. MS: m/z=453.3 (M+1).

Example 87: Synthesis of Compound 146

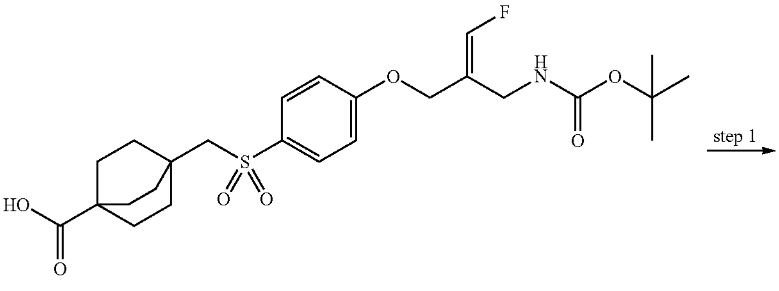

62-4

-continued

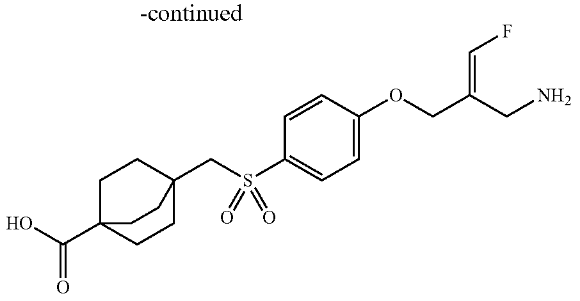

146

Step 1: Compound 146

To a solution of 62-4 (150 mg, 293.20 μmol) in DCM (5 mL) was added HCl/Dioxane (1 mL, 4 M) at 25° C. and stirred for 18 hr. Then, the solution was concentrated to obtain a crude, which was purified by prep-HPLC (column: XBridge@ Prep C18 5 μm 19×150 mm; A: 0.2% $HCO_2H$ water, B: acetonitrile; gradient: 5-60% B; GT: 18 min; flow rate: 15 mL/min) to obtain Compound 146 (33 mg, 80.20 μmol, 27.35% yield, HCOOH salt). $^1H$ NMR (400 MHz, DMSO-d6) δ 7.76 (d, J=8.8 Hz, 2H), 7.16-7.09 (m, 2H), 7.14 (d, J=84.0 Hz, 1H), 4.61 (d, J=3.5 Hz, 2H), 3.07 (s, 2H), 2.61 (s, 2H) 2.30 (s, 2H), 1.93 (q, J=7.2, 6.6 Hz, 4H), 1.55 (d, J=3.9 Hz, 8H) ppm. MS: m/z=412.3 (M+1).

Example 88: SSAO Activity Assay

Amine oxidase activity of recombinant hSSAO, hMAO-A, and hMAO-B isoforms are measured using the MAO-Glo assay kit (Promega, V1402). Ten nL test compounds (with DMSO as vehicle, 0.1% v/v for hSSAO, hMAO-A and hMAO-B) were added into assay plates by Echo, and pre-incubated with 5 μL of enzyme for 30 mins at room temperature before the addition of 5 μL of luminogenic substrate. The substrate concentration is 40 μM for human recombinant SSAO, 40 μM for human recombinant MAO-A, and 4 μM for human recombinant MAO-B. The hSSAO and hMAO-A assays were conducted in the MAO-A reaction buffer in the kit, and the MAO-B assay was conducted in the MAO-B reaction buffer. Oxidation of the substrate was conducted for 1 hr, before the addition of detecting reagent according the manufacture's protocol. The $IC_{50}$ value of the tested compounds was calculated by fitting the dose response curve using a 4-parameter non-linear regression routine. As shown in Table 19, the compounds exhibit potent hSSAO inhibition ("A" means >0 nM and ≤20 nM; "B" means >20 nM and ≤100 nM; "C" means >100 nM and ≤500 nM, "D" means >500 nM).

TABLE 19

SSAO activity of compounds of the application

| Compound No. | SSAO Activity ($IC_{50}$, nM) |
|---|---|
| BI 1467335 (PXS-4728A) | A |
| 1 | A |
| 2 | B |
| 3 or 4 | B |
| 4 or 3 | B |
| 5 | A |
| 6 | B |
| 7 | A |
| 8 | B |
| 9 | A |
| 10 | B |
| 11 | B |
| 12 | B |
| 13 | B |
| 14 | B |
| 15 | A |
| 16 | B |
| 17 | B |
| 18 | A |
| 19 | A |
| 20 | A |
| 21 or 22 | B |
| 22 or 21 | B |
| 23 or 24 | B |
| 24 or 23 | A |
| 25 | B |
| 26 | B |
| 27 | B |
| 28 | A |
| 29 | B |
| 30 | A |
| 31 | B |
| 32 | B |
| 33 | B |
| 34 | B |
| 35 | B |
| 36 | B |
| 37 | A |
| 38 | A |
| 39 | A |
| 40 | B |
| 41 | B |
| 42 | B |
| 43 | C |
| 44 | B |
| 45 | B |
| 46 | B |
| 47 | C |
| 48 | B |
| 49 | B |
| 50 | B |
| 51 | B |
| 52 | B |
| 53 | B |
| 54 | B |
| 55 | B |
| 56 | B |
| 57 | B |
| 58 | C |
| 59 | B |
| 60 | B |
| 61 | A |
| 62 | B |
| 63 | B |
| 64 | A |

TABLE 19-continued

SSAO activity of compounds of the application

| Compound No. | SSAO Activity ($IC_{50}$, nM) |
|---|---|
| 65 | A |
| 66 | A |
| 67 | A |
| 68 | A |
| 69 | A |
| 70 | B |
| 71 | A |
| 72 | A |
| 73 | B |
| 74 | B |
| 75 | A |
| 76 | A |
| 77 | A |
| 78 | B |
| 79 | A |
| 80 | A |
| 81 | A |
| 82 | A |
| 83 | A |
| 84 | A |
| 85 | B |
| 86 | A |
| 87 | A |
| 88 | A |
| 89 | C |
| 90 | A |
| 91 | A |
| 92 | A |
| 93 or 94 | D |
| 94 or 93 | B |
| 95 | C |
| 96 | A |
| 97 | B |
| 98 | B |
| 99 | B |
| 100 | B |
| 101 | B |
| 102 | A |
| 103 | B |
| 104 or 105 | B |
| 105 or 104 | B |
| 106 | B |
| 107 | A |
| 108 | B |
| 109 or 110 | B |
| 110 or 109 | B |
| 111 | B |
| 112 or 113 | B |
| 113 or 112 | A |
| 114 | B |
| 115 | B |
| 116 | B |
| 117 | C |
| 118 | B |
| 119 | B |
| 120 | B |
| 121 | B |
| 122 | B |
| 123 | B |
| 124 | B |
| 125 | B |
| 126 | C |
| 127 | C |
| 128 | C |
| 129 | B |
| 130 | B |
| 131 | B |
| 132 | B |
| 133 | C |
| 134 | C |
| 135 | B |
| 136 or 137 | B |
| 137 or 136 | B |
| 138 | B |
| 139 | A |
| 140 | A |
| 141 | B |
| 142 | A |
| 143 | B |
| 144 | B |
| 145 | B |
| 146 | B |

Example 89: Brain Kpuu Assay

Brain Kpuu assay is composed of Blood-Brain-Barrier (BBB) assay and protein binding assay, which are conducted in ICR mice. Protein binding assays were performed in 96-well plates, using equilibrium dialysis against brain lysate and plasma to calculate $f_{u(brain)}$ and $f_{u(plasma)}$, respectively. BBB assays were conducted in mice at 1 mg/kg IV dosage. Plasma and brain samples were collected at 5 minutes after dosing to analyze compounds concentration ($C_{plasma}$ and $C_{brain}$). The Kpuu value of the tested compounds was calculated by the equation:

$$Kpuu = \frac{c_{brain}}{c_{plasma}} \times \frac{f_{u(brain)}}{f_{u(plasma)}} \quad (1)$$

As shown in Table 20, the compounds of the present application are selective for hSSAO over either hMAO-A or hMAO-B ("A" means<10 μM; "B" means ≥10 and ≤30 μM; "C" means >30 μM). In addition, the results in Table 21 demonstrate that the compounds are poorly brain penetrable.

TABLE 20

MAO-A and MAO-B activity of representative compounds of the application

| Compound No. | MAO-A Activity ($IC_{50}$, μM) | MAO-B Activity ($IC_{50}$, μM) |
|---|---|---|
| BI 1467335 (PXS-4728A) | C | A |
| 1 | C | A |
| 2 | C | A |
| 3 or 4 | C | B |
| 4 or 3 | C | B |
| 5 | C | A |
| 6 | A | A |
| 7 | A | A |
| 8 | B | A |
| 9 | A | A |
| 10 | C | A |
| 11 | C | A |
| 12 | B | A |
| 13 | B | B |
| 14 | B | B |
| 15 | A | A |
| 16 | C | C |
| 17 | C | B |
| 18 | C | B |
| 19 | B | A |
| 20 | B | B |
| 21 or 22 | B | A |
| 22 or 21 | B | A |
| 23 or 24 | C | A |
| 24 or 23 | C | A |
| 25 | C | A |
| 26 | C | A |
| 27 | C | C |

TABLE 20-continued

MAO-A and MAO-B activity of representative compounds of the application

| Compound No. | MAO-A Activity ($IC_{50}$, μM) | MAO-B Activity ($IC_{50}$, μM) |
|---|---|---|
| 28 | C | B |
| 29 | C | C |
| 30 | C | B |
| 31 | C | A |
| 32 | C | C |
| 33 | C | A |
| 34 | C | A |
| 35 | C | B |
| 36 | C | A |
| 37 | C | C |
| 38 | A | A |
| 39 | A | A |
| 40 | B | A |
| 41 | C | C |
| 42 | C | C |
| 43 | B | B |
| 44 | C | C |
| 45 | C | A |
| 46 | C | C |
| 47 | C | C |
| 48 | C | C |
| 49 | C | C |
| 50 | C | C |
| 51 | C | C |
| 52 | C | A |
| 53 | C | C |
| 54 | C | C |
| 55 | C | B |
| 56 | C | B |
| 57 | B | A |
| 58 | C | C |
| 59 | C | C |
| 60 | C | C |
| 61 | C | B |
| 62 | C | B |
| 63 | C | C |
| 64 | C | B |
| 65 | C | B |
| 66 | C | B |
| 67 | C | C |
| 68 | C | C |
| 69 | C | B |
| 70 | C | B |
| 71 | C | B |
| 72 | C | C |
| 73 | C | C |
| 74 | C | C |
| 75 | C | B |
| 76 | C | B |
| 77 | C | C |
| 78 | C | C |
| 79 | C | C |
| 80 | C | B |
| 81 | C | C |
| 82 | C | C |
| 83 | C | B |
| 84 | C | B |
| 85 | C | B |
| 86 | C | A |
| 87 | C | A |
| 88 | C | A |
| 89 | C | B |
| 90 | C | B |
| 91 | C | B |
| 92 | C | B |
| 93 or 94 | C | C |
| 94 or 93 | C | C |
| 95 | C | C |
| 96 | C | B |
| 97 | C | C |
| 98 | C | B |
| 99 | B | C |
| 100 | B | C |
| 101 | C | A |

TABLE 20-continued

MAO-A and MAO-B activity of representative compounds of the application

| Compound No. | MAO-A Activity ($IC_{50}$, μM) | MAO-B Activity ($IC_{50}$, μM) |
|---|---|---|
| 102 | C | A |
| 103 | C | A |
| 104 or 105 | C | C |
| 105 or 104 | C | C |
| 106 | C | C |
| 107 | C | A |
| 108 | C | A |
| 109 or 110 | C | A |
| 110 or 109 | C | A |
| 111 | C | B |
| 112 or 113 | C | C |
| 113 or 112 | C | C |
| 114 | C | C |
| 115 | C | C |
| 116 | C | C |
| 117 | C | C |
| 118 | A | A |
| 119 | B | C |
| 120 | C | C |
| 121 | C | A |
| 122 | C | A |
| 123 | C | C |
| 124 | C | C |
| 125 | C | A |
| 126 | C | B |
| 127 | C | A |
| 128 | C | C |
| 129 | C | B |
| 130 | C | C |
| 131 | C | C |
| 132 | C | A |
| 133 | B | A |
| 134 | B | A |
| 135 | C | C |
| 136 or 137 | C | C |
| 137 or 136 | C | C |
| 138 | C | A |
| 139 | C | A |
| 140 | C | C |
| 141 | C | C |
| 142 | C | C |
| 143 | C | A |
| 144 | C | A |
| 145 | A | B |
| 146 | C | C |

TABLE 21

Brain Kpuu value (t = 5 min) of representative compounds of the application

| Compound No. | Kpuu (mouse, t = 5 min) |
|---|---|
| BI 1467335 (PXS-4728A) | 0.23 |
| 44 | 0.025 |
| 62 | 0.034 |
| 65 | 0.018 |
| 70 | 0.010 |
| 91 | 0.077 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of Formula (Ia) or (Ib):

(Ia)

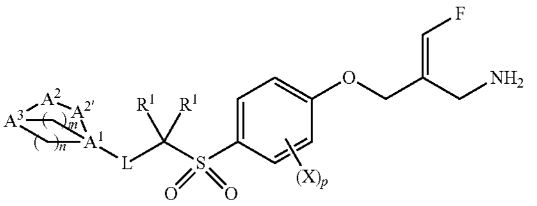

(Ib)

or

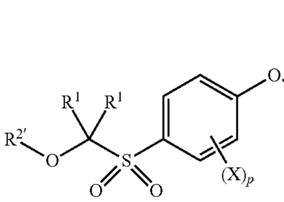

or a pharmaceutically acceptable salt, solvate, stereoisomer, or tautomer thereof, wherein:

each X is independently Cl or F;

p is 0, 1, 2, or 3;

L is absent, —O—, ($C_1$-$C_4$) alkylene, substituted ($C_1$-$C_4$) alkylene, —O—($C_1$-$C_4$) alkylene, substituted —O—($C_1$-$C_4$) alkylene, ($C_1$-$C_4$) alkylene-O—, or substituted ($C_1$-$C_4$) alkylene-O—, wherein the substituted ($C_1$-$C_4$) alkylene, substituted —O—($C_1$-$C_4$) alkylene, or substituted ($C_1$-$C_4$) alkylene-O— is substituted with one or more $L^1$;

each $L^1$ is independently ($C_1$-$C_4$) alkyl, F, or $CF_3$; or two $L^1$, together with the atom to which they are attached, form a 3- to 5-membered cycloalkyl ring;

each $R^1$ is independently H, F, methyl, ethyl, or $CF_3$;

$A^1$ is $CR^{5'}$;

$R^{5'}$ is H, ($C_1$-$C_4$) alkyl, ($C_1$-$C_4$) alkoxy, hydroxy, or cyano;

$A^2$ and $A^{2'}$ are each independently absent, $CH_2$, $CHR^5$, $C(R^5)_2$, NH, $NR^5$, or O, provided that at least one of $A^2$ and $A^{2'}$ is not absent and that $A^2$-$A^{2'}$ is not O—O, O—NH, O—$NR^5$, NH—O, NH—NH, NH—$NR^5$, $NR^5$—O, $NR^5$—NH, or $NR^5$—$NR^5$;

$A^3$ is $CH_2$, $CHR^5$, $C(R^5)_2$, NH, $NR^5$, or O when m is 0, or CH or $CR^5$ when m is 1 or 2, provided that $A^2$-$A^3$ is not O—O, O—NH, O—$NR^5$, NH—O, NH—NH, NH—$NR^5$, $NR^5$—O, $NR^5$—NH, or $NR^5$—$NR^5$;

m is 0, 1, or 2;

n is 1 or 2;

$R^{2'}$ is ($C_1$-$C_4$) alkyl substituted with one or more ($C_1$-$C_4$) alkoxy, ($C_1$-$C_4$) alkoxy, $NR^3C(O)R^4$, $C(O)NR^3R^4$, or heterocyclyl comprising one or two 3- to 6-membering rings and 1 to 3 heteroatoms selected from N and O, wherein the heterocyclyl is optionally substituted with one or more $R^5$;

$R^3$ is H, methyl, or ethyl;

$R^4$ is ($C_1$-$C_4$) alkyl or ($C_3$-$C_{10}$) cycloalkyl optionally substituted with one or more $R^8$; or $R^3$ and $R^4$, together with atom(s) to which they are attached, form a 3- to 6-membered ring optionally comprising one additional heteroatom selected from N and O and optionally substituted with one or more $R^5$;

each $R^5$ is independently ($C_1$-$C_4$) alkyl, ($C_1$-$C_4$) alkoxy, hydroxy, cyano, oxo, $C(O)R^7$, $C(O)NR^7R^{7'}$, $NR^3C(O)R^7$, $NR^3S(O)_2R^4$, $S(O)_2R^4$, ($C_1$-$C_4$) alkyl substituted with one or more hydroxy or $R^6$, ($C_3$-$C_{10}$) cycloalkyl optionally substituted with one or more hydroxy or $R^6$, or heterocyclyl comprising one or two 3- to 6-membering rings and 1 to 3 heteroatoms selected from N and O and optionally substituted with one or more hydroxy or $R^6$; or two $R^5$, together with the atom or atoms to which they are attached, form a 3- to 5-membered saturated or 5- or 6-membered aromatic ring optionally comprising 1 or 2 heteroatoms selected from N and 0;

each $R^6$ is independently $NR^3C(O)R^7$ or $C(O)NR^3R^7$;

each $R^7$ is independently

OH, ($C_1$-$C_4$) alkoxy, ($C_1$-$C_6$) alkyl optionally substituted with one or more ($C_1$-$C_4$) alkoxy, $CF_3$, F, or ($C_3$-$C_{10}$) cycloalkyl, ($C_3$-$C_{10}$) cycloalkyl optionally substituted with one or more $R^8$, or phenyl optionally substituted with one or more $R^8$ each $R^{7'}$ is independently H, methyl, or ethyl; or $R^7$ and $R^{7'}$, together with the atom to which they are attached, form a 3- to 6-membered ring optionally comprising one additional heteroatom selected from N and O and optionally substituted with one or more $R^8$; or $R^3$ and $R^7$, together with atom(s) to which they are attached, form a 3- to 6-membered ring optionally comprising one additional heteroatom selected from N and O and optionally substituted with one or more $R^8$; and each $R^8$ is independently ($C_1$-$C_4$) alkyl, ($C_1$-$C_4$) alkoxy, $CF_3$, OH, or F.

2. The compound of claim 1, wherein the compound is of Formula (Ia'), (Ia2), (Ia2'), (Ia3), (Ia3'), or (Ib'):

(Ia')

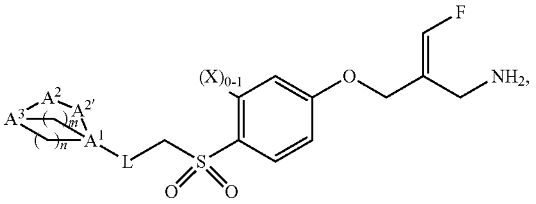

(Ia2)

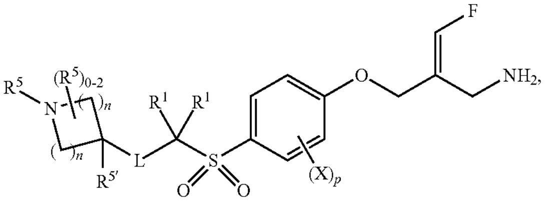

(Ia2')

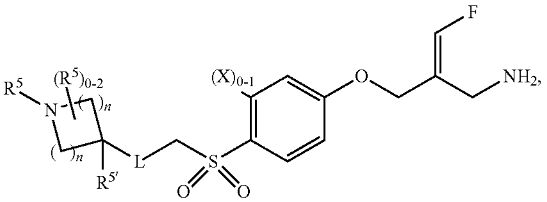

-continued (Ia3)

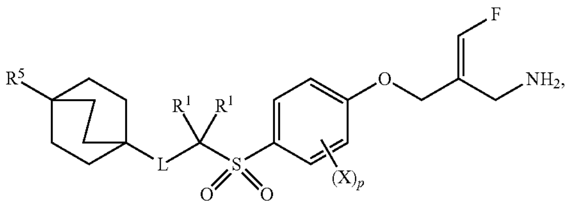

(Ia3')

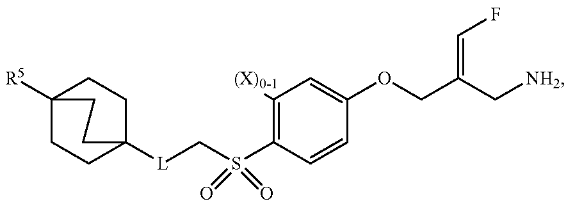

(Ib')

or

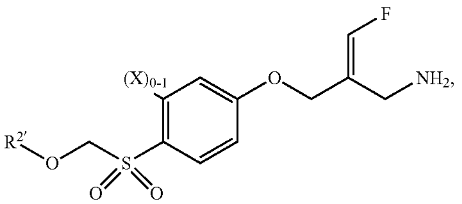

or a pharmaceutically acceptable salt, solvate, stereoisomer, or tautomer thereof.

3. The compound of claim 1, wherein L is absent, —O—, $(C_1-C_2)$ alkylene, substituted $(C_1-C_2)$ alkylene, $(C_1-C_2)$ alkylene-O—, or substituted $(C_1-C_2)$ alkylene-O—.

4. The compound of claim 1, wherein each $L^1$ is independently methyl or two $L^1$, together with the atom to which they are attached, form a cyclopropyl ring.

5. The compound of claim 1, wherein each $R^1$ is H.

6. The compound of claim 1, wherein

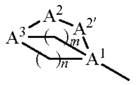

is selected from:

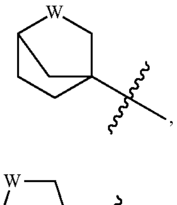

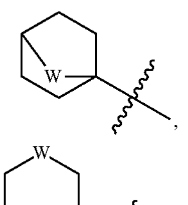

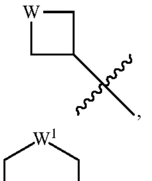

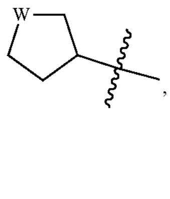

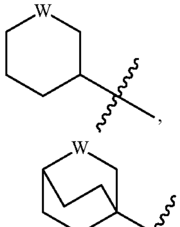

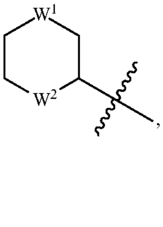

and

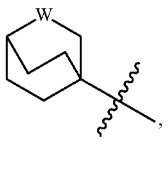

wherein W, $W^1$ and $W^2$ are each independently $CH_2$, $CHR^5$, $C(R^5)_2$, O, NH, or $NR^5$, each optionally substituted with one or more $R^5$.

7. The compound of claim 1, wherein $R^3$ and $R^4$, together with atom(s) to which they are attached, form a 3- to 6-membered ring optionally comprising one additional heteroatom selected from N and O and optionally substituted with one or more $R^5$.

8. The compound of claim 1, wherein at least one $R^5$ is $(C_1-C_4)$ alkyl, $(C_1-C_4)$ alkoxy, hydroxy, cyano, oxo, C(O)$R^7$, C(O)$NR^7R^{7'}$, $NR^3C(O)R^7$, $NR'S(O)_2R^4$, $S(O)_2R^4$, or $(C_1-C_4)$ alkyl substituted with one or more hydroxy or $R^6$.

9. The compound of claim 1, wherein at least one $R^5$ is $(C_3-C_{10})$ cycloalkyl optionally substituted with one or more hydroxy or $R^6$, or heterocyclyl comprising one or two 3- to 6-membering rings and 1 to 3 heteroatoms selected from N and O and optionally substituted with one or more hydroxy or $R^6$; or two $R^5$, together with the atom or atoms to which they are attached, form a 3- to 5-membered saturated or 5- or 6-membered aromatic ring optionally comprising 1 or 2 heteroatoms selected from N and O.

10. The compound of claim 1, wherein at least one $R^7$ is $(C_1-C_4)$ alkoxy, $(C_1-C_6)$ alkyl optionally substituted with one or more $(C_1-C_4)$ alkoxy, $CF_3$, F, or $(C_3-C_{10})$ cycloalkyl.

11. The compound of claim 1, wherein at least one $R^7$ is $(C_3-C_{10})$ cycloalkyl or phenyl optionally substituted with one or more $R^8$.

12. The compound of claim 1, wherein $R^7$ and $R^{7'}$, together with atom(s) to which they are attached, form a 3- to 6-membered ring optionally comprising one additional heteroatom selected from N and O and optionally substituted with one or more $R^8$.

13. The compound of claim 1, wherein $R^3$ and $R^7$, together with atom(s) to which they are attached, form a 3- to 6-membered ring optionally comprising one additional heteroatom selected from N and O and optionally substituted with one or more $R^8$.

14. The compound of claim 1, wherein at least one $R^8$ is $(C_1-C_4)$ alkyl or $(C_1-C_4)$ alkoxy.

15. The compound of claim 1, wherein X is F.

16. A compound selected from (E)-3-fluoro-2-((4-(((tetrahydro-2H-pyran-4-yl)methyl)sulfonyl)phenoxy)methyl)prop-2-en-1-amine, (E)-2-((4-(((5,5-dimethyl-1,4-dioxan-2-yl)methyl)sulfonyl)phenoxy)methyl)-3-fluoroprop-2-en-1-amine, (S,E)-2-((4-(((5,5-dimethyl-1,4-dioxan-2-yl)methyl)sulfonyl)phenoxy)methyl)-3-fluoroprop-2-en-1-amine, (R,E)-2-((4-(((5,5-dimethyl-1,4-dioxan-2-yl)methyl)sulfonyl)phenoxy)methyl)-3-fluoroprop-2-en-1-amine, (E)-3-fluoro-2-((4-(((4-methyltetrahydro-2H-pyran-4-yl)methyl)sulfonyl)phenoxy)methyl)prop-2-en-1-amine, (E)-3-fluoro-2-((3-fluoro-4-(((tetrahydro-2H-pyran-4-yl)methyl)sulfonyl)phenoxy)methyl)prop-2-en-1-amine, (E)-3-fluoro-2-((3-fluoro-4-(((4-methyltetrahydro-2H-pyran-4-yl)methyl)sulfonyl)phenoxy)methyl)prop-2-en-1-amine, (E)-2-((3-chloro-4-(((tetrahydro-2H-pyran-4-yl)methyl)sulfonyl)phenoxy)methyl)-3-fluoroprop-2-en-1-amine, (E)-3-fluoro-2-((2-fluoro-4-(((tetrahydro-2H-pyran-4-yl)methyl)sulfonyl)phenoxy)methyl)prop-2-en-1-amine, (E)-4-(((4-((2-(aminomethyl)-3-fluoroallyl)oxy)phenyl)sulfonyl)methyl)tetrahydro-2H-pyran-4-ol, (E)-3-fluoro-2-((4-(((4-methoxytetrahydro-2H-pyran-4-yl)methyl)sulfonyl)phenoxy)methyl)prop-2-en-1-amine, (E)-4-(((4-((2-(aminomethyl)-3-fluoroallyl)oxy)phenyl)sulfonyl)methyl)tetrahydro-2H-pyran-4-carbonitrile, (E)-4-(((4-((2-(aminomethyl)-3-fluoroallyl)oxy)-2-fluorophenyl)sulfonyl)methyl)tetrahydro-2H-pyran-4-carbonitrile, (1r,4r)-4-(((4-(((E)-2-(aminomethyl)-3-fluoroallyl)oxy)phenyl)sulfonyl)methyl)cyclohexan-1-ol, (1s,4s)-4-(((4-(((E)-2-(aminomethyl)-3-fluoroallyl)oxy)phenyl)sulfonyl)methyl)cyclohexan-1-ol, (E)-N-(1-(4-(((4-((2-(aminomethyl)-3-fluoroallyl)oxy)phenyl)sulfonyl)methyl)bicyclo[2.2.2]octan-1-yl)cyclopropyl)cyclopropanecarboxamide, (E)-4-(((4-((2-(aminomethyl)-3-fluoroallyl)oxy)phenyl)sulfonyl)methyl)bicyclo[2.2.2]octan-1-ol, (E)-1-(4-(((4-((2-(aminomethyl)-3-fluoroallyl)oxy)phenyl)sulfonyl)methyl)bicyclo[2.2.2]octan-1-yl)cyclopropan-1-ol, (E)-3-fluoro-2-((4-((((1r,4r)-4-methoxycyclohexyl)methyl)sulfonyl)phenoxy)methyl)prop-2-en-1-amine, (E)-3-fluoro-2-((4-((((1s,4s)-4-methoxycyclohexyl)methyl)sulfonyl)phenoxy)methyl)prop-2-en-1-amine, (R,E)-3-fluoro-2-((4-(((tetrahydrofuran-3-yl)methyl)sulfonyl)phenoxy)methyl)prop-2-en-1-amine, (S,E)-3-fluoro-2-((4-(((tetrahydrofuran-3-yl)methyl)sulfonyl)phenoxy)methyl)prop-2-en-1-amine, (S,E)-3-fluoro-2-((4-(((tetrahydrofuran-2-yl)methyl)sulfonyl)phenoxy)methyl)prop-2-en-1-amine, (R,E)-3-fluoro-2-((4-(((tetrahydrofuran-2-yl)methyl)sulfonyl)phenoxy)methyl)prop-2-en-1-amine, (E)-3-fluoro-2-((4-((3-methoxy-2-(methoxymethyl)propyl)sulfonyl)phenoxy)methyl)prop-2-en-1-amine, (E)-3-fluoro-2-((4-((((tetrahydro-2H-pyran-4-yl)oxy)methyl)sulfonyl)phenoxy)methyl)prop-2-en-1-amine, (E)-(4-(((4-((2-(aminomethyl)-3-fluoroallyl)oxy)phenyl)sulfonyl)methoxy)piperidin-1-yl)(cyclopentyl)methanone, (E)-3-fluoro-2-((4-((methoxymethyl)sulfonyl)phenoxy)methyl)prop-2-en-1-amine, (E)-3-fluoro-2-((4-(((2-methoxyethoxy)methyl)sulfonyl)phenoxy)methyl)prop-2-en-1-amine, (E)-3-fluoro-2-((4-((((tetrahydro-2H-pyran-4-yl)methoxy)methyl)sulfonyl)phenoxy)methyl)prop-2-en-1-amine, (E)-3-fluoro-2-((4-((((4-methyltetrahydro-2H-pyran-4-yl)methoxy)methyl)sulfonyl)phenoxy)methyl)prop-2-en-1-amine, (E)-4-((((4-((2-(aminomethyl)-3-fluoroallyl)oxy)phenyl)sulfonyl)methoxy)methyl)tetrahydro-2H-pyran-4-carbonitrile, (E)-1-(4-((((4-((2-(aminomethyl)-3-fluoroallyl)oxy)phenyl)sulfonyl)methoxy)methyl)-4-methylpiperidin-1-yl)-2-methylpropan-1-one, (E)-1-(4-((((4-((2-(aminomethyl)-3-fluoroallyl)oxy)phenyl)sulfonyl)methoxy)methyl)-4-methylpiperidin-1-yl)-2,2-dimethylpropan-1-one, (E)-(4-((((4-((2-(aminomethyl)-3-fluoroallyl)oxy)phenyl)sulfonyl)methoxy)methyl)piperidin-1-yl)(1-(trifluoromethyl)cyclopropyl)methanone, (E)-2-((4-((((1,3-dimethoxypropan-2-yl)oxy)methyl)sulfonyl)phenoxy)methyl)-3-fluoroprop-2-en-1-amine, (E)-1-(4-(((4-((2-(aminomethyl)-3-fluoroallyl)oxy)phenyl)sulfonyl)methyl)piperidin-1-yl)-2-methylpropan-1-one, (E)-3-fluoro-2-((4-(((1-(methylsulfonyl)piperidin-4-yl)methyl)sulfonyl)phenoxy)methyl)prop-2-en-1-amine, (E)-(4-(((4-((2-(aminomethyl)-3-fluoroallyl)oxy)phenyl)sulfonyl)methyl)piperidin-1-yl)(4-fluorophenyl)methanone, (E)-(4-(((4-((2-(aminomethyl)-3-fluoroallyl)oxy)phenyl)sulfonyl)methyl)piperidin-1-yl)(3-fluorobicyclo[1.1.1]pentan-1-yl)methanone, (E)-1-(4-(((4-((2-(aminomethyl)-3-fluoroallyl)oxy)phenyl)sulfonyl)methyl)piperidin-1-yl)-2,2-dimethylpropan-1-one, (E)-1-(4-(((4-((2-(aminomethyl)-3-fluoroallyl)oxy)phenyl)sulfonyl)methyl)piperidin-1-yl)-3,3-dimethylbutan-1-one, (E)-adamantan-1-yl(4-(((4-((2-(aminomethyl)-3-fluoroallyl)oxy)phenyl)sulfonyl)methyl)piperidin-1-yl)methanone (E)-(4-(((4-((2-(aminomethyl)-3-fluoroallyl)oxy)phenyl)sulfonyl)methyl)piperidin-1-yl)(cyclopropyl)methanone, (E)-N-(4-(((4-((2-(aminomethyl)-3-fluoroallyl)oxy)phenyl)sulfonyl)methyl)phenyl)isobutyramide, (E)-(4-(((4-((2-(aminomethyl)-3-fluoroallyl)oxy)phenyl)sulfonyl)methyl)phenyl)(pyrrolidin-1-yl)methanone, (E)-(3-(((4-((2-(aminomethyl)-3-fluoroallyl)oxy)phenyl)sulfonyl)methyl)phenyl)(pyrrolidin-1-yl)methanone, (E)-1-(4-(((4-((2-(aminomethyl)-3-fluoroallyl)oxy)phenyl)sulfonyl)methyl)piperidin-1-yl)-2-cyclopropylethan-1-one, (E)-(4-(((4-((2-(aminomethyl)-3-fluoroallyl)oxy)phenyl)sulfonyl)methyl)piperidin-1-yl)(1-(trifluoromethyl)cyclopropyl)methanone, (E)-(4-(((4-((2-(aminomethyl)-3-fluoroallyl)oxy)phenyl)sulfonyl)methyl)piperidin-1-yl)(cyclobutyl)methanone, (E)-(4-(((4-((2-(aminomethyl)-3-fluoroallyl)oxy)phenyl)sulfonyl)methyl)piperidin-1-yl)(3,3-difluorocyclobutyl)methanone, (E)-1-(3-(((4-((2-(aminomethyl)-3-fluoroallyl)oxy)phenyl)sulfonyl)methyl)azetidin-1-yl)-2-methylpropan-1-one, (E)-1-(4-(((4-((2-(aminomethyl)-3-fluoroallyl)oxy)phenyl)sulfonyl)methyl)-4-methylpiperidin-1-yl)-2-methylpropan-1-one, (E)-1-(4-(((4-((2-(aminomethyl)-3-fluoroallyl)oxy)phenyl)sulfonyl)methyl)-4-methylpiperidin-1-yl)-2,2-dimethylpropan-1-one, (E)-(4-(((4-((2-(aminomethyl)-3-fluoroallyl)oxy)phenyl)sulfonyl)methyl)-4-methylpiperidin-1-yl)(1-(trifluoromethyl)cyclopropyl)methanone, (E)-(4-(((4-((2-(aminomethyl)-3-fluoroallyl)oxy)phenyl)sulfonyl)methyl)-4-methylpiperidin-1-yl)(1-methylcyclobutyl)methanone, (E)-(4-(((4-((2-(aminomethyl)-3-fluoroallyl)oxy)phenyl)sulfonyl)methyl)-4-methylpiperidin-1-yl)(1-methylcyclopropyl)methanone, (E)-(4-(((4-((2-(aminomethyl)-3-fluoroallyl)oxy)-2-fluorophenyl)sulfonyl)methyl)piperidin-1-yl)(cyclopentyl)methanone, (E)-1-(4-(((4-((2-(aminomethyl)-3-fluoroallyl)oxy)-2-fluorophenyl)sulfonyl)methyl)piperidin-1-yl)-3,3,3-trifluoropropan-1-one, (E)-(4-(((4-((2-(aminomethyl)-3-fluoroallyl)oxy)-2-chlorophenyl)sulfonyl)methyl)piperidin-1-yl)(cyclopropyl)methanone, (E)-(4-(((4-((2-(aminomethyl)-3-fluoroallyl)oxy)phenyl)sulfonyl)methyl)bicyclo[2.2.2]octan-1-yl)(pyrrolidin-1-yl)methanone, (E)-4-(((4-((2-(aminomethyl)-3-fluoroallyl)oxy)phenyl)sulfonyl)methyl)-N,N-dimethylbicyclo[2.2.2]octane-1-carboxamide, (E)-(4-(((4-((2-(aminomethyl)-3-fluoroallyl)oxy)phenyl)sulfonyl)methyl)bicyclo[2.2.2]octan-1-yl)(4,4-difluoropiperidin-1-yl)methanone, (E)-4-(((4-((2-(aminomethyl)-3-fluoroallyl)oxy)phenyl)sulfonyl)methyl)-N-cyclobutylbicyclo[2.2.2]octane-1-carboxamide, (E)-4-(((4-((2-(aminomethyl)-3-fluoroallyl)oxy)phenyl)sulfonyl)methyl)-N-(2,2,2-trifluoroethyl)bicyclo[2.2.2]octane-1-carboxamide, (E)-4-(((4-((2-(aminomethyl)-3-fluoroallyl)oxy)phenyl)sulfonyl)methyl)-N-(cyclopropylmethyl)bicyclo[2.2.2]octane-1-carboxamide, (E)-4-(((4-((2-(aminomethyl)-3-fluoroallyl)oxy)phenyl)sulfonyl)methyl)-N-(1-methylcyclopropyl)bicyclo[2.2.2]octane-1-carboxamide, (E)-4-(((4-((2-(aminomethyl)-3-fluoroallyl)oxy)phenyl)sulfonyl)methyl)-N-(2-isopropoxyethyl)bicyclo[2.2.2]octane-1-carboxamide, (E)-4-(((4-((2-(aminomethyl)-3-fluoroallyl)oxy)phenyl)sulfonyl)methyl)-N-(3,3-difluorocyclobutyl)bicyclo[2.2.2]octane-1-carboxamide, (E)-4-(((4-((2-(aminomethyl)-3-fluoroallyl)oxy)phenyl)sulfonyl)methyl)-N-(tert-butyl)bicyclo[2.2.2]octane-1-carboxamide, (E)-(4-(((4-((2-(aminomethyl)-3-fluoroallyl)oxy)phenyl)sulfonyl)methyl)bicyclo[2.2.2]octan-1-yl)(azetidin-1-yl)methanone, (E)-(4-(((4-((2-(aminomethyl)-3-fluoroallyl)oxy)phenyl)sulfonyl)methyl)bicyclo[2.2.2]octan-1-yl)(3,3-difluoroazetidin-1-yl)methanone, (E)-4-(((4-((2-(aminomethyl)-3-fluoroallyl)oxy)phenyl)sulfonyl)methyl)-N-cyclopropyl-N-methylbicyclo[2.2.2]octane-1-carboxamide, (E)-4-(((4-((2-(aminomethyl)-3-fluoroallyl)oxy)phenyl)sulfonyl)methyl)-N,N-diethylbicyclo[2.2.2]octane-1-carboxamide, (E)-4-(((4-((2-(aminomethyl)-3-fluoroallyl)oxy)phenyl)sulfonyl)methyl)-N-cyclopropylbicyclo[2.2.2]octane-1-carboxamide, (E)-N-(4-(((4-((2-(aminomethyl)-3-fluoroallyl)oxy)phenyl)sulfonyl)methyl)bicyclo[2.2.2]octan-1-yl)cyclopropanecarboxamide, (E)-N-(3-(((4-((2-(aminomethyl)-3-fluoroallyl)oxy)phenyl)sulfonyl)methyl)bicyclo[1.1.1]pentan-1-yl)pivalamide, (E)-N-(4-(((4-((2-(aminomethyl)-3-fluoroallyl)oxy)phenyl)sulfonyl)methyl)bicyclo[2.2.2]octan-1-yl)-N-methylcyclopropanecarboxamide, (E)-N-(4-(((4-((2-(aminomethyl)-3-fluoroallyl)oxy)phenyl)sulfonyl)methyl)bicyclo[2.2.2]octan-1-yl)-3,3,3-trifluoropropanamide, (E)-N-(4-(((4-((2-(aminomethyl)-3-fluoroallyl)oxy)phenyl)sulfonyl)methyl)bicyclo[2.2.2]octan-1-yl)isobutyramide, (E)-N-(4-(((4-((2-(aminomethyl)-3-fluoroallyl)oxy)phenyl)sulfonyl)methyl)bicyclo[2.2.2]octan-1-yl)cyclopropanesulfonamide, (E)-2-(4-(((4-((2-(aminomethyl)-3-fluoroallyl)oxy)phenyl)sulfonyl)methyl)bicyclo[2.2.2]octan-1-yl)isothiazolidine 1,1-dioxide, (E)-1-(4-(((4-((2-(aminomethyl)-3-fluoroallyl)oxy)phenyl)sulfonyl)methyl)bicyclo[2.2.2]octan-1-yl)-3-methylpyrrolidin-2-one, (E)-N-(4-(((4-((2-(aminomethyl)-3-fluoroallyl)oxy)phenyl)sulfonyl)methyl)bicyclo[2.2.2]octan-1-yl)-2,2-difluorocyclopropane-1-carboxamide, (E)-N-(4-(((4-((2-(aminomethyl)-3-fluoroallyl)oxy)phenyl)sulfonyl)methyl)bicyclo[2.2.2]octan-1-yl)-1-(trifluoromethyl)cyclopropane-1-carboxamide, (E)-N-(4-(((4-((2-(aminomethyl)-3-fluoroallyl)oxy)phenyl)sulfonyl)methyl)bicyclo[2.2.2]octan-1-yl)-1-fluorocyclopropane-1-carboxamide, (E)-4-(((4-((2-(aminomethyl)-3-fluoroallyl)oxy)phenyl)sulfonyl)methyl)bicyclo[2.2.2]octane-1-carbonitrile, N-((1r,4r)-4-(((4-(((E)-2-(aminomethyl)-3-fluoroallyl)oxy)phenyl)sulfonyl)methyl)cyclohexyl)cyclopropanecarboxamide, (E)-4-(((4-((2-(aminomethyl)-3-fluoroallyl)oxy)phenyl)sulfonyl)methyl)-N-cyclobutyl-2-(trifluoromethyl)benzamide, (E)-N-(4-(((4-((2-(aminomethyl)-3-fluoroallyl)oxy)phenyl)sulfonyl)methyl)bicyclo[2.2.2]octan-1-yl)pivalamide, (E)-N-(4-(((4-((2-(aminomethyl)-3-fluoroallyl)oxy)phenyl)sulfonyl)methyl)bicyclo[2.2.2]octan-1-yl)-1-methylcyclopropane-1-carboxamide, (E)-N-(4-(((4-((2-(aminomethyl)-3-fluoroallyl)oxy)phenyl)sulfonyl)methyl)bicyclo[2.2.2]octan-1-yl)cyclobutanecarboxamide, (R,E)-1-(3-((4-((2-(aminomethyl)-3-fluoroallyl)oxy)phenyl)sulfonyl)-2-methylpropyl)pyrrolidin-2-one, (S,E)-1-(3-((4-((2-(aminomethyl)-3-fluoroallyl)oxy)phenyl)sulfonyl)-2-methylpropyl)pyrrolidin-2-one, (E)-3-((4-((2-(aminomethyl)-3-fluoroallyl)oxy)phenyl)sulfonyl)-N-isopropyl-N,2,2-trimethylpropanamide, (E)-N-(3-((4-((2-(aminomethyl)-3-fluoroallyl)oxy)phenyl)sulfonyl)-2,2-dimethylpropyl)-N-methylisobutyramide, (E)-N-(3-((4-((2-(aminomethyl)-3-fluoroallyl)oxy)phenyl)sulfonyl)-2-methylpropyl)-N-ethylisobutyramide, (E)-N-(3-((4-((2-(aminomethyl)-3-fluoroallyl)oxy)phenyl)sulfonyl)-2,2-dimethylpropyl)-N-ethylisobutyramide, (E)-1-(3-(((4-((2-(aminomethyl)-3-fluoroallyl)oxy)phenyl)sulfonyl)methyl)pyrrolidin-1-yl)-2-methylpropan-1-one, (E)-(3-(((4-((2-(aminomethyl)-3-fluoroallyl)oxy)phenyl)sulfonyl)methyl)piperidin-1-yl)(cyclopentyl)methanone, (E)-4-(((4-((2-(aminomethyl)-3-fluoroallyl)oxy)phenyl)sulfonyl)methyl)-1-isopropylpyridin-2 (1H)-one, (E)-6-(((4-((2-(aminomethyl)-3-fluoroallyl)oxy)phenyl)sulfonyl)methyl)-2-isopropylpyridazin-3 (2H)-one, (E)-3-fluoro-2-((4-(((2-(pyrrolidin-1-yl)pyrimidin-5-yl)methyl)sulfonyl)phenoxy)methyl)prop-2-en-1-amine, (R,E)-1-(3-((4-((2-(aminomethyl)-3-fluoroallyl)oxy)phenyl)sulfonyl)-2-methylpropyl)piperidin-2-one, (S,E)-1-(3-((4-((2-(aminomethyl)-3-fluoroallyl)oxy)phenyl)sulfonyl)-2-methylpropyl)piperidin-2-one, (E)-1-((1-(((4-((2-(aminomethyl)-3-fluoroallyl)oxy)phenyl)sulfonyl)methyl)cyclopropyl)methyl)piperidin-2-one, (E)-1-(2-((4-((2-(aminomethyl)-3-fluoroallyl)oxy)phenyl)sulfonyl)ethyl)piperidin-2-one, (S,E)-1-(1-((4-((2-(aminomethyl)-3-fluoroallyl)oxy)phenyl)sulfonyl)propan-2-yl)piperidin-2-one, (R,E)-2-(3-((4-((2-(aminomethyl)-3-fluoroallyl)oxy)phenyl)sulfonyl)-2-methylpropyl)-2-azaspiro[4.4]nonan-1-one, (S,E)-2-(3-((4-((2-(aminomethyl)-3-fluoroallyl)oxy)phenyl)sulfonyl)-2-methylpropyl)-2-azaspiro[4.4]nonan-1-one, (E)-1-(3-((4-((2-(aminomethyl)-3-fluoroallyl)oxy)phenyl)sulfonyl)-2-methylpropyl)-5,5-dimethylpyrrolidin-2-one,
(R,E)-3-fluoro-2-((4-((2-methyl-3-morpholinopropyl)sulfonyl)phenoxy)methyl)prop-2-en-1-amine,
(S,E)-3-fluoro-2-((4-((2-methyl-3-morpholinopropyl)sulfonyl)phenoxy)methyl)prop-2-en-1-amine,
(E)-3-fluoro-2-((3-fluoro-4-((2-methyl-3-morpholinopropyl)sulfonyl)phenoxy)methyl)prop-2-en-1-amine,
(E)-2-((4-((2,2-dimethyl-3-morpholinopropyl)sulfonyl)phenoxy)methyl)-3-fluoroprop-2-en-1-amine,
(E)-3-fluoro-2-((4-(((1-(morpholinomethyl)cyclopropyl)methyl)sulfonyl)phenoxy)methyl)prop-2-en-1-amine,
(E)-1-(((4-((2-(aminomethyl)-3-fluoroallyl)oxy)phenyl)sulfonyl)methyl)pyrrolidin-2-one,
(E)-2-(((4-((2-(aminomethyl)-3-fluoroallyl)oxy)phenyl)sulfonyl)methyl)isoindolin-1-one,
(E)-1-(((4-((2-(aminomethyl)-3-fluoroallyl)oxy)phenyl)sulfonyl)methyl)-3,4-dihydroquinolin-2 (1H)-one,
(E)-1'-(((4-((2-(aminomethyl)-3-fluoroallyl)oxy)phenyl)sulfonyl)methyl)spiro[cyclopropane-1,3'-indolin]-2'-one,
(E)-1-(((4-((2-(aminomethyl)-3-fluoroallyl)oxy)phenyl)sulfonyl)methyl)pyridin-2 (1H)-one,
(E)-N-(((4-((2-(aminomethyl)-3-fluoroallyl)oxy)phenyl)sulfonyl)methyl)-N-methylisobutyramide,
(E)-1-(((4-((2-(aminomethyl)-3-fluoroallyl)oxy)phenyl)sulfonyl)methyl)-5,5-dimethylpyrrolidin-2-one,
(E)-1-(((4-((2-(aminomethyl)-3-fluoroallyl)oxy)-2-chlorophenyl)sulfonyl)methyl)-5,5-dimethylpyrrolidin-2-one,
(E)-1-(((4-((2-(aminomethyl)-3-fluoroallyl)oxy)phenyl)sulfonyl)methyl)-3,3-dimethylpyrrolidin-2-one,
(E)-1-(((4-((2-(aminomethyl)-3-fluoroallyl)oxy)phenyl)sulfonyl)methyl)-4,4-dimethylpyrrolidin-2-one,
(E)-2-(((4-((2-(aminomethyl)-3-fluoroallyl)oxy)phenyl)sulfonyl)methyl)-2-azaspiro[4.4]nonan-1-one,
(E)-2-(((4-((2-(aminomethyl)-3-fluoroallyl)oxy)-2-fluorophenyl)sulfonyl)methyl)-2-azaspiro[4.4]nonan-1-one,
(E)-1-(((4-((2-(aminomethyl)-3-fluoroallyl)oxy)phenyl)sulfonyl)methyl)piperidin-2-one,
(E)-4-(((4-((2-(aminomethyl)-3-fluoroallyl)oxy)phenyl)sulfonyl)methyl)morpholin-3-one,
(E)-4-(((4-((2-(aminomethyl)-3-fluoroallyl)oxy)-2-fluorophenyl)sulfonyl)methyl)morpholin-3-one,
(E)-4-(((4-((2-(aminomethyl)-3-fluoroallyl)oxy)phenyl)sulfonyl)methyl)-5,5-dimethylmorpholin-3-one,
(E)-1-(((4-((2-(aminomethyl)-3-fluoroallyl)oxy)phenyl)sulfonyl)methyl)-4-pivaloylpiperazin-2-one,
(E)-1-(((4-((2-(aminomethyl)-3-fluoroallyl)oxy)phenyl)sulfonyl)methyl)-4-(1-methylcyclobutane-1-carbonyl)piperazin-2-one,
(E)-1-(((4-((2-(aminomethyl)-3-fluoroallyl)oxy)phenyl)sulfonyl)methyl)-4-isopropylpiperazin-2-one,
(5r,8r)-8-(((4-(((E)-2-(aminomethyl)-3-fluoroallyl)oxy)phenyl)sulfonyl)methyl)-2-isopropyl-2-azaspiro[4.5]decan-1-one,
(5s,8s)-8-(((4-(((E)-2-(aminomethyl)-3-fluoroallyl)oxy)phenyl)sulfonyl)methyl)-2-isopropyl-2-azaspiro[4.5]decan-1-one,
(E)-3-(((4-((2-(aminomethyl)-3-fluoroallyl)oxy)phenyl)sulfonyl)methyl)-N-cyclobutylbicyclo[1.1.1]pentane-1-carboxamide,
(Z)—N-(4-(((4-((2-(aminomethyl)-3-fluoroallyl)oxy)phenyl)sulfonyl)methyl)bicyclo[2.2.2]octan-1-yl)cyclopropanecarboxamide,
(Z)-4-(((4-((2-(aminomethyl)-3-fluoroallyl)oxy)phenyl)sulfonyl)methyl)-N-cyclobutylbicyclo[2.2.2]octane-1-carboxamide,
(Z)-4-(((4-((2-(aminomethyl)-3-fluoroallyl)oxy)phenyl)sulfonyl)methyl)-N-(tert-butyl)bicyclo[2.2.2]octane-1-carboxamide,
(Z)—N-(4-(((4-((2-(aminomethyl)-3-fluoroallyl)oxy)phenyl)sulfonyl)methyl)bicyclo[2.2.2]octan-1-yl)pivalamide,
(E)-4-(((4-((2-(aminomethyl)-3-fluoroallyl)oxy)phenyl)sulfonyl)methyl)-N-cyclobutylbicyclo[2.2.1]heptane-1-carboxamide,
(E)-4-(((4-((2-(aminomethyl)-3-fluoroallyl)oxy)phenyl)sulfonyl)methyl)-N-isopropylcyclohexane-1-carboxamide,
(E)-N-(4-(((4-((2-(aminomethyl)-3-fluoroallyl)oxy)phenyl)sulfonyl)methyl)bicyclo[2.2.1]heptan-1-yl)pivalamide, and
(E)-4-(((4-((2-(aminomethyl)-3-fluoroallyl)oxy)phenyl)sulfonyl)methyl)bicyclo[2.2.2]octane-1-carboxylic acid, or a pharmaceutically acceptable salt, solvate, stereoisomer, or tautomer thereof.

17. A pharmaceutical composition comprising a compound of claim 1, or a pharmaceutically acceptable salt, solvate, stereoisomer, or tautomer thereof, and a pharmaceutically acceptable diluent, excipient or carrier.

18. A method of modulating SSAO or treating a SSAO-mediated disorder, comprising administering to a subject in need thereof, a therapeutically effective amount of a compound of claim 1, or a pharmaceutically acceptable salt, solvate, stereoisomer, or tautomer thereof, wherein the SSAO-mediated disorder is liver inflammation, liver fibrosis, nonalcoholic fatty liver disease, nonalcoholic steatohepatitis, or stroke.

19. The compound of claim 16, wherein the compound is selected from the group consisting of:

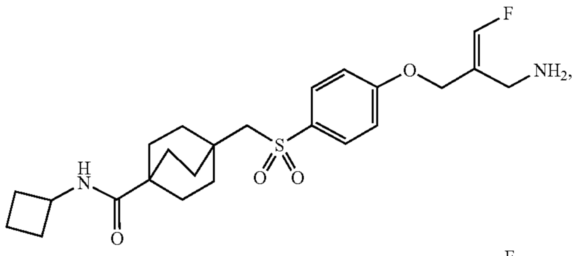

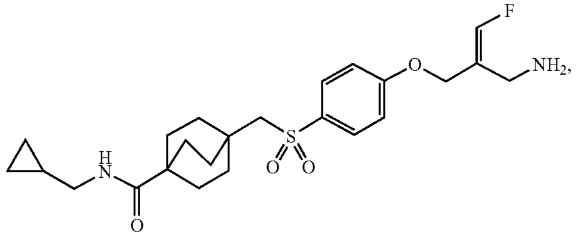

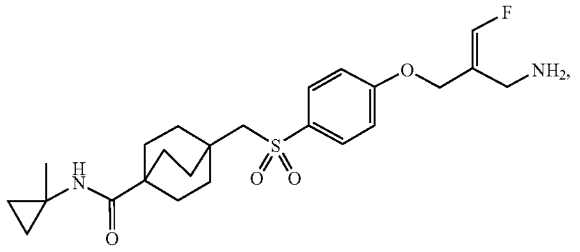

-continued
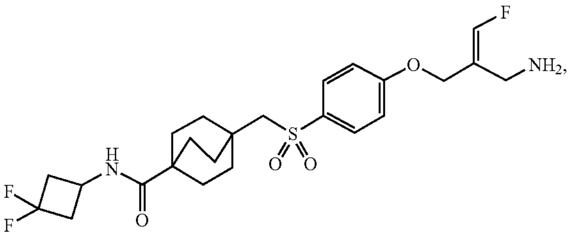
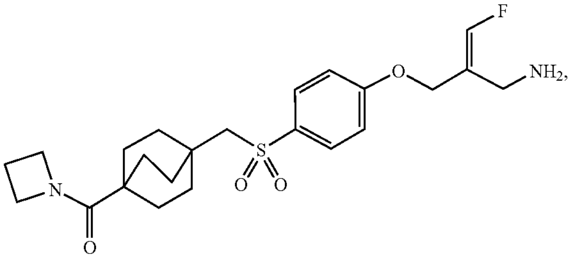
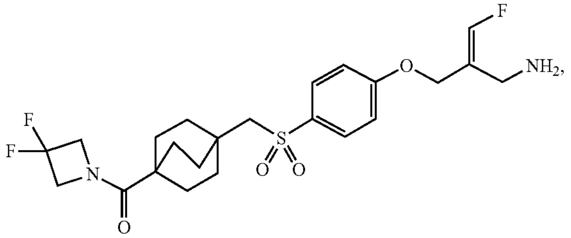
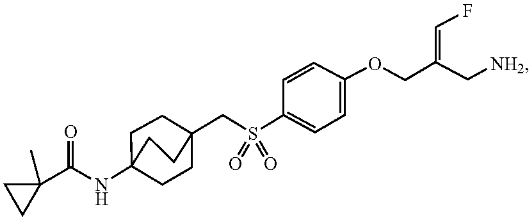
and
-continued
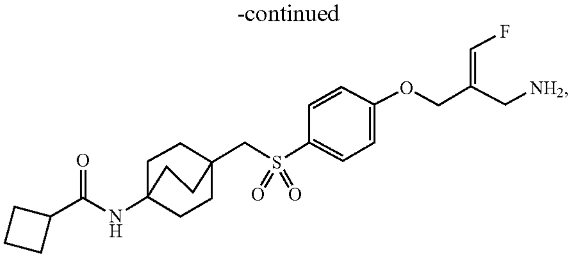
or a pharmaceutically acceptable salt, solvate, stereoisomer, or tautomer thereof.
20. The compound of claim 1, wherein m is 1 or 2.
21. The compound of claim 1, wherein m and n are each 2.
22. The compound of claim 6, wherein
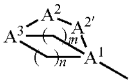
is selected from:
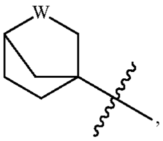,
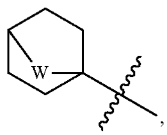,
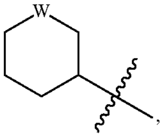,
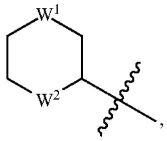,
and
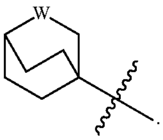.
* * * * *

UNITED STATES PATENT AND TRADEMARK OFFICE

CERTIFICATE OF CORRECTION

PATENT NO. : 11,472,769 B2
APPLICATION NO. : 17/082323
DATED : October 18, 2022
INVENTOR(S) : Zaifang Ren et al.

It is certified that error appears in the above-identified patent and that said Letters Patent is hereby corrected as shown below:

In the Claims

Column 334, Claim 8, Line 11, please replace:
"$R^7$, $C(O)NR^7NR^{7'}$, $NR^3C(O)R^7$, $NR'S(O)_2R^4$, $S(O)_2R^4$, or"
With:
--$R^7$, $C(O)NR^7NR^{7'}$, $NR^3C(O)R^7$, $NR^3S(O)_2R^4$, $S(O)_2R^4$, or--

Signed and Sealed this
Twenty-second Day of November, 2022

Katherine Kelly Vidal
*Director of the United States Patent and Trademark Office*